(12) United States Patent
Webster et al.

(10) Patent No.: US 6,680,188 B2
(45) Date of Patent: Jan. 20, 2004

(54) ISOLATED HUMAN KINASE PROTEINS, NUCLEIC ACID MOLECULES ENCODING HUMAN KINASE PROTEINS, AND USES THEREOF

(75) Inventors: Marion Webster, San Francisco, CA (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 10/238,709

(22) Filed: Sep. 11, 2002

(65) Prior Publication Data

US 2003/0022340 A1 Jan. 30, 2003

Related U.S. Application Data

(62) Division of application No. 09/804,471, filed on Mar. 13, 2001, now Pat. No. 6,479,269.

(51) Int. Cl.[7] .............................. C12N 9/12; C12N 1/20; C12N 15/00; C12N 5/00; C07K 1/00

(52) U.S. Cl. .................. 435/194; 530/350; 435/320.1; 435/325; 435/252.3; 435/6

(58) Field of Search .............................. 435/194, 320.1, 435/252.3, 6, 325; 530/350

(56) References Cited

PUBLICATIONS

Di Cunto et al., J.B.C., 273(45), 29706–29711, 1998.*

Results of BLAST search of SEQ ID No.: 2 against Derwent (FastAlertP and GeneseqP) and NCBI (pataa) Protein Patent Databases on May 29, 2003.

* cited by examiner

*Primary Examiner*—Maryam Monshipouri
(74) *Attorney, Agent, or Firm*—Justin D. Karjala; Celera Genomics

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

4 Claims, 105 Drawing Sheets

```
   1 GGGGAGATGT TGAAGTTCAA ATATGGAGCG CGGAATCCTT TGGATGCTGG
  51 TGCTGCTGAA CCCATTGCCA ACCGGGCCTC CAGGCTGAAT CTGTTCTTCC
 101 AGGGGAAACC ACCCTTTATG ACTCAACAGC AGATGTCTCC TCTTTCCCGA
 151 GAAGGGATAT TAGATGCCCT CTTTGTTCTC TTTGAAGAAT GCAGTCAGCC
 201 TGCTCTGATG AAGATTAAGC ACGTGAGCAA CTTTGTCCGG AAGTATTCCG
 251 ACACCATAGC TGAGTTACAG GAGCTCCAGC CTTCGGCAAA GGACTTCGAA
 301 GTCAGAAGTC TTGTAGGTTG TGGTCACTTT GCTGAAGTGC AGGTGGTAAG
 351 AGAGAAAGCA ACCGGGGACA TCTATGCTAT GAAAGTGATG AAGAAGAAGG
 401 CTTTATTGGC CCAGGAGCAG GTTTCATTTT TTGAGGAAGA GCGGAACATA
 451 TTATCTCGAA GCACAAGCCC GTGGATCCCC CAATTACAGT ATGCCTTTCA
 501 GGACAAAAAT CACCTTTATC TGGTCATGGA ATATCAGCCT GGAGGGGACT
 551 TGCTGTCACT TTTGAATAGA TATGAGGACC AGTTAGATGA AAACCTGATA
 601 CAGTTTTACC TAGCTGAGCT GATTTTGGCT GTTCACAGCG TTCATCTGAT
 651 GGGATACGTG CATCGAGACA TCAAGCCTGA GAACATTCTC GTTGACCGCA
 701 CAGGACACAT CAAGCTGGTG GATTTTGGAT CTGCCGCGAA AATGAATTCA
 751 AACAAGATGG TGAATGCCAA ACTCCCGATT GGGACCCCAG ATTACATGGC
 801 TCCTGAAGTG CTGACTGTGA TGAACGGGGA TGGAAAAGGC ACCTACGGCC
 851 TGGACTGTGA CTGGTGGTCA GTGGGCGTGA TTGCCTATGA GATGATTTAT
 901 GGGAGATCCC CCTTCGCAGA GGGAACCTCT GCCAGAACCT TCAATAACAT
 951 TATGAATTTC CAGCGGTTTT TGAAATTTCC AGATGACCCC AAAGTGAGCA
1001 GTGACTTTCT TGATCTGATT CAAAGCTTGT TGTGCGGCCA GAAAGAGAGA
1051 CTGAAGTTTG AAGGTCTTTG CTGCCATCCT TTCTTCTCTA AAATTGACTG
1101 GAACAACATT CGTAACTCTC CTCCCCCCTT CGTTCCCACC CTCAAGTCCG
1151 ACGATGACAC CTCCAATTTT GATGAACCAG AGAAGAATTC GTGGGTTTCA
1201 TCCTCTCCGT GCCAGCTGAG CCCCTCAGGC TTCTCGGGTG AAGAACTGCC
1251 GTTTGTGGGG TTTTCGTACA GCAAGGCACT GGGGATTCTT GGTAGATCTG
1301 AGTCTGTTGT GTCGGGTCTG GACTCCCCTG CCAAGACTAG CTCCATGGAA
1351 AAGAAACTTC TCATCAAAAG CAAAGAGCTA CAAGACTCTC AGGACAAGTG
1401 TCACAAGGTA TTTATTTCCG CAGCCGGCCT CCTTCCTTGC TCCAGGATCC
1451 TCCCGTCCGT ATATGCCAAG GGATCCGCCC GGGGCCGCTG CTGGCTCTGA
1501 GCCGCCTGAT CCGTA
(SEQ ID NO: 1)
FEATURES:
5'UTR:       1 - 6
Start Codon: 7
Stop Codon:  1498
3'UTR:       1501
```

Homologous proteins:
Top 10 BLAST Hits:

```
                                                              Score   E
Sequences producing significant alignments:                   (bits)  Value
CRA|18000005168810 /altid=gi|3599507 /def=gb|AAC72822.1| (AF086...  888    0.0
CRA|18000005168811 /altid=gi|3599509 /def=gb|AAC72823.1| (AF086...  850    0.0
CRA|18000005161385 /altid=gi|3360512 /def=gb|AAC27932.1| (AF070...  844    0.0
CRA|18000005075416 /altid=gi|7505496 /def=pir||T25808 hypotheti...  352    7e-96
CRA|89000000196974 /altid=gi|7294566 /def=gb|AAF49906.1| (AE003...  347    1e-94
CRA|18000005236627 /altid=gi|5174413 /def=ref|NP_006026.1| CDC4...  346    4e-94
CRA|335001098689373 /altid=gi|11433630 /def=ref|XP_007257.1| CD...  346    4e-94
CRA|18000005123191 /altid=gi|7446379 /def=pir||T14039 protein k...  343    3e-93
CRA|18000005057611 /altid=gi|4505831 /def=ref|NP_003598.1| ser-...  342    6e-93
CRA|18000005067765 /altid=gi|7495847 /def=pir||T25539 hypotheti...  340    2e-92
```

FIGURE 1A

EST:

```
                                                  Score      E
Sequences producing significant alignments:       (bits)   value
gi|11292270 /dataset=dbest /taxon=96...            630     e-178
gi|11369862 /dataset=dbest /taxon=96...            615     e-173
gi|12111020 /dataset=dbest /taxon=96...            517     e-144
gi|12362084 /dataset=dbest /taxon=96...            492     e-136
gi|12349935 /dataset=dbest /taxon=96...            492     e-136
```

FIGURE 1B

```
EXPRESSION INFORMATION FOR MODULATORY USE:
gi|11292270  Brain- glioblastoma
gi|11369862  Uterus tumor
gi|12111020  Colon
gi|12362084  Nervous- normal
gi|12349935  Nervous- tumor
```

Tissue Expression:
Pooled tissues

FIGURE 1C

```
  1 MLKFKYGARN PLDAGAAEPI ANRASRLNLF FQGKPPFMTQ QQMSPLSREG
 51 ILDALFVLFE ECSQPALMKI KHVSNFVRKY SDTIAELQEL QPSAKDFEVR
101 SLVGCGHFAE VQVVREKATG DIYAMKVMKK KALLAQEQVS FFEEERNILS
151 RSTSPWIPQL QYAFQDKNHL YLVMEYQPGG DLLSLLNRYE DQLDENLIQF
201 YLAELILAVH SVHLMGYVHR DIKPENILVD RTGHIKLVDF GSAAKMNSNK
251 MVNAKLPIGT PDYMAPEVLT VMNGDGKGTY GLDCDWWSVG VIAYEMIYGR
301 SPFAEGTSAR TFNNIMNFQR FLKFPDDPKV SSDFLDLIQS LLCGQKERLK
351 FEGLCCHPFF SKIDWNNIRN SPPPFVPTLK SDDDTSNFDE PEKNSWVSSS
401 PCQLSPSGFS GEELPFVGFS YSKALGILGR SESVVSGLDS PAKTSSMEKK
451 LLIKSKELQD SQDKCHKVFI SAAGLLPCSR ILPSVYAKGS ARGRCWL
        (SEQ ID NO:2)
```

FEATURES:
Functional domains and key regions:
Prosite results:

[1] PDOC00004 PS00004 CAMP_PHOSPHO_SITE
cAMP- and cGMP-dependent protein kinase phosphorylation site 78-81  RKYS
------------------------------------------------------------
--
[2] PDOC00005 PS00005 PKC_PHOSPHO_SITE
Protein kinase C phosphorylation site Number of matches: 5
        1      93-95   SAK
        2    248-250   SNK
        3    308-310   SAR
        4    490-492   SAR
        5    378-380   TLK
------------------------------------------------------------
---
[3] PDOC00006 PS00006 CK2_PHOSPHO_SITE
Casein kinase II phosphorylation site Number of matches: 9
        1      83-86   TIAE
        2      93-96   SAKD
        3    140-143   SFFE
        4    361-364   SKID
        5    381-384   SDDD
        6    386-389   SNFD
        7    410-413   SGEE
        8    436-439   SGLD
        9    445-448   SSME
------------------------------------------------------------
----
[4] PDOC00008 PS00008 MYRISTYL
N-myristoylation site Number of matches: 3

FIGURE 2A

```
       1      50-55    GILDAL
       2    474-479    GLLPCS
       3    489-494    GSARGR
-----------------------------------------------------------------
[5] PDOC00100 PS00107 PROTEIN_KINASE_ATP
Protein kinases ATP-binding region signature 103-126    VGCGHFAEVQVVREKATGDIYAMK
-----------------------------------------------------------------
[6] PDOC00100 PS00108 PROTEIN_KINASE_ST
Serine/Threonine protein kinases active-site signature 217-229    YVHRDIKPENILV
```

Membrane spanning structure and domains:
Candidate membrane-spanning segments:
```
 Helix Begin    End    Score Certainity
     1   197    217    0.789 Putative
     2   467    487    0.714 Putative
```

FIGURE 2B

BLAST Alignment to Top Hit:
Alignment to top blast hit:

>CRA|18000005168810 /altid=gi|3599507 /def=gb|AAC72822.1|
(AF086823)
        rho/rac-interacting citron kinase short isoform [Mus
        musculus] /org=Mus musculus /taxon=10090
/dataset=nraa
        /length=494
        Length = 494

Score =  888 bits (2270), Expect = 0.0
 Identities = 432/495 (87%), Positives = 459/495 (92%)
 Frame = +1

Query: 7
MLKFKYGARNPLDAGAAEPIANRASRLNLFFQGKPPFMTQQQMSPLSREGILDALFVLFE 186
MLKFKYG RNP +A A+EPIA+RASRLNLFFQGKPP MTQQQMS LSREG+LDALF LFE
Sbjct: 1 MLKFKYGVRNPPEASASEPIASRASRLNLFFQGKPPLMTQQQMSALSREGMLDALFALFE 60

Query: 187   ECSQPALMKIKHVSNFVRKYSDTIAELQELQPSAKDFEVRSLVGCGHFAEVQVVREKATG 366
             ECSQPALMK+KHVS+FV+KYSDTIAEL+ELQPSA+DFEVRSLVGCGHFAEVQVVREKATG
Sbjct: 61    ECSQPALMKMKHVSSFVQKYSDTIAELRELQPSARDFEVRSLVGCGHFAEVQVVREKATG 120

Query: 367   DIYAMKVMKKKALLAQEQVSFFEEERNILSRSTSPWIPQLQYAFQDKNHLYLVMEYQPGG 546
             D+YAMK+MKKKALLAQEQVSFFEEERNILSRSTSPWIPQLQYAFQDKN+LYLVMEYQPGG
Sbjct: 121   DVYAMKIMKKKALLAQEQVSFFEEERNILSRSTSPWIPQLQYAFQDKNNLYLVMEYQPGG 180

Query: 547   DLLSLLNRYEDQLDENLIQFYLAELILAVHSVHLMGYVHRDIKPENILVDRTGHIKLVDF 726
             D LSLLNRYEDQLDE++IQFYLAELILAVHSVH MGYVHRDIKPENIL+DRTG IKLVDF
Sbjct: 181   DFLSLLNRYEDQLDESMIQFYLAELILAVHSVHQMGYVHRDIKPENILIDRTGEIKLVDF 240

Query: 727   GSAAKMNSNKMVNAKLPIGTPDYMAPEVLTVMNGDGKGTYGLDCDWWSVGVIAYEMIYGR 906
             GSAAKMNSNK V+AKLPIGTPDYMAPEVLTVMN D +GTYGLDCDWWSVGV+AYEM+YG+
Sbjct: 241   GSAAKMNSNK-VDAKLPIGTPDYMAPEVLTVMNEDRRGTYGLDCDWWSVGVVAYEMVYGK 299

Query: 907   SPFAEGTSARTFNNIMNFQRFLKFPDDPKVSSDFLDLIQSLLCGQKERLKFEGLCCHPFF 1086
             +PF EGTSARTFNNIMNFQRFLKFPDDPKVSS+ LDL+QSLLC QKERLKFEGLCCHPFF
Sbjct: 300   TPFTEGTSARTFNNIMNFQRFLKFPDDPKVSSELLDLLQSLLCVQKERLKFEGLCCHPFF 359

Query: 1087  SKIDWNNIRNSPPPFVPTLKSDDDTSNFDEPEKNSWVSSSPCQLSPSGFSGEELPFVGFS 1266
             ++ DWNNIRNSPPPFVPTLKSDDDTSNFDEPEKNSW P FSGEELPFVGFS
Sbjct: 360   ARTDWNNIRNSPPPFVPTLKSDDDTSNFDEPEKNSWAFILCVPAEPLAFSGEELPFVGFS 419

Query: 1267  YSKALGILGRSESVVSGLDSPAKTSSMEKKLLIKSKELQDSQDKCHKVFISAAGLLPCSR 1446
             YSKALG LGRSESVVS LDSPAK SSMEKKLLIKSKELQDSQDKCHKV IS AGL PCSR
Sbjct: 420   YSKALGYLGRSESVVSSLDSPAKVSSMEKKLLIKSKELQDSQDKCHKVSISTAGLRPCSR 479

QuerySIYAEGSAGGHC 494 (SEQ ID NO:4)
: 1447 ILPSVYAKGSARGRC 1491
IL S+YA+GSA G C
Sbjct: 480 ILQ

FIGURE 2C

```
Hmmer search results (Pfam):
Scores for sequence family classification (score includes all domains):
Model      Description                                      Score    E-value   N
--------   -----------                                      -----    -------   ---
PF00069    Eukaryotic protein kinase domain                 219.4    5.5e-62   1
CE00022    CE00022 MAGUK_subfamily_d                         28.0    3.5e-08   1
CE00359    E00359 bone_morphogenetic_protein_receptor        21.4    2.4e-05   1
PF00433    Protein kinase C terminal domain                  15.4    0.0018    1
CE00287    CE00287 PTK_Eph_orphan_receptor                  -56.4    0.00012   1
CE00292    CE00292 PTK_membrane_span                        -91.3    0.0013    1
CE00291    CE00291 PTK_fgf_receptor                        -110.8    0.021     1
CE00286    E00286 PTK_EGF_receptor                         -122.6    0.0015    1
CE00290    CE00290 PTK_Trk_family                          -180.0    0.0073    1
CE00016    CE00016 GSK_glycogen_synthase_kinase            -201.8    1.8e-05   1
```

FIGURE 2D

```
Parsed for domains:
Model     Domain  seq-f seq-t    hmm-f hmm-t       score   E-value
--------  ------  ----- -----    ----- -----       -----   -------
CE00359   1/1      219   269 ..    274   327 ..     21.4   2.4e-05
CE00022   1/1      218   316 ..    143   238 ..     28.0   3.5e-08
CE00292   1/1       97   341 ..      1   288 []    -91.3   0.0013
CE00290   1/1       99   341 ..      1   282 []   -180.0   0.0073
CE00286   1/1       96   341 ..      1   263 []   -122.6   0.0015
CE00291   1/1       97   341 ..      1   285 []   -110.8   0.021
CE00287   1/1       97   358 ..      1   260 []    -56.4   0.00012
PF00069   1/1       97   360 ..      1   278 []    219.4   5.5e-62
PF00433   1/1      361   390 ..      1    32 [.     15.4   0.0018
CE00016   1/1       38   438 ..      1   433 []   -201.8   1.8e-05
```

FIGURE 2E

```
   1 TACACCTAGC AATAGTCATA GAATGCACAA ATCTTCAATG TTAGCAAATA
  51 ATGCCAAACT TTTTTTTCAA ATTTCAAAGA GATTGTATCC ATTTACACGC
 101 CTACGGGTAC TGTATAAGTG TGTGTACTTC CACATCTTCG CAAACACTGT
 151 CACATCCTTT TGTTGTTGTT GTTCTCGAAT TTGAGTGTTA TTCTTTCTCA
 201 CTGTGACTTT ATTTTTCATA TTTTCTGATT ATGAACGAGG TTGACAACTT
 251 TCACACATTT GTTGGTCATC TGGATTTCCT TTTTGGTGAA GTGCCTGTTT
 301 AAGTATCTCG TCTATAATTT ATTTTAAAGT GTCCTTTCAG ACAGTCTCAA
 351 TGACTGTCAC CAACTCCTTG CAGGGCAGTC AGCCCGGAGA TAGAGTAATC
 401 AAGGTAGGTT GAAGTCAAGC TCAAAACATT CGCTGCCTCA GCTGTAGCAG
 451 AGGACCACTG GGCTTCCCCA GGTAACAAGT ACTTCTACCT TAGCCACATG
 501 AGAGAGAAAG AAGACCAGGC AGAGCAGCCT GGCTGCCTTC CTCCTTGCAG
 551 GTGGCCGAGA GCAGGGACA GCGCCTGGC GACCTCCTCA GGGATCCTAG
 601 ATTAACAGTC GCGTCCTCAA ACGCAGCATC CTGCGTAACC GCCAATTTCA
 651 AACTTCCAAG ACCTGCCCTG CTGATTTTGC CCTTCCCTTT TTCCCGTTGG
 701 TCGCGAGTCA AAGGAAGATG CAATTTGATT GGCTCTCCCC TTCACTTTCC
 751 TCCATGCCTT TAGGGACATG GGCGGGGCCT GGCTGAGACG CCCATGTCTA
 801 TCATAGGAGC GGAGACGCTG ATTGGTCCAA ACACGGCTGA GACCCGCCCG
 851 CGCCGTTCCT CGGGTTCAAA CGCGGCGGCG GGAGGCGCGG GCGGAACAG
 901 ATCGCAGACC TGGGGGTTCG CAGAGCGTGA GTCTGATCCC CCAGACCCAA
 951 TTCTACCGCA CCCGGCTCTG CAAGGCCAGG GGAGGGCCGC CTCCACCCAT
1001 ACAAGTCCCG GGTTTCCCTC CCGCCCCGGG GAGGGCGGCG ATTCCACCCC
1051 CAGGGCTGCG GGAGGCCTGG AGGGTCTTCC GGGGCTAGCT GTGCGCGCGC
1101 CCACCTTCCT TGGGAGCCGA GGGGTCAGCC GAGTGGTGCT GGGGCAGGAG
1151 GCTTGCTCCT CCCCTAAACC AGGCGGAGTG CTTTGTCTCT TCAGCTCTGC
1201 CTCCTGTCAG CACTAACTGC ATTATTCTGC CCAGTGTAGT CGGCCGGTTC
1251 CTTATTATCT GCGTGAACTT AGCCATTTAC TTAACCTCTC TGTTTCAGCG
1301 TATTCATACC CCGTGCCCAC CCCATCACCT CATGATGCCC CCGCCTCTTT
1351 CGCTCTGCTC CAGTCCGTCT GGCCTCGCTG TTGCTGGAGA GGCCAGGTCC
1401 TGCCTCAGTG CTTTTGGCTT GGCTGTTTCG TTTGCCACGG ATGTCTTTCT
1451 TTCCCCAGAT ATCAACATGG CTTGCTGGTC ATTCGCTTCA GGTCTTCAAG
1501 TCTTGGGTCA AATGGTGGCT TCTCAGTGAA GTCTTATTTG ACCACACTAA
1551 AAATTGCACC ATCTCACCCC CATTGTCCTT TTCTTGCTCG ATTTTGTTTT
1601 TACCCCATAG CACTTAACAC CTTACAACAA GCTATATATT TTGCTTATTT
1651 CAGTCATTCA TTTAATAACT ATTCGCACCT ATTTGTGTGC CAGGCTATGT
1701 GTGCCCCCAC TGCATGGGGG CAAACATCTC TGCCCTTGTG GAGCTTCCAT
1751 TCTAAGGGGG GAGATAATAA ACACATTTAT AAGTAAGAGA GTATGTCAGA
1801 TAAGTGTATC ATCTCCTGTC ACAGTGAGTT AAAATCTGGT GTTTAATCTC
1851 CATGATTAGA CTGAGCTTCC TAAAACTGGA GTGGTAGCTG ATTTTCACCT
1901 CCTTGTCCCT GATATCTTGA GGGAGATCAG GATCTCTCAG GCCCTTCCTG
1951 CTCAAAACAT AGGACACACT TGACTTTTCT GATATCCTTT CAGCGCCAGT
2001 GGGGAGATGT TGAAGTTCAA ATATGGAGCG CGGAATCCTT TGGATGCTGG
2051 TGCTGCTGAA CCCATTGCCA GCCGGGCCTC CAGGCTGAAT CTGTTCTTCC
2101 AGGTAACAGC CTACCCTGCC AACTTTGCTC ACCTGTGTGT GTCCTTGGAA
2151 TCTCCTTGTC ACTCACCTTT GCTTTTATTT ATTTGTTTAT TTATTTAGAG
2201 TCTCAGTCTC TCAGGCTGGA GTACAGTGG GCAATCTCAG CTCACTGCAA
2251 CCTCCGCCTC CTGGGTTCAA GCGATTCTCC TGCCTCAGCC TCCAGAGTAG
2301 CTGGGACTAC AGCCGCCTGC CACCACACCC GGCTAAATTT TGTATTTTTC
2351 TTTTTAGTAG AGACGGGGTT TCACCATGTT GGCCAGGCTA GGTCGAACT
2401 CCTGACCTCA AGTGATCCAC CTGCCTTGGC CTCCTAAAGT GCTGGGATTA
2451 CAGGCATGAA CCGTGCCCAG CTTGCTTTTA TTATAGGACC AGGGATAATA
2501 TTTTAGGGGA AATTCTGTTT TGTTTTGTTT GAAACAAGGT CTTCTGTCGA
2551 CTCTAGGCCT GTGCCACCAT GCCTGGCTAA TTTTTTAATT TTTTGTAGGG
2601 ATGGGGTCTC ACTGTGTTGC CCAGGCTGAT ATAGAACACC TGACTTCAAG
```

FIGURE 3A

```
2651 TGAGCCTCTT GCCTTGGCCT CCCAAAGCAC TGGGGTTATA GGTGTGAGCC
2701 ACTGCACCTG GCCCTCTATT TAGAGTTTTA TATGCACTGA TTCTTTTGGA
2751 AAAAAGACAC TGTGCAGAAG TAGATAGCTG AACTTGCCTT AGAAGGGAGA
2801 TCTTTTCATA TTTCTCACAC TTTACACTTC TGTACTAAAG TTTATTCATT
2851 CATTGATTGA TTGGTTGCTT GCAAGACAGG GTCTTGCTCT GTGGCTCAGG
2901 CTGGAGTGCA TTGGCACAAT CACGGCTTAC TGCAGCCTTG ACCTCCTGGG
2951 CTCAAACGAT CCTCCCACTT CAGCTTCCTG AGTAGCTGGG ACCACAGGTG
3001 TGTGCCACCA TACCTGGCTA ATTTTTGTAT TTTTTGTAGA GATGAGGTTT
3051 CACCATGTTG CCCAGGCAGG TCTCGAATTC CTGGGCTCAA GTGATCTACT
3101 TGTCACAGCT TCTGCAAGTG TTGGGCTTAC AGGCATAAGC CCCTGTACCA
3151 GGGCAAGTTT GTCCTTTTAT TGAAGAAAGA AAAATAAATG AACAAAGATG
3201 CTTTTTAAAA CTACAATTTC TGTGGGTATA ATCCTATTCA TTTTCATTGC
3251 AGGGATGTTT ATTTTTTAAG ATTTTTTTTT TTTTTTTTTG AGACAGAGTC
3301 TTCGCTGTCG CCCAGGCTGG AGTGCAGTGG CGCGATCTCG GCTCACTGCA
3351 GGCTCTGCCC CCCGGGGTTC ACGCCATTCT CCTGCCTCAG CCTCCCACGT
3401 AGCTGGGACT ACAGGCGCCC GTCACCTCGC CCGGCTAATT TTTTGTATTT
3451 TTAGTAGAGA CGGGGTTTCA CTGTGTTAGC CAGGATGGTA TTTTTTAAGA
3501 TTTTAAAAAA AGTTTTGATG AATACCACAC CTGTTTAACC CTCATTCCTC
3551 TCAAGATACA CATTTCTGTC ACCCCAGATG CGTTAAAACT AATATCATA
3601 AGATTACTTC CAAATAGATT TTTAATTCTT TTGTTTCTGA TGTATGTGGA
3651 ACACTGGTGA AGTAGAAATC CTTGTTTGAT TTATGTATTC GTAAGTCAGG
3701 GGGACAATAG AGACCATGAA GATTTAGAAT TGAATCCCAG TCCCAGCACT
3751 AGTTAGCTGC ATTACTTTGG GTGAGTCAGT TACCTTTTCT GAGTCCATTT
3801 GCTATTCTTT AAAATAGGTT GTAGCCTGTA ATGCCAGTAT TTTCGGAGGC
3851 TGAGGCGGGC GGATTACTTG AGGTCACGGG TTCGAGACCA GCCTGGACAA
3901 CGTGGTGAAA CCCTGTCTCT ACTAAAAATA TAGAAAATTA GCTGGGCATG
3951 GTGGTCGCAT GTACCTGTAA TCCCAGCTAC TTGAAAAGCT GAAGCAGGAG
4001 AATCATTTGA ACCCGGGAGG CGGAGGTTGT CGTGAGCCGA GATGGTGCAC
4051 TGCACTCCAG CCTGGGCGAC AGAGTGGGTA AGACTCCATC TCAAAACAAA
4101 ACAAAACAAA AGAAAACAAA AAAAATAACA TAGAGGTTGT AGTACCTAAT
4151 CCACAGGGTT GTTGTGAGGA TTAGATGAGA TATTCGATTT AAAGCACTTA
4201 GCACCTTGCC TGGCTCTTAG TAAACTCCTT ATAAAAAATG GTAATTATTG
4251 TTAATACTCA GCATAGAATA GTATTAGTTA TAATATTAAT ACTAAATTTG
4301 TTTCCTTAAT AGTAATTATA TTTGGGAAGG TAGTTATGTA GGATACCTGT
4351 AAGATGATGA ATGATGAAGT ATTCTTGATA ACTTTTTTTT TTTTTCCAAA
4401 ATATTGGTAT TGGGTGTTTA AACAGATGAG AGTGGAAACA AATTGAAAGC
4451 TTAGGTTTTT CTGTGGGACC ATCCCCATCA GCATTTTAAG TCTTGACATA
4501 TCTTTCACAA ATGAATAGTC TGTCTTTAAC CTTAGATGGC TGGAGTGCTT
4551 CCACGTTTCA GCCCCTTTAT CATGCTACTT TAAAATATCT CCAACTTGCT
4601 GGGCGTGGTG GCTCACGCCT GTAATCCTAG CAATTTGGGA GGCTGAGGTG
4651 GGTGGATTGC TTGAGGTCAG GAGTTCGAGA GCAGCCCGGG CAACATGGTG
4701 AGCCCCTCCG TTTCTACTAA AAACACAAAA AATAGCTGAC TGTGATGGTG
4751 TGTGCCTGTA GTCCCAGCTA CTCGGGAGGC TGAGGCAGGA GGATCACTTG
4801 AGCCCTAGAG GCAGAGGTTG CAGTGAGCTA AGATTGTGCC ACTGCACTTC
4851 AGCACTTCAG CCTAGGCGAC AGAGCAAGAC CCTGTAAATT AAAAAAAAA
4901 AAAAAAGAA AAGGAAAAAA ATTTCCAACT TATTAAGGGC TTATAGTGTG
4951 CTGATTATGT AATAGTTATG GCTTCCAATG TGTCTGGCAT AGAACTGGCA
5001 TGTTTCTGAG TATCTCACTT CAGCCTCATG ACAGAGGTAA GGACTATTTT
5051 TAATTTAAAC TTTAAATAGG AGGCAACAGG CCAGGTGTGG TGGCTCACAC
5101 CTGTAATCCC AGTACTTTGG GAGGCTGAGG CAGGTGGATT GCTTGAGTCC
5151 AAGAGTTCAA GACTAGCCTG GGCAAAATGG TGAAACCCCA TCTCTACAAA
5201 AAATATAAAT AATTAGTCAG GCATGGCGGT GTGTGCCTGT AGTCCCAGCT
5251 ACTCAGGAGG CTGAGGTGGG GGCATCTCTG GGGCCCCGGA GGCAGAGGTT
```

FIGURE 3B

```
5301 GTAGTGAGTT GAGATTGCAA CACTGCACTC CAGCCTGGGC AACAGAACGA
5351 GACCCTGTTT CTAAATAAAT ACATAAATAG GAGGCAACAG ATATAGACAG
5401 ATATGGAGGT AGGTAAGGCC TTGCCCAAGA TCATACACGT TGGGTTTTGC
5451 AGATGAGGCC AAGATCAGAC TCCATCTTTG GTTGGTCTGA CTCCAAAGGC
5501 TGACCACATA GCCATTGGGC CACAGCACCT GTGCACGTCA GAATTTATTA
5551 AGTATATCTT GTATTAGTC ATTATAACAG GAAGACTTAT GGGTAAACCC
5601 TCAGTTCATC TCTTTTTAAT GCTGAGATCC CCCTGCCCAG TAAAGCTATT
5651 ATTGCAAGTA TAGTATATAC CTATCATTTG CCTTGAGTTA TCAGGTAAGG
5701 ATGCTGTTTG TTCTTTTCCC ATATAGTGCT GTTTGAATGA GGTTGAGATA
5751 CAGTAGCAAT TTTGTTTTCC ATTCAGGTGA GTACCTTAGA CTGAGTGTCA
5801 TTTTGTCTTT TTTACTTCTA CTCAACAGGA TTTCCTGACA TGTTCGAGGT
5851 CAGTGATTGT CAGACTTTCT GAGCCAGCAA AATTTCCCAA ATTGCTGGGT
5901 AGACACAGGT TTTCCAACTT TTTATTTTGC CAAGTAAGGA TATATAAAAA
5951 AAAAATAAAA AGAAAGACCT ATTATTTTCT GGCCCTTGTA TTTCATAAAG
6001 GGCATTTTAA GAAACAACAA GACAGGAAGA ACATCATCTC AGAATAAAGG
6051 ACCATTTTTA AATTTGAATA CATTTAGTTT TATAAAAAAG ATATCATGTG
6101 GTGTTCATTT TTTCTCATTT CACTGCAGGC TGTTGAAAAC TTTGTTAAGA
6151 ACCAGTACTA TATTTGGGAA CCCCTGCTTT AATTGATCTA AACTCTTGAA
6201 GAATAGAAGA AACAAAGCAT TTTATTTTTC TGAGTTACTG GCAACTATTA
6251 CTAAAGTGAC AGATATGGTG GCCTTGAATG CAGTGCTTCC CAAACCTGAT
6301 TGAGGTCTGA CTCTCTTGGG GACCAGGGTC TCATTCTGTT GCCCAGGCTG
6351 GAGTGTGGCA GCACAATCTT GGCTCACTGC AGCCTTTACT TCTTGGGCTC
6401 AAGTGATCCT TCTACCTCAG TCTCACAAGT GGCTAGGACT ACAGGACCAT
6451 GGCACTACAC CTGGCTAATT TTTTTTTGTT TGTTTGTAGA GATGGGATCT
6501 CGCTGTGTTG CCCTGGCTGG TCTTGAACTC CTGGGCTCAA GTGATCCTCC
6551 CACCTTGGCC TCCCAAAGTG CTAGTATTCC AGGTGTGAGC CACCTCTCCC
6601 TGCTGGGGAA CTTGTTAATA AAACAGATTC TAGGCTACAG TCTGGAAAAT
6651 TCTAATTCAT TTGGTTGTGG GGGAGGGGGG CATAGGACCA GAGAATGTGT
6701 TTGTTTGTTT GTTTGTTTTT CTTAAATTCT CCAGTGCTGT TGTGATTCAA
6751 ATGCAGCCGG TCTGTTTCTG TTATCAAGTG CTGTGTAACA AAGCACTCAC
6801 AAAGTTTAAA GCAACAATGA TTTATTTTTT CTTAGGATTC TGTGGGTTGG
6851 CTGGACTCAG CTAGGTAGTT CTGCTTCATC CTGTGATGTC AGCTGGGGTC
6901 ACTTGTGGGG CTACATTCAG CTGGGATTAT GTCTGGGACT GGAACATGTG
6951 GGTGCTGACT GCTGGCTGGG GCACCTTAGT GTTTCTCACA TGGCCTCTCT
7001 TCTCCATGAG GTCTTTCAGT AGTATAGCCC AGGACTCGTA ACTTTTTTTT
7051 TTTTTTTAAG ACAGACTGTC GCCCTGTCGC CCAGGCTGGA GTGCAGTGGC
7101 ACGATCTCTG CTCACTGCAA CCTCCGCCTC CTGGGTTCAA GCAATTCTCC
7151 TGCCCCAGCC TCCCGAGTAG CTGGGATTAC AGGCACGTGC CTCCACGCCC
7201 GGCTAATGTT TGCATTTTTA GTAGAGATGG GGTTTCACCA CGTTGGTCAG
7251 GCTGGTCTCG AACTTCTGAC CTCGCGATCC GCCTGCCTCG GCCTCCCAAA
7301 GTGTTGGAAT TACAGGTGTG AGCCACTGCA CCTGGCTGAC TCGTAACTTT
7351 TTTTGTAAGT AATAAATATT TTAGGCTTTG TGGGTCCTGT AGTCTCTGTT
7401 GCAACCACTC AACTTGGCCA TGGTAGCACA AAAGCAGCTA AAGACAATAT
7451 GTAAATGATG GGTGTAGCTG TGTTCCAGTA AAACTTATAA AAAGTCCGTG
7501 GGCTGGATTT GGTCCAAGGG CTACAGATTG CACACCCCTG GTCTAGCCCA
7551 AGCATCTGTG CATGGTGGCT GGCTTCCCAA AAGTGGAAGC TGCTAAGCTG
7601 CCTTTTTTTT TTTTTTTTTT TTTTTTGAGA GGGAGTCTCA CTGTGTTGCC
7651 TAGGCTGGAG TGCGGTGGTG TGATCTCGGC TCACTGCAAC CTCCATCTCC
7701 CGGGTGCAGG CAATTCTCAT GCCTCAACCT CCCAGGTAGC TGGGATTACG
7751 GGTGCCTACC ACCACGCCTG GCTAATTTTT GTATTTTGGT AGAGACAGGG
7801 TTTCACCATG TTGGCCAGGC TGGTCTCAAA CTCCTGACCT CAAGTGATCC
7851 ACCCGTCTTG GCCTCCCAAA GTGCTGGGAT TACAGATGTG AGCCACCGTG
7901 TCTGGCCGCT TGACAAGCTT CTTAAAGGCA CTGCCCTGAA CTGGCACAGT
```

FIGURE 3C

```
 7951 GTCACTTGTG TCACATTCTT TTGGTTGAAG AGAGTCTCAG AGATGGCACA
 8001 GATTCAAAGG CAGGAGAAAT AGACTCCAGC GCTTAAAGTA AGGAGTAGCA
 8051 TGTGCCTACA GAATTGGAGG AACTGTTGGA GGCCATCTTT GAAGAGAGAC
 8101 CACCACTATC CATGGCTTGG CACGTGGGAA TCACTGCTCT ATACCAGGGT
 8151 TGCAGACTCA TGTCTTTGGG GGCCAGGCAG TGAGTATAAA TGAGTCAAGT
 8201 GGGCCAGTTG GAAGATGGAG TCAGACCTGC AGTGAACTCC CAAACACATC
 8251 TGCTACCGGG AGGGGCAGCA TTACTCAGCT CCAGCTCAGC GTCATCAGGC
 8301 AGGAAGGCGA GGCAGTGTTG CCGGATGTGC CAGTGTTTCA AAAGAAGCCA
 8351 GAGACTCCAT TTTTATTTTT TTGTATGGAA TCTCCTGATT TTGAAATATT
 8401 GGCAGATAAT TCAAATTATC TTAAACACTA CAGGCCAAAC AAAACATATC
 8451 TGTGGGCTAG AGACAGTCTG CCAGTTTGTA ACTATTTCTC CAGATCATGA
 8501 GTAAATTTGG CTTTACGATG GTCACTCAGT TCTTATTACT CTAGGTTGTT
 8551 CAAATGAATT AAAAAAGCTG AAATTATATG AATAAACCCC TGGGCACACA
 8601 TGAAAGAAGT GAAAAACCCA TTGTTTCCTA TTGTAGAAAC ATGGAAGCAT
 8651 GTCAGAGCCA GAGGATCCAG AGGAAATATT CTCACTAGCC TCAGACCCTC
 8701 AGGAGTGAGG GAGCTTTTCT TGTTAATGGC CACGCTTGTG CAGTTTTCCT
 8751 TCCCAGGTGC TGGTGAAAGA AACCCACAGT CTTGGAATCA TGGAAGTGAT
 8801 ACCATAATGA CTGTCAGTTG ACGTTGCTTT AAAGAATGAA GCCACAGAAT
 8851 TGTGCTGTTA GCATGTCGTG AGCAGTTAGT TGAGTTGGTG GCTTGTAATT
 8901 TACTCTGTGT GGATGTTATT GATCAAAGCT TTTCATTATT GACAGTGTCT
 8951 CCATCTGCTG TTTGCTGTTT TTAGGGGAAA CCACCCTTTA TGACTCAACA
 9001 GCAGATGTCT CCTCTTTCCC GAGAAGGGAT ATTAGATGCC CTCTTTGTTC
 9051 TCTTTGAAGA ATGCAGTCAG CCTGCTCTGA TGAAGATTAA GCACGTGAGC
 9101 AACTTTGTCC CGGAAGTGTA AGTTTGGGGA ACTTTTTCTT GAAAACTGTC
 9151 CTGAGAGAGA AAAACTAGAA AGATGCTTGA GGCAGAATGA GTTACTGGTT
 9201 GATAGTAGTC GGTAAGAACT CTGGTTCTAT ATAAGACAGA TCCAGGTTCA
 9251 AATTCAGGCT GCACCTCTTA TAGCTGGGAG ACCAGGTAAG TTGGGCTTCT
 9301 TGGTTGCAAG CGACAAACTT AATTCAAAGA CTGAATTTAG GCCAGGTGCA
 9351 ATGGCTCATA CCTATAATCT CAGCCCTTTG GGAAGCTGAG GTGGGTGAAT
 9401 CGCTTGAGCC CAGGAGTTCA AGACCAGCTT GGGCAACATG GTGAAACCCC
 9451 ATCTCTACAA AAAATACAAA AATTAGCTGG GTATGGTGGC TTGCACCCGT
 9501 GGTCCCAGCT GCTGAGGAGG CTGAGGTGGG AGGATCACTG GAGCCCGGGA
 9551 GGTTGAGGCT CAATGAGCTG TGATTGTGCC ATTGCACTCC AGTCTGGGTG
 9601 ACAGAGTGAG ACCCTGTGTG AATAAAAGAG TGAATTTATT GGCTCATGAA
 9651 ACTGAGAAAT CCAGGAATGA GTTAAGTTTT AGCTTTAGGC ATAGCTAGTT
 9701 CCAGAGACCT CAATAATATC CCGTGGCCCT GTCCTTATAC TCACTCAGGG
 9751 CTGACTTTCT ATTAGGCAGA GTAGGCACGG TGCTTAGGAT CTGTGATATT
 9801 TAATTTTAAT GAATTTAATT ACTTTTAATT AACTGAATTA AATTTTAATT
 9851 TGTTTTAAAA TTATAGGAAA AATGAATATA ATAATGTATA ATGATTCTGG
 9901 ATTACATTCA TCTTTATACT AATGTAGTCA TAAAATATAA TTTTTGTTTT
 9951 TTTTGGAGAC AGAGTCTTGC CCTATTACCC AGGCTGGATT GCAGTGGTAT
10001 ATCATGGCTC ACTGCAGTTT CAACCTTCTA GGCTCAAGCA ATCCTTCCAC
10051 CCCAGTGGCT GGGACTACAG GCTCACACTA CCACGCCCAG CTAATTTTTG
10101 CTTTTTTCTC TGTAGAGATA GGGTCTTACT ATGTTACCCA GGCTGGTTTC
10151 AAACTCCAGG CTTGAAGCAG TCTTCCTGCC TCAGCCTCCC AAAGCTTTGG
10201 GATTACAGGT GTGAGCCACC ATGCCTGGCC CCATAAAATA TAATTTTTGA
10251 ATTCTTTTTT GTTTTTAATG GAGGAAGGGG CTGAGGAAGG CAAAAGTACC
10301 TAGGGCCTAT GAAGTCATAT ATTGGCCTTG CCTTCACCCT GTTTCTGACT
10351 TTGCTTGACT TCCATGTGAT GAGGCAGTTG GCTGTTAGTG TCCCAGTTTC
10401 ATACTCTTAC ATTAGTGTTT TTCAACCAGT GGGTGATTTG ACGTTTTCGG
10451 TTGTCAGAGC TAGTTGGGGG TGGTGGTGTG TGAGTTTGGG GGGAAGGGTC
10501 CTACTGTCAG TTAATGGGTG AGGCCAGAGA TGCCACCAAA CACCTTACAG
10551 TGCACAAAGC AGCCCCCATA ACACAGAATT ATGTAGCCCA CAATGCCAAC
```

FIGURE 3D

```
10601 AGTGCTGAAT TTGAGAAACC CCACCTTGTA CAACATTGCT GTGCAACCAA
10651 CCACCCTAAA TATTACTGAC TTAAAACAAT AGTCACTGTG GCTGGGCGCG
10701 GTGGCTCATG CGTGTAAGCC CAGCGCTTTG GGAGGCTGAG GCGGCGGATC
10751 ACTTGAGGTC AGGAGTTCCA GACCAGCCTG GCCAACATGG TGAAACCTTG
10801 TCTCTACTAA AAATACAAGA ATTAGCTGAA TGTGGCAGCG GGCGCCTGTA
10851 ATCCCAGCCA TTTGGGAGGC AGAGGCAGGA GAATCGCTTG AACCTGGGAG
10901 GTGGAGGTTG CAGTGAGCCA AGATCTCACC ATTGCACTCC AGCTTGGGCA
10951 ATGAGTGAGA CTCTGTCTTA AAAAAAAAAA AAAGTTATTG TATTACCTCT
11001 TGTGTGTGTA GGTTAATTGG ACTCAGCTGG GGATTCCTCT GCTCTGTATT
11051 ACATTGGCCA GGATTGCAGT CACCTGGGGC TCTCCTGGGC TGGAATGTGT
11101 GAGAGGGCTT ACTCAGTGTT TGGTGCCCTG GCTTGGAGGC TGGGCCCAGC
11151 TGGGCCTCTC TCTCTTCATG AAGTTTCAGG GCCTTTTGCT GTCCACATGG
11201 CACCTCTATG TGGTCTCCAA ATCAGAAGTC AAGGAACTAC AGCCTGTGAT
11251 GCCTATTTTG TAAAGAAGGT TTTACTGGAA CACAGCCCTA CCCATGTGTT
11301 TGTACAGTGC CTATGGCTGC TTTCACATCA TAACAGCATT TTATTTCATT
11351 TTATTTATTT TTTTTTGAGA CAAAGTCTCA CTCTGGCTGG AGTGCAGCAG
11401 CACAATCATA GCTCACTGCA GCCTCCAACT CTTGGGCTCA AGCAATCCTC
11451 CTGTCTCAGC CTCCTCAGTA GCTAGTACTA CAGGCCCATG CCACCACTAA
11501 TGGCTAATTT TTTAATTTTG TGTAGAGATG GGACCTTGTG AGATTGCCTA
11551 GGCTGGTCTT GAACTCCTGG CCTCAAGAAA TCCTCCCACC TTGGCCTCCC
11601 AAAATGCTTG GATTACAGGC ATGAGCCACT GTGCCCAGCC CACAACAGCA
11651 TTTGAGTAGT TGTGATAGAG ACCAAATGGC CTACAAAGCC CAAAATAGTT
11701 CCTGTTTGGC CCATTTCGAA AAGGCTTGCT GACCTCTGAG CTACATGGTC
11751 TCTCTAGCAG GACAGCCTCG ACGGTAGCTC AGGTTTCCAA AACACAAAAG
11801 TGGAAGCTGC CAGGCTTTCT TAGGGGTTAT CCTAGGAGGG ACATAGGATC
11851 TCTTTGACTG CATTTTATTG TTTGATGCAT GCTCTGGGC TGCTCAAATT
11901 CCACCTGAGA GGAAACTACA CAAGGTCATG AATCCCAAGA GGACTGGGGC
11951 ATTGGGTGCT ATTTTTGGAG ACTGGCTACC ACACCCTGCC CAATGGTAAT
12001 CTTCCCTTAT CTAGATTAAT ACAACCCCAG GGAAGATTCT AACTTGGCTC
12051 TGCTTTGGGT CATTTGCCTC CCTGGAGGTG AGGTGTTGTG ATCGGTTTTG
12101 TTGGAATGCC CAAAGGGGTC AGGGCAGTGT GATTACCAGG ACCTCATGGA
12151 ATGGGGATG CGTGGTTATG CAAAGGAGCC GGGGATGCTG GGTAGAAAAA
12201 AAATCAGCAT ATGTTCACTA TAGTGCTCTT CAGTATTTTA CATGTACTTT
12251 GTTCTCAGTT TTCTCATCTG TAAAATAGGA ATAATGTATA TCCTTTTTTT
12301 TTTTTTTTTT TTGGAGTCTT GCTCTGTTGT CCAGGCTGGA GTACAGTGGC
12351 ACAATCTCAG CTCACTGCAA CCTCCGCATC CCGGGTTCAA GTGATTCTCC
12401 TGCCTCAGCC TCCTCAGTAG CTGGGACTAC AGGCGTGCAC CACCACACTC
12451 AGCTAGTTTT TGTATTTTA GTAGAGATGG GGTTTCGCCA TGTTGGCCAG
12501 GCTGGTCTCA AACTCCTGAC CTCAAGTGAT CTGCCTGCCT CGGCCTCCGA
12551 AAGTGCTGGA ATTACAGGCA TGAGCCACCA CGCCCATTGG GAATAATGTA
12601 TATCTAATGA GGCTGTGTTG GAATTGAATG AGTTAATGCA CAGACCAGAT
12651 TTGTCATGTT GCCTGGCCCA TAGGAGACAA TAAATGGTAC CCAGTATTAA
12701 TAACTGTGAA TGTCAACAAC ATTTAATATA TTGTATATCT TCAAAATGTA
12751 CTTGAGGTAT TTGTTCATCA TTCTGTTTTT GTTTGAATAA GCTCGTGCCT
12801 TCTTTTTGTG AATATTTAAA TTTATAAGTA GCGAGTGGGA GGGGAAGGAA
12851 GTTATGTGAT GAGGCTAGCT TACTGAGCCA TCTGCAGGCA CCTTCATTAG
12901 TCTTGAGACT GTCCTCTGGT TACTTAACAG CAGTGAATTA TCTAGAATCA
12951 TTTAGTGATC AGAAGACTTG GTTTAGTGGA ATGTAGATTT TTTTCTAATA
13001 GACCCCTCTT CCAGGGAAAT GTTTCATATT TTTGAAGAGG TTTCCTGGGG
13051 AGTGTTTAAG AGGCCATGAT TGAAAATGGG TGATTACATT AGTGTGTTTT
13101 CTATTCCTCC CCTTTTTGAG TTTCTGTTTT GGAATGTAAG CTTTGTTTTT
13151 CTACGTGGAG AAGGGTCCCT CAGCTGCTTC TGCCCAGGTT TTTTGAATCT
13201 TCCTATAGGG ATGGAGATTT TCTTTGGGGA CTGTTAGAGA AAATGGAATA
```

FIGURE 3E

```
13251 GAGTGTAGCT CTGAAGGAGA AGGATGTCTC CAGCAGAAGT ACCTCTAGCC
13301 TTGGGCCAAG GGAGGGAAGG GAAGGGAACG AGCATCTGGG AACCAGGGAA
13351 GGGATTTTTG TCTTTCTTAA TTACTCTTAC ATCCCCAGTG CCCAAAATAG
13401 TGTCTGGCAT ATGTTAAGTC CTTAGTAAAT ACTTGTTGAA TGAGTGTATG
13451 CTCAGTGAAC AAAATAAATG GCAAACATTA AGCACAGTAT CAGATAATTT
13501 GTGTAAAAAA TATACAGCAG TGTTATACTA AAACTTGCAC AGAGGCCAGG
13551 TGCAGTGGCT CACGCCTGTA ATCCCAGCAC TGGGAGGCCG AGGTGGGCAG
13601 ATCTTTGAGC TCAGGAGTTT GAGACCAACC TGGGCAACAT GCTGAAACCC
13651 TGTCTATACA AAAATACAA AAAGTAGCTG GGCATGGGG ACGCACATCT
13701 GTGGTCCCAG CTACTTGGGA GGCTGAGGCT GGAGTAATTG CTTGAAGCTG
13751 GGAGGTGGAG GTTGCAGTAA GCCAAGATTG TGCCACTGCA CCCCAGCCTG
13801 GGTGACAGAG TAAGACCCTG TCTCAAAACA CAAAACAACA CCCCCTTCAA
13851 AAAAAATCCA AAACCACCAC CACAACAAAA AAACTTACAC AGAAAAGTGT
13901 TGATAATTGT CAAAATTGGG CTGTTATTGG CAATTTGACA GTAGCTGAAT
13951 TACTACCATT TGAGCTATAT TCACTATAGA TAAGATCTTC AATATATTTA
14001 CAACTTTAGT ACTAATGGGA AAATGATAAC TTTTGAAAAG TTTTTTTTTT
14051 TTCTTATTGC AAACAATACA CAATACAATG TTAAATATAG AAGGTTAAAC
14101 GTGCATCTGA GTCTGTTTGG GCTGCGATAA TAGATACCTT AGACTTGGCA
14151 ATTTATAAAC AATAGAAATT CATTGCTGAC AGTTGTGAAG ACTGGGAAGT
14201 CCAAGATCAA GGCGCCAGCG AATCTGGTAT CTGGTGATGG CTCCCTGCTT
14251 CAAAAATGGC GCCTTCTTGC TGCATCTTCA CCTGGCAGAA GGGGCAAACA
14301 TGAGTCCTTC AGCTTCTTTT TTTTTTTTTT TCTATGTTTA AAACTTTTGG
14351 TCCGGCGTGG TGGCTCATGC CTGTAATCCT AGCACTTTGG GAGGCCGAGG
14401 CAGGTGCATC ATGAGGTCAA GAGATCGAGA CCATCCTGGC CAACATGGTG
14451 AAACCCCCCC GTCTCTATAC TAAAAATACA AAAATTAGCC AGGCATGGTG
14501 GCGTGTGCTT GTAGTCCCAG CTACTCAGGA GGCTGAGGCA GGAGAATTGC
14551 TTGAACCTGG GAGGCAGAGG TTGCAGTGAG CCAAGATTGC GCCACTGCAC
14601 TCCAGCCTGG CAACAGAGTA AGACTCCGTC TCAAAACAAA CAAACAAAAA
14651 AAACAAAAAA AAACTTTTAT TTTAGGTTCA TGGGTAAATG TACAGGTTTG
14701 TTATGTAGGT AAACTTGTCT TGGGGTTTGT TATAGATTAT TTCGTCACCC
14751 AGGTACTAAG CCTAGTAACC AATAGTTATT TTTTCAGATT GTCCTCCCTC
14801 CTCCCACCCT CTGTCCTCTA GTAGGCTCCA ATGTCTGTTG TTCCCTTCTT
14851 AGTGTCCTTG TGTTCTCATC CTTTAGCTCC CATTTATATG TGAGAACATG
14901 TGGTATTTGG TTTTCTGTTC CTGCATTAGT TTGCTAAGGA TAATGTCAGC
14951 CTCTTTTTTT TTTTTTTTTT TTTTTTTGAT ACAGAGTCTC GCTCTGTTGC
15001 CCAGGTTGGA GTGCAGTGGT GCGATCTTGG CTCACTGCAA CCTCTGCCTC
15051 CCGGGTTCAA GTGATTCTCT TGCCTTAGCC TCCTGAGTAG CTGGGACTAC
15101 AGGTGCGCAC CACCATGCCA GGCTAATTTT TGTATTTTAG TAGAGATAGG
15151 GTTTCACCAT GCTGGCCACG CTGGTCTCCA ACTCTTGACC TTGTGATCCG
15201 CCGGCCTCGT CTTTTTCCCA AAGTGCTGAG ATTACAGGTG TGAGTCACTG
15251 CACCCGGCCC AATGTCAGCC TCTTTTTTAG GGAAGTGATT TAATCACTTC
15301 CCTAAAAGTC CTACCTCGTT TTTTTTTTTG GTTTTTTCTT TTTTTTTTTT
15351 TTTTTTTTTT TTTTTTTTTA GGTAGAGTCT TGCTCTGTCA CCCAGGCTGG
15401 AGTGCAGTGG TGCGATCTTG GCTCACTGCA ACCTCCACCT CCTGAGTTCA
15451 AGCAATTCTC CTGCCTCAGC CTCCTGAGTA GCTGGGATTA TAGGTGCCTG
15501 CCACCACGCC TGGCTAATTT TTTTGTATTT TTAGTAGAGT TGGGGTTTCA
15551 CCATGTTGGC CAGGCTGGTC TTGAACTCCT GACCTCAAGT GATCTGCCCA
15601 AAATGCTGGG ATTACAGGCG GGAGCCACTG TGGCCAGCCC CTGCAAGTCC
15651 TACCTCTTAA TAGTATTACA CTGGGGATTA CATTTCAACA TGAATTTTGT
15701 AGGGGCGAGG GGCACAAACG TTTAGAATAT AGCACATCAC ATACATAGTG
15751 AGAGAAAAAT CCCTCAAAAT CTTACCTGAG ACAATCACTG CCAACAGATT
15801 GCTGTATAGT GTGCCAATTT TGTTTGTGTG TGTGTGTGCC TTAAAAATAT
15851 TTATTATGGA AATTTAAAAA CGTACCCCAA GGTGGCCAGG TGTAGGGCTC
```

FIGURE 3F

```
15901 ACGCCTGTAA TCCTGGCACT TTGGGAGCCC GAGGTGGGTG TATTACTTGA
15951 GGTCAGGAGT TTGAGACCAG CCTGGCCAAA ATGGTGATAC CAGTCTCCTA
16001 AAAATACAAA AATTAGCCGG GTGTGGTGGG CACCTGTAGT TCCAGCTACT
16051 CGGGAGACCA AGTCATGAGA ATTGCTTGAA CCCTGGAGGC AGAGGTTGCA
16101 GTGAGCCAAG ACCATGCCAC TGCACTCCAG CCAGGGTGAC AGAGTGAGAC
16151 TCCATCCTAG TAAACAAACA AACAAACAAA CAAACCAACT AACCAACCAG
16201 GATAAAACTC CCTGTCTGTA AGGAGTATGT GTTCTAATGG ATACTGAGCC
16251 ATCTTGTTCT GTTTAACATG TGCCTAATGT TCTTTTATAT GGGCGGACTT
16301 GTAGGTTGTT TCAACTTTTC TGTTGATGAA CCTTTAGGTG GTTTCTGATT
16351 ATTTTTGTGT TACAACAGTT TTCATCATTC ACATCTTTGT ATGCATCTTT
16401 TTTGAGCACA TGTGCAAGTA TTTCTGTGGA CAATGGATGA TTCCTAGAAA
16451 TTGAAAGTTT GGATTACTGT GTTCCAAAAA AGGAAGCAAT ACACCCAGCT
16501 ATGTTGGCTT TTGCTCTTGG GTCCAGATGA TTATCTGACA AAGTTATTCT
16551 CTGATTGCAT TTTCTTTTCT TTTCTTTTCT TTTTTTTTTT TGAGATGGAG
16601 TTTCGCTCTT GTTGCCCAGG TTGGAGTGCA ATGGCGCGAT CTTGGCTCAC
16651 TGCAACCTCT GCCTCCCAGG TTCAAGCGAT TCTCCTGCCT CAGCCTCCTA
16701 AGTAGCTGGC ATTGCAGGCA TGCGCCACGA CACCTGGCTA ATTTTTTGTA
16751 TTTTTAGTAG AGATGGGATT TCTCCATATT GGTCAGGCTG GTCTTGAACT
16801 CTTGACCTCA GGTGATCCAC CCGCTTCAGC CTCCCAAAGT GCTGGGATTA
16851 CAGGCGTGAG CCACAGTGCC TGGCCCTCTG ACTGCATTTT CACAGTGTTT
16901 TGGGTCCTTA TCTCTACCTC AGTACCTCAA TATTCAGTGC CCACTGGGCC
16951 CTTAGATACT GCAGCTAAAA GTGCACAGGG GTGGAGTGAT GTGACGGTTT
17001 TGGGGTCACA GAAGCAGCTG GTATAGAGAG AAGTTGTGAA GTTTTTTTTT
17051 TTTTTCCTGA GACAGAGTCT CGCTGTATCC CCTAGGCTGG AGTGCAGTGG
17101 CTTGATCTCG GCTCACTGCA ACCTCTGTCT CCCTGGTTCA AGTGATTCTT
17151 ATGCCTCAGC CTCCCGAGTA GCTGGGATTA TAGGCATGTG TCACCATACC
17201 CAGCTAATTT TTGTGTTTTT AGTAGAGATG GGGTTTCACC ATGTTGGCCA
17251 GGCTGGTCTT GAGCTCCTGA CCTCAGGTGA TCCGCCCACC TGGGCCTCCC
17301 AAAGTGCTGG GATTACAGGC CTGAGCCATT GCGCCTGGTC TTTTTTTTTT
17351 TTTTTTAAGT AATCATAGGC TTGAATGTAG CCTCTCATCT GTTCACCTTA
17401 ATAATCCAAA AGCCTTTAGA TAAAGAAATG GAGATTTGGA ATGGCTTCTC
17451 AGAATTCCAA GAGAGTATTG TCATGGTTTT GCCTGCAAAG CACCGTGGTC
17501 TGTCTCCTTG TGCAGTTGAG AAAGCTGGTG GTCGCCACTG ACAGGCCCAG
17551 AGTTATTAAG TTGGACACTG CTTTAAGCAA CTTTGTAAAC AATCCAAGGC
17601 ATACTAGAGA ATTAGGAGAG ATTGGCTTTG TGTATGAGCA ATAACAAAAT
17651 CAAGTTCAAT CCAGCAAGTT TTTGGGGAAT TATAATTCAA AACTCAAATA
17701 CTTGATCTGG AAGAAACTTG GAAAGAGGGA AGGAAGACAG GCTTGTTACA
17751 GCATTGTCAG GGTAAAAGGA AAATACCGTG CAGCTTTTAA TTTTGCTTCT
17801 TCATGGCATT CCCCATGTAG GTGCCCTAGA TTTGTTTTTT ACAGTGGTCA
17851 CGACTTCATG TGGATCCACC CACCACTCTT GCCTGGTTCC CCAAGGGACC
17901 AAGGGAAGGT GTATTCAGGA TGATTGCTGA AGTGAGGGGT GGGGTCTGTG
17951 GCTGAGAAGA CTCTCAATAC CGCGGCACTC ATTATAAGCC TCTGACACAG
18001 GAGATTTCAA CTCCACCCGT GCAACAAAGG AACAGGGTGG GCAAGAGTAG
18051 TTACAGTTGC AGGCTGAGTG CGATGGTTCA TGCCTGTAAT CCCAGTGCTT
18101 TGGAAGCCA AGGTGGGAGG ATTGCTTGAG TCTAGGAGTT TGAGACCAGC
18151 CTGGGTGACA TAATGAGACC CTACCTGTAC AAAAAAATTT TAAAAATTAG
18201 CCAGATTGGT GGTGTGCGCC TATAGTCCCA GCTACTCTGG AGAATGAGGT
18251 GGGTGAGGGT CCCTTGAGTC CAGGAGTTCG AGGCTGCAGT GAGTTATGAT
18301 TCTATGATTT CACCACTGCA TTCCAGCCTG GGCGACAGAG CAAGATTGTG
18351 TTCTTTTTTT TTTTGAGAC GGAGTCTCAC TCTGTCACCC AGGCTGAAGT
18401 GCAGTGGTAC GATCTCTGCT CACTACAACC TGCACCTCCC AGGTTCAAGT
18451 GATTCTCTCC CTCAGCCTCC CGAGCAGCTG AGATTAAAAG CGGCCGCTTG
18501 TGTGCAGCTA ATTTTTGTAT TGTTAGTAGA GATGGGGTTT CATCATGTTG
```

FIGURE 3G

```
18551 GTCAGGCTTG TCTTGAACTC CTGACCTCAG GTGATCCACC CGCCTCGCCC
18601 TCCCAAAATG CTGGGATTAC AGGCGTGAGC TACTGCGCCC AGCCATTTGT
18651 GTCTCTTAAA AAAAAAACTA AGAAAATGAA AAAAATGACA TTGGCCAATT
18701 CATTAAAATG CCACTCACTG ACTGTGGTAT GAAATGGCTT TCCCTTTGAT
18751 GGACCGAGTC TGTCTCATTG TGTGAGCCAC TTGCAGGGCT GAGTATGACT
18801 CTGGAATGTA GCTCCTAACC TTATCTGCTG CCCAGCCATT GAAATGGCCA
18851 TCCCTTCCAG TTCCCAGAAG ATTCCAGTGT GTGTTTGGGA TTTTAAGACA
18901 GTCTCTTGGT CTTCAGTGTG GCATCTTTCT GCCGGATTTT CCAGGATAAT
18951 TTTGATTATA AGCATTGCAT TGCCCTTGGT GTGTAATGCC TGTGTATGAT
19001 GCTGTTCCCT TGTAACGTGC AGGATTAAAT TTTTGGGTCA GCCACTGCTG
19051 CTCCCCTTCA TTCCTGCAGG TCATTAGAGT CATCGTACAT TTAGCGATGT
19101 CTCAGATCAG TGTATCTAGA GTGTTAATAA ACATGTTAGA TTCCAAATCT
19151 ACTGTCCATT TAATCCATAC TTCATACGTT GAGGATCTCT GACTGAAAGA
19201 TTAGACTTGG AAAAATAATA AGACTGTATG GTAAGAAAAC TATAGTTGCA
19251 AATCCATTTG GACATGTAGT ATGTCAGCCC TGCAGAGCAG ATGTCAGAAC
19301 CCCATTTAGT TCTCTGAGTG CTAAGCCCTT CTGCCCACCA CGCTGTTTTT
19351 TTTTTTTGAG ATGGAGTCTC GCTCTGTCAC TCAGGCTGGA GTGCAGTGGT
19401 GTGATCTCGG CTCACTGCAA GCTCTGTCTC CCAGGTTCAC GCCATTCTCC
19451 TGCCTCAGCC TCCCAAGTAG CTGGGACTAC AGGTGCTCAC CACCATGCCC
19501 AGCTAATTTT TTGTATGTTT TTGGTAGAGA CGGGGTTTCA CTGTGTTAGC
19551 CAGGATGGTC TGGATCTCCT GACCTTGTGA TCCACCCGCT TCGGCCTCCC
19601 AAAGTGCTGG GATTACAGGC GTGAGCCACT GCTCCTGGCC CCCACGCCTT
19651 TTTTTTTTTT TGGAGACAGA GTTTCACTCT GTCACCCAGA TTGGAGTGCT
19701 GTGGCACAAT CTCAGCTCAT TGTGTCCTCT GCCTCCCAGG TTCAAGTGAT
19751 TCTTGTGCCT CAGCCTCCTG AGTAGGTGGA ATTACAGGCG TGCACCACAA
19801 CACCTGGCTA ATTTTTGTAT TTTTAGTAGA GATGGGGTTT CACCATGTTG
19851 GCCAGGCTGG TCTCGATCTC CTGACCTCCA GTGATCCACT TGCCTAGGCC
19901 TCCCAAAGTG TTGGGATTAC AGGCGTCAGC CACCATGCCT GGACCCCTCT
19951 GCCCCTTTAA GCACTGCCAC ATATTAGATC TACGAAGGCT TTATGGATAC
20001 AATCCAAGGA AGATGAACCT TGGGCTAGTG GGATAAAACT AAGCGCATGT
20051 AGTTAGAATG GAATGATCTG GAAACCAGGT CCCAAGTTGG TCTAAATTAG
20101 ACTCATGTTG ACTATGTCAC ACTGTAAACC AGTCTAAATG CTAATAAGCA
20151 TGCTTGACCA AACACTGCCC TGCAGCCTTC AGAGAGGAAG AAGGAAAACA
20201 TAATTTGTAT CCTCTCTCCC TATTTTCTGA GTCTATGGGA TTCAAATTGT
20251 AGCTGCCATG GAAACTGTAC TTTGGAATTT CTAGAGCCCT TAATTTTAAC
20301 TTAACATATA AAAACACTTT TGTACTGATT TTATAATTAT TCATGATGGA
20351 TGAGAAAGTG AATGTCTTTG ACAGTGAGGG AAGCTATCCG AATGCTATTT
20401 TCTTTTTTTT TTTTCTTTCA TAAAGATGCA TATATTTGCA TGCTTTATTT
20451 ACCTGGGGCT AACTCTTGCA TCTTTTGCAG ATTCCGACAC CATAGCTGAG
20501 TTACAGGAGC TCCAGCCTTC GGCAAAGGAC TTCGAAGTCA GAAGTCTTGT
20551 AGGTTGTGGT CACTTTGCTG AAGTGCAGGT GGTAAGAGAG AAAGCAACCG
20601 GGGACATCTA TGCTATGAAA GTGATGAAGA AGAAGGCTTT ATTGGCCCAG
20651 GAGCAGGTAG GAGGATTTTA ACATCATGCT TTTCCACTTT CTGTACCGGA
20701 GTGTTCATTG CAAAGACGAT AATCTGCTGC ACTGGCGTCT AGGATCAAGC
20751 ACGTTTTCCT CTGTGACTCT ATATTTAATT ATAGTTGGGG CAAAAAGGTC
20801 TCTCATGTTC TTAGCTCATC TTCTTGAACT GATGTTGGCT AATTTTGAAG
20851 GCTCACAAAT TCCTCTTGAT GTATCATGTT TCTATCGTTG TAATTTATTT
20901 CAGAACCAAG GTGGCCTTTT AGCTAATGAA TTTAAGATGA TCTTTTATGA
20951 CCATTAGCTG AGGACTCAGG ATATACATAT GGTGGGGTGA ATCAGATTGC
21001 TTTTGTACAC GCTTTAGGTA TTTGTGTTGT GGGCATATGG ATTTGGTTTT
21051 AAAACAGGCC TTTGAAGAAA TCAAATAACA TTCTTTGTTA TGTGGCTAGG
21101 GAGTTGCTTG TTTGAGAGCA GGTAGAACGT TATCTTTTTT GTTGTGGTAT
21151 TTTTCTTTCT TTTAAACAAG GCTACTGTCT CTAGACATAT TGATTCATTT
```

FIGURE 3H

```
21201 GCTGTGTTTT AGAGAGATGG CCGTCAGCCT TGGAATTCAG AGAGTAATTT
21251 ATTACTTACA GACATTTTAG TGCACATGAT ATGTCTGATA ATGTACCCAG
21301 CTCTGCAGGA AGCTTGCAAA AGGAATAGAA GTCCCATGGT TGCTATTTTC
21351 AGTGTTTAAA AACAACCTTG GAAAGTGGAG GAAAAATGCA AATGTATAAA
21401 GCAGGTGCTT ACCAGCTAAA GTATCACAGA AGTGGGAGAG CAATTAGCAA
21451 ATTAATTAAC GATGATGTGA GGGGAGATGT TGTGGGTGAG CAAGGGACAG
21501 TTAGGGACAG TTCTCACCGA TGGGGGGAAA TGTAGGTTCT CGGCAGAGAG
21551 AAGTGATGAG AACATGTTGG GTAGAAGTGT GACATTCTGG AGTACTAGAA
21601 TGCTATGCAA GTGTGTGTGT GTGGGTGTGT GTGTGTGTTC AGTGGTTCAG
21651 AACAGACTGG GAAATGGCGA AATGAGGACA TTTGGGTGGG GAGGGGGAAA
21701 TGGGTGGGAA ACTCAAGAAC CTTTTTTTAA AAAATTGTGG TAAAATATAT
21751 ATAACATAAA GTGTACCATT TTAACCATTT TTAAATGTGC AACTGAGTGG
21801 TATTCAGTGC ATTCATGATG TTGTACAACC ATGACCGCTC TCCATTTCTA
21851 GAATTTTTCT ATCATCCCAA ACAGAAACTC TCTATCCATT ATACAATACC
21901 TCCCCATTCC CCCAAGAACC AGTTTTTGAA TTGCAGTTTA CTTTGTGAGG
21951 CTGTTGGGGA TTATTTAGGC CTCTGGAAGG AGGAGGTTGG GATCAGAGTC
22001 TGGCCCTGTG GACTTCAATG ACTTTGTGTG GCCTCCAATC AGAGAAGCAG
22051 CGGAGGGCAG GAAGCTGCTT GTCAGAATCT GAGAGTGATG TGGCTTCTTT
22101 GTTTAGCAAT AAAATGTGAG CACATAATAG AAAGGAAAAG TGACAGGACA
22151 TGGCAGATAA TTTGGAAGAG AGGAGTGGAA GATGCTCACT CAGCCTCCCA
22201 GCTCCTGAGA AAGAACTGTG TCTCATCAGT TCATACTACC TGAGCATCTG
22251 TTGTATCTGG TGTGTTTCTA GGTCCTGGAG AAGAGGCATT ACGTGTAGCC
22301 CTGACCTTGT GATGCTTATG TTTTTGATGG GAAATAGTGC GTGTAAAAAG
22351 AAAATAATCC AACAGGCCAC ACGGCAGGCA AACAATAGAG ATATTCAAAT
22401 AGGTATACCT TCCTCCAGGT GAATGGCCTG AAATGACCGT GTGGAAGTGT
22451 GGGCTGGGGG CTTATAAAAT TATACACATA CAGGCGCTAA CTAAAGCCGC
22501 CTATTCATTC CTTAAGAGGA TGCATAGAAA AGAAAAGTAG GGTCCTTAAC
22551 TGAGCCATTT GGAATTTAAG GGCATGAGAG AAGCCAGCAC AAGCAGTGAA
22601 GGGAAGGAAA AGAAGTGCCC GAGAGGAGGG AGGGATGCTG TTCTGCAGAC
22651 AAGGCCTGCC GCCTGGGAGA GGCCCGCACG CCCACCCAGG GTTCTCTGAC
22701 AGCTGGAAGG GGTCTTCAGA GACTGTTTAT ATTTTATTTA TTTATTTATT
22751 TATTTATTTT GAGACAGAGT CTCTGTCACC CAGGCTGGAG TGCAGTGGTG
22801 CGATCTCAGC TCACTGCAAG CTCCGCCTCC CAGGTTCACA CCATTCTCCT
22851 ATCTCAGCCT CCCGAGTAGC TGGGACTACA GGCGCCTGCC ACAATGCCCG
22901 GCTAATTTTT TTGTAATTTT AGTAGAGACG GGGTTTTACC TCGTTAGCCA
22951 GGATGGTCTT GATCTCCTGA CCTCATGATT CGCCCACCTC GGCCTCCCAA
23001 AGTGCTGGGA TTACAGGTGT GAGCCACTGT GCCTGGCCGA CTGTTTCTAC
23051 TATTTTAGAG AGAGGGTCTC ACTGTCATCT GTGCTGGAAT GCAGTGATGC
23101 AGTCATAGCT CACTGCACCC TCAAACTCCT GGGCTTAAGC GACCCTCCCG
23151 CCTCAGCCTC TTAAGTAGCT GGGACCATAG GCATGTGCTG CCACACCCAG
23201 TTAACTTTAT TATTTATTTA TTTATTTAGA GAATGAGTCT CATTCTGTTG
23251 CCCAGGCTAG AGGTGCAGTG GCACGATCTC GGCTCACTGC AACCCCGCCT
23301 CCCAGGTTCA AGCGATTCTT CTTGCTCAGC CTCCTGAATA GCTGGGATTA
23351 CAGGCACCTG CCACCACACC TGGCTAATTT TTGTATTTTT AGTGCAGAGG
23401 GGGGGGTTTC ACCATGTTGG TCAGGCTGGT CTCGAACTCC TGACCTTGTG
23451 ATCTGCCTGC CTCGGCCTCC CAAAGTGCTG GGATTACAGG CGTGAGCCAC
23501 CGTGCCCGGC CCACTTTATT ATTTTAAAAA CATTGTTTTA TTTTTATTTT
23551 TTTGAGACAG AGTCCGCTGG AGTTCAGTGG CCGGATCTCA CTCACTGCAA
23601 CCTCTGCCTC CTGGGTTCAA GTGATTCTTG TGCTTCAGCC TCTCTAGTAG
23651 CTGGGACTAC AGGCGGGTGC CACCATGCCT GGCTAATGTT TTTTGTATCT
23701 TTTTAGTAGA GACGGGGTTT TGCCCATGTT GGCCAGGCTG GTCTCGAACT
23751 CCTGACCTCA AGTGATCTGC CCACTTTAGC CTCTCAAAGT ACTTGGGATT
23801 ACAGGCGTGA GCCACTGTGG CTAGCCCCCA GCTAACTTTA AAAAAAATT
```

FIGURE 3I

```
23851 TTGTGGGCCG GGTGCAGTGG CTCACGCCTG TAATCCCAGC ACTTTGGAGG
23901 CCAAGCAGGG CGGATCACTT GAGGTCGGGA GTTTGAGACC AGCCTGACCA
23951 ACATGGAGAA ACCCTGTCTC TACTAAAAAT ACAAAAAATT AGCCGGGTGT
24001 GGTGGTGCAT GCCTGTAATC CCAGCTACTT GGGAGCTGAG GCAGGAGAAT
24051 TGCTTGAATC TGGGAGGCAG AGGTTGCAGT GAGCTTAGAT CACGCCACTG
24101 CACTACAGCC TGGGCAACAA GAGCGAACAC TCCGTCTCAA AAAAAAAAAA
24151 TAAATTATGT AGAGGTGGGA TCTCCCTATG TTGCCCGGAC TGGTCTTGAA
24201 CTCCTGGCCT CAAGTGATCC TTCCATCTCC CCCTCCCAAA GTGTTGGGAT
24251 TACAGGCATG AGCCACCCCT CCTGGCTGAG ACTGCTTATT TTATTTATTT
24301 TTAATTTTTT TTGTTTTGAG ACTGCTTATT TTAATGGAAG CTTCAGGGGT
24351 CAGACGGGGT CAGACAGAGT CATTGGTGAG CAAGCAAAGG TGTAGACTGT
24401 TCAGTTCAGC CTTCCTTGGA CACCTTTTAT GTGCCAGACA AAAGAAGGAT
24451 CAGCATATCA GGTGCAGTAA ATTATTGGGG TTATGTTGGT GTTTCCCAAA
24501 TGTGTTAGAT TTATCCCTGG TAGTGTTAAA TCTCATGATT TTAGGTAGTA
24551 TATGGACAAC CTATGTAAAA ACATTTAATA GTTTAATATT AACTAGCATA
24601 TCAAAACCTG TGACTTTGCT CACGCCTGTA ATCCCAGCAC TTTGGGAGGC
24651 CAAGGCGGGA GGATGGTTTG GGCCAGGAG TTTGAGGCCA GCCTAGGTAA
24701 CATGGTGAGA CCCTGTCTCT AAAACAAAAC AAAACAAAAC AAACAAACAA
24751 ACAAATAAAC AAATCCCCTG TAACTTGTTC TAACAATAAC CTAAACAATT
24801 TTTTATTTAA AATTAAATAA AAAAATTGAA ACAGTAACCA TTTTTTTTTT
24851 TTTTTTTGGA GACAGAGTCT TGCTTTGTCA CCTAGTCTAG AGTGCAGTGG
24901 CACAATCTCT GCTCACTGCA ACCTCTGCCT TCAAACAATT CTCCTGCCTC
24951 AGGCTTCTGA GTAGGTGGGA TTGATTACAG GTGCACTCCA CCATGCCCAG
25001 CTAATTTTTG TATTTTTAGT AGAGACGGGG TTTCACCATG TTGGCTAGGC
25051 TAGTCTTGAA CTCCTGACCT GCAGTAGTCC ACGTGCCTTG GCCTCCCAAA
25101 GTGCTGGGAT TACAATCACA AATTTATAGA AAAGTTGCAA GTACCATGTA
25151 GTCAGGGTTC TTAAGAGAAA TGGAACCAGT AGGAGATAGA TATATAATCA
25201 TCTCCTAGGA TTATAAGTTG ACACATAAGA CTAACCGTCA CATACAGTAT
25251 AAACAACTTT TTTTCTTAAA CCATTTGATA GATACACACA CACTGATATA
25301 CATAGAATAT ATATACACAC ACACAGAATG TATATACACA TAGAATATAT
25351 GTGCATACAG AATATATACA CAGAAATATA TATGTACACA TGCATAGAAT
25401 ATATTTACAT ATATATGCAT ATATATAATT TATTTATTTT AAGCAGTTGA
25451 TTTATACAGT TTTTGTTTTT GTTTTTTTTT TGAGACAGAG TCTCACTCTG
25501 TCACCCAGGC TAGAGTGCAG TGGCGAGATC TCAGCTCACT GCAACCTCTG
25551 CCCCCGGGTT CCAGTGATTC TCCTGCCTCA GCTCCACAAG TAGCACACCA
25601 CCATGCCCAG CTAATTTTTG TATTTTTTTT AGTAGAGACG AGGTTTCATC
25651 ATGTTGGCCA GGCTGGTCTC GAACTCCTGA CCTCAAGTGA TCCGCCCGCC
25701 TTGGCCTCCC AAAGTGCTGG GATTTCAGGC GTGAGCCACC ACACCTGGCT
25751 CCCATAATGT CTTTTAGAAT AAAACGATCG AGTTGAGGAT CACACGTGAC
25801 ACTTAATTGT CCTGTCTCTT TAGTCTCCTT CAATCTGGAG CAGTTCTTTG
25851 ATTTTTCCTG GACTCTCATG ACCTTGACAA TTCTGATGAT TATAGGCCAG
25901 TTATTTTGTA AAATTTGAAT TTGTCTGATG TTGCTTATGT TTAGATTTAG
25951 GGTCTTGGTC TTTGGCCGGA ATATCTCAGA CAAGATGCTC TGTTCTTATT
26001 GCATCAGAGC AGAAGACTCT CTGTTTCAGT TGATCACATT TATGTTGATG
26051 CTCACTTTGA TCACTTGATT AAGGTGGTGT CAGTTATGCC TTTCTACTTG
26101 TAGGGTTACT CCTTCCTCCT TCGTGATTTT ATTTATTTTA TTTTTCTTAG
26151 AGACAGGGTC TTGCTTGGTT GCCCAAGCTG GAGTGCAGTG GTGGGATCTT
26201 GGCTCACTGC AGCCTTGAAC TCCTGGGCTC AAGTAATCCA CCTGCCACAG
26251 CCTCCTGAGT AACTGGGACT GTAAGCGAAC ACCACCACAC CCAGCTACTT
26301 TTTGTATTGT AGAGATGGGG TCTCACTGTG TTGTCCAGGC TGGTCTGTAA
26351 CTCCTGGCCT CAAGCAGTCT TCCGGCCTTG GCCTCCCGAA GTGCTGGGAT
26401 TACAGGCATG AGCCACTGCA CCCAGCCTCC TTTGTAATTA AAAAGTATT
26451 TTATGGGGAG TTACTTTCAA GTGATGGAAA TATTTTATAT CTATGTGGAC
```

FIGURE 3J

```
26501 TTGGATTTTC CTATTTCAGT CAGTGAGTTA TAATCCATTT CTGTCACTAG
26551 TTTTATACTT AAATTGTTCC CAACTTGGCC ACTGAGAACC TTTTTAGGTT
26601 AGCTTTTGTG TCCTTTTCAC ATGTCTCCAA GATTCATTGA ATACTTTCCT
26651 GCTTTCTGGT ATAGCAAGAT GTTCAGGTTC TTTTGGTACT TTTACTTTCT
26701 CTGCCCTGGC TCTGGCATCA GTCATTTCTC AGAGGAGCCC TGTGCCTTTC
26751 AGTGGACAAT GGTGTTTAGA GGCCAAGATC TGGACATTGG GTGTTTTCAT
26801 TGCTACCGGT GTGTCACTAC TCCCAGACCC CTTTCAGTGG ACAGCACTAA
26851 GGAATACACA TACGTATATA CAATATATCC ACCTACACAT GTGCGTGCAC
26901 TCACACACAC ACATATACAT TACATCTATA TTTGTGTATC CATGTCTATA
26951 TATTGAAAAT TGTGGCTGGG CACAGTGGCT TATGCCTTTA ATCTCAGCAT
27001 TTTGGGAGGC TGAGGCAAGA GGATCACCTG AAGCCAGGAG TTCAACACCA
27051 GCTTGGGAAA CAGAGAGAGA CTCTGTCTCT ACAAAAATAA AAAGGGAAAA
27101 CCATGAGTTC ACACCCGTGC CCCCAGTTCC AATCCAACTT CACAGGGTTC
27151 ATTTTAGTTT TCACCCTTTC CATGTTTGTA ATTCTCTTCT CTGACATTAT
27201 ACCCTTAATA TGTTTACTTA TTTTATGCAT CTGTATGCAT CCAATCTACT
27251 GTCTTTGTTG GTATCCCACC TCCCCTTGGT GGGTCCAGAT AATCTGCTCT
27301 GGGTTGCCCT TTCACGTGGA TGTCTTCCTT ACCCTGTGTG GGCCTGTGAT
27351 ACTGGGCTGC CCCCACACAT GAGTGCTGCC CTCCTCACGT TGCTTGGGAC
27401 GGCACTGTGT CCTGGGCCAC CATGACTTTT CTCATAACTA GCGTGGATGC
27451 TTACCTTGTT CCACACCAGT GAATGGCTTC AGGAAGAGAA GAGGAAGAGA
27501 AAAATATTTA CATTTAAAGA AAGGTAGTTT AAAGAAATAT GTTAGGTAAA
27551 GAATTGAGCA GGTAATATAC GGAGCTGGCA AAAATTGTGA CCAAAGTAGG
27601 TGAATGATTG AGATTTATGC AATTCTGGGC TAAGTGACAG CCCCTTCCCT
27651 TTCCCTTCCC TTCCCCTTCC CTTCCCTTTT CTTCCCTTTC CCTTCCCTTT
27701 CCTTCCCTTT CCCTTCCCCT TCCCTTCCCT TTCCTTCCCT TTCCCTCTTC
27751 TTCCTTCCTT CCTTCTGTTT TCTTTTCCCT TCTTTCCTTT GCCTTTTTTT
27801 TTTTTTTAAA GCTAGAAACA TCAGTTTAGG CATAAAGACA GAGGAAAAGG
27851 CTTCTTTTTC CTCTCACAGT TCTTTATAAT TGTCTAAGCA GTTTCTTTTT
27901 TCCCTAGGTT TCATTTTTTG AGGAAGAGCG GAACATATTA TCTCGAAGCA
27951 CAAGCCCGTG GATCCCCCAA TTACAGTATG CCTTTCAGGA CAAAAATCAC
28001 CTTTATCTGG TGAGTCTTTA CATCTGTCTC TCTGGAATTA GCCTAGCACT
28051 CTGACACTCA GATGCCTGTG GTAGAACTGA ATGTTGTTCT TGCCCATGTG
28101 GTCTCATTCA TGCAAAGACT TTCTTACCTT ACAGGTGTCT CCCTGGTTTC
28151 CTCGTTATAA AGATCAAGAG CTAACCCATT TAGAAACAGC CTCATTGGGC
28201 TGAACGTGGT GGCTCACGCC TGTAATCCCA GCATTTTGGG AGGCCGAGGC
28251 GGGTGGATCA CGAGGTCAGG AGATCAAGAC CATCCTGGCT AACACAGTGA
28301 AACCCCGTCT CTACTAAAAA TACAGAAAAA TTAGCCGGGC ATGGTGTCGG
28351 GTGCCTGTAG TCCCAGCTAC TCAGGTGGCT AAGGCAGGAC AATCGCTTGA
28401 ACCTGGGAAG CGGAGCTTGC AGTGAGCCGA GATTGCGCCA CTGCACTCCA
28451 GCCTGGGTGA CAGAGCAAGA CTCTATCTCA AAAAAAAAAA AAAGAAAAAA
28501 AAAGAAACAG CCTCATTGAC AGTTGGATAT TGTAGCTGTG GCTTTCAGGC
28551 AATAATAGGG AATCATTTAT TGGGGAATAG TCTGTCATTA TGTATAAGAT
28601 AATCTTGCTT TAATTTTTAA AAACTTCCTG TGTTAGCTTG CTTAGGATTA
28651 AAAAAATGAT AATAGTGCAT GGTTGTTATA AGAAAATGCA AACACTGCAG
28701 ACATGCATGA AGTTGAAGGG AAAGCCCCCC ATTTTCTTTT CCTTTTCTTT
28751 TTTTTTGAGA CAGAGTCTCG CTTTGTCACC CAGGCTGGAG TGCGGTGGCA
28801 CTATCTCGGC TCACTGCAAT CTCCACCTCC CAGGTTCAAG AGATTCTTCT
28851 GCCTCAGCTT CCCTAGTAGC TGGGATTACA GGCACGTGTC ACCACGCCCA
28901 ACTAATTTTT GTATTTTTAG TAGAGATGGG GTTTTACCAC GTTGGCCGGG
28951 CTGGCCGCAA ACTCCTGACC TCAAATGATC CACCTGCCTC GGCCTCCCAA
29001 AGTGTTGTGA TTACAGGAGT GAGCCACTGT GCCCGGCCTC TCCGTTTTAT
29051 TTTCTAATCC TCCTCCCTAG GGGAAGAAAT GTTAAATGGT TACATAAGCT
29101 TTCCCTTTCT GACCCTTAAC TGTGCTCTGT AGGAGCATGG TGGGGGATGT
```

FIGURE 3K

```
29151 TTCTTTTCTT TTCTTCTTTT TTTGAGACCA GGTCTCACTT TGCCACCCAG
29201 GCTGGAGTTC AGTGGCATGA ACATGGCTCA CTGCAGCCTC GACTTCCTGG
29251 GCTCCAGCAA ACCTCCCACC TCAGCCTCCC GGGCATACAC CACTGTGCCT
29301 GGCTAATTTT TGTATTTTTA GTAGAGACGG GGTTTTGCCA TGTTGCCCAG
29351 GCTGGTTTCG AAGTCCTGAG CTCAAGAGAT CTTCCTGCCT TGGCCTTCCA
29401 AAGTGCTGGG ATTACAGGTG TGAGCCACCA TGCCCAGCTC CGGTGGGGGA
29451 TATTTCTATA TCCACATGTG TATAGTTTAC TTTATAAAAA TGGTATGTTA
29501 CTCTGTGCTT GGCTCTCCAG CTTGCTGTTG CCTTTCACCA GTGTATCCCA
29551 GACATCCTTT CTTCCTTGTC AGTAACGCAG GTCTACTTTA TTCTTTGAGC
29601 AGTGGCATAA TTTTCCCTGA TGTGTATATA TCATAAGTTA GAGAATGCTA
29651 AAATTCATTT TGGGGCCTTG TTTAGGTTCT TGAGGGATTA AATTCCTAAA
29701 TTTAACAAGT GTATCCTGGA AACAATTTTT GTTCCTGATT CAGCCCTTAA
29751 AAGAGGACTA TCATGTTACC TTGAATGGAG ATAAACAGGC TCACGTAAGA
29801 GAAAAGGGTA AGAGGGATGA ACTCCCACTT ATCTTAAACT TCTACTGGCC
29851 CGTTTTTGGG GAATTTGCTG CTTTTATTCC TGACCTAAAA TAAATAAGTT
29901 TATGTGTCTT GGTTTCATAT TAGTTGAGAA CCCAGTGCCT GGAGAGAAGT
29951 TTTCCTTGTC CTCTGAGTGA GGACATTCAC ATATGAATCT ATTGGCAGAC
30001 TGGCTTTGAC TGACCACACG TGCCTTCAGA ACCAATGCCA CAGCTCTTAG
30051 GTTTATGGCC TGAAACACCC TTTCCTTACA TATTGCCTTA GAAACTTTCC
30101 TTCCTTGAGA CATGGGGCAT GGAACCCTCA CCTTCACAGA TGACCTTGGT
30151 GTGTTTCTAG GGTTGCTGGT GTTCCAGGAC ATCTGTTGCA GATGCAGTAT
30201 TTACCTTGTG CTCTCTGCAT CATAAGCAGC TTCTCATGTT TGAATGTATT
30251 AACAGACTTT TAATTTTTTT TATTTTTGAG ACAAAGTCTC ACTCTGTCAC
30301 CCAGGCTAGT GTTACCCAGG CTGGAGTGCA ATGGCTCAAT CTCAGCTCAC
30351 TGCAACCTCC ACCTCCTGGG TTCAAGCGAT TCTCTTGCCT CAGCCTCCCG
30401 AGTAGCTGGG ATTACAGGTG CATGACACCA CGCCCTGCTA ATTTTTGTAT
30451 TTTTAGTAGA GACGGGGTTT CGCCATGTTG GTGGGCTGG TCTCAAACTC
30501 CTGACCTCAG ATGATCTGCC CGCCTTGGCC TCCCAAAGTG CTGGGATTAC
30551 AGGCGTGAGC CACTGCGCCT TTTCTTTTCA TTTTTTTTCT GAGATGGAGT
30601 CTTTCTCTGT CACCAGGCTG GAGTACAGTC ATGCAATCTC AGCTCACTGC
30651 AACTTCCACC TCCTGGGTTA AAGTGATTCT CCTGTCTTAG CCTCCTGTGT
30701 AGCTGGGACT ACAGGCGTGT GCCACTGTGC CCAGCTAATT TTTATATTTT
30751 TAGTAGAGAC GGGGTTTTGC CATGTGGGTT AGGCTGGTCT TGAACTCCTG
30801 ACCTCAGGTG ATCCACCCGT CTTGGCCTCC CAAAGTGCTG GGTTATAGG
30851 CGTGAGCCAC TGTGCCCAGC CTCAGGCTTC TTTATTAAGA AGAAGTTCGG
30901 GCCAGGTGTG GTGGCTTACA CCTGTAATCC CAGCAATTTG GGAGGCCGAG
30951 GTGGGCAGAT CAGGAGGTCA GGAGATCGAG ACCATCCTGG CTAACATGGT
31001 GAAACCTCGT CTCTACTAAA AATATAAAAA ATTAGGCAGG TATGGTGGCG
31051 GGTGCCTGTA GTCCCAGCTA CTCGGGAGGC TGAGGGAGGA GAACGGTGTG
31101 AACCTGGGAG GCGGAGCTTG CAGTGAGCCC AGATTGTGCC AGTGCACTCC
31151 AGCCTGGGTG ACAGAGCGAG GCTCCGTCTC AAGAAAAAAA AAAAAGACGT
31201 TCCCTTGAAA CAACAGGGCT TTTGTTTGTT TTGGTTTGTG TTTGTTTGTT
31251 ATTGTTGTTT TAGATACGTA TTTTTTTCTT TCTTTTTTTT TTTTAAGTGA
31301 TGATGTCTCT GTTGCAGTGG CATGATCATA GCTCACTGTA ACCTCAAATT
31351 GCAGGGCTCA AGTGATTCTC CTGCTTCACC TTCCTGATTA GCTGGGACAA
31401 CAGGTACAAA CCACCATGCC TAGCGAATTT TTAAATTTTT CATAGAGACT
31451 AGGGTCTCAC TATGTTGCCT AGGCTGGTTT CGAACTCCTG GCCCCAAGTC
31501 ATCCTCCTGC CTTGGCTTCC CAAATTGTTG GGATCACAGG CATGAATCAC
31551 CACACCCAGC CTATTTTTAG ATATTTTAAT TCGAGCTCTA CAGGAGGTTT
31601 AGAACACTAG CTTGTGAAGA TAAACTTCAT TTTCAAGGCC ACACAGAATC
31651 TAAGTGGTCC TGGAATTAGG AAGGGCTTTG ATTTTTTGGA CCAAAGTTGA
31701 GAGTCCACAG TTTTCTGGTC TACCTTGCAC TGCTCCATAA ACTCATATTT
31751 CTTTTCTCTG AGCTGAAGAG CTCCCCTTCT TGGTGTCTAG TCTCAGGCAA
```

FIGURE 3L

```
31801 CTTATTCTTA AAAGTAAGCA TTATTGAAAT GCTTTGGGAT TTTCACATCA
31851 TCAAGGTCCA TTTTGGTAGA GGCACTGACA GATTTTGAGT GTTCTGTGTG
31901 AAGGAACTCA GTTGAGGATT TAGTGGTCCA TGTGGCAGGC TACTGCTCAG
31951 TAGCTTCAGG GAAACCACTG CTTGCCTCCC CTGTGGCCAG TGAGGATGAT
32001 CAGAGGAGTC CCAGCAGGAA TGCCCAAATG TAGTTTTCTT ACATGTTGAT
32051 GGGAGTGCAT TGTTTCATGT CTAAACAGTT CTCAAATCAC ATCTTCAGGA
32101 GGGTACTATC TGGGCACTTT GATAATTTCT CACTTTGATG TCACCGTTCT
32151 TATTACCATC ACCTAGTTTT GTCATAGTAG AAATAACTTT CCTTTTTCTG
32201 TGTGTGTGTG TGTGTGTGTG TGTGTGTGTG TGTGTGTGTT TTGAGATGGA
32251 GTCTTGCCGT GTTGCCCAGG CTGTAGTGCA GTGGCGTGTT CTCGGCTCAC
32301 TGCAACCTCT GCCTCCGGGT TCTCCTGCC TCAGCCTCCC GAGTAGTTGG
32351 GATTACAGGC GTGTGACACC ACGCCTGGCT CATTTTTGTA TTTTCAGTAG
32401 AGATGGGGTT TCACCACTTT GGCCAGGCTG GTCTTGAACT CCTGACCTTG
32451 TGATCCGCCC ACCTTGACCT CCCAAAGTGC TGGGATTGCA GGTGTGAGCC
32501 ACCACGCCTG GCTTTTTTTT TTTTTTTTTT TGAGACAGAG TCTTGCTCTG
32551 TTGCCCAGGC TGGAGTGCAG TGGCGGGATC TTGGCTCACT GCAGCCTCCA
32601 CCTCCTAGGT TCAAGCAATT CTTCTGCCTC AGCCTCCTGA GTAGCTGGGA
32651 TTACAGGTGC CCACCACCAT GTCCGGCAAA TTTTTGTATT TTTAGTAGAG
32701 ACGGGTTTC ACCATGTTGG CCAGGCTGGT TTCTAACTCC TGACCCCAGG
32751 TGATCCGCCT GCCTCAGCCT CCCAGAGTGA TGGAATTACA GGCATGAGCC
32801 ACTGCGCCTG GCCACCTTTG TCTTCTTAGT TGTGGATTTA ACTGCTGTGG
32851 ACATCTGCTT GGGCATAGCC TTCCGGAGT ACCTCTTGGA TTGGGACTGT
32901 CTGTGGGTTT CTGTGCTAGG ACAGGCTCCC AGATGTAGGA GGCTTCCCCA
32951 ATGATCTCAC CACTGGCATC GGCATCCTTA GCTTCTACTC AGCTTTTCCA
33001 TCTGCCATCT TGCAAGATGG AAGGTTGTTT TGTTTTTGTT TTTGTTTTTT
33051 GGTTTATTTT TTTTGAGATA GAGTCTCGCT CTGTTGCCAA GGCTGGAGTT
33101 CAGTGGCGCA ATCTCGGCTC AGTGCAACCT CCACCTCCTG GGTTCAAGTG
33151 ATTCACCTGC CTCAGCCTCT GGAGTAGCTG GGATTACAGG CGCGTGCCAC
33201 CATGTTCGTT TAATTTTTTG TATTTTAGT AGAGACGGGG TTTCACCGTG
33251 TTAGCCAGGA TGGTCTCGAT CTTCTGACCT CATGATCCGC CTGCTTCAGC
33301 CTCCCAGAGT GCTGGGATTA CAGGCGTGAG CCACCGTGCC CAGCCTAGGA
33351 GGGTTCTTAA TGCAGCTGTT TTTTGGAGTT CTGGTTGCCT CAGCACACTG
33401 CTACTTGGGT CAATGACATT TTTACTCCCT TGTTTTGTAG CTCAATTGGG
33451 TATTACTGAT GGGATTTTGT AATTATTAAT ATTTTCTTGT CTCCATTTTC
33501 TTCTCAAGTA CTTTGTTGCT TTTGAGTAAA ATGCTTGCTA AGGGTATAGT
33551 TTTCACATAA AAGCTCAAAT TTAGCATGGA AATTAAGATA TGCTCATACG
33601 TCTGCCATCC CTTATCTGTA ATTCTGAAAT ACCTAGAGTT CTGAATAACC
33651 TCAAATTCTT TTGTTACTTG TTTATCAGCA AAACCTGATT TGAACTCAGT
33701 TTTTGGCAAA ACTTGATCCA AGCTCTCTTA AGGCTCTTTT TAGTCTTTAT
33751 TCATTCCCTT TAGTGTGACT TCCCATTTTG CTATAAAATT ATGAGTGTGT
33801 TTGATTACAA GGTGATGTCC CAGACCCTAC TGAGGGTGTT ACATAATATA
33851 AACTGTATGT ATGGCTGGGC GCGGTGGCTT ATACCTGTAA TCCCAGCAAC
33901 TTTGGGAGGC CGAGGCGAGC GGATAACCTT AGTTCAGGAG TTCAAGCCCA
33951 GCCTGGCCAA CATGGTGAAA CCCCGTCTCT ACTAAGAATA CAAAAATTAG
34001 CCAGGCATGA TGGTGGGCGC CTGTAATCCC AGCTACTCCT TAGGCTGAGG
34051 CAGGAGAATC ACTTGAACCC AGGAGGTGGA GGTTGCAGTG AGCCAAGGTC
34101 ATGCCACTGC ACTCCAGCCT GGGCGACAAA GCAAGAATCT GTCTCAAAAA
34151 AAAAAAAAAA AAAGTGTGTG TACCACTTTA CCTTTCTAAA ATCTGAAAAA
34201 TTCTGAATCT GGAAACCCAT TCTGCTTCAA GATAAATGGA TCCTAGATTT
34251 ATATCGGTAC CGTACAGTCC TGAAATTCCA TCCTATCTAT TGGCCACTTT
34301 TACATCAACA AACCTTTGAA GTTTGGGGAA ACTTACATAT CACGCTCCCT
34351 TGGCAGTTGA ACATTATTTA TTTATTTTGA GATGGAGTAC TCGCTTTGCC
34401 CAGGCTGGAG TGCAGTGGCG CGATCTTGGC TCACTGCAAC CTCTGCCTCC
```

FIGURE 3M

```
34451 CGGGTTCAAG CAATTCTCCT GCCTCAGCCT CCTGAGTAGC TGGGATTATA
34501 GGCATGCAAC ACCATGCCCA GCTAATTTTT GTCTTTTTAG TAGAGACGGG
34551 GTTTCACTAT GTTAACCAGG CTGTTCTCGA ACTCCTGACC TTGTAATCTT
34601 CCCTCCTCGG CCTCCCAAAG TGCTGGAATT ACAGGCGTGA ACCACCACGC
34651 CTGGCCCTGA AGATACATTT TAAATCAATG AAAAAAACAA CAGGATTCTA
34701 CCTCCTATGG TATATCCCTC CTGGCTGTCT CTTCTCTCCA GTCTTGCCTC
34751 TGCTGTGTGG GTTTCAGGCA TCCATCTTCT CTACTCTGAA TTACTGTGAT
34801 AACCTCTGAA GTATTTTCCC TGCCATCTGT CTGGCCCTTC TCCCAGGTCT
34851 TCCACATACT GCAGCCAAGT CAGCCCGCTG TTGAAACCCT TCAAGACTCC
34901 CTGCTGTCCT CTGGATGAAG TCCAGACTCT TCCACGTGAC TTACCAGGCC
34951 TTTCTTGCAC TTGTCCCCAG CCACTTACTG TTTCTCTCTT TCTACCTTAA
35001 CATCCTGAAC TTCCTTTGGT TCTTTGACCT TGCCTCTGAC CTTTTTCCAT
35051 GCTGTTCACT CTTTCCCTGT TCACCTTGCT AACTCCTCTT TCTCTTTCTG
35101 GGTTGGATCA GATTTCACTT CTTCCAGAAG CCCTTCCTAG ACCCTATACT
35151 TCTGGAATGG CGCCTTTTGA CTGTACGCTC ATTGCACCCT GTACTTCTCC
35201 TTTATGAGTG GGTGCTGGTC TGTCCCACTA GGCTACTTCA TCCATAAAGG
35251 GAGAGTAGAG CTTTACCAAG TCAATGCTTA AGCAATATTT ATTGGATGAA
35301 TGTGTGATTA ATTTCATAGA AATTTGATGT GCATTCAAAT TTACTTATTG
35351 TATTACGGAA CTTGCATTAT ATTCTCAGTG GAGTTATTTT CTTTCACGTG
35401 TGTAATTCAA GATAGACTCA GTGAGATTTT CAAAATTTGG AATGCAGTGC
35451 AAGGAAATTG AACTTGAGTT CTTTTGCATT TTGATGGTTA AAAATTTCCC
35501 ATTTGTGGTG ACATACCACA ATAAGCCAGT GAATGTGGCT TATTGTTTTC
35551 TGGTCTATAG AAAATTGTCG CAAACTCTGT CATAATGTCT GGTTCTATAT
35601 AACAAAGCTA GTCCTGTATT CTGCATGTGG CTGATGGAAA CAGTGCTCTG
35651 TTGATCTGGT TCATGAAGAA ATCTGTTCAA TTCTGCATAA CAGATGCCTT
35701 CATCAGTGTC CTTCCATGAA GGAGCTGATC TTCACAAAGA ACACATAGTT
35751 TTGCATCCCA CCACTTGCAG TATTTTTTTT TTTTTTTTTT TTTTTTTGAG
35801 ATGCAGTCTC GCTCTGTCAC CCTGGCTGGA GTGCAGTGGC ATGATCTCAG
35851 CTCAGTGCAA CCTCTACCTC CTGGGTTCAA TTGATTCTCC TGCCTCAGCC
35901 TCCTGAGTAG CTGGGATTAC AGGCGCACAC CACCATGCCT GGCTAATTTT
35951 TGTTGTTTTA GTAGAGACGG AGTTTCACCA TATTGGTCAG GCTGGTCTCA
36001 AACTCTTGAC CTCATGATCT GCCTGCCTTG GCGTCCCAAA GTGTTGGGAT
36051 TACAGGCGTG AGTCACTGTG CCCTGCCAGT ATTGTTTTGT CTAAATTATT
36101 TGTGCTGATG TTTTTCCTAC TGTGGTTTTC TTCAGATTAC CCTTGCTCTG
36151 AGCCTGCAAT TGACTCATGA ACTTCTTTTC CATGTTCTAA CCTTACAATG
36201 ACTTCCTTGT GTTCACTCCA AATGTTTTTC CCTGGTTGCA TGTAGAGATG
36251 TATTAGCTAA GGTACATGCT TAGCTGCTGT ATCAAAGAGA CCCTAATGTA
36301 CAACCCAGGC TGGTAGAGCA GCTCTGCTGT ATGTGTTAAT TCAGGGACCC
36351 AGGTTCCTTC CATGTTGTGA CTCCCCCCTT CCTTAGGATG TTGTCTTCTT
36401 TTACATGGCT GAAGTTGGGC CATTTCATGT CTCTGTTCCA GCTGCCTGGT
36451 AGGAAAAAAG AACAGAAATT CAGAGTAAGC AAATTCTTTT TCTATAGATG
36501 GATGCGGAAG TTGGACACAT CATTTCCTCT CACATTTTCT CGGCCAGAAC
36551 GTAGTCATGT GACTGCACGT CTAGCTGCTA AGGAGACTGG GAATTTACTG
36601 TCGGCTGTGT GGCCTCTGTC AAGCTAAAAT TCTTATTACT GTGGAATAAG
36651 GGAAGGATGG ATTTGGGGGC ACAATTAATA GTCTGTCACA GAGGCTAAAA
36701 CAGCTGCTTT TGGCTGGGCA CGGTGGCTCA CACATGTAAT TTCAGCACTT
36751 TGGGAGGCCG AGGCAAGTGG ATCACTTGAG ATCAGGAATT TGAGACCAGC
36801 CTGGCCAACA TGGTGAAACC CTGTCTCTCC TAAAAATATA GAAATTAGCC
36851 GGGCATGGTG GCGGGTACCT GTAATCCGAG CTACTCCAGA GGTTGAGGCA
36901 GGAGAATTGC TTGAACCTGG AAGGCAGAGG TTGCAGTGAG CCAAGATGGT
36951 GCCACTGCAC TCCAGCCTGG GCGACAGAGC AAGACTCCAT CTCAAAAAAA
37001 AAAAAAAAGG TTAAATAAAC AGCTGCTTTT GTAGGTGATA CAAGGTACAG
37051 CTAAGCTTTG AAGCCAGGCC TGTAGTTTCA CCTTCCATAT TCTTACTCAA
```

FIGURE 3N

```
37101 GGCATTATAC TTCTGGATCT GAAACCACTG GATCTGATGC CCTGCTTGGG
37151 ATGAGTTCTT TATATTATCT TGCTTTCAAC CCACACCTGT GTAATTTTAT
37201 GGGCAGCGTT TGTTTCCTAT ATAGGAACAA TTTGAAAGTG GGCTGTTTCT
37251 AGGCTTTCAT GAATAGCAGG CTATGCTGTC ATTGGGAATC TGGAGGGAGT
37301 TAATGAACAC AACTTCATTG TTTACTTTAG TGAAATGTGG CAGCTTATGA
37351 TAGTTTTGAC AGTGAGACAT GTGCTGTTTT GATCTCTCAG CTAAGATTAT
37401 CTGATTTTTC AGGCATGTCT CAAAACTCAC CAGGCCTGCT CACATGCTGC
37451 TGCTTCTGAA GCCAGGGTTT GGAAACCAGC TGCCCATCAG AATGAGGCTG
37501 TGACTTAGAA TATTGGTTCT TGTTTTATTA CCATTCCTTG TTTGGTCTCT
37551 CCAGAGTCAC TGGCCTTTTC CGCTTCAATT TTCTTATCGG TGAAATGAGA
37601 TATTAATTCC TCTTATTGAC TTCAATTCAA TTGCTGAGTG TATTGTTGCC
37651 TTTGGGAAGT TCTTTGAGTT TTCTGTGCCT TTGAAATAGT TGTTTTTTTT
37701 TATTCTGGTG TTTTGAGGCA TGTTTCAAGT GAGTGCATTT ACACTTCTAC
37751 CATTTTAGGA GCCACAATTC AGTTATGTTG TCCCAGCTTG CTTGGCCCCA
37801 TCCCCAGAGT TTCTGATTCA GTAGGTCTGG GGTGGGGCCC AATAATTTGC
37851 ATTTCTTCTT CTTTTTTCGA GACAGAGTCT GACTGTGTCA TCCAAGCTGG
37901 AGTGCAGTGG CACGATCGTA GCTCATTGTA GCCTCAAACT CCTGGGCTCA
37951 AGCCGTCCTC CCACCTCACC CTCCTGAGTA GCTGGGACTA TAGGCATATA
38001 CTACCATGCC CTGCCACCTT TTTAATTTTT TGTAAGGATG GGGGTCTCAC
38051 TGTGTTGCTC AGGCTGGTCT TGAATTCCTG GGCTGAAGTG ATCCTCCTGC
38101 TTCAGCCTCC CCAAATGCCG GCATTCCTGG CATGAGCCAC TGCACTTGGC
38151 CAAGACTTTG CATTTCTAAC TAGTTTCCAG GTAATGCTGC TGCTGGTGTA
38201 GGGACCTCAT TTTGAGAACC ATTGTTCTAT AGCTGTAGCT ATAGTTAGTT
38251 TCTGGTTATA GCTTCTTCCT TTTGTCCCTT CAGTAATAGT GTACACATCC
38301 GAAATCCCTG TCCTTGCTCT TTCAGGCCCA GGCATGGTAT CTGGTCCTCT
38351 TCTGTTGCTA GCCCTGGGGT GCTTCATCAT CCCAAGTTTA TTTTTCTTCT
38401 CCTAACCTGA ACCTTTGTAA ATAGCCCCTT CCCTAATGAA CGTCCTCAAT
38451 TCCCTGTTTT GCGTGTCCTG TCTGTTTCTT GGCAAGACTC TGGATGATTC
38501 AGTACTCAAT GAGGATTTTT CGCATAGATG GATGAAACAG GCTGGGTTTC
38551 ATGTTTTCTA AGATAAAGGT GCTTCTCTCT TTTTCTCTTG GTCACTTTGA
38601 CCAAGAAGAA AATAACAGAG TTTTTATTCT CAAGAAGAAT AATATCGGGG
38651 CCACTCTGCT CAGAGGCCAC TCTGCTTTGA GGACCCCTTC TCTCCTCCCT
38701 CATGCCAAAG ATCAGGAACA TTGGGCAGAG CGGATAACGA TGCCGCCAGC
38751 GTCATTACAT TTTCACGGCA CTTTCAGTTG TGCTGAGCGT GCAAACATTT
38801 CAAGGAGACA TTTCTAAGAG GTGGCTAGCA CAGCATGCCT CTAATGCCCT
38851 ATGTGAATTG GAATAGAGTA CTAAAGAACT GTTCAATATT CACCCCATCC
38901 CCGCATATGC AAGCATGCAC GTGGGTTCAT TGTATATGTG TGTGTGCACG
38951 TGTGCACAGA CACATTTGTC CTTCGTTTCA AATGCAACAC AATGGATGGA
39001 AATTGCCTTC CTGGTACTGG GGTATGGATG CAAACACCAA CAGAGAAGCA
39051 GCCGCTACTT CCAAACTGAA CACATGTGAG ATTTGCCCTT TAATTAGCAT
39101 CTGCAGCTGC TGCCATCAGA AGGGTCTGTC TCTGTTGGCC TGAAAGTCTT
39151 TGCTTTAAAA GAGCAAGTCC ATTATAGCTC CAAGCCAGGC TCGTCTGTCA
39201 GCTGCTGTGC TTTCTCTGCC ATCAGCGGGG TTGCCACATT GTTTTGGGCT
39251 GTTTCACTCT AGGACTCTTT CCTCCTCCTG TGCCCCCAGC CTTTGATTAC
39301 CATGCCTTGG TGATCCTCAT TTGGGTGACC TGCAGCTGCT CATTGTGTGT
39351 GCAGGAGACA TCTCCAGTCC TTGTAAGGAG GGAAGATCAC TGGCTTCAGT
39401 GCTGATGGAC TGGTTATTTT CCAGCCCTTT GTCGTCAGTG ATCTTGTCTT
39451 GATATGCAGA AAGGCTCCAG GTAGTCACTG AAAAAAATAT AAGCAGCAGA
39501 GGTGATGGCT ATATGAAAGT CACGTTTCAT CAAGGGCATT GCTGCTATGG
39551 AAACTTTCAA TTCACTTGGA GTAGGGAGCC ATATTGGTTC CACAGCCTCC
39601 TCAGCAGTGG GTCCCAACAC AGTGCTGGGC TAGCTGCCTC TGAATCACCG
39651 CAGTAGCTCC TTTTACTATA GATTCCTGGG TCCCACCCAT GGAATGTGAT
39701 CCATGAAGTC TGGGGTTATT CCCTGGAATC CTTTAAGCTC CCTAAGTGGT
```

FIGURE 3O

```
39751 TGGGATGGGA AAGAGATATG CTTTATGTTA CTATACTTCT TATTATTATT
39801 ATTTTAAAAT TCTTGCCGGG CGCAGTGGCT CACACCTGTA ATCCCAGCAC
39851 ATTGGGAGAC CGAGGCGGGT GGATCACTTG AGGTCAGGAG TTCGAGACTG
39901 GCCTGGCCAA CATGATGAAA TCCCGTCTCT ACTAAAAATA CAAAAATTAG
39951 CTGGGCATGG TGGCGCATGA CTGTAGTCCC AGCCACTCCG GAGGCTGAGG
40001 CAGGAGAATC GCTTGAACCC GGGAGGCAGA GGTTGCAGTG AGCCGAGATC
40051 GTGGCACTGC ACTCCAGCCT GGGTAACAGA GTGAGACTTC ATCTCAAAAA
40101 AAACCCAAAA AAACAAAACT CTTTTTCATT ATACCGGAAC GTCAGCTTTA
40151 TGGAGTCGGG GATTTTTTCT GTTTTATTCA CTGCTGTTTC CCTAACATCT
40201 AGAATAGTGG CTGGCACGAT AGGCACTCAA GTATTGATTT AGATGAGTCT
40251 ATTTTATTTT CTTTTAAATT TTTAATTTTT ATTAGAGGTG GGGTCTGGCT
40301 TTGTTGCCCA AGCTGGTCTC AAAACTCCTG GCCTCAAGCG ATTGTACTGC
40351 CTCAGCCTCC CAAAGGGCTA GGATAGGCAT GAGCCAACAT GCCTGGCTTG
40401 TCTTATTTTT AACAAGCACT TCTGGTGATT CTGATGGACA ATCAGGCTTG
40451 GGAAGTTCTA ACCTAGAGGA CCTACAGTTG TCTTGGGGTA GAAGCCAAGG
40501 CTATCCTGGT TTTTAGAATC AGTGCCTTAC TGGGCATCTC TGAAGAGTAA
40551 AAGTCAGGGA CAGAGTTACA TTTTTGGACA AAACCAGATG CTGTGAATGG
40601 ACTCTTGGTC ACAACCTGGG TGGCGACTTG GTCCTTAACT TCTTCATCAT
40651 TTTCTGCTGA CCCTGTTCTT TGGTTCACAG CAAGTCACCT GATAAGAAGA
40701 CTCAAAGACT GCTAGTTTGT TACTTTAGAT GATGCTTTTG GAACCTCTTG
40751 GTACCATTTT AACAATCCAA ACGTATTTTA TGAAAGCACT CAAGTCCTGG
40801 GTCTTTATTG TATCTTTAAG CTCTAACAGC ATGATGATTG AATAAGCTGT
40851 GGTTGGCCAC ACACAAGCCA TCTTCCCCAT GGCCTCCATT CATACTAGAA
40901 TGAGCAGCTA TACCCCAGTA GTATAGTTTT GGGATATGGG TAACATCTTG
40951 GGATAGCCAC ATTTACTTAG TAAATGTCTG GCTTACATTC TCCTAATGGT
41001 GCACTGTTGG AATTTTTGGT GTGGTAACCT GGAATAGTGT TGGTGGGTCA
41051 AGTTTGATTA GCATCTTTGA TAAGGACCCG GTCTATTTAG AGGTTTGTCA
41101 TTGAGTGTGT CTGTTTTGGC CTCATGTTGT GAAGCATGCT GTGTAGCAGC
41151 TGTTGTAATT TTTGTTGCTT GTTTTCTCAA TCAACCCTGG TTTTGAAGAA
41201 ATGGGAAGTT GTTCCACTCT TAGACTGATC TGACTTGGGA GGGGATTTTC
41251 AGTTCAGGAA GTTGGATCTT CTGAATGGAA GCAAAGAATA CATGTCTTTT
41301 TGCCACTTTA CAAGCTGGCT CTTGTTTTCT GAACTATTTT ACTGGTCATT
41351 GCAAATAGAA TGTCAGGAGT AGCTGCCAAA TACTAAGTTG TGTTCAGTTT
41401 GTCAGTTCTT AAGAGTTGCC GGTGGCTGCT CTGCTATGCG TATGACTTTC
41451 TCAGCCTTAA ACTTACAAGC CATACTGTTT TTTTCACATC TTTAATACAG
41501 CCATAGGAAA TTTATAACTG TGGCGTGTCG TCATAAATAT GCATTGTTCT
41551 TATTTTAAGA CATTTCAGTA CTAAAAGTAT AAGTACTTCT GTTATTATCT
41601 GTGAATTTCT TTCCTTCTTC TTTTTTTGGA TATTTAAGAC CTTTTCGATG
41651 TCAATATATA TTTAAAACAG ACATATAAAT TAGCATTCAC CCACATACCC
41701 AGGGCCTATG GAGAACCAGG TTGGGATGAG TGGGTGAGCT ACAGGCAGCC
41751 AGGTGGCTCC TGTGGGCTCC TCGAGGACTG GGGTGAGTAA CTAATGTCTG
41801 CTAGGAACTT GGGGGAAAGA AGGTGTGTAT GTTAGGTGCT GCCCCCTTCT
41851 AAGTGTTCCT CTTGTTCATA ATTGATTTTT TTTTTTTTTT TTTTTTTTTT
41901 TTTAGAAGGA GTCTCGCTCT GTTGCCAGGC TGGAGTGCAG TGGTGTGATC
41951 TCAGCTCACT GCAACCTCTG CCTCCCGGGT TCAAGTGATT CTCCTGCCTC
42001 AGCCTCCCGA GTAGCTGGGA CTACAGGCAT GCACCACCAT GCCCAGCTAA
42051 TTTTTGTATT TTNNNNNNNN NNNNNNNNNN NNNNNNNNNN NNNNNNNNNN
42101 NNNNNNNNNN NNNNNNNNNN NNNNNNNNNN NNNNNNNNNN NNNNNNNNNN
42151 NNNNNNNNNN NNNNNNNNNN NNNNNNNNNN NNNNNNNNNN NNNNNNNNNN
42201 NNNNNNNNNN NNNNNNNNNN NNNNNNNNNN NNNNNNNNNN NNNNNNNNNN
42251 NNNNNNNNNN NNNNNNNNNN NNNNNNNNNN NNNNNNNNNN NNNNNNNNNN
42301 NNNNNNNNNN NNNNNNNNNN NNNNNNNNNN NNNNNNNNNN NNNNNNNNNN
42351 NNNNNNNNNN NNNNNNNNNN NNNNNNNNNN NNNNNNNNNN NNNNNNNNNN
```

FIGURE 3P

```
42401 NNNNNNNNNN NNNNNNNNNN NNNNNNNNNN NNNNNNNNNN NNNNNNNNNN
42451 NNNNNNNNNN NNNNNNNNNN NNNNNNNNNN NNNNNNNNNN NNNNNNNNNN
42501 NNNNNNNNNN NNNNNNNNNN NNNNNNNNNN NNNNNNNNNN NNNNNNNNNN
42551 NNNNNNNNNN NNNNNNNNNN NNNNNNNNNN NNNNNNNNNN NNNNNNNNNN
42601 NNNNNNNNNN NNNNNNNNNN NNNNNNNNNN NNNNNNNNNN NNNNNNNNNN
42651 NNNNNNNNNN NNNNNNNNNN NNNNNNNNNN NNNNNNNNNN NNNNNNNNNN
42701 NNNNNNNNNN NNNNNNNNNN NNNNNNNNNN NNNNNNNNNN NNNNNNNNNN
42751 NNNNNNNNNN NNNNNNNNNN NNNNNNNNNN NNNNNNNNNN NNNNNNNNNN
42801 NNNNNNNNNN NNNNNNNNNN NNNNNNNNNN NNNNNNNNNN NNNNNNNNNN
42851 NNNNNNNNNN NNNNNNNNNN NNNNNNNNNN NNNNNNNNNN NNNNNNNNNN
42901 NNNNNNNNNN NNNNNNNNNN NNNNNNNNNN NNNNNNNNNN NNNNNNNNNN
42951 NNNNNNNNNN NNNNNNNNNN NNNNNNNNNN NNNNNNNNNN NNNNNNNNNN
43001 NNNNNNNNNN NNNNNNNNNN NNNNNNNNNN NNNNNNNNNN NNNNNNNNNN
43051 NNNNNNNNNN NNNNNNNNNN NNNNNNNNNN NNNNNNNNNN NNNNNNNNNN
43101 NNNNNNNNNN NNNNNNNNNN NNNNNNNNNN NNNNNNNNNN NNNNNNNNNN
43151 NNNNNNNNNN NNNNNNNNNN NNNNNNNNNN NNNNNNNNNN NNNNNNNNNN
43201 NNNNNNNNNN NNNNNNNNNN NNNNNNNNNN NNNNNNNNNN NNNNNNNNNN
43251 NNNNNNNNNN NNNNNNNNNN NNNNNNNNNN NNNNNNNNNN NNNNNNNNNN
43301 NNNNNNNNNN NNNNNNNNNN NNNNNNNNNN NNNNNNNNNN NNNNNNNNNN
43351 NNNNNNNNNN NNNNNNNNNN NNNNNNNNNN NNNNNNNNNN NNNNNNNNNN
43401 NNNNNNNNNN NNNNNNNNNN NNNNNNNNNN NNNNNNNNNN NNNNNNNNNN
43451 NNNNNNNNNN NNNNNNNNNN NNNNNNNNNN NNNNNNNNNN NNNNNNNNNN
43501 NNNNNNNNNN NNNNNNNNNN NNNNNNNNNN NNNNNNNNNN NNNNNNNNNN
43551 NNNNNNNNNN NNNNNNNNNN NNNNNNNNNN NNNNNNNNNN NNNNNNNNNN
43601 NNNNNNNNNN NNNNNNNNNN NNNNNNNNNN NNNNNNNNNN NNNNNNNNNN
43651 NNNNNNNNNN NNNNNNNNNN NNNNNNNNNN NNNNNNNNNN NNNNNNNNNN
43701 NNNNNNNNNN NNNNNNNNNN NNNNNNNNNN NNNNNNNNNN NNNNNNNNNN
43751 NNNNNNNNNN NNNNNNNNNN NNNNNNNNNN NNNNNNNNNN NNNNNNNNNN
43801 NNNNNNNNNN NNNNNNNNNN NNNNNNNNNN NNNNNNNNNN NNNNNNNNNN
43851 NNNNNNNNNN NNNNNNNNNN NNNNNNNNNN NNNNNNNNNN NNNNNNNNNN
43901 NNNNNNNNNN NNNNNNNNNN NNNNNNNNNN NNNNNNNNNN NNNNNNNNNN
43951 NNNNNNNNNN NNNNNNNNNN NNNNNNNNNN NNNNNNNNNN NNNNNNNNNN
44001 NNNNNNNNNN NNNNNNNNNN NNNNNNNNNN NNNNNNNNNN NNNNNNNNNN
44051 NNNNNNNNNN NNNNNNNNNN NNNNNNNNNN NNNNNNNNNN NNNNNNNNNN
44101 NNNNNNNNNN NNNNNNNNNN NNNNNNNNNN NNNNNNNNNN NNNNNNNNNN
44151 NNNNNNNNNN NNNNNNNNNN NNNNNNNNNN NNNNNNNNNN NNNNNNNNNN
44201 NNNNNNNNNN NNNNNNNNNN NNNNNNNNNN NNNNNNNNNN NNNNNNNNNN
44251 NNNNNNNNNN NNNNNNNNNN NNNNNNNNNN NNNNNNNNNN NNNNNNNNNN
44301 NNNNNNNNNN NNNNNNNNNN NNNNNNNNNN NNNNNNNNNN NNNNNNNNNN
44351 NNNNNNNNNN NNNNNNNNNN NNNNNNNNNN NNNNNNNNNN NNNNNNNNNN
44401 NNNNNNNNNN NNNNNNNNNN NNNNNNNNNN NNNNNNNNNN NNNNNNNNNN
44451 NNNNNNNNNN NNNNNNNNNN NNNNNNNNNN NNNNNNNNNN NNNNNNNNNN
44501 NNNNNNNNNN NNNNNNNNNN NNNNNNNNNN NNNNNNNNNN NNNNNNNNNN
44551 NNNNNNNNNN NNNNNNNNNN NNNNNNNNNN NNNNNNNNNN NNNNNNNNNN
44601 NNNNNNNNNN NNNNNNNNNN NNNNNNNNNN NNNNNNNNNN NNNNNNNNNN
44651 NNNNNNNNNN NNNNNNNNNN NNNNNNNNNN NNNNNNNNNN NNNNNNNNNN
44701 NNNNNNNNNN NNNNNNNNNN NNNNNNNNNN NNNNNNNNNN NNNNNNNNNN
44751 NNNNNNNNNN NNNNNNNNNN NNNNNNNNNN NNNNNNNNNN NNNNNNNNNN
44801 NNNNNNNNNN NNNNNNNNNN NNNNNNNNNN NNNNNNNNNN NNNNNNNNNN
44851 NNNNNNNNNN NNNNNNNNNN NNNNNNNNNN NNNNNNNNNN NNNNNNNNNN
44901 NNNNNNNNNN NNNNNNNNNN NNNNNNNNNN NNNNNNNNNN NNNNNNNNNN
44951 NNNNNNNNNN NNNNNNNNNN NNNNNNNNNN NNNNNNNNNN NNNNNNNNNN
45001 NNNNNNNNNN NNNNNNNNNN NNNNNNNNNN NNNNNNNNNN NNNNNNNNNN
```

FIGURE 3Q

```
45051 NNNNNNNNNN NNNNNNNNNN NNNNNNNNNN NNNNNNNNNN NNNNNNNNNN
45101 NNNNNNNNNN NNNNNNNNNN NNNNNNNNNN NNNNNNNNNN NNNNNNNNNN
45151 NNNNNNNNNN NNNNNNNNNN NNNNNNNNNN NNNNNNNNNN NNNNNNNNNN
45201 NNNNNNNNNN NNNNNNNNNN NNNNNNNNNN NNNNNNNNNN NNNNNNNNNN
45251 NNNNNNNNNN NNNNNNNNNN NNNNNNNNNN NNNNNNNNNN NNNNNNNNNN
45301 NNNNNNNNNN NNNNNNNNNN NNNNNNNNNN NNNNNNNNNN NNNNNNNNNN
45351 NNNNNNNNNN NNNNNNNNNN NNNNNNNNNN NNNNNNNNNN NNNNNNNNNN
45401 NNNNNNNNNN NNNNNNNNNN NNNNNNNNNN NNNNNNNNNN NNNNNNNNNN
45451 NNNNNNNNNN NNNNNNNNNN NNNNNNNNNN NNNNNNNNNN NNNNNNNNNN
45501 NNNNNNNNNN NNNNNNNNNN NNNNNNNNNN NNNNNNNNNN NNNNNNNNNN
45551 NNNNNNNNNN NNNNNNNNNN NNNNNNNNNN NNNNNNNNNN NNNNNNNNNN
45601 NNNNNNNNNN NNNNNNNNNN NNNNNNNNNN NNNNNNNNNN NNNNNNNNNN
45651 NNNNNNNNNN NNNNNNNNNN NNNNNNNNNN NNNNNNNNNN NNNNNNNNNN
45701 NNNNNNNNNN NNNNNNNNNN NNNNNNNNNN NNNNNNNNNN NNNNNNNNNN
45751 NNNNNNNNNN NNNNNNNNNN NNNNNNNNNN NNNNNNNNNN NNNNNNNNNN
45801 NNNNNNNNNN NNNNNNNNNN NNNNNNNNNN NNNNNNNNNN NNNNNNNNNN
45851 NNNNNNNNNN NNNNNNNNNN NNNNNNNNNN NNNNNNNNNN NNNNNNNNNN
45901 NNNNNNNNNN NNNNNNNNNN NNNNNNNNNN NNNNNNNNNN NNNNNNNNNN
45951 NNNNNNNNNN NNNNNNNNNN NNNNNNNNNN NNNNNNNNNN NNNNNNNNNN
46001 NNNNNNNNNN NNNNNNNNNN NNNNNNNNNN NNNNNNNNNN NNNNNNNNNN
46051 NNNNNNNNNN NNNNNNNNNN NNNNNNNNNN NNNNNNNNNN NNNNNNNNNN
46101 NNNNNNNNNN NNNNNNNNNN NNNNNNNNNN NNNNNNNNNN NNNNNNNNNN
46151 NNNNNNNNNN NNNNNNNNNN NNNNNNNNNN NNNNNNNNNN NNNNNNNNNN
46201 NNNNNNNNNN NNNNNNNNNN NNNNNNNNNN NNNNNNNNNN NNNNNNNNNN
46251 NNNNNNNNNN NNNNNNNNNN NNNNNNNNNN NNNNNNNNNN NNNNNNNNNN
46301 NNNNNNNNNN NNNNNNNNNN NNNNNNNNNN NNNNNNNNNN NNNNNNNNNN
46351 NNNNNNNNNN NNNNNNNNNN NNNNNNNNNN NNNNNNNNNN NNNNNNNNNN
46401 NNNNNNNNNN NNNNNNNNNN NNNNNNNNNN NNNNNNNNNN NNNNNNNNNN
46451 NNNNNNNNNN NNNNNNNNNN NNNNNNNNNN NNNNNNNNNN NNNNNNNNNN
46501 NNNNNNNNNN NNNNNNNNNN NNNNNNNNNN NNNNNNNNNN NNNNNNNNNN
46551 NNNNNNNNNN NNNNNNNNNN NNNNNNNNNN NNNNNNNNNN NNNNNNNNNN
46601 NNNNNNNNNN NNNNNNNNNN NNNNNNNNNN NNNNNNNNNN NNNNNNNNNN
46651 NNNNNNNNNN NNNNNNNNNN NNNNNNNNNN NNNNNNNNNN NNNNNNNNNN
46701 NNNNNNNNNN NNNNNNNNNN NNNNNNNNNN NNNNNNNNNN NNNNNNNNNN
46751 NNNNNNNNNN NNNNNNNNNN NNNNNNNNNN NNNNNNNNNN NNNNNNNNNN
46801 NNNNNNNNNN NNNNNNNNNN NNNNNNNNNN NNNNNNNNNN NNNNNNNNNN
46851 NNNNNNNNNN NNNNNNNNNN NNNNNNNNNN NNNNNNNNNN NNNNNNNNNN
46901 NNNNNNNNNN NNNNNNNNNN NNNNNNNNNN NNNNNNNNNN NNNNNNNNNN
46951 NNNNNNNNNN NNNNNNNNNN NNNNNNNNNN NNNNNNNNNN NNNNNNNNNN
47001 NNNNNNNNNN NNNNNNNNNN NNNNNNNNNN NNNNNNNNNN NNNNNNNNNN
47051 NNNNNNNNNN NNNNNNNNNN NNNNNNNNNN NNNNNNNNNN NNNNNNNNNN
47101 NNNNNNNNNN NNNNNNNNNN NNNNNNNNNN NNNNNNNNNN NNNNNNNNNN
47151 NNNNNNNNNN NNNNNNNNNN NNNNNNNNNN NNNNNNNNNN NNNNNNNNNN
47201 NNNNNNNNNN NNNNNNNNNN NNNNNNNNNN NNNNNNNNNN NNNNNNNNNN
47251 NNNNNNNNNN NNNNNNNNNN NNNNNNNNNN NNNNNNNNNN NNNNNNNNNN
47301 NNNNNNNNNN NNNNNNNNNN NNNNNNNNNN NNNNNNNNNN NNNNNNNNNN
47351 NNNNNNNNNN NNNNNNNNNN NNNNNNNNNN NNNNNNNNNN NNNNNNNNNN
47401 NNNNNNNNNN NNNNNNNNNN NNNNNNNNNN NNNNNNNNNN NNNNNNNNNN
47451 NNNNNNNNNN NNNNNNNNNN NNNNNNNNNN NNNNNNNNNN NNNNNNNNNN
47501 NNNNNNNNNN NNNNNNNNNN NNNNNNNNNN NNNNNNNNNN NNNNNNNNNN
47551 NNNNNNNNNN NNNNNNNNNN NNNNNNNNNN NNNNNNNNNN NNNNNNNNNN
47601 NNNNNNNNNN NNNNNNNNNN NNNNNNNNNN NNNNNNNNNN NNNNNNNNNN
47651 NNNNNNNNNN NNNNNNNNNN NNNNNNNNNN NNNNNNNNNN NNNNNNNNNN
```

FIGURE 3R

| | | | | |
|---|---|---|---|---|
| 47701 NNNNNNNNNN | NNNNNNNNNN | NNNNNNNNNN | NNNNNNNNNN | NNNNNNNNNN |
| 47751 NNNNNNNNNN | NNNNNNNNNN | NNNNNNNNNN | NNNNNNNNNN | NNNNNNNNNN |
| 47801 NNNNNNNNNN | NNNNNNNNNN | NNNNNNNNNN | NNNNNNNNNN | NNNNNNNNNN |
| 47851 NNNNNNNNNN | NNNNNNNNNN | NNNNNNNNNN | NNNNNNNNNN | NNNNNNNNNN |
| 47901 NNNNNNNNNN | NNNNNNNNNN | NNNNNNNNNN | NNNNNNNNNN | NNNNNNNNNN |
| 47951 NNNNNNNNNN | NNNNNNNNNN | NNNNNNNNNN | NNNNNNNNNN | NNNNNNNNNN |
| 48001 NNNNNNNNNN | NNNNNNNNNN | NNNNNNNNNN | NNNNNNNNNN | NNNNNNNNNN |
| 48051 NNNNNNNNNN | NNNNNNNNNN | NNNNNNNNNN | NNNNNNNNNN | NNNNNNNNNN |
| 48101 NNNNNNNNNN | NNNNNNNNNN | NNNNNNNNNN | NNNNNNNNNN | NNNNNNNNNN |
| 48151 NNNNNNNNNN | NNNNNNNNNN | NNNNNNNNNN | NNNNNNNNNN | NNNNNNNNNN |
| 48201 NNNNNNNNNN | NNNNNNNNNN | NNNNNNNNNN | NNNNNNNNNN | NNNNNNNNNN |
| 48251 NNNNNNNNNN | NNNNNNNNNN | NNNNNNNNNN | NNNNNNNNNN | NNNNNNNNNN |
| 48301 NNNNNNNNNN | NNNNNNNNNN | NNNNNNNNNN | NNNNNNNNNN | NNNNNNNNNN |
| 48351 NNNNNNNNNN | NNNNNNNNNN | NNNNNNNNNN | NNNNNNNNNN | NNNNNNNNNN |
| 48401 NNNNNNNNNN | NNNNNNNNNN | NNNNNNNNNN | NNNNNNNNNN | NNNNNNNNNN |
| 48451 NNNNNNNNNN | NNNNNNNNNN | NNNNNNNNNN | NNNNNNNNNN | NNNNNNNNNN |
| 48501 NNNNNNNNNN | NNNNNNNNNN | NNNNNNNNNN | NNNNNNNNNN | NNNNNNNNNN |
| 48551 NNNNNNNNNN | NNNNNNNNNN | NNNNNNNNNN | NNNNNNNNNN | NNNNNNNNNN |
| 48601 NNNNNNNNNN | NNNNNNNNNN | NNNNNNNNNN | NNNNNNNNNN | NNNNNNNNNN |
| 48651 NNNNNNNNNN | NNNNNNNNNN | NNNNNNNNNN | NNNNNNNNNN | NNNNNNNNNN |
| 48701 NNNNNNNNNN | NNNNNNNNNN | NNNNNNNNNN | NNNNNNNNNN | NNNNNNNNNN |
| 48751 NNNNNNNNNN | NNNNNNNNNN | NNNNNNNNNN | NNNNNNNNNN | NNNNNNNNNN |
| 48801 NNNNNNNNNN | NNNNNNNNNN | NNNNNNNNNN | NNNNNNNNNN | NNNNNNNNNN |
| 48851 NNNNNNNNNN | NNNNNNNNNN | NNNNNNNNNN | NNNNNNNNNN | NNNNNNNNNN |
| 48901 NNNNNNNNNN | NNNNNNNNNN | NNNNNNNNNN | NNNNNNNNNN | NNNNNNNNNN |
| 48951 NNNNNNNNNN | NNNNNNNNNN | NNNNNNNNNN | NNNNNNNNNN | NNNNNNNNNN |
| 49001 NNNNNNNNNN | NNNNNNNNNN | NNNNNNNNNN | NNNNNNNNNN | NNNNNNNNNN |
| 49051 NNNNNNNNNN | NNNNNNNNNN | NNNNNNNNNN | NNNNNNNNNN | NNNNNNNNNN |
| 49101 NNNNNNNNNN | NNNNNNNNNN | NNNNNNNNNN | NNNNNNNNNN | NNNNNNNNNN |
| 49151 NNNNNNNNNN | NNNNNNNNNN | NNNNNNNNNN | NNNNNNNNNN | NNNNNNNNNN |
| 49201 NNNNNNNNNN | NNNNNNNNNN | NNNNNNNNNN | NNNNNNNNNN | NNNNNNNNNN |
| 49251 NNNNNNNNNN | NNNNNNNNNN | NNNNNNNNNN | NNNNNNNNNN | NNNNNNNNNN |
| 49301 NNNNNNNNNN | NNNNNNNNNN | NNNNNNNNNN | NNNNNNNNNN | NNNNNNNNNN |
| 49351 NNNNNNNNNN | NNNNNNNNNN | NNNNNNNNNN | NNNNNNNNNN | NNNNNNNNNN |
| 49401 NNNNNNNNNN | NNNNNNNNNN | NNNNNNNNNN | NNNNNNNNNN | NNNNNNNNNN |
| 49451 NNNNNNNNNN | NNNNNNNNNN | NNNNNNNNNN | NNNNNNNNNN | NNNNNNNNNN |
| 49501 NNNNNNNNNN | NNNNNNNNNN | NNNNNNNNNN | NNNNNNNNNN | NNNNNNNNNN |
| 49551 NNNNNNNNNN | NNNNNNNNNN | NNNNNNNNNN | NNNNNNNNNN | NNNNNNNNNN |
| 49601 NNNNNNNNNN | NNNNNNNNNN | NNNNNNNNNN | NNNNNNNNNN | NNNNNNNNNN |
| 49651 NNNNNNNNNN | NNNNNNNNNN | NNNNNNNNNN | NNNNNNNNNN | NNNNNNNNNN |
| 49701 NNNNNNNNNN | NNNNNNNNNN | NNNNNNNNNN | NNNNNNNNNN | NNNNNNNNNN |
| 49751 NNNNNNNNNN | NNNNNNNNNN | NNNNNNNNNN | NNNNNNNNNN | NNNNNNNNNN |
| 49801 NNNNNNNNNN | NNNNNNNNNN | NNNNNNNNNN | NNNNNNNNNN | NNNNNNNNNN |
| 49851 NNNNNNNNNN | NNNNNNNNNN | NNNNNNNNNN | NNNNNNNNNN | NNNNNNNNNN |
| 49901 NNNNNNNNNN | NNNNNNNNNN | NNNNNNNNNN | NNNNNNNNNN | NNNNNNNNNN |
| 49951 NNNNNNNNNN | NNNNNNNNNN | NNNNNNNNNN | NNNNNNNNNN | NNNNNNNNNN |
| 50001 NNNNNNNNNN | NNNNNNNNNN | NNNNNNNNNN | NNNNNNNNNN | NNNNNNNNNN |
| 50051 NNNNNNNNNN | NNNNNNNNNN | NNNNNNNNNN | NNNNNNNNNN | NNNNNNNNNN |
| 50101 NNNNNNNNNN | NNNNNNNNNN | NNNNNNNNNN | NNNNNNNNNN | NNNNNNNNNN |
| 50151 NNNNNNNNNN | NNNNNNNNNN | NNNNNNNNNN | NNNNNNNNNN | NNNNNNNNNN |
| 50201 NNNNNNNNNN | NNNNNNNNNN | NNNNNNNNNN | NNNNNNNNNN | NNNNNNNNNN |
| 50251 NNNNNNNNNN | NNNNNNNNNN | NNNNNNNNNN | NNNNNNNNNN | NNNNNNNNNN |
| 50301 NNNNNNNNNN | NNNNNNNNNN | NNNNNNNNNN | NNNNNNNNNN | NNNNNNNNNN |

FIGURE 3S

```
50351 NNNNNNNNNN NNNNNNNNNN NNNNNNNNNN NNNNNNNNNN NNNNNNNNNN
50401 NNNNNNNNNN NNNNNNNNNN NNNNNNNNNN NNNNNNNNNN NNNNNNNNNN
50451 NNNNNNNNNN NNNNNNNNNN NNNNNNNNNN NNNNNNNNNN NNNNNNNNNN
50501 NNNNNNNNNN NNNNNNNNNN NNNNNNNNNN NNNNNNNNNN NNNNNNNNNN
50551 NNNNNNNNNN NNNNNNNNNN NNNNNNNNNN NNNNNNNNNN NNNNNNNNNN
50601 NNNNNNNNNN NNNNNNNNNN NNNNNNNNNN NNNNNNNNNN NNNNNNNNNN
50651 NNNNNNNNNN NNNNNNNNNN NNNNNNNNNN NNNNNNNNNN NNNNNNNNNN
50701 NNNNNNNNNN NNNNNNNNNN NNNNNNNNNN NNNNNNNNNN NNNNNNNNNN
50751 NNNNNNNNNN NNNNNNNNNN NNNNNNNNNN NNNNNNNNNN NNNNNNNNNN
50801 NNNNNNNNNN NNNNNNNNNN NNNNNNNNNN NNNNNNNNNN NNNNNNNNNN
50851 NNNNNNNNNN NNNNNNNNNN NNNNNNNNNN NNNNNNNNNN NNNNNNNNNN
50901 NNNNNNNNNN NNNNNNNNNN NNNNNNNNNN NNNNNNNNNN NNNNNNNNNN
50951 NNNNNNNNNN NNNNNNNNNN NNNNNNNNNN NNNNNNNNNN NNNNNNNNNN
51001 NNNNNNNNNN NNNNNNNNNN NNNNNNNNNN NNNNNNNNNN NNNNNNNNNN
51051 NNNNNNNNNN NNNNNNNNNN NNNNNNNNNN NNNNNNNNNN NNNNNNNNNN
51101 NNNNNNNNNN NNNNNNNNNN NNNNNNNNNN NNNNNNNNNN NNNNNNNNNN
51151 NNNNNNNNNN NNNNNNNNNN NNNNNNNNNN NNNNNNNNNN NNNNNNNNNN
51201 NNNNNNNNNN NNNNNNNNNN NNNNNNNNNN NNNNNNNNNN NNNNNNNNNN
51251 NNNNNNNNNN NNNNNNNNNN NNNNNNNNNN NNNNNNNNNN NNNNNNNNNN
51301 NNNNNNNNNN NNNNNNNNNN NNNNNNNNNN NNNNNNNNNN NNNNNNNNNN
51351 NNNNNNNNNN NNNNNNNNNN NNNNNNNNNN NNNNNNNNNN NNNNNNNNNN
51401 NNNNNNNNNN NNNNNNNNNN NNNNNNNNNN NNNNNNNNNN NNNNNNNNNN
51451 NNNNNNNNNN NNNNNNNNNN NNNNNNNNNN NNNNNNNNNN NNNNNNNNNN
51501 NNNNNNNNNN NNNNNNNNNN NNNNNNNNNN NNNNNNNNNN NNNNNNNNNN
51551 NNNNNNNNNN NNNNNNNNNN NNNNNNNNNN NNNNNNNNNN NNNNNNNNNN
51601 NNNNNNNNNN NNNNNNNNNN NNNNNNNNNN NNNNNNNNNN NNNNNNNNNN
51651 NNNNNNNNNN NNNNNNNNNN NNNNNNNNNN NNNNNNNNNN NNNNNNNNNN
51701 NNNNNNNNNN NNNNNNNNNN NNNNNNNNNN NNNNNNNNNN NNNNNNNNNN
51751 NNNNNNNNNN NNNNNNNNNN NNNNNNNNNN NNNNNNNNNN NNNNNNNNNN
51801 NNNNNNNNNN NNNNNNNNNN NNNNNNNNNN NNNNNNNNNN NNNNNNNNNN
51851 NNNNNNNNNN NNNNNNNNNN NNNNNNNNNN NNNNNNNNNN NNNNNNNNNN
51901 NNNNNNNNNN NNNNNNNNNN NNNNNNNNNN NNNNNNNNNN NNNNNNNNNN
51951 NNNNNNNNNN NNNNNNNNNN NNNNNNNNNN NNNNNNNNNN NNNNNNNNNN
52001 NNNNNNNNNN NNNNNNNNNN NNNNNNNNNN NNNNNNNNNN NNNNNNNNNN
52051 NNNNNNNNNN NNNNNNNNNN NNNNNNNNNN NNNNNNNNNN NNNNNNNNNN
52101 NNNNNNNNNN NNNNNNNNNN NNNNNNNNNN NNNNNNNNNN NNNNNNNNNN
52151 NNNNNNNNNN NNNNNNNNNN NNNNNNNNNN NNNNNNNNNN NNNNNNNNNN
52201 NNNNNNNNNN NNNNNNNNNN NNNNNNNNNN NNNNNNNNNN NNNNNNNNNN
52251 NNNNNNNNNN NNNNNNNNNN NNNNNNNNNN NNNNNNNNNN NNNNNNNNNN
52301 NNNNNNNNNN NNNNNNNNNN NNNNNNNNNN NNNNNNNNNN NNNNNNNNNN
52351 NNNNNNNNNN NNNNNNNNNN NNNNNNNNNN NNNNNNNNNN NNNNNNNNNN
52401 NNNNNNNNNN NNNNNNNNNN NNNNNNNNNN NNNNNNNNNN NNNNNNNNNN
52451 NNNNNNNNNN NNNNNNNNNN NNNNNNNNNN NNNNNNNNNN NNNNNNNNNN
52501 NNNNNNNNNN NNNNNNNNNN NNNNNNNNNN NNNNNNNNNN NNNNNNNNNN
52551 NNNNNNNNNN NNNNNNNNNN NNNNNNNNNN NNNNNNNNNN NNNNNNNNNN
52601 NNNNNNNNNN NNNNNNNNNN NNNNNNNNNN NNNNNNNNNN NNNNNNNNNN
52651 NNNNNNNNNN NNNNNNNNNN NNNNNNNNNN NNNNNNNNNN NNNNNNNNNN
52701 NNNNNNNNNN NNNNNNNNNN NNNNNNNNNN NNNNNNNNNN NNNNNNNNNN
52751 NNNNNNNNNN NNNNNNNNNN NNNNNNNNNN NNNNNNNNNN NNNNNNNNNN
52801 NNNNNNNNNN NNNNNNNNNN NNNNNNNNNN NNNNNNNNNN NNNNNNNNNN
52851 NNNNNNNNNN NNNNNNNNNN NNNNNNNNNN NNNNNNNNNN NNNNNNNNNN
52901 NNNNNNNNNN NNNNNNNNNN NNNNNNNNNN NNNNNNNNNN NNNNNNNNNN
52951 NNNNNNNNNN NNNNNNNNNN NNNNNNNNNN NNNNNNNNNN NNNNNNNNNN
```

FIGURE 3T

53001 NNNNNNNNNN NNNNNNNNNN NNNNNNNNNN NNNNNNNNNN NNNNNNNNNN
53051 NNNNNNNNNN NNNNNNNNNN NNNNNNNNNN NNNNNNNNNN NNNNNNNNNN
53101 NNNNNNNNNN NNNNNNNNNN NNNNNNNNNN NNNNNNNNNN NNNNNNNNNN
53151 NNNNNNNNNN NNNNNNNNNN NNNNNNNNNN NNNNNNNNNN NNNNNNNNNN
53201 NNNNNNNNNN NNNNNNNNNN NNNNNNNNNN NNNNNNNNNN NNNNNNNNNN
53251 NNNNNNNNNN NNNNNNNNNN NNNNNNNNNN NNNNNNNNNN NNNNNNNNNN
53301 NNNNNNNNNN NNNNNNNNNN NNNNNNNNNN NNNNNNNNNN NNNNNNNNNN
53351 NNNNNNNNNN NNNNNNNNNN NNNNNNNNNN NNNNNNNNNN NNNNNNNNNN
53401 NNNNNNNNNN NNNNNNNNNN NNNNNNNNNN NNNNNNNNNN NNNNNNNNNN
53451 NNNNNNNNNN NNNNNNNNNN NNNNNNNNNN NNNNNNNNNN NNNNNNNNNN
53501 NNNNNNNNNN NNNNNNNNNN NNNNNNNNNN NNNNNNNNNN NNNNNNNNNN
53551 NNNNNNNNNN NNNNNNNNNN NNNNNNNNNN NNNNNNNNNN NNNNNNNNNN
53601 NNNNNNNNNN NNNNNNNNNN NNNNNNNNNN NNNNNNNNNN NNNNNNNNNN
53651 NNNNNNNNNN NNNNNNNNNN NNNNNNNNNN NNNNNNNNNN NNNNNNNNNN
53701 NNNNNNNNNN NNNNNNNNNN NNNNNNNNNN NNNNNNNNNN NNNNNNNNNN
53751 NNNNNNNNNN NNNNNNNNNN NNNNNNNNNN NNNNNNNNNN NNNNNNNNNN
53801 NNNNNNNNNN NNNNNNNNNN NNNNNNNNNN NNNNNNNNNN NNNNNNNNNN
53851 NNNNNNNNNN NNNNNNNNNN NNNNNNNNNN NNNNNNNNNN NNNNNNNNNN
53901 NNNNNNNNNN NNNNNNNNNN NNNNNNNNNN NNNNNNNNNN NNNNNNNNNN
53951 NNNNNNNNNN NNNNNNNNNN NNNNNNNNNN NNNNNNNNNN NNNNNNNNNN
54001 NNNNNNNNNN NNNNNNNNNN NNNNNNNNNN NNNNNNNNNN NNNNNNNNNN
54051 NNNNNNNNNN NNNNNNNNNN NNNNNNNNNN NNNNNNNNNN NNNNNNNNNN
54101 NNNNNNNNNN NNNNNNNNNN NNNNNNNNNN NNNNNNNNNN NNNNNNNNNN
54151 NNNNNNNNNN NNNNNNNNNN NNNNNNNNNN NNNNNNNNNN NNNNNNNNNN
54201 NNNNNNNNNN NNNNNNNNNN NNNNNNNNNN NNNNNNNNNN NNNNNNNNNN
54251 NNNNNNNNNN NNNNNNNNNN NNNNNNNNNN NNNNNNNNNN NNNNNNNNNN
54301 NNNNNNNNNN NNNNNNNNNN NNNNNNNNNN NNNNNNNNNN NNNNNNNNNN
54351 NNNNNNNNNN NNNNNNNNNN NNNNNNNNNN NNNNNNNNNN NNNNNNNNNN
54401 NNNNNNNNNN NNNNNNNNNN NNNNNNNNNN NNNNNNNNNN NNNNNNNNNN
54451 NNNNNNNNNN NNNNNNNNNN NNNNNNNNNN NNNNNNNNNN NNNNNNNNNN
54501 NNNNNNNNNN NNNNNNNNNN NNNNNNNNNN NNNNNNNNNN NNNNNNNNNN
54551 NNNNNNNNNN NNNNNNNNNN NNNNNNNNNN NNNNNNNNNN NNNNNNNNNN
54601 NNNNNNNNNN NNNNNNNNNN NNNNNNNNNN NNNNNNNNNN NNNNNNNNNN
54651 NNNNNNNNNN NNNNNNNNNN NNNNNNNNNN NNNNNNNNNN NNNNNNNNNN
54701 NNNNNNNNNN NNNNNNNNNN NNNNNNNNNN NNNNNNNNNN NNNNNNNNNN
54751 NNNNNNNNNN NNNNNNNNNN NNNNNNNNNN NNNNTTCTAA TAACTGTGCT
54801 TTCTACTACA TTAAGCCTAT TTTTTTTTTT TTTTTTTTTT TTTGAGATGG
54851 AGTCTTGCTC TGTTACCCAG GCTGGAGTGC AGTGGCACAA TATCGGCTCA
54901 CTGCAACCCT GCCTCCTGGG TTCAAGCGAT TTTCCTGCCT CAGCCTCCTG
54951 AGTAGCTGGG ATCACGGGTG CCCACCACCA TGCCTGGCTA ATTTTTGTAT
55001 TTTTAGTAGA GATGGGGTTT CACCATGTTG GCTAGGCTGG TCTTGAACTC
55051 TTGACCTTAG GTGATCCGCC TGCCTCGGCC TCCCAAAGTA TTGGGATTAC
55101 AGGCATGAGC CACTGTGCCT AGCCTGTGAA GCTCATTTCT TAAGGCTCTG
55151 ATAAATGTAT ATGTTTTAGT TTCAACCAAA AGGAAAAGGA ACGTATTTCC
55201 TAGATTTTTG TATCTCACCT AATTTTCATC TTTCTGGAAT GCTTAATACA
55251 TATTTTTATG TACATACATT ATTTGTTATT CTTGAGCCTC CTCTTGAGTG
55301 AAAATTTCCC CTTAGATGAC TCTTGGAGCT AATTTATTTC CTTCCCTTTA
55351 GCTCACTCAC TCATTCAATC ATTCAATAAC GAGTGCGTTA TCATACCAGG
55401 TACTGTTAGG TAGCAGGTTT ACAGGGATGA GCAGAAGAAG CAGGCCCTCT
55451 CTGCCTTCTT TCTTTTTTCAT CACACTGAAA TCACAGCGCA TTGTGTGTGT
55501 GCAAAAGTAG AGTGCAGAGG GAACATGCAG AAAGGAGTTA TAGGATAGAA
55551 AAGGTAGCCA AGGAAAGCAG CAAGAACAGC ATGATTTGTT CAGGGATCTT
55601 TAAATAGCTC ATCATTGTTG GACAGCAAAG GGAGAGATGG GGAACGTGGC

FIGURE 3U

```
55651 AAGATGAGAT GAGAAGGGGA GCCGGGGTCA AGCCATGGAG GACGCTGAAC
55701 CCCTACAAAG GAACTAAGCC TATTGATGTG AACAGGCCAC TTATTTTGGG
55751 AACACGCCTT TGGTCCAAAG GGAAGAGGGC ACGAAACTTC CTTCTCTAAA
55801 AAACAAAAAA AAAGAAACTT GCATATATGA GAAATACTTT CTTCACTTTG
55851 CAGCATGAGA AACGGAATCC CTACTAAGGA AATAATTCTC TTATTTTTTT
55901 TGGAACAGCG GTTTTTGAAA TTTCCAGATG ACCCCAAAGT GAGCAGTGAC
55951 TTTCTTGATC TGATTCAAAG CTTGTTGTGC GGCCAGAAAG AGAGACTGAA
56001 GTTTGAAGGT CTTTGCTGCC ATCCTTTCTT CTCTAAAATT GACTGGAACA
56051 ACATTCGTAA CTGTAAGTAG GGCTGTTTTC CTTAATTTGG GATGTTGGGA
56101 TTATGAAACA CTCAAGAGAG ATCTGAGATT GTTCTGGCCC AAAGAAGCTT
56151 CTGTAAATTA CATAAATAAA GGCTTTAATT ATCTACAGGA GTAGTAAAGG
56201 CTAATGATGT AGCTGTCTTT GAGTAATAAT TCTGCCTTAA AATTGTTTGT
56251 GTAGAACTGG GTCATTTATC AAACTCTGTG TTTATGTGGC CTTTAGAATA
56301 TTATCCCTCA GTAAGTTAGA GGCACAGATT AATGGAGTTT GAAGGTTGTC
56351 ACTTGGTTTG ACACAGTTTC TTCCAAAAAA GTGGATCTAG GTATTTCATT
56401 CACATATCAG GAAAAAGACT CAGATTAGGC AACATGCCCA GGTTGTTCTG
56451 CTAATGGCTG AGTTTAAACA AAACCATAA ACACCTCCCT GTGTTTATTC
56501 ATTTGTTTCC CTCGATAATA TTTGTCTTTG CTCACAAGCA TGTAAAACCT
56551 ATAATGTATA TGCACAGTAG ATTCATTCAT ACATCACTTT TTATAATCAG
56601 TTAGTGCAAA CTGAATGAAT TCATTAAAAA CAAAGACCTG GTTTATTATC
56651 AACAGAAACC ACACAATGCT CTTTTTTCTT TTACCAGTTG GTGATCTTTT
56701 AAAAATCCTT TTAATTCTTG GATGTGTTGT TGATTGAATG TGTTCTACTG
56751 AATGATCAGC ACGGATTAGA GCCAGTAGGA AAGCAGTTAT CCTGTTTGAG
56801 TATGTGTTTT GTTTTTGGTG ATGGAGGGAG GTTGGGAAAT GGAATCTGTT
56851 TCTAGGTGTC AAAACCAGGC TTCTGATTGG AGATGTGTTA TAATTATAAT
56901 TGCTTGCACC TTCAGCTAGG ACATAGTATG GTAAAAAATC AGTATTGTCC
56951 AGTTGTAAAC CATTTTGATG GTTTCTCTAA CCTTCTGCTG AAATATTTAA
57001 GTAGGTAGCA TTTCCATAAA TCTTTCTTGG CAAATGTTTT TATTATTCGG
57051 GTGGCCACAT TGCTTTATTT TTCTAAATAA ATAGACATCT CCCCCCAAAT
57101 CTCCAAGGTT CAGACCTTCT AATCAGTAAT ATATTTTCAG GGCATTCTTC
57151 CTTTTATGCT TTTAGAAAGA TGTAATAGAC TTTCTTTTAG ATGCTGTTCA
57201 AGTACTTAAT CTTTTCTTGT CTTGCCTTTT TATCTCTGTA ATCTTCTTGA
57251 ATAAGCAGTT AATTTTTTTT ATTCATGAAC CTGCTGATCA TGTCTAAGAA
57301 TGTATCTCCA CTTAAGTAAG TCAGTGAATG GTGATTACCT GAGTAGAGTT
57351 AAAGTAGTCC CCCACCCTCC TATCTGTGGC ACATATGTTC CAAGTCTCCC
57401 AGTGGATGTG TGAAACTGAT GATAGTACTG AAACCCATCT ACCTTTTTTC
57451 CTGTGCATAC ATACCTATGT TATATAAAGC TTAACTTATA AATTAGGCAT
57501 AATATATTTG ACTCCAGCT CCCAGTGTAG TGGCTCTGAA GACTCACAAA
57551 ATGTATTTGC TTTAAAAAAT TCTTTTTTTT TTTTTTGAGA CGGAGTTTTG
57601 CTCTTGTTGC CCAGGCTGGA GTGCAGTGGT GCGACCTCAG CTCACTGCAA
57651 CCTCCGCCTC TTGGGTTCAA GCGATTCTCC TGCCTCAGCC TCCCAAGTAG
57701 CTGGGATTAT AGGCATGCAC CACCACACCC AGCTAATTTT CTATTTTTCG
57751 TAGAAACGGT TTTTCCATGT TGGTCAGGCT GATCTTGAAC TCCTGACCTC
57801 AGGTGATCTG CCTGCCTCGG CCTTCCAAAG TGCTGGGATT ACAGGTGTGA
57851 GCCACCACGC CTGGCAAAA AATTCTTTTA ATTTAAGTAA ATCTTTATTT
57901 ATTTACTTTT GAGACAGAGT CTCACTCTGT GGGCCAGGCA GGAATGCAGT
57951 GGTGTGATCA CGGCTCACTG CAGCCTCGAC CTCCCATGCT CAAGCAGTCC
58001 TCCCACCTCA GCCTCCTAAG TAGCTAGGAC TACAGGTGTG TGCCATCACA
58051 CTCTGCTAAT TTTTTTGTAT TTGTAGAGAC GCGGTTTCAC CAGGTTGCCC
58101 AGGCTGGTCT TGAACTCCTG AGCTCAAGTG ATCCTCCTGC TTTGGCCTCC
58151 CAAAATACTG GGATTACAGG CGTGAGCCAT TGCACCCAGC CCTAATTTTA
58201 ATAAATCTTT TATTTTGGAA TAGTATTAGA TTTATAGAAA AGTTGCAAAG
58251 ATAGTATGGA AGAGTTCCCA CATACCCTTC ACCCAGTTTT CCCCAACGTT
```

FIGURE 3V

```
58301 AACTCTTTTT TATATTTATT TATTTATTTT TTGAGACACA GTCTTCCCGT
58351 CGCCCAGGCT GGAGTGTGGT GGCACGATCT CGGCTCACTG CAACCTCCGC
58401 CTCCTGGGTT CAAGTGATTC TTCTGCCTCA GCCTCCGAGT AGCTGGGACC
58451 ACAGGTGTGC GCCACCATGC CCGGCTACTT TTTGTATTTT CAGTAGAGAC
58501 AGGGTTTCAC CATGTTGGTC AGGCTGATCT CAAGCTCCTG ACCTCAGGTG
58551 ATCTGCCTAC CTTAGCCTCC CAAAGTGCTG GGATTACAGA CATGAGCCAC
58601 CGCACCCAGC CCCCAGTGTT AACTCTTACA TAACAGTGTC ACTGTCTAAG
58651 TGTTTGAAAA ACTATTTGTC AAAACTAATA TTGGTACATT ATTGTTAACT
58701 ACACTTCAGA CTTTTTTTGG ATTTTACCAA TTCTCCCACT CATGTCCCTT
58751 TTCTGTTTCA GGAATCAATC CGTGGTACCA TATTGCAGTT AGGGTGTTTA
58801 TATTTGATGG GACTGGTCCT AGTTTAGATA CTTAGTGTAG CTCAGCCAGC
58851 AGGTGGGATC TTCATGCCCA CCGAGGATTG GTATTGTGTT TTCCTGGTGG
58901 TTTTATGGCA TTTCCGACTA TGCAGAGAGG CATGGTATTA ACTTCAGTGT
58951 CTCCTAGCAA ATTTTCCTGT TTTTCACCAA CCTCTGATCC CTGCATTATT
59001 TGCAATCAAC TCAGAGATTT GTGATTGAAA ACATTGCTTG ACTCCATGCT
59051 CTTTAAGCTA TTTTCTAACT AGGTAACTGT AACATAAATT ATGCTTTTAT
59101 CTAGCACTGT TTTTCATAAA CACATGTTGA GTGATTTTCA TCAACCGAAA
59151 TACTTCGAAT CATTAAGTTT CCCAAGTTCA TGGATGCTGC TTAAATGCCT
59201 GGTGGTTCCA GGCTGTCGAA TATTTCTGCC TTCTGCAATA AGAGATTGTC
59251 CCTTGTTAAA AGCAACATTA GCCTTTGTGC GGTTTCACCC CCAATTCTTC
59301 TTTTTCTTGT TGTAACCAAT GAAAGGAAGT ACTGCTTAAC ACAGCAGGTA
59351 ATAATCTTCT AAAACTCATT ATCTCAAGAG GTGGTCCTGG CAGGATATAT
59401 AAATGCAATT TAAGAAAGGT CTTGGCAAAT TTATGAATGA CAGAACTGGG
59451 AGTGGCTACC GAGAGAAACT AGGATGCGCC TTTGCTTTGA CACTGAGGTC
59501 AGGCGTAGCT TCTGTACCCT CCTGGGTCCT GCCTCTTGGG GTTGCTGCAG
59551 GCAGCACCCC ATGAACCAGG CATCTGACCC AGTTCCAGGA TACTTATTCT
59601 TCCAGCAAGT CGAACACTCT GTGATGAGTG ACTGCCATGC TCATGGGTCA
59651 CCAGGCTCTC ATTATTCTGT TTCATTTCCA GCCTCCACA AGATTGGTTT
59701 TTCAGCTGCT TATTTATTAT TATCATTATT TCAAGGCTGC TTTCCAAGTT
59751 TCAGTGGGGG GTTTCCTAAG CGTACCAGCT GCCCTGGTTG TGCAGTTCCG
59801 GTGATGTTTC AGATGCTGGG CCGGATTCTG GCTGTACCCA GCCTGATCTT
59851 TCTGGGCTTC AGGAAAGCTG AAGCCAATCA GAGCTCCTCT TTCATGCCTT
59901 TGGGATTATG CTTACCTTGC CTGGCATCGT GTACCTGCTC CCATCCATGG
59951 GAAAGTTTTG CTGTCTGGTA CTGTCTTCTA TCAACATCTT TTAAGATATC
60001 TTCCCCCGAG GCATCGTGAT GTCAACGGAA CCAGCACACT TGTACGTTTT
60051 ATGCAAGACT GCCATATCTC AACAGTGAGA AATGCATAAT GGAAGTGGTG
60101 ATCACGGATT ATTTCCTAGG ACATTATGGC TAATGCGCTA GAGAACTCGG
60151 ATGGTCTGTT GCGTCTGACA TGGGCTTTTT CTCTTGAGTT GTCTTTCTTT
60201 TGCTATTCTC TGAAAGAAAC AATTCTTGCC ACATGATCCT GATTTTTCAG
60251 GTCCTCAGCA TTTGTTAGCA GAAAGTACAC TTTGTTTCCA TCCGGCAGTG
60301 ACTCAGTGGT GGTCCCATGC TGATGAAACG CTGAGATAGT CTTCTTCCAA
60351 ATAGGTATCG TTTTGATTGT TGCTGCTTAT TTGCTAGCTG GCCCTCAATA
60401 GTGACAATGA AACCTCAAGT GTATAATATG GTTGCTCAGT AATCCTGAGG
60451 GAAGACAGTC TTTGGTTTGG GGGATAGGGA TTCTGTGCCT ACTTAGCTTC
60501 AGGTGAAAGT CTTACAAATT TTTGTGTGTA GAAATAAGCA CCATGTACCT
60551 CCTTGGGTTT TTTCTTTTTT TTTCTAGTCC TTTAGTATGG TCAACAATAT
60601 TGTTTAGGGA GTACCTATTC TGTGCTAACC ACTAGGCATT CAAGTATATT
60651 ACACTATGCT CCTTCAAAAC ACTTCTGTCA AATGTAAGGA TTATTATACC
60701 CATTTTACAG ATGTGGTTAC TGTGGTAACT TGGCCAAGGT CATAGGGCAA
60751 GTGAATAAGG GATTCTGGAT TTGGGTGGAG GTCTGTGTGA TTCCAAAGCC
60801 CATGCTCTTT CTACAATACT ATATATGCCT TTGCATAAGT TATTGTTATT
60851 AGTAATAATA TTTGTGATGA TGGCAAATAA TAAACCATGT CACACTAGAG
60901 AGTGATTTAA TCTCTAGGTC TATTTAAGAA CATTTGGAAT TGCAGGAATT
```

FIGURE 3W

```
60951 GGATTTTTTTT TTTTTTTTAA GTGATGGAGT CTTGCCATCT TTGCCCAGGC
61001 TGGTCTCAAA CTTGTGGGCT CAAGTGATCA TCCTCCCTCT GCCTCCCAAA
61051 GTGATGGGAT TACAGATATG AGCCACCATG CCCAGCCTAG AATTGCAGGA
61101 ATTTTTGAAT TGATGATTCA TTCTGATATT TGAATTTCTA CAGTATGTTA
61151 AGTGCAATGT CAGGTGCTGG TGCTGTGGCT CCATTGATGA ACACATTTGG
61201 GTATGGCCCT ACCTTCATTG AATTTAGAGT CTAAGAGCCT AACCGGTCTT
61251 TTGCTTGAAT AGAGCTGTAG TCCTGTTAAA TTGCTGTACC TCCAAATGGT
61301 GGGAAGTTTA ATGCTTCGTA GGCCTCCCCT CACTAGTTTA CTGAACCACA
61351 TGTGCTTGAT TTTTTTTTGA GATGGGGTCT CGCTCTGTTG CCCAGGCCGG
61401 AGTGCAGTGG CGTGATCTCG GCTCACTGCA AGCTCCGCCT CCCAGGTTCA
61451 CGCCATTCTT CTGCCTCAGC CTCCCGAGTA GCTGGGACTA CAGGTGCCCG
61501 CCAACACGCC CGGCTAATTT TTTTGTATTT TTAGTAGAGA CAGGGTTTTA
61551 CCATGTTAGC CAGGATGGTC TCGGTCTGCT GACCTCGTGA TCCACCTGCC
61601 TCAGCCTCCC AAAGTGCTGG GATTACAGGC ATGAGCCACT GTGCCTGGCC
61651 CCACATGTGC TTGATTTTAA GCAAAATACA GACTATAGGC TGTGACCTGG
61701 TGATCTCTTC CCCACATACA GCATCCTGCT AACCTATAAC TCTCCCCATG
61751 TCTCAGATCT AGCCTGGGAA AGGACAATGT TGGATCGATG GCCCACTTCT
61801 AATCTTGGGA TTTCTAATCT CAAGATGAGT TGAGAAGACT CAGGATGTGT
61851 CCTGTTTTCT GTTTATTTAG AACAGGGTTT CTCAGCCTTG GCACTGTTGA
61901 CATTTGGGGC CAGATAATTC TTTGCTGTGG GGGCTGTTGT GTGAATTGCA
61951 GGATGTTGAA CAGCATCGCT GTGCTTTCTC CATGGATACC AGTAGCACCC
62001 TCCCCCTGCA GTTGCAACAA CCAAAAATGA CTCTAGACAT TGCCCAGTCT
62051 CCCCTTGGGG GCTACAGTCA CCTTCAGTTG AGAACCATTG ATTTAGAAGA
62101 ATTGGCCAGG TTATTATCAG GAGAGGGAAC ATCACAGTAA TCTGAATCTC
62151 TCAATACTGC CACTGTTACT GTTAACGAAC AGCAAAACTA TTACGTGGAG
62201 GCAGTAGGAC CTTGCTACTC AGAGTGTGGT CCGTGGACCG GCAGCATCGG
62251 AATCATCTAG GAGCTTGTTA GAGCTTCAGA GACTCAGGCC TACTGAGTCA
62301 GAAGCTGCAT TTTAATAAGG ATCCCCAGGG GATTTCTGTG CATATTAGAG
62351 TTGTGAAGCC CTGCAAGAGG AAGAAATTGG ATGCTAGCCT CAGAGTTTCT
62401 TGCTCATCTT TGTGGGTCTT CCTCGTTTTG TCTTCGGGCT TAAGGTATGG
62451 GGAGGCCACT TTTTGGCTCA GGACTCCTAT GGGTGAATGG GACTGCTTAG
62501 AACTGCTGGG TTTTAGGCCT TGCTTTGAGG AATTTAAAGC TTTTCTCTTA
62551 GATGGACATT ACATCGTTCA TATACTTCAA AATGGTGGTT TGACCTAATC
62601 TCTGCCTTCT GATAGCAAAA AGATATTTCC TTGACTCCCT GAACCCCACT
62651 TTACTGTTGT CCCATATTGG ATTTTAATTA AGGGTGGAAT AAGTATTCTT
62701 CACTAACATG TTTATACATG TATGATATTA CCATGCCATT TATTGAGTGC
62751 CTAGTATGTG CCAGGAGCTC TGCAAAGTGC TTTATGCTTA TTATTGTTCC
62801 ATTTATTCTT CCCCAAACCT CTGTGAGGCA GGTCCTATCA CTAGTCCACA
62851 ATACAAATGA GGTCATGGAG CCCGAAGTTG GCAGTGGTAG GAATCAAACT
62901 CAGGTCTCCC TGACTCTAAA TTCTCTTTGC CTTTGTTTTT TTGAAAAAGT
62951 GGTATAGCCC ATAGCAGAAA ATTCACATTA TACAGAAGGT TATACGGCGA
63001 AAAATGCCTC CTTCCCACCC CACGCTCAAC CCCTCTCCCT CAAGCGAACC
63051 ACTATTGTCA GTTTCTCATA GAACTTTCCA GAATATTCTA TGCTCCTATA
63101 ACACTAGCAC AACCTATCCT CTTAACAACA TCTTTATGCT GCCTCCCAAG
63151 AATTCAGTAA TTTTTTTTTT TTTGAGATGG AGTTTTGCTC TAGTTGCCCA
63201 GGCTGGAGTG CAATGGCGTG ATCTCGGCTC ATTGCAACCT CTGCCTCCCA
63251 CGTTCAAGTG ATTCTCTTGC CTCAGCCTCC CGAGTAGCTG GGATTACAGG
63301 CATGCGCCAC TATGCTTGGC TAATTTTGTA TTTTTAGTAG AGATGGGGTT
63351 TCTCCATGTT GGTCAGGCTG GTCTTGAACT CCCAACCTCA GGTAATCCGC
63401 CCACCTCGGC CTCCCAAAGT GTTGAGATTA CAGGCGTGAG CCACCGCACC
63451 TGGCCAAATT CAGTAATTTT TATTGGCAGG TTATTTTCCC GCATCATTGA
63501 AATGAATGAA GCAATCTTTA TACTTCATTC ATTTAAGCAT GGCCCTACCA
63551 TGCTTATCCT TCGAATCTGC CACTCAGCCA TTGGTTTCTG ATAAGCAGTG
```

FIGURE 3X

63601 CTCTTCTCAA ATGAAAACCC CTTATGGCTT TTTTTTTTTT TTAAACAAGG
63651 CCACAGGTGA TATCATGATT TTGACATTAT TTTTTCATTT ATTTTGTTTA
63701 GTGTCCTGCC TTTAGAATTG CATTATCTCA ATGGCTTGTG CATTTAGTGT
63751 GTGTGTGTGT GTGTGTGTTG TGTGTGTGTG TGTGTGGTAT GTGAGCACGC
63801 ACATATTTGT TTTGGGCCCT TTTTTTTTTT TTTTTTGAGA CAGAGTCTTC
63851 CTCTGTCAGC CAGGCTGGAG TGCAGTGGCA CAATCTCGGC TCACTGCAAC
63901 TTCTGCCTCC TGGGTTCAAG CAATTCTCCT GCCTCAGCCT CCCACGCAGC
63951 TGGGATTACA GGCATGCGCC ACCACGCCTG GCTAATTTTT TTGTATTTTT
64001 AGTAGAGACG GGTTTCACCG TGTTGGCCAG GCTGGTCTCG AACTCCTGAC
64051 CTCAGGTAAT CCGCCCGCCT CGGCCTCCCA AAGTGCTGGG ATTACAGGCG
64101 TGATGTTTTG GGCCTTTTAA AGTTCATCTT GTTTGTGTAT TCATTTGTTT
64151 GGGGCCTTTT AAAGTTCTTC TTGTTTGAGG CTTCCTGTCA TTTGAAGGGT
64201 TATCTGGTCA TGTTTTGTTT TCTAAGCTAG TTCCATGAGG ATCATAGATA
64251 TGCTTCTCTG TTAGGCTTGG TTGGCCCTTA AACTTGTCTT CCTTTTGGAC
64301 ACTCACTTAC TTCAGGGGCA GGAGGAAGTG AGGAAGAGGA GTTGGGTCTG
64351 TTTGGAGTAT CAGCATGGAC GGGAAGGGGA GCAAGAGGGA TGGGATGGTA
64401 AAGTAGTGAT GGTAGAAATT CAACTTACTA GACCAGGAGC GTGTGGGCGC
64451 CACCTACTAA AACAAAAAAG GAATAATGAA GAGCTATAGT CAGTAGCTCT
64501 TATAATCTCT TATGGGATAT GTAGGCAAAT ATTTATGTGT CTCTTCGGGG
64551 CTGTTCTGTT TTTAGAAGGT AAATGATTGG TAAGAAAAAA TAGGCCAAAA
64601 AGAGCTAAAT GCTTATGAAT TAGGATTATA GGATTTTCCC CCACTAGTCT
64651 GAATTTAGAA GCTACTTCCA GAGATGTCAA AAATATGTAA TATTCTACTT
64701 TATTCCAAGA TAAATTGAGG GCAACTTATT CTAGAAATAA TTGCAATATT
64751 AAAAATATAA CAATGAATAA ATAGAGAAAT CTAGATGAAA GGAGTATGAG
64801 GATAGGGAAA TAAAGTTAGG GTTGAAAGTA AAAACAAGGA AGTTCCTGTT
64851 AAGTTGCCAA AGGAAGAATG ATTTGGGACT CTCAGTCTCC CAGTGACCAA
64901 AGCAGAAAGG AGAATATAAA CAGTTACAAG AGCCCCAGTC GCATGAAAAA
64951 AAAGTCCAGA ATGCTCTGCT CAGAGGAGAC CCAATTTTCT GAATACTGAG
65001 CCCTGAGGAA TTTCACCACT GGGTTTCCCA TAAATGAGAC CCCCTGTGAC
65051 CTGGTGGGCC CCATCCCTCG GAAGTGTACC CTGGCATTTC CATAGGACTG
65101 CTTCCTTCTG GGCCTCTTAG TGCAAGCCAG CAGTGCAATG CCACATCCAA
65151 GTTTGGTAAA TCAATTCTAA GTGAGATAAA TTAATGCCTT TTTTGGGGGA
65201 AGATGGGAAA CAGAGTGGGT TTGTTGGAGA GCCCATAAAT TGGAGTCTTC
65251 AACCCTTAAA TTCTCACTTG CGGGAAAACC TTTCACAACC AAGCAAACGT
65301 GGAAATGATT TGGCCAAAGA TTCAAAATTA TATTAAACAT CTGGGACTAT
65351 ATTCAGCAGC CAACTTTCTA ATCAATTCTA TGAGTGTGGT GATTGCAGTT
65401 ATGCTCATTT TCTGAGGGTG AAGTTTGGAT AGAACTAAAA AGGGCGGTTG
65451 GCAGGAATCA AAAGAGATGA AAGCCTCAGG ACAAAGAGTT AGAGGCCCAG
65501 GTGGTTCATG ACTGAGAGTT TGGAAATGAT TTCTGGTGTC TCACTTCAGA
65551 GAAATAAAT ATAGCCAACT CTGTTCATCC GTGGTGATGG AACATTCAAC
65601 TACAGCACTG GCAGTTTGGG ATCTAAGACC ACCCTTCCAG CACTTCAAAA
65651 TTCTGACTTA TAAAGGACAC ACACAAAGAA CAGATAGCCA GATAGAGACC
65701 AAAATACCCA CTTTATTCTT GGCAGGGCAA GCACCCAGTA AGCTCTGATG
65751 CAGGGCTCTG GTAAATTTGC CCATCCTACC AACAGAGAAG AATGGTGGCC
65801 TCCCCTCATG AACGGGGTCG GAGGGGGGCC TTGCCACAAC AGGGGGCCTG
65851 ATGGAAATAA GGGGGACAAG AGTGTTCGGT TGGTTGAGTG CCTGCTATGC
65901 CTGTGCCTAG GCAGTAAAAG GGGAAGTTTT AAGTTTGGCC CTTACTTTCA
65951 AGACATAGTA ATTCTACCTT CTAGTAAAAC ATGGCCAAAT AAATGTCTGC
66001 TTTTCATGAG CCAGATAACC TCCTTCTTCT TTATTGGAGG AGTGAGTAGA
66051 AGGGTGAGAC TAGCCGGGTG CGATGTCTCC AACCTGGGCG AAAGAGCAAG
66101 ACTCCATCTC AAAAAAAAAA AAAAAATTA AGAATAAATC TTTTCACTGT
66151 TGGAGAAAAG TTTTGAGAGG CCGAGGTGAG AGGATCACTT GAGGCCAGGA
66201 GTTTGAGACT AGCCTGGGCA ACATAGCAAG ACCCCTGTCT CTATCAAAAA

FIGURE 3Y

```
66251 ATAATAATAA AAAAAGCTAG CTGGGTATGG TGGTGTGCAC CTGTAATCCC
66301 AGCTACTTGG GAGGCTGAGG TGGGAGGATT GCTTGAGCCC AGGAGTTCAA
66351 GCTTATAGTG AACTATGATT GCACCCCTGC ACTCCCTCCT GGGCATCAGA
66401 GTGAGACACT GTCTCTAAAA AAAAAAAGTT GGAGAAAAGG ATACTAAAGA
66451 GATAAAAGGG TACTAAAGAG ATCGGGAAGG CAGCAAAGAA TGAATCTAGT
66501 CTGATGTGTT ATTGGGTGTA CGTAATTCAT GGCGGAAGGT GCTGAAAGGG
66551 AAGGTTGCCT GGGCCTACAG CAAGCAGGTG CTGATGAACT AGCTCCTTTG
66601 CTATTACTTA AATGTGTCCT GGTTGGGCCA GATGTGGTGG CTCACACCTG
66651 TAATCCCAGC ACTTTGGGAG GCCAAGGCGG ACGGATCACT TGAGGTCAGG
66701 AGTTCGAGAC CAGCCTGGCC AACATGGTAA AACCCCGTCT CTACTAAAAA
66751 TACAAAAAAA GTATCCAGGC ATGGTGGCAG GTGCTTGTAA TCCCAGCTAC
66801 TTGGGAGGCT GAAGCATGAG AATTCCTTGA ACCCGGGAGG TGGAGGTTGC
66851 AGTGAGCCGA GATCATGCCA CTGCACTTCC AACCTGGGCA AAAGAGCAAG
66901 ACTGAGTTCT CAAAAAAAAA AAAAAAAAA ATTCCTGGGG AATATCCACC
66951 AGGGTGAAAA ATTGGGTATA TCCAAATTCA GCTTTGCAAA GAAATGCACT
67001 CATGACTAGT TGCAATTTGA AACGTTCCTC TTCTGAGTAT TTCTAGCCTA
67051 TGTAGGTGTT TCACAGATTG CTGAGTACCT AGACTGAGAG GGAGAGAAAA
67101 AAACAAAGTA AAGCTAAAAT GTTAAGAAGT CTGGTTAAAG TGCAATCCAG
67151 AAGTGAGGGA AAGCATCTCT AAAAGTATGA ATCTTTGGGG AAACATAACT
67201 TGATTACCAA AAACTTAATA TTAAGCAGCC TCATAGGAAC ATGGCTTTTG
67251 GGTATGGCGA GAGCCAGCTA GAGCTCACAT CTCCATTGAA ATCCACCACC
67301 AGAGAGGTTA TCTGCCTAGT TGTTGGCAGC CAGACCCTGG CATTGTTTAG
67351 ATTGATTGAT GGAAGGCTAC TTTGGGAATG CTGGCTTCCT TATTCATTGA
67401 CTTTAAAGAC AGCATTGTAA AAATTGATCA CCAGCCCAAA TCAATGTTAC
67451 CCTGAAGTAT TTTTATGACT TTTTGGGGAG GCAAAGAGAT GGGATAATTT
67501 TTGATTTATT TAAGTCTATT GCAAACTGGA ACTCCTTTGT CTTCTTTTTG
67551 AACTACCTTT TTTGTTTTTT TGAGAGAGAG TCTTGCTTTG TTACCCAGAC
67601 TAGAAAGCAG TGATGCAGTC ACAGCTGACT GCAGCCTTGA CCTCCCAGAC
67651 TCCGATGATC CTCCCATCTC TCCCATGTGC ATCACCACAC CCGGCTAATT
67701 TTTTGTATTT TTTGTAGAGA CAGGGTTTTG CCATGTTGCC CAGGCTGGTC
67751 TTGAACTCCT AGACTGAAGT GATCCACCTG CTTTGGCCTC CTAAAATGCT
67801 GGGATTACAA GTGTTAGCCA CCAGGCCCGG TCTTGAACTT CGTATATACA
67851 GTGTGTTGTG TGGGCAAGTC ATGCCTGACC ACTTCCTAGT GGGAGGGGAG
67901 AAACTAGAGG GCTTGCCTGA GGCTTTAGGC AATGTAATCT GTTCTCTTGG
67951 GATCAATTAC TTATGCATAT TTAGTAGCCA GCTCTATTTG CTGATCACCT
68001 AATCTGTTCT CTTCGTTCAT TCCCATGAGA CTTCGATATG GGATATCTTC
68051 CTCTTCTTCC CATTGCAGCC TTTTCTCTCA GAGTTGTTCC CATGATAAGA
68101 ACTCCCATCA AAATCTCTGC TCTAACATCA GTTGTCAGAT TTTGCCACTT
68151 TTTTTTTTTT TTTTTTTCTG AGATGATGGA ATCTCACTCT GCTGCCCAGG
68201 CTGGAGGCAG TGCCACCATC TCGGCTCATT GCAACCTCTG TCTCCCGGGT
68251 TTGAGGGATT CTCCTGCCTC AGCCTCCCGA GTAGCTGAGA TTACAGGAGC
68301 ACCCCACCAC TCCAGGCTAA TTTTTGTATT TTTTTTAGTA GAGATGGGCT
68351 TTCACCATAT TGGCCAGGTT GGTCTCAAAC TCCTGACCTT AAATGATCTG
68401 CCTGTCTCTG CTTCCCAAAG TGCTGGGATT ACAGGTGTGA GCCACTACGC
68451 CCAGCCACAT TTTGTTACTT CTTTCTGTAA CCTGAATGTG GAAAAACTCA
68501 CTGTCTTTCC TCCACTCTCA CACCATAACT GTCAACACCA CAGAAGACTT
68551 CTGTGACCAA ATATGTGGTC ACCACCAAGC AAGCAGTAAG TTCTGCAGTG
68601 GACACCACTA GGCGTCCTCC AGTTCAGTTC TGGCACTATC CGCCTGGAGA
68651 TAGGGCTCAA TCCCACAGGT GGAGGTCTCA GTCCCCAAGA ATGTCCCCTC
68701 TTCAGGCACC AGTTGCAAGT CCAGGCCTCT GGAACTTCTC GCTGACTGGC
68751 TTCAAATTGG GGTTCCTGCA GCCCCCTCTT TGAGTTCAAT TAATTGGCTA
68801 GAGCTGCTCA CAGAACTTGG GAAAACACAT TTACTGGTTT ATTCTAAAGG
68851 ACATTGCAAA GGATAAAGAT GAAGAAATGC ATAGGGCGAG GTATGGGGGA
```

FIGURE 3Z

```
68901 AGGGTTGCGA GCTTCCACGC CCTCCCTGGT CGCCCTCCAG GAACCTCCAC
68951 GTGTTCAGCT ATCCGGAAGC TCTCCAAACT CTGTCCTCTT GGGACCTTTC
69001 ATGGAGACGC CATTGGATAG GCATGATCAA CAACCATGTA GAAATGGGAT
69051 TGCACGAAAA GGCTATGATC TAATCCTCAT AGGCTGAGTG GGGAATCCCA
69101 GCAAGGCCTG TTTGTTCAGA TCCTTCTGTA GCATTCATTC CTCCAGGTTA
69151 TGGGGCAGGA CCCCTTCTGA AATGGGGTCT TCTGACCTAC AATCAGACAA
69201 GGCAGAGGAA ATTTCTTTAT GGCCAGCTCC AAGTCAGAAA GGTGGGGGAA
69251 GATTAGAGTC CTGCCTTGAG CAGATGAAAG GAGGGCTGGA GGAGGTCAGA
69301 GAGAGAGAGA TTCTGTTTTT CAAGGCCTGC TTCTAAAGCC TAAAGCACCC
69351 CTAAATAACA AAAGATTGTA ACAAGGACTA TGGGAGTCAT AAGCCAGGAA
69401 CCGTGGATGA AAACCTATAT ATATGTATAT ATATATCTCA TAATAATTCA
69451 AACCTGTCTC CTGTTAATCC CATCCTCTCT GTTTCTGTTA TCATTTCCTT
69501 AGTGTAGATC TGCCTAAGTG TAGAATTTGT AGAATTTGTC ATGTTGACTA
69551 TTGTAGACTT GTCTTTTAGA GTTTCTAGCA CTAGCCTCTT CCACCCATCA
69601 CTATTGAGAT GATTGTATCC GTCTCAGTAC TGACACTAAC CCAGCACTCT
69651 GGTTTTACAT CTGTCAATCC ATCAAGACTT CACTTTCACT TTCTTCCCTG
69701 CCTCATTATT CACTATGCTC TTGGGCCATT GCTCTGGCTT CTGGGGCTTT
69751 TCTAAAGTAG CACTTTTCCC CACTCCAGCC CATGAAGATA CCTTTTAACC
69801 AGCTCTTGAG ATTAAATCCC CTCCGTGACA CTTTCCTGCA GGAACTTGCA
69851 AAAAAGTACT GCATTCCCCA CTGGCAAAAC TTGCCATCAG CCAGTTTATG
69901 TATTCTCTGC TTTTCACACC CATATCTTGA CCTCTGAACA ACACACATAT
69951 TCTCCTCTTC ATTTATTTCA CAGTTCTGTC TTCATAACAT TGATAAGTAT
70001 GATCACATTA GCGCTCTAGA TTTTAAGCAA CTGGAAGATA GCTATTTTTT
70051 TGGTACTCTT CCTTTAAATT TGAACATAGT GTCTAATTAG TCAATTAACA
70101 TTTTTTTAAA AGGGCGAGGG ACATCATGGT AGAGAGAACG AAGTTGAACG
70151 TGTTTTTGGT TGAATATTAG CGCATGCCCA CTGTATTCTA GGCACAGTCC
70201 TGATTCATTA TATCATCACA CAATAATTAT TTATGTGCCT TCATCCTTTA
70251 TGACACAGTG CTGGCTCTTA TTCATCTCCC ATTTCTGCAA TCCATGGTGA
70301 TGATTAAAAG TCTTAGGAGT TTTACGAGGC TCAGTATTTT TTTTTTTTAA
70351 TATGCTAGTT CTTCATGAAT ACATTGGGTA CTCTGAAGCA TATCATTTCC
70401 TGGGTTTCCT GAAGTGGTAT GTTGCGTGGA ATGGCACATT AGGTCTAAAT
70451 AATTATCCCC TATGTAAGGT TCTTGTTTTT CATTCATTCT CTTAAAAAAT
70501 AGATATTAAA CATTAAATAA GGACAGCCAG GTATTGTTTG AGGTGTTAGT
70551 GGGCTATGCT AAAAAATCAA AGGTGGGAAT GAGGCAGCTG GAGCTCAAAG
70601 GAGCATGTTA GAAGGAGTCC CAAGAGGACA AATCCATTTG GTTCTTCTTT
70651 CCTTGTTTTT TTTCGAATAT TTTTGAGGAT GATAATTTTT TTCCCCTCAA
70701 AAGCTTTTAA TGAATGTTAG GATTAAAAAA GAGAGAGAGA GAATTTATAG
70751 AAGAGAAATT AACTATAGCT CCTAAAATAG CTCTTTGTTT CTGAAAGCCT
70801 TGATTCTGCT ATCTATTTTA TAACTGAAAC AAAAACAAAA ACAAAAACAA
70851 AAAACAACCT CAAGAAGTTA CTTGTATAGC CTCTGCCACT AAGGAGACTG
70901 TGTTCTGATG TTACCTCAAA CAGGCTGATT TATTAAAATA TTTAAAAATA
70951 TATATGGAAA TATTTTTTTC TATTTTTTTT TTTAGTGGCT TTTCCCAGTG
71001 AACAATAGGT CTTACTATAT GATTTCTTAT TTGTCATTAG TGAATGTGGT
71051 GGGTATGTGG CAGCTGGGGG AGCTGATGAT TTTATAATAC TGTATCAGAA
71101 ATGATTAGTG TAGGTACTTA TTAACATATT TCTCAGACAG AACAATCTTG
71151 ACTTTTAAAA CCTCTTCATT TAATTCAAAC ATCAAGTACC CTGTTTGTGG
71201 CCTGTGTTAT GTTAGGTGCT CTCTTTACAA GACCTATTTT CTTGCTATTT
71251 AATTATATAT TTGCTTAGCA AATATTTACT CTGCACCTAC TAGGTACCTG
71301 GCACTGTGCT GTGTACTGAG GTGCCATGTG TACCTCCATC AACATAGACT
71351 CAAGATCAAT ATGATTTCAG TGAACTAAAA ATACCTTTAT TGAAGCAAAA
71401 AAAAATCACA TTTTGTAAGG ATCAAAAAAG AGACATTTTA TATAAGGTAC
71451 AAGAAATAGA AGAATTATAT CCCCAAGATA TATGTGATAA CATACTTGTT
71501 AGTTTTTGGA CGTGACCAGA TTTTACACAA TCCTTAAAAA ATGCAGCAAC
```

FIGURE 3AA

```
71551 CAGATTTTAA AGTAGTTCTC TAATCTCTCT TTCTGTGCCC CATTAGATGT
71601 ATATTGGATC TTCTCATTCT GTCTTTGTCT TTTGACCTCT CATGTTTTCC
71651 GTCTCTTTGT CTCTGTGTGT TGCATTGTAC ACAAATGCTT CTTGAACTGT
71701 GGTGTGCACA TGAATCACCT GGGGACCTTG TTACAACGTA GGTTCTGATT
71751 CCATGGGTAT GGGGCAGGGC CTGAGATTCT TAGAGAATTA AATTCTAACC
71801 AGCTCCTGAG TGGTGGTGAT AATGCCAGTG TGTAGACCAT AGCTTAAGTA
71851 TCAAGGTTCT ATGTGATTCC CTCAGATCTA ACTGCTAGTT CACTAAGTTT
71901 CTCTTCAGCT GTATCTAGTC TGCTATTTAA CATATTCAGT GAATTTTTAA
71951 CCTTAAATTC AAGAACAAGA CTTTTTATTT CTGGAAGTTC AGTTTGGTTC
72001 CTTTCAAATG TACCTGGTTC TTTTTCAAAG TGTCATGTTC TTTGATAAGA
72051 ATTTCTACTA ATTTACCTTG ATAATAAAAA TTTGTTTCAT GGCTCATTTT
72101 AGATTGTTCT TTTATCTGCA GTTTTTGGAG GGCTAATTCT CCCATTTCTT
72151 GTATCTGTTG TTGCACCCGT AAGGTGTAGT TGTTGATTTT TACTTTTTAA
72201 TTGTGAATTT ATTTCTGGTA GGGATTGGAA GGAGGTTGTT GGGGTGGGGG
72251 TGGGGTGGGG AGAAAATCCT GTGTGCCCTG GGTTGCAAAA ACACCCCTAC
72301 AAGTTGTTCT CCACTTGCAT CTGCCAGTGC TCCAAGGGCT CAGTGATCCT
72351 GGACCAGTAG TCATGATAAT TTCTTGAATT GTAACAGGAT ACTGTAAATG
72401 TGGACACTCT ACCTGAGGTT ACTGCTTCTT TCTATCTGCT TTATTTCCTT
72451 CCCACTGAAG GGCCCTGGAC AAGGGTAAAC ATCTCATCAC TTTCTGGGTG
72501 GCAGAATATT TCCAGTTCCC CCACTTCTTT TTGGCTTAAG GCTGTGGCTT
72551 TTTCCTCTGC CTGAATGTGG CCCTAAGAAG CCCTTCTTTT CAAACTTTCC
72601 TGTTGTACTT GACCGACTAG CTGTCTAGAG GTTTATATCC CTAGCTTTTA
72651 ATCTTTGCTG TGAATATCTT ACCTGTTACC AGCTAGTATA TTTCACATTG
72701 ACTTCTCTTT CCTTTTTTTT TTTTTTTTTT TTTTTGAGAC GGTGTTTCGC
72751 TCTTGTTCCC CAGGCTGGAG TGCAGTGGCA CGATCTTGGC TCACTGCAAC
72801 CTCCACCTCC CAGGTTCAAG CGATTCTCTT GCCTCAGCCT CCCAAGTAGC
72851 TGGGACTACA GGCATGCACC ATCACATCTG GCTAATTTTT TTGTATTTTT
72901 AATAGAGATG GGGTTTTACC ATGTTGGCCA GGCTGGCCTT GAACTCCTGA
72951 CCTCAGGTGA TCCACCTGCC TCGCCCTCCC AAGGTGCTGG GATTACAGGC
73001 ATGAGCCACT GTGCCTGGCC TACTTCTTCT TCCTTTTAAC TTGAAGATTA
73051 TCTGCCCCTT TTTCTAATCT TAACCGCATT AAGCTGGCTT TGAGCATGGC
73101 AAGAGTTTTA TAGATGAATC TTATTTTATA GTACAGGATT TCAAAATCAT
73151 AATTATTTCA CTGAGGGTGG CTTTTACCCT CCATTAATTA TACTTCTCAC
73201 TCAGAAATGG AATTCTATTT TGGTCTCCTA AAGATAAATT AGTATATAGT
73251 GGAAAGGAAT TATAAAGTTC TGCTAGGAAT TAAATGATAT GATTAACACA
73301 AACATCCACA TGGATGTGTC TCTGCCCTGT GCAGGAAAGA TGAACATTCA
73351 GTACAGATTC TGCTCTATGT CACTAGCTTT CAAGACCTGC AGGTTCTCTC
73401 CTAAGCATGC AATTCCTGTG AGCAGTAGCA ATAATAGCAG GTCATATTTG
73451 TGGAGTGATT ACTGTATGCT AAGAACTGTG GTAAACACTT TTATATGGAT
73501 TATTTTATTT AAACCTCCTA ATAGTCCATT GAAATAGATA TTGCCATGTT
73551 GAAAACTGAG GTTCAGAGAG GTTAAGTGAC TTACCCAGTG TCACAGAACT
73601 AGTAAGTGGT GCAGCTGGGA TTTGAACTGA GATTCCAGAA CAATTGCCAT
73651 TAACCACTTT GCTTCCATAT TAGTATCATC TGCAAATCTC TCTCCATAAA
73701 TTTCCTCAGT CTTTATCTGA GTTCCTTAT TTCAGGAAGG AAAACTTCTG
73751 TTTTTGATCC TTATGAAATA CAATTTCCAT TAAAACTTTT TTTTTTTGCT
73801 ATTAAAAAAG GTACCGGATA ATTGAAACCA GACTGGATTT GAGCCTGTGT
73851 TGATGGAAGT ACACATGGGA TGTGGGCTGA AGTGTTCAAT CTAATTTTTC
73901 TTTCCATCAG CTAATTTTTA AAGTATTAAG CAAGTAGATT CTGACACTAA
73951 CAGGGAAGAT TTAAATTCTC TTGAGAGACT GGAGGTGTTA AATAATTTTC
74001 TGGTAGTGCA CATTTTACAT CTTAAATCTT CCTCACTCTC CCACCTCATC
74051 TCAATGTACC TGAAGCTCTG GGAATGTTCT TTTGTACTTC TCAGGAACAG
74101 CCAGACCTCT GGCTTCATCT CCTCTCCCCT CCACATCCCT TTCCTGCTCC
74151 AATTACTTCC CAGCGCCACT TGGATGTTGT TGTCATCGGG GAACTTTGGA
```

FIGURE 3BB

```
74201 AACAGCCAGA TTTTTTTGGA GTCTGTAAGC AGAAAACAGA CTGCTTGCTG
74251 CTCATATCTG GCACCCAGCT TTGTCCAGAA AACGAGGAGT TAAAAAGAAG
74301 TCTGGGCTGT GAAGGGCTGT GACAACTGTC CTAGGGGGAG CTCTAGCGAG
74351 CCCTGGCGGG CAGTGACTCA TGCTGCTCTG TCACTGGGAT CAGCACTGGC
74401 CCCTGGCAGG CAGGCGGCAG CCAGGTGGGG TTCCAGCCAG AGCACGCACG
74451 CACGGAGCCG GGAGCATGCA GCCTGCACTG CGGGGGATGT GATGCTCGGC
74501 TCTAACTCGC CTGGCTGGCC CGCCACGGAC GCCTCAGCTT GCAACCATGG
74551 TAACGTTTCT GGCGGGGGAC ACCCCGGGA GCCCACCGCG ATGGGCAGCC
74601 TCCTGGTGAC TGATGGACGA GTGTCCACCT CCCAGACCGA GAGCGCTTAG
74651 TAGGTCGGAG GAAGTGGAGA GGATGTAACA CGCCCCAGC CGGGAGTGAA
74701 GCCCTGAGGA GGTAGGAGCC GCATATGTCC ATCCGTGCAT TCCCACCGTC
74751 AGCGCGCAGG GGTGCTGTAG ATCACCGGTA GGAACTTTAT TTGGCTGGTG
74801 CTTCATTATG CTGATTAAAC TGCAGTGGAT TTGATGGGCA TGATTGCGCT
74851 GGGGAAGATG CATAATGAAC TAAAAAAAAA AAAAAGTGGT TAATAAGATC
74901 TCGGAGTCGA CTTGTCCGGG TATGAATGAA GTAGACTGCA GTGGTATCCT
74951 AACAGGAGTT CCAGAACCTC ACACATCCCT TTTCCTGGTC CTTCCTCTTA
75001 TCCCGGTTAA TCCACGAAAT GTAGAAGTTC CATCTTATTT CAACGATTAG
75051 TGCTAATCAT TAATAATTTA GACCTGTCTG GAGGAGGGAA TCCATAGGTT
75101 TAGGTCTCCT AGCATCCTGG CACTAGCCAG CAGCTGCTCT GTAGGAGCCT
75151 TCTGGAAACA GCAGGAAGGA GCGGCTTCCC CACGAGTTCC CCAAGTGCTT
75201 TCGTTGGCCC AAGTGCTTTC GTTGGCCCAA GTGACCTGTT TGAGTTTGCT
75251 CTTCAGTTTA CCCCAGGCGG GAAGGCAGCC TGTCTGCGGG TTGGTGGCCA
75301 TGTTGGCAGA GAAGGGGTTA ATCTCTTGTT GCTGTAGGAG CCGAGGTTGC
75351 GAGCTAGATT GAAAGCAGGC GCTGCAGTGC CATCGCCAGC GCCGAAGGAG
75401 TAAGACGATC TTCTCCGCAA CAGTGTTGAA TCCGGCTGAA ATTTTTTTTC
75451 CTCCCCGCCT CCTTTCTTGT TTTTCTTTAA CCAGCTCCTC CCCCCTTCGT
75501 TCCCACCCTC AAGTCTGACG ATGACACCTC CAATTTTGAT GAACCAGAGA
75551 AGAATTCGTG GGTTTCATCC TCTCCGTGCC AGCTGAGCCC CTCAGGCTTC
75601 TCGGGTGAAG AACTGCCGTT TGTGGGGTTT TCGTACAGCA AGGCACTGGG
75651 GATTCTTGGT AGATCTGAGT AAGTGAAAAT TTGACTTTCT AAAGGGACCT
75701 GCATTGATGC AAGGCTTTTG GAGCCAAAGG TGGTGGTGGG GGGGTGGGGG
75751 AATAGGTGGG GGGAGTGCAG TGGAGGGAAG CTGCTAGTCA CCTGCATTGG
75801 GAAAGCAGTC TACCTGTTAG GGCTTTGCGG GGGTAGCCTG TTAATATTCT
75851 CATTTTGCAG TGTGTAAGGT ACCTGTTCCT GTCTGTGGTA TGATAATTGT
75901 CAATTGGGTA CTTTGGGTTA GTTTTCCAAT CTTTGGTCTT CTTTAAAGGG
75951 GAGAGAGTGG GAGATTTCCA GCAGTGCAGA TCCCCGGTCA AAGGAGAAAT
76001 GTGCAGGAGT TAAGATGAGC TGCCCATCTA TCTAACCATC TATGTATCTG
76051 TCTCTCAAGT GGGTGGATGG GGGTTGCTAT CTTGGCTGTA TAAAGAATCC
76101 TAAAAACCTT GTCTCATAAG CTAGAGGTTT CCTGATGGGT TTAACTGAGC
76151 TGCAAGTGGC TGAACCAGAG CTCTAACAGA GAGATGGTGC TCGGCTCCTC
76201 TCCAAGTATG CTGCAAGATC AGGGATCTGG CAGCTGAGCC TCTCTGAGCT
76251 GGTGGAGCGC TGGCAGCCAG AGAAAGCCCC GTTACTGTGA GCCACCAGGA
76301 GGGAGTGTGA TGTAGCCGAG TCATTGATTC ACAGAAACTG GGCTTCATAG
76351 GGGGAAAAAA AACCAGGAGA CTAGAAAATG GAAATATAAA TATCACTGTA
76401 AACCTCTTGA TCTGGTAGGT CTTTCTCCAT TCTCATAAAA GCTATTGAAA
76451 AATGCATTAA CAGAGCACTT GGAATTAGAG GGTCGAGGCT TCCAGGAGCC
76501 TCCTGGAATT TCTGTAAAAT GCAGTAGCTT CTGTGGATGT GGGAGGTCAG
76551 TATCTTGCCT CATTCTCTCA TGATACAATG ACATTCTGTT TTCAGAGGAG
76601 TGAGTTCCCC AGAAGATCTT GGACTGATGG TGTTATTTGC CAGCCACCCT
76651 GGTCCCTGCA CTTTCAGGTT CTCAGAGGGT AATGTTGGGT TAGTTGCTGC
76701 CCACTTAGGA GACGAGCAGA ATTTGATATT CTTCTTGGCA GCATCTTTCC
76751 CTCTTTGTGG TATTTGTAGC TTAGATATCG ATTTATAGGG ATGTTATGTT
76801 GGTTCCTGGA TGGTGTCTCC CTATGGGTGC TATTTTGACA GTAACGTTCC
```

FIGURE 3CC

```
76851 TGAAAAGATT TCAGAGTGTT GTGGGGAATT GGGCATTTGA TACGAAATAA
76901 GGTTGTGGGC TGTGATTGAA TGTGAGGGAG GTTTTTATGT TGCAAGATGT
76951 TGAAGTGGTC TTTCTTGATC CCCTCTCTGG GGGCTGGGTT TCAAATTCAG
77001 GTTGGATTTT GGTAGTGTTA GATGTGCCTC TCTGTCTGAT TTGCTCCACA
77051 ACCCCAAAGC AATCTGGATG GTGGTGGGAG AGGCAGAGTG CTAACTAGCT
77101 GTTGAATGTG CCATCAGATG GGTTTGAAAC GGCTCAGCAG GATTGGGAGG
77151 TTTTGCCATT GGCATCAAAG AGCAGGGCAG AAGCGGAGGC CTGATGTTGA
77201 AGGATGCATG GTTAGTGGGC AGTATAACCT TGACACACGC AGCACACTGA
77251 AGGTCACACG TCGTACTGGA AGGACGTGTG GAGAGTTCTA GTTCTGGTTA
77301 GCAGTGGGCT GGCTGGGTCA GAATGCAAGC TTGCTTGGGT GTTGGTCAGT
77351 GATCTGAAAG ACGAGGGAGG ATTCGAGGGA GTTAGATTTC AGGGGAAAAG
77401 GCAGAATGAT ATGGGAGATC TTAGGCATTG CAATTAATCT GAAGCAGTGT
77451 GTGATTAATT GCTTATTTTT CAGGAAGACT TGAATGACAT CTTTCTGTTT
77501 CTCACAGAAA GCTCAGTTTA GGGAGCTCTC TGACAGGGAC ATCTCAGTAT
77551 TAAGGCTGAG GCACTCGATA AATATTTGTT GATTTAATTT ACCTATGATC
77601 CTTTCCTCCA GAAGTGTTTA TATTGCTTAT TGTATTTGAA GATGTGCTAT
77651 CTCACCTCTG GTAGTTTAAA CTATATCCTT AGAGCACAAA ACGAGCTGCT
77701 GTTCCTGACC CAACAGAATG TTTAATAAGA TTCTTATTTC AAAAAAGGTC
77751 CATGCAAATA AAACTGTGTA TTTCTTATTT GGACGATGGC ATCAGAGTAT
77801 TCCTATCATT GGGGAACTTT AACGTTTTTT CAAAGCTTGG CAACGGGGTT
77851 GGAATCAGAA AGATTTTCTT TCATCTTGCG TCTTGTTATG TGTTATTGCT
77901 ATTGGACTTG GCTACTCTGC TGTAGGCAGC CCTGTGGGTG ATACCTACAA
77951 GCATCATTTT AGAAATTCAT CCACCTGTTG GATGTAGATG ACCCTGGACA
78001 TATCAGATTG TGATTAATTA GAAATCTAAT AAAAGAGAGG CAGTGATGAA
78051 ATTACTTAGC AGCTCCTGCA GTTTTATTGA CAAAATTTAC TTGGAGAGAG
78101 GGGGAGACAT TTTCTGGGGG TACCACCTTT GCTGCCAGCG ACCCTGTGTT
78151 TCTTCCTGAG TTTCTTTTTC TTTTCTCACC ATTTTCAGCA TCACAGGTTT
78201 TTATTTACAC ACATTGATTA CCTGTGCTGT TACTCATTCT TCACACCACT
78251 GAGGAAATTG CAGATGCTGC TGTACTGTGC TAGGTAAATT GACCTCAGAT
78301 TTGTTACCAG TGAATTGAAT GAAATGTTCA GAGGTGGAGC TGAATGAACG
78351 AGGAGTTTTT GTGGAGAAAT TGGCAGTGAG AATGATTTAA ATTCTGTGAT
78401 AGCTCCTCGT TTTTTGGGAT CCTTATTTTG GGACCCCAGA CTATTTTTAA
78451 GCCATTGAGT GCATCATTAT TTTAGGCTGA GCAAGAATCT TGATGACAGC
78501 GTTTCAATGG CTGAGGCGTA GTGGGAGTTC CTTGCAGCTT GAGTTGGTGG
78551 GAGCTGGAGA GTTTCTAGAG AACTAGGTTT GGTTGTCTTT GGGGTGGGGT
78601 TATGGTGAAA TTAGTCTTGG AGAGTGAGTA GCTGTCTGAT GCTTCTTTTC
78651 CTTTTTAACC AGCAAGAGCC CAAACCAAAT CCCCAAGCTC TGAATGCCTG
78701 GCTGTTCCTC TCAGCCTTTC TTTGCTTGAA CTTGACAATA GTAGGGTAGT
78751 AACAGGAAAC AGCATGTTAA AGTTTTAAAA ATAAAATAGA TCTCAGCTCT
78801 TTTCCTTCCC ATTAGCAAGG GGTACATTTA TTTAGGTTTT TCCTTCTAGA
78851 TTGAGGCACT GCCTCATTTA AGTTCTTGGT GAAGCCATGC ATTTCTGCAA
78901 ACCATAAGTA TAAACTCTAG AACGGGGGTG TCCAATCTTT TGGCTTCCTT
78951 GGGCCACATG GGAAGAAGAA GAATTGTCTT GAGGCACACA TAAAATACAC
79001 TAATGATAGC TGATGAGCTA AAAAAAAAAA AAAACTCATA AAGTTTTAAG
79051 AAAGCTTACA AACTTGTAAG TTTTGAGCCA CATTAAAAAC CATCCTGGGC
79101 TGCATGCAGC CCCCGGGGCC TTGGGTTGGA CAAGCTTGCT GTAGAAGGTA
79151 AAAATCAGTT GGTTTTATGT TTTTGTTTTA AACATGCTGG TTGTATGCTT
79201 TTGGAAGAGT TGGGGAACAC TGAGGGTAAT GGGATCTTGA TGGGGCTGGA
79251 ATTTGTGGGA AGATGGTGTC TGGGTAGGCT GTTTTTAGGA AGGGGCACTC
79301 TCTTCCTTTT GATTCAGAGA TTTTTCCTTT CTTTTCGGGT GGTTCTGAAA
79351 ACACAGCGAT GGATCCAGGC ATTCAAACAC CATGGAGGAA GGAAGAGTGG
79401 CTGTTGCCAT TGCTTCCCGA GTTTTCTGGG AACCAGTTTT TGGTGCCTCT
79451 TCCTTGCTCT ACTGGGGCTT CTCTGCATGT CAGTTTCTTC AACTGCGAAG
```

FIGURE 3DD

```
79501 TGGAAGGACA GCGATACTTT TCTTACAGGA CTTTTGCGGG GATGGATGAA
79551 ATACGTAAAA CACTTGGTCT AGTACCTGGC ACATGGAAAA GCCTTGGTAA
79601 ATGTTCACTG TTGTTATTTT TGTTATTACT AATACACTAG TCCATGTATG
79651 TATAGTGTCC TCCTATACAC ACCAAGAGAA TATGGAAAGG ACTCAGCAAT
79701 GATTAGGTAG TCCAAAGTCA TACCAGATTG GAAACCAAGC TTCCCAGGCC
79751 CTGGGACTTT TCTGCTAGAG ACACTTCACG GTTCTGACCA ACTACAAAGA
79801 GTTAATATGC AGTTGCCAAA TACCTGTTGG TAAAAGGTGG ATGTTGGGGA
79851 GGAGTGGATT GGGGAACAGA ATTAGAAGGT CCAGTCCCAG AATGGGTACC
79901 TTCCCATCAA GTTGAACAAG TCAAAACAGG TTATGTTGAA ACAACTGAGA
79951 GAAAGTAAAG CAAACACCAT TGCTGCAGAA TATCATGGTA CAAATTGGAC
80001 ATCTTTGGGA GTTAGCGGAG TAAGGCAAAA TCCAGTGAGG GACGCTTAAT
80051 GGGTAATGCC AATTCACAAT TCTTGTTAAA TTACATTGCT GATCTTCCTT
80101 GGAATGTCTG TCCATTCCCC CAAGTAGACT GTGATCTCAA GGCAAGGCTG
80151 GGTCTTATTC ATCCTGGTTT TCCTGGAGCA GTAAATACTT GTGCTGGGAC
80201 TGGGCTTATA AGCATACTAA TGGAAAGTAA AATATTTGGG TTGGTTTTTT
80251 AAAAAGACAG TGGATTTGGA TCAGTGGAGA GGAAGGTAGA GGGAATTTCA
80301 GGTGGGCAGG GTGCTAACAA CAGCCCATCC TTACAGGGCA CCAACTGTGT
80351 TCTAGGCTGT GTTCCAACCA CTTTACACAG ATGAATTCAT TTAAATTGCA
80401 CAACCAGCCC AAGAGGAAGG TACCATTATT ATTCTCATTT TGGATGTGAG
80451 GAAACTGAGG CGTGGGGAGA TCAAACAACT TGCCTAAAGT TATGTAGCTT
80501 TGAGTGGCTT AGCTGAGATT TGAACCCTGT GGGTATAAAC GCCACAGATG
80551 GGAAATTTGT GTGGGGTACC CAGGTTCATG TGCTTGTTAG AAGTGGAAGC
80601 TATTTGTAGA GAATCACGAA TGATGAGGTT GGGGCAGGGT GTGATGGGAG
80651 CTGACAGGCA GGTCTAAATG CTGGGATTCA TTTTCAGTCT CTGTGTTTAT
80701 TGAGTAGGTA GACGGATAG CTCTTGGATT TCTCAGATTT TTTCCTCTTT
80751 TCATTTAGAG ACTCTTATCT GGTGTGTGTG TGCCCGCACA CATACATAAA
80801 CCCACGCGTA TATACTCTTT CCCTGAATGT TCTTATTTGC TAAAGCTTAA
80851 GCTTGGCAAA GAGAGGAAAC TGCACTGACC TTACTCTCCA CCATATCTTC
80901 AGGCTGATCA TACACAAGTT GCTTAATAAG CATTTGGTTA ATCCATCTAA
80951 ATCATTCTTA TGGCTGCAAC TCTCATTTTG TTGATGACTC TACTATCTAT
81001 GTCTATTCAC ATCTACATTT TGTACTTTTG TTTGCCTCCC ATCTGTCCTG
81051 GGATGGCTGA TACCAGTGGA AGACAGCCTG AACTCTCCAA TCAGTCCTGT
81101 TTCCTTTTTA TGAAATACTT GGAGGTTGGA GGATCTTCCC TTAAAAAGTG
81151 TTTTCCTTTC TACATCCAGC CAAAGGCTCT TGGTCCTTGT GCTTGCTACC
81201 TAGATCCCTA TTGGAAAGAG TCTTGCCTGC AATTTGATTT TTTAAATAGC
81251 AGCAATAACA GAGTCGTCTC TGCTACACGA AGACATGCAT CTGCTGTATT
81301 TCCCAGACAA GTTCAAAAAC CTTAACTAGC TTCTGCCCAT GGTTATTGCT
81351 CTCAAGTGCC TTGTGTTGTT CCCATCCCCT CATTATCTGG ATTAGATGTT
81401 TAACATTTGC CTGTGTGTGT TGTGTTGGAT TTTCTCCTCT CCTCTTGCTC
81451 ATTCAATTTC TTCCTTCTCT TAGCCAAGCA CAGCTTGTTC TCCTACTTGC
81501 CTTATTCTGT TCTCTATTTA GACTGTGCGT GCCTGCCTTG CAGCCCTGGC
81551 AGGACCATTC CACCGCCTTC TCATTTGTCT TAAAGATACC TTTAGGAAAT
81601 CTAATCCAGA CAATCCTAGC CCAGTCCTGA AGATTAGGCT CCAGAAGATC
81651 TGTCAAGTGT GTTTTTTGCT GGCCTACACA TGCTAATTTG CATGGTTGCC
81701 TGGGATCCCT TAAGAAGACA GTCATTGACT AAATGGCGCT ACATGTTCCC
81751 AAGCTCTGCG CCAGTCTGGC AACTCTTCCT TTGTCTACGT GAATTTCTCC
81801 TAGTTCTTTC TGCTTTGCTT GCTGTTCATC TCCTGACCTC TCTCCGACAA
81851 ACTTCCTGAA AGAAGAGCCT GCACTCAACA CCTCTTTTTT CCACCTCTTC
81901 AACAATACTG AAATGACTGT CTCAGAAGCC GTTGATTGTA CCTAACCACC
81951 AAATCTGGTG ATTTCCATCT CACCACGTGA TACCATTAAT ACTACCTTTC
82001 TTCGAGACAA CGTTCTACTT TCTTCTCTTC TGTATTATGG ACACTTGGTT
82051 TCCCTCCTAC CTCTCTGACT GTCATTCTCA CTCTTTTGTG GCTGCCATCA
82101 GGCTCTTGCA ATGTACGTAC CATCTCCTCA AGTTCCATCC TCAGTTATCT
```

FIGURE 3EE

```
82151 TTCTAGTTGG TTCTTGGTGA TCTCATTCAG TTCCTTGACT TTAGTTCTTA
82201 CCTCCCCATG GCCTCCTCCC ATCGTACACT GTGTTCCTCA TCACCAGGAT
82251 GTTTTACCAG TTTCTCACCA TCCCATCCTC TGTTCCCTTC CTACATAGAC
82301 AGACCCACTC GCTCACTCAG TAAGCCACTA GGTGCTAGTT TTGGCTTCTT
82351 CATTTTATGT AAGAAACTAC CACCTTCCCT ACCCTTCTAG GCAAGAAAGC
82401 TGAGTCATCG TAAATTCTTT TCTGCCTCCC CCGCCATCCC ATCAGTTGCC
82451 AATTTCTCCA AGTGGTGCCT CTAGGATGCC ACTTGCATCC ATACCCATCT
82501 TTCTTCCTCA TTGGCACCCA TCATGGACTC TTGCTTGGTC TGGTGCAGTA
82551 GCCTCCTCAG TGATTCCCTT GCCTCTGGTT TTCCTGGCTG TAATCCATTC
82601 TCCACAAAGG GTGGAATTCT TCCAAAGCAT AGGTTGGATG ATGTCATTCA
82651 CCGGCTTACA CCTTCAACAG CATCCCAGTG TGCTCATAAT TAATGGCTGC
82701 TCCTGAACTT GGTATTCAGT CTTGGTATGC CAAGACCCCA GCCTGCCGGC
82751 TCATTTGTGT CTCCTCATCC CCTACTGAAT CACTTCAATA GTGTTGTCTG
82801 GCCAAGCTGT TCAAGGCTCA TTAAGGACAG GACCAGGTCT TCCTTCTTTT
82851 GCCTGAAACA GTGCCTTGCC CCTGGCAGGT CTTCAATGAA CATTTGTTGA
82901 ATTGAATTAG ACTAAAATGG CCAGGGATTA TACCAATTCC TTCTGCACAG
82951 TGTAGACAAC TGCTAATGGA ACCTGTTTTC TGTAGAGCAC TTCTTGTGTT
83001 CCCAGAACTA TGCGAGTACT TTATGTGCAT TATCTCATTA AATCATCACA
83051 ATCTCACTGT AACTCTATGA GGTAGCTGAT ATTATCCCCA TTTTACAAAT
83101 GAAGACACTG ATTCAGGAAG ATTAGATTAT TTTCCTGAGG TTCTGAAGGT
83151 AGAAACACAT CTAAGACTTG GAGCAATATC TGGTTGCCTC TAGACCACTG
83201 TACTATCTAC CCTGCCTCTA AGAGCCATGA CTTTGCTAGA TTATGCAGGA
83251 GTTATGGACT TGTCTAATAG TAAAGGTAAA AGAATTGGTT TTAATGAGAA
83301 TCTACTCTTC TAGGTACTAT TCTGAGTGCC TGACAAGCAT TCTCATGTAG
83351 ACCCAGCAAT AACTCATTAT TTTACAGATA GAGAAAATGA TGATCATGAT
83401 GCTTGGGTTA CTTCTTAGGT TCACTCAGCT CACATCTGGC AGAGGGTGGT
83451 CAACTTTTCC AAGTTTTAAC TTATTTATTT ATTTATTTTG AGACAGAGTC
83501 TCATTCTGTT GCCCACGCTG GAGTACGGTG ACACAATCTC AGCTTATTGC
83551 AACCTCCGCC TCCCAGGTTC AAGCGATTCT TGTGCCTCAG CCTCCCGTGT
83601 AGCTGGGATT ACAGGTGCCT GCCACCACGC CCAGCTAATT TTGTTTTTGT
83651 ATTTTTAGTA GAGGCTGGGT TTCACCATGT TGGCCAGGCC TGTCTTGAAC
83701 TCCTGACCTC AAGTGATCTG CCAGCCTCGG CCTCCCAAAG TGTTGTGATT
83751 ACAGATGTGA GCCACCACGC CTGGCTCAAC TTTTAACTTT AGAACTGATA
83801 TAAACATGCC TATTTTTTTG GGACTGACTG TAGCATACCC ATTCAAAGTC
83851 CAGGCTTTGG AATCAGACAG ACGTGGGCTG AACTCAGGGT TTCACCCCTT
83901 GCTTGTTGTG TGAATGAGAC ATTTCACTGC TTTCAGCCTC AATTCCCTCA
83951 TCTGTAAAGT GGAAGGTGTA AGGTCGCCTA TCTGATAGGT TTGCCATGGG
84001 GATATGAAGC ACACTTAGTG TTGGTGCCAT GAGTAGAATG AGTGTTCATT
84051 TCATATTTGT TAATGTTATT TAGGTCCGAG GATGGGTATG GGGTGCTTTG
84101 GACTCTCTTT TTCTCCCTGC TTCCGCCTTA TAAAGACATC TTGCTGGTTT
84151 CTGCCCATTG AGAGAATCCA GCTCCACGTG GGGGGCCTGA CAGATGTCCT
84201 AATATCTCCA TCCAATTTTT TACTCTGAAT GGAGTCTGTG ATGTATCACT
84251 TCAACCTGCA CTTTCTATAA AATGCTCTCC AGGCTTCTGG TAGGATCCAG
84301 TGCCAGTGGG AAGTGTGCAT GTTCCCAGCC TAGATGTCAC ATGCTCCCAC
84351 CCACCCTGGA AGCACTTGGG TATCCCCTGG ATGGGTAAGT CTGTGTGTCA
84401 TTGTGCCATT CCTGTCTCAG AACCAATGCT GGGCATCTCT ACTTGCAGGT
84451 GCTGGAAAGC TTTTTCATGC CAGCATACAT GCAGCACACT TCTCATTTTG
84501 GATTCCTTTA TCCCACGGTG ACCTTTAAAC TGGCTGCCTG GGGGCACAGA
84551 AGTACTAGCA CACCATTCAC TTATTTATTC ATTCATTCAT TCATTCATTC
84601 ATTCACTCAA CAAATATATT GTTCTAGTCC TTAAGGCACA ACTCTGAGCA
84651 AGACAGGTAA GGTCTTTACT CTCAAGAAGC TAGCATTTGG TGGGGAGAAA
84701 CAAAGGAGAA ATAACTACTG TGCACATGTG AGGCAATTGC AGATGGTGGT
84751 CTGCAGAATT GGGATTGAGA CTGCCTGGGG GTGGCCACTT TAGACTGGGT
```

FIGURE 3FF

```
84801 CCGCAAGGAA AGGTTCTCTG AGCTGAGCAT GAGTATTTGT TCAAGAAGGC
84851 TGAGTTGCAT CCCAAGGTGA CACAGCTTTT AAGCCCACAC TGAGCAGCTC
84901 TGAGGTCCTA GGGGCTGTTC GAGAACCTGG GATATAGCAC TGACTATGAG
84951 ACAAAAATCC CTGTCTTCAT GGAGCTTACA TGATGGGGGC AGATTCACAT
85001 TCATTCATTT GTTCATTAAT TCATTAATTC ATTCAGCTAT TTGAGAGCCT
85051 ACTATGTGCC AAGCACTTTC TAGGCACTGG AGAAGTAACA GTGAATGCAA
85101 AGGAGCAAGC ATCCCTGCCC ACACAGAGTG CATTCTTCCA GAATATCAAT
85151 AAGGAGTCGG TTAGCAAAAA TAAGTGGGAA GAGTATTCCA GAGAGAGGAA
85201 AAAAGGGCAA AGGCCCTGAG GCTGCCACTA ACCTATGGGT GCTCAATGAA
85251 CAGAAGGCAT GTTTGGGTAG GGGGTACTTA AGGATACACA AGGAACATGG
85301 TCTGAGCTGA GGTCATCAGG GCCTTTAGGT ATGGACTTTG CTCTAAATTG
85351 CACTGAGTAG GAAGCTTTTG CAGGATTTTG AATAGGGTCA TGGAATATCT
85401 GGGTCTTATT TCACAAAGTG TGCCTCTGAC CATTGTGTGG AGGGTGGATA
85451 GTGAGGGACA AGAGTTGGAT CCAGGGAGGT AAGTGTGGTT ATTGCAGTCA
85501 TCCCAGGTGA GAGGCAATGA AATTAACCTG CAAAGTGAGG CACTGGCTTA
85551 GAGGTGGGAA CTGAATTAAA AATCATGGGA CTAGCTATTC TTTTATTAAT
85601 AGCATGATTT TTGATAAATG ATTCTGGAGC TACATATTAA TCATTTCAAA
85651 GCAAGTGCTC TAATTTAACT AGAGACCACT GCTGGTTGTG TGTGTGAGTG
85701 CATATGTGTG TATGTATATG AGTATGTGTG GTGTGTGTCA GTATGTATAT
85751 GTGTGTATGG TATATATATA AATATATATA TTGTGTGTGG TGGGGGAGGG
85801 GGGGTGCCCC AAAGCTAGAC AGACTCTGAC TGTCTTTAGG GGAATAGTGT
85851 TTTTGATATT TCCAGGTGTT CCTGATGGGC ACCATTGTTA TTTTATTTTA
85901 TTTTTATTTT ATTTTTGAGA CGGAGTCTCA CTCTGTCGCC AGGCTGGAGT
85951 GCAGTGGCGC TATCTCGGCT CAAGACAACC TCCGCCTCCC AGGTTCAAGC
86001 AATTCTCCTG CCTCAGCCTC CCGAGTAGCT AGGACTACAG GTGCGTGCCA
86051 CCACACCCGG CCACCATTGT GTATTTTAAA GTGTGCTTAT AAAATTAGTT
86101 CAGAGCCAGA TGTGGTGGCC CACGCCTGTA ATCCAAGCAC TTTGGGAGGC
86151 CGAGGCGGGT GGATCATGAG GTCAGGAGAC CGAGACCATC CTTGCCAACG
86201 GGGTGGTGAA ACCCCATCTC TACTAAAAAT ACAAAAAAAT TAGCTGGGTA
86251 CAGTGGCGCG TGCCTGTAGT CCCAACTACT CCGGAGGACA AGGCAGGAGA
86301 ATTGCTTGAA CCTGGGAGGT AGAGGTTGCA GTGAGCCGAG ATCGCACCAC
86351 TGCACTCCAG CCTGGTGACA GAACAAGACT CCATCTCTAA ATAAATAAAT
86401 AAAACAAGTT CACAAATTTC GGAATGCTCA ATCTTAAAAG CCAGTATATT
86451 TTTGGAAACG GAATGCTGAT GAGTTTTTTA TTTTTTGCAG CATATTACAT
86501 CTTGCAGTTG CATGTATTTT TAGTGCTGTT GGCCAGCACT AAAGGTGGGG
86551 CCCTCAGCTG AGCTAATTTT GAGTCCCCTC ATTTTGGCTT CAAGTATACT
86601 CATTCTTGGT TTTCCCAAGA ATATCTGGGA TTTGTGATCT GTGTTATCTG
86651 TGGTTTGGTG TCGTATTTTG CAGGCATAGG GTCCTATTCC TAAGGGAATA
86701 AATGGATGGC TTGATGCTTA AGCACGAACT TAATCATCGC AGTAGTGATT
86751 AAAGAGTATT CAACATGTAC ACTTGCTTGT AGGAAGGAGT ACACATTGTA
86801 TTCTCTTTTG ATATGCAATA TTTTATTCAT AGCCCTATTA AGTAATTTTT
86851 TTTAACAAAG TTATATGGAT TATTTACAGG TACATCACGG GAAAACTGCA
86901 TTTTATAATT TTCACTGAAA TGTTGAGGTT ACATGTAAAG CAATTTTTAT
86951 GTCATATCTG ATACATTTTA AGAAAACATG TCTTCCTGTT ACAGCGGTAA
87001 TGACCATGCC TGCTCTTTCT TCTGTGTCAT ATGCCATTAT CCCTATTAAT
87051 ACTCTTTGGG CTTCTATAAT TATAAAGCAG ATGTGTATAT CAGGGAGAGA
87101 TGTTGATTTC AGAGTAAGTT TTTCTAGAAA ATAGAAGCTG GAAAAAAAG
87151 GAAACCCAA ACTTGGCTTC GTGCTCGAAG AGACAGCACT GCTGTGTGTG
87201 GGCGGGTGGC TGCGTGCACC CGCTGCTCAG AAGTGCCTTT TCTCTCCATG
87251 GGGATAACTG GCTGTGTATC CGAGATGTGG CCAGGAGTAG GCAAGCAACG
87301 TGTGGGCAGG CTGCATGTTC TTTTATTAGC ATCTTCATTG TACTGCATCT
87351 CGTCGAGCCC AGAGCATGAA CTGGCCTGGG TTTCTAATAT CTACCCTGCT
87401 TCCCACCTAA TTACTCCCCT GAACCCTAAA GTGAGGGAGG GAGAGTTGCT
```

FIGURE 3GG

```
87451 CTTGTGGGGT GAGCTTTCCC TGGGGTGGCT GTGAACCAAC CTGGCATGTG
87501 GATGTTCTTG GGTATCCAGA GCTGTCCTGG ACTCAGGCTT GGAGTCAGCT
87551 TCTTAGCACT GAATGCAGCC AGTCATGGAT GGAGGTCACT GTATCTCACA
87601 TGTTCCGCTC TCCCTTTCCT CCATGACCTT GCCCCTCTGA GCCTCTGTAG
87651 CACTTTTCTT GAGTGTGTCC AAGGCCATCT AGCTAAGAAG TAGCAGAAAT
87701 GGGATTTGAA GCCATGACTG TTTGGTGATA GAGCCTCAGC TTTGAACTGG
87751 GGTTCTACTG CCTGGCACCC CTGCACAAAT CATGGTAACG TGGTAGGAGA
87801 ACATAGAGGT ATAGGGCAAG CCCCTCCTTA ATGCCATGAA TAATACCCAT
87851 CTTATAGGAT TGTGGGGAGG ACTCAGTGAA GTAACCCGTG AAGCACTAAA
87901 CACGTGCCTG ACACGTGCTC AATAAATGAG CACTTGTCCT GATGACAAAG
87951 GTCGTGGCAT TAATTCTCTC TCCTAGGTTG TTACTTCCTT GAGGACAGGA
88001 ATTGTGGCTT CCTTAATGGC CACTGCAGCA GAGTTTCTCA AGTTGGCACT
88051 ATTGACATTT TGGGCTGGAT AATTCTTGTT GTGGGAGCTG TCCTGTGGAT
88101 TGTAGGATGT TGAGCAGCAT CTTTGGCCTC TACCCGCTAC ATATTAATAG
88151 CACCCCTAGT CATGAAAATA AAATGTCTAG ACATTGCCAA ACTGCCCCTG
88201 TTGAGAACCA CTGGTCTGCA GGTATCTCTC ATGGGGATCA CAGGGCTTTT
88251 ATATTCTCTT CTCTGTCTCT CTCTCTCCCT CTCTGGGTGT CTCTCTCTCT
88301 CACACACACG CTTAGAGAAG GTGGTTAAAA AAAATTTTGT TGAAGTTTGA
88351 GAATTTTGAG AACAAAGGAA AAATTTTGGA AGGCATTTTA ATGAACAGAT
88401 AGACTCTGTC CCATTCCATG GTCAACAGAA TTTCATAATT AGATAGTTTG
88451 TTTACTGCAA CTCTGCACCC CATTGCCCAT CATTTTAGAG TTCCAACCAG
88501 TTAGAGGATT TTTCTTGCAA ACTTTCCTTA AAGCAGTGAT AGTATCAGCT
88551 CTTTAAATAA TACTATGCTT GATGAAGTGG TACTTTTCGG GATAATTTGA
88601 GACCAGCCGA CTTGCTGCTT GAAGAGGACA GGGCTATATT TGGTAATAAT
88651 ATATATGTGA TAATATGTAT GTAATATTAT TATAATGTAA TATACAATAA
88701 TATTTGGTGT AACTGGTGAC TCTGAGGCCA GTCTTTGATC GAACCTCTCA
88751 AGCTATGATT TACATTATGG TCAATGTTAG CATAATGCAA TTATCAGCAA
88801 TCACTTGCTG TTGCTTTGAA AGTCAGAAGG ATGGCTAATA AAAATCTTAG
88851 AAAAAGAAAA CAGGCTGGGC GCAGTGGCTC ACCCCTGTAA TCCCAGCACT
88901 TTGGGAGGCT GAGGCGGGCA GATCATGAGG TCAGGAGATC GAGACCATCC
88951 TGGCCAACAT GGTGAAACCC CATCTGTACT AGAATACAAA AAAAAAAAAA
89001 AAATTTGCTG GGCGTGGTGG CGTGCGCCTG TAGTCCCAGC TACTCGGGAG
89051 CTGAGTCAGG GGAATCGCTT GAACCCGGGA GGTGGAGGTT GCAGTGAGCC
89101 GAGATTGTGC CACTGCACTC CAGCCTGGTG ACAGAGTGAG ACTCCGTCTC
89151 AAACAAAACA AAACAAAACA AAAACAAAA AAAGAAAATC TTAGAAAAAG
89201 AAAATAAATT GTAATATTTC AGAATATTTG TTGGGGAGGA TATGTGTGCT
89251 CAAGAAATAT ATACTGAGAA CTTACCATTG ATGCTAGAGA TTGAATTGCC
89301 CCATGTCTAC ATGAAAAATG AATAGAATAT AAACATTTTA AATTGAGCCA
89351 TGTCTATCTG TATTATATTT CTTTTATAGA AATTCATGGA AATGGTATAT
89401 TTTAACTGAA TTATTAACAC TGGGACAAT AGGCTTTAAT CATTATCTAA
89451 TACCTGTACG TTGTTTTGAA ATTCATAGCC CACCACCATT AATTTCAAAA
89501 TTGGGTTCTT ACTCAAAGAG TGATGAAAAG GCACCAGTAC CAAATGGTCT
89551 GGCCAAAATG CTACATGGAA CTAAATGCTG GGGATGGTCA TACAATGAGT
89601 TTTAAGTGGC TAGACCCTAA ATCAGAAGCA CTTTCTTCTA ATTAGCACCA
89651 TGGTTCTTAA TCCTTTCTGT ACATTACAAT CGCTCAGCAG CTTAATACAA
89701 ATGTTGCTTC CCGGGGCCAC ACTCCACATC TTTCTGACTC TCTGATTTAA
89751 TTGGTCCGAA TGGGGCCTAT ACATCAGGTG TTTTTTAAAA GGTCTCCAAG
89801 TGATTCTAAT GTGTACCTGC ATTGAGGACC AGGGAAGGTG TAGGAAGCCT
89851 GATAACCTTT ACTCTCCAGC CTCATCCTCC AATCCCATGA TTGTTTATGG
89901 GATTGTTGCT ACACACCCAG CTTAGTCATA GCATTCTTAC TCTAGCTTTT
89951 TTTTAGATGC AATTTTTATT TATTCTTAAA GAAAAAGATT TCTTTAGCAC
90001 CTTTATTCTA AAGAGCTCTT AATTGCTGTG CTTAGAACTT CTAAACAGTG
90051 AGCATTTGTC AAACATAGAA TAGCAGAATG AAGGGGTTGG ACCTCGGGTG
```

FIGURE 3HH

```
90101 AGGAGGGCTG TCGCATGGTC TCTTTCGAGT GCCGGCGGGT GGGGGCTGCA
90151 CATCTCCTCG CTTCTGGGCC CATTGATAAG TGACCTAAAA GTGCCTTTCG
90201 TTTTTTTTGG TGGGGGGTGA AAAAGCAATC TGTTTTGTAC CCACAGCGGT
90251 GCACTTTAAA CAGGAAGCCC TACTGGGGCC AGCCTTCTAT GTGTCATTAA
90301 GTTTTTCACG CCACATCCTA CCTATCATCA TGCACCCATG TCATCGTTCT
90351 TTTAAAGGGT GCCAGTTTTT TGCTTAAGCA CAAGGAGCTG TGACCTGTGT
90401 TGTCATCCCT GATGCATGTC ATGCATGTGA CTTCATGACA TGTGGGTGAC
90451 TTTTGATCTC TGAAGGACCA GGGACCCAGT CTGTGGATCA CCACTCTCTC
90501 CGTGGGTGGT TTGGGTCTTG TTCTCTAGCC CACCCAGCCA GGTGCAATTA
90551 GGAATAAAGG AAATAGCAAA GGAATTTTGC TCAAGGCCAT GCCAAGCATT
90601 TCATCTCATA TGAAAAGGAA AAGAGAGAGA GTGTGTGTGT GTTGGCTAGA
90651 TTTAGGTAGA AAACAGGCTG GTGAGAAGCG TAGAACTTGG TTAAAATTTC
90701 TAGCCAAAAG TAAGATTTTT AAAAAGATTT ATTTCTGGAT CCAATCCCTG
90751 TTGCCCATTT CTATGAATAA TCACCATTTG TTTTAATGTG AATAATAGCA
90801 CACAGCAAAT TCAGCCCCCT GAGTTTTACC ATTTTAAGCA ATTGCTTTAG
90851 GCCCGTGAGG CATGTACTAT TTATGAAGTT GCATGGGTAG TAATGGAAAA
90901 CACAACAATG ACAGTAGTAA CAGGTGACAT TTGTCGAACA CTTGCAGTGT
90951 GCCAGGCACT GTGCTGAGAG CATTACATGC ATTATTTCAT TTAATCCTTC
91001 CAAGAACTCT TTGAAGTAGG TTGGTAATTA TGGCCATTTT ACAATTGAGG
91051 AAACTGAGGT TCGGAGATGT CAAATAACTA GTCAGTGGTG GGGGTCAGAT
91101 TTTTCTTTTT TTTTTAAATT TATTTGCTTT TTTTTTTTTT TTTTTTGAGA
91151 CGGAGTCTCA CTCTGTTGCC CAGGCTGAGT GCTGTGGTGC CATCTTGGCT
91201 CACTGCAAGT TCCGCCTCCC GGGTTCACGC CATTCTCCTG CCTCAGCCTC
91251 CGGAGTAGCT GGGACTACAG GCGCCCACCA CCAGGCCTGG CTAATTTTTT
91301 GTATTTTTAG TAGAGACGAG GTTTCACCGT GTTAGCCAGG ATGGTCTGGA
91351 TCTCCTGACC TCGTGATCCG CTTGCCTCGG CCCCCCAAAG TGCTGAGATT
91401 ACAGGCATCA GCCACCGCGC CCGGCCTATT TGTTTTTTTT TTTAAGAGAC
91451 AAGGTCTTGC TGTGTTACCC AGACTGGAGT GCAGTGGTAC AATCGTAGCT
91501 CACTGTAGCC TTGAACTCCT GGGCTCGAGC GATCCTCCCA CCCCAGCCTC
91551 CCACGTAGCT GGGACTAGAG GCATGAGCCA CTATGCCCGA CTCATTTTTA
91601 AACATTTTTT ATAGAGACGG CTGGGTGTGG TACCTGTAAT CCCAGCACTT
91651 TGGGAGACTG AGGCGGGCGG ATTGCTTGAG CCCAGGAATT TGAGACCAGC
91701 CTGGGCAACA TGGAGAAACC CCGTGTCTAC AAAAAATACA AAAATCAGCT
91751 GGGTGTGGTG GTGCGTGCCT GTAGTTCCAG TTACTGGGGA GGCTGAGGTA
91801 AGAGAATCAC TTGAGTCTGG GAAGTCGAGG CTGCAGTGAC CTGGGACCAC
91851 CGCACTCCAG CCTGGGCATC GGAGTGAGAC TGTCTTTCAA AAAATAATTT
91901 ATTTATTTAT TTTAAAAATA GAGACAGGGT ATTGCTGTGT TGCCCAGGCC
91951 CGTCTTGAAC TTCTGGCCTC AAGTGATCCT TCTGCCTCGG CCTCCCAAAG
92001 TGTTGAGATT ATAGGCATGT GCCACTGTGC CCAGCCTGAG ATTTTGAACA
92051 GAGGAGCATG ATGCTGGGCG TTGACTCATT TGGCTGTGAG TGTGGAAAGC
92101 TGTCACTGGA GTACAGCAAG TCAGCACTAT CAAGCCAGCC CTTGTCATTG
92151 CCAGGAGCTG CGGGGAGAGA GGTGTTTTGC ATTGCTGCAG GGAACTGACC
92201 TCTTTTAGTC AGGGAAGTAG TTTGGGCAGT AGAAAGCAGA ACTTGCACCT
92251 GCTGGTAAGA TCTGAGTGGT CACTGACAAC CAGCTCTGCA ACCCTGTTAC
92301 CAGGGCAACA AAGATGGGCC CAGGGGTAGT GGTGGGCTCT GCCACATCTC
92351 TCTGTGCATA AGAACCTTTG GCCACTTGCT CTGGCCTTGT CTTTCACCAA
92401 TCCCAGTGTT CATATCCAGT GTACCAACCA CTGAGGGCAG CTGTCCTGGA
92451 ATCTGTCTCT CATCTCTGCC CATAATTAAC TGCTTCTGGG CACAGTGCAT
92501 GAGTTACATA GATGAGTGTG GGTAAGTTTG CCCTTTCTGT GGGGGGAGCA
92551 TCCTTTTGGT CCACTCTCAG GAGGGCATCC TATGTTATTT TTGTGATATT
92601 TTCCTAAGAG TTGTATAAGC AAGTGCATCA AGCCAACTTG TCTACCCCAG
92651 CTCCCTCTTG AGACCAGCAG AAACTATTTA TCAACTGGCA GTTTACGTAA
92701 CCTCTCTGGG CCTCAATTTC CTCATATAAA ATGAGGATAA TAAATCGTAT
```

FIGURE 3II

```
92751 CTGCTCATAG AGTTGCTGTG GGGAGTAAAG AGTTCAAATG TATCTGTCAG
92801 TGAAGGAAAA AAGAAAAAAA AACAAAAACA AAGAGTTCAA ATATATCTAG
92851 CGTTCAAACA GAACCAGGTA TGCAGCCAGT GCCCAATAGG TGTATGAGTT
92901 TCCTATGGCC AATGTAACAA ATGACCACAA ACTTAGTGGC TTAAAACAAC
92951 ACACATTTAT TATTTTACAG TTCTGGAGGT CAGAAGTCTA AGATGATGCC
93001 AGGCTTGGTG GCTCAAGCCT GTAATCCCAG CACTTTGGGA GGCTGAGGTG
93051 GCAGGATCAC TTGAGGTCAG GAGTTCCAGA CTAGCCTAGC CAACATGGTG
93101 AAACCCCATC TCTACTAAAA ATACAAAAAT TAGTCAGGCA CGGTCACGAG
93151 CACCTGTAAT CCCAACTACT CAGGAGGCTG AGGCAGGAGA ATTGCTTGAA
93201 CCCAGGAGGT GGAGGTTGCA GTGAGCCGAG GTTGCAGTGA GCCGAGGTTG
93251 CACCACTGCA CTCCAGCCTG GGCAACAGAA CGCGACCCTG TTTCCAAGAA
93301 AAAAAAAAAG TCCGGGATGA GTTTTACTGG GCTGAGATCA GTGTAGACAA
93351 GGCTGCCCTC TCTCTGGAGG CTCTAGGGCA GAATCTGTTT CCTTGTCTTT
93401 TCCAGCTTCT AGAGGTTGCC TGCATTCCTT GGCTTGTGGC CCCTTCCTCC
93451 GTGTTCAAAG CCATTGGTGT AACATCTTCA GGTCTCTGTG ACTCCGATCC
93501 TTGCTTCCAT CTTATAAGGA TCCTTGTGAT TTCATTGTAC CCATCCAGAT
93551 ATCCCAGGAG AATCTTTCCA TCCCAAGATC CATAACTTAA ATCCCATCTG
93601 CAAAGTCCCT TTTGCCATGT GTGGTAATAT ATTCACAGCT TGCAGAGATC
93651 AGGACATGGG CATCTTTGGG AAACGGGAAG GGGGCATTAT TTGACCTAAC
93701 ATCAAGAGCA TGAGATGTTT TTGTAAAATG AAACAAATGT TGCAGCTTCC
93751 TAATGCAGCT TCTTAGGCCC ACCTGCAGGC CCCCTTGACG TTGGTTTTTC
93801 TCTACCTAGG TCTGTTGTGT CGGGTCTGGA CTCCCCTGCC AAGACTAGCT
93851 CCATGGAAAA GAAACTTCTC ATCAAAAGCA AAGAGCTACA AGACTCTCAG
93901 GACAAGTGTC ACAAGGTATT TATTTCCGCA GCCGGCCTCC TTCCTTGCTC
93951 CAGGATCCTC CCGTCCGTAT ATGCCAAGGG ATCCGCCCGG GGCCGCTGCT
94001 GGCTCTGAGC CGCCTGATCC GTAGAGAGTG AGGCGCTCCT GCCTTCGCTG
94051 AAGTCGCGCC TCCAGCAGCT CAGAGGGAGA TGAATTCGGG CCTTGCTGTT
94101 GCTGTAAATC CTTTAAATCT AAACCAGAGG AGGCCCTGGA TTTAAACAGT
94151 CCGTTTCTCA GCATGACCCA GCCAGATGTC TGCTTCTTCC GGCAGGTGGC
94201 CTGGGTCCTC ACCTGTGGCT GAGATACATC CCATCTGCTT TGAGTGATGC
94251 GAAGTCTCTC TTCCTAGTCT TTTAAAACTC CTGCTTATGT CACTGCGGCC
94301 ACTGTGTTGA TTACGCTCAA CGTCTCTTAA CATTCACTGT TCCTGCCCAG
94351 AGGCAACGCT CTGGAAACTA ATAAGTCACT GCTTGCCTGG GACTCCTAAG
94401 AGTGCAGACG AATAAATATC TCCTTGCCCT GTCCTGGATT TGTCCTCTAG
94451 ATCTTTGCAA GGAGATGGGG GGGGATCAAG ATGGATTTGG GATAAAATTA
94501 AAGTGACGTC TGCAAAAACA AAACAAAAAC AAAAGCAAAC AGGTGAAAAA
94551 TGATGATTGT GGCTTCCTTG CTAACTGGGT TAGAGAAGTG ATCAAGTGTG
94601 AACCGGGACT TGAATGAGAG GAGTGACTTA GCATTTGGTG ACTGTCCTTA
94651 ACGAAGAACT GTGCGCTCCT GGGCGAAGAA ACAATGGTAT TTCCATCCCA
94701 ACTTAACTTT TGGCGAATTA GCCTTAGCCC AGACCACCAG GTGGTTTCGG
94751 AGGCTACTTG AGATGTGATT GCTCCTAATG AACCTCCACG GGCCTTTTTA
94801 ACCTGTCGAT GTGTTTATTT CAGATGGAGC AGGAAATGAC CCGGTTACAT
94851 CGGAGAGTGT CAGAGGTGGA GGCTGTGCTT AGTCAGAAGG AGGTGGAGCT
94901 GAAGGCCTCT GAGACTCAGA GATCCCTCCT GGAGCAGGAC CTTGCTACCT
94951 ACATCACAGA ATGCAGTGTG AGCCTTCCCT GAAGCCCCCT TCCCTTGGAG
95001 GTGGCACTTC CTGTTGTGTG TGTCTCATCC TGTTTCATGA TGACTCCATG
95051 AGGCACATCA CAGCCAATGG CAGAGAGTAG AGAGAGGGAG AGCACAAAAG
95101 CAAGATCTGT GTTTTGCAGA GTAGTGAGAG CCAGGCGTAA GGTCCCCAAG
95151 AAATGAGATT GGACTCATTT CCAGCAGAAA GTGCAGGTAG ACGGCTGGTA
95201 CCATGGAGTC TGGAGATGGG AGTAATTCAT CTTTGCCGCA AGTTGCAAAA
95251 GATCTTAACA TCTCCCATCC CAGCCTCTGT GGTCTGCGTT GTGTCTGACA
95301 TGAGCAGCCT TGAGAACCAG ACTCCCAACT ATGTACAAGA AAACTTACTT
95351 TCAATCTTCC TGACATCAAA TTTTCCATTG GCCAGAACCA GTGTAGTGAC
```

FIGURE 3JJ

```
95401 AAGAAAATAG CCTTGAAAAC CCAGACCCTC TGTCATTATT TACCATGTGA
95451 CTTTCATTTT TTCTTTCCTT CACAAGAGTA GACTGTCTTC TTCTCCATTG
95501 TCTTGTTAAA TTTTTCATTC AGGTGTTTTT TAATGTGCCC AATTAAACAG
95551 TCTCAAGAAG TTGAATCACA CATTTCTAAA GTTTTTTTCA CAAGGGAGAG
95601 GAAATCTATA GAACGTGGCT GATTAAGAAT AACTGCTATG TTTCCATTCC
95651 AGACTTGGCT GCCTTTCAGT GGTGGGTGAA GTTATTCAGC TATGTATTTC
95701 AGATATAGAT TTCAGTGCCA TTGAAGCATT AAGGGATTCT TATGGATGAA
95751 AGGTGTCCAG GAAAAATAAG CCAGGAGGTA GAAATAGACC ACTTGGAGTC
95801 TTAAATGACA ACTGGGCAGA GGATATGAAG TCATTGCTAC TTTGAAAGAG
95851 GCATATGTAC TTTAGGGCCC ACAAATAACT GTAGAAAACA CTTTGTAGCT
95901 ATCCACATGG TGGCTGTAAT AGCTACTGGG TCTTAATAGG TTTTAGTCCT
95951 GAACATGCAA GTAAGTATCT CCTAGGACAG GTAGATGGTG GCAGGAGACA
96001 GGCTGATGCA GTTTCCGGCT GGACTAATTT TTGTATTGTT AGTAGAGATG
96051 GGGTTTCATC ATGTTGGTCA GGCTTGTCTT GAACTCCTGA CCTCAGGTGA
96101 TCCACCCGCC TCGCCCTCCC AAAATGCTGG GATTACAGGC GTGAGCTACT
96151 GCGCCCAGCC ATTTGTGTCT CTTAAAAAAA AAACTAAGAA AATGAAAAAA
96201 ATGACATTGG CCAATTCATT AAAATGCCAC TCACTGACTG TGGTATGAAA
96251 TGGCTTTCCC TTTGATGGAC CGAAGTCTGT CTCATTGTGT GAGCCACTTG
96301 CAGGGCTGAG TATGACTNNN NNNNNNNNNN NNNNNNNNNN NNNNNNNNNN
96351 NNNNNNNNNN NNNNNNNNNN NNNNNNNNNN NNNNNNNNNN NNNNNNNNNN
96401 NNNNNNNNNN NNNNNNNNNN NNNNNNNNNN NNNNNNNNNN NNNNNNNNNN
96451 NNNNNNNNNN NNNNNNNNNN NNNNNNNNNN NNNNNNNNNN NNNNNNNNNN
96501 NNNNNNNNNN NNNNNNNNNN NNNNNNNNNN NNNNNNNNNN NNNNNNNNNN
96551 NNNNNNNNNN NNNNNNNNNN NNNNNNNNNN NNNNNNNNNN NNNNNNNNNN
96601 NNNNNNNNNN NNNNNNNNNN NNNNNNNNNN NNNNNNNNNN NNNNNNNNNN
96651 NNNNNNNNNN NNNNNNNNNN NNNNNNNNNN NNNNNNNNNN NNNNNNNNNN
96701 NNNNNNNNNN NNNNNNNNNN NNNNNNNNNN NNNNNNNNNN NNNNNNNNNN
96751 NNNNNNNNNN NNNNNNNNNN NNNNNNNNNN NNNNNNNNNN NNNNNNNNNN
96801 NNNNNNNNNN NNNNNNNNNN NNNNNNNNNN NNNNNNNNNN NNNNNNNNNN
96851 NNNNNNNNNN NNNNNNNNNN NNNNNNNNNN NNNNNNNNNN NNNNNNNNNN
96901 NNNNNNNNNN NNNNNNNNNN NNNNNNNNNN NNNNNNNNNN NNNNNNNNNN
96951 NNNNNNNNNN NNNNNNNNNN NNNNNNNNNN NNNNNNNNNN NNNNNNNNNN
97001 NNNNNNNNNN NNNNNNNNNN NNNNNNNNNN NNNNNNNNNN NNNNNNNNNN
97051 NNNNNNNNNN NNNNNNNNNN NNNNNNNNNN NNNNNNNNNN NNNNNNNNNN
97101 NNNNNNNNNN NNNNNNNNNN NNNNNNNNNN NNNNTCGGCC TCCCAAGTGC
97151 TGGGATTACA GGCGTGAGCC ACTGCTCCTG GCCCCCACGC CTTTTTTTTT
97201 TTTTGGAGAC AGAGTTTCAC TCTGTCACCC AGATTGGAGT GCTGTGGCAC
97251 AATCTCAGCT CATTGTGTCC TCTGCCTCCC AGGTTCAAGT GATTCTTGTG
97301 CCTCAGCCTC CTGAGTAGGT GGAATTACAG GCGTGCACCA CAACACCTGG
97351 CTAATTTTTG TATTTTTAGT AGAGATGGGG TTTCACCATG TTGGCCAGGC
97401 TGGTCTCGAT CTCCTGACCT CCAGTGATCC ACTTGCCTAG GCCTCCCAAA
97451 GTGTTGGGAT TACAGGCGTC AGCCACCATG CCTGGACCCC TCTGCCCCTT
97501 TAAGCACTGC CACATATTAG ATCTACGAAG GCTTTATGGA TACAATCCAA
97551 GGAAGATGAA CCTTGGGCTA GTGGGATAAA ACTAAGCGCA TGTAGTTAGA
97601 ATGGAATGAT CTGGAAACCA GGTCCCAAGT TGGTCTAAAT TAGACTCATG
97651 TTGACTATGT CACACTGTAA ACCAGTCTAA ATGCTAATAA GCATGCTTGA
97701 CCAAACACTG CCCTGCAGCC TTCAGAGAGG AAGAAGGAAA ACATAATTTG
97751 TATCCTCTCT CCCTATTTTC TGAGTCTATG GGATTCAAAT TGTAGCTGCC
97801 ATGGAAACTG TACTTTGGAA TTTCTAGAGC CCTTAATTTT AACTTAACAT
97851 ATAAAAACAC TTTTGTACTG ATTTTATAAT TATTCATGAT GGATGAGAAA
97901 GTGAATGTCT TTGACAGTGA GGGAAGCTAT CCGAATGCTA TTTTCTTTTT
97951 TTTTTTTCTT TCATAAAGAT GCATATATTT GCATGCTTTA TTTACCTGGG
98001 GCTAACTCTT GCATCTTTTG CAGATTCCGA CACCATAGCT GAGTTACAGG
```

FIGURE 3KK

```
98051  AGCTCCAGCC TTCGGCAAAG GACTTCGAAG TCAGAAGTCT TGTAGGTTGT
98101  GGTCACTTTG CTGAAGTGCA GGTGGTAAGA GAGAAAGCAA CCGGGGACAT
98151  CTATGCTATG AAAGTGATGA AGAAGAAGGC TTTATTGGCC CAGGAGCAGG
98201  TAGGAGGATT TTAACATCAT GCTTTTCCAC TTTCTGTACC GGAGTGTTCA
98251  TTGCAAAGAC GATAATCTGC TGCACTGGCG TCTAGGATCA AGCACGTTTT
98301  CCTCTGTGAC TCTATATTTA ATTATAGTTG GGGCAAAAAG GTCTCTCATG
98351  TTCTTAGCTC ATCTTCTTGA ACTGATGTTG GCTAATTTTG AAGGCTCACA
98401  AATTCCTCTT GATGTATCAT GTTTCTATCG TTGTAATTTA TTTCAGAACC
98451  AAGGTGGCCT TTTAGCTAAT GAATTTAAGA TGATCTTTTA TGACCATTAG
98501  CTGAGGACTC AGGATATACA TATGGTGGGG TGAATCAGAT TGCTTTTGTA
98551  CACGCTTTAG GTATTTGTGT TGTGGGCATA TGGATTTGGT TTTAAAACAG
98601  GCCTTTGAAG AAATCAAATA ACATTCTTTG TTATGTGGCT AGGGAGTTGC
98651  TTGTTTGAGA GCAGGTAGAA CGTTATCTTT TTTGTTGTGG TATTTTTCTT
98701  TCTTTTAAAC AAGGCTACTG TCTCTAGACA TATTGATTCA TTTGCTGTGT
98751  TTTAGAGAGA TGGCCGTCAG CCTTGGAATT CAGAGAGTAA TTTATTACTT
98801  ACAGACATTT TAGTGCACAT GATATGTCTG ATAATGTACC CAGCTCTGCA
98851  GGAAGCTTGC AAAAGGAATA GAAGTCCCAT GGTTGCTATT TCAGTGTTT
98901  AAAAACAACC TTGGAAAGTG GAGGAAAAAT GCAAATGTAT AAAGCAGGTG
98951  CTTACCAGCT AAAGTATCAC AGAAGTGGGA GAGCAATTAG CAAATTAATT
99001  AACGATGATG TGAGGGGAGA TGTTGTGGGT GAGCAAGGGA CAGTTAGGGA
99051  CAGTTCTCAC CGATGGGGGG AAATGTAGGT TCTCGGCAGA GAGAAGTGAT
99101  GAGAACATGT TGGGTAGAAG TGTGACATTC TGGAGTACTA GAATGCTATG
99151  CAAGTGTGTG TGTGTGGGTG TGTGTGTGT TTCAGTGGTT CAGAACAGAC
99201  TGGGAAATGG CGAAATGAGG ACATTTGGGT GGGGAGGGGG AAATGGGTGG
99251  GAAACTCAAG AACCTTTTTT TAAAAAATTG TGGTAAAATA TATATAACAT
99301  AAAGTGTACC ATTTTAACCA TTTTTAAATG TGCAACTGAG TGGTATTCAG
99351  TGCATTCATG ATGTTGTACA ACCATGACCG CTCTCCATTT CTAGAATTTT
99401  TCTATCATCC CAAACAGAAA CTCTCTATCC ATTATACAAT ACCTCCCAT
99451  TCCCCCAAGA ACCAGTTTTT GAATTGCAGT TTACTTTGTG AGGCTGTTGG
99501  GGATTATTTA GGCCTCTGGA AGGAGGAGGT TGGGATCAGA GTCTGGCCCT
99551  GTGGACTTCA ATGACTTTGT GTGGCCTCCA ATCAGAGAAG CAGCGGAGGG
99601  CAGGAAGCTG CTTGTCAGAA TCTGAGAGTG ATGTGGCTTC TTTGTTTAGC
99651  AATAAAATGT GAGCACATAA TAGAAAGGAA AAGTGACAGG ACATGGCAGA
99701  TAATTTGGAA GAGAGGAGTG GAAGATGCTC ACTCAGCCTC CCAGCTCCTG
99751  AGAAAGAACT GTGTCTCATC AGTTCATACT ACCTGAGCAT CTGTTGTATC
99801  TGGTGTGTTT CTAGGTACCT GGAGAAGAGG CATTACGTGT AGCCCTGACC
99851  TTGTGATGCT TATGTTTTTG ATGGGAAATA GTGCGTGTAA AAAGAAAATA
99901  ATCCAACAGG CCACACGGCA GGCAAACAAT AGAGATATTC AAATAGGTAT
99951  ACCTTCCTCC AGGTGAATGG CCTGAAATGA CCGTGTGGAA GTGTGGGCTG
100001 GGGGCTTATA AAATTATACA CATACAGGCG CTAACTAAAG CCGCCTATTC
100051 ATTCCTTAAG AGGATGCATA GAAAAGAAAA GTAGGGTCCT TTAACTGAGC
100101 CCATTTGAAT TTAGGGCCTG AGAGAAGCAG CACAAGCAGT GAAGGGAAGA
100151 AAAAGAAGTG CCCGAGAGGA GGGAGGGATT CTGTTCTGCA GACAAGGCCT
100201 GCCGCCTGGG AGAGGCCCGC ACGCCCACCC AGGGTTCTCT GACAGCTGGA
100251 AGGGGTCTTC AGAGACTGTT TATATTTTAT TTATTTATTT ATTTATTTAT
100301 TNTGAGACAG AGTCTCTGTC ACCCAGGCTG GAGTGCAGTG GTGCGATCTC
100351 AGCTCACTGC AAGCTCCGCC TCCCAGGTTC ACACCATTCT CCTATCTCAG
100401 CCTCCCGAGT AGCTGGGACT ACAGGCGCCT GCCACAATGC CCGGCTAATT
100451 TTTTTGTAAT TTTAGTAGAG ACGGGGTTTT ACCTGCGTTA GCCAGGTATG
100501 GTCTTGATCT CCTGACCTCA TGATTCGCCC ACCTCGGCCT CCCAAAGTGC
100551 TGGGATTACA GGTGTGAGCC ACTGTGCCTG GCCGACTGTT TCTACTATTT
100601 TAGAGAGAGG GTCTCACTGT CATCTGTGCT GGAATGCAGT GATGCAGTCA
100651 TAGCTCACTG CACCCTCAAA CTCCTGGGCT TAAGCGACCC TCCCGCCTCA
```

FIGURE 3LL

```
100701 GCCTCTTAAG TAGCTGGGAC CATAGGCATG TGCTGCCACA CCCAGTTAAC
100751 TTTATTATTT ATTTATTTAT TTAGAGAATG AGTCTCATTC TGTTGCCCAG
100801 GCTAGAGGTG CAGTGGCACG ATCTCGGCTC ACTGCAACCC CGCCTCCCAG
100851 GTTCAAGCGA TTCTTCTTGC TCAGCCTCCT GAATAGCTGG GATTACAGGC
100901 ACCTGCCACC ACACCTGGCT AATTTTTGTA TTTTTAGTGC AGAGGGGGGN
100951 NNNNNNNNNN NNNNNNNNNN NNNNNNNNNN NNNNNNNNNN NNNNNNNNNN
101001 NNNNNNNNNN NNNNNNNNNN NNNNNNNNNN NNNNNNNNNN NNNNNNNNNN
101051 NNNNNNNNNN NNNNNNNNNN NNNNNNNNNN NNNNNNNNNN NNNNNNNNNN
101101 NNNNNNNNNN NNNNNNNNNN NNNNNNNNNN NNNNNNNNNN NNNNNNNNNN
101151 NNNNNNNNNN NNNNNNNNNN NNNNNNNNNN NNNNNNNNNN NNNNNNNNNN
101201 NNNNNNNNNN NNNNNNNNNN NNNNNNNNNN NNNNNNNNNN NNNNNNNNNN
101251 NNNNNNNNNN NNNNNNNNNN NNNNNNNNNN NNNNNNNNNN NNNNNNNNNN
101301 NNNNNNNNNN NNNNNNNNNN NNNNNNNNNN NNNNNNNNNN NNNNNNNNNN
101351 NNNNNNNNNN NNNNNNNNNN NNNNNNNNNN NNNNNNNNNN NNNNNNNNNN
101401 NNNNNNNNNN NNNNNNNNNN NNNNNNNNNN NNNNNNNNNN NNNNNNNNNN
101451 NNNNNNNNNN NNNNNNNNNN NNNNNNNNNN NNNNNNNNNN NNNNNNNNNN
101501 NNNNNNNNNN NNNNNNNNNN NNNNNNNNNN NNNNNNNNNN NNNNNNNNNN
101551 NNNNNNNNNN NNNNNNNNNN NNNNNNNNNN NNNNNNNNNN NNNNNNNNNN
101601 NNNNNNNNNN NNNNNNNNNN NNNNNNNNNN NNNNNNNNNN NNNNNNNNNN
101651 NNNNNNNNNN NNNNNNNNNN NNNNNNNNNN NNNNNNNNNN NNNNNNNNNN
101701 NNNNNNNNNN NNNNNNNNNN NNNNNNNNNN NNNNNNNNNN NNNNNNNNNN
101751 NNNNNNNNNN NNNNNNNNNN NNNNNNNNNN NNNNNNNNNN NNNNNNNNNN
101801 NNNNNNNNNN NNNNNNNNNN NNNNNNNNNN NNNNNNNNNN NNNNNNNNNN
101851 NNNNNNNNNN NNNNNNNNNN NNNNNNNNNN NNNNNNNNNN NNNNNNNNNN
101901 NNNNNNNNNN NNNNNNNNNN NNNNNNNNNN NNNNNNNNNN NNNNNNNNNN
101951 NNNNNNNNNN NNNNNNNNNN NNNNNNNNNN NNNNNNNNNN NNNNNNNNNN
102001 NNNNNNNNNN NNNNNNNNNN NNNNNNNNNN NNNNNNNNNN NNNNNNNNNN
102051 NNNNNNNNNN NNNNNNNNNN NNNNNNNNNN NNNNNNNNNN NNNNNNNNNN
102101 NNNNNNNNNN NNNNNNNNNN NNNNNNNNNN NNNNNNNNNN NNNNNNNNNN
102151 NNNNNNNNNN NNNNNNNNNN NNNNNNNNNN NNNNNNNNNN NNNNNNNNNN
102201 NNNNNNNNNN NNNNNNNNNN NNNNNNNNNN NNNNNNNNNN NNNNNNNNNN
102251 NNNNNNNNNN NNNNNNNNNN NNNNNNNNNN NNNNNNNNNN NNNNNNNNNN
102301 NNNNNNNNNN NNNNNNNNNN NNNNNNNNNN NNNNNNNNNN NNNNNNNNNN
102351 NNNNNNNNNN NNNNNNNNNN NNNNNNNNNN NNNNNNNNNN NNNNNNNNNN
102401 NNNNNNNNNN NNNNNNNNNN NNNNNNNNNN NNNNNNNNNN NNNNNNNNNN
102451 NNNNNNNNNN NNNNNNNNNN NNNNNNNNNN NNNNNNNNNN NNNNNNNNNN
102501 NNNNNNNNNN NNNNNNNNNN NNNNNNNNNN NNNNNNNNNN NNNNNNNNNN
102551 NNNNNNNNNN NNNNNNNNNN NNNNNNNNNN NNNNNNNNNN NNNNNNNNNN
102601 NNNNNNNNNN NNNNNNNNNN NNNNNNNNNN NNNNNNNNNN NNNNNNNNNN
102651 NNNNNNNNNN NNNNNNNNNN NNNNNNNNNN NNNNNNNNNN NNNNNNNNNN
102701 NNNNNNNNNN NNNNNNNNNN NNNNNNNNNN NNNNNNNNNN NNNNNNNNNN
102751 NNNNNNNNNN NNNNNNNNNN NNNNNNNNNN NNNNNNNNNN NNNNNNNNNN
102801 NNNNNNNNNN NNNNNNTATA TGTGCATACA GAATATATAC ACAGAAATAT
102851 ATATGTACAC ATGCATAGAA TATATTTACA TATATATGCA TATATATAAT
102901 TTATTTATTT TAAGCAGTTG ATTTATACAG TTTTTGTTTT TGTTTTTTTT
102951 TTGAGACAGA GTCTCACTCT GTCACCCAGG CTAGAGTGCA GTGGCGAGAT
103001 CTCAGCTCAC TGCAACCTCT GCCCCCGGGT TCCAGTGATT CTCCTGCCTC
103051 AGCTCCACAA GTAGCACACC ACCATGCCCA GCTAATTTTT GTATTTTTTT
103101 TAGTAGAGAC GAGGTTTCAT CATGTTGGCC AGGCTGGTCT CGAACTCCTG
103151 ACCTCAAGTG ATCCGCCCGC CTTGGCCTCC CAAAGTGCTG GGATTTCAGG
103201 CGTGAGCCAC CACACCTGGC TCCCATAATG TCTTTTAGAA TAAAACGATC
103251 GAGTTGAGGA TCACACGTGA CACTTAATTG TCCTGTCTCT TTAGTCTCCT
103301 TCAATCTGGA GCAGTTCTTT GATTTTTCCT GGACTCTCAT GACCTTGACA
```

FIGURE 3MM

```
103351 ATTCTGATGA TTATAGGCCA GTTATTTTGT AAAATTTGAA TTTGTCTGAT
103401 GTTGCTTATG TTTAGATTTA GGGTCTTGGT CTTTGGCCGG AATATCTCAG
103451 ACAAGATGCT CTGTTCTTAT TGCATCAGAG CAGAAGACTC TCTGTTTCAG
103501 TTGATCACAT TTATGTTGAT GCTCACTTTG ATCACTTGAT TAAGGTGGTG
103551 TCAGTTATGC CTTTCTACTT GTAGGGTTAC TCCTTCCTCC TTCGTGATTT
103601 TATTTATTTT ATTTTTCTTA GAGACAGGGT CTTGCTTGGT TGCCCAAGCT
103651 GGAGTGCAGT GGTGGGATCT TGGCTCACTG CAGCCTTGAA CTCCTGGGCT
103701 CAAGTAATCC ACCTGCCACA GCCTCCTGAG TAACTGGGAC TGTAAGCGAA
103751 CACCACCACA CCCAGCTACT TTTTGTATTG TAGAGATGGG GTCTCACTGT
103801 GTTGTCCAGG CTGGTCTGTA ACTCCTGGCC TCAAGCAGTC TTCCGGCCTT
103851 GGCCTCCCGA AGTGCTGGGA TTACAGGCAT GAGCCACTGC ACCCAGCCTC
103901 CTTTGTAATT AAAAAAGTAT TTTATGGGGA GTTACTTTCA AGTGATGGAA
103951 ATATTTTATA TCTATGTGGA CTTGGATTTT CCTATTTCAG TCAGTGAGTT
104001 ATAATCCATT TCTGTCACTA GTTTTATACT TAAATTGTTC CCAACTTGGC
104051 CACTGAGAAC CTTTTTAGGT TAGCTTTTGT GTCCTTTTCA CATGTCTCCA
104101 AGATTCATTG AATACTTTCC TGCTTTCTGG TATAGCAAGA TGTTCAGGTT
104151 CTTTTGGTAC TTTTACTTTC TCTGCCCTGG CTCTGGCATC AGTCATTTCT
104201 CAGAGGAGCC CTGTGCCTTT CAGTGGACAA TGGTGTTTAG AGGCCAAGAT
104251 CTGGACATTG GGTGTTTTCA TTGCTACCGG TGTGTCACTA CTCCCAGACC
104301 CCTTTCAGTG GACAGCACTA AGGAATACAC ATACGTATAT ACAATATATC
104351 CACCTACACA TGTGCGTGCA CTCACACACA CACATATACA TTACATCTAT
104401 ATTTGTGTAT CCATGTCTAT ATATTGAAAA TTGTGGCTGG GCACAGTGGC
104451 TTATGCCTTT AATCTCAGCA TTTTGGGAGG CTGAGGCAAG AGGATCACCT
104501 GAAGCCAGGA GTTCAACACC AGCTTGGGAA ACAGAGAGAG ACTCTGTCTC
104551 TACAAAAATA AAAAGGGAAA ACCATGAGTT CACACCCGTG CCCCCAGTTC
104601 CAATCCAACT TCACAGGGTT CATTTTAGTT TTCACCCTTT CCATGTTTGT
104651 AATTCTCTTC TCTGACATTA TACCCTTAAT ATGTTTACTT ATTTTATGCA
104701 TCTGTATGCA TCCAATCTAC TGTCTTTGTT GGTATCCCAC CTCCCCTTGG
104751 TGGGTCCAGA TAATCTGCTC TGGGTTGCCC TTTCACGTGG ATGTCTTCCT
104801 TACCCTGTGT GGGCCTGTGA TACTGGGCTG CCCCCACACA TGAGTGCTGC
104851 CCTCCTCACG TTGCTTGGGA CGGCACTGTG TCCTGGGCCA CCATGACTTT
104901 TCTCATAACT AGCGTGGATG CTTACCTTGT TCCACACCAG TGAATGGCTT
104951 CAGGAAGAGA AGAGGAAGAG AAAAATATTT ACATTTAAAG AAAGGTAGTT
105001 TAAAGAAATA TGTTAGGTAA AGAATTGAGC AGGTAATATA CGGAGCTGGC
105051 AAAAATTGTG ACCAAAGTAG GTGAATGATT GAGATTTATG CAATTCTGGG
105101 CTAAGTGACA GCCCCTTCCC TTTCCCTTCC CTTCCCCTTC CCTTCCCTTT
105151 TCTTCCCTTT CCCTTCCCTT TCCTTCCCTT TCCCTTCCCC TTCCCTTCCC
105201 TTTCCTTCCC TTTCCCTCTT CTTCCTTCCT TCCTTCTGTT TTCTTTTCCC
105251 TTCTTTCCTT TGCCTTTTTT TTTTTTTTAA AGCTAGAAAC ATCAGTTTAG
105301 GCATAAAGAC AGAGGAAAAG GCTTCTTTTT CCTCTCACAG TTCTTTATAA
105351 TTGTCTAAGC AGTTTCTTTT TTCCCTAGGT TTCATTTTTT GAGGAAGAGC
105401 GGAACATATT ATCTCGAAGC ACAAGCCCGG GATCCCCCAA TTANNNNNNN
105451 NNNNNNNNNN NNNNNNNNNN NNNNNNNNNN NNNNNNNNNN NNNNNNNNNN
105501 NNNNNNNNNN NNNNNNNNNN NNNNNNNNNN NNNNNNNNNN NNNNNNNNNN
105551 NNNNNNNNNN NNNNNNNNNN NNNNNNNNNN NNNNNNNNNN NNNNNNNNNN
105601 NNNNNNNNNN NNNNNNNNNN NNNNNNNNNN NNNNNNNNNN NNNNNNNNNN
105651 NNNNNNNNNN NNNNNNNNNN NNNNNNNNNN NNNNNNNNNN NNNNNNNNNN
105701 NNNNNNNNNN NNNNNNNNNN NNNNNNNNNN NNNNNNNNNN NNNNNNNNNN
105751 NNNNNNNNNN NNNNNNNNNN NNNNNNNNNN NNNNNNNNNN NNNNNNNNNN
105801 NNNNNNNNNN NNNNNNNNNN NNNNNNNNNN NNNNNNNNNN NNNNNNNNNN
105851 NNNNNNNNNN NNNNNNNNNN NNNNNNNNNN NNNNNNNNNN NNNNNNNNNN
105901 NNNNNNNNNN NNNNNNNNNN NNNNNNNNNN NNNNNNNNNN NNNNNNNNNN
105951 NNNNNNNNNN NNNNNNNNNN NNNNNNNNNN NNNNNNNNNN NNNNNNNNNN
```

FIGURE 3NN

```
106001 NNNNNNNNNN NNNNNNNNNN NNNNNNNNNN NNNNNNNNNN NNNNNNNNNN
106051 NNNNNNNNNN NNNNNNNNNN NNNNNNNNNN NNNNNNNNNN NNNNNNNNNN
106101 NNNNNNNNNN NNNNNNNNNN NNNNNNNNNN NNNNNNNNNN NNNNNNNNNN
106151 NNNNNNNNNN NNNNNNNNNN NNNNNNNNNN NNNNNNNNNN NNNNNNNNNN
106201 NNNNNNNNNN NNNNNNNNNN NNNNNNNNNN NNNNNNNNNN NNNNNNNNNN
106251 NNNNNNNNNN NNNNNNNNNN NNNNNNNNNN NNNNNNNNNN NNNNNNNNNN
106301 NNNNNNNNNN NNNNNNNNNN NNNNNNNNNN NNNNNNNNNN NNNNNNNNNN
106351 NNNNNNNNNN NNNNNNNNNN NNNNNNNNNN NNNNNNNNNN NNNNNNNNNN
106401 NNNNNNNNNN NNNNNNNNNN NNNNNNNNNN NNNNNNNNNN NNNNNNNNNN
106451 NNNNNNNNNN NNNNNNNNNN NNNNNNNNNN NNNNNNNNNN NNNATGGAGT
106501 CTTGCTCTGT TGTCCAGGCT GGAGTGCAGT GGTGTGATCT TGGCTCACTG
106551 CAACCTCCGC CTCCTGGGTT GAAGCGATTC TCCTGCCTCA GCCCCCTGAA
106601 TAGCTGGGAT TACAGGCATG TGCCACCACG CCTGGCTAAT TTTTGTATTT
106651 TTAATAGACA CGGGGTTTCA CCATGTTGGT CAGGCTGGTC TCGAACTCCT
106701 GACCTCAGGT GATCTGCATG CCTAGGCCTC CCAAAGTGCT GGGATTACAG
106751 GCATGAGCCA CTGCGCCTGG CCAACTTATT TAACTTTTTT GAGACAGGGT
106801 CTCACTCTGT CACCCAGGCT GGAGTGCAGT GGCATGATCA TGGCTCACTG
106851 CAGCCTCAAA TTGCAGGGCT CAAGTGATTC TCCTGCTTCA CCTTCCTGAT
106901 TAGCTGGGAC AACAGGTACA AACCACCATG CCTAGCTAAT TTTTAAATTT
106951 TCTGTAGAGA CTAGGGTCTC ACTATGTTGC CCAGGCTGGT TTCGAACTCC
107001 TGAGCTCAAG AGATCTTCCT GCCTTGGCCT TCCAAAGTGC TGGGATTACA
107051 GGTGTGAGCC CCATGCCCAG CTCCGGTGGG GGATATTTCT ATATCCACAT
107101 GTGTATAGTT TACTTTATAA AAATGGTATG TTACTCTGTG CTTGGCTCTC
107151 CAGCTTGCTG TTGCCTTTCA CCAGTGTATC CCAGACATCC TTTCTTCCTT
107201 GTCAGTAACG CAGGTCTACT TTATTCTTTG AGCAGTGGCA TAATTTTCCC
107251 TGATGTGTAT ATATCATAAG TTAGAGAATG CTAAAATTCA TTTTGGGGCC
107301 TTGTTTAGGT TCTTGAGGGA TTAAATTCCT AAATTTAACA AGTGTATCCT
107351 GGAAACAATT TTTGTTCCTG ATTCAGCCCT TAAAAGAGGA CTATCATGTT
107401 ACCTTGAATG GAGATAAACA GGCTCACGTA AGAGAAAAGG GTAAGAGGGA
107451 TGAACTCCCA CTTATCTTAA ACTTCTACTG GCCCGTTTTT GGGGAATTTG
107501 CTGCTTTTAT TCCTGACCTA AAATAAATAA GTTTATGTGT CTTGGTTTCA
107551 TATTAGTTGA GAACCCAGTG CCTGGAGAGA AGTTTTCCTT GTCCTCTGAG
107601 TGAGGACATT CACATATGAA TCTATTGGCA GACTGGCTTT GACTGACCAC
107651 ACGTGCCTTC AGAACCAATG CCACAGCTCT TAGGTTTATG GCCTGAAACA
107701 CCCTTTCCTT ACATATTGCC TTAGAAACTT TCCTTCCTTG AGACATGGGG
107751 CATGGAACCC TCACCTTCAC AGATGACCTT GGTGTGTTTC TAGGGTTGCT
107801 GGTGTTCCAG GACATCTGTT GCAGATGCAG TATTTACCTT GTGCTCTCTG
107851 CATCATAAGC AGCTTCTCAT GTTTGAATGT ATTAACAGAC TTTTAATTTT
107901 TTTTATTTTT GAGACAAAGT CTCACTCTGT CACCCAGGCT AGTGTTACCC
107951 AGGCTGGAGT GCAATGNNNN NNNNNNNNNN NNNNNNNNNN NNNNNNNNNN
108001 NNNNNNNNNN NNNNNNNNNN NNNNNNNNNN NNNNNNNNNN NNNNNNNNNN
108051 NNNNNNNNNN NNNNNNNNNN NNNNNNNNNN NNNNNNNNNN NNNNNNNNNN
108101 NNNNNNNNNN NNNNNNNNNN NNNNNNNNNN NNNNNNNNNN NNNNNNNNNN
108151 NNNNNNNNNN NNNNNNNNNN NNNNNNNNNN NNNNNNNNNN NNNNNNNNNN
108201 NNNNNNNNNN NNNNNNNNNN NNNNNNNNNN NNNNNNNNNN NNNNNNNNNN
108251 NNNNNNNNNN NNNNNNNNNN NNNNNNNNNN NNNNNNNNNN NNNNNNNNNN
108301 NNNNNNNNNN NNNNNNNNNN NNNNNNNNNN NNNNNNNNNN NNNNNNNNNN
108351 NNNNNNNNNN NNNNNNNNNN NNNNNNNNNN NNNNNNNNNN NNNNNNNNNN
108401 NNNNNNNNNN NNNNNNNNNN NNNNNNNNNN NNNNNNNNNN NNNNNNNNNN
108451 NNNNNNNNNN NNNNNNNNNN NNNNNNNNNN NNNNNNNNNN NNNNNNNNNN
108501 NNNNNNNNNN NNNNNNNNNN NNNNNNNNNN NNNNNNNNNN NNNNNNNNNN
108551 NNNNNNNNNN NNNNNNNNNN NNNNNNNNNN NNNNNNNNNN NNNNNNNNNN
108601 NNNNNNNNNN NNNNNNNNNN NNNNNNNNNN NNNNNNNNNN NNNNNNNNNN
```

FIGURE 3OO

```
108651 NNNNNNNNNN NNNNNNNNNN NNNNNNNNNN NNNNNNNNNN NNNNNNNNNN
108701 NNNNNNNNNN NNNNNNNNNN NNNNNNNNNN NNNNNNNNNN NNNNNNNNNN
108751 NNNNNNNNNN NNNNNNNNNN NNNNNNNNNN NNNNNNNNNN NNNNNNNNNN
108801 NNNNNNNNNN NNNNNNNNNN NNNNNNNNNN NNNNNNNNNN NNNNNNNNNN
108851 NNNNNNNNNN NNNNNNNNNN NNNNNNNNNN NNNNNNNNNN NNNNNNNNNN
108901 NNNNNNNNNN NNNNNNNNNN NNNNNNNNNN NNNNNNNNNN NNNNNNNNNN
108951 NNNNNNNNNN NNNNNNNNNN NNNNNNNNNN NNNNNNNNNN NNNNNNNNNN
109001 NNNNNNNNNN NNNNNNNNNN NNNNNNNNNN NNNNNNNNNN NNNNNNNNNN
109051 NNNNNNNNNN NNNNNNNNNN NNNNNNNNNN NNNNNNNNNN NNNNNNNNNN
109101 NNNNNNNNNN NNNNNNNNNN NNNNNNNNNN NNNNNNNNNN NNNNNNNNNN
109151 NNNNNNNNNN NNNNNNNNNN NNNNNNNNNN NNNNNNNNNN NNNNNNNNNN
109201 NNNNNNNNNN NNNNNNNNNN NNNNNNNNNN NNNNNNNNNN NNNNNNNNNN
109251 NNNNNNNNNN NNNNNNNNNN NNNNNNNNNN NNNNNNNNNN NNNNNNNNNN
109301 NNNNNNNNNN NNNNNNNNNN NNNNNNNNNN NNNNNNNNNN NNNNNNNNNN
109351 NNNNNNNNNN NNNNNNNNNN NNNNNNNNNN NNNNNNNNNN NNNNNNNNNN
109401 NNNNNNNNNN NNNNNNNNNN NNNNNNNNNN NNNNNNNNNN NNNNNNNNNN
109451 NNNNNNNNNN NNNNNNNNNN NNNNNNNNNN NNNNNNNNNN NNNNNNNNNN
109501 NNNNNNNNNN NNNNNNNNNN NNNNNNNNNN NNNNNNNNNN NNNNNNNNNN
109551 NNNNNNNNNN NNNNNNNNNN NNNNNNNNNN NNNNNNNNNN NNNNNNNNNN
109601 NNNNNNNNNN NNNNNNNNNN NNNNNNNNNN NNNNNNNNNN NNNNNNNNNN
109651 NNNNNNNNNN NNNNNNNNNN NNNNNNNNNN NNNNNNNNNN NNNNNNNNNN
109701 NNNNNNNNNN NNNNNNNNNN NNNNNNNNNN NNNNNNNNNN NNNNNNNNNN
109751 NNNNNNNNNN NNNNNNNNNN NNNNNNNNNN NNNNNNNNNN NNNNNNNNNN
109801 NNNNNNNNNN NNNNNNNNNN NNNNNNNNNN NNNNNNNNNN NNNNNNNNNN
109851 NNNNNNNNNN NNNNNNNNNN NNNNNNNNNN NNNNNNNNNN NNNNNNNNNN
109901 NNNNNNNNNN NNNNNNNNNN NNNNNNNNNN NNNNNNNNNN NNNNNNNNNN
109951 NNNNNNNNNN NNNNNNNNNN NNNNNNNNNN NNNNNNNNNN NNNNNNNNNN
110001 NNNNNNNNNN NNNNNNNNNN NNNNNNNNNN NNNNNNNNNN NNNNNNNNNN
110051 NNNNNNNNNN NNNNNNNNNN NNNNNNNNNN NNNNNNNNNN NNNNNNNNNN
110101 NNNNNNNNNN NNNNNNNNNN NNNNNNNNNN NNNNNNNNNN NNNNNNNNNN
110151 NNNNNNNNNN NNNNNNNNNN NNNNNNNNNN NNNNNNNNNN NNNNNNNNNN
110201 NNNNNNNNNN NNNNNNNNNN NNNNNNNNNN NNNNNNNNNN NNNNNNNNNN
110251 NNNNNNNNNN NNNNNNNNNN NNNNNNNNNN NNNNNNNNNN NNNNNNNNNN
110301 NNNNNNNNNN NNNNNNNNNN NNNNNNNNNN NNNNNNNNNN NNNNNNNNNN
110351 NNNNNNNNNN NNNNNNNNNN NNNNNNNNNN NNNNNNNNNN NNNNNNNNNN
110401 NNNNNNNNNN NNNNNNNNNN NNNNNNNNNN NNNNNNNNNN NNNNNNNNNN
110451 NNNNNNNNNN NNNNNNNNNN NNNNNNNNNN NNNNNNNNNN NNNNNNNNNN
110501 NNNNNNNNNN NNNNNNNNNN NNNNNNNNNN NNNNNNNNNN NNNNNNNNNN
110551 NNNNNNNNNN NNNNNNNNNN NNNNNNNNNN NNNNNNNNNN NNNNNNNNNN
110601 NNNNNNNNNN NNNNNNNNNN NNNNNNNNNN NNNNNNNNNN NNNNNNNNNN
110651 NNNNNNNNNN NNNNNNNNNN NNNNNNNNNN NNNNNNNNNN NNNNNNNNNN
110701 NNNNNNNNNN NNNNNNNNNN NNNNNNNNNN NNNNNNNNNN NNNNNNNNNN
110751 NNNNNNNNNN NNNNNNNNNN NNNNNNNNNN NNNNNNNNNN NNNNNNNNNN
110801 NNNNNNNNNN NNNNNNNNNN NNNNNNNNNN NNNNNNNNNN NNNNNNNNNN
110851 NNNNNNNNNN NNNNNNNNNN NNNNNNNNNN NNNNNNNNNN NNNNNNNNNN
110901 NNNNNNNNNN NNNNNNNNNN NNNNNNNNNN NNNNNNNNNN NNNNNNNNNN
110951 NNNNNNNNNN NNNNNNNNNN NNNNNNNNNN NNNNNNNNNN NNNNNNNNNN
111001 NNNNNNNNNN NNNNNNNNNN NNNNNNNNNN NNNNNNNNNN NNNNNNNNNN
111051 NNNNNNNNNN NNNNNNNNNN NNNNNNNNNN NNNNNNNNNN NNNNNNNNNN
111101 NNNNNNNNNN NNNNNNNNNN NNNNNNNNNN NNNNNNNNNN NNNNNNNNNN
111151 NNNNNNNNNN NNNNNNNNNN NNNNNNNNNN NNNNNNNNNN NNNNNNNNNN
111201 NNNNNNNNNN NNNNNNNNNN NNNNNNNNNN NNNNNNNNNN NNNNNNNNNN
111251 NNNNNNNNNN NNNNNNNNNN NNNNNNNNNN NNNNNNNNNN NNNNNNNNNN
```

FIGURE 3PP

```
111301 NNNNNNNNNN NNNNNNNNNN NNNNNNNNNN NNNNNNNNNN NNNNNNNNNN
111351 NNNNNNNNNN NNNNNNNNNN NNNNNNNNNN NNNNNNNNNN NNNNNNNNNN
111401 NNNNNNNNNN NNNNNNNNNN NNNNNNNNNN NNNNNNNNNN NNNNNNNNNN
111451 NNNNNNNNNN ATATTGAATC TGTGCAAAGT CAGCTATCAG TCTGATTGCC
111501 CTATCCCACA AATTGCATCC CAGGAGATGA TTAGATGCAA TAGGTGAAAG
111551 TTTTCATGTT CCTCAGTGGC ATTCAGTGCA TGAACAACCA TTGTCCACCT
111601 AATTCCTCTG CATCTACAGC AAGAAATAGA ATTTTTGTGG AGACTTAACA
111651 TGCTGTGTCT TACTTACATA TGTATGCAAA AAAAAAAAAA AAAGTCACTT
111701 TTTTTCTTTT TTGAGACCGA GTCTTGCTCT GTGGCCCAGG CTGGAGCACA
111751 ATCACGGCTC ACTGTAACCT CCGCTACCCA GGTTCAAGTG ATTCTCCTGC
111801 CTCAGCCTCC TTGAGTAGCT GGGACTACAG GCACGTGCCA CCATGCCCAG
111851 CTAATTTTTG TACTTTTAGT AGAAATGGGG TTTTGCCATG TTGGCCAGGC
111901 TGGTCTCGAA CTCCTGACCT CAGGTGATCC ACCTGTCTTG GCCTCCCAAA
111951 GTGTGGGATT ACAGGCGTGA ACCACCAACG CCTGGCCCTG AAGATACATT
112001 TTAAATCAAT GAAAAAAAAC AACAGGATTC TACCTCCTAT GGTATATCCC
112051 TCCTGGCTGT CTCTTCTCTC CAGTCTTGCC TCTGCTGTGT GGGTTTCAGG
112101 CATCCATCTT CTCTACTCTG AATTACTGTG ATAACCTCTG AAGTATTTTC
112151 CCTGCCATCT GTCTGGCCCT TCTCCCAGGT CTTCCACATA CTGCAGCCAA
112201 GTCAGCCCGC TGTTGAAACC CTTCAAGACT CCCTGCTGTC CTCTGGATGA
112251 AGTCCAGACT CTTCCACGTG ACTTACCAGG CCTTTCTTGC ACTTGTCCCC
112301 AGCCACTTAC TGTTTCTCTC TTTCTACCTT AACATCCTGA ACTTCCTTTG
112351 GTTCTTTGAC CTTGCCTCTG ACCTTTTTCC ATGCTGTTCA CTCTTTCCCT
112401 GTTCACCTTG CTAACTCCTC TTTCTCTTTC TGGGTTGGAT CAGATTTCAC
112451 TTCTTCCAGA AGCCCTTCCT AGACCCTATA CTTCTGGAAT GGCGCCTTTT
112501 GACTGTACGC TCATTGCACC CTGTACTTCT CCTTTATGAG TGGGTGCTGG
112551 TCTGTCCCAC TAGGCTACTT CATCCATAAA GGGAGAGTAG AGCTTTACCA
112601 AGTCAATGCT TAAGCAATAT TTATTGGATG AATGTGTGAT TAATTTCATA
112651 GAAATTTGAT GTGCATTCAA ATTTACTTAT TGTATTACGG AACTTGCATT
112701 ATATTCTCAG TGGAGTTATT TTCTTTCACG TGTGTAATTC AAGATAGACT
112751 CAGTGAGATT TTCAAAATTT GGAATGCAGT GCAAGGAAAT TGAACTTGAG
112801 TTCTTTTGCA TTTTGATGGT TAAAAATTTC CCATTTGTGG TGACATACCA
112851 CAATAAGCCA GTGAATGTGG CTTATTGTTT TCTGGTCTAT AGAAAATTGT
112901 CGCAAACTCT GTCATAATGT CTGGTTCTAT ATAACAAAGC TAGTCCTGTA
112951 TTCTGCATGT GGCTGATGGA AACAGTGCTC TGTTGATCTG GTTCATGAAG
113001 AAATCTGTTC AATTCTGCAT AACAGATGCC TTCATCAGTG TCCTTCCATG
113051 AAGGAGCTGA TCTTCACAAA GAACACATAG TTTTGCATCC CACCACTTGC
113101 AGTNNNNNNN NNNNNNNNNN NNNNNNNNNN NNNNNNNNNN NNNNNNNNNN
113151 NNNNNNNNNN NNNNNNNNNN NNNNNNNNNN NNNNNNNNNN NNNNNNNNNN
113201 NNNNNNNNNN NNNNNNNNNN NNNNNNNNNN NNNNNNNNNN NNNNNNNNNN
113251 NNNNNNNNNN NNNNNNNNNN NNNNNNNNNN NNNNNNNNNN NNNNNNNNNN
113301 NNNNNNNNNN NNNNNNNNNN NNNNNNNNNN NNNNNNNNNN NNNNNNNNNN
113351 NNNNNNNNNN NNNNNNNNNN NNNNNNNNNN NNNNNNNNNN NNNNNNNNNN
113401 NNNNNNNCCT ACTGTGGTTT TCTTCAGAAT TACCCTTGCT CTGAGCCTGC
113451 AATTGACTCA TGAACTTCTT TTCCATGTTC TAACCTTACA ATGACTTCCT
113501 TGTGTTCACT CCAAATGTTT TTCCCTGGTT GCATGTAGAG ATGTATTAGC
113551 TAAGGTACAT GCTTAGCTGC TGTATCAAAG AGACCCTAAT GTACAACCCA
113601 GGCTGGTAGA GCAGCTCTGC TGTATGTGTT AATTCAGGGA CCCAGGTTCC
113651 TTCCATGTTG TGACTCCCCC CTTCCTTAGG ATGTTGTCTT CTTTTACATG
113701 GCTGAAGTTG GGCCATTTCA TGTCTCTGTT CCAGCTGCCT GGTAGGAAAA
113751 AAGAACAGAA ATTCAGAGTA AGCAAATTCT TTTTCTATAG ATGGATGCGG
113801 AAGTTGGACA CATCATTTCC TCTCACATTT TCTCGGCCAG AACGTAGTCA
113851 TGTGACTGCA CGTCTAGCTG CTAAGGAGAC TGGGAATTTA CTGTCGGCTG
113901 TGTGGCCTCT GTCAAGCTAA AATTCTTATT ACTGTGGAAT AAGGGAAGGA
```

FIGURE 3QQ

```
113951 TGGATTTGGG GGCACAATTA ATAGTCTGTC ACAGAGGCTA AAACAGCTGC
114001 TTTTGGCTGG GCACGGTGGC TCACACATGT AATTTCAGCA CTTTGGGAGG
114051 CCGAGGCAAG TGGATCACTT GAGATCAGGA ATTTGAGACC AGCCTGGCCA
114101 ACATGGTGAA ACCCTGTCTC TCCTAAAAAT ATAGAAATTA GCCGGGCATG
114151 GTGGCGGGTA CCTGTAATCC GAGCTACTCC AGAGGTTGAG GCAGGAGAAT
114201 TGCTTGAACC TGGAAGGCAG AGGTTGCAGT GAGCCAAGAT GGTGCCACTG
114251 CACTCCAGCC TGGGCGACAG AGCAAGACTC CATCTCAAAA AAAAAAAAAA
114301 AGGTTAAATA AACAGCTGCT TTTGTAGGTG ATACAAGGTA CAGCTAAGCT
114351 TTGAAGCCAG GCCTGTAGTT TCACCTTCCA TATTCTTACT CAAGGCATTA
114401 TACTTCTGGA TCTGAAACCA CTGGATCTGA TGCCCTGCTT GGGATGAGTT
114451 CTTTATATTA TCTTGCTTTC AACCCACACC TGTGTAATTT TATGGGCAGC
114501 GTTTGTTTCC TATATAGGAA CAATTTGAAA GTGGGCTGTT TCTAGGCTTT
114551 CATGAATAGC AGGCTATGCT GTCATTGGGA ATCTGGAGGG AGTTAATGAA
114601 CACAACTTCA TTGTTTACTT TAGTGAAATG TGGCAGCTTA TGATAGTTTT
114651 GACAGTGAGA CATGTGCTGT TTTGATCTCT CAGCTAAGAT TATCTGATTT
114701 TTCAGGCATG TCTCAAAACT CACCAGGCCT GCTCACATGC TGCTGCTTCT
114751 GAAGCCAGGG TTTGGAAACC AGCTGCCCAT CAGAATGAGG CTGTGACTTA
114801 GAATATTGGT TCTTGTTTTA TTACCATTCC TTGTTTGGTC TCTCCAGAGT
114851 CACTGGCCTT TTCCGCTTCA ATTTTCTTAT CGGTGAAATG AGATATTAAT
114901 TCCTCTTATT GACTTCAATT CAATTGCTGA GTGTATTGTT GCCTTTGGGA
114951 AGTTCTTTGA GTTTTCTGTG CCTTTGAAAT AGTTGTTTTT TTTTATTCTG
115001 GTGTTTTGAG GCATGTTTCA AGTGAGTGCA TTTACACTTC TACCATTTTA
115051 GGAGCCACAA TTCAGTTATG TTGTCCCAGC TTGCTTGGCC CCATCCCCAG
115101 AGTTTCTGAT TCAGTAGGTC TGGGGTGGGG CCCAATAATT TGCATTTCTT
115151 CTTCTTTTTT CGAGACAGAG TCTGACTGTG TCATCCAAGC TGGAGTGCAG
115201 TGGCACGATC GTAGCTCATT GTAGCCTCAA ACTCCTGGGC TCAAGCCGTC
115251 CTCCCACCTC ACCCTCCTGA GTAGCTGGGA CTATAGGCAT ATACTACCAT
115301 GCCCTGCCAC CTTTTTAATT TTTTGTAAGG ATGGGGGTCT CACTGTGTTG
115351 CTCAGGCTGG TCTTGAATTC CTGGGCTGAA GTGATCCTCC TGCTTCAGCC
115401 TCCCCAAATG CCGGCATTCC TGGCATGAGC CACTGCACTT GGCCAAGACT
115451 TTGCATTTCT AACTAGTTTC CAGGTAATGC TGCTGCTGGT GTAGGGACCT
115501 CATTTTGAGA ACCATTGTTC TATAGCTGTA GCTATAGTTA GTTTCTGGTT
115551 ATAGCTTCTT CCTTTTGTCC CTTCAGTAAT AGTGTACACA TCCGAAATCC
115601 CTGTCCTTGC TCTTTCAGGC CCAGGCATGG TATCTGGTCC TCTTCTGTTG
115651 CTAGCCCTGG GGTGCTTCAT CATCCCAAGT TTATTTTTCT TCTCCTAACC
115701 TGAACCTTTG TAAATAGCCC CTTCCCTAAT GAACGTCCTC AATTCCCTGT
115751 TTTGCGTGTC CTGTCTGTTT CTTGGCAAGA CTCTGGATGA TTCAGTACTC
115801 AATGAGGATT TTTCGCATAG ATGGATGAAA CAGGCTGGGT TTCATGTTTT
115851 CTAAGATAAA GGTGCTTCTC TCTTTTTCTC TTGGTCACTT TGACCAAGAA
115901 GAAAATAACA GAGTTTTTAT TCTCAAGAAG AATAATATCG GGCCACTCT
115951 GCTCAGAGGC CACTCTGCTT TGAGGACCCC TTCTCTCCTC CCTCATGCCA
116001 AAGATCAGGA ACATTGGGCA GAGCGGATAA CGATGCCGCC AGCGTCATTA
116051 CATTTTCACG GCACTTTCAG TTGTGCTGAG CGTGCAAACA TTTCAAGGAG
116101 ACATTTCTAA GAGGTGGCTA GCACAGCATG CCTCTAATGC CCTATGTGAA
116151 TTGGAATAGA GTACTAAAGA ACTGTTCAAT ATTCACCCCA TCCCCGCATA
116201 TGCAAGCATG CACGTGGGTT CATTGTATAT GTGTGTGTGC ACGTGTGCAC
116251 AGACACATTT GTCCTTCGTT TCAAATGCAA CACAATGGAT GGAAATTGCC
116301 TTCCTGGTAC TGGGGTATGG ATGCAAACAC CAACAGAGAA GCAGCCGCTA
116351 CTTCCAAACT GAACACATGT GAGATTTGCC CTTTAATTAG CATCTGCAGC
116401 TGCTGCCATC AGAAGGGTCT GTCTCTGTTG GCCTGAAAGT CTTTGCTTTA
116451 AAAGAGCAAG TCCATTATAG CTCCAAGCCA GGCTCGTCTG TCAGCTGCTG
116501 TGCTTTCTCT GCCATCAGCG GGGTTGCCAC ATTGTTTTGG GCTGTTTCAC
116551 TCTAGGACTC TTTCCTCCTC CTGTGCCCCC AGCCTTTGAT TACCATGCCT
```

FIGURE 3RR

```
116601 TGGTGATCCT CATTTGGGTG ACCTGCAGCT GCTCATTGTG TGTGCAGGAG
116651 ACATCTCCAG TCCTTGTAAG GAGGGAAGAT CACTGGCTTC AGTGCTGATG
116701 GACTGGTTAT TTTCCAGCCC TTTGTCGTCA GTGATCTTGT CTTGATATGC
116751 AGAAAGGCTC CAGGTAGTCA CTGAAAAAAA TATAAGCAGC AGAGGTGATG
116801 GCTATATGAA AGTCACGTTT CATCAAGGGC ATTGCTGCTA TGGAAACTTT
116851 CAATTCACTT GGAGTAGGGA GCCATATTGG TTCCACAGCC TCCTCAGCAG
116901 TGGGTCCCAA CACAGTGCTG GGCTAGCTGC CTCTGAATCA CCGCAGTAGC
116951 TCCTTTTACT ATAGATTCCT GGGTCCCACC CATGGAATGT GATCCATGAA
117001 GTCTGGGGTT ATTCCCTGGA ATCCTTTAAG CTCCCTAAGT GGTTGGGATG
117051 GGAAAGAGAT ATGCTTTATG TTACTATACT TCTTATTATT ATTATTTTAA
117101 AATTCTTGCC GGGCGCAGTG GCTCACACCT GTAATCCCAG CACATTGGGA
117151 GACCGAGGCG GGTGGATCAC TTGAGGTCAG GAGTTCGAGA CTGGCCTGGC
117201 CAACATGATG AAATCCCGTC TCTACTAAAA ATACAAAAAT TAGCTGGGCA
117251 TGGTGGCGCA TGACTGTAGT CCCAGCCACT CCGGAGGCTG AGGCAGGAGA
117301 ATCGCTTGAA CCCGGGAGGC AGAGGTTGCA GTGAGCCGAG ATCGTGGCAC
117351 TGCACTCCAG CCTGGGTAAC AGAGTGAGAC TTCATCTCAA AAAAAACCCA
117401 AAAAAACAAA ACTCTTTTTC ATTATACCGG AACGTCAGCT TTATGGAGTC
117451 GGGGATTTTT TCTGTTTTAT TCACTGCTGT TTCCCTAACA TCTAGAATAG
117501 TGGCTGGCAC GATAGGCACT CAAGTATTGA TTTAGATGAG TCTATTTTAT
117551 TTTCTTTTAA ATTTTTAATT TTTATTAGAG GTGGGGTCTG GCTTTGTTGC
117601 CCAAGCTGGT CTCAAAACTC CTGGCCTCAA GCGATTGTAC TGCCTCAGCC
117651 TCCCAAAGGG CTAGGATAGG CATGAGCCAA CATGCCTGGC TTGTCTTATT
117701 TTTAACAAGC ACTTCTGGTG ATTCTGATGG ACAATCAGGC TTGGGAAGTT
117751 CTAACCTAGA GGACCTACAG TTGTCTTGGG GTAGAAGCCA AGGCTATCCT
117801 GGTTTTTAGA ATCAGTGCCT TACTGGGCAT CTCTGAAGAG TAAAAGTCAG
117851 GGACAGAGTT ACATTTTTGG ACAAAACCAG ATGCTGTGAA TGGACTCTTG
117901 GTCACAACCT GGGTGGCGAC TTGGTCCTTA ACTTCTTCAT CATTTTCTGC
117951 TGACCCTGTT CTTTGGTTCA CAGCAAGTCA CCTGATAAGA AGACTCAAAG
118001 ACTGCTAGTT TGTTACTTTA GATGATGCTT TTGGAACCTC TTGGTACCAT
118051 TTTAACAATC CAAACGTATT TTATGAAAGC ACTCAAGTCC TGGGTCTTTA
118101 TTGTATCTTT AAGCTCTAAC AGCATGATGA TTGAATAAGC TGTGGTTGGC
118151 CACACACAAG CCATCTTCCC CATGGCCTCC ATTCATACTA GAATGAGCAG
118201 CTATACCCCA GTAGTATAGT TTGGGATAT GGGTAACATC TTGGGATAGC
118251 CACATTTACT TAGTAAATGT CTGGCTTACA TTCTCCTAAT GGTGCACTGT
118301 TGGAATTTTT GGTGTGGTAA CCTGGAATAG TGTTGGTGGG TCAAGTTTGA
118351 TTAGCATCTT TGATAAGGAC CCGGTCTATT TAGAGGTTTG TCATTGAGTG
118401 TGTCTGTTTT GGCCTCATGT TGTGAAGCAT GCTGTGTAGC AGCTGTTGTA
118451 ATTTTTGTTG CTTGTTTTCT CAATCAACCC TGGTTTTGAA GAAATGGGAA
118501 GTTGTTCCAC TCTTAGACTG ATCTGACTTG GGAGGGGATT TCAGTTCAG
118551 GAAGTTGGAT CTTCTGAATG GAAGCAAAGA ATACATGTCT TTTTGCCACT
118601 TTACAAGCTG GCTCTTGTTT TCTGAACTAT TTTACTGGTC ATTGCAAATA
118651 GAATGTCAGG AGTAGCTGCC AAATACTAAG TTGTGTTCAG TTTGTCAGTT
118701 CTTAAGAGTT GCCGGTGGCT GCTCTGCTAT GCGTATGACT TTCTCAGCCT
118751 TAAACTTACA AGCCATACTG TTTTTTTCAC ATCTTTAATA CAGCCATAGG
118801 AAATTTATAA CTGTGGCGTG TCGTCATAAA TATGCATTGT TCTTATTTTA
118851 AGACATTTCA GTACTAAAAG TATAAGTACT TCTGTTATTA TCTGTGAATT
118901 TCTTTCCTTC TTCTTTTTTT GGATATTTAA GACCTTTTCG ATGTCAATAT
118951 ATATTTAAAA CAGACATATA AATTAGCATT CACCCACATA CCCAGGGCCT
119001 ATGGAGAACC AGGTTGGGAT GAGTGGGTGA GCTACAGGCA GCCAGGTGGC
119051 TCCTGTGGGC TCCTCGAGGA CTGGGGTGAG TAACTAATGT CTGCTAGGAA
119101 CTTGGGGGAA AGAAGGTGTG TATGTTAGGT GCTGCCCCCT TCTAAGTGTT
119151 CCTCTTGTTC ATAATTGAGT TTTTTTTTTT TTTTTTTTTT TTTTAGAAGG
119201 AGTCTCGCTC TGTTGCCAGG CTGGAGTGCA GTGGTGTGAT CTCAGCTCAC
```

FIGURE 3SS

```
119251 TGCAACCTCT GCCTCCCGGG TTCAAGTGAT TCTCCTGCCT CAGCCTCCCG
119301 AGTAGCTGGG ACTACAGGCA TGCACCACCA TGCCCAGCTA ATTTTTGTAT
119351 TTTTAGTAAA GACGGGGTTT CACCATGTTG GCCAGGGTGG TCTCGATCTC
119401 TTGACCTTGT GATCCGCCTG CCTCGGCCTC CCAAAGTGCT GGGATTACAG
119451 GTGTGAGCCA CTGTGCCCAG CCCATAAATC AAAATTTTTT CAGCAATTGT
119501 TATACAAGTG GAACCTTACT CTTCAAATGC AATTGTCCAG TGTCTGGCTT
119551 AATGTCTGCT GTTGTCAGAA ACCATGTGAA TGGAGTAGAT TCCCAGGTTA
119601 TAAGGAGCCC CCAGGGAGGA TGCGCGAGTC ACTGGCTTCT CCAGGGGTCT
119651 CTGGTTTGGG GTTGCCTTGG TGCTGGGCAC ACTTCCTGGA GATTTTACTG
119701 GACCAGCCTG AGGCCTTTGG GGCTCTGTGC AGATGCTCTA CTTCTGACTT
119751 GTCTAGAGCT TTCTTCTAAT TCTGGACTAA AAGCAAGCAG GAGTTTGGAG
119801 GATGATGGTG AGAATTCACA TCCCCGAGTT GGCTTTTGGA ATGCAGTAGT
119851 TTGTGAGATT TAGTGTTTTT TTTAAGAAGT ATATTCAGAT CTTGCCTTTT
119901 TCCCAGAAAG CATATGAGAC AACTTCCAAG ACATTTATAG CATGGCTAAT
119951 AAAATGGGAA ATCAGGGCGA AGGACAGGAG AACTCAATAA GGGTTAACAT
120001 GGCTACAGCG ATTGTCTAAA TGGGTTCTTT TTGCTGGCCA GAGCAGAAAG
120051 GATCATGCAG TAAAGTGGGG GGGAAGAAAG GGAATTGAAT GGTAGGTGAA
120101 GACTTCATGT TGGTGCCAGG CACTGTGCCA GGCCCTCCTA GGACCTTGTC
120151 TTACTCAATC CTCACACAGT GCTGCAAGAG GATTAGTCTT ATCCCTGTTT
120201 TAGAGAGGAT GAAACTGAAA GGCAGCGAGG TGAAGTCACC AGCAGGAGGC
120251 TGAAGCCGCC CAGGCTAACT GGCCTTATAG CTACCTAGGG ACTCAGGAAT
120301 ATCACACCTG TTTATCATCA AAAGGAGAAA GGATTTCAGT TCCTTGGGGT
120351 AGAAGAGTTT CTTTTTGCTA ATCAAACATT TTACTTGAGG CTTCATATTC
120401 TTCTTCAAGA TTTTTTTCCT GTGTATGTAC CAACACATGT AATAATTCCT
120451 TGTTTATTTC AAAAAAGGGG TTGTACTTTA TTCTTTACAA GATTTCACTT
120501 TATATTGTCA TGGACAATTT TCCATGGCAG TATGAATAAA TGGAATCTGT
120551 TTGTTTTTAA TATCTTTGTC TTATCCCATT GTTTACATAT GTCATATTTT
120601 AGCCAGTCTC TAACTGATGG ATAGCTGAAT GATTTCCATG TTTTTTTCCC
120651 CTGTTACAAA CAATACTGCA AGGAATCTAT TTATCTTTCT ATTTATCTGC
120701 AAACTATTGT AAGTACCTGT AAATTGTTAG AAGTGGAATT ACTAGGTCAA
120751 AGGGGATATT TTCACATTTA AATTTTGAAT AGAGGCTGTC AGTTGCCTTC
120801 CACACTGACT ATAAAAGGAA AAGATTGTAT CACATTTATT GCAAGCCTTC
120851 TGTATTCTGC TGGGTGCTGA GGGGAATACA GAAAGGATAT AAGAGTGGTT
120901 GCCCTCTAGG AATATCCGTC TACACTGTAC CTAATCCTAG GGAATGTCTG
120951 GGGTGTCAAC TTGTGGGTGG GAAAGTGGGT GGATTTAATT CAACTGTTCA
121001 AGCTTGCCTT GCAAACACTG TGCATGGTGT CTGGGACTAG TCTTTCATTA
121051 TATTGATTCC CCTGGGTAAC AGATGTAATT TCCTTAGGGC AGGGACTTCA
121101 TCCTACATGA CTTACAGCGT GCCTTACACA TCTTCTTTGC TTTGTGGAGA
121151 CCTTGTTATT ATAACACGTC AGGTGATATT CGAGGATCTA ATTGAGGCAT
121201 TCCCTATTTT TGGGTGTGTG AAGAATTAAT AACTTTGGCA TTCTATACAG
121251 GTCATGGAAT ATCAGCCTGG AGGGGACTTG CTGTCACTTT TGAATAGATA
121301 TGAGGACCAG TTAGATGAAA ACCTGATACA GTTTTACCTA GCTGAGCTGA
121351 TTTTGGCTGT TCACAGCGTT CATCTGATGG GATACGTGCA TCGGTAAGTG
121401 AGACTCTGGT AGCATTTTTA TGCTGAGGAT TTTCCTGTGT CGCATAAGAG
121451 TTCCTGCATG GAAATGAGTG GATGAGTGAT TTCAAGATCA AGATAACGCC
121501 NNNNNNNNNN NNNNNNNNNN NNNNNNNNNN NNNNNNNNNN NNNNNNNNNN
121551 NNNNNNNNNN NNNNNNNNNN NNNNNNNNNN NNNNNNNNNN NNNNNNNNNN
121601 NNNNNNNNNN NNNNNNNNNN NNNNNNNNNN NNNNNNNNNN NNNNNNNNNN
121651 NNNNNNNNNN NNNNNNNNNN NNNNNNNNNN NNNNNNNNNN NNNNNNNNNN
121701 NNNNNNNNNN NNNNNNNNNN NNNNNNNNNN NNNNNNNNNN NNNNNNNNNN
121751 NNNNNNNNNN NNNNNNNNNN NNNNNNNNNN NNNNNNNNNN NNNNNNNNNN
121801 NNNNNNNNNN NNNNNNNNNN NNNNNNNNNN NNNNNNNNNN NNNNNNNNNN
121851 NNNNNNNNNN NNNNNNNNNN NNNNNNNNNN NNNNNNNNNN NNNNNNNNNN
```

FIGURE 3TT

```
121901 NNNNNNNNNN NNNNNNNNNN NNNNNNNNNN NNNNNNNNNN NNNNNNNNNN
121951 NNNNNNNNNN NNNNNNNNNN NNNNNNNNNN NNNNNNNNNN NNNNNNNNNN
122001 NNNNNNNNNN NNNNNNNNNN NNNNNNNNNN NNNNNNNNNN NNNNNNNNNN
122051 NNNNNNNNNN NNNNNNNNNN NNNNNNNNNN NNNNNNNNNN NNNNNNNNNN
122101 NNNNNNNNNN NNNNNNNNNN NNNNNNNNNN NNNNNNNNNN NNNNNNNNNN
122151 NNNNNNNNNN NNNNNNNNNN NNNNNNNNNN NNNNNNNNNN NNNNNNNNNN
122201 NNNNNNNNNN NNNNNNNNNN NNNNNNNNNN NNNNNNNNNN NNNNNNNNNN
122251 NNNNNNNNNN NNNNNNNNNN NNNNNNNNNN NNNNNNNNNN NNNNNNNNNN
122301 NNNNNNNNNN NNNNNNNNNN NNNNNNNNNN NNNNNNNNNN NNNNNNNNNN
122351 NNNNNNNNNN NNNNNNNNNN NNNNNNNNNN NNNNNNNNNN NNNNNNNNNN
122401 NNNNNNNNNN NNNNNNNNNN NNNNNNNNNN NNNNNNNNNN NNNNNNNNNN
122451 NNNNNNNNNN NNNNNNNNNN NNNNNNNNNN NNNNNNNNNN NNNNNNNNNN
122501 NNNNNNNNNN NNNNNNNNNN NNNNNNNNNN NNNNNNNNNN NNNNNNNNNN
122551 NNNNNNNNNN NNNNNNNNNN NNNNNNNNNN NNNNNNNNNN NNNNNNNNNN
122601 NNNNNNNNNN NNNNNNNNNN NNNNNNNNNN NNNNNNNNNN NNNNNNNNNN
122651 NNNNNNNNNN NNNNNNNNNN NNNNNNNNNN NNNNNNNNNN NNNNNNNNNN
122701 NNNNNNNNNN NNNNNNNNNN NNNNNNNNNN NNNNNNNNNN NNNNNNNNNN
122751 NNNNNNNNNN NNNNNNNNNN NNNNNNNNNN NNNNNNNNNN NNNNNNNNNN
122801 NNNNNNNNNN NNNNNNNNNN NNNNNNNNNN NNNNNNNNNN NNNNNNNNNN
122851 NNNNNNNNNN NNNNNNNNNN NNNNNNNNNN NNNNNNNNNN NNNNNNNNNN
122901 NNNNNNNNNN NNNNNNNNNN NNNNNNNNNN NNNNNNNNNN NNNNNNNNNN
122951 NNNNNNNNNN NNNNNNNNNN NNNNNNNNNN NNNNNNNNNN NNNNNNNNNN
123001 NNNNNNNNNN NNNNNNNNNN NNNNNNNNNN NNNNNNNNNN NNNNNNNNNN
123051 NNNNNNNNNN NNNNNNNNNN NNNNNNNNNN NNNNNNNNNN NNNNNNNNNN
123101 NNNNNNNNNN NNNNNNNNNN NNNNNNNNNN NNNNNNNNNN NNNNNNNNNN
123151 NNNNNNNNNN NNNNNNNNNN NNNNNNNNNN NNNNNNNNNN NNNNNNNNNN
123201 NNNNNNNNNN NNNNNNNNNN NNNNNNNNNN NNNNNNNNNN NNNNNNNNNN
123251 NNNNNNNNNN NNNNNNNNNN NNNNNNNNNN NNNNNNNNNN NNNNNNNNNN
123301 NNNNNNNNNN NNNNNNNNNN NNNNNNNNNN NNNNNNNNNN NNNNNNNNNN
123351 NNNNNNNNNN NNNNNNNNNN NNNNNNNNNN NNNNNNNNNN NNNNNNNNNN
123401 NNNNNNNNNN NNNNNNNNNN NNNNNNNNNN NNNNNNNNNN NNNNNNNNNN
123451 NNNNNNNNNN NNNNNNNNNN NNNNNNNNNN NNNNNNNNNN NNNNNNNNNN
123501 NNNNNNNNNN NNNNNNNNNN NNNNNNNNNN NNNNNNNNNN NNNNNNNNNN
123551 NNNNNNNNNN NNNNNNNNNN NNNNNNNNNN NNNNNNNNNN NNNNNNNNNN
123601 NNNNNNNNNN NNNNNNNNNN NNNNNNNNNN NNNNNNNNNN NNNNNNNNNN
123651 NNNNNNNNNN NNNNNNNNNN NNNNNNNNNN NNNNNNNNNN NNNNNNNNNN
123701 NNNNNNNNNN NNNNNNNNNN NNNNNNNNNN NNNNAAAAAA CTGATGCTAG
123751 TGAAAATGCA TAATTTAAGA GGTTAGAGAA GCTGCTCTTC AAAATGCCCC
123801 CCAAGTCTGA GAGTTAAATC CTTTACATAA AGGACAATAT GTAAAATTTT
123851 CTTTTTTCTTT TTTCTTTTTT TTTGAGACGG AGTCTCGCTC TGTCCCCCAG
123901 GCTGGAGTGC AGTGGCGCGA TCTCGGCTCA CTGCAAGCTC CGCCCCCCTG
123951 GGTTCACGCC ATTCTCCTGC CTCAGCCTCC CGAGTAGCTG GGACTGCAAG
124001 CGCCCGCCAC CATGCCCAGC TAATTTTTTG TATTTTTAGT AGAGACGGGG
124051 TTTCACCGTG TTAGCCAGGA TGGTCTCGAT CTCCTGACCT CGTGATCCAC
124101 TCGCTTCGGC CTCCCAAAGT GCTGGGATTA CAGGCATAAG CCACTGCGCC
124151 CGGCTCTTTT TTTTCTTAAA CTGCTTCCAG AAAAGTGGAT ATTATTAGGT
124201 TGATGTTAAG AAAAGGCTTG GAGTTGCATT AACTTTTTGC TTTCTAGCAT
124251 CTGGCCTGTC TGTTCTGCAG ACCTGAGACC TACTTGAGAT AATTTTCTTG
124301 GTGTTCAGGC CCTTGGAAAA ATAAGTTCCC TATGTTGTCC AGTGTCAAAG
124351 TTTCTCAACC TCAGCACTAT TCTTTTTTTC AGGTTATTTT CTTGTAATCT
124401 GTTCACTTGA TCATTACATT AAGAATTAGA TTATATTGCT ATAACTACAA
124451 AGCATTTTAT GTTTTAAAAA TTATGTACAA TTTAGAAACA GGCATGAAAA
124501 CTTAGGTATT AAATTTAGTG GAATAAAGCA CAGAAAAAAA GTTAAAATAA
```

FIGURE 3UU

```
124551 TGCAGTTTTA TCACTTAGGA TTAAACATTT ATATGGGCCG GGTGTAGTGC
124601 CTCACACCTG TAATCCCAGC ACGTTTGGAG GTCGAGGCGG GAGGATTGCT
124651 GGAGTTTGAG ACCAGCCTGG GCAACAAAAT GAGACCTAGT CTCTACAAAA
124701 AATCAAAAAA TTAGCCAGAC ATGGTAGTAC ATGCTTGTAG CTCCAGCCAC
124751 ATGGGAGGCC AAGACAGTAG GATCGCTGGA GCGAAGGAGG TTGAGGCTGC
124801 AATGACCGTG TTTGCACCAT TGCATTCCAG CCTGGGCGAC AGAACAAGAC
124851 CCTGTCTTAA AACAAATTTA TATGCTGCAT TCGTGAAATT AAAAAAAAAT
124901 CATGGATTTA GAAATAAATT GAAGCAAGGT ACATTGACAG TGTAACCTCA
124951 GCACTACTGA CATTTTGATC TGAATAATTC TTTGTTGTGG GGGATGCGCT
125001 GTATAAGATG TTTAGCTGCA TCCCTGACTC CTACCTCCTA GATGCCATTA
125051 GCACCCTCCC CTCCAGATGT GATAACCAAA AATGTCTCTA GACATTGCCA
125101 GATGTGCCTG GGGTAGGAGG GTTGGGGGAA GTGGGGTTTG AGAACCCTTA
125151 GTTGATCATG CCTGCAGTAG GTTGAGAAGC ATCAGAAAGC TAATTAATTA
125201 GACAGGAATA TGTGTTTGCA GTAAGAAAAC CTCAGCAAAC TAATCAAGTT
125251 CCAAAGTTAC TGCTTGGTAA ATAAATAGGA ATTAAGAATA AGACCCTATC
125301 TCTGTGTCTG GGGTCATTCT CTTCGGAGCT CTTGGTGGAG AGACAGGGTT
125351 CCCAGTTTCA ATTTTTTAGT GCTTCAGACT GCCCTTTTCA GTTATAATTG
125401 TAACAACCTT CACTCCAGGT GGGGAGCCTC CCAGGTTTAT TTACAACAAG
125451 GCTCAATCTC TGATTATTTT GGTCAAGGAG ATATGACACT CTATACCACA
125501 CACTTGAGAA TATTGCCTCT CTTTTTCTCT TGAGCTTTTA GGGTTGGAAC
125551 GTGACAGGCA GATAAGGAAT TTTTTGCATT AAGTGCAAAG TCCTTTTTCT
125601 TATAGAAGAG CAATAATCTG CACACTAGAT CAAGTCAAGT GTGGATATAA
125651 AATTATAATT TTTGGGGGGA TATTTTTAAT AGTGGTTTTG GGTTAAACAT
125701 ATTTCCTTTA AATGAAATGT CTGTAGGCCT AAAGTAGGTT CTAAATGTTG
125751 CCTGTACTCA TAGTATACCA TATAAAATAT AATCCACATT TACTGGAACT
125801 ACCATATATT ACTTACCCCA AATCAATCAA TCCCTTCCCT ATCACCCCCA
125851 CGTAAGATCT TCGTATTTTG GATACCTGTG AATCTTAGAT CTGTTCAGTT
125901 TTCCATTATC CATTGTCTTA TTTCAAGCTT CTCATTCAGA ATGTTGCTTT
125951 GGAGTATTTT CTGTTAGTAA ACACAGGGCC TAGTGACTCT AGGACCTGCT
126001 GTGTGACTTA GGTCACCCAC TTCACTTTAT TAGAATCTCA AAGAATGGTG
126051 AACAGCTGAG TTCCAATCTG TCTCATTTGG CTCTCATGAA AACAGTCATA
126101 AGGAGATTGT AGATAAACCA CATTATATAG CATAGTAAGT GATAATCAAC
126151 CCCATTTGGC AGTTGCAACC CCACAAGAGA TAGCCCTTTT TAGATTTGTG
126201 TAGGAGTGAA AAGCTTTATT TTCCACAAGA GGAACGACAT AGTAAGAACT
126251 CCTTTCCCCC CTGCTTCTGC AGGTATATGC TTATGCCCTA GGCAACTTGA
126301 TGGGTAAAGT TAGGTTTAAA TAGTTTTATT TGTAAGCTCT TCTCTTCTCT
126351 TCTCTTCTCT TCTCTTCTCT TCTCTTCTCT TCTTTTCTTT CAAGACAGAG
126401 TCTTGCTCTG TCACCCAGGC TGGAGTGCAG TGGGCGACCT TGGCTCACTG
126451 CAACCTCCGC CTCCTGGGTT CAAGAGATTC TCCTGCCTCA GCTCCCCGAG
126501 TAGCTGGGAT TACAGGTGCC CGCCACCATG CCTGGCTAAT TTTTGTATTT
126551 TTAGTAGAGA TGGGGTTTCA CCATGTTGAA GCATTTTAGG AAAGGGGTTA
126601 GGAGGAGGAA GACANNNNNN NNNNNNNNNN NNNNNNNNNN NNNNNNNNNN
126651 NNNNNNNNNN NNNNNNNNNN NNNNNTCTC CCCCTTTCTC CCAAAATATG
126701 GCAGACTCTT CTGTCCCCTA GTCATTCTCA TATAGTCTTC TGAACTTGTT
126751 TATTTTCTTC CCTGTTAATA CAGTAAAAAT TAACTAAGTT GGCCAGGAGT
126801 GGTGGCACAT GCCTGTAATC CCAGCACTTT GGGAGGCCGA GGCGAGCAGA
126851 TCACCTGAGG TCAGGAGTTT GAGACCAGCC TGGCCAACAT GGTGAAACCC
126901 TGTCTCTACT AAAAAAAAAT TGTAAAAGTT AGCTGGGTGT GGTGGTGCGC
126951 ACCTGTAGTC CCAGCTATTC GGGAGGCTGA GGCAGGAGAA TTGCTTGAAC
127001 CCAGGGGCTG GAGGTTGCAG TGAGCCAAGA TCGCGCCACT GCACTCTAGC
127051 CTGGGCGACA GAGCAGTCTT TAAAAAAAAA AAAAATTAA CTAAGTTAAG
127101 TAGTACTTGG GCCCTATCAG ATAGTGTCCT CCTGCAGGCA GGCTGGGCCC
127151 CTACTACAGT TTCACTTTTA ATATCTCACC GAGATTAGCT GACTGAATTG
```

FIGURE 3VV

```
127201 CCACCAGAGG AGAGTGAAAG CATATTGCAA AATCATAATC AGGACATGTG
127251 AGATTATGTG TTGAACAGGT TTAATGTGCT TGGGGGTCAG TGACTAATGG
127301 GAACTTAGCA GTCATTAACT GTCATTAAAA ACGTTTGTTA ATTACTATTA
127351 CACACTTAGA GATTTGTTAA TTAACAAAGA GTAATGCCTT TGCTAATCAC
127401 TATTATGCAC TTAAGAGGAA GCCAGTGGGT ATTTTTCCCT TCATAGCTTT
127451 CTAGTACAAA TTAATAAAAT TTAGAAAATT AGAAAATGAT TGTGCATAAA
127501 TGTGTATAAT CATGTATCTG TTAGGGGCA  AAAATTAGTT GGGGAATTAT
127551 CTTTCTTTGA TAAGTCTTAT CATTAGTTTG AAAATGGGGC ATTGGCAATT
127601 CATACTGTTT GGCTGGGTTG TCCTGAGAAA CACTCCCCAG TCAATTCTGT
127651 TTTTGCAACT CTTTGGTTGT GAACAAGTGA CTGCCCTGTG AGCTGCAAAT
127701 AAGGAGAACT GAATATTCCT GAACAGTCTG TGGCAATAAA AATGAAATCC
127751 AGTAAGTGCA AATGGTATGT ATTCAACAAT TGCGTAGTTA GGTCCTGCAA
127801 GGTAATTAGA CATAAAGGAT AAGTATTTAA TCAACAATAT AGTAGCATTT
127851 TCATTACCTA GTCAAATCAA GATGTTACAG TTTTCCTTCT CTTGTTTTGT
127901 TATTTAAAAA ATATCTATTG TGGCCAGGCT CCGTGGCTCA CACTTGTAAT
127951 CCCAGCACTT TGGGAGGCCA AGATGGGTGG ATCACGAGGT CAAGAGATCG
128001 AGACCATCCT GGCCAAACAT AGTGAAACCC CGTCTCTACT AAAAATACAA
128051 AAATTATCTG GGTGTGGTGG CATGCACCTG TAGTCGCAGT TACTCGAGAG
128101 GCTGAGGCAA GAGAATTGCT TGAACCTGGG AGGAGGAGGT TGCAGTGAGC
128151 TGAGATCGCA GCACTGCACT CCAGCCTGGT GACAGAGCGA GACTCCATCT
128201 CGGAAAAAAA AAAAAATCTA TTGGTTATTG TTGGTGCATT TTAACCAAAA
128251 CCCTTTAGTT TAACCCTAAC CTGTGCTGAG CTCTTTAACA TTTACATACA
128301 TATTAAAAAA CAGAATCAGC CCAGATTTCC CAACATATTA AGTCTTCTCC
128351 TTGACTTAAG CTACTTTCAG TTCTTCAAGC TTAAGTCACC CTGTGGTTTT
128401 GTCTTAGGCC AAATATTTTC CCCTTTGTCT CCCCTTCTGT CTATCAAGCC
128451 AAGCCTGCCT GTGGGTTTTG GATAGTGTGA CCATCTGGCT TTCTTGAAGG
128501 GGCACTTACA GGGGAAGTTT TATTGCCCAA ACCGGTGGAC AATCCATGTC
128551 AGGAATGATT ATATCACACT GCTTTCTGGG TTTAGGGCTT GGAAAAACCT
128601 GTATCAGAGC GTGGGCCCTA GGGAAGAGGT AAAAAGAGAG GAGAGGGAAG
128651 AATAGGTCTG TTTCATATAA CGAGAAAGTC TCATGGCAGA GGAATGGATG
128701 AGATTCAAGT TACAGGCTGG AAGAGCTTCA TCCAGAATCA GCCCCGGGGA
128751 GAGGAGACCT CATCACGTCC TCACTAAACA TTCACTTTCC TCTCCACACC
128801 CAGTTAAAGT AAAGCAAATT TACTTCCTTG GTGAAAAGCC CAGCCTTCAA
128851 GGTATGTGGA CTTACCCACA AAATCTCTTG GCTCACTCAG TTTCACTTAC
128901 CATCGTTTAA TGAGGAAAAA GTTCTTTTGT ACCATGTAAC TGCTGACCTG
128951 AGAGAAGCCC ATTATGATAT AGAGTTATAG GACAGCTGGC CAACACACTA
129001 TATAGCTAAA ATCAGGGCCT CTCTGTTTTG ATGGGAGAA  AAGTTAGAGA
129051 AGGAATCTTT AGACTTCAAA TTTCATGGCT CAGTAAAACG TCAAAATAAT
129101 TTTGAAGACC AAAGGGGTTG CCAGCTTACT AGGCTGCCTA GACAGGGTG
129151 GGTATGAGGG GAAGAAAGCC TGCTTCTTTC ATCAACAGCA TATCCAGAAA
129201 CAAAGGACAT TTAAACACTA AAAAAGTCAG AAGGACAAAT TCTCAGAAAA
129251 AAAGGACAGT CCTTTAAATG GGTTACATTT AGCTTTATAA AATGCCCTCC
129301 TGTATTGTCC TAATCTTTCT TTGCCAAGGT CAAGTGCTTG GGTGCCATTG
129351 GATTATAAGC CCCTGGGTTT CTGAACGGTG GGGGAGGGAA CCACAGGAAC
129401 AAGGGTTAGG GGTGAGGAAA AAGAACTCAT TAACCTTGGG CCCTGGGTGG
129451 AAGTTAATTA TCATGTCTTG CCCTGTGGGT GGGTTGAAGT AGGAACGTTA
129501 ATTCCAAAGG CAGTTTTCCA AATTTTTGAA CTTGAGATTT GTAATATTAT
129551 CTTGCCAGTT AGCCACCAGT TCTCTTCTCT TTTTTCTTTT CTTTTCTTAC
129601 AGTCTCGCTG TCACCCAGGC TGCAGTGTAA TGGCGCAATC TTGGCTCACT
129651 GCAACCTCCG CCTCCCAGGT TCAAGCGATT CTTGTGCCTC AGCCTCCCGA
129701 GTAGCTGGGA CCACAGGTGT GCACCACCAC ACCTGACTAA TTTTTGTATT
129751 TTTAATAGAG ATGGGGCTTC ACCATGTTGG CCATGCTGGT CTCAAACTCC
129801 TGGCCTCAAA TGATCCACCC ACCTTGGCCT CCCAAAGTGT TGGGATTACA
```

FIGURE 3WW

```
129851 GGCATGGGCC ACTGCACCTG GCCAACTGCC AGTTTTCTAG TAATGGTTAG
129901 GTTGATATTT TAGATTCATT TTTAGAGTTT ATTATCATTT TGCTGTTATC
129951 ATAAGAGAAG TTCCATCATG TCAATAACTT GTATTAGGAA AGACATCTTC
130001 CATTCCCGGT ATATCCAACT CTCATTCGTA TAACTGAAGG CTGTGTGTAT
130051 ATCATCAACA ATTCTTGCCC TTTTGCCCTT GGATTGCATT ATATGCTGTG
130101 TGCTTTTTTT TTTTTTTAAA TTAGTAAAGC GTTTGCATTT CCTGACAGTG
130151 TGCCACTTGA CAGCTGGTTT AAGTGCCTGG GAGAATAGTA ATCAGTGGCA
130201 AATCAGCTTG TGTCTGAAAT GTGGCTGTTG GCAGTCTACT TGAGGATAAT
130251 TGAAAGTTTG CTGTATTCGT TTTATTGATG GGATTCTAGG TGAATGCCAA
130301 ACTCCGATT GGGACCCCAG ATTACATGGC TCCTGAAGTG CTGACTGTGA
130351 TGAACGGGGA TGGAAAAGGC ACCTACGGCC TGGACTGTGA CTGGTGGTCA
130401 GTGGGCGTGA TTGCCTATGA GATGATTTAT GGGAGATCCC CCTTCGCAGA
130451 GGGAACCTCT GCCAGAACCT TCAATAACAT TATGAATTTC CAGGTAAAGA
130501 GTCCTTAGAA GATTTCGAAG TCACATTGAG AAACGTTATT TAAAAATTGT
130551 GCGAATGAGG CTGGGCCGTG GGTGGCTCAT GCCTGTAATC CCGGCACTTT
130601 GGGAGGCCGA GGTGGGTGGA TCACGAGGTC AGGAGATCGA GACCATCCTG
130651 GCTAACATGG TGAAACCCCA TCTCTACTAA AAAATACAAA AAAATTAGCC
130701 AGTTGTGGTG GTGGGCGCCT GTAGTCCCAG CTANNNNNNN NNNNNNNNNN
130751 NNNNNNNNNN NNNNNNNNNN NNNNNNNNNN NNNNNNNNNN NNNNNNNNNN
130801 NNNNNNNNNN NNNNNNNNNN NNNNNNNNNN NNNNNNNNNN NNNNNNNNNN
130851 NNNNNNNNNN NNNNNNNNNN NNNNNNNNNN NNNNNNNNNN NNNNNNNNNN
130901 NNNNNNNNNN NNNNNNNNNN NNNNNNNNNN NNNNNNNNNN NNNNNNNNNN
130951 NNNNNNNNNN NNNNNNNNNN NNNNNNNNNN NNNNNNNNNN NNNNNNNNNN
131001 NNNNNNNNNN NNNNNNNNNN NNNNNNNNNN NNNNNNNNNN NNNNNNNNNN
131051 NNNNNNNNNN NNNNNNNNNN NNNNNNNNNN NNNNNNNNNN NNNNNNNNNN
131101 NNNNNNNNNN NNNNNNNNNN NNNNNNNNNN NNNNNNNNNN NNNNNNNNNN
131151 NNNNNNNNNN NNNNNNNNNN NNNNNNNNNN NNNNNNNNNN NNNNNNNNNN
131201 NNNNNNNNNN NNNNNNNNNN NNNNNNNNNN NNNNNNNNNN NNNNNNNNNN
131251 NNNNNNNNNN NNNNNNNNNN NNNNNNNNNN NNNNNNNNNN NNNNNNNNNN
131301 NNNNNNNNNN NNNNNNNNNN NNNNNNNNNN NNNNNNNNNN NNNNNNNNNN
131351 NNNNNNNNNN NNNNNNNNNN NNNNNNNNNN NNNNNNNNNN NNNNNNNNNN
131401 NNNNNNNNNN NNNNNNNNNN NNNNNNNNNN NNNNNNNNNN NNNNNNNNNN
131451 NNNNNNNNNN NNNNNNNNNN NNNNNNNNNN NNNNNNNNNN NNNNNNNNNN
131501 NNNNNNNNNN NNNNNNNNNN NNNNNNNNNN NNNNNNNNNN NNNNNNNNNN
131551 NNNNNNNNNN NNNNNNNNNN NNNNNNNNNN NNNNNNNNNN NNNNNNNNNN
131601 NNNNNNNNNN NNNNNNNNNN NNNNNNNNNN NNNNNNNNNN NNNNNNNNNN
131651 NNNNNNNNNN NNNNNNNNNN NNNNNNNNNN NNNNNNNNNN NNNNNNNNNN
131701 NNNNNNNNNN NNNNNNNNNN NNNNNNNNNN NNNNNNNNNN NNNNNNNNNN
131751 NNNNNNNNNN NNNNNNNNNN NNNNNNNNNN NNNNNNNNNN NNNNNNNNNN
131801 NNNNNNNNNN NNNNNNNNNN NNNNNNNNNN NNNNNNNNNN NNNNNNNNNN
131851 NNNNNNNNNN NNNNNNNNNN NNNNNNNNNN NNNNNNNNNN NNNNNNNNNN
131901 NNNNNNNNNN NNNNNNNNNN NNNNNNNNNN NNNNNNNNNN NNNNNNNNNN
131951 NNNNNNNNNN NNNNNNNNNN NNNNNNNNNN NNNNNNNNNN NNNNNNNNNN
132001 NNNNNNNNNN NNNNNNNNNN NNNNNNNNNN NNNNNNNNNN NNNNNNNNNN
132051 NNNNNNNNNN NNNNNNNNNN NNNNNNNNNN NNNNNNNNNN NNNNNNNNNN
132101 NNNNNNNNNN NNNNNNNNNN NNNNNNNNNN NNNNNNNNNN NNNNNNNNNN
132151 NNNNNNNNNN NNNNNNNNNN NNNNNNNNNN NNNNNNNNNN NNNNNNNNNN
132201 NNNNNNNNNN NNNNNNNNNN NNNNNNNNNN NNNNNNNNNN NNNNNNNNNN
132251 NNNNNNNNNN NNNNNNNNNN NNNNNNNNNN NNNNNNNNNN NNNNNNNNNN
132301 NNNNNNNNNN NNNNNNNNNN NNNNNNNNNN NNNNNNNNNN NNNNNNNNNN
132351 NNNNNNNNNN NNNNNNNNNN NNNNNNNNNN NNNNNNNNNN NNNNNNNNNN
132401 NNNNNNNNNN NNNNNNNNNN NNNNNNNNNN NNNNNNNNNN NNNNNNNNNN
132451 NNNNNNNNNN NNNNNNNNNN NNNNNNNNNN NNNNNNNNNN NNNNNNNNNN
```

FIGURE 3XX

```
132501 NNNNNNNNNN NNNNNNNNNN NNNNNNNNNN NNNNNNNNNN NNNNNNNNNN
132551 NNNNNNNNNN NNNNNNNNNN NNNNNNNNNN NNNNNNNNNN NNNNNNNNNN
132601 NNNNNNNNNN NNNNNNNNNN NNNNNNNNNN NNNNNNNNNN NNNNNNNNNN
132651 NNNNNNNNNN NNNNNNNNNN NNNNNNNNNN NNNNNNNNNN NNNNNNNNNN
132701 NNNNNNNNNN NNNNNNNNNN NNNNNNNNNN NNNNNNNNNN NNNNNNNNNN
132751 NNNNNNNNNN NNNNNNNNNN NNNNNNNNNN NNNNNNNNNN NNNNNNNNNN
132801 NNNNNNNNNN NNNNNNNNNN NNNNNNNNNN NNNNNNNNNN NNNNNNNNNN
132851 NNNNNNNNNN NNNNNNNNNN NNNNNNNNNN NNNNNNNNNN NNNNNNNNNN
132901 NNNNNNNNNN NNNNNNNNNN NNNNNNNNNN NNNNNNNNNN NNNNNNNNNN
132951 NNNNNNNNNN NNNNNNNNNN NNNNNNNNNN NNNNNNNNNN NNNNNNNNNN
133001 NNNNNNNNNN NNNNNNNNNN NNNNNNNNNN NNNNNNNNNN NNNNNNNNNN
133051 NNNNNNNNNN NNNNNNNNNN NNNNNNNNNN NNNNNNNNNN NNNNNNNNNN
133101 NNNNNNNNNN NNNNNNNNNN NNNNNNNNNN NNNNNNNNNN NNNNNNNNNN
133151 NNNNNNNNNN NNNNNNNNNN NNNNNNNNNN NNNNNNNNNN NNNNNNNNNN
133201 NNNNNNNNNN NNNNNNNNNN NNNNNNNNNN NNNNNNNNNN NNNNNNNNNN
133251 NNNNNNNNNN NNNNNNNNNN NNNNNNNNNN NNNNNNNNNN NNNNNNNNNN
133301 NNNNNNNNNN NNNNNNNNNN NNNNNNNNNN NNNNNNNNNN NNNNNNNNNN
133351 NNNNNNNNNN NNNNNNNNNN NNNNNNNNNN NNNNNNNNNN NNNNNNNNNN
133401 NNNNNNNNNN NNNNNNNNNN NNNNNNNNNN NNNNNNNNNN NNNNNNNNNN
133451 NNNNNNNNNN NNNNNNNNNN NNNNNNNNNN NNNNNNNNNN NNNNNNNNNN
133501 NNNNNNNNNN NNNNNNNNNN NNNNNNNNNN NNNNNNNNNN NNNNNNNNNN
133551 NNNNNNNNNN NNNNNNNNNN NNNNNNNNNN NNNNNNNNNN NNNNNNNNNN
133601 NNNNNNNNNN NNNNNNNNNN NNNNNNNNNN NNNNNNNNNN NNNNNNNNNN
133651 NNNNNNNNNN NNNNNNNNNN NNNNNNNNNN NNNNNNNNNN NNNNNNNNNN
133701 NNNNNNNNNN NNNNNNNNNN NNNNNNNNNN NNNNNNNNNN NNNNNNNNNN
133751 NNNNNNNNNN NNNNNNNNNN NNNNNNNNNN NNNNNNNNNN NNNNNNNNNN
133801 NNNNNNNNNN NNNNNNNNNN NNNNNNNNNN NNNNNNNNNN NNNNNNNNNN
133851 NNNNNNNNNN NNNNNNNNNN NNNNNNNNNN NNNNNNNNNN NNNNNNNNNN
133901 NNNNNNNNNN NNNNNNNNNN NNNNNNNNNN NNNNNNNNNN NNNNNNNNNN
133951 NNNNNNNNNN NNNNNNNNNN NNNNNNNNNN NNNNNNNNNN NNNNNNNNNN
134001 NNNNNNNNNN NNNNNNNNNN NNNNNNNNNN NNNNNNNNNN NNNNNNNNNN
134051 NNNNNNNNNN NNNNNNNNNN NNNNNNNNNN NNNNNNNNNN NNNNNNNNNN
134101 NNNNNNNNNN NNNNNNNNNN NNNNNNNNNN NNNNNNNNNN NNNNNNNNNN
134151 NNNNNNNNNN NNNNNNNNNN NNNNNNNNNN NNNNNNNNNN NNNNNNNNNN
134201 NNNNNNNNNN NNNNNNNNNN NNNNNNNNNN NNNNNNNNNN NNNNNNNNNN
134251 NNNNNNNNNN NNNNNNNNNN NNNNNNNNNN NNNNNNNNNN NNNNNNNNNN
134301 NNNNNNNNNN NNNNNNNNNN NNNNNNNNNN NNNNNNNNNN NNNNNNNNNN
134351 NNNNNNNNNN NNNNNNNNNN NNNNNNNNNN NNNNNNNNNN NNNNNNNNNN
134401 NNNNNNNNNN NNATTGCTTT ATTTTTCTAA ATAAATAGAC ATCTCCCCCC
134451 AAATCTCCAA GGTTCAGACC TTCTAATCAG TAATATATTT TCAGGGCATT
134501 CTTCCTTTTA TGCTTTTAGA AAGATGTAAT AGACTTTCTT TTAGATGCTG
134551 TTCAAGTACT TAATCTTTTC TTGTCTTGCC TTTTTATCTC TGTAATCTTC
134601 TTGAATAAGC AGTTAATTTT TTTTATTCAT GAACCTGCTG ATCATGTCTA
134651 AGAATGTATC TCCACTTAAG TAAGTCAGTG AATGGTGATT ACCTGAGTAG
134701 AGTTAAAGTA GTCCCCCACC CTCCTATCTG TGGCACATAT GTTCCAAGTC
134751 TCCCAGTGGA TGTGTGAAAC TGATGATAGT ACTGAAACCC ATCTACCTTT
134801 TTTCCTGTGC ATACATACCT ATGTTATATA AAGCTTAACT TATAAATTAG
134851 GCATAATATA TTTGACTCCC AGCTCCAGT GTAGTGGCTC TGCAGACTCA
134901 CAAAATGTAT TTGCTTTAAA AAATTCTTTT TTTTTTTTTT GAGACGGAGT
134951 TTTGCTCTTG TTGCCCAGGC TGGAGTGCAG TGGTGCGACC TCAGCTCACT
135001 GCAACCTCCG CCTCTTGGGT TCAAGCGATT CTCCTGCCTC AGCCTCCCAA
135051 GTAGCTGGGA TTATAGGCAT GCACCACCAC ACCCAGCTAA TTTTCTATTT
135101 TTCGTAGAAA CGGTTTTTCC ATGTTGGTCA GGCTGATCTT GAACTCCTGA
```

FIGURE 3YY

```
135151 CCTCAGGTGA TCTGCCTGCC TCGGCCTTCC AAAGTGCTGG GATTACAGGT
135201 GTGAGCCACC ACGCCTGGCC AAAAAATTCT TTTAATTTAA GTAAATCTTT
135251 ATTTATTTAC TTTTGAGACA GAGTCTCACT CTGTGGGCCA GGCAGGAATG
135301 CAGTGGTGTG ATCACGGCTC ACTGCAGCCT CGACCTCCCA TGCTCAAGCA
135351 GTCCTCCCAC CTCAGCCTCC TAAGTAGCTA GGACTACAGG TGTGTGCCAT
135401 CACACTCTGC TAATTTTTTT GTATTTGTAG AGACGCGGTT TCACCAGGTT
135451 GCCCAGGCTG GTCTTGAACT CCTGAGCTCA AGTGATCCTC CTGCTTTGGC
135501 CTCCCAAAAT ACTGGGATTA CAGGCGTGAG CCATTGCACC CAGCCCTAAT
135551 TTTAATAAAT CTTTTATTTT GGAATAGTAT TAGATTTATA GAAAAGTTGC
135601 AAAGATAGTA TGGAAGAGTT CCCACATACC CTTCACCCAG TTTTCCCCAA
135651 NNNNNNNNNN NNNNNNNNNN NNNNNNNNNN NNNNNNNNNN NNNNNNNNNN
135701 TATTTATTTA TTTATTTTTT GAGACACAGT CTTCCCGTCG CCCAGGCTGG
135751 AGTGTGGTGG CACGATCTCG GCTCACTGCA ACCTCCGCCT CCTGGGTTCA
135801 AGTGATTCTT CTGCCTCAGC CTCCGAGTAG CTGGGACCAC AGGTGTGCGC
135851 CACCATGCCC GGCTACTTTT TGTATTTTCA GTAGAGACAG GGTTTCACCA
135901 TGTTGGTCAG GCTGATCTCA AGCTCCTGAC CTCAGGTGAT CTGCCTACCT
135951 TAGCCTCCCA AAGTGCTGGG ATTACAGACA TGAGCCACCG CACCCAGCCC
136001 CCAGTGTTAA CTCTTACATA ACAGTGTCAC TGTCTAAGTG TTTGAAAAAC
136051 TATTTGTCAA AACTAATATT GGTACATTAT TGTTAACTAC ACTTCAGACT
136101 TTTTTTGGAT TTTACCAATT CTCCCACTCA TGTCCCTTTT CTGTTTCAGG
136151 AATCAATCCG TGGTACCATA TTGCAGTTAG GGTGTTTATA TTTGATGGGA
136201 CTGGTCCTAG TTTAGATACT TAGTGTAGCT CAGCCAGCAG GTGGGATCTT
136251 CATGCCCACC GAGGATTGGT ATTGTGTTTT CCTGGTGGTT TTATGGCATT
136301 TCCGACTATG CAGAGAGGCA TGGTATTAAC TTCAGTGTCT CCTAGCAAAT
136351 TTTCCTGTTT TTCACCAACC TCTGATCCCT GCATTATTTG CAATCAACTC
136401 AGAGATTTGT GATTGAAAAC ATTGCTTGAC TCCATGCTCT TTAAGCTATT
136451 TTCTAACTAG GTAACTGTAA CATAAATTAT GCTTTTATCT AGCACTGTTT
136501 TTCATAAACA CATGTTGAGT GATTTTCATC AACCGAAATA CTTCGAATCA
136551 TTAAGTTTCC CAAGTTCATG GATGCTGCTT AAATGCCTGG TGGTTCCAGG
136601 CTGTCGAATA TTTCTGCCTT CTGCAATAAG AGATTGTCCC TTGTTAAAAG
136651 CAACATTAGC CTTTGTGCGG TTTCACCCCC AATTCTTCTT TTTCTTGTTG
136701 TAACCAATGA AAGGAAGTAC TGCTTAACAC AGCAGGTAAT AATCTTCTAA
136751 AACTCATTAT CTCAAGAGGT GGTCCTGGCA GGATATATAA ATGCAATTTA
136801 AGAAAGGTCT TGGCAAATTT ATGAATGACA GAACTGGGAG TGGCTACCGA
136851 GAGAAACTAG GATGCGCCTT TGCTTTGACA CTGAGGTCAG GCGTAGCTTC
136901 TGTACCCTCC TGGGTCCTGC CTCTTGGGGT TGCTGCAGGC AGCACCCCAT
136951 GAACCAGGCA TCTGACCCAG TTCAGGATA CTTATTCTTC CAGCAAGTCG
137001 AACACTCTGT GATGAGTGAC TGCCATGCTC ATGGGTCACC AGGCTCTCAT
137051 TATTCTGTTT CATTTCCAGC CTCCCACAAG ATTGGTTTTT CAGCTGCTTA
137101 TTTATTATTA TCATTATTTC AAGGCTGCTT TCCAAGTTTC AGTGGGGGGT
137151 TTCCTAAGCG TACCAGCTGC CCTGGTTGTG CAGTTCCGGT GATGTTTCAG
137201 ATGCTGGGCC GGATTCTGGC TGTACCCAGC CTGATCTTTC TGGGCTTCAG
137251 GAAAGCTGAA GCCAATCAGA GCTCCTCTTT CATGCCTTTG GGATTATGCT
137301 TACCTTGCCT GGCATCGTGT ACCTGCTCCC ATCCATGGGA AAGTTTTGCT
137351 GTCTGGTACT GTCTTCTATC AACATCTTTT AAGATATCTT CCCCCGAGGC
137401 ATCGTGATGT CAACGGAACC AGCACACTTG TACGTTTTAT GCAAGACTGC
137451 CATATCTCAA CAGTGAGAAA TGCATAATGG AAGTGGTGAT CACGGATTAT
137501 TTCCTAGGAC ATTATGGCTA ATGCGCTAGA GAACTCGGAT GGTCTGTTGC
137551 GTCTGACATG GGCTTTTTCT CTTGAGTTGT CTTTCTTTTG CTATTCTCTG
137601 AAAGAAACAA TTCTTGCCAC ATGATCCTGA TTTTTCAGGT CCTCAGCATT
137651 TGTTAGCAGA AAGTACACTT TGTTTCCATC CGGCAGTGAC TCAGTGGTGG
137701 TCCCATGCTG ATGAAACGCT GAGATAGTCT TCTTCCAAAT AGGTATCGTT
137751 TTGATTGTTG CTGCTTATTT GCTAGCTGGC CCTCAATAGT GACAATGAAA
```

FIGURE 3ZZ

```
137801 CCTCAAGTGT ATAATATGGT TGCTCAGTAA TCCTGAGGGA AGACAGTCTT
137851 TGGTTTGGGG GATAGGGATT CTGTGCCTAC TTAGCTTCAG GTGAAAGTCT
137901 TACAAATTTT TGTGTGTAGA AATAAGCACC ATGTACCTCC TTGGGTTTTT
137951 TCTTTTTTTT TCTAGTCCTT TAGTATGGTC AACAATATTG TTTAGGGAGT
138001 ACCTATTCTG TGCTAACCAC TAGGCATTCA AGTATATTAC ACTATGCTCC
138051 TTCAAAACAC TTCTGTCAAA TGTAAGGATT ATTATACCCA TTTTACAGAT
138101 GTGGTTACTG TGGTAACTTG GCCAAGGTCA TAGGGCAAGT GAATAAGGGA
138151 TTCTGGATTT GGGTGGAGGT CTGTGTGATT CCAAAGCCCA TGCTCTTTCT
138201 ACAATACTAT ATATGCCTTT GCATAAGTTA TTGTTATTAG TAATAATATT
138251 TGTGATGATG GCAAATAATA AACCATGTCA CACTAGAGAG TGATTTAATC
138301 TCTAGGTCTA TTTAAGAACA TTTGGAATTG CAGGAATTGG ATTTTTTTTT
138351 TTTTTTAAGT GATGGAGTCT TGCCATCTTT GCCCAGGCTG GTCTCAAACT
138401 TGTGGGCTCA AGTGATCATC CTCCCTCTGC CTCCCAAAGT GATGGGATTA
138451 CAGATATGAG CCACCATGCC CAGCCTAGAA TTGCAGGAAT TTTTGAATTG
138501 ATGATTCATT CTGATATTTG AATTTCTACA GTATGTTAAG TGCAATGTCA
138551 GGTGCTGGTG CTGTGGCTCC ATTGATGAAC ACATTTGGGT ATGGCCCTAC
138601 CTTCATTGAA TTTAGAGTCT AAGAGCCTAA CCGGTCTTTT GCTTGAATAG
138651 AGCTGTAGTC CTGTTAAATT GCTGTACCTC CAAATGGTGG GAAGTTTAAT
138701 GCTTCGTAGG CCTCCCCTCA CTAGTTTACT GAACCACATG TGCTTGATTT
138751 TTTTTTGANN NNNNNNNNNN NNNNNNNNNN NNNNNNNNNN NNNNNNNNNN
138801 NNNNNNNNNN NNNNNNNNNN NNNNNNNNNN CTCACTGCAA GCTCCGCCTC
138851 CCAGGTTCAC GCCATTCTTC TGCCTCAGCC TCCCGAGTAG CTGGGACTAC
138901 AGGTGCCCGC CAACACGGCC CGGCTAATTT TTTTGTATTT TTAGTAGAGA
138951 CAGGGTTTTA CCATGTTAGC CAGGATGGTC TCGGTCTGCT GACCTCGTGA
139001 TCCACCTGCC TCAGCCTCCC AAAGTGCTGG GATTACAGGC ATGAGCCACT
139051 GTGCCTGGCC CCACATGTGC TTGATTTTAA GCAAAATACA GACTATAGGC
139101 TGTGACCTGG TGATCTCTTC CCCACATACA GCATCCTGCT AACCTATAAC
139151 TCTCCCCATG TCTCAGATCT AGCCTGGGAA AGGACAATGT TGGATCGATG
139201 GCCCACTTCT AATCTTGGGA TTTCTAATCT CAAGATGAGT TGAGAAGACT
139251 CAGGATGTGT CCTGTTTTCT GTTTATTTAG AACAGGGTTT CTCAGCCTTG
139301 GCACTGTTGA CATTTGGGGC CAGATAATTC TTTGCTGTGG GGGCTGTTGT
139351 GTGAATTGCA GGATGTTGAA CAGCATCGCT GTGCTTTCTC CATGGATACC
139401 AGTAGCACCC TCCCCCTGCA GTTGCAACAA CCAAAAATGA CTCTAGACAT
139451 TGCCCAGTCT CCCCTTGGGG GCTACAGTCA CCTTCAGTTG AGAACCATTG
139501 ATTTAGAAGA ATTGGCCAGG TTATTATCAG GAGAGGGAAC ATCACAGTAA
139551 TCTGAATCTC TCAATACTGC CACTGTTACT GTTAACGAAC AGCAAAACTA
139601 TTACGTGGAG GCAGTAGGAC CTTGCTACTC AGAGTGTGGT CCGTGGACCG
139651 GCAGCATCGG AATCATCTAG GAGCTTGTTA GAGCTTCAGA GACTCAGGCC
139701 TACTGAGTCA GAAGCTGCAT TTTAATAAGG ATCCCCAGGG GATTTCTGTG
139751 CATATTAGAG TTGTGAAGCC CTGCAAGAGG AAGAAATTGG ATGCTAGCCT
139801 CAGAGTTTCT TGCTCATCTT TGTGGGTCTT CCTACGTTTT GTCTTCGGGC
139851 TTAAGGTATG GGGAGGCCAC TTTTTGGCTC AGGACTCCTA TGGGTGAATG
139901 GGACTGCTTA GAACTGCTGG GTTTTAGGCC TTGCTTTGAG GAATTTAAAG
139951 CTTTTCTCTT AGATGGACAT TACATCGTTC ATATACTTCA AAATGGTGGT
140001 TTGACCTAAT CTCTGCCTTC TGATAGCAAA AAGATATTTC CTTGACTCCC
140051 TGAACCCCAC TTTACTGTTG TCCCATATTG GATTTTAATT AAGGGTGGAA
140101 TAAGTATTCT TCACTAACAT GTTTATACAT GTATGATATT ACCATGCCAT
140151 TTATTGAGTG CCTAGTATGT GCCAGGAGCT CTGCAAAGTG CTTTATGCTT
140201 ATTATTGTTC CATTTATTCT TCCCCAAACC TCTGTGAGGC AGGTCCTATC
140251 ACTAGTCCAC AATACAAATG AGGTCATGGA GCCCGAAGTT GGCAGTGGTA
140301 GGAATCAAAC TCAGGTCTCC CTGACTCTAA ATTCTCTTTG CCTTTGTTTT
140351 TTTGAAAAAG TGGTATAGCC CATAGCAGAA AATTCACATT ATACAGAAGG
140401 TTATACGGCG AAAAATGCCT CCTTCCCACC CCACGCTCAA CCCCTCTCCC
```

FIGURE 3AAA

```
140451 TCAAGCGGAA CCACTATTGT CAGTTTCTCA TAGAACTTTC CAGAATATTC
140501 TATGCTCCTA TAACACTAGC ACAACCTATC CTCTTAACAA CATCTTTATG
140551 CTGCCTCCCA AGAATTCAGT AATTTTTTTT TTTTTGAGAT GGAGTTTTGC
140601 TCTAGTTGCC CAGGCTGGAG TGCAATGGCG TGATCTCGGC TCATTGCAAC
140651 CTCTGCCTCC CACGTTCAAG TGATTCTCTT GCCTCAGCCT CCCGAGTAGC
140701 TGGGATTACA GGCATGCGCC ACTATGCTTG GCTAATTTTG TATTTTTAGT
140751 AGAGATGGGG TTTCTCCCAT GTTGGTCAGG CTGGTCTTGA ACTCCCAACC
140801 TCAGGTAATC CGCCCACCTC GGCCTCCCAA AGTGTTGAGA TTACAGGCGT
140851 GAGCCACCGC ACCTGGCCAA ATTCAGTAAT TTTTATTGGC AGGTTATTTT
140901 CCCGCATCAT TNNNNNNNNN NNNNNNNNNN NNNNNNNNNN NNNNNNNNNN
140951 NNNNNNNNNN NNNNNNNNNN NNNNNNNNNN NNNNNNNNNN NNNNNNNNNN
141001 NNNNNNNNNN NNNNNNNNNN NNNNNNNNNN NNNNNNNNNN NNNNNNNNNN
141051 NNNNNNNNNN NNNNNNNNNN NNNNNNNNNN NNNNNNNNNN NNNNNNNNNN
141101 NNNNNNNNNN NNNNNNNNNN NNNNNNNNNN NNNNNNNNNN NNNNNNNNNN
141151 NNNNNNNNNN NNNNNNNNNN NNNNNNNNNN NNNNNNNNNN NNNNNNNNNN
141201 NNNNNNNNNN NNNNNNNNNN NNNNNNNNNN NNNNNNNNNN NNNNNNNNNN
141251 NNNNNNNNNN NNNNNNNNNN NNNNNNNNNN NNNNNNNNNN NNNNNNNNNN
141301 NNNNNNNNNN NNNNNNNNNN NNNNNNNNNN NNNNNNNNNN NNNNNNNNNN
141351 NNNNNNNNNN NNNNNNNNNN NNNNNNNNNN NNNNNNNNNN NNNNNNNNNN
141401 NNNNNNNNNN NNNNNNNNNN NNNNNNNNNN NNNNNNNNNN NNNNNNNNNN
141451 NNNNNNNNNN NNNNNNNNNN NNNNNNNNNN NNNNNNNNNN NNNNNNNNNN
141501 NNNNNNNNNN NNNNNNNNNN NNNNNNNNNN NNNNNNNNNN NNNNNNNNNN
141551 NNNNNNNNNN NNNNNNNNNN NNNNNNNNNN NNNNNNNNNN NNNNNNNNNN
141601 NNNNNNNNNN NNNNNNNNNN NNNNNNNNNN NNNNNNNNNN NNNNNNNNNN
141651 NNNNNNNNNN NNNNNNNNNN NNNNNNNNNN NNNNNNNNNN NNNNNNNNNN
141701 NNNNNNNNNN NNNNNNNNNN NNNNNNNNNN NNNNNNNNNN NNNNNNNNNN
141751 NNNNNNNNNN NNNNNNNNNN NNNNNNNNNN NNNNNNNNNN NNNNNNNNNN
141801 NNNNNNNNNN NNNNNNNNNN NNNNNNNNNN NNNNNNNNNN NNNNNNNNNN
141851 NNNNNNNNNN NNNNNNNNNN NNNNNNNNNN NNNNNNNNNN NNNNNNNNNN
141901 NNNNNNNNNN NNNNNNNNNN NNNNNNNNNN NNNNNNNNNN NNNNNNNNNN
141951 NNNNNNNNNN NNNNNNNNNN NNNNNNNNNN NNNNNNNNNN NNNNNNNNNN
142001 NNNNNNNNNN NNNNNNNNNN NNNNNNNNNN NNNNNNNNNN NNNNNNNNNN
142051 NNNNNNNNNN NNNNNNNNNN NNNNNNNNNN NNNNNNNNNN NNNNNNNNNN
142101 NNNNNNNNNN NNNNNNNNNN NNNNNNNNNN NNNNNNNNNN NNNNNNNNNN
142151 NNNNNNNNNN NNNNNNNNNN NNNNNNNNNN NNNNNNNNNN NNNNNNNNNN
142201 NNNNNNNNNN NNNNNNNNNN NNNNNNNNNN NNNNNNNNNN NNNNNNNNNN
142251 NNNNNNNNNN NNNNNNNNNN NNNNNNNNNN NNNNNNNNNN NNNNNNNNNN
142301 NNNNNNNNNN NNNNNNNNNN NNNNNNNNNN NNNNNNNNNN NNNNNNNNNN
142351 NNNNNNNNNN NNNNNNNNNN NNNNNNNNNN NNNNNNNNNN NNNNNNNNNN
142401 NNNNNNNNNN NNNNNNNNNN NNNNNNNNNN NNNNNNNNNN NNNNNNNNNN
142451 NNNNNNNNNN NNNNNNNNNN NNNNNNNNNN NNNNNNNNNN NNNNNNNNNN
142501 NNNNNNNNNN NNNNNNNNNN NNNNNNNNNN NNNNNNNNNN NNNNNNNNNN
142551 NNNNNNNNNN NNNNNNNNNN NNNNNNNNNN NNNNNNNNNN NNNNNNNNNN
142601 NNNNNNNNNN NNNNNNNNNN NNNNNNNNNN NNNNNNNNNN NNNNNNNNNN
142651 NNNNNNNNNN NNNNNNNNNN NNNNNNNNNN NNNNNNNNNN NNNNNNNNNN
142701 NNNNNNNNNN NNNNNNNNNN NNNNNNNNNN NNNNNNNNNN NNNNNNNNNN
142751 NNNNNNNNNN NNNNNNNNNN NNNNNNNNNN NNNNNNNNNN NNNNNNNNNN
142801 NNNNNNNNNN NNNNNNNNNN NNNNNNNNNN NNNNNNNNNN NNNNNNNNNN
142851 NNNNNNNNNN NNNNNNNNNN NNNNNNNNNN NNNNNNNNNN NNNNNNNNNN
142901 NNNNNNNNNN NNNNNNNNNN NNNNNNNNNN NNNNNNNNNN NNNNNNNNNN
142951 NNNNNNNNNN NNNNNNNNNN NNNNNNNNNN NNNNNNNNNN NNNNNNNNNN
143001 NNNNNNNNNN NNNNNNNNNN NNNNNNNNNN NNNNNNNNNN NNNNNNNNNN
143051 NNNNNNNNNN NNNNNNNNNN NNNNNNNNNN NNNNNNNNNN NNNNNNNNNN
```

FIGURE 3BBB

```
143101 NNNNNNNNNN NNNNNNNNNN NNNNNNNNNN NNNNNNNNNN NNNNNNNNNN
143151 NNNNNNNNNN NNNNNNNNNN NNNNNNNNNN NNNNNNNNNN NNNNNNNNNN
143201 NNNNNNNNNN NNNNNNNNNN NNNNNNNNNN NNNNNNNNNN NNNNNNNNNN
143251 NNNNNNNNNN NNNNNNNNNN NNNNNNNNNN NNNNNNNNNN NNNNNNNNNN
143301 NNNNNNNNNN NNNNNNNNNN NNNNNNNNNN NNNNNNNNNN NNNNNNNNNN
143351 NNNNNNNNNN NNNNNNNNNN NNNNNNNNNN NNNNNNNNNN NNNNNNNNNN
143401 NNNNNNNNNN NNNNNNNNNN NNNNNNNNNN NNNNNNNNNN NNNNNNNNNN
143451 NNNNNNNNNN NNNNNNNNNN NNNNNNNNNN NNNNNNNNNN NNNNNNNNNN
143501 NNNNNNNNNN NNNNNNNNNN NNNNNNNNNN NNNNNNNNNN NNNNNNNNNN
143551 NNNNNNNNNN NNNNNNNNNN NNNNNNNNNN NNNNNNNNNN NNNNNNNNNN
143601 NNNNNNNNNN NNNNNNNNNN NNNNNNNNNN NNNNNNNNNN NNNNNNNNNN
143651 NNNNNNNNNN NNNNNNNNNN NNNNNNNNNN NNNNNNNNNN NNNNNNNNNN
143701 NNNNNNNNNN NNNNNNNNNN NNNNNNNNNN NNNNNNNNNN NNNNNNNNNN
143751 NNNNNNNNNN NNNNNNNNNN NNNNNNNNNN NNNNNNNNNN NNNNNNNNNN
143801 NNNNNNNNNN NNNNNNNNNN NNNNNNNNNN NNNNNNNNNN NNNNNNNNNN
143851 NNNNNNNNNN NNNNNNNNNN NNNNNNNNNN NNNNNNNNNN NNNNNNNNNN
143901 NNNNNNNNNN NNNNNNNNNN NNNNNNNNNN NNNNNNNNNN NNNNNNNNNN
143951 NNNNNNNNNN NNNNNNNNNN NNNNNNNNNN NNNNNNNNNN NNNNNNNNNN
144001 NNNNNNNNNN NNNNNNNNNN NNNNNNNNNN NNNNNNNNNN NNNNNNNNNN
144051 NNNNNNNNNN NNNNNNNNNN NNNNNNNNNN NNNNNNNNNN NNNNNNNNNN
144101 NNNNNNNNNN NNNNNNNNNN NNNNNNNNNN NNNNNNNNNN NNNNNNNNNN
144151 NNNNNNNNNN NNNNNNNNNN NNNNNNNNNN NNNNNNNNNN NNNNNNNNNN
144201 NNNNNNNNNN NNNNNNNNNN NNNNNNNNNN NNNNNNNNNN NNNNNNNNNN
144251 NNNNNNNNNN NNNNNNNNNN NNNNNNNNNN NNNNNNNNNN NNNNNNNNNN
144301 NNNNNNNNNN NNNNNNNNNN NNNNNNNNNN NNNNNNNNNN NNNNNNNNNN
144351 NNNNNNNNNN NNNNNNNNNN NNNNNNNNNN NNNNNNNNNN NNNNNNNNNN
144401 NNNNNNNNNN NNNNNNNNNN NNNNNNNNNN NNNNNNNNNN NNNNNNNNNN
144451 NNNNNNNNNN NNNNNNNNNN NNNNNNNNNN NNNNNNNNNN NNNNNNNNNN
144501 NNNNNNNNNN NNNNNNNNNN NNNNNNNNNN NNNNNNNNNN NNNNNNNNNN
144551 NNNNNNNNNN NNNNNNNNNN NNNNNNNNNN NNNNNNNNNN NNNNNNNNNN
144601 NNNNNNNNNN NNNNNNNNNN NNNNNNNNNN NNNNNNNNNN NNNNNNNNNN
144651 NNNNNNNNNN NNNNNNNNNN NNNNNNNNNN NNNNNNNNNN NNNNNNNNNN
144701 NNNNNNNNNN NNNNNNNNNN NNNNNNNNNN NNNNNNNNNN NNNNNNNNNN
144751 NNNNNNNNNN NNNNNNNNNN NNNNNNNNNN NNNNNNNNNN NNNNNNNNNN
144801 NNNNNNNNNN NNNNNNNNNN NNNNNNNNNN NNNNNNNNNN NNNNNNNNNN
144851 NNNNNNNNNN NNNNNNNNNN NNNNNNNNNN NNNNNNNNNN NNNNNNNNNN
144901 NNNNNNNNNN NNNNNNNNNN NNNNNNNNNN NNNNNNNNNN NNNNNNNNNN
144951 NNNNNNNNNN NNNNNNNNNN NNNNNNNNNN NNNNNNNNNN NNNNNNNNNN
145001 NNNNNNNNNN NNNNNNNNNN NNNNNNNNNN NNNNNNNNNN NNNNNNNNNN
145051 NNNNNNNNNN NNNNNNNNNN NNNNNNNNNN NNNNNNNNNN NNNNNNNNNN
145101 NNNNNNNNNN NNNNNNNNNN NNNNNNNNNN NNNNNNNNNN NNNNNNNNNN
145151 NNNNNNNNNN NNNNNNNNNN NNNNNNNNNN NNNNNNNNNN NNNNNNNNNN
145201 NNNNNNNNNN NNNNNNNNNN NNNNNNNNNN NNNNNNNNNN NNNNNNNNNN
145251 NNNNNNNNNN NNNNNNNNNN NNNNNNNNNN NNNNNNNNNN NNNNNNNNNN
145301 NNNNNNNNNN NNNNNNNNNN NNNNNNNNNN NNNNNNNNNN NNNNNNNNNN
145351 NNNNNNNNNN NNNNNNNNNN NNNNNNNNNN NNNNNNNNNN NNNNNNNNNN
145401 NNNNNNNNNN NNNNNNNNNN NNNNNNNNNN NNNNNNNNNN NNNNNNNNNN
145451 NNNNNNNNNN NNNNNNNNNN NNNNNNNNNN NNNNNNNNNN NNNNNNNNNN
145501 NNNNNNNNNN NNNNNNNNNN NNNNNNNNNN NNNNNNNNNN NNNNNNNNNN
145551 NNNNNNNNNN NNNNNNNNNN NNNNNNNNNN NNNNNNNNNN NNNNNNNNNN
145601 NNNNNNNNNN NNNNNNNNNN NNNNNNNNNN NNNNNNNNNN NNNNNNNNNN
145651 NNNNNNNNNN NNNNNNNNNN NNNNNNNNNN NNNNNNNNNN NNNNNNNNNN
145701 NNNNNNNNNN NNNNNNNNNN NNNNNNNNNN NNNNNNNNNN NNNNNNNNNN
```

FIGURE 3CCC

```
145751 NNNNNNNNNN NNNNNNNNNN NNNNNNNNNN NNNNNNNNNN NNNNNNNNNN
145801 NNNNNNNNNN NNNNNNNNNN NNNNNNNNNN NNNNNNNNNN NNNNNNNNNN
145851 NNNNNNNNNN NNNNNNNNNN NNNNNNNNNN NNNNNNNNNN NNNNNNNNNN
145901 NNNNNNNNNN NNNNNNNNNN NNNNNNNNNN NNNNNNNNNN NNNNNNNNNN
145951 NNNNNNNNNN NNNNNNNNNN NNNNNNNNNN NNNNNNNNNN NNNNNNNNNN
146001 NNNNNNNNNN NNNNNNNNNN NNNNNNNNNN NNNNNNNNNN NNNNNNNNNN
146051 NNNNNNNNNN NNNNNNNNNN NNNNNNNNNN NNNNNNNNNN NNNNNNNNNN
146101 NNNNNNNNNN NNNNNNNNNN NNNNNNNNNN NNNNNNNNNN NNNNNNNNNN
146151 NNNNNNNNNN NNNNNNNNNN NNNNNNNNNN NNNNNNNNNN NNNNNNNNNN
146201 NNNNNNNNNN NNNNNNNNNN NNNNNNNNNN NNNNNNNNNN NNNNNNNNNN
146251 NNNNNNNNNN NNNNNNNNNN NNNNNNNNNN NNNNNNNNNN NNNNNNNNNN
146301 NNNNNNNNNN NNNNNNNNNN NNNNNNNNNN NNNNNNNNNN NNNNNNNNNN
146351 NNNNNNNNNN NNNNNNNNNN NNNNNNNNNN NNNNNNNNNN NNNNNNAATT
146401 CAAAACCTGT CTCCTGTTAA TCCCATCCTC TCTGTTTCTG TTATCATTTC
146451 CTTAGTGTAG ATCTGCCTAA GTGTAGAATT TGTAGAATTT GTCATGTTGA
146501 CTATTGTAGA CTTGTCTTTT AGAGTTTCTA GCACTAGCCT CTTCCACCCA
146551 TCACTATTGA GATGATTGTA TCCGTCTCAG TACTGACACT AACCCAGCAC
146601 TCTGGTTTTA CATCTGTCAA TCCATCAAGA CTTCACTTTC ACTTTCTTCC
146651 CTGCCTCATT ATTCACTATG CTCTTGGGCC ATTGCTCTGG CTTCTGGGGC
146701 TTTTCTAAAG TAGCACTTTT CCCCACTCCA GCCCATGAAG ATACCTTTTA
146751 ACCAGCTCTT GAGATTAAAT CCCCTCCGTG ACACTTTCCT GCAGGAACTT
146801 GCAAAAAGT ACTGCATTCC CCACTGGCAA AACTTGCCAT CAGCCAGTTT
146851 ATGTATTCTC TGCTTTTCAC ACCCATATCT TGACCTCTGA ACAACACACA
146901 TATTCTCCTC TTCATTTATT TCACAGTTCT GTCTTCATAA CATTGATAAG
146951 TATGATCACA TTAGCGCTCT AGATTTTAAG CAACTGGAAG ATAGCTATTT
147001 TTTTGGTACT CTTCCTTTAA ATTTGAACAT AGTGTCTAAT TAGTCAATTA
147051 ACATTTTTTT AAAAGGGCGA GGGACATCAT GGTAGAGAGA ACGAAGTTGA
147101 ACGTGTTTTT GGTTGAATAT TAGCGCATGC CCACTGTATT CTAGGCACAG
147151 TCCTGATTCA TTATATCATC ACACAATAAT TATTTATGTG CCTTCATCCT
147201 TTATGACACA GTGCTGGCTC TTATTCATCT CCCATTTCTG CAATCCATGG
147251 TGATGATTAA AAGTCTTAGG AGTTTTACGA GGCTCAGTAT TTTTTTTTTT
147301 TAATATGCTA GTTCTTCATG AATACATTGG GTACTCTGAA GCATATCATT
147351 TCCTGGGTTT CCTGAAGTGG TATGTTGCGT GGAATGGCAC ATTAGGTCTA
147401 AATAATTATC CCCTATGTAA GGGGTCTTGT TTTTCATTCA TTCTCTTAAA
147451 AAATAGATAT TAAACATTAA ATAAGGACAG CCAGGNNNNN NNNNNNNNNN
147501 NNNNNNNNNN NNNNNNNNNN NNNNNNNNNN NNNNNNNNNN NNNNNNNNNN
147551 NNNNNNNNNN NNNNNNNNNN NNNNNNNNNN NNNNNNNNNN NNNNNNNNNN
147601 NNNNNNNNNN NNNNNNNNNN NNNNNNNNNN NNNNNNNNNN NNNNNNNNNN
147651 NNNNNNNNNN NNNNNNNNNN NNNNNNNNNN NNNNNNNNNN NNNNNNNNNN
147701 NNNNNNNNNN NNNNNNNNNN NNNNNNNNNN NNNNNNNNNN NNNNNNNNNN
147751 NNNNNNNNNN NNNNNNNNNN NNNNNNNNNN NNNNNNNNNN NNNNNNNNNN
147801 NNNNNNNNNN NNNNNNNNNN NNNNNNNNNN NNNNNNNNNN NNNNNNNNNN
147851 NNNNNNNNNN NNNNNNNNNN NNNNNNNNNN NNNNNNNNNN NNNNNNNNNN
147901 NNNNNNNNNN NNNNNNNNNN NNNNNNNNNN NNNNNNNNNN NNNNNNNNNN
147951 NNNNNNNNNN NNNNNNNNNN NNNNNNNNNN NNNNNNNNNN NNNNNNNNNN
148001 NNNNNNNNNN NNNNNNNNNN NNNNNNNNNN NNNNNNNNNN NNNNNNNNNN
148051 NNNNNNNNNN NNNNNNNNNN NNNNNNNNNN NNNNNNNNNN NNNNNNNNNN
148101 NNNNNNNNNN NNNNNNNNNN NNNNNNNNNN NNNNNNNNNN NNNNNNNNNN
148151 NNNNNNNNNN NNNNNNNNNN NNNNNNNNNN NNNNNNNNNN NNNNNNNNNN
148201 NNNNNNNNNN NNNNNNNNNN NNNNNNNNNN NNNNNNNNNN NNNNNNNNNN
148251 NNNNNNNNNN NNNNNNNNNN NNNNNNNNNN NNNNNNNNNN NNNNNNNNNN
148301 NNNNNNNNNN NNNNNNNNNN NNNNNNNNNN NNNNNNNNNN NNNNNNNNNN
148351 NNNNNNNNNN NNNNNNNNNN NNNNNNNNNN NNNNNNNNNN NNNNNNNNNN
```

FIGURE 3DDD

```
148401 NNNNNNNNNN NNNNNNNNNN NNNNNNNNNN NNNNNNNNNN NNNNNNNNNN
148451 NNNNNNNNNN NNNNNNNNNN NNNNNNNNNN NNNNNNNNNN NNNNNNNNNN
148501 NNNNNNNNNN NNNNNNNNNN NNNNNNNNNN NNNNNNNNNN NNNNNNNNNN
148551 NNNNNNNNNN NNNNNNNNNN NNNNNNNNNN NNNNNNNNNN NNNNNNNNNN
148601 NNNNNNNNNN NNNNNNNNNN NNNNNNNNNN NNNNNNNNNN NNNNNNNNNN
148651 NNNNNNNNNN NNNNNNNNNN NNNNNNNNNN NNNNNNNNNN NNNNNNNNNN
148701 NNNNNNNNNN NNNNNNNNNN NNNNNNNNNN NNNNNNNNNN NNNNNNNNNN
148751 NNNNNNNNNN NNNNNNNNNN NNNNNNNNNN NNNNNNNNNN NNNNNNNNNN
148801 NNNNNNNNNN NNNNNNNNNN NNNNNNNNNN NNNNNNNNNN NNNNNNNNNN
148851 NNNNNNNNNN NNNNNNNNNN NNNNNNNNNN NNNNNNNNNN NNNNNNNNNN
148901 NNNNNNNNNN NNNNNNNNNN NNNNNNNNNN NNNNNNNNNN NNNNNNNNNN
148951 NNNNNNNNNN NNNNNNNNNN NNNNNNNNNN NNNNNNNNNN NNNNNNNNNN
149001 NNNNNNNNNN NNNNNNNNNN NNNNNNNNNN NNNNNNNNNN NNNNNNNNNN
149051 NNNNNNNNNN NNNNNNNNNN NNNNNNNNNN NNNNNNNNNN NNNNNNNNNN
149101 NNNNNNNNNN NNNNNNNNNN NNNNNNNNNN NNNNNNNNNN NNNNNNNNNN
149151 NNNNNNNNNN NNNNNNNNNN NNNNNNNNNN NNNNNNNNNN NNNNNNNNNN
149201 NNNNNNNNNN NNNNNNNNNN NNNNNNNNNN NNNNNNNNNN NNNNNNNNNN
149251 NNNNNNNNNN NNNNNNNNNN NNNNNNNNNN NNNNNNNNNN NNNNNNNNNN
149301 NNNNNNNNNN NNNNNNNNNN NNNNNNNNNN NNNNNNNNNN NNNNNNNNNN
149351 NNNNNNNNNN NNNNNNNNNN NNNNNNNNNN NNNNNNNNNN NNNNNNNNNN
149401 NNNNNNNNNN NNNNNNNNNN NNNNNNNNNN NNNNNNNNNN NNNNNNNNNN
149451 NNNNNNNNNN NNNNNNNNNN NNNNNNNNNN NNNNNNNNNN NNNNNNNNNN
149501 NNNNNNNNNN NNNNNNNNNN NNNNNNNNNN NNNNNNNNNN NNNNNNNNNN
149551 NNNNNNNNNN NNNNNNNNNN NNNNNNNNNN NNNNNNNNNN NNNNNNNNNN
149601 NNNNNNNNNN NNNNNNNNNN NNNNNNNNNN NNNNNNNNNN NNNNNNNNNN
149651 NNNNNNNNNN NNNNNNNNNN NNNNNNNNNN NNNNNNNNNN NNNNNNNNNN
149701 NNNNNNNNNN NNNNNNNNNN NNNNNNNNNN NNNNNNNNNN NNNNNNNNNN
149751 NNNNNNNNNN NNNNNNNNNN NNNNNNNNNN NNNNNNNNNN NNNNNNNNNN
149801 NNNNNNNNNN NNNNNNNNNN NNNNNNNNNN NNNNNNNNNN NNNNNNNNNN
149851 NNNNNNNNNN NNNNNNNNNN NNNNNNNNNN NNNNNNNNNN NNNNNNNNNN
149901 NNNNNNNNNN NNNNNNNNNT TCCTTTTTTT TTTTTTTTTT TTTTTTGAGA
149951 CGGTGTTTCG CTCTTGTTCC CCAGGCTGGA GTGCAGTGGC ACGATCTTGG
150001 CTCACTGCAA CCTCCACCTC CCAGGTTCAA GCGATTCTCT TGCCTCAGCC
150051 TCCCAAGTAG CTGGGACTAC AGGCATGCAC CATCACATCT GGCTAATTTT
150101 TTTGTATTTT TAATAGAGAT GGGGTTTTAC CATGTTGGCC AGGCTGGCCT
150151 TGAACTCCTG ACCTCAGGTG ATCCACCTGC CTCGCCCTCC CAAGGTGCTG
150201 GGATTACAGG CATGAGCCAC TGTGCCTGGC CTACTTCTTC TTCCTTTTAA
150251 CTTGAAGATT ATCTGCCCCT TTTTCTAATC TTAACCGCAT TAAGCTGGCT
150301 TTGAGCATGG CAAGAGTTTT ATAGATGAAT CTTATTTTAT AGTACAGGAT
150351 TTCAAAATCA TAATTATTTC ACTGAGGGTG GCTTTTACCC TCCATTAATT
150401 ATACTTCTCA CTCAGAAATG GAATTCTATT TTGGTCTCCT AAAGATAAAT
150451 TAGTATATAG TGGAAAGGAA TTATAAAGTT CTGCTAGGAA TTAAATGATA
150501 TGATTAACAC AAACATCCAC ATGGATGTGT CTCTGCCCTG TGCAGGAAAG
150551 ATGAACATTC AGTACAGATT CTGCTCTATG TCACTAGCTT TCAAGACCTG
150601 CAGGTTCTCT CCTAAGCATG CAATTCCTGT GAGCAGTAGC AATAATAGCA
150651 GGTCATATTT GTGGAGTGAT TACTGTATGC TAAGAACTGT GGTAAACACT
150701 TTTATATGGA TTATTTTATT TAAACCTCCT AATAGTCCAT TGAAATAGAT
150751 ATTGCCATGT TGAAAACTGA GGTTCAGAGA GGTTAAGTGA CTTACCCAGT
150801 GTCACAGAAC TAGTAAGTGG TGCAGCTGGG ATTTGAACTG AGATTCCAGA
150851 ACAATTGCCA TTAACCACTT TGCTTCCATA TTAGTATCAT CTGCAAATCT
150901 CTCTCCATAA ATTTCCTCAG TCTTTATCTG AGTTTCCTTA TTTCAGGAAG
150951 GAAAACTTCT GTTTTTGATC CTTATGAAAT ACAATTTCCA TTAAAACTTT
151001 TTTTTTTTGC TATTAAAAAA GGTACCGGAT AATTGAAACC AGACTGGATT
```

FIGURE 3EEE

```
151051 TGAGCCTGTG TTGATGGAAG TACACATGGG ATGTGGGCTG AAGTGTTCAA
151101 TCTAATTTTT CTTTCCATCA GCTAATTTTT AAAGTATTAA GCAAGTAGAT
151151 TCTGACACTA ACAGGGAAGA TTTAAATTCT CTTGAGAGAC TGGAGGTGTT
151201 AAATAATTTT CTGGTAGTGC ACATTTTACA TCTTAAATCT TCCTCACTCT
151251 CCCACCTCAT CTCAATGTAC CTGAAGCTCT GGGAATGTTC TTTTGTACTT
151301 CTCAGGAACA GCCAGACCTC TGGCTTCATC TCCTCTCCCC TCCACATCCC
151351 TTTCCTGCTC CAATTACTTC CCAGCGCCAC TTGGATGTTG TTGTCATCGG
151401 GGAACTTTGG AAACAGCCAG ATTTTTTTGG AGTCTGTAAG CAGAAAACAG
151451 ACTGCTTGCT GCTCATATCT GGCACCCAGC TTTGTCCAGA AAACGAGGAG
151501 TTAAAAAGAA GTCTGGGCTG TGAAGGGCTG TGACAACTGT CCTAGGGGGA
151551 GCTCTAGCGA GCCCTGGCGG GCAGTGACTC ATGCTGCTCT GTCACTGGGA
151601 TCAGCACTGG CCCCTGGCAG GCAGGCGGCA GCCAGGTGGG GTTCCAGCCA
151651 GAGCACGCAC GCACGGAGCC GGGAGCATGC AGCCTGCACT GCGGGGGATG
151701 TGATGCTCGG CTCTAACTCG CCTGGCTGGC CCGCCACGGA CGCCTCAGCT
151751 TGCAACCATG GTAACGTTTC TGGCGGGGA CACCCCGGG AGCCCACCGC
151801 GATGGGCAGC CTCCTGGTGA CTGATGGACG AGTGTCCACC TCCCAGACCG
151851 AGAGCGCTTA GTAGGTCGGA GGAAGTGGAG AGGATGTAAC ACGCCCCAG
151901 CCGGGAGTGA AGCCCTGAGG AGGTAGGAGC CGCATATGTC CATCCGTGCA
151951 TTCCCACCGT CAGCGCGCAG GGGTGCTGTA GATCACCGGT AGGAACTTTA
152001 TTTGGCTGGT GCTTCATTAT GCTGATTAAA CTGCAGTGGA TTTGATGGGC
152051 ATGATTGCGC TGGGGAAGAT GCATAATGAA CTAAAAAAAA AAAAAAGTGG
152101 TTAATAAGAT CTCGGAGTCG ACTTGTCCGG GTATGAATGA AGTAGACTGC
152151 AGTGGTATCC TAACAGGAGT TCCAGAACCT CACACATCCC TTTTCCTGGT
152201 CCTTCCTCTT ATCCCGGTTA ATCCACGAAA TGTAGAAGTT CCATCTTATT
152251 TCAACGATTA GTGCTAATCA TTAATAATTT AGACCTGTCT GGAGGAGGGA
152301 ATCCATAGGT TTAGGTCTCC TAGCATCCTG GCACTAGCCA GCAGCTGCTC
152351 TGTAGGAGCC TTCTGGAAAC AGCAGGAAGG AGCGGCTTCC CCACGAGTTC
152401 CCCAAGTGCT TTCGTTGGCC CAAGTGCTTT CGTTGGCCCA AGTGACCTGT
152451 TTGAGTTTGC TCTTCAGTTT ACCCCAGGCG GGAAGGCAGC CTGTCTGCGG
152501 GTTGGTGGCC ATGTTGGCAG AGAAGGGGTT AATCTCTTGT TGCTGTAGGA
152551 GCCGAGGTTG CGAGCTAGAT TGAAAGCAGG CGCTGCAGTG CCATCGCCAG
152601 CGCCAAGGA GTAAGACGAT CTTCTCCGCA ACAGTGTTGA ATCCGGCTGA
152651 AATTTTTTTT CCTCCCCGCC TCCTTTCTTG TTTTTCTTTA ACCAGCTCCT
152701 CCCCCCTTCG TTCCCACCCT CAAGTCTGAC GATGACACCT CCAATTTTGA
152751 TGAACCAGAG AAGAATTCGT GGGTTTCATC CTCTCCGTGC CAGCTGAGCC
152801 CCTCAGGCTT CTCGGGTGAA GAACTGCCGT TTGTGGGGTT TTCGTACAGC
152851 AAGGCACTGG GGATTCTTGG TAGATCTGAG TAAGTGAAAA TTTGACTTTC
152901 TAAAGGGACC TGCATTGATG CAAGGCTTTT GGAGCCAAAG GTGGTGGTGG
152951 GGGGGTGGGG GAATAGGTGG GGGGAGTGCA GTGGAGGGAA GCTGCTAGTC
153001 ACCTGCATTG GGAAAGCAGT CTACCTGTTA GGGCTTTGCG GGGGTAGCCT
153051 GTTAATATTC TCATTTTGCA GTGTGTAAGG TACCTGTTCC TGTCTGTGGT
153101 ATGATAATTG TCAATTGGGT ACTTTGGGTT AGTTTTCCAA TCTTTGGTCT
153151 TCTTTAAAGG GGAGAGAGTG GGAGATTTCC AGCAGTGCAG ATCCCCGGTC
153201 AAAGGAGAAA TGTGCAGGAG TTAAGATGAG CTGCCCATCT ATCTAACCAT
153251 CTATGTATCT GTCTCTCAAG TGGGTGGATG GGGGTTGCTA TCTTGGCTGT
153301 ATAAAGAATC CTAAAAACCT TGTCTCATAA GCTAGAGGTT TCCTGATGGG
153351 TTTAACTGAG CTGCAAGTGG CTGAACCAGA GCTCTAACAG AGAGATGGTG
153401 CTCGGCTCCT CTCCAAGTAT GCTGCAAGAT CAGGGATCTG GCAGCTGAGC
153451 CTCTCTGAGC TGGTGGAGCG CTGGCAGCCA GAGAAAGCCC CGTTACTGTG
153501 AGCCACCAGG AGGGAGTGTG ATGTAGCCGA GTCATTGATT CACAGAAACT
153551 GGGCTTCATA GGGGGAAAAA AAACCAGGAG ACTAGAAAAT GGAAATATAA
153601 ATATCACTGT AAACCTCTTG ATCTGGTAGG TCTTTCTCCA TTCTCATAAA
153651 AGCTATTGAA AAATGCATTA ACAGAGCACT TGGAATTAGA GGGTCGAGGC
```

FIGURE 3FFF

```
153701 TTCCAGGAGC CTCCTGGAAT TTCTGTAAAA TGCAGTAGCT TCTGTGGATG
153751 TGGGAGGTCA GTATCTTGCC TCATTCTCTC ATGATACAAT GACATTCTGT
153801 TTTCAGAGGA GTGAGTTCCC CAGAAGATCT TGGACTGATG GTGTTATTTG
153851 CCAGCCACCC TGGTCCCTGC ACTTTCAGGT TCTCAGAGGG TAATGTTGGG
153901 TTAGTTGCTG CCCACTTAGG AGACGAGCAG AATTTGATAT TCTTCTTGGC
153951 AGCATCTTTC CCTCTTTGTG GTATTTGTAG CTTAGATATC GATTTATAGG
154001 GATGTTATGT TGGTTCCTGG ATGGTGTCTC CCTATGGGTG CTATTTTGAC
154051 AGTAACGTTC CTGAAAAGAT TTCAGAGTGT TGTGGGGAAT TGGGCATTTG
154101 ATACGAAATA AGGTTGTGGG CTGTGATTGA ATGTGAGGGA GGTTTTTATG
154151 TTGCAAGATG TTGAAGTGGT CTTTCTTGAT CCCCTCTCTG GGGGCTGGGT
154201 TTCAAATTCA GGTTGGATTT TGGTAGTGTT AGATGTGCCT CTCTGTCTGA
154251 TTTGCTCCAC AACCCCAAAG CAATCTGGAT GGTGGTGGGA GAGGCAGAGT
154301 GCTAACTAGC TGTTGAATGT GCCATCAGAT GGGTTTGAAA CGGCTCAGCA
154351 GGATTGGGAG GTTTTGCCAT TGGCATCAAA GAGCAGGGCA GAAGCGGAGG
154401 CCTGATGTTG AAGGATGCAT GGTTAGTGGG CAGTATAACC TTGACACACG
154451 CAGCACACTG AAGGTCACAC GTCGTACTGG AAGGACGTGT GGAGAGTTCT
154501 AGTTCTGGTT AGCAGTGGGC TGGCTGGGTC AGAATGCAAG CTTGCTTGGG
154551 TGTTGGTCAG TGATCTGAAA GACGAGGGAG GATTCGAGGG AGTTAGATTT
154601 CAGGGGAAAA GGCAGAATGA TATGGGAGAT CTTAGGCATT GCAATTAATC
154651 TGAAGCAGTG TGTGATTAAT TGCTTATTTT TCAGGAAGAC TTGAATGACA
154701 TCTTTCTGTT TCTCACAGAA AGCTCAGTTT AGGGAGCTCT CTGACAGGGA
154751 CATCTCAGTA TTAAGGCTGA GGCACTCGAT AAATATTTGT TGATTTAATT
154801 TACCTATGAT CCTTTCCTCC AGAAGTGTTT ATATTGCTTA TTGTATTTGA
154851 AGATGTGCTA TCTCACCTCT GGTAGTTTAA ACTATATCCT TAGAGCACAA
154901 AACGAGCTGC TGTTCCTGAC CCAACAGAAT GTTTAATAAG ATTCTTATTT
154951 CAAAAAAGGT CCATGCAAAT AAAACTGTGT ATTTCTTATT TGGACGATGG
155001 CATCAGAGTA TTCCTATCAT TGGGGAACTT TAACGTTTTT TCAAAGCTTG
155051 GCAACGGGGT TGGAATCAGA AAGATTTTCT TTCATCTTGC GTCTTGTTAT
155101 GTGTTATTGC TATTGGACTT GGCTACTCTG CTGTAGGCAG CCCTGTGGGT
155151 GATACCTACA AGCATCATTT TAGAAATTCA TCCACCTGTT GGATGTAGAT
155201 GACCCTGGAC ATATCAGATT GTGATTAATT AGAAATCTAA TAAAAGAGAG
155251 GCAGTGATGA AATTACTTAG CAGCTCCTGC AGTTTTATTG ACAAAATTTA
155301 CTTGGAGAGA GGGGGAGACA TTTTCTGGGG GTACCACCTT TGCTGCCAGC
155351 GACCCTGTGT TTCTTCCTGA GTTTCTTTTT CTTTTCTCAC CATTTTCAGC
155401 ATCACAGGTT TTTATTTACA CACATTGATT ACCTGTGCTG TTACTCATTC
155451 TTCACACCAC TGAGGAAATT GCAGATGCTG CTGTACTGTG CTAGGTAAAT
155501 TGACCTCAGA TTTGTTACCA GTGAATTGAA TGAAATGTTC AGAGGTGGAG
155551 CTGAATGAAC GAGGAGTTTT TGTGGAGAAA TTGGCAGTGA GAATGATTTA
155601 AATTCTGTGA TAGCTCCTCG TTTTTTGGGA TCCTTATTTT GGGACCCCAG
155651 ACTATTTTTA AGCCATTGAG TGCATCATTA TTTTAGGCTG AGCAAGAATC
155701 TTGATGACAG CGTTTCAATG GCTGAGGCGT AGTGGGAGTT CCTTGCAGCT
155751 TGAGTTGGTG GGAGCTGGAG AGTTTCTAGA GAACTAGGTT TGGTTGTCTT
155801 TGGGGTGGGG TTATGGTGAA ATTAGTCTTG GAGAGTGAGT AGCTGTCTGA
155851 TGCTTCTTTT CCTTTTTAAC CAGCAAGAGC CCAAACCAAA TCCCCAAGCT
155901 CTGAATGCCT GGCTGTTCCT CTCAGCCTTT CTTTGCTTGA ACTTGACAAT
155951 AGTAGGGTAG TAACAGGAAA CAGCATGTTA AAGTTTTAAA AATAAAATAG
156001 ATCTCAGCTC TTTTCCTTCC CATTAGCAAG GGGTACATTT ATTTAGGTTT
156051 TTCCTTCTAG ATTGAGGCAC TGCCTCATTT AAGTTCTTGG TGAAGCCATG
156101 CATTTCTGCA AACCATAAGT ATAAACTCTA GAACGGGGGT GTCCAATCTT
156151 TTGGCTTCCT TGGGCCACAT GGGAAGAAGA AGAATTGTCT TGAGGCACAC
156201 ATAAAATACA CTAATGATAG CTGATGAGCT AAAAAAAAAA AAAAACTCAT
156251 AAAGTTTTAA GAAAGCTTAC AAACTTGTAA GTTTTGAGCC ACATTAAAAA
156301 CCATCCTGGG CTGCATGCAG CCCCCGGGGC CTTGGGTTGG ACAAGCTTGC
```

FIGURE 3GGG

156351 TGTAGAAGGT AAAAATCAGT TGGTTTTATG TTTTTGTTTT AAACATGCTG
156401 GTTGTATGCT TTTGGAAGAG TTGGGGAACA CTGAGGGTAA TGGGATCTTG
156451 ATGGGGCTGG AATTTGTGGG AAGATGGTGT CTGGGTAGGC TGTTTTTAGG
156501 AAGGGGCACT CTCTTCCTTT TGATTCAGAG ATTTTTCCTT TCTTTTCGGG
156551 TGGTTCTGAA AACACAGCGA TGGATCCAGG CATTCAAACA CCATGGAGGA
156601 AGGAAGAGTG GCTGTTGCCA TTGCTTCCCG AGTTTTCTGG GAACCAGTTT
156651 TTGGTGCCTC TTCCTTGCTC TACTGGGGCT TCTCTGCATG TCAGTTTCTT
156701 CAACTGCGAA GTGGAAGGAC AGCGATACTT TTCTTACAGG ACTTTTGCGG
156751 GGATGGATGA AATACGTAAA ACACTTGGTC TAGTACCTGG CACATGGAAA
156801 AGCCTTGGTA AATGTTCACT GTTGTTATTT TTGTTATTAC TAATACACTA
156851 GTCCATGTAT GTATAGTGTC CTCCTATACA CACCAAGAGA ATATGGAAAG
156901 GACTCAGCAA TGATTAGGTA GTCCAAAGTC ATACCAGATT GGAAACCAAG
156951 CTTCCCAGGC CCTGGGACTT TTCTGCTAGA GACACTTCAC GGTTCTGACC
157001 AACTACAAAG AGTTAATATG CAGTTGCCAA ATACCTGTTG GTAAAAGGTG
157051 GATGTTGGGG AGGAGTGGAT TGGGGAACAG AATTAGAAGG TCCAGTCCCA
157101 GAATGGGTAC CTTCCCATCA AGTTGAACAA GTCAAAACAG GTTATGTTGA
157151 AACAACTGAG AGAAAGTAAA GCAAACACCA TTGCTGCAGA ATATCATGGT
157201 ACAAATTGGA CATCTTTGGG AGTTAGCGGA GTAAGGCAAA ATCCAGTGAG
157251 GGACGCTTAA TGGGTAATGC CAATTCACAA TTCTTGTTAA ATTACATTGC
157301 TGATCTTCCT TGGAATGTCT GTCCATTCCC CCAAGTAGAC TGTGATCTCA
157351 AGGCAAGGCT GGGTCTTATT CATCCTGGTT TTCCTGGAGC AGTAAATACT
157401 TGTGCTGGGA CTGGGCTTAT AAGCATACTA ATGGAAAGTA AAATATTTGG
157451 GTTGGTTTTT TAAAAAGACA GTGGATTTGG ATCAGTGGAG AGGAAGGTAG
157501 AGGGAATTTC AGGTGGGCAG GGTGCTAACA ACAGCCCATC CTTACAGGGC
157551 ACCAACTGTG TTCTAGGCTG TGTTCCAACC ACTTTACACA GATGAATTCA
157601 TTTAAATTGC ACAACCAGCC CAAGAGGAAG GTACCATTAT TATTCTCATT
157651 TTGGATGTGA GGAAACTGAG GCGTGGGGAG ATCAAACAAC TTGCCTAAAG
157701 TTATGTAGCT TTGAGTGGCT TAGCTGAGAT TTGAACCCTG TGGGTATAAA
157751 TGCCACAGAT GGGAAATTTG TGTGGGGTAC CCCAGGGTTC ATGTGCTTGT
157801 TAGAAGTGGA AGCTATTTGT AGAGAATCAC GAATGATGAG GTTGGGGCAG
157851 GGTGTGATGG GAGCTGACAG GCAGGTCTAA ATGCTGGGAT TCCATTTTCA
157901 GTCTCTGTGT TTATTGAGTA GGTAGACGGT ATAGCTCTTG GATTTCTCAG
157951 ATTTTTTCCT CTTTTCATTT AGAGACTCTT ATCTGGTGTG TGTGTGCCCG
158001 CACACATACA TAAACCCACG CGTATATACT CTTTCCCTGA ATGTTCTTAT
158051 TTGCTAAAGC TTAAGCTTGG CAAAGAGAGG AAACTGCACT GACCTTACTC
158101 TCCACCATAT CTTCAGGCTG ATCATACACA AGTTGCTTAA TAAGCATTTG
158151 GTTAATCCAT CTAAATCATT CTTATGGCTG CAACTCTCAT TTTGTTGATG
158201 ACTCTACTAT CTATGTCTAT TCACATCTAC ATTTTGTACT TTTGTTTGCC
158251 TCCCATCTGT CCTGGGATGG CTGATACCAG TGGAAGACAG CCTGAACTCT
158301 CCAATCAGTC CTGTTTCCTT TTTATGAAAT ACTTGGAGGT TGGAGGATCT
158351 TCCCTTAAAA AGTGTTTTCC TTTCTACATC CAGCCAAAGG CTCTTGGTCC
158401 TTGTGCTTGC TACCTAGATC CCTATTGGAA AGAGTCTTGC CTGCAATTTG
158451 ATTTTTTAAA TAGCAGCAAT AACAGAGTCG TCTCTGCTAC ACGAAGACAT
158501 GCATCTGCTG TATTTCCCAG ACAAGTTCAA AAACCTTAAC TAGCTTCTGC
158551 CCATGGTTAT TGCTCTCAAG TGCCTTGTGT TGTTCCCATC CCCTCATTAT
158601 CTGGATTAGA TGTTTAACAT TTGCCTGTGT GTGTTGTGTT GGATTTTCTC
158651 CTCTCCTCTT GCTCATTCAA TTTCTTCCTT CTCTTAGCCA AGCACAGCTT
158701 GTTCTCCTAC TTGCCTTATT CTGTTCTCTA TTTAGACTGT GCGTGCCTGC
158751 CTTGCAGCCC TGGCAGGACC ATTCCACCGC CTTCTCATTT GTCTTAAAGA
158801 TACCTTTAGG AAATCTAATC CAGACAATCC TAGCCCAGTC CTGAAGATTA
158851 GGCTCCAGAA GATTCTGTCA AGTGTGTTTT TTGCTGGCCT ACACATGCTA
158901 ATTTGCATGG TTGCCTGGGA TCCCTTAAGA AGACAGTCAT TGACTAAATG
158951 GCGCTACATG TTCCCAAGCT CTGCGCCAGT CTGGCAACTC TTCCTTTGTC

FIGURE 3HHH

| | | | | |
|---|---|---|---|---|
| 159001 | TACGTGAATT | TCTCCTAGTT | CTTTCTGCTT | TGCTTGCTGT | TCATCTCCTG |
| 159051 | ACCTCTCTCC | GACAAACTTC | NNNNNNNNNN | NNNNNNNNNN | NNNNNNNNNN |
| 159101 | NNNNNNNNNN | NNNNNNNNNN | NNNNNNNNNN | NNNNNNNNNN | NNNNNNNNNN |
| 159151 | NNNNNNNNNN | NNNNNNNNNN | NNNNNNNNNN | NNNNNNNNNN | NNNNNNNNNN |
| 159201 | NNNNNNNNNN | NNNNNNNNNN | NNNNNNNNNN | NNNNNNNNNN | NNNNNNNNNN |
| 159251 | NNNNNNNNNN | NNNNNNNNNN | NNNNNNNNNN | NNNNNNNNNN | NNNNNNNNNN |
| 159301 | NNNNNNNNNN | NNNNNNNNNN | NNNNNNNNNN | NNNNNNNNNN | NNNNNNNNNN |
| 159351 | NNNNNNNNNN | NNNNNNNNNN | NNNNNNNNNN | NNNNNNNNNN | NNNNNNNNNN |
| 159401 | NNNNNNNNNN | NNNNNNNNNN | NNNNNNNNNN | NNNNNNNNNN | NNNNNNNNNN |
| 159451 | NNNNNNNNNN | NNNNNNNNNN | NNNNNNNNNN | NNNNNNNNNN | NNNNNNNNNN |
| 159501 | NNNNNNNNNN | NNNNNNNNNN | NNNNNNNNNN | NNNNNNNNNN | NNNNNNNNNN |
| 159551 | NNNNNNNNNN | NNNNNNNNNN | NNNNNNNNNN | NNNNNNNNNN | NNNNNNNNNN |
| 159601 | NNNNNNNNNN | NNNNNNNNNN | NNNNNNNNNN | NNNNNNNNNN | NNNNNNNNNN |
| 159651 | NNNNNNNNNN | NNNNNNNNNN | NNNNNNNNNN | NNNNNNNNNN | NNNNNNNNNN |
| 159701 | NNNNNNNNNN | NNNNNNNNNN | NNNNNNNNNN | NNNNNNNNNN | NNNNNNNNNN |
| 159751 | NNNNNNNNNN | NNNNNNNNNN | NNNNNNNNNN | NNNNNNNNNN | NNNNNNNNNN |
| 159801 | NNNNNNNNNN | NNNNNNNNNN | NNNNNNNNNN | NNNNNNNNNN | NNNNNNNNNN |
| 159851 | NNNNNNNNNN | NNNNNNNNNN | NNNNNNNNNN | NNNNNNNNNN | NNNNNNNNNN |
| 159901 | NNNNNNNNNN | NNNNNNNNNN | NNNNNNNNNN | NNNNNNNNNN | NNNNNNNNNN |
| 159951 | NNNNNNNNNN | NNNNNNNNNN | NNNNNNNNNN | NNNNNNNNNN | NNNNNNNNNN |
| 160001 | NNNNNNNNNN | NNNNNNNNNN | NNNNNNNNNN | NNNNNNNNNN | NNNNNNNNNN |
| 160051 | NNNNNNNNNN | NNNNNNNNNN | NNNNNNNNNN | NNNNNNNNNN | NNNNNNNNNN |
| 160101 | NNNNNNNNNN | NNNNNNNNNN | NNNNNNNNNN | NNNNNNNNNN | NNNNNNNNNN |
| 160151 | NNNNNNNNNN | NNNNNNNNNN | NNNNNNNNNN | NNNNNNNNNN | NNNNNNNNNN |
| 160201 | NNNNNNNNNN | NNNNNNNNNN | NNNNNNNNNN | NNNNNNNNNN | NNNNNNNNNN |
| 160251 | NNNNNNNNNN | NNNNNNNNNN | NNNNNNNNNN | NNNNNNNNNN | NNNNNNNNNN |
| 160301 | NNNNNNNNNN | NNNNNNNNNN | NNNNNNNNNN | NNNNNNNNNN | NNNNNNNNNN |
| 160351 | NNNNNNNNNN | NNNNNNNNNN | NNNNNNNNNN | NNNNNNNNNN | NNNNNNNNNN |
| 160401 | NNNNNNNNNN | NNNNNNNNNN | NNNNNNNNNN | NNNNNNNNNN | NNNNNNNNNN |
| 160451 | NNNNNNNNNN | NNNNNNNNNN | NNNNNNNNNN | NNNNNNNNNN | NNNNNNNNNN |
| 160501 | NNNNNNNNNN | NNNNNNNNNN | NNNNNNNNNN | NNNNNNNNNN | NNNNNNNNNN |
| 160551 | NNNNNNNNNN | NNNNNNNNNN | NNNNNNNNNN | NNNNNNNNNN | NNNNNNNNNN |
| 160601 | NNNNNNNNNN | NNNNNNNNNN | NNNNNNNNNN | NNNNNNNNNN | NNNNNNNNNN |
| 160651 | NNNNNNNNNN | NNNNNNNNNN | NNNNNNNNNN | NNNNNNNNNN | NNNNNNNNNN |
| 160701 | NNNNNNNNNN | NNNNNNNNNN | NNNNNNNNNN | NNNNNNNNNN | NNNNNNNNNN |
| 160751 | NNNNNNNNNN | NNNNNNNNNN | NNNNNNNNNN | NNNNNNNNNN | NNNNNNNNNN |
| 160801 | NNNNNNNNNN | NNNNNNNNNN | NNNNNNNNNN | NNNNNNNNNN | NNNNNNNNNN |
| 160851 | NNNNNNNNNN | NNNNNNNNNN | NNNNNNNNNN | NNNNNNNNNN | NNNNNNNNNN |
| 160901 | NNNNNNNNNN | NNNNNNNNNN | NNNNNNNNNN | NNNNNNNNNN | NNNNNNNNNN |
| 160951 | NNNNNNNNNN | NNNNNNNNNN | NNNNNNNNNN | NNNNNNNNNN | NNNNNNNNNN |
| 161001 | NNNNNNNNNN | NNNNNNNNNN | NNNNNNNNNN | NNNNNNNNNN | NNNNNNNNNN |
| 161051 | NNNNNNNNNN | NNNNNNNNNN | NNNNNNNNNN | NNNNNNNNNN | NNNNNNNNNN |
| 161101 | NNNNNNNNNN | NNNNNNNNNN | NNNNNNNNNN | NNNNNNNNNN | NNNNNNNNNN |
| 161151 | NNNNNNNNNN | NNNNNNNNNN | NNNNNNNNNN | NNNNNNNNNN | NNNNNNNNNN |
| 161201 | NNNNNNNNNN | NNNNNNNNNN | NNNNNNNNNN | NNNNNNNNNN | NNNNNNNNNN |
| 161251 | NNNNNNNNNN | NNNNNNNNNN | NNNNNNNNNN | NNNNNNNNNN | NNNNNNNNNN |
| 161301 | NNNNNNNNNN | NNNNNNNNNN | NNNNNNNNNN | NNNNNNNNNN | NNNNNNNNNN |
| 161351 | NNNNNNNNNN | NNNNNNNNNN | NNNNNNNNNN | NNNNNNNNNN | NNNNNNNNNN |
| 161401 | NNNNNNNNNN | NNNNNNNNNN | NNNNNNNNNN | NNNNNNNNNN | NNNNNNNNNN |
| 161451 | NNNNNNNNNN | NNNNNNNNNN | NNNNNNNNNN | NNNNNNNNNN | NNNNNNNNNN |
| 161501 | NNNNNNNNNN | NNNNNNNNNN | NNNNNNNNNN | NNNNNNNNNN | NNNNNNNNNN |
| 161551 | NNNNNNNNNN | NNNNNNNNNN | NNNNNNNNNN | NNNNNNNNNN | NNNNNNNNNN |
| 161601 | NNNNNNNNNN | NNNNNNNNNN | NNNNNNNNNN | NNNNNNNNNN | NNNNNNNNNN |

FIGURE 3III

```
161651 NNNNNNNNNN NNNNNNNNNN NNNNNNNNNN NNNNNNNNNN NNNNNNNNNN
161701 NNNNNNNNNN NNNNNNNNNN NNNNNNNNNN NNNNNNNNNN NNNNNNNNNN
161751 NNNNNNNNNN NNNNNNNNNN NNNNNNNNNN NNNNNNNNNN NNNNNNNNNN
161801 NNNNNNNNNN NNNNNNNNNN NNNNNNNNNN NNNNNNNNNN NNNNNNNNNN
161851 NNNNNNNNNN NNNNNNNNNN NNNNNNNNNN NNNNNNNNNN NNNNNNNNNN
161901 NNNNNNNNNN NNNNNNNNNN NNNNNNNNNN NNNNNNNNNN NNNNNNNNNN
161951 NNNNNNNNNN NNNNNNNNNN NNNNNNNNNN NNNNNNNNNN NNNNNNNNNN
162001 NNNNNNNNNN NNNNNNNNNN NNNNNNNNNN NNNNNNNNNN NNNNNNNNNN
162051 NNNNNNNNNN NNNNNNNNNN NNNNNNNNNN NNNNNNNNNN NNNNNNNNNN
162101 NNNNNNNNNN NNNNNNNNNN NNNNNNNNNN NNNNNNNNNN NNNNNNNNNN
162151 NNNNNNNNNN NNNNNNNNNN NNNNNNNNNN NNNNNNNNNN NNNNNNNNNN
162201 NNNNNNNNNN NNNNNNNNNN NNNNNNNNNN NNNNNNNNNN NNNNNNNNNN
162251 NNNNNNNNNN NNNNNNNNNN NNNNNNNNNN NNNNNNNNNN NNNNNNNNNN
162301 NNNNNNNNNN NNNNNNNNNN NNNNNNNNNN NNNNNNNNNN NNNNNNNNNN
162351 NNNNNNNNNN NNNNNNNNNN NNNNNNNNNN NNNNNNNNNN NNNNNNNNNN
162401 NNNNNNNNNN NNNNNNNNNN NNNNNNNNNN NNNNNNNNNN NNNNNNNNNN
162451 NNNNNNNNNN NNNNNNNNNN NNNNNNNNNN NNNNNNNNNN NNNNNNNNNN
162501 NNNNNNNNNN NNNNNNNNNN NNNNNNNNNN NNNNNNNNNN NNNNNNNNNN
162551 NNNNNNNNNN NNNNNNNNNN NNNNNNNNNN NNNNNNNNNN NNNNNNNNNN
162601 NNNNNNNNNN NNNNNNNNNN NNNNNNNNNN NNNNNNNNNN NNNNNNNNNN
162651 NNNNNNNNNN NNNNNNNNNN NNNNNNNNNN NNNNNNNNNN NNNNNNNNNN
162701 NNNNNNNNNN NNNNNNNNNN NNNNNNNNNN NNNNNNNNNN NNNNNNNNNN
162751 NNNNNNNNNN NNNNNNNNNN NNNNNNNNNN NNNNNNNNNN NNNNNNNNNN
162801 NNNNNNNNNN NNNNNNNNNN NNNNNNNNNN NNNNNNNNNN NNNNNNNNNN
162851 NNNNNNNNNN NNNNNNNNNN NNNNNNNNNN NNNNNNNNNN NNNNNNNNNN
162901 NNNNNNNNNN NNNNNNNNNN NNNNNNNNNN NNNNNNNNNN NNNNNNNNNN
162951 NNNNNNNNNN NNNNNNNNNN NNNNNNNNNN NNNNNNNNNN NNNNNNNNNN
163001 NNNNNNNNNN NNNNNNNNNN NNNNNNNNNN NNNNNNNNNN NNNNNNNNNN
163051 NNNNNNNNNN NNNNNNNNNN NNNNNNNNNN NNNNNNNNNN NNNNNNNNNN
163101 NNNNNNNNNN NNNNNNNNNN NNNNNNNNNN NNNNNNNNNN NNNNNNNNNN
163151 NNNNNNNNNN NNNNNNNNNN NNNNNNNNNN NNNNNNNNNN NNNNNNNNNN
163201 NNNNNNNNNN NNNNNNNNNN NNNNNNNNNN NNNNNNNNNN NNNNNNNNNN
163251 NNNNNNNNNN NNNNNNNNNN NNNNNNNNNN NNNNNNNNNN NNNNNNNNNN
163301 NNNNNNNNNN NNNNNNNNNN NNNNNNNNNN NNNNNNNNNN NNNNNNNNNN
163351 NNNNNNNNNN NNNNNNNNNN NNNNNNNNNN NNNNNNNNNN NNNNNNNNNN
163401 NNNNNNNNNN NNNNNNNNNN NNNNNNNNNN NNNNNNNNNN NNNNNNNNNN
163451 NNNNNNNNNN NNNNNNNNNN NNNNNNNNNN NNNNNNNNNN NNNNNNNNNN
163501 NNNNNNNNNN NNNNNNNNNN NNNNNNNNNN NNNNNNNNNN NNNNNNNNNN
163551 NNNNNNNNNN NNNNNNNNNN NNNNNNNNNN NNNNNNNNNN NNNNNNNNNN
163601 NNNNNNNNNN NNNNNNNNNN NNNNNNNNNN NNNNNNNNNN NNNNNNNNNN
163651 NNNNNNNNNN NNNNNNNNNN NNNNNNNNNN NNNNNNNNNN NNNNNNNNNN
163701 NNNNNNNNNN NNNNNNNNNN NNNNNNNNNN NNNNNNNNNN NNNNNNNNNN
163751 NNNNNNNNNN NNNNNNNNNN NNNNNNNNNN NNNNNNNNNN NNNNNNNNNN
163801 NNNNNNNNNN NNNNNNNNNN NNNNNNNNNN NNNNNNNNNN NNNNNNNNNN
163851 NNNNNNNNNN NNNNNNNNNN NNNNNNNNNN NNNNNNNNNN NNNNNNNNNN
163901 NNNNNNNNNN NNNNNNNNNN NNNNNNNNNN NNNNNNNNNN NNNNNNNNNN
163951 NNNNNNNNNN NNNNNNNNNN NNNNNNNNNN NNNNNNNNNN NNNNNNNNNN
164001 NNNNNNNNNN NNNNNNNNNN NNNNNNNNNN NNNNNNNNNN NNNNNNNNNN
164051 NNNNNNNNNN NNNNNNNNNN NNNNNNNNNN NNNNNNNNNN NNNNNNNNNN
164101 NNNNNNNNNN NNNNNNNNNN NNNNNNNNNN NNNNNNNNNN NNNNNNNNNN
164151 NNNNNNNNNN NNNNNNNNNN NNNNNNNNNN NNNNNNNNNN NNNNNNNNNN
164201 NNNNNNNNNN NNNNNNNNNN NNNNNNNNNN NNNNNNNNNN NNNNNNNNNN
164251 NNNNNNNNNN NNNNNNNNNN NNNNNNNNNN NNNNNNNNNN NNNNNNNNNN
```

FIGURE 3JJJ

```
164301 NNNNNNNNNN NNNNNNNNNN NNNNNNNNNN NNNNNNNNNN NNNNNNNNNN
164351 NNNNNNNNNN NNNNNNNNNN NNNNATTTCA GAGTAAGTTT TTCTAGAAAA
164401 TAGAAGCTGG AAAAAAAAGG AAAACCCAAA CTTGGCTTCG TGCTCGAAGA
164451 GACAGCACTG CTGTGTGTGG GCGGGTGGCT GCGTGCACCC GCTGCTCAGA
164501 AGTGCCTTTT CTCTCCATGG GGATAACTGG CTGTGTATCC GAGATGTGGC
164551 CAGGAGTAGG CAAGCAACGT GTGGGCAGGC TGCATGTTCT TTTATTAGCA
164601 TCTTCATTGT ACTGCATCTC GTCGAGCCCA GAGCATGAAC TGGCCTGGGT
164651 TTCTAATATC TACCCTGCTT CCCACCTAAT TACTCCCCTG AACCCTAAAG
164701 TGAGGGAGGG AGAGTTGCTC TTGTGGGGTG AGCTTTCCCT GGGGTGGCTG
164751 TGAACCAACC TGGCATGTGG ATGTTCTTGG GTATCCAGAG CTGTCCTGGA
164801 CTCAGGCTTG GAGTCAGCTT CTTAGCACTG AATGCAGCCA GTCATGGATG
164851 GAGGTCACTG TATCTCACAT GTTCCGCTCT CCCTTTCCTC CATGACCTTG
164901 CCCCTCTGAG CCTCTGTAGC ACTTTTCTTG AGTGTGTCCA AGGCCATCTA
164951 GCTAAGAAGT AGCAGAAATG GGATTTGAAG CCATGACTGT TTGGTGATAG
165001 AGCCTCAGCT TTGAACTGGG GTTCTACTGC CTGGCACCCC TGCACAAATC
165051 ATGGTAACGT GGTAGGAGAA CATAGAGGTA TAGGGCAAGC CCCTCCTTAA
165101 TGCCATGAAT AATACCCATC TTATAGGATT GTGGGGAGGA CTCAGTGAAG
165151 TAACCCGTGA AGCACTAAAC ACGTGCCTGA CACGTGCTCA ATAAATGAGC
165201 ACTTGTCCTG ATGACAAAGG TCGTGGCATT AATTCTCTCT CCTAGGTTGT
165251 TACTTCCTTG AGGACAGGAA TTGTGGCTTC CTTAATGGCC ACTGCAGCAG
165301 AGTTTCTCAA GTTGGCACTA TTGACATTTT GGGCTGGATA ATTCTTGTTG
165351 TGGGAGCTGT CCTGTGGATT GTAGGATGTT GAGCAGCATC TTTGGCCTCT
165401 ACCCGCTACA TATTAATAGC ACCCTAGTC ATGAAAATAA AATGTCTAGA
165451 CATTGCCAAA CTGCCCCTGT TGAGAACCAC TGGTCTGCAG GTATCTCTCA
165501 TGGGGATCAC AGGGCTTTTA TATTCTCTTC TCTGTCTCTC TCTCTCCCTC
165551 TCTGGGTGTC TCTCTCTCTC ACACACACGC TTAGAGAAGG TGGTTAAAAA
165601 AAATTTTGTT GAAGTTTGAG AATTTTGAGA ACAAAGGAAA AATTTTGGAA
165651 GGCATTTTAA TGAACAGATA GACTCTGTCC CATTCCATGG TCAACAGAAT
165701 TTCATAATTA GATAGTTTGT TTACTGCAAC TCTGCACCCC ATTGCCCATC
165751 ATTTTAGAGT TCCAACCAGT TAGAGGATTT TTCTTGCAAA CTTTCCTTAA
165801 AGCAGTGATA GTATCAGCTC TTTAAATAAT ACTATGCTTG ATGAAGTGGT
165851 ACTTTTCGGG ATAATTTGAG ACCAGCCGAC TTGCTGCTTG AAGAGGACAG
165901 GGCTATATTT GGTAATAATA TATATGTGAT AATATGTATG TAATATTATT
165951 ATAATGTAAT ATACAATAAT ATTTGGTGTA ACTGGTGACT CTGAGGCCAG
166001 TCTTTGATCG AACCTCTCAA GCTATGATTT ACATTATGGT CAATGTTAGC
166051 ATAATGCAAT TATCAGCAAT CACTTGCTGT TGCTTTGAAA GTCAGAAGGA
166101 TGGCTAATAA AAATCTTAGA AAAAGAAAAC AGGCCGGGTG CAGTGGCTCA
166151 CCCCTGTAAT CCCAGCACTT TGGGAGGCTG AGGCGGACAG ATCATGAGGT
166201 CAGGAGATCG AGACCATCCT GGCCAACATG GTGAAACCCC ATCTGTACTA
166251 GAATACAAAA AAAAAAAAAA AATTTGCTGG GCGTGGTGGC GTGCGCCTGT
166301 AGTCCCAGCT ACTCGGGAGC TGAGTCAGGG GAATCGCTTG AACCCGGGAG
166351 GTGGAGGTTG CAGTGAGCCG AGATTGTGCC ACTGCACTCC AGCCTGGTGA
166401 CAGAGTGAGA CTCCGTCTCA AACAAACAA AACAAACAA AAACAAAAA
166451 AAGAAAATCT TAGAAAAGA AAATAAATTG TAATATTTCA GAATATTTGT
166501 TGGGGAGGAT ATGTGTGCTC AAGAAATATA TACTGAGAAC TTACCATTGA
166551 TGCTAGAGAT TGAATTGCCC CATGTCTACA TGAAAAATGA ATAGAATATA
166601 AACATTTTAA ATTGAGCCAT GTCTATCTGT ATTATATTTC TTTTATAGAA
166651 ATTCATGGAA ATGGTATATT TTAACTGAAT TATTAACACT GGGGACAATA
166701 GGCTTTAATC ATTATCTAAT ACCTGTACGT TGTTTTGAAA TTCATAGCCC
166751 ACCACCATTA ATTTCAAAAT TGGGTTCTTA CTCAAAGAGT GATGAAAAGG
166801 CACCAGTACC AAATGGTCTG GCCAAAATGC TACATGGAAC TAAATGCTGG
166851 GGATGGTCAT ACAATGAGTT TTAAGTGGCT AGACCCTAAA TCAGAAGCAC
166901 TTTCTTCTAA TTAGCACCAT GGTTCTTAAT CCTTTCTGTA CATTACAATC
```

FIGURE 3KKK

```
166951 GCTCAGCAGC TTAATACAAA TGTTGCTTCC CGGGGCCACA CTCCACATCT
167001 TTCTGACTCT CTGATTTAAT TGGTCCGAAT GGGGCCTATA CATCAGGTGT
167051 TTTTTAAAAG GTCTCCAAGT GATTCTAATG TGTACCTGCA TTGAGGACCA
167101 GGGAAGGTGT AGGAAGCCTG ATAACCTTTA CTCTCCAGCC TCATCCTCCA
167151 ATCCCATGAT TGTTTATGGG ATTGTTGCTA CACACCCAGC TTAGTCATAG
167201 CATTCTTACT CTAGCTTTTT TTTAGATGCA ATTTTTATTT ATTCTTAAAG
167251 AAAAAGATTT CTTTAGCACC TTTATTCTAA AGAGCTCTTA ATTGCTGTGC
167301 TTAGAACTTC TAAACAGTGA GCATTTGTCA AACATAGAAT AGCAGAATGA
167351 AGGGGTTGGA CCTCGGGTGA GGAGGGCTGT CGCATGGTCT CTTTCGAGTG
167401 CCGGCGGGTG GGGGCTGCAC ATCTCCTCGC TTCTGGGCCC ATTGATAAGT
167451 GACCTAAAAG TGCCTTTCGT TTTTTTTGGT GGGGGGTGAA AAAGCAATCT
167501 GTTTTGTACC CACAGCGGTG CACTTTAAAC AGGAAGCCCT ACTGGGGCCA
167551 GCCTTCTATG TGTCATTAAG TTTTTCACGC CACATCCTAC CTATCATCAT
167601 GCACCCATGT CATCGTTCTT TTAAAGGGTG CCAGTTTTTT GCTTAAGCAC
167651 AAGGAGCTGT GACCTGTGTT GTCATCCCTG ATGCATGTCA TGCATGTGAC
167701 TTCATGACAT GTGGGTGACT TTTGATCTCT GAAGGACCAG GGACCCAGTC
167751 TGTGGATCAC CACTCTCTCC GTGGGTGGTT TGGGTCTTGT TCTCTAGCCC
167801 ACCCAGCCAG GTGCAATTAG GAATAAAGGA AATAGCAAAG GAATTTTGCT
167851 CAAGGCCATG CCAAGCATTT CATCTCATAT GAAAAGGAAA AGAGAGAGAG
167901 TGTGTGTGTG TTGGCTAGAT TTAGGTAGAA AACAGGCTGG TGAGAAGCGT
167951 AGAACTTGGT TAAAATTTCT AGCCAAAAGT AAGATTTTTA AAAAGATTTA
168001 TTTCTGGATC CAATCCCTGT TGCCCATTTC TATGAATAAT CACCATTTGT
168051 TTTAATGTGA ATAATAGCAC ACAGCAAATT CAGCCCCCTG AGTTTTACCA
168101 TTTTAAGCAA TTGCTTTAGG CCCGTGAGGC ATGTACTATT TATGAAGTTG
168151 CATGGGTAGT AATGGAAAAC ACAACAATGA CAGTAGTAAC AGGTGACATT
168201 TGTCAACACA TTGCAGTGTG CCAGGCACTG TGCTGAGAGC ATTACATGCA
168251 TTATTTCATT TAATCCTTCC AAGAACTCTT TGAAGTAGGT TGGTAATTAT
168301 GGCCATTTTA CAATTGAGGA AACTGAGGTT CGGAGATGTC AAATAACTAG
168351 TCAGTGGTGG GGTCAGATTT TTCTTTTTTT TTTAAATTTA TTTGCTTTTT
168401 TTTTTTTTTT TTTTTTTTTG AGACGGAGTC TCACTCTGTT GCCCAGGCTG
168451 ANNNNNNNNN NNNNNNNNNN NNNNNNNNNN NNNNNNNNNN NNNNNNNNNN
168501 NNNNNNNNNN NNNNNNNNNN NNNNNNNNNN NNNNNNNNNN NNNNNNNNNN
168551 NNNNNNNNNN NNNNNNNNNN NNNNNNNNNN NNNNNNNNNN NNNNNNNNNN
168601 NNNNNNNNNN NNNNNNNNNN NNNNNNNNNN NNNNNNNNNN NNNNNNNNNN
168651 NNNNNNNNNN NNNNNNNNNN NNNNNNNNNN NNNNNNNNNN NNNNNNNNNN
168701 NNNNNNNNNN NNNNNNNNNN NNNNNNNNNN NNNNNNNNNN NNNNNNNNNN
168751 NNNNNNNNNN NNNNNNNNNN NNNNNNNNNN NNNNNNNNNN NNNNNNNNNN
168801 NNNNNNNNNN NNNNNNNNNN NNNNNNNNNN NNNNNNNNNN NNNNNNNNNN
168851 NNNNNNNNNN NNNNNNNNNN NNNNNNNNNN NNNNNNNNNN NNNNNNNNNN
168901 NNNNNNNNNN NNNNNNNNNN NNNNNNNNNN NNNNNNNNNN NNNNNNNNNN
168951 NNNNNNNNNN NNNNNNNNNN NNNNNNNNNN NNNNNNNNNN NNNNNNNNNN
169001 NNNNNNNNNN NNNNNNNNNN NNNNNNNNNN NNNNNNNNNN NNNNNNNNNN
169051 NNNNNNNNNN NNNNNNNNNN NNNNNNNNNN NNNNNNNNNN NNNNNNNNNN
169101 NNNNNNNNNN NNNNNNNNNN NNNNNNNNNN NNNNNNNNNN NNNNNNNNNN
169151 NNNNNNNNNN NNNNNNNNNN NNNNNNNNNN NNNNNNNNNN NNNNNNNNNN
169201 NNNNNNNNNN NNNNNNNNNN NNNNNNNNNN NNNNNNNNNN NNNNNNNNNN
169251 NNNNNNNNNN NNNNNNNNNN NNNNNNNNNN NNNNNNNNNN NNNNNNNNNN
169301 NNNNNNNNNN NNNNNNNNNN NNNNNNNNNN NNNNNNNNNN NNNNNNNNNN
169351 NNNNNNNNNN NNNNNNNNNN NNNNNNNNNN NNNNNNNNNN NNNNNNNNNN
169401 NNNNNNNNNN NNNNNNNNNN NNNNNNNNNN NNNNNNNNNN NNNNNNNNNN
169451 NNNNNNNNNN NNNNNNNNNN NNNNNNNNNN NNNNNNNNNN NNNNNNNNNN
169501 NNNNNNNNNN NNNNNNNNNN NNNNNNNNNN NNNNNNNNNN NNNNNNNNNN
169551 NNNNNNNNNN NNNNNNNNNN NNNNNNNNNN NNNNNNNNNN NNNNNNNNNN
```

FIGURE 3LLL

```
169601 NNNNNNNNNN NNNNNNNNNN NNNNNNNNNN NNNNNNNNNN NNNNNNNNNN
169651 NNNNNNNNNN NNNNNNNNNN NNNNNNNNNN NNNNNNNNNN NNNNNNNNNN
169701 NNNNNNNNNN NNNNNNNNNN NNNNNNNNNN NNNNNNNNNN NNNNNNNNNN
169751 NNNNNNNNNN NNNNNNNNNN NNNNNNNNNN NNNNNNNNNN NNNNNNNNNN
169801 NNNNNNNNNN NNNNNNNNNN NNNNNNNNNN NNNNNNNNNN NNNNNNNNNN
169851 NNNNNNNNNN NNNNNNNNNN NNNNNNNNNN NNNNNNNNNN NNNNNNNNNN
169901 NNNNNNNNNN NNNNNNNNNN NNNNNNNNNN NNNNNNNNNN NNNNNNNNNN
169951 NNNNNNNNNN NNNNNNNNNN NNNNNNNNNN NNNNNNNNNN NNNNNNNNNN
170001 NNNNNNNNNN NNNNNNNNNN NNNNNNNNNN NNNNNNNNNN NNNNNNNNNN
170051 NNNNNNNNNN NNNNNNNNNN NNNNNNNNNN NNNNNNNNNN NNNNNNNNNN
170101 NNNNNNNNNN NNNNNNNNNN NNNNNNNNNN NNNNNNNNNN NNNNNNNNNN
170151 NNNNNNNNNN NNNNNNNNNN NNNNNNNNNN NNNNNNNNNN NNNNNNNNNN
170201 NNNNNNNNNN NNNNNNNNNN NNNNNNNNNN NNNNNNNNNN NNNNNNNNNN
170251 NNNNNNNNNN NNNNNNNNNN NNNNNNNNNN NNNNNNNNNN NNNNNNNNNN
170301 NNNNNNNNNN NNNNNNNNNN NNNNNNNNNN NNNNNNNNNN NNNNNNNNNN
170351 NNNNNNNNNN NNNNNNNNNN NNNNNNNNNN NNNNNNNNNN NNNNNNNNNN
170401 NNNNNNNNNN NNNNNNNNNN NNNTGGCTTA AAACAACACA CATTTATTAT
170451 TTTACAGTTC TGGAGGTCAG AAGTCTAAGA TGATGCCAGG CTTGGTGGCT
170501 CAAGCCTGTA ATCCCAGCAC TTTGGGAGGC TGAGGTGGCA GGATCACTTG
170551 AGGTCAGGAG TTCCAGACTA GCCTAGCCAA CATGGTGAAA CCCCATCTCT
170601 ACTAAAAATA CAAAAATTAG TCAGGCACGG TCACGAGCAC CTGTAATCCC
170651 AACTACTCAG GAGGCTGAGG CAGGAGAATT GCTTGAACCC AGGAGGTGGA
170701 GGTTGCAGTG AGCCGAGGTT GCAGTGAGCC GAGGTTGCAC CACTGCACTC
170751 CAGCCTGGGC AACAGAACGC GACCCTGTTT CCAAGAAAAA AAAAAAGTCC
170801 GGGATGAGTT TTACTGGGCT GAGATCAGTG TAGACAAGGC TGCCCTCTCT
170851 CTGGAGGCTC TAGGGCAGAA TCTGTTTCCT TGTCTTTTCC AGCTTCTAGA
170901 GGTTGCCTGC ATTCCTTGGC TTGTGGCCCC TTCCTCCGTG TTCAAAGCCA
170951 TTGGTGTAAC ATCTTCAGGT CTCTGTGACT CCGATCCTTG CTTCCATCTT
171001 ATAAGGATCC TTGTGATTTC ATTGTACCCA TCCAGATATC CCAGGAGAAT
171051 CTTTCCATCC CAAGATCCAT AACTTAAATC CCATCTGCAA AGTCCCTTTT
171101 GCCATGTGTG GTAATATATT CACAGCTTGC AGAGATCAGG ACATGGGCAT
171151 CTTTGGGAAA CGGGAAGGGG GCATTATTTG ACCTAACATC AAGAGCATGA
171201 GATGTTTTTG TAAAATGAAA CAAATGTTGC AGCTTCCTAA TGCAGCTTCT
171251 TAGGCCCACC TGCAGGCCCC CTTGACGTTG GTTTTTCTCT ACCTAGGTCT
171301 GTTGTGTCGG GTCTGGACTC CCCTGCCAAG ACTAGCTCCA TGGAAAAGAA
171351 ACTTCTCATC AAAAGCAAAG AGCTACAAGA CTCTCAGGAC AAGTGTCACA
171401 AGGTATTTAT TTCCGCAGCC GGCCTCCTTC CTTGCTCCAG GATCCTCCCG
171451 TCCGTATATG CCAAGGGATC CGCCCGGGGC CGCTGCTGGC TCTGAGCCGC
171501 CTGATCCGTA GAGAGTGAGG CGCTCCTGCC TTCGCTGAAG TCGCGCCTCC
171551 AGCAGCTCAG AGGGAGATGA ATTCGGGCCT TGCTGTTGCT GTAAATCCTT
171601 TAAATCTAAA CCAGAGGAGG CCCTGGATTT AAACAGTCCG TTTCTCAGCA
171651 TGACCCAGCC AGATGTCTGC TTCTTCCGGC AGGTGGCCTG GGTCCTCACC
171701 TGTGGCTGAG ATACATCCCA TCTGCTTTGA GTGATGCGAA GTCTCTCTTC
171751 CTAGTCTTTT AAAACTCCTG CTTATGTCAC TGCGGCCACT GTGTTGATTA
171801 CGCTCAACGT CTCTTAACAT TCACTGTTCC TGCCCAGAGG CAACGCTCTG
171851 GAAACTAATA AGTCACTGCT TGCCTGGGAC TCCTAAGAGT GCAGACGAAT
171901 AAATATCTCC TTGCCCTGTC CTGGATTTGT CCTCTAGATC TTTGCAAGGA
171951 GATGGGGGGG GATCAAGATG GATTTGGGAT AAAATTAAAG TGACGTCTGC
172001 AAAAACAAAA CAAAAACAAA AGCAAACAGG TGAAAAATGA TGATTGTGGC
172051 TTCCTTGCTA ACTGGGTTAG AGAAGTGATC AAGTGTGAAC CGGGACTTGA
172101 ATGAGAGGAG TGACTTAGCA TTTGGTGACT GTCCTTAACG AAGAACTGTG
172151 CGCTCCTGGG CGAAGAAACA ATGGTATTTC CATCCCAACT TAACTTTTGG
172201 CGAATTAGCC TTAGCCCAGA CCACCAGGTG GTTTCGGAGG CTACTTGAGA
```

FIGURE 3MMM

```
172251 TGTGATTGCT CCTAATGAAC CTCCACGGGC CTTTTTAACC TGTCGATGTG
172301 TTTATTTCAG ATGGAGCAGG AAATGACCCG GTTACATCGG AGAGTGTCAG
172351 AGGTGGAGGC TGTGCTTAGT CAGAAGGAGG TGGAGCTGAA GGCCTCTGAG
172401 ACTCAGAGAT CCCTCCTGGA GCAGGACCTT GCTACCTACA TCACAGAATG
172451 CAGTGTGAGC CTTCCCTGAA GCCCCCTTCC CTTGGAGGTG GCACTTCCTG
172501 TTGTGTGTGT CTCATCCTGT TTCATGATGA CTCCATGAGG CACATCACAG
172551 CCAATGGCAG AGAGTAGAGA GAGGGAGAGC ACAAAAGCAA GATCTGTGTT
172601 TTGCAGAGTA GTGAGAGCCA GGCGTAAGGT CCCCAAGAAA TGAGATTGGA
172651 CTCATTTCCA GCAGAAAGTG CAGGTAGACG GCTGGTACCA TGGAGTCTGG
172701 AGATGGGAGT AATTCATCTT TGCCGCAAGT TGCAAAAGAT CTTAACATCT
172751 CCCATCCCAG CCTCTGTGGT CTGCGTTGTG TCTGACATGA GCAGCCTTGA
172801 GAACCAGACT CCCAACTATG TACAAGAAAA CTTACTTTCA ATCTTCCTGA
172851 CATCAAATTT TCCATTGGCC AGAACCAGTG TAGTGACAAG AAAATAGCCT
172901 TGAAAACCCA GACCCTCTGT CATTATTTAC CATGTGACTT TCATTTTTTC
172951 TTTCCTTCAC AAGAGTAGAC TGTCTTCTTC TCCATTGTCT TGTTAAATTT
173001 TTCATTCAGG TGTTTTTTAA TGTGCCCAAT TAAACAGTCT CAAGAAGTTG
173051 AATCACACAT TTCTAAAGTT TTTTTCACAA GGGAGAGGAA ATCTATAGAA
173101 CGTGGCTGAT TAAGAATAAC TGCTATGTTT CCATTCCAGA CTTGGCTGCC
173151 TTTCAGTGGT GGGTGAAGTT ATTCAGCTAT GTATTTCAGA TATAGATTTC
173201 AGTGCCATGA AGCATAAGGG NNNNNNNNNN NNNNNNNNNN NNNNNNNNNN
173251 NNNNNNNNNN NNNNNNNNNN NNNNNNNNNN NNNNNNNNNN NNNNNNNNNN
173301 NNNNNNNNNN NNNNNNNNNN NNNNNNNNNN NNNNNNNNNN NNNNNNNNNN
173351 NNNNNNNNNN NNNNNNNNNN NNNNNNNNNN NNNNNNNNNN NNNNNNNNNN
173401 NNNNNNNNNN NNNNNNNNNN NNNNNNNNNN NNNNNNNNNN NNNNNNNNNN
173451 NNNNNNNNNN NNNNNNNNNN NNNNNNNNNN NNNNNNNNNN NNNNNNNNNN
173501 NNNNNNNNNN TGATTCTCCT GCCTCAGCCT CCCGAGTAGC TGGGACTACA
173551 GGCATGCACC ACCATGCCCA GCTAATTTTT GTATTTTTAG TAAAGACGGG
173601 GTTTCACCAT GTTGGCCAGG GTGGTCTCGA TCTCTTGACC TTGTGATCCG
173651 CCTGCCTCGG CCTCCCAAAG TGCTGGGATT ACAGGTGTGA GCCACTGTGC
173701 CCAGCCCATA AATCAAAATT TTTTCAGCAA TTGTTATACA AGTGGAACCT
173751 TACTCTTCAA ATGCAATTGT CCAGTGTCTG GCTTAATGTC TGCTGTTGTC
173801 AGAAACCATG TGAATGGAGT AGATTCCCAG GTTATAAGGA GCCCCAGGG
173851 AGGATGCGCG AGTCACTGGC TTCTCCAGGG GTCTCTGGTT TGGGGTTGCC
173901 TTGGTGCTGG GCACACTTCC TGGAGATTTT ACTGGACCAG CCTGAGGCCT
173951 TTGGGGCTCT GTGCAGATGC TCTACTTCTG ACTTGTCTAG AGCTTTCTTC
174001 TAATTCTGGA CTAAAAGCAA GCAGGAGTTT GGAGGATGAT GGTGAGAATT
174051 CACATCCCCG AGTTGGCTTT TGGAATGCAG TAGTTTGTGA GATTTAGTGT
174101 TTTTTTTAAG AAGTATATTC AGATCTTGCC TTTTTCCCAG AAAGCATATG
174151 AGACAACTTC CAAGACATTT ATAGCATGGC TAATAAAATG GGAAATCAGG
174201 GCGAAGGACA GGAGAACTCA ATAAGGGTTA ACATGGCTAC AGCGATTGTC
174251 TAAATGGGTT CTTTTTGCTG GCCAGAGCAG AAAGGATCAT GCAGTAAAGT
174301 GGGGGGGAAG AAAGGGAATT GAATGGTAGG TGAAGACTTC ATGTTGGTGC
174351 CAGGCACTGT GCCAGGCCCT CCTAGGACCT TGTCTTACTC AATCCTCACA
174401 CAGTGCTGCA AGAGGATTAG TCTTATCCCT GTTTTAGAGA GGATGAAACT
174451 GAAAGGCAGC GAGGTGAAGT CACCAGCAGG AGGCTGAAGC CGC
(SEQ ID NO:3)
```

FEATURES:
Start:     2007
Exon:      2007-2102
Intron:    2103-8974
Exon:      8975-9117
Intron:    9118-15407

FIGURE 3NNN

Exon:       15408-15409
Intron:     15410-20480
Exon:       20481-20656
Intron:     20657-27907
Exon:       27908-28013
Intron:     28014-72738
Exon:       72739-72741
Intron:     72742-105286
Exon:       105287-105294
Intron:     105295-121265
Exon:       121266-121393
Intron:     121394-123900
Exon:       123901-123911
Intron:     123912-126394
Exon:       126395-126467
Intron:     126468-129602
Exon:       129603-129609
Intron:     129610-130289
Exon:       130290-130493
Intron:     130494-149974
Exon:       149975-150024
Intron:     150025-150920
Exon:       150921-151021
Intron:     151022-152695
Exon:       152696-152879
Intron:     152880-171296
Exon:       171297-171492
Stop:       171493

SNPs:

| DNA Position | Major | Minor | Domain | Protein Position | Major | Minor |
|---|---|---|---|---|---|---|
| 10267 | - | T | Intron | | | A |
| 11548 | C | T | Intron | | | |
| 13169 | G | C | Intron | | | |
| 16643 | T | C | Intron | | | |
| 22293 | A | G | Intron | | | |
| 24151 | T | C | Intron | | | |
| 24523 | G | T | Intron | | | |
| 25268 | G | A | Intron | | | |
| 29374 | A | G | Intron | | | |
| 29795 | G | A | Intron | | | |
| 30861 | T | C | Intron | | | |
| 32238 | G | - | Intron | | | |
| 32242 | T | - | Intron | | | |
| 37658 | A | G | Intron | | | |
| 37749 | A | G | Intron | | | |
| 39924 | C | T | Intron | | | |
| 55645 | C | T | Intron | | | |
| 57539 | A | C | Intron | | | |

FIGURE 3000

| | | | | |
|---|---|---|---|---|
| 58604 | C | G | A | Intron |
| 58861 | T | G | | Intron |
| 59060 | G | A | | Intron |
| 59518 | C | A | | Intron |
| 59802 | T | C | | Intron |
| 60083 | T | G | | Intron |
| 60525 | T | C | | Intron |
| 61078 | A | G | | Intron |
| 63026 | T | C | | Intron |
| 63231 | G | A | | Intron |
| 65298 | C | T | | Intron |
| 66172 | C | T | | Intron |
| 66244 | T | C | | Intron |
| 66700 | G | A | | Intron |
| 67029 | G | T | | Intron |
| 67140 | A | G | | Intron |
| 68038 | G | A | | Intron |
| 69852 | G | A | | Intron |
| 71083 | T | C | | Intron |
| 71098 | G | A | | Intron |
| 71445 | A | C | | Intron |
| 71981 | C | A | | Intron |
| 72366 | T | A | | Intron |
| 73797 | T | - | | Intron |
| 74416 | G | A | | Intron |
| 74664 | G | C | | Intron |
| 76330 | T | C | | Intron |
| 78181 | A | G | | Intron |
| 78685 | C | A | | Intron |
| 79926 | G | A | | Intron |
| 80198 | G | A | | Intron |
| 80540 | T | C | | Intron |
| 81810 | C | T | | Intron |
| 82211 | G | A | | Intron |
| 82304 | C | G | | Intron |
| 82452 | A | G | | Intron |
| 82539 | T | A | | Intron |
| 83079 | A | G | | Intron |
| 83350 | T | G | | Intron |
| 83407 | A | G | | Intron |
| 83434 | G | A | | Intron |
| 83527 | A | G | | Intron |
| 83699 | G | A | | Intron |
| 83729 | A | G | | Intron |
| 84000 | T | G | | Intron |
| 84034 | C | T | | Intron |
| 84213 | C | T | | Intron |
| 84803 | A | G | | Intron |
| 85027 | G | A | | Intron |
| 85275 | A | T | | Intron |
| 87009 | T | C | | Intron |
| 87888 | G | A | | Intron |
| 88136 | G | A | | Intron |

FIGURE 3PPP

| | | | | | |
|---|---|---|---|---|---|
| 88231 | G | A | Intron | | |
| 88482 | A | G | Intron | | |
| 88608 | C | A | Intron | | |
| 88866 | T | C | Intron | | |
| 88870 | C | T | Intron | | |
| 88918 | G | A | Intron | | |
| 88940 | C | T | Intron | | |
| 89133 | A | G | Intron | | |
| 89260 | T | C | Intron | | |
| 89298 | G | T | Intron | | |
| 89682 | G | A | Intron | | |
| 89757 | C | T | Intron | | |
| 89817 | C | T | Intron | | |
| 90248 | G | A | Intron | | |
| 90283 | G | C | Intron | | |
| 90506 | C | G | Intron | | |
| 90607 | C | T | Intron | | |
| 92329 | A | G | Intron | | |
| 92912 | C | A | Intron | | |
| 95043 | A | G | Intron | | |
| 95227 | T | C | Intron | | |
| 107428 | G | A | Intron | | |
| 114951 | A | G | Intron | | |
| 115042 | A | G | Intron | | |
| 117217 | C | T | Intron | | |
| 120452 | A | G | Intron | | |
| 124035 | G | A | T | Intron | |
| 124589 | C | T | | Intron | |
| 125136 | G | - | | Intron | |
| 125856 | G | T | | Intron | |
| 126256 | C | T | | Intron | |
| 127332 | C | T | | Intron | |
| 128302 | G | A | | Intron | |
| 129122 | C | T | | Intron | |
| 129376 | T | C | | Intron | |
| 134893 | A | C | | Intron | |
| 136001 | C | G | | Intron | |
| 136249 | T | G | | Intron | |
| 136448 | G | A | | Intron | |
| 136906 | C | A | | Intron | |
| 137190 | T | C | | Intron | |
| 137471 | T | G | | Intron | |
| 137913 | T | C | | Intron | |
| 138466 | A | G | | Intron | |
| 146805 | G | A | | Intron | |
| 151008 | T | - | | Exon | 365 | C |
| 151627 | G | A | | Intron | |
| 151875 | G | C | | Intron | |
| 153541 | T | C | | Intron | |
| 155392 | A | G | | Intron | |
| 155896 | C | A | | Intron | |
| 157137 | G | A | | Intron | |
| 157409 | G | A | | Intron | |

FIGURE 3QQQ

| | | | |
|---|---|---|---|
| 164675 | T | C | Intron |
| 165157 | G | A | Intron |
| 165405 | G | A | Intron |
| 165500 | G | A | Intron |
| 165751 | A | G | Intron |
| 165877 | C | A | Intron |
| 166135 | T | C | Intron |
| 166139 | C | T | Intron |
| 166187 | G | A | Intron |
| 166209 | C | T | Intron |
| 166402 | A | G | Intron |
| 166529 | T | C | Intron |
| 166567 | G | T | Intron |
| 166951 | G | A | Intron |
| 167026 | C | T | Intron |
| 167086 | C | T | Intron |
| 167517 | G | A | Intron |
| 167552 | G | C | Intron |
| 167775 | C | G | Intron |
| 167876 | C | T | Intron |
| 172530 | A | G | Beyond ORF(3') |
| 172714 | T | C | Beyond ORF(3') |
| 173811 | C | T | Beyond ORF(3') |
| 173812 | C | T G | Beyond ORF(3') |

Context:

DNA
Position

10267    TTGCCCTATTACCCAGGCTGGATTGCAGTGGTATATCATGGCTCACTGCAGTTTCAACCT
TCTAGGCTCAAGCAATCCTTCCACCCCAGTGGCTGGGACTACAGGCTCACACTACCACGC
CCAGCTAATTTTTGCTTTTTTTCTCTGTAGAGATAGGGTCTTACTATGTTACCCAGGCTGG
TTTCAAACTCCAGGCTTGAAGCAGTCTTCCTGCCTCAGCCTCCCAAAGCTTTGGGATTAC
AGGTGTGAGCCACCATGCCTGGCCCCATAAAATATAATTTTTGAATTCTTTTTTGTTTTT
[-,T,A]
 ATGGAGGAAGGGGCTGAGGAAGGCAAAAGTACCTAGGGCCTATGAAGTCATATATTGGCC
TTGCCTTCACCCTGTTTCTGACTTTGCTTGACTTCCATGTGATGAGGCAGTTGGCTGTTA
GTGTCCCAGTTTCATACTCTTACATTAGTGTTTTTCAACCAGTGGGTGATTTGACGTTTT
CGGTTGTCAGAGCTAGTTGGGGGTGGTGGTGTGTGAGTTTGGGGGGAAGGGTCCTACTGT
CAGTTAATGGGTGAGGCCAGAGATGCCACCAAACACCTTACAGTGCACAAAGCAGCCCCC

11548    GATGCCTATTTTGTAAAGAAGGTTTTACTGGAACACAGCCCTACCCATGTGTTTGTACAG
TGCCTATGGCTGCTTTCACATCATAACAGCATTTTATTTCATTTTATTTATTTTTTTTTG
AGACAAAGTCTCACTCTGGCTGGAGTGCAGCAGCACAATCATAGCTCACTGCAGCCTCCA
ACTCTTGGGCTCAAGCAATCCTCCTGTCTCAGCCTCCTCAGTAGCTAGTACTACAGGCCC
ATGCCACCACTAATGGCTAATTTTTTTAATTTTGTGTAGAGATGGGACCTTGTGAGATTGC
[C,T]
 TAGGCTGGTCTTGAACTCCTGGCCTCAAGAAATCCTCCCACCTTGGCCTCCCAAAATGCT
TGGATTACAGGCATGAGCCACTGTGCCCAGCCCACAACAGCATTTGAGTAGTTGTGATAG
AGACCAAATGGCCTACAAAGCCCAAAATAGTTCCTGTTTGGCCCATTTCGAAAAGGCTTG
CTGACCTCTGAGCTACATGGTCTCTCTAGCAGGACAGCCTCGACGGTAGCTCAGGTTTCC
AAAACACAAAAGTGGAAGCTGCCAGGCTTTCTTAGGGGTTATCCTAGGAGGGACATAGGA

13169    CTTACTGAGCCATCTGCAGGCACCTTCATTAGTCTTGAGACTGTCCTCTGGTTACTTAAC
AGCAGTGAATTATCTAGAATCATTTAGTGATCAGAAGACTTGGTTTAGTGGAATGTAGAT

FIGURE 3RRR

```
         TTTTTTCTAATAGACCCCTCTTCCAGGGAAATGTTTCATATTTTTGAAGAGGTTTCCTGG
         GGAGTGTTTAAGAGGCCATGATTGAAAATGGGTGATTACATTAGTGTGTTTTCTATTCCT
         CCCCTTTTTGAGTTTCTGTTTTGGAATGTAAGCTTTGTTTTTCTACGTGGAGAAGGGTCC
         [G,C]
           TCAGCTGCTTCTGCCCAGGTTTTTTGAATCTTCCTATAGGGATGGAGATTTTCTTTGGGG
         ACTGTTAGAGAAAATGGAATAGAGTGTAGCTCTGAAGGAGAAGGATGTCTCCAGCAGAAG
         TACCTCTAGCCTTGGGCCAAGGGAGGGAAGGGAAGGGAACGAGCATCTGGGAACCAGGGA
         AGGGATTTTTGTCTTTCTTAATTACTCTTACATCCCCAGTGCCCAAAATAGTGTCTGGCA
         TATGTTAAGTCCTTAGTAAATACTTGTTGAATGAGTGTATGCTCAGTGAACAAAATAAAT

16643    TTCTGATTATTTTTGTGTTACAACAGTTTTCATCATTCACATCTTTGTATGCATCTTTTT
         TGAGCACATGTGCAAGTATTTCTGTGGACAATGGATGATTCCTAGAAATTGAAAGTTTGG
         ATTACTGTGTTCCAAAAAAGGAAGCAATACACCCAGCTATGTTGGCTTTTGCTCTTGGGT
         CCAGATGATTATCTGACAAAGTTATTCTCTGATTGCATTTTCTTTTCTTTTCTTTTCTTT
         TTTTTTTTTGAGATGGAGTTTCGCTCTTGTTGCCCAGGTTGGAGTGCAATGGCGCGATCT
         [T,C]
         GGCTCACTGCAACCTCTGCCTCCCAGGTTCAAGCGATTCTCCTGCCTCAGCCTCCTAAGT
         AGCTGGGATTGCAGGCATGCGCCACGACACCTGGCTAATTTTTTGTATTTTTAGTAGAGA
         TGGGATTTTCTCCATATTGGTCAGGCTGGTCTTGAACTCTTGACCTCAGGTGATCCACCCG
         CTTCAGCCTCCCAAAGTGCTGGGATTACAGGCGTGAGCCACAGTGCCTGGCCCTCTGACT
         GCATTTTCACAGTGTTTTGGGTCCTTATCTCTACCTCAGTACCTCAATATTCAGTGCCCA

22293    TCAGAGTCTGGCCCTGTGGACTTCAATGACTTTGTGTGGCCTCCAATCAGAGAAGCAGCG
         GAGGGCAGGAAGCTGCTTGTCAGAATCTGAGAGTGATGTGGCTTCTTTGTTTAGCAATAA
         AATGTGAGCACATAATAGAAAGGAAAAGTGACAGGACATGGCAGATAATTTGGAAGAGAG
         GAGTGGAAGATGCTCACTCAGCCTCCCAGCTCCTGAGAAAGAACTGTGTCTCATCAGTTC
         ATACTACCTGAGCATCTGTTGTATCTGGTGTGTTTCTAGGTCCTGGAGAAGAGGCATTAC
         [A,G]
         TGTAGCCCTGACCTTGTGATGCTTATGTTTTTGATGGGAAATAGTGCGTGTAAAAAGAAA
         ATAATCCAACAGGCCACACGGCAGGCAAACAATAGAGATATTCAAATAGGTATACCTTCC
         TCCAGGTGAATGGCCTGAAATGACCGTGTGGAAGTGTGGGCTGGGGGCTTATAAAATTAT
         ACACATACAGGCGCTAACTAAAGCCGCCTATTCATTCCTTAAGAGGATGCATAGAAAAGA
         AAAGTAGGGTCCTTAACTGAGCCATTTGGAATTTAAGGGCATGAGAGAAGCCAGCACAAG

24151    TTGTGGGCCGGGTGCAGTGGCTCACGCCTGTAATCCCAGCACTTTGGAGGCCAAGCAGGG
         CGGATCACTTGAGGTCGGGAGTTTGAGACCAGCCTGACCAACATGGAGAAACCCTGTCTC
         TACTAAAAATACAAAAAATTAGCCGGGTGTGGTGGTGCATGCCTGTAATCCCAGCTACTT
         GGGAGCTGAGGCAGGAGAATTGCTTGAATCTGGGAGGCAGAGGTTGCAGTGAGCTTAGAT
         CACGCCACTGCACTACAGCCTGGGCAACAAGAGCGAACACTCCGTCTCAAAAAAAAAAAA
         [T,C]
         AAATTATGTAGAGGTGGGATCTCCCTATGTTGCCCGGACTGGTCTTGAACTCCTGGCCTC
         AAGTGATCCTTCCATCTCCCCCTCCCAAAGTGTTGGGATTACAGGCATGAGCCACCCCTC
         CTGGCTGAGACTGCTTATTTTATTTATTTTTAATTTTTTTTGTTTTGAGACTGCTTATTT
         TAATGGAAGCTTCAGGGGTCAGACGGGGTCAGACAGAGTCATTGGTGAGCAAGCAAAGGT
            GTAGACTGTTCAGTTCAGCCTTCCTTGGACACCTTTTATGTGCCAGACAAAAGAAGGATC

24523    CCATCTCCCCCTCCCAAAGTGTTGGGATTACAGGCATGAGCCACCCCTCCTGGCTGAGAC
         TGCTTATTTTATTTATTTTTAATTTTTTTTGTTTTGAGACTGCTTATTTTAATGGAAGCT
         TCAGGGGTCAGACGGGGTCAGACAGAGTCATTGGTGAGCAAGCAAAGGTGTAGACTGTTC
         AGTTCAGCCTTCCTTGGACACCTTTTATGTGCCAGACAAAAGAAGGATCAGCATATCAGG
         TGCAGTAAATTATTGGGGTTATGTTGGTGTTTCCCAAATGTGTTAGATTTATCCCTGGTA
         [G,T]
         TGTTAAATCTCATGATTTTAGGTAGTATATGGACAACCTATGTAAAAACATTTAATAGTT
              TAATATTAACTAGCATATCAAAACCTGTGACTTTGCTCACGCCTGTAATCCCAGCACTTT
         GGGAGGCCAAGGCGGGAGGATGGTTTGGGCCCAGGAGTTTGAGGCCAGCCTAGGTAACAT
         GGTGAGACCCTGTCTCTAAAACAAAACAAAACAAACAAACAAACAAATAAACAAA
         TCCCCTGTAACTTGTTCTAACAATAACCTAAACAATTTTTTATTTAAAATTAAATAAAAA

25268    GGATTGATTACAGGTGCACTCCACCATGCCCAGCTAATTTTTGTATTTTTAGTAGAGACG
         GGGTTTCACCATGTTGGCTAGGCTAGTCTTGAACTCCTGACCTGCAGTAGTCCACGTGCC
         TTGGCCTCCCAAAGTGCTGGGATTACAATCACAAATTTATAGAAAAGTTGCAAGTACCAT
         GTAGTCAGGGTTCTTAAGAGAAATGGAACCAGTAGGAGATAGATATATAATCATCTCCTA
         GGATTATAAGTTGACACATAAGACTAACCGTCACATACAGTATAAACAACTTTTTTTCTT
         [G,A]
         AACCATTTGATAGATACACACACACTGATATACATAGAATATATATACACACACACAGAA
```

FIGURE 3SSS

```
        TGTATATACACATAGAATATATGTGCATACAGAATATATACACAGAAATATATATGTACA
        CATGCATAGAATATATTTACATATATATGCATATATATAATTTATTTATTTTAAGCAGTT
        GATTTATACAGTTTTTGTTTTTGTTTTTTTTTTGAGACAGAGTCTCACTCTGTCACCCAG
        GCTAGAGTGCAGTGGCGAGATCTCAGCTCACTGCAACCTCTGCCCCCGGGTTCCAGTGAT

29374   AAGAAATGTTAAATGGTTACATAAGCTTTCCCTTTCTGACCCTTAACTGTGCTCTGTAGG
        AGCATGGTGGGGATGTTTCTTTTCTTTTCTTCTTTTTTTGAGACCAGGTCTCACTTTGC
           CACCCAGGCTGGAGTTCAGTGGCATGAACATGGCTCACTGCAGCCTCGACTTCCTGGGCT
        CCAGCAAACCTCCCACCTCAGCCTCCCGGGCATACACCACTGTGCCTGGCTAATTTTTGT
        ATTTTTAGTAGAGACGGGGTTTTGCCATGTTGCCCAGGCTGGTTTCGAAGTCCTGAGCTC
        [A,G]
        AGAGATCTTCCTGCCTTGGCCTTCCAAAGTGCTGGGATTACAGGTGTGAGCCACCATGCC
        CAGCTCCGGTGGGGATATTTCTATATCCACATGTGTATAGTTTACTTTATAAAAATGGT
        ATGTTACTCTGTGCTTGGCTCTCCAGCTTGCTGTTGCCTTTCACCAGTGTATCCCAGACA
        TCCTTTCTTCCTTGTCAGTAACGCAGGTCTACTTTATTCTTTGAGCAGTGGCATAATTTT
        CCCTGATGTGTATATATCATAAGTTAGAGAATGCTAAAATTCATTTTGGGGCCTTGTTTA

29795   ATGTTACTCTGTGCTTGGCTCTCCAGCTTGCTGTTGCCTTTCACCAGTGTATCCCAGACA
        TCCTTTCTTCCTTGTCAGTAACGCAGGTCTACTTTATTCTTTGAGCAGTGGCATAATTTT
        CCCTGATGTGTATATATCATAAGTTAGAGAATGCTAAAATTCATTTTGGGGCCTTGTTTA
        GGTTCTTGAGGGATTAAATTCCTAAATTTAACAAGTGTATCCTGGAAACAATTTTTGTTC
        CTGATTCAGCCCTTAAAAGAGGACTATCATGTTACCTTGAATGGAGATAAACAGGCTCAC
        [G,A]
        TAAGAGAAAAGGGTAAGAGGGATGAACTCCCACTTATCTTAAACTTCTACTGGCCCGTTT
        TTGGGGAATTTGCTGCTTTTATTCCTGACCTAAAATAAATAAGTTTATGTGTCTTGGTTT
        CATATTAGTTGAGAACCCAGTGCCTGGAGAGAAGTTTTCCTTGTCCTCTGAGTGAGGACA
        TTCACATATGAATCTATTGGCAGACTGGCTTTGACTGACCACACGTGCCTTCAGAACCAA
        TGCCACAGCTCTTAGGTTTATGGCCTGAAACACCCTTTCCTTACATATTGCCTTAGAAAC

30861   CACTGCGCCTTTTCTTTTCATTTTTTTTCTGAGATGGAGTCTTTCTCTGTCACCAGGCTG
        GAGTACAGTCATGCAATCTCAGCTCACTGCAACTTCCACCTCCTGGGTTAAAGTGATTCT
        CTGTCTTAGCCTCCTGTGTAGCTGGGACTACAGGCGTGTGCCACTGTGCCCAGCTAATT
        TTTATATTTTTAGTAGAGACGGGGTTTTGCCATGTGGGTTAGGCTGGTCTTGAACTCCTG
        ACCTCAGGTGATCCACCCGTCTTGGCCTCCCAAAGTGCTGGGGTTATAGGCGTGAGCCAC
        [T,C]
        GTGCCCAGCCTCAGGCTTCTTTATTAAGAAGAAGTTCGGGCCAGGTGTGGTGGCTTACAC
        CTGTAATCCCAGCAATTTGGGAGGCCGAGGTGGGCAGATCAGGAGGTCAGGAGATCGAGA
        CCATCCTGGCTAACATGGTGAAACCTCGTCTCTACTAAAAATATAAAAAATTAGGCAGGT
        ATGGTGGCGGGTGCCTGTAGTCCCAGCTACTCGGGAGGCTGAGGGAGGAGAACGGTGTGA
        ACCTGGGAGGCGGAGCTTGCAGTGAGCCCAGATTGTGCCAGTGCACTCCAGCCTGGGTGA

32238   GGCTACTGCTCAGTAGCTTCAGGGAAACCACTGCTTGCCTCCCCTGTGGCCAGTGAGGAT
        GATCAGAGGAGTCCCAGCAGGAATGCCCAAATGTAGTTTTCTTACATGTTGATGGGAGTG
        CATTGTTTCATGTCTAAACAGTTCTCAAATCACATCTTCAGGAGGGTACTATCTGGGCAC
        TTTGATAATTTCTCACTTTGATGTCACCGTTCTTATTACCATCACCTAGTTTTGTCATAG
        TAGAAATAACTTTCCTTTTTCTGTGTGTGTGTGTGTGTGTGTGTGTGTGTGTGTGTGTGT
        [G,-]
        TTTTGAGATGGAGTCTTGCCGTGTTGCCCAGGCTGTAGTGCAGTGGCGTGTTCTCGGCTC
        ACTGCAACCTCTGCCTCCCGGGTTCTCCTGCCTCAGCCTCCCGAGTAGTTGGGATTACAG
        GCGTGTGACACCACGCCTGGCTCATTTTTGTATTTTCAGTAGAGATGGGGTTTCACCACT
        TTGGCCAGGCTGGTCTTGAACTCCTGACCTTGTGATCCGCCCACCTTGACCTCCCAAAGT
        GCTGGGATTGCAGGTGTGAGCCACCACGCCTGGCTTTTTTTTTTTTTTTTTGAGACAG

32242   ACTGCTCAGTAGCTTCAGGGAAACCACTGCTTGCCTCCCCTGTGGCCAGTGAGGATGATC
           AGAGGAGTCCCAGCAGGAATGCCCAAATGTAGTTTTCTTACATGTTGATGGGAGTGCATT
        GTTTCATGTCTAAACAGTTCTCAAATCACATCTTCAGGAGGGTACTATCTGGGCACTTTG
        ATAATTTCTCACTTTGATGTCACCGTTCTTATTACCATCACCTAGTTTTGTCATAGTAGA
        AATAACTTTCCTTTTTCTGTGTGTGTGTGTGTGTGTGTGTGTGTGTGTGTGTGTGTGTTT
        [T,-]
        GAGATGGAGTCTTGCCGTGTTGCCCAGGCTGTAGTGCAGTGGCGTGTTCTCGGCTCACTG
        CAACCTCTGCCTCCCGGGTTCTCCTGCCTCAGCCTCCCGAGTAGTTGGGATTACAGGCGT
        GTGACACCACGCCTGGCTCATTTTTGTATTTTCAGTAGAGATGGGGTTTCACCACTTTGG
        CCAGGCTGGTCTTGAACTCCTGACCTTGTGATCCGCCCACCTTGACCTCCCAAAGTGCTG
        GGATTGCAGGTGTGAGCCACCACGCCTGGCTTTTTTTTTTTTTTTTTTTGAGACAGAGTC
```

FIGURE 3TTT

| | |
|---|---|
| 37658 | GACAGTGAGACATGTGCTGTTTTGATCTCTCAGCTAAGATTATCTGATTTTTCAGGCATG<br>TCTCAAAACTCACCAGGCCTGCTCACATGCTGCTGCTTCTGAAGCCAGGGTTTGGAAACC<br>AGCTGCCCATCAGAATGAGGCTGTGACTTAGAATATTGGTTCTTGTTTTATTACCATTCC<br>TTGTTTGGTCTCTCCAGAGTCACTGGCCTTTTCCGCTTCAATTTTCTTATCGGTGAAATG<br>AGATATTAATTCCTCTTATTGACTTCAATTCAATTGCTGAGTGTATTGTTGCCTTTGGGA<br>[A,G]<br>GTTCTTTGAGTTTTCTGTGCCTTTGAAATAGTTGTTTTTTTTTATTCTGGTGTTTTGAGG<br>CATGTTTCAAGTGAGTGCATTTACACTTCTACCATTTTAGGAGCCACAATTCAGTTATGT<br>TGTCCCAGCTTGCTTGGCCCCATCCCCAGAGTTTCTGATTCAGTAGGTCTGGGGTGGGGC<br>CCAATAATTTGCATTTCTTCTTCTTTTTTCGAGACAGAGTCTGACTGTGTCATCCAAGCT<br>GGAGTGCAGTGGCACGATCGTAGCTCATTGTAGCCTCAAACTCCTGGGCTCAAGCCGTCC |
| 37749 | GCTGCTTCTGAAGCCAGGGTTTGGAAACCAGCTGCCCATCAGAATGAGGCTGTGACTTAG<br>AATATTGGTTCTTGTTTTATTACCATTCCTTGTTTGGTCTCTCCAGAGTCACTGGCCTTT<br>TCCGCTTCAATTTTCTTATCGGTGAAATGAGATATTAATTCCTCTTATTGACTTCAATTC<br>AATTGCTGAGTGTATTGTTGCCTTTGGGAAGTTCTTTGAGTTTTCTGTGCCTTTGAAATA<br>GTTGTTTTTTTTTATTCTGGTGTTTTGAGGCATGTTTCAAGTGAGTGCATTTACACTTCT<br>[A,G]<br>CCATTTTAGGAGCCACAATTCAGTTATGTTGTCCCAGCTTGCTTGGCCCCATCCCCAGAG<br>TTTCTGATTCAGTAGGTCTGGGGTGGGGCCCAATAATTTGCATTTCTTCTTCTTTTTTCG<br>AGACAGAGTCTGACTGTGTCATCCAAGCTGGAGTGCAGTGGCACGATCGTAGCTCATTGT<br>AGCCTCAAACTCCTGGGCTCAAGCCGTCCTCCCACCTCACCCTCCTGAGTAGCTGGGACT<br>ATAGGCATATACTACCATGCCCTGCCACCTTTTTAATTTTTTGTAAGGATGGGGGTCTCA |
| 39924 | GCTGGGCTAGCTGCCTCTGAATCACCGCAGTAGCTCCTTTTACTATAGATTCCTGGGTCC<br>CACCCATGGAATGTGATCCATGAAGTCTGGGGTTATTCCCTGGAATCCTTTAAGCTCCCT<br>AAGTGGTTGGGATGGGAAAGAGATATGCTTTATGTTACTATACTTCTTATTATTATTATT<br>TTAAAATTCTTGCCGGGCGCAGTGGCTCACACCTGTAATCCCAGCACATTGGGAGACCGA<br>GGCGGGTGGATCACTTGAGGTCAGGAGTTCGAGACTGGCCTGGCCAACATGATGAAATCC<br>[C,T]<br>GTCTCTACTAAAAATACAAAAATTAGCTGGGCATGGTGGCGCATGACTGTAGTCCCAGCC<br>ACTCCGGAGGCTGAGGCAGGAGAATCGCTTGAACCCGGGAGGCAGAGGTTGCAGTGAGCC<br>GAGATCGTGGCACTGCACTCCAGCCTGGGTAACAGAGTGAGACTTCATCTCAAAAAAAAC<br>CCAAAAAAACAAAACTCTTTTTCATTATACCGGAACGTCAGCTTTATGGAGTCGGGGATT<br>TTTTCTGTTTTATTCACTGCTGTTTCCCTAACATCTAGAATAGTGGCTGGCACGATAGGC |
| 55645 | CCTTTAGCTCACTCACTCATTCAATCATTCAATAACGAGTGCGTTATCATACCAGGTACT<br>GTTAGGTAGCAGGTTTACAGGGATGAGCAGAAGAAGCAGGCCCTCTCTGCCTTCTTTCTT<br>TTTCATCACACTGAAATCACAGCGCATTGTGTGTGTGCAAAAGTAGAGTGCAGAGGGAAC<br>ATGCAGAAAGGAGTTATAGGATAGAAAAGGTAGCCAAGGAAAGCAGCAAGAACAGCATGA<br>TTTGTTCAGGGATCTTTAAATAGCTCATCATTGTTGGACAGCAAAGGGAGAGATGGGGAA<br>[C,T]<br>GTGGCAAGATGAGATGAGAAGGGGAGCCGGGGTCAAGCCATGGAGGACGCTGAACCCCTA<br>CAAAGGAACTAAGCCTATTGATGTGAACAGGCCACTTATTTTGGGAACACGCCTTTGGTC<br>CAAAGGGAAGAGGGCACGAAACTTCCTTCTCTAAAAAACAAAAAAAAAGAAACTTGCATA<br>TATGAGAAATACTTTCTTCACTTTGCAGCATGAGAAACGGAATCCCTACTAAGGAAATAA<br>TTCTCTTATTTTTTTTGGAACAGCGGTTTTTGAAATTTCCAGATGACCCCAAAGTGAGCA |
| 57539 | TAATCTTCTTGAATAAGCAGTTAATTTTTTTTATTCATGAACCTGCTGATCATGTCTAAG<br>AATGTATCTCCACTTAAGTAAGTCAGTGAATGGTGATTACCTGAGTAGAGTTAAAGTAGT<br>CCCCCACCCTCCTATCTGTGGCACATATGTTCCAAGTCTCCCAGTGGATGTGTGAAACTG<br>ATGATAGTACTGAAACCCATCTACCTTTTTTCCTGTGCATACATACCTATGTTATATAAA<br>GCTTAACTTATAAATTAGGCATAATATATTTGACTCCCAGCTCCCAGTGTAGTGGCTCTG<br>[A,C]<br>AGACTCACAAAATGTATTTGCTTTAAAAAAATTCTTTTTTTTTTTTTTTGAGACGGAGTTTT<br>GCTCTTGTTGCCCAGGCTGGAGTGCAGTGGTGCGACCTCAGCTCACTGCAACCTCCGCCT<br>CTTGGGTTCAAGCGATTCTCCTGCCTCAGCCTCCCAAGTAGCTGGGATTATAGGCATGCA<br>CCACCACACCCAGCTAATTTTCTATTTTTCGTAGAAACGGTTTTTCCATGTTGGTCAGGC<br>TGATCTTGAACTCCTGACCTCAGGTGATCTGCCTGCCTCGGCCTTCCAAAGTGCTGGGAT |
| 58604 | TCTTTTTTATATTTATTTATTTATTTTTTGAGACACAGTCTTCCCGTCGCCCAGGCTGGA<br>GTGTGGTGGCACGATCTCGGCTCACTGCAACCTCCGCCTCCTGGGTTCAAGTGATTCTTC<br>TGCCTCAGCCTCCGAGTAGCTGGGACCACAGGTGTGCGCCACCATGCCCGGCTACTTTTT<br>GTATTTTCAGTAGAGACAGGGTTTCACCATGTTGGTCAGGCTGATCTTGAAGCTCCTGACC |

FIGURE 3UUU

```
         TCAGGTGATCTGCCTACCTTAGCCTCCCAAAGTGCTGGGATTACAGACATGAGCCACCGC
         [C,G,A]
            CCCAGCCCCCAGTGTTAACTCTTACATAACAGTGTCACTGTCTAAGTGTTTGAAAAACTA
         TTTGTCAAAACTAATATTGGTACATTATTGTTAACTACACTTCAGACTTTTTTTGGATTT
         TACCAATTCTCCCACTCATGTCCCTTTTCTGTTTCAGGAATCAATCCGTGGTACCATATT
         GCAGTTAGGGTGTTTATATTTGATGGGACTGGTCCTAGTTTAGATACTTAGTGTAGCTCA
         GCCAGCAGGTGGGATCTTCATGCCCACCGAGGATTGGTATTGTGTTTTCCTGGTGGTTTT
```

58861
```
         CTTAGCCTCCCAAAGTGCTGGGATTACAGACATGAGCCACCGCACCCAGCCCCCAGTGTT
         AACTCTTACATAACAGTGTCACTGTCTAAGTGTTTGAAAAACTATTTGTCAAAACTAATA
         TTGGTACATTATTGTTAACTACACTTCAGACTTTTTTTGGATTTTACCAATTCTCCCACT
         CATGTCCCTTTTCTGTTTCAGGAATCAATCCGTGGTACCATATTGCAGTTAGGGTGTTTA
         TATTTGATGGGACTGGTCCTAGTTTAGATACTTAGTGTAGCTCAGCCAGCAGGTGGGATC
         [T,G]
         TCATGCCCACCGAGGATTGGTATTGTGTTTTCCTGGTGGTTTTATGGCATTTCCGACTAT
         GCAGAGAGGCATGGTATTAACTTCAGTGTCTCCTAGCAAATTTTCCTGTTTTTCACCAAC
         CTCTGATCCCTGCATTATTTGCAATCAACTCAGAGATTTGTGATTGAAAACATTGCTTGA
         CTCCATGCTCTTTAAGCTATTTTCTAACTAGGTAACTGTAACATAAATTATGCTTTTATC
         TAGCACTGTTTTTCATAAACACATGTTGAGTGATTTTCATCAACCGAAATACTTCGAATC
```

59060
```
         AGGAATCAATCCGTGGTACCATATTGCAGTTAGGGTGTTTATATTTGATGGGACTGGTCC
         TAGTTTAGATACTTAGTGTAGCTCAGCCAGCAGGTGGGATCTTCATGCCCACCGAGGATT
         GGTATTGTGTTTTCCTGGTGGTTTTATGGCATTTCCGACTATGCAGAGAGGCATGGTATT
         AACTTCAGTGTCTCCTAGCAAATTTTCCTGTTTTTCACCAACCTCTGATCCCTGCATTAT
         TTGCAATCAACTCAGAGATTTGTGATTGAAAACATTGCTTGACTCCATGCTCTTTAAGCT
         [G,A]
         TTTTCTAACTAGGTAACTGTAACATAAATTATGCTTTTATCTAGCACTGTTTTTCATAAA
         CACATGTTGAGTGATTTTCATCAACCGAAATACTTCGAATCATTAAGTTTCCCAAGTTCA
         TGGATGCTGCTTAAATGCCTGGTGGTTCCAGGCTGTCGAATATTTCTGCCTTCTGCAATA
         AGAGATTGTCCCTTGTTAAAAGCAACATTAGCCTTTGTGCGGTTTCACCCCCAATTCTTC
         TTTTTCTTGTTGTAACCAATGAAAGGAAGTACTGCTTAACACAGCAGGTAATAATCTTCT
```

59518
```
         GAATATTTCTGCCTTCTGCAATAAGAGATTGTCCCTTGTTAAAAGCAACATTAGCCTTTG
         TGCGGTTTCACCCCCAATTCTTCTTTTTCTTGTTGTAACCAATGAAAGGAAGTACTGCTT
         AACACAGCAGGTAATAATCTTCTAAAACTCATTATCTCAAGAGGTGGTCCTGGCAGGATA
         TATAAATGCAATTTAAGAAAGGTCTTGGCAAATTTATGAATGACAGAACTGGGAGTGGCT
         ACCGAGAGAAACTAGGATGCGCCTTTGCTTTGACACTGAGGTCAGGCGTAGCTTCTGTAC
         [C,A]
         CTCCTGGGTCCTGCCTCTTGGGGTTGCTGCAGGCAGCACCCCATGAACCAGGCATCTGAC
         CCAGTTCCAGGATACTTATTCTTCCAGCAAGTCGAACACTCTGTGATGAGTGACTGCCAT
         GCTCATGGGTCACCAGGCTCTCATTATTCTGTTTCATTTCCAGCCTCCCACAAGATTGGT
         TTTTCAGCTGCTTATTTATTATTATCATTATTTCAAGGCTGCTTTCCAAGTTTCAGTGGG
         GGGTTTCCTAAGCGTACCAGCTGCCCTGGTTGTGCAGTTCCGGTGATGTTTCAGATGCTG
```

59802
```
         GGCGTAGCTTCTGTACCCTCCTGGGTCCTGCCTCTTGGGGTTGCTGCAGGCAGCACCCCA
         TGAACCAGGCATCTGACCCAGTTCCAGGATACTTATTCTTCCAGCAAGTCGAACACTCTG
         TGATGAGTGACTGCCATGCTCATGGGTCACCAGGCTCTCATTATTCTGTTTCATTTCCAG
         CCTCCCACAAGATTGGTTTTTCAGCTGCTTATTTATTATTATCATTATTTCAAGGCTGCT
         TTCCAAGTTTCAGTGGGGGGTTTCCTAAGCGTACCAGCTGCCCTGGTTGTGCAGTTCCGG
         [T,C]
         GATGTTTCAGATGCTGGGCCGGATTCTGGCTGTACCCAGCCTGATCTTTCTGGGCTTCAG
         GAAAGCTGAAGCCAATCAGAGCTCCTCTTTCATGCCTTTGGGATTATGCTTACCTTGCCT
         GGCATCGTGTACCTGCTCCCATCCATGGGAAAGTTTTGCTGTCTGGTACTGTCTTCTATC
         AACATCTTTTAAGATATCTTCCCCCGAGGCATCGTGATGTCAACGGAACCAGCACACTTG
         TACGTTTTATGCAAGACTGCCATATCTCAACAGTGAGAAATGCATAATGGAAGTGGTGAT
```

60083
```
         CCTGGTTGTGCAGTTCCGGTGATGTTTCAGATGCTGGGCCGGATTCTGGCTGTACCCAGC
         CTGATCTTTCTGGGCTTCAGGAAAGCTGAAGCCAATCAGAGCTCCTCTTTCATGCCTTTG
         GGATTATGCTTACCTTGCCTGGCATCGTGTACCTGCTCCCATCCATGGGAAAGTTTTGCT
         GTCTGGTACTGTCTTCTATCAACATCTTTTAAGATATCTTCCCCCGAGGCATCGTGATGT
         CAACGGAACCAGCACACTTGTACGTTTTATGCAAGACTGCCATATCTCAACAGTGAGAAA
         [T,G]
         GCATAATGGAAGTGGTGATCACGGATTATTTCCTAGGACATTATGGCTAATGCGCTAGAG
         AACTCGGATGGTCTGTTGCGTCTGACATGGGCTTTTTCTCTTGAGTTGTCTTTCTTTTGC
         TATTCTCTGAAAGAAACAATTCTTGCCACATGATCCTGATTTTTCAGGTCCTCAGCATTT
```

FIGURE 3VVV

```
              GTTAGCAGAAAGTACACTTTGTTTCCATCCGGCAGTGACTCAGTGGTGGTCCCATGCTGA
              TGAAACGCTGAGATAGTCTTCTTCCAAATAGGTATCGTTTTGATTGTTGCTGCTTATTTG

60525         CTTGCCACATGATCCTGATTTTTCAGGTCCTCAGCATTTGTTAGCAGAAAGTACACTTTG
              TTTCCATCCGGCAGTGACTCAGTGGTGGTCCCATGCTGATGAAACGCTGAGATAGTCTTC
              TTCCAAATAGGTATCGTTTTGATTGTTGCTGCTTATTTGCTAGCTGGCCCTCAATAGTGA
              CAATGAAACCTCAAGTGTATAATATGGTTGCTCAGTAATCCTGAGGGAAGACAGTCTTTG
              GTTTGGGGGATAGGGATTCTGTGCCTACTTAGCTTCAGGTGAAAGTCTTACAAATTTTTG
              [T,C]
              GTGTAGAAATAAGCACCATGTACCTCCTTGGGTTTTTTCTTTTTTTTTCTAGTCCTTTAG
              TATGGTCAACAATATTGTTTAGGGAGTACCTATTCTGTGCTAACCACTAGGCATTCAAGT
              ATATTACACTATGCTCCTTCAAAACACTTCTGTCAAATGTAAGGATTATTATACCCATTT
              TACAGATGTGGTTACTGTGGTAACTTGGCCAAGGTCATAGGGCAAGTGAATAAGGGATTC
              TGGATTTGGGTGGAGGTCTGTGTGATTCCAAAGCCCATGCTCTTTCTACAATACTATATA

61078         GAGGTCTGTGTGATTCCAAAGCCCATGCTCTTTCTACAATACTATATATGCCTTTGCATA
              AGTTATTGTTATTAGTAATAATATTTGTGATGATGGCAAATAATAAACCATGTCACACTA
              GAGAGTGATTTAATCTCTAGGTCTATTTAAGAACATTTGGAATTGCAGGAATTGGATTTT
              TTTTTTTTTTTAAGTGATGGAGTCTTGCCATCTTTGCCCAGGCTGGTCTCAAACTTGTGG
              GCTCAAGTGATCATCCTCCCTCTGCCTCCCAAAGTGATGGGATTACAGATATGAGCCACC
              [A,G]
              TGCCCAGCCTAGAATTGCAGGAATTTTTGAATTGATGATTCATTCTGATATTTGAATTTC
              TACAGTATGTTAAGTGCAATGTCAGGTGCTGGTGCTGTGGCTCCATTGATGAACACATTT
              GGGTATGGCCCTACCTTCATTGAATTTAGAGTCTAAGAGCCTAACCGGTCTTTTGCTTGA
              ATAGAGCTGTAGTCCTGTTAAATTGCTGTACCTCCAAATGGTGGGAAGTTTAATGCTTCG
              TAGGCCTCCCCTCACTAGTTTACTGAACCACATGTGCTTGATTTTTTTTTGAGATGGGGT

63026         TATTACCATGCCATTTATTGAGTGCCTAGTATGTGCCAGGAGCTCTGCAAAGTGCTTTAT
              GCTTATTATTGTTCCATTTATTCTTCCCCAAACCTCTGTGAGGCAGGTCCTATCACTAGT
              CCACAATACAAATGAGGTCATGGAGCCCGAAGTTGGCAGTGGTAGGAATCAAACTCAGGT
              CTCCCTGACTCTAAATTCTCTTTGCCTTTGTTTTTTTGAAAAAGTGGTATAGCCCATAGC
              AGAAAATTCACATTATACAGAAGGTTATACGGCGAAAAATGCCTCCTTCCCACCCCACGC
              [T,C]
              CAACCCCTCTCCCTCAAGCGAACCACTATTGTCAGTTTCTCATAGAACTTTCCAGAATAT
              TCTATGCTCCTATAACACTAGCACAACCTATCCTCTTAACAACATCTTTATGCTGCCTCC
              CAAGAATTCAGTAATTTTTTTTTTTTGAGATGGAGTTTTGCTCTAGTTGCCCAGGCTGG
              AGTGCAATGGCGTGATCTCGGCTCATTGCAACCTCTGCCTCCCACGTTCAAGTGATTCTC
              TTGCCTCAGCCTCCCGAGTAGCTGGGATTACAGGCATGCGCCACTATGCTTGGCTAATTT

63231         CTTTGTTTTTTTGAAAAAGTGGTATAGCCCATAGCAGAAAATTCACATTATACAGAAGGT
              TATACGGCGAAAAATGCCTCCTTCCCACCCCACGCTCAACCCCTCTCCCTCAAGCGAACC
              ACTATTGTCAGTTTCTCATAGAACTTTCCAGAATATTCTATGCTCCTATAACACTAGCAC
              AACCTATCCTCTTAACAACATCTTTATGCTGCCTCCCAAGAATTCAGTAATTTTTTTTTT
              TTTGAGATGGAGTTTTGCTCTAGTTGCCCAGGCTGGAGTGCAATGGCGTGATCTCGGCTC
              [G,A]
              TTGCAACCTCTGCCTCCCACGTTCAAGTGATTCTCTTGCCTCAGCCTCCCGAGTAGCTGG
              GATTACAGGCATGCGCCACTATGCTTGGCTAATTTTGTATTTTTAGTAGAGATGGGGTTT
              CTCCATGTTGGTCAGGCTGGTCTTGAACTCCCAACCTCAGGTAATCCGCCCACCTCGGCC
              TCCCAAAGTGTTGAGATTACAGGCGTGAGCCACCGCACCTGGCCAAATTCAGTAATTTTT
              ATTGGCAGGTTATTTTCCCGCATCATTGAAATGAATGAAGCAATCTTTATACTTCATTCA

65298         GAGCCCTGAGGAATTTCACCACTGGGTTTCCCATAAATGAGACCCCCTGTGACCTGGTGG
              GCCCCATCCCTCGGAAGTGTACCCTGGCATTTCCATAGGACTGCTTCCTTCTGGGCCTCT
              TAGTGCAAGCCAGCAGTGCAATGCCACATCCAAGTTTGGTAAATCAATTCTAAGTGAGAT
              AAATTAATGCCTTTTTTGGGGGAAGATGGGAAACAGAGTGGGTTTGTTGGAGAGCCCATA
              AATTGGAGTCTTCAACCCTTAAATTCTCACTTGCGGGAAAACCTTTCACAACCAAGCAAA
              [C,T]
              GTGGAAATGATTTGGCCAAAGATTCAAAATTATATTAAACATCTGGGACTATATTCAGCA
              GCCAACTTTCTAATCAATTCTATGAGTGTGGTGATTTGCAGTTATGCTCATTTTCTGAGGG
              TGAAGTTTGGATAGAACTAAAAAGGGCGGTTGGCAGGAATCAAAAGAGATGAAAGCCTCA
              GGACAAAGAGTTAGAGGCCCAGGTGGTTCATGACTGAGAGTTTGGAAATGATTTCTGGTG
              TCTCACTTCAGAGAAAATAAATATAGCCAACTCTGTTCATCCGTGGTGATGGAACATTCA

66172         GTGTTCGGTTGGTTGAGTGCCTGCTATGCCTGTGCCTAGGCAGTAAAAGGGGAAGTTTTA
              AGTTTGGCCCTTACTTTCAAGACATAGTAATTCTACCTTCTAGTAAAACATGGCCAAATA
```

FIGURE 3WWW

```
        AATGTCTGCTTTTCATGAGCCAGATAACCTCCTTCTTCTTTATTGGAGGAGTGAGTAGAA
        GGGTGAGACTAGCCGGGTGCGATGTCTCCAACCTGGGCGAAAGAGCAAGACTCCATCTCA
        AAAAAAAAAAAAAAAAATTAAGAATAAATCTTTTCACTGTTGGAGAAAAGTTTTGAGAGGC
        [C,T]
        GAGGTGAGAGGATCACTTGAGGCCAGGAGTTTGAGACTAGCCTGGGCAACATAGCAAGAC
        CCCTGTCTCTATCAAAAAATAATAATAAAAAAAGCTAGCTGGGTATGGTGGTGTGCACCT
        GTAATCCCAGCTACTTGGGAGGCTGAGGTGGGAGGATTGCTTGAGCCCAGGAGTTCAAGC
        TTATAGTGAACTATGATTGCACCCCTGCACTCCCTCCTGGGCATCAGAGTGAGACACTGT
        CTCTAAAAAAAAAAAAGTTGGAGAAAAGGATACTAAAGAGATAAAAGGGTACTAAAGAGAT

66244   ACTTTCAAGACATAGTAATTCTACCTTCTAGTAAAACATGGCCAAATAAATGTCTGCTTT
        TCATGAGCCAGATAACCTCCTTCTTCTTTATTGGAGGAGTGAGTAGAAGGGTGAGACTAG
        CCGGGTGCGATGTCTCCAACCTGGGCGAAAGAGCAAGACTCCATCTCAAAAAAAAAAAAA
        AAAATTAAGAATAAATCTTTTCACTGTTGGAGAAAAGTTTTGAGAGGCCGAGGTGAGAGG
        ATCACTTGAGGCCAGGAGTTTGAGACTAGCCTGGGCAACATAGCAAGACCCCTGTCTCTA
        [T,C]
        CAAAAAATAATAATAAAAAAAGCTAGCTGGGTATGGTGGTGTGCACCTGTAATCCCAGCT
        ACTTGGGAGGCTGAGGTGGGAGGATTGCTTGAGCCCAGGAGTTCAAGCTTATAGTGAACT
        ATGATTGCACCCCTGCACTCCCTCCTGGGCATCAGAGTGAGACACTGTCTCTAAAAAAAA
        AAAGTTGGAGAAAAGGATACTAAAGAGATAAAAGGGTACTAAAGAGATCGGGAAGGCAGC
        AAAGAATGAATCTAGTCTGATGTGTTATTGGGTGTACGTAATTCATGGCGGAAGGTGCTG

66700   AGTGAGACACTGTCTCTAAAAAAAAAAAAGTTGGAGAAAAGGATACTAAAGAGATAAAAGG
        GTACTAAAGAGATCGGGAAGGCAGCAAAGAATGAATCTAGTCTGATGTGTTATTGGGTGT
        ACGTAATTCATGGCGGAAGGTGCTGAAAGGGAAGGTTGCCTGGGCCTACAGCAAGCAGGT
        GCTGATGAACTAGCTCCTTTGCTATTACTTAAATGTGTCCTGGTTGGGCCAGATGTGGTG
        GCTCACACCTGTAATCCCAGCACTTTGGGAGGCCAAGGCGGACGGATCACTTGAGGTCAG
        [G,A]
        AGTTCGAGACCAGCCTGGCCAACATGGTAAAACCCCGTCTCTACTAAAAATACAAAAAAA
        GTATCCAGGCATGGTGGCAGGTGCTTGTAATCCCAGCTACTTGGGAGGCTGAAGCATGAG
        AATTCCTTGAACCCGGGAGGTGGAGGTTGCAGTGAGCCGAGATCATGCCACTGCACTTCC
        AACCTGGGCAAAAGAGCAAGACTGAGTTCTCAAAAAAAAAAAAAAAAAAAATTCCTGGGG
        AATATCCACCAGGGTGAAAAATTGGGTATATCCAAATTCAGCTTTGCAAAGAAATGCACT

67029   AAAACCCCGTCTCTACTAAAAATACAAAAAAAGTATCCAGGCATGGTGGCAGGTGCTTGT
        AATCCCAGCTACTTGGGAGGCTGAAGCATGAGAATTCCTTGAACCCGGGAGGTGGAGGTT
        GCAGTGAGCCGAGATCATGCCACTGCACTTCCAACCTGGGCAAAAGAGCAAGACTGAGTT
        CTCAAAAAAAAAAAAAAAAAAAATTCCTGGGGAATATCCACCAGGGTGAAAAATTGGGTA
        TATCCAAATTCAGCTTTGCAAAGAAATGCACTCATGACTAGTTGCAATTTGAAACGTTCC
        [G,T]
        CTTCTGAGTATTTCTAGCCTATGTAGGTGTTTCACAGATTGCTGAGTACCTAGACTGAGA
        GGGAGAGAAAAAAACAAAGTAAAGCTAAAATGTTAAGAAGTCTGGTTAAAGTGCAATCCA
        GAAGTGAGGGAAAGCATCTCTAAAAGTATGAATCTTTGGGGAAACATAACTTGATTACCA
        AAAACTTAATATTAAGCAGCCTCATAGGAACATGGCTTTTGGGTATGGCGAGAGCCAGCT
        AGAGCTCACATCTCCATTGAAATCCACCACCAGAGAGGTTATCTGCCTAGTTGTTGGCAG

67140   GTGGAGGTTGCAGTGAGCCGAGATCATGCCACTGCACTTCCAACCTGGGCAAAAGAGCAA
        GACTGAGTTCTCAAAAAAAAAAAAAAAAAAAATTCCTGGGGAATATCCACCAGGGTGAAA
        AATTGGGTATATCCAAATTCAGCTTTGCAAAGAAATGCACTCATGACTAGTTGCAATTTG
        AAACGTTCCTCTTCTGAGTATTTCTAGCCTATGTAGGTGTTTCACAGATTGCTGAGTACC
        TAGACTGAGAGGGAGAGAAAAAAACAAAGTAAAGCTAAAATGTTAAGAAGTCTGGTTAAA
        [A,G]
        TGCAATCCAGAAGTGAGGGAAAGCATCTCTAAAAGTATGAATCTTTGGGGAAACATAACT
        TGATTACCAAAAACTTAATATTAAGCAGCCTCATAGGAACATGGCTTTTGGGTATGGCGA
        GAGCCAGCTAGAGCTCACATCTCCATTGAAATCCACCACCAGAGAGGTTATCTGCCTAGT
        TGTTGGCAGCCAGACCCTGGCATTGTTTAGATTGATTGATGGAAGGCTACTTTGGGAATG
        CTGGCTTCCTTATTCATTGACTTTAAAGACAGCATTGTAAAAATTGATCACCAGCCCAAA

68038   GCCCAGGCTGGTCTTGAACTCCTAGACTGAAGTGATCCACCTGCTTTGGCCTCCTAAAAT
        GCTGGGATTACAAGTGTTAGCCACCAGGCCCGGTCTTGAACTTCGTATATACAGTGTGTT
        GTGTGGGCAAGTCATGCCTGACCACTTCCTAGTGGGAGGGGAGAAACTAGAGGGCTTGCC
        TGAGGCTTTAGGCAATGTAATCTGTTCTCTTGGGATCAATTACTTATGCATATTTAGTAG
        CCAGCTCTATTTGCTGATCACCTAATCTGTTCTCTTCGTTCATTCCCATGAGACTTCGAT
        [G,A]
        TGGGATATCTTCCTCTTCTTCCCATTGCAGCCTTTTCTCTCAGAGTTGTTCCCATGATAA
```

FIGURE 3XXX

```
          GAACTCCCATCAAAATCTCTGCTCTAACATCAGTTGTCAGATTTTGCCACTTTTTTTTTTT
          TTTTTTTTTCTGAGATGATGGAATCTCACTCTGCTGCCCAGGCTGGAGGCAGTGCCACCA
          TCTCGGCTCATTGCAACCTCTGTCTCCCGGGTTTGAGGGATTCTCCTGCCTCAGCCTCCC
          GAGTAGCTGAGATTACAGGAGCACCCCACCACTCCAGGCTAATTTTTGTATTTTTTTTAG

69852     GGCTTTTCTAAAGTAGCACTTTTCCCCACTCCAGCCCATGAAGATACCTTTTAACCAGCT
          CTTGAGATTAAATCCCCTCCGTGACACTTTCCTGCAGGAACTTGCAA
          [G,A]
          AAAGTACTGCATTCCCCACTGGCAAAACTTGCCATCAGCCAGTTTATGTATTCTCTGCTT
          TTCACACCCATATCTTGACCTCTGAACAACACACATATTCTCCTCTT

71083     CTTTGTTTCTGAAAGCCTTGATTCTGCTATCTATTTTATAACTGAAACAAAAACAAAAAC
          AAAAACAAAAAACAACCTCAAGAAGTTACTTGTATAGCCTCTGCCACTAAGGAGACTGTG
          TTCTGATGTTACCTCAAACAGGCTGATTTATTAAAATATTTAAAAATATATATGGAAATA
          TTTTTTTCTATTTTTTTTTTTTAGTGGCTTTTCCCAGTGAACAATAGGTCTTACTATATGA
          TTTCTTATTTGTCATTAGTGAATGTGGTGGGTATGTGGCAGCTGGGGGAGCTGATGATTT
          [T,C]
          ATAATACTGTATCAGAAATGATTAGTGTAGGTACTTATTAACATATTTCTCAGACAGAAC
          AATCTTGACTTTTAAAACCTCTTCATTTAATTCAAACATCAAGTACCCTGTTTGTGGCCT
          GTGTTATGTTAGGTGCTCTCTTTACAAGACCTATTTTCTTGCTATTTAATTATATATTTG
          CTTAGCAAATATTTACTCTGCACCTACTAGGTACCTGGCACTGTGCTGTGTACTGAGGTG
          CCATGTGTACCTCCATCAACATAGACTCAAGATCAATATGATTTCAGTGAACTAAAAATA

71098     CCTTGATTCTGCTATCTATTTTATAACTGAAACAAAAACAAAAACAAAAACAAAAAACAA
          CCTCAAGAAGTTACTTGTATAGCCTCTGCCACTAAGGAGACTGTGTTCTGATGTTACCTC
          AAACAGGCTGATTTATTAAAATATTTAAAAATATATATGGAAATATTTTTTTTCTATTTTT
          TTTTTTAGTGGCTTTTCCCAGTGAACAATAGGTCTTACTATATGATTTCTTATTTGTCAT
          TAGTGAATGTGGTGGGTATGTGGCAGCTGGGGGAGCTGATGATTTTATAATACTGTATCA
          [G,A]
          AAATGATTAGTGTAGGTACTTATTAACATATTTCTCAGACAGAACAATCTTGACTTTTAA
          AACCTCTTCATTTAATTCAAACATCAAGTACCCTGTTTGTGGCCTGTGTTATGTTAGGTG
          CTCTCTTTACAAGACCTATTTTCTTGCTATTTAATTATATATTTGCTTAGCAAATATTTA
          CTCTGCACCTACTAGGTACCTGGCACTGTGCTGTGTACTGAGGTGCCATGTGTACCTCCA
          TCAACATAGACTCAAGATCAATATGATTTCAGTGAACTAAAAATACCTTTATTGAAGCAA

71445     ATCTTGACTTTTAAAACCTCTTCATTTAATTCAAACATCAAGTACCCTGTTTGTGGCCTG
          TGTTATGTTAGGTGCTCTCTTTACAAGACCTATTTTCTTGCTATTTAATTATATATTTGC
          TTAGCAAATATTTACTCTGCACCTACTAGGTACCTGGCACTGTGCTGTGTACTGAGGTGC
          CATGTGTACCTCCATCAACATAGACTCAAGATCAATATGATTTCAGTGAACTAAAAATAC
          CTTTATTGAAGCAAAAAAAAAATCACATTTTGTAAGGATCAAAAAAGAGACATTTTATATA
          [A,C]
          GGTACAAGAAATAGAAGAATTATATCCCCAAGATATATGTGATAACATACTTGTTAGTTT
          TTGGACGTGACCAGATTTTACACAATCCTTAAAAAATGCAGCAACCAGATTTTAAAGTAG
          TTCTCTAATCTCTCTTTCTGTGCCCCATTAGATGTATATTGGATCTTCTCATTCTGTCTT
          TGTCTTTTGACCTCTCATGTTTTCCGTCTCTTTGTCTCTGTGTGTTGCATTGTACACAAA
          TGCTTCTTGAACTGTGGTGTGCACATGAATCACCTGGGGACCTTGTTACAACGTAGGTTC

71981     ACAAATGCTTCTTGAACTGTGGTGTGCACATGAATCACCTGGGGACCTTGTTACAACGTA
          GGTTCTGATTCCATGGGTATGGGGCAGGGCCTGAGATTCTTAGAGAATTAAATTCTAACC
          AGCTCCTGAGTGGTGGTGATAATGCCAGTGTGTAGACCATAGCTTAAGTATCAAGGTTCT
          ATGTGATTCCCTCAGATCTAACTGCTAGTTCACTAAGTTTCTCTTCAGCTGTATCTAGTC
          TGCTATTTAACATATTCAGTGAATTTTTAACCTTAAATTCAAGAACAAGACTTTTTATTT
          [C,A]
          TGGAAGTTCAGTTTGGTTCCTTTCAAATGTACCTGGTTCTTTTTCAAAGTGTCATGTTCT
          TTGATAAGAATTTCTACTAATTTACCTTGATAATAAAAATTTGTTTCATGGCTCATTTTA
          GATTGTTCTTTTATCTGCAGTTTTTGGAGGGCTAATTCTCCCATTTCTTGTATCTGTTGT
          TGCACCCGTAAGGTGTAGTTGTTGATTTTTACTTTTTAATTGTGAATTTATTTCTGGTAG
          GGATTGGAAGGAGGTTGTTGGGGTGGGGGTGGGGTGGGGAGAAAATCCTGTGTGCCCTGG

72366     CCTTGATAATAAAAATTTGTTTCATGGCTCATTTTAGATTGTTCTTTTATCTGCAGTTTT
          TGGAGGGCTAATTCTCCCATTTCTTGTATCTGTTGTTGCACCCGTAAGGTGTAGTTGTTG
          ATTTTTACTTTTTAATTGTGAATTTATTTCTGGTAGGGATTGGAAGGAGGTTGTTGGGGT
          GGGGGTGGGGTGGGGAGAAAATCCTGTGTGCCCTGGGTTGCAAAAACACCCCTACAAGTT
          GTTCTCCACTTGCATCTGCCAGTGCTCCAAGGGCTCAGTGATCCTGGACCAGTAGTCATG
```

FIGURE 3YYY

```
         [T,A]
         TAATTTCTTGAATTGTAACAGGATACTGTAAATGTGGACACTCTACCTGAGGTTACTGCT
         TCTTTCTATCTGCTTTATTTCCTTCCCACTGAAGGGCCCTGGACAAGGGTAAACATCTCA
         TCACTTTCTGGGTGGCAGAATATTTCCAGTTCCCCCACTTCTTTTTGGCTTAAGGCTGTG
         GCTTTTTCCTCTGCCTGAATGTGGCCCTAAGAAGCCCTTCTTTTCAAACTTTCCTGTTGT
         ACTTGACCGACTAGCTGTCTAGAGGTTTATATCCCTAGCTTTTAATCTTTGCTGTGAATA

73797    GGATTATTTTATTTAAACCTCCTAATAGTCCATTGAAATAGATATTGCCATGTTGAAAAC
         TGAGGTTCAGAGAGGTTAAGTGACTTACCCAGTGTCACAGAACTAGTAAGTGGTGCAGCT
         GGGATTTGAACTGAGATTCCAGAACAATTGCCATTAACCACTTTGCTTCCATATTAGTAT
         CATCTGCAAATCTCTCTCCATAAATTTCCTCAGTCTTTATCTGAGTTTCCTTATTTCAGG
         AAGGAAAACTTCTGTTTTTGATCCTTATGAAATACAATTTCCATTAAAACTTTTTTTTTT
         [T,-]
         GCTATTAAAAAAGGTACCGGATAATTGAAACCAGACTGGATTTGAGCCTGTGTTGATGGA
         AGTACACATGGGATGTGGGCTGAAGTGTTCAATCTAATTTTTCTTTCCATCAGCTAATTT
         TTAAAGTATTAAGCAAGTAGATTCTGACACTAACAGGGAAGATTTAAATTCTCTTGAGAG
         ACTGGAGGTGTTAAATAATTTTCTGGTAGTGCACATTTTACATCTTAAATCTTCCTCACT
         CTCCCACCTCATCTCAATGTACCTGAAGCTCTGGGAATGTTCTTTTGTACTTCTCAGGAA

74416    CATCTCCTCTCCCCTCCACATCCCTTTCCTGCTCCAATTACTTCCCAGCGCCACTTGGAT
         GTTGTTGTCATCGGGGAACTTTGGAAACAGCCAGATTTTTTTGGAGTCTGTAAGCAGAAA
         ACAGACTGCTTGCTGCTCATATCTGGCACCCAGCTTTGTCCAGAAAACGAGGAGTTAAAA
         AGAAGTCTGGGCTGTGAAGGGCTGTGACAACTGTCCTAGGGGGAGCTCTAGCGAGCCCTG
         GCGGGCAGTGACTCATGCTGCTCTGTCACTGGGATCAGCACTGGCCCCTGGCAGGCAGGC
         [G,A]
         GCAGCCAGGTGGGGTTCCAGCCAGAGCACGCACGCACGGAGCCGGGAGCATGCAGCCTGC
         ACTGCGGGGGATGTGATGCTCGGCTCTAACTCGCCTGGCTGGCCCGCCACGGACGCCTCA
         GCTTGCAACCATGGTAACGTTTCTGGCGGGGGACACCCCGGGAGCCCACCGCGATGGGC
         AGCCTCCTGGTGACTGATGGACGAGTGTCCACCTCCCAGACCGAGAGCGCTTAGTAGGTC
         GGAGGAAGTGGAGAGGATGTAACACGCCCCCAGCCGGGAGTGAAGCCCTGAGGAGGTAGG

74664    TGACTCATGCTGCTCTGTCACTGGGATCAGCACTGGCCCCTGGCAGGCAGGCGGCAGCCA
         GGTGGGGTTCCAGCCAGAGCACGCACGCACGGAGCCGGGAGCATGCAGCCTGCACTGCGG
         GGGATGTGATGCTCGGCTCTAACTCGCCTGGCTGGCCCGCCACGGACGCCTCAGCTTGCA
         ACCATGGTAACGTTTCTGGCGGGGGACACCCCGGGAGCCCACCGCGATGGGCAGCCTCC
         TGGTGACTGATGGACGAGTGTCCACCTCCCAGACCGAGAGCGCTTAGTAGGTCGGAGGAA
         [G,C]
         TGGAGAGGATGTAACACGCCCCCAGCCGGGAGTGAAGCCCTGAGGAGGTAGGAGCCGCAT
         ATGTCCATCCGTGCATTCCCACCGTCAGCGCGCAGGGGTGCTGTAGATCACCGGTAGGAA
         CTTTATTTGGCTGGTGCTTCATTATGCTGATTAAACTGCAGTGGATTTGATGGGCATGAT
         TGCGCTGGGGAAGATGCATAATGAACTAAAAAAAAAAAAAAAGTGGTTAATAAGATCTCGG
         AGTCGACTTGTCCGGGTATGAATGAAGTAGACTGCAGTGGTATCCTAACAGGAGTTCCAG

76330    ATCTAACCATCTATGTATCTGTCTCTCAAGTGGGTGGATGGGGGTTGCTATCTTGGCTGT
         ATAAAGAATCCTAAAAACCTTGTCTCATAAGCTAGAGGTTTCCTGATGGGTTTAACTGAG
         CTGCAAGTGGCTGAACCAGAGCTCTAACAGAGAGATGGTGCTCGGCTCCTCTCCAAGTAT
         GCTGCAAGATCAGGGATCTGGCAGCTGAGCCTCTCTGAGCTGGTGGAGCGCTGGCAGCCA
         GAGAAAGCCCCGTTACTGTGAGCCACCAGGAGGGAGTGTGATGTAGCCGAGTCATTGATT
         [T,C]
         ACAGAAACTGGGCTTCATAGGGGGAAAAAAAACCAGGAGACTAGAAAATGGAAATATAAA
         TATCACTGTAAACCTCTTGATCTGGTAGGTCTTTCTCCATTCTCATAAAAGCTATTGAAA
         AATGCATTAACAGAGCACTTGGAATTAGAGGGTCGAGGCTTCCAGGAGCCTCCTGGAATT
         TCTGTAAAATGCAGTAGCTTCTGTGGATGTGGGAGGTCAGTATCTTGCCTCATTCTCTCA
         TGATACAATGACATTCTGTTTTCAGAGGAGTGAGTTCCCCAGAAGATCTTGGACTGATGG

78181    TCTTGTTATGTGTTATTGCTATTGGACTTGGCTACTCTGCTGTAGGCAGCCCTGTGGGTG
         ATACCTACAAGCATCATTTTAGAAATTCATCCACCTGTTGGATGTAGATGACCCTGGACA
         TATCAGATTGTGATTAATTAGAAATCTAATAAAAGAGAGGCAGTGATGAAATTACTTAGC
         AGCTCCTGCAGTTTTATTGACAAAATTTACTTGGAGAGAGGGGGAGACATTTTCTGGGGG
         TACCACCTTTGCTGCCAGCGACCCTGTGTTTCTTCCTGAGTTTCTTTTTCTTTTCTCACC
         [A,G]
         TTTTCAGCATCACAGGTTTTTATTTACACACATTGATTACCTGTGCTGTTACTCATTCTT
         CACACCACTGAGGAAATTGCAGATGCTGCTGTACTGTGCTAGGTAAATTGACCTCAGATT
         TGTTACCAGTGAATTGAATGAAATGTTCAGAGGTGGAGCTGAATGAACGAGGAGTTTTTG
         TGGAGAAATTGGCAGTGAGAATGATTTAAATTCTGTGATAGCTCCTCGTTTTTTGGGATC
```

FIGURE 3ZZZ

```
         CTTATTTTGGGACCCCAGACTATTTTTAAGCCATTGAGTGCATCATTATTTTAGGCTGAG
78685    ATTTAAATTCTGTGATAGCTCCTCGTTTTTTGGGATCCTTATTTTGGGACCCCAGACTAT
         TTTTAAGCCATTGAGTGCATCATTATTTTAGGCTGAGCAAGAATCTTGATGACAGCGTTT
         CAATGGCTGAGGCGTAGTGGGAGTTCCTTGCAGCTTGAGTTGGTGGGAGCTGGAGAGTTT
         CTAGAGAACTAGGTTTGGTTGTCTTTGGGGTGGGGTTATGGTGAAATTAGTCTTGGAGAG
         TGAGTAGCTGTCTGATGCTTCTTTTCCTTTTTAACCAGCAAGAGCCCAAACCAAATCCCC
         [C,A]
         AGCTCTGAATGCCTGGCTGTTCCTCTCAGCCTTTCTTTGCTTGAACTTGACAATAGTAGG
         GTAGTAACAGGAAACAGCATGTTAAAGTTTTAAAAATAAAATAGATCTCAGCTCTTTTCC
         TTCCCATTAGCAAGGGGTACATTTATTTAGGTTTTTCCTTCTAGATTGAGGCACTGCCTC
         ATTTAAGTTCTTGGTGAAGCCATGCATTTCTGCAAACCATAAGTATAAACTCTAGAACGG
         GGGTGTCCAATCTTTTGGCTTCCTTGGGCCACATGGGAAGAAGAAGAATTGTCTTGAGGC

79926    TTACTAATACACTAGTCCATGTATGTATAGTGTCCTCCTATACACACCAAGAGAATATGG
         AAAGGACTCAGCAATGATTAGGTAGTCCAAAGTCATACCAGATTGGAAACCAAGCTTCCC
         AGGCCCTGGGACTTTTCTGCTAGAGACACTTCACGGTTCTGACCAACTACAAAGAGTTAA
         TATGCAGTTGCCAAATACCTGTTGGTAAAAGGTGGATGTTGGGGAGGAGTGGATTGGGGA
         ACAGAATTAGAAGGTCCAGTCCCAGAATGGGTACCTTCCCATCAAGTTGAACAAGTCAAA
         [G,A]
         CAGGTTATGTTGAAACAACTGAGAGAAAGTAAAGCAAACACCATTGCTGCAGAATATCAT
         GGTACAAATTGGACATCTTTGGGAGTTAGCGGAGTAAGGCAAAATCCAGTGAGGGACGCT
         TAATGGGTAATGCCAATTCACAATTCTTGTTAAATTACATTGCTGATCTTCCTTGGAATG
         TCTGTCCATTCCCCCAAGTAGACTGTGATCTCAAGGCAAGGCTGGGTCTTATTCATCCTG
         GTTTTCCTGGAGCAGTAAATACTTGTGCTGGGACTGGGCTTATAAGCATACTAATGGAAA

80198    ACCTTCCCATCAAGTTGAACAAGTCAAAACAGGTTATGTTGAAACAACTGAGAGAAAGTA
         AAGCAAACACCATTGCTGCAGAATATCATGGTACAAATTGGACATCTTTGGGAGTTAGCG
         GAGTAAGGCAAAATCCAGTGAGGGACGCTTAATGGGTAATGCCAATTCACAATTCTTGTT
         AAATTACATTGCTGATCTTCCTTGGAATGTCTGTCCATTCCCCCAAGTAGACTGTGATCT
         CAAGGCAAGGCTGGGTCTTATTCATCCTGGTTTTCCTGGAGCAGTAAATACTTGTGCTGG
         [G,A]
         ACTGGGCTTATAAGCATACTAATGGAAAGTAAAATATTTGGGTTGGTTTTTTAAAAAGAC
         AGTGGATTTGGATCAGTGGAGAGGAAGGTAGAGGGAATTTCAGGTGGGCAGGGTGCTAAC
         AACAGCCCATCCTTACAGGGCACCAACTGTGTTCTAGGCTGTGTTCCAACCACTTTACAC
         AGATGAATTCATTTAAATTGCACAACCAGCCCAAGAGGAAGGTACCATTATTATTCTCAT
         TTTGGATGTGAGGAAACTGAGGCGTGGGGAGATCAAACAACTTGCCTAAAGTTATGTAGC

80540    GTTGGTTTTTAAAAAGACAGTGGATTTGGATCAGTGGAGAGGAAGGTAGAGGGAATTTC
         AGGTGGGCAGGGTGCTAACAACAGCCCATCCTTACAGGGCACCAACTGTGTTCTAGGCTG
         TGTTCCAACCACTTTACACAGATGAATTCATTTAAATTGCACAACCAGCCCAAGAGGAAG
         GTACCATTATTATTCTCATTTTGGATGTGAGGAAACTGAGGCGTGGGGAGATCAAACAAC
         TTGCCTAAAGTTATGTAGCTTTGAGTGGCTTAGCTGAGATTTGAACCCTGTGGGTATAAA
         [T,C]
         GCCACAGATGGGAAATTTGTGTGGGGTACCCAGGTTCATGTGCTTGTTAGAAGTGGAAGC
         TATTTGTAGAGAATCACGAATGATGAGGTTGGGGCAGGGTGTGATGGGAGCTGACAGGCA
         GGTCTAAATGCTGGGATTCATTTTCAGTCTCTGTGTTTATTGAGTAGGTAGACGGTATAG
         CTCTTGGATTTCTCAGATTTTTTCCTCTTTTCATTTAGAGACTCTTATCTGGTGTGTGTG
         TGCCCGCACACATACATAAACCCACGCGTATATACTCTTTCCCTGAATGTTCTTATTTGC

81810    TTCTCTATTTAGACTGTGCGTGCCTGCCTTGCAGCCCTGGCAGGACCATTCCACCGCCTT
         CTCATTTGTCTTAAAGATACCTTTAGGAAATCTAATCCAGACAATCCTAGCCCAGTCCTG
         AAGATTAGGCTCCAGAAGATCTGTCAAGTGTGTTTTTGCTGGCCTACACATGCTAATTT
         GCATGGTTGCCTGGGATCCCTTAAGAAGACAGTCATTGACTAAATGGCGCTACATGTTCC
         CAAGCTCTGCGCCAGTCTGGCAACTCTTCCTTTGTCTACGTGAATTTCTCCTAGTTCTTT
         [C,T]
         TGCTTTGCTTGCTGTTCATCTCCTGACCTCTCTCCGACAAACTTCCTGAAAGAAGAGCCT
         GCACTCAACACCTCTTTTTTCCACCTCTTCAACAATACTGAAATGACTGTCTCAGAAGCC
         GTTGATTGTACCTAACCACCAAATCTGGTGATTTCCATCTCACCACGTGATACCATTAAT
         ACTACCTTTCTTCGAGACAACGTTCTACTTTCTTCTTCTGTATTATGGACACTTGGTT
         TCCCTCCTACCTCTCTGACTGTCATTCTCACTCTTTTGTGGCTGCCATCAGGCTCTTGCA

82211    AAATGACTGTCTCAGAAGCCGTTGATTGTACCTAACCACCAAATCTGGTGATTTCCATCT
         CACCACGTGATACCATTAATACTACCTTTCTTCGAGACAACGTTCTACTTTCTTCTCTTC
         TGTATTATGGACACTTGGTTTCCCTCCTACCTCTCTGACTGTCATTCTCACTCTTTTGTG
```

FIGURE 3AAAA

```
           GCTGCCATCAGGCTCTTGCAATGTACGTACCATCTCCTCAAGTTCCATCCTCAGTTATCT
           TTCTAGTTGGTTCTTGGTGATCTCATTCAGTTCCTTGACTTTAGTTCTTACCTCCCCATG
           [G,A]
           CCTCCTCCCATCGTACACTGTGTTCCTCATCACCAGGATGTTTTACCAGTTTCTCACCAT
           CCCATCCTCTGTTCCCTTCCTACATAGACAGACCCACTCGCTCACTCAGTAAGCCACTAG
           GTGCTAGTTTTGGCTTCTTCATTTTATGTAAGAAACTACCACCTTCCCTACCCTTCTAGG
           CAAGAAAGCTGAGTCATCGTAAATTCTTTTCTGCCTCCCCCGCCATCCCATCAGTTGCCA
           ATTTCTCCAAGTGGTGCCTCTAGGATGCCACTTGCATCCATACCCATCTTTCTTCCTCAT

82304    GAGACAACGTTCTACTTTCTTCTTCTGTATTATGGACACTTGGTTTCCCTCCTACCTC
           TCTGACTGTCATTCTCACTCTTTTGTGGCTGCCATCAGGCTCTTGCAATGTACGTACCAT
           CTCCTCAAGTTCCATCCTCAGTTATCTTTCTAGTTGGTTCTTGGTGATCTCATTCAGTTC
           CTTGACTTTAGTTCTTACCTCCCCATGGCCTCCTCCCATCGTACACTGTGTTCCTCATCA
           CCAGGATGTTTTACCAGTTTCTCACCATCCCATCCTCTGTTCCCTTCCTACATAGACAGA
           [C,G]
           CCACTCGCTCACTCAGTAAGCCACTAGGTGCTAGTTTTGGCTTCTTCATTTTATGTAAGA
           AACTACCACCTTCCCTACCCTTCTAGGCAAGAAAGCTGAGTCATCGTAAATTCTTTTCTG
           CCTCCCCCGCCATCCCATCAGTTGCCAATTTCTCCAAGTGGTGCCTCTAGGATGCCACTT
           GCATCCATACCCATCTTTCTTCCTCATTGGCACCCATCATGGACTCTTGCTTGGTCTGGT
           GCAGTAGCCTCCTCAGTGATTCCCTTGCCTCTGGTTTTCCTGGCTGTAATCCATTCTCCA

82452    TCTAGTTGGTTCTTGGTGATCTCATTCAGTTCCTTGACTTTAGTTCTTACCTCCCCATGG
           CCTCCTCCCATCGTACACTGTGTTCCTCATCACCAGGATGTTTTACCAGTTTCTCACCAT
           CCCATCCTCTGTTCCCTTCCTACATAGACAGACCCACTCGCTCACTCAGTAAGCCACTAG
           GTGCTAGTTTTGGCTTCTTCATTTTATGTAAGAAACTACCACCTTCCCTACCCTTCTAGG
           CAAGAAAGCTGAGTCATCGTAAATTCTTTTCTGCCTCCCCCGCCATCCCATCAGTTGCCA
           [A,G]
           TTTCTCCAAGTGGTGCCTCTAGGATGCCACTTGCATCCATACCCATCTTTCTTCCTCATT
           GGCACCCATCATGGACTCTTGCTTGGTCTGGTGCAGTAGCCTCCTCAGTGATTCCCTTGC
           CTCTGGTTTTCCTGGCTGTAATCCATTCTCCACAAAGGGTGGAATTCTTCCAAAGCATAG
           GTTGGATGATGTCATTCACCGGCTTACACCTTCAACAGCATCCCAGTGTGCTCATAATTA
           ATGGCTGCTCCTGAACTTGGTATTCAGTCTTGGTATGCCAAGACCCCAGCCTGCCGGCTC

82539    CATCACCAGGATGTTTTACCAGTTTCTCACCATCCCATCCTCTGTTCCCTTCCTACATAG
           ACAGACCCACTCGCTCACTCAGTAAGCCACTAGGTGCTAGTTTTGGCTTCTTCATTTTAT
           GTAAGAAACTACCACCTTCCCTACCCTTCTAGGCAAGAAAGCTGAGTCATCGTAAATTCT
           TTTCTGCCTCCCCCGCCATCCCATCAGTTGCCAATTTCTCCAAGTGGTGCCTCTAGGATG
           CCACTTGCATCCATACCCATCTTTCTTCCTCATTGGCACCCATCATGGACTCTTGCTTGG
           [T,A]
           CTGGTGCAGTAGCCTCCTCAGTGATTCCCTTGCCTCTGGTTTTCCTGGCTGTAATCCATT
           CTCCACAAAGGGTGGAATTCTTCCAAAGCATAGGTTGGATGATGTCATTCACCGGCTTAC
           ACCTTCAACAGCATCCCAGTGTGCTCATAATTAATGGCTGCTCCTGAACTTGGTATTCAG
           TCTTGGTATGCCAAGACCCCAGCCTGCCGGCTCATTTGTGTCTCCTCATCCCCTACTGAA
           TCACTTCAATAGTGTTGTCTGGCCAAGCTGTTCAAGGCTCATTAAGGACAGGACCAGGTC

83079    ATCACTTCAATAGTGTTGTCTGGCCAAGCTGTTCAAGGCTCATTAAGGACAGGACCAGGT
           CTTCCTTCTTTTGCCTGAAACAGTGCCTTGCCCCTGGCAGGTCTTCAATGAACATTTGTT
           GAATTGAATTAGACTAAAATGGCCAGGGATTATACCAATTCCTTCTGCACAGTGTAGACA
           ACTGCTAATGGAACCTGTTTTCTGTAGAGCACTTCTTGTGTTCCCAGAACTATGCGAGTA
           CTTTATGTGCATTATCTCATTAAATCATCACAATCTCACTGTAACTCTATGAGGTAGCTG
           [A,G]
           TATTATCCCCATTTTACAAATGAAGACACTGATTCAGGAAGATTAGATTATTTTCCTGAG
           GTTCTGAAGGTAGAAACACATCTAAGACTTGGAGCAATATCTGGTTGCCTCTAGACCACT
           GTACTATCTACCCTGCCTCTAAGAGCCATGACTTTGCTAGATTATGCAGGAGTTATGGAC
           TTGTCTAATAGTAAAGGTAAAAGAATTGGTTTTAATGAGAATCTACTCTTCTAGGTACTA
           TTCTGAGTGCCTGACAAGCATTCTCATGTAGACCCAGCAATAACTCATTATTTTACAGAT

83350    AATCTCACTGTAACTCTATGAGGTAGCTGATATTATCCCCATTTTACAAATGAAGACACT
           GATTCAGGAAGATTAGATTATTTTCCTGAGGTTCTGAAGGTAGAAACACATCTAAGACTT
           GGAGCAATATCTGGTTGCCTCTAGACCACTGTACTATCTACCCTGCCTCTAAGAGCCATG
           ACTTTGCTAGATTATGCAGGAGTTATGGACTTGTCTAATAGTAAAGGTAAAAGAATTGGT
           TTTAATGAGAATCTACTCTTCTAGGTACTATTCTGAGTGCCTGACAAGCATTCTCATGTA
           [T,G]
           ACCCAGCAATAACTCATTATTTTACAGATAGAGAAAATGATGATCATGATGCTTGGGTTA
           CTTCTTAGGTTCACTCAGCTCACATCTGGCAGAGGGTGGTCAACTTTTCCAAGTTTTAAC
```

FIGURE 3BBBB

```
              TTATTTATTTATTTATTTTGAGACAGAGTCTCATTCTGTTGCCCACGCTGGAGTACGGTG
              ACACAATCTCAGCTTATTGCAACCTCCGCCTCCCAGGTTCAAGCGATTCTTGTGCCTCAG
              CCTCCCGTGTAGCTGGGATTACAGGTGCCTGCCACCACGCCCAGCTAATTTTGTTTTTGT

83407     ACTGATTCAGGAAGATTAGATTATTTTCCTGAGGTTCTGAAGGTAGAAACACATCTAAGA
              CTTGGAGCAATATCTGGTTGCCTCTAGACCACTGTACTATCTACCCTGCCTCTAAGAGCC
              ATGACTTTGCTAGATTATGCAGGAGTTATGGACTTGTCTAATAGTAAAGGTAAAAGAATT
              GGTTTTAATGAGAATCTACTCTTCTAGGTACTATTCTGAGTGCCTGACAAGCATTCTCAT
              GTAGACCCAGCAATAACTCATTATTTTACAGATAGAGAAAATGATGATCATGATGCTTGG
              [A,G]
              TTACTTCTTAGGTTCACTCAGCTCACATCTGGCAGAGGGTGGTCAACTTTTCCAAGTTTT
              AACTTATTTATTTATTTATTTTGAGACAGAGTCTCATTCTGTTGCCCACGCTGGAGTACG
              GTGACACAATCTCAGCTTATTGCAACCTCCGCCTCCCAGGTTCAAGCGATTCTTGTGCCT
              CAGCCTCCCGTGTAGCTGGGATTACAGGTGCCTGCCACCACGCCCAGCTAATTTTGTTTT
              TGTATTTTTAGTAGAGGCTGGGTTTCACCATGTTGGCCAGGCCTGTCTTGAACTCCTGAC

83434     CCTGAGGTTCTGAAGGTAGAAACACATCTAAGACTTGGAGCAATATCTGGTTGCCTCTAG
              ACCACTGTACTATCTACCCTGCCTCTAAGAGCCATGACTTTGCTAGATTATGCAGGAGTT
              ATGGACTTGTCTAATAGTAAAGGTAAAAGAATTGGTTTTAATGAGAATCTACTCTTCTAG
              GTACTATTCTGAGTGCCTGACAAGCATTCTCATGTAGACCCAGCAATAACTCATTATTTT
              ACAGATAGAGAAAATGATGATCATGATGCTTGGGTTACTTCTTAGGTTCACTCAGCTCAC
              [G,A]
              TCTGGCAGAGGGTGGTCAACTTTTCCAAGTTTTAACTTATTTATTTATTTATTTTGAGAC
              AGAGTCTCATTCTGTTGCCCACGCTGGAGTACGGTGACACAATCTCAGCTTATTGCAACC
              TCCGCCTCCCAGGTTCAAGCGATTCTTGTGCCTCAGCCTCCCGTGTAGCTGGGATTACAG
              GTGCCTGCCACCACGCCCAGCTAATTTTGTTTTTGTATTTTTAGTAGAGGCTGGGTTTCA
              CCATGTTGGCCAGGCCTGTCTTGAACTCCTGACCTCAAGTGATCTGCCAGCCTCGGCCTC

83527     ATGACTTTGCTAGATTATGCAGGAGTTATGGACTTGTCTAATAGTAAAGGTAAAAGAATT
              GGTTTTAATGAGAATCTACTCTTCTAGGTACTATTCTGAGTGCCTGACAAGCATTCTCAT
              GTAGACCCAGCAATAACTCATTATTTTACAGATAGAGAAAATGATGATCATGATGCTTGG
              GTTACTTCTTAGGTTCACTCAGCTCACATCTGGCAGAGGGTGGTCAACTTTTCCAAGTTT
              TAACTTATTTATTTATTTATTTTGAGACAGAGTCTCATTCTGTTGCCCACGCTGGAGTAC
              [A,G]
              GTGACACAATCTCAGCTTATTGCAACCTCCGCCTCCCAGGTTCAAGCGATTCTTGTGCCT
              CAGCCTCCCGTGTAGCTGGGATTACAGGTGCCTGCCACCACGCCCAGCTAATTTTGTTTT
              TGTATTTTTAGTAGAGGCTGGGTTTCACCATGTTGGCCAGGCCTGTCTTGAACTCCTGAC
              CTCAAGTGATCTGCCAGCCTCGGCCTCCCAAAGTGTTGTGATTACAGATGTGAGCCACCA
              CGCCTGGCTCAACTTTTAACTTTAGAACTGATATAAACATGCCTATTTTTTTGGGACTGA

83699     ATGCTTGGGTTACTTCTTAGGTTCACTCAGCTCACATCTGGCAGAGGGTGGTCAACTTTT
              CCAAGTTTTAACTTATTTATTTATTTATTTTGAGACAGAGTCTCATTCTGTTGCCCACGC
              TGGAGTACGGTGACACAATCTCAGCTTATTGCAACCTCCGCCTCCCAGGTTCAAGCGATT
              CTTGTGCCTCAGCCTCCCGTGTAGCTGGGATTACAGGTGCCTGCCACCACGCCCAGCTAA
              TTTTGTTTTTGTATTTTTAGTAGAGGCTGGGTTTCACCATGTTGGCCAGGCCTGTCTTGA
              [G,A]
              CTCCTGACCTCAAGTGATCTGCCAGCCTCGGCCTCCCAAAGTGTTGTGATTACAGATGTG
              AGCCACCACGCCTGGCTCAACTTTTAACTTTAGAACTGATATAAACATGCCTATTTTTTT
              GGGACTGACTGTAGCATACCCATTCAAAGTCCAGGCTTTGGAATCAGACAGACGTGGGCT
              GAACTCAGGGTTTCACCCCTTGCTTGTTGTGTGAATGAGACATTTCACTGCTTTCAGCCT
              CAATTCCCTCATCTGTAAAGTGGAAGGTGTAAGGTCGCCTATCTGATAGGTTTGCCATGG

83729     CTCACATCTGGCAGAGGGTGGTCAACTTTTCCAAGTTTTAACTTATTTATTTATTTATTT
              TGAGACAGAGTCTCATTCTGTTGCCCACGCTGGAGTACGGTGACACAATCTCAGCTTATT
              GCAACCTCCGCCTCCCAGGTTCAAGCGATTCTTGTGCCTCAGCCTCCCGTGTAGCTGGGA
              TTACAGGTGCCTGCCACCACGCCCAGCTAATTTTGTTTTTGTATTTTTAGTAGAGGCTGG
              GTTTCACCATGTTGGCCAGGCCTGTCTTGAACTCCTGACCTCAAGTGATCTGCCAGCCTC
              [A,G]
              GCCTCCCAAAGTGTTGTGATTACAGATGTGAGCCACCACGCCTGGCTCAACTTTTAACTT
              TAGAACTGATATAAACATGCCTATTTTTTTGGGACTGACTGTAGCATACCCATTCAAAGT
              CCAGGCTTTGGAATCAGACAGACGTGGGCTGAACTCAGGGTTTCACCCCTTGCTTGTTGT
              GTGAATGAGACATTTCACTGCTTTCAGCCTCAATTCCCTCATCTGTAAAGTGGAAGGTGT
              AAGGTCGCCTATCTGATAGGTTTGCCATGGGGATATGAAGCACACTTAGTGTTGGTGCCA

84000     CTCCTGACCTCAAGTGATCTGCCAGCCTCGGCCTCCCAAAGTGTTGTGATTACAGATGTG
```

FIGURE 3CCCC

```
         AGCCACCACGCCTGGCTCAACTTTTAACTTTAGAACTGATATAAACATGCCTATTTTTTT
         GGGACTGACTGTAGCATACCCATTCAAAGTCCAGGCTTTGGAATCAGACAGACGTGGGCT
         GAACTCAGGGTTTCACCCCTTGCTTGTTGTGTGAATGAGACATTTCACTGCTTTCAGCCT
         CAATTCCCTCATCTGTAAAGTGGAAGGTGTAAGGTCGCCTATCTGATAGGTTTGCCATGG
         [T,G]
         GATATGAAGCACACTTAGTGTTGGTGCCATGAGTAGAATGAGTGTTCATTTCATATTTGT
         TAATGTTATTTAGGTCCGAGGATGGGTATGGGGTGCTTTGGACTCTCTTTTTTCTCCCTGC
         TTCCGCCTTATAAAGACATCTTGCTGGTTTCTGCCCATTGAGAGAATCCAGCTCCACGTG
         GGGGGCCTGACAGATGTCCTAATATCTCCATCCAATTTTTTACTCTGAATGGAGTCTGTG
         ATGTATCACTTCAACCTGCACTTTCTATAAAATGCTCTCCAGGCTTCTGGTAGGATCCAG

84034    CCCAAAGTGTTGTGATTACAGATGTGAGCCACCACGCCTGGCTCAACTTTTAACTTTAGA
         ACTGATATAAACATGCCTATTTTTTTGGGACTGACTGTAGCATACCCATTCAAAGTCCAG
         GCTTTGGAATCAGACAGACGTGGGCTGAACTCAGGGTTTCACCCCTTGCTTGTTGTGTGA
         ATGAGACATTTCACTGCTTTCAGCCTCAATTCCCTCATCTGTAAAGTGGAAGGTGTAAGG
         TCGCCTATCTGATAGGTTTGCCATGGGGATATGAAGCACACTTAGTGTTGGTGCCATGAG
         [C,T]
         AGAATGAGTGTTCATTTCATATTTGTTAATGTTATTTAGGTCCGAGGATGGGTATGGGGT
         GCTTTGGACTCTCTTTTTCTCCCTGCTTCCGCCTTATAAAGACATCTTGCTGGTTTCTGC
         CCATTGAGAGAATCCAGCTCCACGTGGGGGGCCTGACAGATGTCCTAATATCTCCATCCA
         ATTTTTTACTCTGAATGGAGTCTGTGATGTATCACTTCAACCTGCACTTTCTATAAAATG
         CTCTCCAGGCTTCTGGTAGGATCCAGTGCCAGTGGGAAGTGTGCATGTTCCCAGCCTAGA

84213    AATGAGACATTTCACTGCTTTCAGCCTCAATTCCCTCATCTGTAAAGTGGAAGGTGTAAG
         GTCGCCTATCTGATAGGTTTGCCATGGGGATATGAAGCACACTTAGTGTTGGTGCCATGA
         GTAGAATGAGTGTTCATTTCATATTTGTTAATGTTATTTAGGTCCGAGGATGGGTATGGG
         GTGCTTTGGACTCTCTTTTTCTCCCTGCTTCCGCCTTATAAAGACATCTTGCTGGTTTCT
         GCCCATTGAGAGAATCCAGCTCCACGTGGGGGGCCTGACAGATGTCCTAATATCTCCATC
         [C,T]
         AATTTTTTACTCTGAATGGAGTCTGTGATGTATCACTTCAACCTGCACTTTCTATAAAAT
         GCTCTCCAGGCTTCTGGTAGGATCCAGTGCCAGTGGGAAGTGTGCATGTTCCCAGCCTAG
         ATGTCACATGCTCCCACCCACCCTGGAAGCACTTGGGTATCCCCTGGATGGGTAAGTCTG
         TGTGTCATTGTGCCATTCCTGTCTCAGAACCAATGCTGGGCATCTCTACTTGCAGGTGCT
         GGAAAGCTTTTTCATGCCAGCATACATGCAGCACACTTCTCATTTTGGATTCCTTTATCC

84803    TTCCTTTATCCCACGGTGACCTTTAAACTGGCTGCCTGGGGGCACAGAAGTACTAGCACA
         CCATTCACTTATTTATTCATTCATTCATTCATTCATTCATTCACTCAACAAATATATTGT
         TCTAGTCCTTAAGGCACAACTCTGAGCAAGACAGGTAAGGTCTTTACTCTCAAGAAGCTA
         GCATTTGGTGGGGAGAAACAAAGGAGAAATAACTACTGTGCACATGTGAGGCAATTGCAG
         ATGGTGGTCTGCAGAATTGGGATTGAGACTGCCTGGGGGTGGCCACTTTAGACTGGGTCC
         [A,G]
         CAAGGAAAGGTTCTCTGAGCTGAGCATGAGTATTTGTTCAAGAAGGCTGAGTTGCATCCC
         AAGGTGACACAGCTTTTAAGCCCACACTGAGCAGCTCTGAGGTCCTAGGGGCTGTTCGAG
         AACCTGGGATATAGCACTGACTATGAGACAAAAATCCCTGTCTTCATGGAGCTTACATGA
         TGGGGGCAGATTCACATTCATTCATTTGTTCATTAATTCATTAATTCATTCAGCTATTTG
         AGAGCCTACTATGTGCCAAGCACTTTCTAGGCACTGGAGAAGTAACAGTGAATGCAAAGG

85027    TGTGAGGCAATTGCAGATGGTGGTCTGCAGAATTGGGATTGAGACTGCCTGGGGGTGGCC
         ACTTTAGACTGGGTCCGCAAGGAAAGGTTCTCTGAGCTGAGCATGAGTATTTGTTCAAGA
         AGGCTGAGTTGCATCCCAAGGTGACACAGCTTTTAAGCCCACACTGAGCAGCTCTGAGGT
         CCTAGGGGCTGTTCGAGAACCTGGGATATAGCACTGACTATGAGACAAAAATCCCTGTCT
         TCATGGAGCTTACATGATGGGGGCAGATTCACATTCATTCATTTGTTCATTAATTCATTA
         [G,A]
         TTCATTCAGCTATTTGAGAGCCTACTATGTGCCAAGCACTTTCTAGGCACTGGAGAAGTA
         ACAGTGAATGCAAAGGAGCAAGCATCCCTGCCCACACAGAGTGCATTCTTCCAGAATATC
         AATAAGGAGTCGGTTAGCAAAAATAAGTGGGAAGAGTATTCCAGAGAGAGGAAAAAAGGG
         CAAAGGCCCTGAGGCTGCCACTAACCTATGGGTGCTCAATGAACAGAAGGCATGTTTGGG
         TAGGGGGTACTTAAGGATACACAAGGAACATGGTCTGAGCTGAGGTCATCAGGGCCTTTA

85275    CTTACATGATGGGGGCAGATTCACATTCATTCATTTGTTCATTAATTCATTAATTCATTC
         AGCTATTTGAGAGCCTACTATGTGCCAAGCACTTTCTAGGCACTGGAGAAGTAACAGTGA
         ATGCAAAGGAGCAAGCATCCCTGCCCACACAGAGTGCATTCTTCCAGAATATCAATAAGG
         AGTCGGTTAGCAAAAATAAGTGGGAAGAGTATTCCAGAGAGAGGAAAAAAGGGCAAAGGC
         CCTGAGGCTGCCACTAACCTATGGGTGCTCAATGAACAGAAGGCATGTTTGGGTAGGGGG
         [A,T]
```

FIGURE 3DDDD

ACTTAAGGATACACAAGGAACATGGTCTGAGCTGAGGTCATCAGGGCCTTTAGGTATGGA
CTTTGCTCTAAATTGCACTGAGTAGGAAGCTTTTGCAGGATTTTGAATAGGGTCATGGAA
TATCTGGGTCTTATTTCACAAAGTGTGCCTCTGACCATTGTGTGGAGGGTGGATAGTGAG
GGACAAGAGTTGGATCCAGGGAGGTAAGTGTGGTTATTGCAGTCATCCCAGGTGAGAGGC
AATGAAATTAACCTGCAAAGTGAGGCACTGGCTTAGAGGTGGGAACTGAATTAAAAATCA

87009   GCTTGATGCTTAAGCACGAACTTAATCATCGCAGTAGTGATTAAAGAGTATTCAACATGT
        ACACTTGCTTGTAGGAAGGAGTACACATTGTATTCTCTTTTGATATGCAATATTTTATTC
        ATAGCCCTATTAAGTAATTTTTTTTAACAAAGTTATATGGATTATTTACAGGTACATCAC
        GGGAAAACTGCATTTTATAATTTTCACTGAAATGTTGAGGTTACATGTAAAGCAATTTTT
        ATGTCATATCTGATACATTTTAAGAAAACATGTCTTCCTGTTACAGCGGTAATGACCATG
        [T,C]
        CTGCTCTTTCTTCTGTGTCATATGCCATTATCCCTATTAATACTCTTTGGGCTTCTATAA
        TTATAAAGCAGATGTGTATATCAGGGAGAGATTTGATTTCAGAGTAAGTTTTTCTAGAA
        AATAGAAGCTGGAAAAAAAAGGAAAACCCAAACTTGGCTTCGTGCTCGAAGAGACAGCAC
        TGCTGTGTGTGGGCGGTGGCTGCGTGCACCCGCTGCTCAGAAGTGCCTTTTCTCTCCAT
        GGGGATAACTGGCTGTGTATCCGAGATGTGGCCAGGAGTAGGCAAGCAACGTGTGGGCAG

87888   ACTGTATCTCACATGTTCCGCTCTCCCTTTCCTCCATGACCTTGCCCCTCTGAGCCTCTG
        TAGCACTTTTCTTGAGTGTGTCCAAGGCCATCTAGCTAAGAAGTAGCAGAAATGGGATTT
        GAAGCCATGACTGTTTGGTGATAGAGCCTCAGCTTTGAACTGGGGTTCTACTGCCTGGCA
        CCCCTGCACAAATCATGGTAACGTGGTAGGAGAACATAGAGGTATAGGGCAAGCCCCTCC
        TTAATGCCATGAATAATACCCATCTTATAGGATTGTGGGGAGGACTCAGTGAAGTAACCC
        [G,A]
        TGAAGCACTAAACACGTGCCTGACACGTGCTCAATAAATGAGCACTTGTCCTGATGACAA
        AGGTCGTGGCATTAATTCTCTCTCCTAGGTTGTTACTTCCTTGAGGACAGGAATTGTGGC
        TTCCTTAATGGCCACTGCAGCAGAGTTTCTCAAGTTGGCACTATTGACATTTTGGGCTGG
        ATAATTCTTGTTGTGGGAGCTGTCCTGTGGATTGTAGGATGTTGAGCAGCATCTTTGGCC
        TCTACCCGCTACATATTAATAGCACCCCTAGTCATGAAAATAAAATGTCTAGACATTGCC

88136   ATGAATAATACCCATCTTATAGGATTGTGGGGAGGACTCAGTGAAGTAACCCGTGAAGCA
        CTAAACACGTGCCTGACACGTGCTCAATAAATGAGCACTTGTCCTGATGACAAAGGTCGT
        GGCATTAATTCTCTCTCCTAGGTTGTTACTTCCTTGAGGACAGGAATTGTGGCTTCCTTA
        ATGGCCACTGCAGCAGAGTTTCTCAAGTTGGCACTATTGACATTTTGGGCTGGATAATTC
        TTGTTGTGGGAGCTGTCCTGTGGATTGTAGGATGTTGAGCAGCATCTTTGGCCTCTACCC
        [G,A]
        CTACATATTAATAGCACCCCTAGTCATGAAAATAAAATGTCTAGACATTGCCAAACTGCC
        CCTGTTGAGAACCACTGGTCTGCAGGTATCTCTCATGGGGATCACAGGGCTTTTATATTC
        TCTTCTCTGTCTCTCTCTCCCTCTCTGGGTGTCTCTCTCTCTCACACACACGCTTAGA
        GAAGGTGGTTAAAAAAAATTTTGTTGAAGTTTGAGAATTTTGAGAACAAAGGAAAAATTT
        TGGAAGGCATTTTAATGAACAGATAGACTCTGTCCCATTCCATGGTCAACAGAATTTCAT

88231   CACTTGTCCTGATGACAAAGGTCGTGGCATTAATTCTCTCTCCTAGGTTGTTACTTCCTT
        GAGGACAGGAATTGTGGCTTCCTTAATGGCCACTGCAGCAGAGTTTCTCAAGTTGGCACT
        ATTGACATTTTGGGCTGGATAATTCTTGTTGTGGGAGCTGTCCTGTGGATTGTAGGATGT
        TGAGCAGCATCTTTGGCCTCTACCCGCTACATATTAATAGCACCCCTAGTCATGAAAATA
        AAATGTCTAGACATTGCCAAACTGCCCCTGTTGAGAACCACTGGTCTGCAGGTATCTCTC
        [G,A]
        TGGGGATCACAGGGCTTTTATATTCTCTTCTCTGTCTCTCTCTCTCCCTCTCTGGGTGTC
        TCTCTCTCTCACACACACGCTTAGAGAAGGTGGTTAAAAAAAATTTTGTTGAAGTTTGAG
        AATTTTGAGAACAAAGGAAAAATTTTGGAAGGCATTTTAATGAACAGATAGACTCTGTCC
        CATTCCATGGTCAACAGAATTTCATAATTAGATAGTTTGTTTACTGCAACTCTGCACCCC
        ATTGCCCATCATTTTAGAGTTCCAACCAGTTAGAGGATTTTTCTTGCAAACTTTCCTTAA

88482   CATTGCCAAACTGCCCCTGTTGAGAACCACTGGTCTGCAGGTATCTCTCATGGGGATCAC
        AGGGCTTTTATATTCTCTTCTCTGTCTCTCTCTCTCCCTCTCTGGGTGTCTCTCTCTCTC
        ACACACACGCTTAGAGAAGGTGGTTAAAAAAAATTTTGTTGAAGTTTGAGAATTTTGAGA
        ACAAAGGAAAAATTTTGGAAGGCATTTTAATGAACAGATAGACTCTGTCCCATTCCATGG
        TCAACAGAATTTCATAATTAGATAGTTTGTTTACTGCAACTCTGCACCCCATTGCCCATC
        [A,G]
        TTTTAGAGTTCCAACCAGTTAGAGGATTTTTCTTGCAAACTTTCCTTAAAGCAGTGATAG
        TATCAGCTCTTTAAATAATACTATGCTTGATGAAGTGGTACTTTTCGGGATAATTTGAGA
        CCAGCCGACTTGCTGCTTGAAGAGGACAGGGCTATATTTGGTAATAATATATATGTGATA
        ATATGTATGTAATATTATTATAATGTAATATACAATAATATTTGGTGTAACTGGTGACTC
        TGAGGCCAGTCTTTGATCGAACCTCTCAAGCTATGATTTACATTATGGTCAATGTTAGCA

FIGURE 3EEEE

88608    ACGCTTAGAGAAGGTGGTTAAAAAAAATTTTGTTGAAGTTTGAGAATTTTGAGAACAAAG
GAAAAATTTTGGAAGGCATTTTAATGAACAGATAGACTCTGTCCCATTCCATGGTCAACA
GAATTTCATAATTAGATAGTTTGTTTACTGCAACTCTGCACCCCATTGCCCATCATTTTA
GAGTTCCAACCAGTTAGAGGATTTTTCTTGCAAACTTTCCTTAAAGCAGTGATAGTATCA
GCTCTTTAAATAATACTATGCTTGATGAAGTGGTACTTTTCGGGATAATTTGAGACCAGC
[C,A]
GACTTGCTGCTTGAAGAGGACAGGGCTATATTTGGTAATAATATATATGTGATAATATGT
ATGTAATATTATTATAATGTAATATACAATAATATTTGGTGTAACTGGTGACTCTGAGGC
CAGTCTTTGATCGAACCTCTCAAGCTATGATTTACATTATGGTCAATGTTAGCATAATGC
AATTATCAGCAATCACTTGCTGTTGCTTTGAAAGTCAGAAGGATGGCTAATAAAAATCTT
AGAAAAAGAAAACAGGCTGGGCGCAGTGGCTCACCCCTGTAATCCCAGCACTTTGGGAGG

88866    TGCTTGATGAAGTGGTACTTTTCGGGATAATTTGAGACCAGCCGACTTGCTGCTTGAAGA
GGACAGGGCTATATTTGGTAATAATATATATGTGATAATATGTATGTAATATTATTATAA
TGTAATATACAATAATATTTGGTGTAACTGGTGACTCTGAGGCCAGTCTTTGATCGAACC
TCTCAAGCTATGATTTACATTATGGTCAATGTTAGCATAATGCAATTATCAGCAATCACT
TGCTGTTGCTTTGAAAGTCAGAAGGATGGCTAATAAAAATCTTAGAAAAAGAAAACAGGC
[T,C]
GGGCGCAGTGGCTCACCCCTGTAATCCCAGCACTTTGGGAGGCTGAGGCGGGCAGATCAT
GAGGTCAGGAGATCGAGACCATCCTGGCCAACATGGTGAAACCCCATCTGTACTAGAATA
CAAAAAAAAAAAAAAAATTTGCTGGGCGTGGTGGCGTGCGCCTGTAGTCCCAGCTACTCG
GGAGCTGAGTCAGGGGAATCGCTTGAACCCGGGAGGTGGAGGTTGCAGTGAGCCGAGATT
GTGCCACTGCACTCCAGCCTGGTGACAGAGTGAGACTCCGTCTCAAACAAAACAAAACAA

88870    TGATGAAGTGGTACTTTTCGGGATAATTTGAGACCAGCCGACTTGCTGCTTGAAGAGGAC
AGGGCTATATTTGGTAATAATATATATGTGATAATATGTATGTAATATTATTATAATGTA
ATATACAATAATATTTGGTGTAACTGGTGACTCTGAGGCCAGTCTTTGATCGAACCTCTC
AAGCTATGATTTACATTATGGTCAATGTTAGCATAATGCAATTATCAGCAATCACTTGCT
GTTGCTTTGAAAGTCAGAAGGATGGCTAATAAAAATCTTAGAAAAAGAAAACAGGCTGGG
[C,T]
GCAGTGGCTCACCCCTGTAATCCCAGCACTTTGGGAGGCTGAGGCGGGCAGATCATGAGG
TCAGGAGATCGAGACCATCCTGGCCAACATGGTGAAACCCCATCTGTACTAGAATACAAA
AAAAAAAAAAAAATTTGCTGGGCGTGGTGGCGTGCGCCTGTAGTCCCAGCTACTCGGGAG
CTGAGTCAGGGGAATCGCTTGAACCCGGGAGGTGGAGGTTGCAGTGAGCCGAGATTGTGC
CACTGCACTCCAGCCTGGTGACAGAGTGAGACTCCGTCTCAAACAAAACAAAACAAAACA

88918    CTTGAAGAGGACAGGGCTATATTTGGTAATAATATATATGTGATAATATGTATGTAATAT
TATTATAATGTAATATACAATAATATTTGGTGTAACTGGTGACTCTGAGGCCAGTCTTTG
ATCGAACCTCTCAAGCTATGATTTACATTATGGTCAATGTTAGCATAATGCAATTATCAG
CAATCACTTGCTGTTGCTTTGAAAGTCAGAAGGATGGCTAATAAAAATCTTAGAAAAAGA
AAACAGGCTGGGCGCAGTGGCTCACCCCTGTAATCCCAGCACTTTGGGAGGCTGAGGCGG
[G,A]
CAGATCATGAGGTCAGGAGATCGAGACCATCCTGGCCAACATGGTGAAACCCCATCTGTA
CTAGAATACAAAAAAAAAAAAAAAATTTGCTGGGCGTGGTGGCGTGCGCCTGTAGTCCCA
GCTACTCGGGAGCTGAGTCAGGGGAATCGCTTGAACCCGGGAGGTGGAGGTTGCAGTGAG
CCGAGATTGTGCCACTGCACTCCAGCCTGGTGACAGAGTGAGACTCCGTCTCAAACAAAA
CAAAACAAAACAAAAAACAAAAAAGAAAATCTTAGAAAAGAAAATAAATTGTAATATT

88940    TTGGTAATAATATATATGTGATAATATGTATGTAATATTATTATAATGTAATATACAATA
ATATTTGGTGTAACTGGTGACTCTGAGGCCAGTCTTTGATCGAACCTCTCAAGCTATGAT
TTACATTATGGTCAATGTTAGCATAATGCAATTATCAGCAATCACTTGCTGTTGCTTTGA
AAGTCAGAAGGATGGCTAATAAAAATCTTAGAAAAAGAAAACAGGCTGGGCGCAGTGGCT
CACCCCTGTAATCCCAGCACTTTGGGAGGCTGAGGCGGGCAGATCATGAGGTCAGGAGAT
[C,T]
GAGACCATCCTGGCCAACATGGTGAAACCCCATCTGTACTAGAATACAAAAAAAAAAAAA
AAATTTGCTGGGCGTGGTGGCGTGCGCCTGTAGTCCCAGCTACTCGGGAGCTGAGTCAGG
GGAATCGCTTGAACCCGGGAGGTGGAGGTTGCAGTGAGCCGAGATTGTGCCACTGCACTC
CAGCCTGGTGACAGAGTGAGACTCCGTCTCAAACAAAACAAAACAAAACAAAAACAAAA
AAAGAAAATCTTAGAAAAAGAAAATAAATTGTAATATTTCAGAATATTTGTTGGGGAGGA

89133       GGCTAATAAAAATCTTAGAAAAAGAAAACAGGCTGGGCGCAGTGGCTCACCCCTGTAATC
CCAGCACTTTGGGAGGCTGAGGCGGGCAGATCATGAGGTCAGGAGATCGAGACCATCCTG
GCCAACATGGTGAAACCCCATCTGTACTAGAATACAAAAAAAAAAAAAAAAATTTGCTGGG

FIGURE 3FFFF

```
              CGTGGTGGCGTGCGCCTGTAGTCCCAGCTACTCGGGAGCTGAGTCAGGGGAATCGCTTGA
              ACCCGGGAGGTGGAGGTTGCAGTGAGCCGAGATTGTGCCACTGCACTCCAGCCTGGTGAC
              [A,G]
              GAGTGAGACTCCGTCTCAAACAAAACAAAACAAAACAAAAAACAAAAAAAGAAAATCTTA
              GAAAAGAAAATAAATTGTAATATTTCAGAATATTTGTTGGGGAGGATATGTGTGCTCAA
              GAAATATATACTGAGAACTTACCATTGATGCTAGAGATTGAATTGCCCCATGTCTACATG
              AAAAATGAATAGAATATAAACATTTTAAATTGAGCCATGTCTATCTGTATTATATTTCTT
              TTATAGAAATTCATGGAAATGGTATATTTTAACTGAATTATTAACACTGGGGACAATAGG

89260     TGGTGAAACCCCATCTGTACTAGAATACAAAAAAAAAAAAAATTTGCTGGGCGTGGTG
              GCGTGCGCCTGTAGTCCCAGCTACTCGGGAGCTGAGTCAGGGGAATCGCTTGAACCCGGG
              AGGTGGAGGTTGCAGTGAGCCGAGATTGTGCCACTGCACTCCAGCCTGGTGACAGAGTGA
              GACTCCGTCTCAAACAAAACAAAACAAAACAAAAAACAAAAAAGAAAATCTTAGAAAAA
              GAAAATAAATTGTAATATTTCAGAATATTTGTTGGGGAGGATATGTGTGCTCAAGAAATA
              [T,C]
              ATACTGAGAACTTACCATTGATGCTAGAGATTGAATTGCCCCATGTCTACATGAAAAATG
              AATAGAATATAAACATTTTAAATTGAGCCATGTCTATCTGTATTATATTTCTTTTATAGA
              AATTCATGGAAATGGTATATTTTAACTGAATTATTAACACTGGGGACAATAGGCTTTAAT
              CATTATCTAATACCTGTACGTTGTTTTGAAATTCATAGCCCACCACCATTAATTTCAAAA
              TTGGGTTCTTACTCAAAGAGTGATGAAAAGGCACCAGTACCAAATGGTCTGGCCAAAATG

89298     AAAAAATTTGCTGGGCGTGGTGGCGTGCGCCTGTAGTCCCAGCTACTCGGGAGCTGAGTC
              AGGGGAATCGCTTGAACCCGGGAGGTGGAGGTTGCAGTGAGCCGAGATTGTGCCACTGCA
              CTCCAGCCTGGTGACAGAGTGAGACTCCGTCTCAAACAAAACAAAACAAAACAAAAACA
              AAAAAGAAAATCTTAGAAAAGAAAATAAATTGTAATATTTCAGAATATTTGTTGGGGA
              GGATATGTGTGCTCAAGAAATATATACTGAGAACTTACCATTGATGCTAGAGATTGAATT
              [G,T]
              CCCCATGTCTACATGAAAAATGAATAGAATATAAACATTTTAAATTGAGCCATGTCTATC
              TGTATTATATTTCTTTTATAGAAATTCATGGAAATGGTATATTTTAACTGAATTATTAAC
              ACTGGGGACAATAGGCTTTAATCATTATCTAATACCTGTACGTTGTTTTGAAATTCATAG
              CCCACCACCATTAATTTCAAAATTGGGTTCTTACTCAAAGAGTGATGAAAAGGCACCAGT
              ACCAAATGGTCTGGCCAAAATGCTACATGGAACTAAATGCTGGGGATGGTCATACAATGA

89682     ATTCATGGAAATGGTATATTTTAACTGAATTATTAACACTGGGGACAATAGGCTTTAATC
              ATTATCTAATACCTGTACGTTGTTTTGAAATTCATAGCCCACCACCATTAATTTCAAAAT
              TGGGTTCTTACTCAAAGAGTGATGAAAAGGCACCAGTACCAAATGGTCTGGCCAAAATGC
              TACATGGAACTAAATGCTGGGGATGGTCATACAATGAGTTTTAAGTGGCTAGACCCTAAA
              TCAGAAGCACTTTCTTCTAATTAGCACCATGGTTCTTAATCCTTTCTGTACATTACAATC
              [G,A]
              CTCAGCAGCTTAATACAAATGTTGCTTCCCGGGGCCACACTCCACATCTTTCTGACTCTC
              TGATTTAATTGGTCCGAATGGGGCCTATACATCAGGTGTTTTTTAAAAGGTCTCCAAGTG
              ATTCTAATGTGTACCTGCATTGAGGACCAGGGAAGGTGTAGGAAGCCTGATAACCTTTAC
              TCTCCAGCCTCATCCTCCAATCCCATGATTGTTTATGGGATTGTTGCTACACACCCAGCT
              TAGTCATAGCATTCTTACTCTAGCTTTTTTTTAGATGCAATTTTTATTTATTCTTAAAGA

89757     TACGTTGTTTTGAAATTCATAGCCCACCACCATTAATTTCAAAATTGGGTTCTTACTCAA
              AGAGTGATGAAAAGGCACCAGTACCAAATGGTCTGGCCAAAATGCTACATGGAACTAAAT
              GCTGGGGATGGTCATACAATGAGTTTTAAGTGGCTAGACCCTAAATCAGAAGCACTTTCT
              TCTAATTAGCACCATGGTTCTTAATCCTTTCTGTACATTACAATCGCTCAGCAGCTTAAT
              ACAAATGTTGCTTCCCGGGGCCACACTCCACATCTTTCTGACTCTCTGATTTAATTGGTC
              [C,T]
              GAATGGGGCCTATACATCAGGTGTTTTTTAAAAGGTCTCCAAGTGATTCTAATGTGTACC
              TGCATTGAGGACCAGGGAAGGTGTAGGAAGCCTGATAACCTTTACTCTCCAGCCTCATCC
              TCCAATCCCATGATTGTTTATGGGATTGTTGCTACACACCCAGCTTAGTCATAGCATTCT
              TACTCTAGCTTTTTTTTAGATGCAATTTTTATTTATTCTTAAAGAAAAAGATTTCTTTAG
              CACCTTTATTCTAAAGAGCTCTTAATTGCTGTGCTTAGAACTTCTAAACAGTGAGCATTT

89817     AGAGTGATGAAAAGGCACCAGTACCAAATGGTCTGGCCAAAATGCTACATGGAACTAAAT
                GCTGGGGATGGTCATACAATGAGTTTTAAGTGGCTAGACCCTAAATCAGAAGCACTTTCT
              TCTAATTAGCACCATGGTTCTTAATCCTTTCTGTACATTACAATCGCTCAGCAGCTTAAT
              ACAAATGTTGCTTCCCGGGGCCACACTCCACATCTTTCTGACTCTCTGATTTAATTGGTC
              CGAATGGGGCCTATACATCAGGTGTTTTTTAAAAGGTCTCCAAGTGATTCTAATGTGTAC
              [C,T]
              TGCATTGAGGACCAGGGAAGGTGTAGGAAGCCTGATAACCTTTACTCTCCAGCCTCATCC
```

FIGURE 3GGGG

```
         TCCAATCCCATGATTGTTTATGGGATTGTTGCTACACACCCAGCTTAGTCATAGCATTCT
         TACTCTAGCTTTTTTTTAGATGCAATTTTTATTTATTCTTAAAGAAAAAGATTTCTTTAG
         CACCTTTATTCTAAAGAGCTCTTAATTGCTGTGCTTAGAACTTCTAAACAGTGAGCATTT
         GTCAAACATAGAATAGCAGAATGAAGGGGTTGGACCTCGGGTGAGGAGGGCTGTCGCATG

90248    TTTTTTTAGATGCAATTTTTATTTATTCTTAAAGAAAAAGATTTCTTTAGCACCTTTATT
         CTAAAGAGCTCTTAATTGCTGTGCTTAGAACTTCTAAACAGTGAGCATTTGTCAAACATA
         GAATAGCAGAATGAAGGGGTTGGACCTCGGGTGAGGAGGGCTGTCGCATGGTCTCTTTCG
         AGTGCCGGCGGGTGGGGGCTGCACATCTCCTCGCTTCTGGGCCCATTGATAAGTGACCTA
         AAAGTGCCTTTCGTTTTTTTTGGTGGGGGGTGAAAAAGCAATCTGTTTTGTACCCACAGC
         [G,A]
           GTGCACTTTAAACAGGAAGCCCTACTGGGGCCAGCCTTCTATGTGTCATTAAGTTTTTCA
         CGCCACATCCTACCTATCATCATGCACCCATGTCATCGTTCTTTTAAAGGGTGCCAGTTT
         TTTGCTTAAGCACAAGGAGCTGTGACCTGTGTTGTCATCCCTGATGCATGTCATGCATGT
         GACTTCATGACATGTGGGTGACTTTTGATCTCTGAAGGACCAGGGACCCAGTCTGTGGAT
         CACCACTCTCTCCGTGGGTGGTTTGGGTCTTGTTCTCTAGCCCACCCAGCCAGGTGCAAT

90283    AAAAGATTTCTTTAGCACCTTTATTCTAAAGAGCTCTTAATTGCTGTGCTTAGAACTTCT
         AAACAGTGAGCATTTGTCAAACATAGAATAGCAGAATGAAGGGGTTGGACCTCGGGTGAG
         GAGGGCTGTCGCATGGTCTCTTTCGAGTGCCGGCGGGTGGGGGCTGCACATCTCCTCGCT
         TCTGGGCCCATTGATAAGTGACCTAAAAGTGCCTTTCGTTTTTTTTGGTGGGGGGTGAAA
         AAGCAATCTGTTTTGTACCCACAGCGGTGCACTTTAAACAGGAAGCCCTACTGGGGCCAG
         [G,C]
           CTTCTATGTGTCATTAAGTTTTTTCACGCCACATCCTACCTATCATCATGCACCCATGTCA
         TCGTTCTTTTAAAGGGTGCCAGTTTTTTGCTTAAGCACAAGGAGCTGTGACCTGTGTTGT
         CATCCCTGATGCATGTCATGCATGTGACTTCATGACATGTGGGTGACTTTTGATCTCTGA
         AGGACCAGGGACCCAGTCTGTGGATCACCACTCTCTCCGTGGGTGGTTTGGGTCTTGTTC
         TCTAGCCCACCCAGCCAGGTGCAATTAGGAATAAAGGAAATAGCAAAGGAATTTTGCTCA

90506    TTTGGTGGGGGGTGAAAAAGCAATCTGTTTTGTACCCACAGCGGTGCACTTTAAACAGGA
         AGCCCTACTGGGGCCAGCCTTCTATGTGTCATTAAGTTTTTCACGCCACATCCTACCTAT
         CATCATGCACCCATGTCATCGTTCTTTTAAAGGGTGCCAGTTTTTTGCTTAAGCACAAGG
         AGCTGTGACCTGTGTTGTCATCCCTGATGCATGTCATGCATGTGACTTCATGACATGTGG
         GTGACTTTTGATCTCTGAAGGACCAGGGACCCAGTCTGTGGATCACCACTCTCTCCGTGG
         [C,G]
           TGGTTTGGGTCTTGTTCTCTAGCCCACCCAGCCAGGTGCAATTAGGAATAAAGGAAATAG
         CAAAGGAATTTTGCTCAAGGCCATGCCAAGCATTTCATCTCATATGAAAAGGAAAAGAGA
         GAGAGTGTGTGTGTGTTGGCTAGATTTAGGTAGAAAACAGGCTGGTGAGAAGCGTAGAAC
         TTGGTTAAAATTTCTAGCCAAAAGTAAGATTTTTAAAAAGATTTATTTCTGGATCCAATC
         CCTGTTGCCCATTTCTATGAATAATCACCATTTGTTTTAATGTGAATAATAGCACACAGC

90607    CACGCCACATCCTACCTATCATCATGCACCCATGTCATCGTTCTTTTAAAGGGTGCCAGT
         TTTTTGCTTAAGCACAAGGAGCTGTGACCTGTGTTGTCATCCCTGATGCATGTCATGCAT
         GTGACTTCATGACATGTGGGTGACTTTTGATCTCTGAAGGACCAGGGACCCAGTCTGTGG
         ATCACCACTCTCTCCGTGGGTGGTTTGGGTCTTGTTCTCTAGCCCACCCAGCCAGGTGCA
         ATTAGGAATAAAGGAAATAGCAAAGGAATTTTGCTCAAGGCCATGCCAAGCATTTCATCT
         [C,T]
         ATATGAAAAGGAAAAGAGAGAGAGTGTGTGTGTTGGCTAGATTTAGGTAGAAAACAGG
         CTGGTGAGAAGCGTAGAACTTGGTTAAAATTTCTAGCCAAAAGTAAGATTTTTAAAAAGA
         TTTATTTCTGGATCCAATCCCTGTTGCCCATTTCTATGAATAATCACCATTTGTTTTAAT
         GTGAATAATAGCACACAGCAAATTCAGCCCCCTGAGTTTTACCATTTTAAGCAATTGCTT
         TAGGCCCGTGAGGCATGTACTATTTATGAAGTTGCATGGGTAGTAATGGAAAACACAACA

92329    GCCCAGCCTGAGATTTTGAACAGAGGAGCATGATGCTGGGCGTTGACTCATTTGGCTGTG
         AGTGTGGAAAGCTGTCACTGGAGTACAGCAAGTCAGCACTATCAAGCCAGCCCTTGTCAT
         TGCCAGGAGCTGCGGGGAGAGAGGTGTTTTGCATTGCTGCAGGGAACTGACCTCTTTTAG
         TCAGGGAAGTAGTTTGGGCAGTAGAAAGCAGAACTTGCACCTGCTGGTAAGATCTGAGTG
         GTCACTGACAACCAGCTCTGCAACCCTGTTACCAGGGCAACAAAGATGGGCCCAGGGGTA
         [A,G]
            TGGTGGGCTCTGCCACATCTCTCTGTGCATAAGAACCTTTGGCCACTTGCTCTGGCCTTG
         TCTTTCACCAATCCCAGTGTTCATATCCAGTGTACCAACCACTGAGGGCAGCTGTCCTGG
         AATCTGTCTCTCATCTCTGCCCATAATTAACTGCTTCTGGGCACAGTGCATGAGTTACAT
         AGATGAGTGTGGGTAAGTTTGCCCTTTCTGTGGGGGAGCATCCTTTTGGTCCACTCTCA
         GGAGGGCATCCTATGTTATTTTTGTGATATTTTCCTAAGAGTTGTATAAGCAAGTGCATC
```

FIGURE 3HHHH

92912  TGTATAAGCAAGTGCATCAAGCCAACTTGTCTACCCCAGCTCCCTCTTGAGACCAGCAGA
AACTATTTATCAACTGGCAGTTTACGTAACCTCTCTGGGCCTCAATTTCCTCATATAAAA
TGAGGATAATAAATCGTATCTGCTCATAGAGTTGCTGTGGGGAGTAAAGAGTTCAAATGT
ATCTGTCAGTGAAGGAAAAAGAAAAAAAAACAAAAACAAAGAGTTCAAATATATCTAGC
GTTCAAACAGAACCAGGTATGCAGCCAGTGCCCAATAGGTGTATGAGTTTCCTATGGCCA
[C,A]
TGTAACAAATGACCACAAACTTAGTGGCTTAAAACAACACACATTTATTATTTTACAGTT
CTGGAGGTCAGAAGTCTAAGATGATGCCAGGCTTGGTGGCTCAAGCCTGTAATCCCAGCA
CTTTGGGAGGCTGAGGTGGCAGGATCACTTGAGGTCAGGAGTTCCAGACTAGCCTAGCCA
ACATGGTGAAACCCCATCTCTACTAAAAATACAAAAATTAGTCAGGCACGGTCACGAGCA
CCTGTAATCCCAACTACTCAGGAGGCTGAGGCAGGAGAATTGCTTGAACCCAGGAGGTGG

95043  GGTTTCGGAGGCTACTTGAGATGTGATTGCTCCTAATGAACCTCCACGGGCCTTTTTAAC
CTGTCGATGTGTTTATTTCAGATGGAGCAGGAAATGACCCGGTTACATCGGAGAGTGTCA
GAGGTGGAGGCTGTGCTTAGTCAGAAGGAGGTGGAGCTGAAGGCCTCTGAGACTCAGAGA
TCCCTCCTGGAGCAGGACCTTGCTACCTACATCACAGAATGCAGTGTGAGCCTTCCCTGA
AGCCCCCTTCCCTTGGAGGTGGCACTTCCTGTTGTGTGTGTCTCATCCTGTTTCATGATG
[A,G]
CTCCATGAGGCACATCACAGCCAATGGCAGAGAGTAGAGAGAGGGAGAGCACAAAAGCAA
GATCTGTGTTTTGCAGAGTAGTGAGAGCCAGGCGTAAGGTCCCCAAGAAATGAGATTGGA
CTCATTTCCAGCAGAAAGTGCAGGTAGACGGCTGGTACCATGGAGTCTGGAGATGGGAGT
AATTCATCTTTGCCGCAAGTTGCAAAAGATCTTAACATCTCCCATCCCAGCCTCTGTGGT
CTGCGTTGTGTCTGACATGAGCAGCCTTGAGAACCAGACTCCCAACTATGTACAAGAAAA

95227  TCCTGGAGCAGGACCTTGCTACCTACATCACAGAATGCAGTGTGAGCCTTCCCTGAAGCC
CCCTTCCCTTGGAGGTGGCACTTCCTGTTGTGTGTGTCTCATCCTGTTTCATGATGACTC
CATGAGGCACATCACAGCCAATGGCAGAGAGTAGAGAGAGGGAGAGCACAAAAGCAAGAT
CTGTGTTTTGCAGAGTAGTGAGAGCCAGGCGTAAGGTCCCCAAGAAATGAGATTGGACTC
ATTTCCAGCAGAAAGTGCAGGTAGACGGCTGGTACCATGGAGTCTGGAGATGGGAGTAAT
[T,C]
CATCTTTGCCGCAAGTTGCAAAAGATCTTAACATCTCCCATCCCAGCCTCTGTGGTCTGC
GTTGTGTCTGACATGAGCAGCCTTGAGAACCAGACTCCCAACTATGTACAAGAAAACTTA
CTTTCAATCTTCCTGACATCAAATTTTCCATTGGCCAGAACCAGTGTAGTGACAAGAAAA
TAGCCTTGAAAACCCAGACCCTCTGTCATTATTTACCATGTGACTTTCATTTTTTCTTTC
CTTCACAAGAGTAGACTGTCTTCTTCTCCATTGTCTTGTTAAATTTTTCATTCAGGTGTT

107428  ATGTTACTCTGTGCTTGGCTCTCCAGCTTGCTGTTGCCTTTCACCAGTGTATCCCAGACA
TCCTTTCTTCCTTGTCAGTAACGCAGGTCTACTTTATTCTTTGAGCAGTGGCATAATTTT
CCCTGATGTGTATATATCATAAGTTAGAGAATGCTAAAATTCATTTTGGGGCCTTGTTTA
GGTTCTTGAGGGATTAAATTCCTAAATTTAACAAGTGTATCCTGGAAACAATTTTTGTTC
CTGATTCAGCCCTTAAAAGAGGACTATCATGTTACCTTGAATGGAGATAAACAGGCTCAC
[G,A]
TAAGAGAAAAGGGTAAGAGGGATGAACTCCCACTTATCTTAAACTTCTACTGGCCCGTTT
TTGGGGAATTTGCTGCTTTTATTCCTGACCTAAAATAAATAAGTTTATGTGTCTTGGTTT
CATATTAGTTGAGAACCCAGTGCCTGGAGAGAAGTTTTCCTTGTCCTCTGAGTGAGGACA
TTCACATATGAATCTATTGGCAGACTGGCTTTGACTGACCACACGTGCCTTCAGAACCAA
TGCCACAGCTCTTAGGTTTATGGCCTGAAACACCCTTTCCTTACATATTGCCTTAGAAAC

114951  GACAGTGAGACATGTGCTGTTTTGATCTCTCAGCTAAGATTATCTGATTTTTCAGGCATG
TCTCAAAACTCACCAGGCCTGCTCACATGCTGCTGCTTCTGAAGCCAGGGTTTGGAAACC
AGCTGCCCATCAGAATGAGGCTGTGACTTAGAATATTGGTTCTTTGTTTTTATTACCATTCC
TTGTTTGGTCTCTCCAGAGTCACTGGCCTTTTCCGCTTCAATTTTCTTATCGGTGAAATG
AGATATTAATTCCTCTTATTGACTTCAATTCAATTGCTGAGTGTATTGTTGCCTTTGGGA
[A,G]
GTTCTTTGAGTTTTCTGTGCCTTTGAAATAGTTGTTTTTTTTTATTCTGGTGTTTTGAGG
CATGTTTCAAGTGAGTGCATTTACACTTCTACCATTTTAGGAGCCACAATTCAGTTATGT
TGTCCCAGCTTGCTTGGCCCCATCCCCAGAGTTTCTGATTCAGTAGGTCTGGGGTGGGGC
CCAATAATTTGCATTTCTTCTTCTTTTTTCGAGACAGAGTCTGACTGTGTCATCCAAGCT
GGAGTGCAGTGGCACGATCGTAGCTCATTGTAGCCTCAAACTCCTGGGCTCAAGCCGTCC

115042  GCTGCTTCTGAAGCCAGGGTTTGGAAACCAGCTGCCCATCAGAATGAGGCTGTGACTTAG
AATATTGGTTCTTGTTTTATTACCATTCCTTGTTTGGTCTCTCCAGAGTCACTGGCCTTT
TCCGCTTCAATTTTCTTATCGGTGAAATGAGATATTAATTCCTCTTATTGACTTCAATTC
AATTGCTGAGTGTATTGTTGCCTTTGGGAAGTTCTTTGAGTTTTCTGTGCCTTTGAAATA
GTTGTTTTTTTTTATTCTGGTGTTTTGAGGCATGTTTCAAGTGAGTGCATTTACACTTCT

FIGURE 3IIII

```
              [A,G]
              CCATTTTAGGAGCCACAATTCAGTTATGTTGTCCCAGCTTGCTTGGCCCCATCCCCAGAG
              TTTCTGATTCAGTAGGTCTGGGGTGGGGCCCAATAATTTGCATTTCTTCTTCTTTTTTCG
              AGACAGAGTCTGACTGTGTCATCCAAGCTGGAGTGCAGTGGCACGATCGTAGCTCATTGT
              AGCCTCAAACTCCTGGGCTCAAGCCGTCCTCCCACCTCACCCTCCTGAGTAGCTGGGACT
              ATAGGCATATACTACCATGCCCTGCCACCTTTTTAATTTTTTGTAAGGATGGGGGTCTCA

117217        GCTGGGCTAGCTGCCTCTGAATCACCGCAGTAGCTCCTTTTACTATAGATTCCTGGGTCC
              CACCCATGGAATGTGATCCATGAAGTCTGGGGTTATTCCCTGGAATCCTTTAAGCTCCCT
              AAGTGGTTGGGATGGGAAAGAGATATGCTTTATGTTACTATACTTCTTATTATTATTATT
              TTAAAATTCTTGCCGGGCGCAGTGGCTCACACCTGTAATCCCAGCACATTGGGAGACCGA
              GGCGGGTGGATCACTTGAGGTCAGGAGTTCGAGACTGGCCTGGCCAACATGATGAAATCC
              [C,T]
              GTCTCTACTAAAAATACAAAAATTAGCTGGGCATGGTGGCGCATGACTGTAGTCCCAGCC
              ACTCCGGAGGCTGAGGCAGGAGAATCGCTTGAACCCGGGAGGCAGAGGTTGCAGTGAGCC
              GAGATCGTGGCACTGCACTCCAGCCTGGGTAACAGAGTGAGACTTCATCTCAAAAAAAAC
              CCAAAAAAACAAAACTCTTTTTCATTATACCGGAACGTCAGCTTTATGGAGTCGGGGATT
              TTTTCTGTTTTATTCACTGCTGTTTCCCTAACATCTAGAATAGTGGCTGGCACGATAGGC

120452        TACTCAATCCTCACACAGTGCTGCAAGAGGATTAGTCTTATCCCTGTTTTAGAGAGGATG
              AAACTGAAAGGCAGCGAGGTGAAGTCACCAGCAGGAGGCTGAAGCCGCCCAGGCTAACTG
              GCCTTATAGCTACCTAGGGACTCAGGAATATCACACCTGTTTATCATCAAAAGGAGAAAG
              GATTTCAGTTCCTTGGGGTAGAAGAGTTTCTTTTTGCTAATCAAACATTTTACTTGAGGC
              TTCATATTCTTCTTCAAGATTTTTTTCCTGTGTATGTACCAACACATGTAATAATTCCTT
              [A,G]
              TTTATTTCAAAAAAGGGGTTGTACTTTATTCTTTACAAGATTTCACTTTATATTGTCATG
              GACAATTTTCCATGGCAGTATGAATAAATGGAATCTGTTTGTTTTTAATATCTTTGTCTT
              ATCCCATTGTTTACATATGTCATATTTTAGCCAGTCTCTAACTGATGGATAGCTGAATGA
              TTTCCATGTTTTTTTCCCCTGTTACAAACAATACTGCAAGGAATCTATTTATCTTTCTAT
              TTATCTGCAAACTATTGTAAGTACCTGTAAATTGTTAGAAGTGGAATTACTAGGTCAAAG

124035        AAAAAACTGATGCTAGTGAAAATGCATAATTTAAGAGGTTAGAGAAGCTGCTCTTCAAAA
              TGCCCCCCAAGTCTGAGAGTTAAATCCTTTACATAAAGGACAATATGTAAAATTTTCTTT
              TTCTTTTTTCTTTTTTTTTGAGACGGAGTCTCGCTCTGTCCCCAGGCTGGAGTGCAGTG
              GCGCGATCTCGGCTCACTGCAAGCTCCGCCCCCCTGGGTTCACGCCATTCTCCTGCCTCA
              GCCTCCCGAGTAGCTGGGACTGCAAGCGCCCGCCACCATGCCCAGCTAATTTTTTGTATT
              [G,A,T]
              TTAGTAGAGACGGGGTTTCACCGTGTTAGCCAGGATGGTCTCGATCTCCTGACCTCGTGA
              TCCACTCGCTTCGGCCTCCCAAAGTGCTGGGATTACAGGCATAAGCCACTGCGCCCGGCT
              CTTTTTTTTCTTAAACTGCTTCCAGAAAAGTGGATATTATTAGGTTGATGTTAAGAAAAG
              GCTTGGAGTTGCATTAACTTTTTGCTTTCTAGCATCTGGCCTGTCTGTTCTGCAGACCTG
              AGACCTACTTGAGATAATTTTCTTGGTGTTCAGGCCCTTGGAAAAATAAGTTCCCTATGT

124589        ATAATTTTCTTGGTGTTCAGGCCCTTGGAAAAATAAGTTCCCTATGTTGTCCAGTGTCAA
              AGTTTCTCAACCTCAGCACTATTCTTTTTTTCAGGTTATTTTCTTGTAATCTGTTCACTT
              GATCATTACATTAAGAATTAGATTATATTGCTATAACTACAAAGCATTTTATGTTTTAAA
              AATTATGTACAATTTAGAAACAGGCATGAAAACTTAGGTATTAAATTTAGTGGAATAAAG
              CACAGAAAAAAAGTTAAAATAATGCAGTTTTATCACTTAGGATTAAACATTTATATGGGC
              [C,T]
              GGGTGTAGTGCCTCACACCTGTAATCCCAGCACGTTTGGAGGTCGAGGCGGGAGGATTGC
              TGGAGTTTGAGACCAGCCTGGGCAACAAAATGAGACCTAGTCTCTACAAAAAATCAAAAA
              ATTAGCCAGACATGGTAGTACATGCTTGTAGCTCCAGCCACATGGGAGGCCAAGACAGTA
              GGATCGCTGGAGCGAAGGAGGTTGAGGCTGCAATGACCGTGTTTGCACCATTGCATTCCA
              GCCTGGGCGACAGAACAAGACCCTGTCTTAAAACAAATTTATATGCTGCATTCGTGAAAT

125136        GCGACAGAACAAGACCCTGTCTTAAAACAAATTTATATGCTGCATTCGTGAAATTAAAAA
              AAAATCATGGATTTAGAAATAAATTGAAGCAAGGTACATTGACAGTGTAACCTCAGCACT
              ACTGACATTTTGATCTGAATAATTCTTTGTTGTGGGGGATGCGCTGTATAAGATGTTTAG
              CTGCATCCCTGACTCCTACCTCCTAGATGCCATTAGCACCCTCCCCTCCAGATGTGATAA
              CCAAAAATGTCTCTAGACATTGCCAGATGTGCCTGGGGTAGGAGGGTTGGGGGAAGTGGG
              [G,-]
              TTTGAGAACCCTTAGTTGATCATGCCTGCAGTAGGTTGAGAAGCATCAGAAAGCTAATTA
              ATTAGACAGGAATATGTGTTTGCAGTAAGAAAACCTCAGCAAACTAATCAAGTTCCAAAG
              TTACTGCTTGGTAAATAAATAGGAATTAAGAATAAGACCCTATCTCTGTGTCTGGGGTCA
              TTCTCTTCGGAGCTCTTGGTGGAGAGACAGGGTTCCCAGTTTCAATTTTTTAGTGCTTCA
```

FIGURE 3JJJJ

```
          GACTGCCCTTTTCAGTTATAATTGTAACAACCTTCACTCCAGGTGGGGAGCCTCCCAGGT
125856    AGGCAGATAAGGAATTTTTTGCATTAAGTGCAAAGTCCTTTTTCTTATAGAAGAGCAATA
          ATCTGCACACTAGATCAAGTCAAGTGTGGATATAAAATTATAATTTTTGGGGGGATATTT
          TTAATAGTGGTTTTGGGTTAAACATATTTCCTTTAAATGAAATGTCTGTAGGCCTAAAGT
          AGGTTCTAAATGTTGCCTGTACTCATAGTATACCATATAAAATATAATCCACATTTACTG
          GAACTACCATATATTACTTACCCCAAATCAATCAATCCCTTCCCTATCACCCCCACGTAA
          [G,T]
          ATCTTCGTATTTTGGATACCTGTGAATCTTAGATCTGTTCAGTTTTCCATTATCCATTGT
          CTTATTTCAAGCTTCTCATTCAGAATGTTGCTTTGGAGTATTTTCTGTTAGTAAACACAG
          GGCCTAGTGACTCTAGGACCTGCTGTGTGACTTAGGTCACCCACTTCACTTTATTAGAAT
          CTCAAAGAATGGTGAACAGCTGAGTTCCAATCTGTCTCATTTGGCTCTCATGAAAACAGT
          CATAAGGAGATTGTAGATAAACCACATTATATAGCATAGTAAGTGATAATCAACCCCATT

126256    ATTTTCTGTTAGTAAACACAGGGCCTAGTGACTCTAGGACCTGCTGTGTGACTTAGGTCA
          CCCACTTCACTTTATTAGAATCTCAAAGAATGGTGAACAGCTGAGTTCCAATCTGTCTCA
          TTTGGCTCTCATGAAAACAGTCATAAGGAGATTGTAGATAAACCACATTATATAGCATAG
          TAAGTGATAATCAACCCCATTTGGCAGTTGCAACCCCACAAGAGATAGCCCTTTTTAGAT
          TTGTGTAGGAGTGAAAAGCTTTATTTTCCACAAGAGGAACGACATAGTAAGAACTCCTTT
          [C,T]
          CCCCCTGCTTCTGCAGGTATATGCTTATGCCCTAGGCAACTTGATGGGTAAAGTTAGGTT
          TAAATAGTTTTATTTGTAAGCTCTTCTCTTCTCTTCTCTTCTCTTCTCTTCTCTTCTCTT
          CTCTTCTTTTCTTTCAAGACAGAGTCTTGCTCTGTCACCCAGGCTGGAGTGCAGTGGGCG
          ACCTTGGCTCACTGCAACCTCCGCCTCCTGGGTTCAAGAGATTCTCCTGCCTCAGCTCCC
          CGAGTAGCTGGGATTACAGGTGCCCGCCACCATGCCTGGCTAATTTTTGTATTTTTAGTA

127332    CGCGCCACTGCACTCTAGCCTGGGCGACAGAGCAGTCTTTAAAAAAAAAAAAAAATTAAC
          TAAGTTAAGTAGTACTTGGGCCCTATCAGATAGTGTCCTCCTGCAGGCAGGCTGGGCCCC
          TACTACAGTTTCACTTTTAATATCTCACCGAGATTAGCTGACTGAATTGCCACCAGAGGA
          GAGTGAAAGCATATTGCAAAATCATAATCAGGACATGTGAGATTATGTGTTGAACAGGTT
          TAATGTGCTTGGGGGTCAGTGACTAATGGGAACTTAGCAGTCATTAACTGTCATTAAAAA
          [C,T]
          GTTTGTTAATTACTATTACACACTTAGAGATTTGTTAATTAACAAAGAGTAATGCCTTTG
          CTAATCACTATTATGCACTTAAGAGGAAGCCAGTGGGTATTTTTCCCTTCATAGCTTTCT
          AGTACAAATTAATAAAATTTAGAAAATTAGAAAATGATTGTGCATAAATGTGTATAATCA
          TGTATCTGTTAGGGGCAAAAATTAGTTGGGGAATTATCTTTCTTTGATAAGTCTTATCA
          TTAGTTTTGAAAATGGGGCATTGGCAATTCATACTGTTTGGCTGGGTTGTCCTGAGAAACA

128302    GACCATCCTGGCCAAACATAGTGAAACCCCGTCTCTACTAAAAATACAAAAATTATCTGG
          GTGTGGTGGCATGCACCTGTAGTCGCAGTTACTCGAGAGGCTGAGGCAAGAGAATTGCTT
          GAACCTGGGAGGAGGAGGTTGCAGTGAGCTGAGATCGCAGCACTGCACTCCAGCCTGGTG
          ACAGAGCGAGACTCCATCTCGGAAAAAAAAAAAAAATCTATTGGTTATTGTTGGTGCATTT
          TAACCAAAACCCTTTAGTTTAACCCTAACCTGTGCTGAGCTCTTTAACATTTACATACAT
          [G,A]
          TTAAAAAACAGAATCAGCCCAGATTTCCCAACATATTAAGTCTTCTCCTTGACTTAAGCT
          ACTTTCAGTTCTTCAAGCTTAAGTCACCCTGTGGTTTTGTCTTAGGCCAAATATTTTCCC
          CTTTGTCTCCCCTTCTGTCTATCAAGCCAAGCCTGCCTGTGGGTTTTGGATAGTGTGACC
          ATCTGGCTTTCTTGAAGGGGCACTTACAGGGGAAGTTTTATTGCCCAAACCGGTGGACAA
          TCCATGTCAGGAATGATTATATCACACTGCTTTCTGGGTTTAGGGCTTGGAAAAACCTGT

129122    ACTTCCTTGGTGAAAAGCCCAGCCTTCAAGGTATGTGGACTTACCCACAAAATCTCTTGG
          CTCACTCAGTTTCACTTACCATCGTTTAATGAGGAAAAAGTTCTTTTGTACCATGTAACT
          GCTGACCTGAGAGAAGCCCATTATGATATAGAGTTATAGGACAGCTGGCCAACACACTAT
          ATAGCTAAAATCAGGGCCTCTCTGTTTTGATGGGGAGAAAAGTTAGAGAAGGAATCTTTA
          GACTTCAAATTTTCATGGCTCAGTAAAACGTCAAAATAATTTTGAAGACCAAAGGGGTTGC
          [C,T]
          AGCTTACTAGGCTGCCTAGACAGGGGTGGGTATGAGGGGAAGAAAGCCTGCTTCTTTCAT
          CAACAGCATATCCAGAAACAAAGGACATTTAAACACTAAAAAAGTCAGAAGGACAAATTC
          TCAGAAAAAAAGGACAGTCCTTTAAATGGGTTACATTTAGCTTTATAAAATGCCCTCCTG
          TATTGTCCTAATCTTTCTTTGCCAAGGTCAAGTGCTTGGGTGCCATTGGATTATAAGCCC
          CTGGGTTTCTGAACGGTGGGGGAGGGAACCACAGGAACAAGGGTTAGGGGTGAGGAAAAA

129376    TGGCTCAGTAAAACGTCAAAATAATTTTGAAGACCAAAGGGGTTGCCAGCTTACTAGGCT
          GCCTAGACAGGGGTGGGTATGAGGGGAAGAAAGCCTGCTTCTTTCATCAACAGCATATCC
          AGAAACAAAGGACATTTAAACACTAAAAAAGTCAGAAGGACAAATTCTCAGAAAAAAAGG
```

FIGURE 3KKKK

```
         ACAGTCCTTTAAATGGGTTACATTTAGCTTTATAAAATGCCCTCCTGTATTGTCCTAATC
         TTTCTTTGCCAAGGTCAAGTGCTTGGGTGCCATTGGATTATAAGCCCCTGGGTTTCTGAA
         [T,C]
         GGTGGGGGAGGGAACCACAGGAACAAGGGTTAGGGGTGAGGAAAAAGAACTCATTAACCT
         TGGGCCCTGGGTGGAAGTTAATTATCATGTCTTGCCCTGTGGGTGGGTTGAAGTAGGAAC
         GTTAATTCCAAAGGCAGTTTTCCAAATTTTTGAACTTGAGATTTGTAATATTATCTTGCC
         AGTTAGCCACCAGTTCTCTTCTCTTTTTTCTTTTCTTTTCTTACAGTCTCGCTGTCACCC
         AGGCTGCAGTGTAATGGCGCAATCTTGGCTCACTGCAACCTCCGCCTCCCAGGTTCAAGC

134893   TAATCTTCTTGAATAAGCAGTTAATTTTTTTTATTCATGAACCTGCTGATCATGTCTAAG
         AATGTATCTCCACTTAAGTAAGTCAGTGAATGGTGATTACCTGAGTAGAGTTAAAGTAGT
         CCCCCACCCTCCTATCTGTGGCACATATGTTCCAAGTCTCCCAGTGGATGTGTGAAACTG
         ATGATAGTACTGAAACCCATCTACCTTTTTTCCTGTGCATACATACCTATGTTATATAAA
         GCTTAACTTATAAATTAGGCATAATATATTTGACTCCCAGCTCCCAGTGTAGTGGCTCTG
         [A,C]
         AGACTCACAAAATGTATTTGCTTTAAAAAATTCTTTTTTTTTTTTTTGAGACGGAGTTTT
         GCTCTTGTTGCCCAGGCTGGAGTGCAGTGGTGCGACCTCAGCTCACTGCAACCTCCGCCT
         CTTGGGTTCAAGCGATTCTCCTGCCTCAGCCTCCCAAGTAGCTGGGATTATAGGCATGCA
         CCACCACACCCAGCTAATTTTCTATTTTTCGTAGAAACGGTTTTTCCATGTTGGTCAGGC
         TGATCTTGAACTCCTGACCTCAGGTGATCTGCCTGCCTCGGCCTTCCAAAGTGCTGGGAT

136001   TATTTATTTATTTATTTTTTGAGACACAGTCTTCCCGTCGCCCAGGCTGGAGTGTGGTGG
         CACGATCTCGGCTCACTGCAACCTCCGCCTCCTGGGTTCAAGTGATTCTTCTGCCTCAGC
         CTCCGAGTAGCTGGGACCACAGGTGTGCGCCACCATGCCCGGCTACTTTTTGTATTTTCA
         GTAGAGACAGGGTTTCACCATGTTGGTCAGGCTGATCTCAAGCTCCTGACCTCAGGTGAT
         CTGCCTACCTTAGCCTCCCAAAGTGCTGGGATTACAGACATGAGCCACCGCACCCAGCCC
         [C,G]
         CAGTGTTAACTCTTACATAACAGTGTCACTGTCTAAGTGTTTGAAAAACTATTTGTCAAA
         ACTAATATTGGTACATTATTGTTAACTACACTTCAGACTTTTTTTGGATTTTACCAATTC
         TCCCACTCATGTCCCTTTTCTGTTTCAGGAATCAATCCGTGGTACCATATTGCAGTTAGG
         GTGTTTATATTTGATGGGACTGGTCCTAGTTTAGATACTTAGTGTAGCTCAGCCAGCAGG
         TGGGATCTTCATGCCCACCGAGGATTGGTATTGTGTTTTCCTGGTGGTTTTATGGCATTT

136249   CTTAGCCTCCCAAAGTGCTGGGATTACAGACATGAGCCACCGCACCCAGCCCCCAGTGTT
         AACTCTTACATAACAGTGTCACTGTCTAAGTGTTTGAAAAACTATTTGTCAAAACTAATA
         TTGGTACATTATTGTTAACTACACTTCAGACTTTTTTTGGATTTTACCAATTCTCCCACT
         CATGTCCCTTTTCTGTTTCAGGAATCAATCCGTGGTACCATATTGCAGTTAGGGTGTTTA
         TATTTGATGGGACTGGTCCTAGTTTAGATACTTAGTGTAGCTCAGCCAGCAGGTGGGATC
         [T,G]
         TCATGCCCACCGAGGATTGGTATTGTGTTTTCCTGGTGGTTTTATGGCATTTCCGACTAT
         GCAGAGAGGCATGGTATTAACTTCAGTGTCTCCTAGCAAATTTTCCTGTTTTTCACCAAC
         CTCTGATCCCTGCATTATTTGCAATCAACTCAGAGATTTGTGATTGAAAACATTGCTTGA
         CTCCATGCTCTTTAAGCTATTTTCTAACTAGGTAACTGTAACATAAATTATGCTTTTATC
         TAGCACTGTTTTTCATAAACACATGTTGAGTGATTTTCATCAACCGAAATACTTCGAATC

136448   AGGAATCAATCCGTGGTACCATATTGCAGTTAGGGTGTTTATATTTGATGGGACTGGTCC
         TAGTTTAGATACTTAGTGTAGCTCAGCCAGCAGGTGGGATCTTCATGCCCACCGAGGATT
         GGTATTGTGTTTTCCTGGTGGTTTTATGGCATTTCCGACTATGCAGAGAGGCATGGTATT
         AACTTCAGTGTCTCCTAGCAAATTTTCCTGTTTTTCACCAACCTCTGATCCCTGCATTAT
         TTGCAATCAACTCAGAGATTTGTGATTGAAAACATTGCTTGACTCCATGCTCTTTAAGCT
         [G,A]
         TTTTCTAACTAGGTAACTGTAACATAAATTATGCTTTTATCTAGCACTGTTTTTCATAAA
         CACATGTTGAGTGATTTTCATCAACCGAAATACTTCGAATCATTAAGTTTCCCAAGTTCA
         TGGATGCTGCTTAAATGCCTGGTGGTTCCAGGCTGTCGAATATTTCTGCCTTCTGCAATA
         AGAGATTGTCCCTTGTTAAAAGCAACATTAGCCTTTGTGCGGTTTCACCCCCAATTCTTC
         TTTTTCTTGTTGTAACCAATGAAAGGAAGTACTGCTTAACACAGCAGGTAATAATCTTCT

136906   GAATATTTCTGCCTTCTGCAATAAGAGATTGTCCCTTGTTAAAAGCAACATTAGCCTTTG
         TGCGGTTTCACCCCCAATTCTTCTTTTTCTTGTTGTAACCAATGAAAGGAAGTACTGCTT
         AACACAGCAGGTAATAATCTTCTAAAACTCATTATCTCAAGAGGTGGTCCTGGCAGGATA
         TATAAATGCAATTTAAGAAAGGTCTTGGCAAATTTATGAATGACAGAACTGGGAGTGGCT
         ACCGAGAGAAACTAGGATGCGCCTTTGCTTTGACACTGAGGTCAGGCGTAGCTTCTGTAC
         [C,A]
         CTCCTGGGTCCTGCCTCTTGGGGTTGCTGCAGGCAGCACCCCATGAACCAGGCATCTGAC
         CCAGTTCCAGGATACTTATTCTTCCAGCAAGTCGAACACTCTGTGATGAGTGACTGCCAT
```

FIGURE 3LLLL

```
            GCTCATGGGTCACCAGGCTCTCATTATTCTGTTTCATTTCCAGCCTCCCACAAGATTGGT
            TTTTCAGCTGCTTATTTATTATTATCATTATTTCAAGGCTGCTTTCCAAGTTTCAGTGGG
            GGGTTTCCTAAGCGTACCAGCTGCCCTGGTTGTGCAGTTCCGGTGATGTTTCAGATGCTG

137190      GGCGTAGCTTCTGTACCCTCCTGGGTCCTGCCTCTTGGGGTTGCTGCAGGCAGCACCCCA
            TGAACCAGGCATCTGACCCAGTTCCAGGATACTTATTCTTCCAGCAAGTCGAACACTCTG
            TGATGAGTGACTGCCATGCTCATGGGTCACCAGGCTCTCATTATTCTGTTTCATTTCCAG
            CCTCCCACAAGATTGGTTTTTTCAGCTGCTTATTTATTATTATCATTATTTCAAGGCTGCT
            TTCCAAGTTTCAGTGGGGGGTTTCCTAAGCGTACCAGCTGCCCTGGTTGTGCAGTTCCGG
            [T,C]
            GATGTTTCAGATGCTGGGCCGGATTCTGGCTGTACCCAGCCTGATCTTTCTGGGCTTCAG
            GAAAGCTGAAGCCAATCAGAGCTCCTCTTTCATGCCTTTGGGATTATGCTTACCTTGCCT
            GGCATCGTGTACCTGCTCCCATCCATGGGAAAGTTTTGCTGTCTGGTACTGTCTTCTATC
            AACATCTTTTAAGATATCTTCCCCCGAGGCATCGTGATGTCAACGGAACCAGCACACTTG
            TACGTTTTATGCAAGACTGCCATATCTCAACAGTGAGAAATGCATAATGGAAGTGGTGAT

137471      CCTGGTTGTGCAGTTCCGGTGATGTTTCAGATGCTGGGCCGGATTCTGGCTGTACCCAGC
            CTGATCTTTCTGGGCTTCAGGAAAGCTGAAGCCAATCAGAGCTCCTCTTTCATGCCTTTG
            GGATTATGCTTACCTTGCCTGGCATCGTGTACCTGCTCCCATCCATGGGAAAGTTTTGCT
            GTCTGGTACTGTCTTCTATCAACATCTTTTAAGATATCTTCCCCCGAGGCATCGTGATGT
            CAACGGAACCAGCACACTTGTACGTTTTATGCAAGACTGCCATATCTCAACAGTGAGAAA
            [T,G]
            GCATAATGGAAGTGGTGATCACGGATTATTTCCTAGGACATTATGGCTAATGCGCTAGAG
            AACTCGGATGGTCTGTTGCGTCTGACATGGGCTTTTTCTCTTGAGTTGTCTTTCTTTTGC
            TATTCTCTGAAAGAAACAATTCTTGCCACATGATCCTGATTTTTCAGGTCCTCAGCATTT
            GTTAGCAGAAAGTACACTTTGTTTCCATCCGGCAGTGACTCAGTGGTGGTCCCATGCTGA
            TGAAACGCTGAGATAGTCTTCTTCCAAATAGGTATCGTTTTGATTGTTGCTGCTTATTTG

137913      CTTGCCACATGATCCTGATTTTTCAGGTCCTCAGCATTTGTTAGCAGAAAGTACACTTTG
            TTTCCATCCGGCAGTGACTCAGTGGTGGTCCCATGCTGATGAAACGCTGAGATAGTCTTC
            TTCCAAATAGGTATCGTTTTGATTGTTGCTGCTTATTTGCTAGCTGGCCCTCAATAGTGA
            CAATGAAACCTCAAGTGTATAATATGGTTGCTCAGTAATCCTGAGGGAAGACAGTCTTTG
            GTTTGGGGGATAGGGATTCTGTGCCTACTTAGCTTCAGGTGAAAGTCTTACAAATTTTTG
            [T,C]
            GTGTAGAAATAAGCACCATGTACCTCCTTGGGTTTTTTCTTTTTTTTTTCTAGTCCTTTAG
            TATGGTCAACAATATTGTTTAGGGAGTACCTATTCTGTGCTAACCACTAGGCATTCAAGT
            ATATTACACTATGCTCCTTCAAAACACTTCTGTCAAATGTAAGGATTATTATACCCATTT
            TACAGATGTGGTTACTGTGGTAACTTGGCCAAGGTCATAGGGCAAGTGAATAAGGGATTC
            TGGATTTGGGTGGAGGTCTGTGTGATTCCAAAGCCCATGCTCTTTCTACAATACTATATA

138466      GAGGTCTGTGTGATTCCAAAGCCCATGCTCTTTCTACAATACTATATATGCCTTTGCATA
            AGTTATTGTTATTAGTAATAATATTTGTGATGATGGCAAATAATAAACCATGTCACACTA
            GAGAGTGATTTAATCTCTAGGTCTATTTAAGAACATTTGGAATTGCAGGAATTGGATTTT
            TTTTTTTTTTTAAGTGATGGAGTCTTGCCATCTTTGCCCAGGCTGGTCTCAAACTTGTGG
            GCTCAAGTGATCATCCTCCCTCTGCCTCCCAAAGTGATGGGATTACAGATATGAGCCACC
            [A,G]
            TGCCCAGCCTAGAATTGCAGGAATTTTTTGAATTGATGATTCATTCTGATATTTGAATTTC
            TACAGTATGTTAAGTGCAATGTCAGGTGCTGGTGCTGTGGCTCCATTGATGAACACATTT
            GGGTATGGCCCTACCTTCATTGAATTTAGAGTCTAAGAGCCTAACCGGTCTTTTGCTTGA
            ATAGAGCTGTAGTCCTGTTAAATTGCTGTACCTCCAAATGGTGGGAAGTTTAATGCTTCG
            TAGGCCTCCCCTCACTAGTTTACTGAACCACATGTGCTTGATTTTTTTTGA

146805      GGCTTTTCTAAAGTAGCACTTTTCCCCACTCCAGCCCATGAAGATACCTTTTAACCAGCT
            CTTGAGATTAAATCCCCTCCGTGACACTTTCCTGCAGGAACTTGCAA
            [G,A]
            AAAGTACTGCATTCCCCACTGGCAAAACTTGCCATCAGCCAGTTTATGTATTCTCTGCTT
            TTCACACCCATATCTTGACCTCTGAACAACACACATATTCTCCTCTT

151008      GGATTATTTTATTTAAACCTCCTAATAGTCCATTGAAATAGATATTGCCATGTTGAAAAC
            TGAGGTTCAGAGAGGTTAAGTGACTTACCCAGTGTCACAGAACTAGTAAGTGGTGCAGCT
            GGGATTTGAACTGAGATTCCAGAACAATTGCCATTAACCACTTTGCTTCCATATTAGTAT
            CATCTGCAAATCTCTCTCCATAAATTTCCTCAGTCTTTATCTGAGTTTCCTTATTTCAGG
            AAGGAAAACTTCTGTTTTTGATCCTTATGAAATACAATTTCCATTAAAACTTTTTTTTTT
            [T,-]
            GCTATTAAAAAAGGTACCGGATAATTGAAACCAGACTGGATTTGAGCCTGTGTTGATGGA
```

FIGURE 3MMMM

```
           AGTACACATGGGATGTGGGCTGAAGTGTTCAATCTAATTTTTCTTTCCATCAGCTAATTT
           TTAAAGTATTAAGCAAGTAGATTCTGACACTAACAGGGAAGATTTAAATTCTCTTGAGAG
           ACTGGAGGTGTTAAATAATTTTCTGGTAGTGCACATTTTACATCTTAAATCTTCCTCACT
           CTCCCACCTCATCTCAATGTACCTGAAGCTCTGGGAATGTTCTTTTGTACTTCTCAGGAA

151627   CATCTCCTCTCCCCTCCACATCCCTTTCCTGCTCCAATTACTTCCCAGCGCCACTTGGAT
           GTTGTTGTCATCGGGGAACTTTGGAAACAGCCAGATTTTTTTGGAGTCTGTAAGCAGAAA
           ACAGACTGCTTGCTGCTCATATCTGGCACCCAGCTTTGTCCAGAAAACGAGGAGTTAAAA
           AGAAGTCTGGGCTGTGAAGGGCTGTGACAACTGTCCTAGGGGGAGCTCTAGCGAGCCCTG
           GCGGGCAGTGACTCATGCTGCTCTGTCACTGGGATCAGCACTGGCCCCTGGCAGGCAGGC
           [G,A]
           GCAGCCAGGTGGGGTTCCAGCCAGAGCACGCACGCACGGAGCCGGGAGCATGCAGCCTGC
           ACTGCGGGGGATGTGATGCTCGGCTCTAACTCGCCTGGCTGGCCCGCCACGGACGCCTCA
           GCTTGCAACCATGGTAACGTTTCTGGCGGGGGACACCCCCGGGAGCCCACCGCGATGGGC
           AGCCTCCTGGTGACTGATGGACGAGTGTCCACCTCCCAGACCGAGAGCGCTTAGTAGGTC
           GGAGGAAGTGGAGAGGATGTAACACGCCCCCAGCCGGGAGTGAAGCCCTGAGGAGGTAGG

151875   TGACTCATGCTGCTCTGTCACTGGGATCAGCACTGGCCCCTGGCAGGCAGGCGGCAGCCA
           GGTGGGGTTCCAGCCAGAGCACGCACGCACGGAGCCGGGAGCATGCAGCCTGCACTGCGG
           GGGATGTGATGCTCGGCTCTAACTCGCCTGGCTGGCCCGCCACGGACGCCTCAGCTTGCA
           ACCATGGTAACGTTTCTGGCGGGGGACACCCCCGGGAGCCCACCGCGATGGGCAGCCTCC
           TGGTGACTGATGGACGAGTGTCCACCTCCCAGACCGAGAGCGCTTAGTAGGTCGGAGGAA
           [G,C]
           TGGAGAGGATGTAACACGCCCCCAGCCGGGAGTGAAGCCCTGAGGAGGTAGGAGCCGCAT
           ATGTCCATCCGTGCATTCCCACCGTCAGCGCGCAGGGGTGCTGTAGATCACCGGTAGGAA
           CTTTATTTGGCTGGTGCTTCATTATGCTGATTAAACTGCAGTGGATTTTGATGGGCATGAT
           TGCGCTGGGGAAGATGCATAATGAACTAAAAAAAAAAAAAAGTGGTTAATAAGATCTCGG
           AGTCGACTTGTCCGGGTATGAATGAAGTAGACTGCAGTGGTATCCTAACAGGAGTTCCAG

153541   ATCTAACCATCTATGTATCTGTCTCTCAAGTGGGTGGATGGGGGTTGCTATCTTGGCTGT
           ATAAAGAATCCTAAAAACCTTGTCTCATAAGCTAGAGGTTTCCTGATGGGTTTAACTGAG
           CTGCAAGTGGCTGAACCAGAGCTCTAACAGAGAGATGGTGCTCGGCTCCTCTCCAAGTAT
           GCTGCAAGATCAGGGATCTGGCAGCTGAGCCTCTCTGAGCTGGTGGAGCGCTGGCAGCCA
           GAGAAAGCCCCGTTACTGTGAGCCACCAGGAGGGAGTGTGATGTAGCCGAGTCATTGATT
           [T,C]
           ACAGAAACTGGGCTTCATAGGGGGAAAAAAAACCAGGAGACTAGAAAATGGAAATATAAA
           TATCACTGTAAACCTCTTGATCTGGTAGGTCTTTCTCCATTCTCATAAAAGCTATTGAAA
           AATGCATTAACAGAGCACTTGGAATTAGAGGGTCGAGGCTTCCAGGAGCCTCCTGGAATT
           TCTGTAAAATGCAGTAGCTTCTGTGGATGTGGGAGGTCAGTATCTTGCCTCATTCTCTCA
           TGATACAATGACATTCTGTTTTCAGAGGAGTGAGTTCCCCAGAAGATCTTGGACTGATGG

155392   TCTTGTTATGTGTTATTGCTATTGGACTTGGCTACTCTGCTGTAGGCAGCCCTGTGGGTG
           ATACCTACAAGCATCATTTTAGAAATTCATCCACCTGTTGGATGTAGATGACCCTGGACA
           TATCAGATTGTGATTAATTAGAAATCTAATAAAAGAGAGGCAGTGATGAAATTACTTAGC
           AGCTCCTGCAGTTTTATTGACAAAATTTACTTGGAGAGAGGGGGAGACATTTTCTGGGGG
           TACCACCTTTGCTGCCAGCGACCCTGTGTTTCTTCCTGAGTTTCTTTTTCTTTTCTCACC
           [A,G]
           TTTTCAGCATCACAGGTTTTTATTTACACACATTGATTACCTGTGCTGTTACTCATTCTT
           CACACCACTGAGGAAATTGCAGATGCTGCTGTACTGTGCTAGGTAAATTGACCTCAGATT
           TGTTACCAGTGAATTGAATGAAATGTTCAGAGGTGGAGCTGAATGAACGAGGAGTTTTTG
           TGGAGAAATTGGCAGTGAGAATGATTTAAATTCTGTGATAGCTCCTCGTTTTTTGGGATC
           CTTATTTTGGGACCCCAGACTATTTTTAAGCCATTGAGTGCATCATTATTTTAGGCTGAG

155896   ATTTAAATTCTGTGATAGCTCCTCGTTTTTTGGGATCCTTATTTTGGGACCCCAGACTAT
           TTTTAAGCCATTGAGTGCATCATTATTTTAGGCTGAGCAAGAATCTTGATGACAGCGTTT
           CAATGGCTGAGGCGTAGTGGGAGTTCCTTGCAGCTTGAGTTGGTGGGAGCTGGAGAGTTT
           CTAGAGAACTAGGTTTGGTTGTCTTTGGGGTGGGGTTATGGTGAAATTAGTCTTGGAGAG
           TGAGTAGCTGTCTGATGCTTCTTTTCCTTTTTAACCAGCAAGAGCCCAAACCAAATCCCC
           [C,A]
           AGCTCTGAATGCCTGGCTGTTCCTCTCAGCCTTTCTTTGCTTGAACTTGACAATAGTAGG
           GTAGTAACAGGAAACAGCATGTTAAAGTTTTAAAAATAAAATAGATCTCAGCTCTTTTCC
           TTCCCATTAGCAAGGGGTACATTTATTTAGGTTTTTCCTTCTAGATTGAGGCACTGCCTC
           ATTTAAGTTCTTGGTGAAGCCATGCATTTCTGCAAACCATAAGTATAAACTCTAGAACGG
           GGGTGTCCAATCTTTTGGCTTCCTTGGGCCACATGGGAAGAAGAAGAATTGTCTTGAGGC
```

FIGURE 3NNNN

| | |
|---|---|
| 157137 | TTACTAATACACTAGTCCATGTATGTATAGTGTCCTCCTATACACACCAAGAGAATATGG<br>AAAGGACTCAGCAATGATTAGGTAGTCCAAAGTCATACCAGATTGGAAACCAAGCTTCCC<br>AGGCCCTGGGACTTTTCTGCTAGAGACACTTCACGGTTCTGACCAACTACAAAGAGTTAA<br>TATGCAGTTGCCAAATACCTGTTGGTAAAAGGTGGATGTTGGGGAGGAGTGGATTGGGGA<br>ACAGAATTAGAAGGTCCAGTCCCAGAATGGGTACCTTCCCATCAAGTTGAACAAGTCAAA<br>[G,A]<br>CAGGTTATGTTGAAACAACTGAGAGAAAGTAAAGCAAACACCATTGCTGCAGAATATCAT<br>GGTACAAATTGGACATCTTTGGGAGTTAGCGGAGTAAGGCAAAATCCAGTGAGGGACGCT<br>TAATGGGTAATGCCAATTCACAATTCTTGTTAAATTACATTGCTGATCTTCCTTGGAATG<br>TCTGTCCATTCCCCCAAGTAGACTGTGATCTCAAGGCAAGGCTGGGTCTTATTCATCCTG<br>GTTTTCCTGGAGCAGTAAATACTTGTGCTGGGACTGGGCTTATAAGCATACTAATGGAAA |
| 157409 | ACCTTCCCATCAAGTTGAACAAGTCAAAACAGGTTATGTTGAAACAACTGAGAGAAAGTA<br>AAGCAAACACCATTGCTGCAGAATATCATGGTACAAATTGGACATCTTTGGGAGTTAGCG<br>GAGTAAGGCAAAATCCAGTGAGGGACGCTTAATGGGTAATGCCAATTCACAATTCTTGTT<br>AAATTACATTGCTGATCTTCCTTGGAATGTCTGTCCATTCCCCCAAGTAGACTGTGATCT<br>CAAGGCAAGGCTGGGTCTTATTCATCCTGGTTTTCCTGGAGCAGTAAATACTTGTGCTGG<br>[G,A]<br>ACTGGGCTTATAAGCATACTAATGGAAAGTAAAATATTTGGGTTGGTTTTTTAAAAAGAC<br>AGTGGATTTGGATCAGTGGAGAGGAAGGTAGAGGGAATTTCAGGTGGGCAGGGTGCTAAC<br>AACAGCCCATCCTTACAGGGCACCAACTGTGTTCTAGGCTGTGTTCCAACCACTTTACAC<br>AGATGAATTCATTTAAATTGCACAACCAGCCCAAGAGGAAGGTACCATTATTATTCTCAT<br>TTTGGATGTGAGGAAACTGAGGCGTGGGGAGATCAAACAACTTGCCTAAAGTTATGTAGC |
| 164675 | ATTTCAGAGTAAGTTTTTCTAGAAAATAGAAGCTGGAAAAAAAAGGAAAACCCAAACTTG<br>GCTTCGTGCTCGAAGAGACAGCACTGCTGTGTGTGGGCGGGTGGCTGCGTGCACCCGCTG<br>CTCAGAAGTGCCTTTTCTCTCCATGGGGATAACTGGCTGTGTATCCGAGATGTGGCCAGG<br>AGTAGGCAAGCAACGTGTGGGCAGGCTGCATGTTCTTTTATTAGCATCTTCATTGTACTG<br>CATCTCGTCGAGCCCAGAGCATGAACTGGCCTGGGTTTCTAATATCTACCCTGCTTCCCA<br>[T,C]<br>CTAATTACTCCCCTGAACCCTAAAGTGAGGGAGGGAGAGTTGCTCTTGTGGGGTGAGCTT<br>TCCCTGGGGTGGCTGTGAACCAACCTGGCATGTGGATGTTCTTGGGTATCCAGAGCTGTC<br>CTGGACTCAGGCTTGGAGTCAGCTTCTTAGCACTGAATGCAGCCAGTCATGGATGGAGGT<br>CACTGTATCTCACATGTTCCGCTCTCCCTTTCCTCCATGACCTTGCCCCTCTGAGCCTCT<br>GTAGCACTTTTCTTGAGTGTGTCCAAGGCCATCTAGCTAAGAAGTAGCAGAAATGGGATT |
| 165157 | ACTGTATCTCACATGTTCCGCTCTCCCTTTCCTCCATGACCTTGCCCCTCTGAGCCTCTG<br>TAGCACTTTTCTTGAGTGTGTCCAAGGCCATCTAGCTAAGAAGTAGCAGAAATGGGATTT<br>GAAGCCATGACTGTTTGGTGATAGAGCCTCAGCTTTGAACTGGGGTTCTACTGCCTGGCA<br>CCCCTGCACAAATCATGGTAACGTGGTAGGAGAACATAGAGGTATAGGGCAAGCCCCTCC<br>TTAATGCCATGAATAATACCCATCTTATAGGATTGTGGGGAGGACTCAGTGAAGTAACCC<br>[G,A]<br>TGAAGCACTAAACACGTGCCTGACACGTGCTCAATAAATGAGCACTTGTCCTGATGACAA<br>AGGTCGTGGCATTAATTCTCTCTCCTAGGTTGTTACTTCCTTGAGGACAGGAATTGTGGC<br>TTCCTTAATGGCCACTGCAGCAGAGTTTCTCAAGTTGGCACTATTGACATTTTGGGCTGG<br>ATAATTCTTGTTGTGGGAGCTGTCCTGTGGATTGTAGGATGTTGAGCAGCATCTTTGGCC<br>TCTACCCGCTACATATTAATAGCACCCCTAGTCATGAAAATAAAATGTCTAGACATTGCC |
| 165405 | ATGAATAATACCCATCTTATAGGATTGTGGGGAGGACTCAGTGAAGTAACCCGTGAAGCA<br>CTAAACACGTGCCTGACACGTGCTCAATAAATGAGCACTTGTCCTGATGACAAAGGTCGT<br>GGCATTAATTCTCTCTCCTAGGTTGTTACTTCCTTGAGGACAGGAATTGTGGCTTCCTTA<br>ATGGCCACTGCAGCAGAGTTTCTCAAGTTGGCACTATTGACATTTTGGGCTGGATAATTC<br>TTGTTGTGGGAGCTGTCCTGTGGATTGTAGGATGTTGAGCAGCATCTTTGGCCTCTACCC<br>[G,A]<br>CTACATATTAATAGCACCCCTAGTCATGAAAATAAAATGTCTAGACATTGCCAAACTGCC<br>CCTGTTGAGAACCACTGGTCTGCAGGTATCTCTCATGGGGATCACAGGGCTTTTATATTC<br>TCTTCTCTGTCTCTCTCTCTCCCTCTGGGTGTCTCTCTCTCTCACACACACGCTTAGA<br>GAAGGTGGTTAAAAAAAATTTTGTTGAAGTTTGAGAATTTTGAGAACAAAGGAAAAATTT<br>TGGAAGGCATTTTAATGAACAGATAGACTCTGTCCCATTCCATGGTCAACAGAATTTCAT |
| 165500 | CACTTGTCCTGATGACAAAGGTCGTGGCATTAATTCTCTCTCCTAGGTTGTTACTTCCTT<br>GAGGACAGGAATTGTGGCTTCCTTAATGGCCACTGCAGCAGAGTTTCTCAAGTTGGCACT<br>ATTGACATTTTGGGCTGGATAATTCTTGTTGTGGGAGCTGTCCTGTGGATTGTAGGATGT<br>TGAGCAGCATCTTTGGCCTCTACCCGCTACATATTAATAGCACCCCTAGTCATGAAAATA<br>AAATGTCTAGACATTGCCAAACTGCCCCTGTTGAGAACCACTGGTCTGCAGGTATCTCTC |

FIGURE 30000

```
          [G,A]
          TGGGGATCACAGGGCTTTTATATTCTCTTCTCTGTCTCTCTCTCTCCCTCTCTGGGTGTC
          TCTCTCTCTCACACACACGCTTAGAGAAGGTGGTTAAAAAAAATTTTGTTGAAGTTTGAG
          AATTTTGAGAACAAAGGAAAAATTTTGGAAGGCATTTTAATGAACAGATAGACTCTGTCC
          CATTCCATGGTCAACAGAATTTCATAATTAGATAGTTTGTTTACTGCAACTCTGCACCCC
          ATTGCCCATCATTTTAGAGTTCCAACCAGTTAGAGGATTTTTCTTGCAAACTTTCCTTAA

165751    CATTGCCAAACTGCCCCTGTTGAGAACCACTGGTCTGCAGGTATCTCTCATGGGATCAC
          AGGGCTTTTATATTCTCTTCTCTGTCTCTCTCTCTCCCTCTCTGGGTGTCTCTCTCTCTC
          ACACACACGCTTAGAGAAGGTGGTTAAAAAAAATTTTGTTGAAGTTTGAGAATTTTGAGA
          ACAAAGGAAAAATTTTGGAAGGCATTTTAATGAACAGATAGACTCTGTCCCATTCCATGG
          TCAACAGAATTTCATAATTAGATAGTTTGTTTACTGCAACTCTGCACCCCATTGCCCATC
          [A,G]
          TTTTAGAGTTCCAACCAGTTAGAGGATTTTTCTTGCAAACTTTCCTTAAAGCAGTGATAG
          TATCAGCTCTTTAAATAATACTATGCTTGATGAAGTGGTACTTTTCGGGATAATTTGAGA
          CCAGCCGACTTGCTGCTTGAAGAGGACAGGGCTATATTTGGTAATAATATATATGTGATA
          ATATGTATGTAATATTATTATAATGTAATATACAATAATATTTGGTGTAACTGGTGACTC
          TGAGGCCAGTCTTTGATCGAACCTCTCAAGCTATGATTTACATTATGGTCAATGTTAGCA

165877    ACGCTTAGAGAAGGTGGTTAAAAAAAATTTTGTTGAAGTTTGAGAATTTTGAGAACAAAG
          GAAAAATTTTGGAAGGCATTTTAATGAACAGATAGACTCTGTCCCATTCCATGGTCAACA
          GAATTTCATAATTAGATAGTTTGTTTACTGCAACTCTGCACCCCATTGCCCATCATTTTA
          GAGTTCCAACCAGTTAGAGGATTTTTCTTGCAAACTTTCCTTAAAGCAGTGATAGTATCA
          GCTCTTTAAATAATACTATGCTTGATGAAGTGGTACTTTTCGGGATAATTTGAGACCAGC
          [C,A]
          GACTTGCTGCTTGAAGAGGACAGGGCTATATTTGGTAATAATATATATGTGATAATATGT
          ATGTAATATTATTATAATGTAATATACAATAATATTTGGTGTAACTGGTGACTCTGAGGC
          CAGTCTTTGATCGAACCTCTCAAGCTATGATTTACATTATGGTCAATGTTAGCATAATGC
          AATTATCAGCAATCACTTGCTGTTGCTTTGAAAGTCAGAAGGATGGCTAATAAAAATCTT
          AGAAAAAGAAAACAGGCCGGGTGCAGTGGCTCACCCCTGTAATCCCAGCACTTTGGGAGG

166135    TGCTTGATGAAGTGGTACTTTTCGGGATAATTTGAGACCAGCCGACTTGCTGCTTGAAGA
          GGACAGGGCTATATTTGGTAATAATATATATGTGATAATATGTATGTAATATTATTATAA
          TGTAATATACAATAATATTTGGTGTAACTGGTGACTCTGAGGCCAGTCTTTGATCGAACC
          TCTCAAGCTATGATTTACATTATGGTCAATGTTAGCATAATGCAATTATCAGCAATCACT
          TGCTGTTGCTTTGAAAGTCAGAAGGATGGCTAATAAAAATCTTAGAAAAAGAAAACAGGC
          [T,C]
          GGGTGCAGTGGCTCACCCCTGTAATCCCAGCACTTTGGGAGGCTGAGGCGGACAGATCAT
          GAGGTCAGGAGATCGAGACCATCCTGGCCAACATGGTGAAACCCCATCTGTACTAGAATA
          CAAAAAAAAAAAAAAAATTTGCTGGGCGTGGTGGCGTGCGCCTGTAGTCCCAGCTACTCG
          GGAGCTGAGTCAGGGGAATCGCTTGAACCCGGGAGGTGGAGGTTGCAGTGAGCCGAGATT
          GTGCCACTGCACTCCAGCCTGGTGACAGAGTGAGACTCCGTCTCAAACAAAACAAAACAA

166139    TGATGAAGTGGTACTTTTCGGGATAATTTGAGACCAGCCGACTTGCTGCTTGAAGAGGAC
          AGGGCTATATTTGGTAATAATATATATGTGATAATATGTATGTAATATTATTATAATGTA
          ATATACAATAATATTTGGTGTAACTGGTGACTCTGAGGCCAGTCTTTGATCGAACCTCTC
          AAGCTATGATTTACATTATGGTCAATGTTAGCATAATGCAATTATCAGCAATCACTTGCT
          GTTGCTTTGAAAGTCAGAAGGATGGCTAATAAAAATCTTAGAAAAAGAAAACAGGCCGGG
          [C,T]
          GCAGTGGCTCACCCCTGTAATCCCAGCACTTTGGGAGGCTGAGGCGGACAGATCATGAGG
          TCAGGAGATCGAGACCATCCTGGCCAACATGGTGAAACCCCATCTGTACTAGAATACAAA
          AAAAAAAAAAAATTTGCTGGGCGTGGTGGCGTGCGCCTGTAGTCCCAGCTACTCGGGAG
          CTGAGTCAGGGGAATCGCTTGAACCCGGGAGGTGGAGGTTGCAGTGAGCCGAGATTGTGC
          CACTGCACTCCAGCCTGGTGACAGAGTGAGACTCCGTCTCAAACAAAACAAAACAAAACA

166187    CTTGAAGAGGACAGGGCTATATTTGGTAATAATATATATGTGATAATATGTATGTAATAT
          TATTATAATGTAATATACAATAATATTTGGTGTAACTGGTGACTCTGAGGCCAGTCTTTG
          ATCGAACCTCTCAAGCTATGATTTACATTATGGTCAATGTTAGCATAATGCAATTATCAG
          CAATCACTTGCTGTTGCTTTGAAAGTCAGAAGGATGGCTAATAAAAATCTTAGAAAAAGA
          AAACAGGCCGGGTGCAGTGGCTCACCCCTGTAATCCCAGCACTTTGGGAGGCTGAGGCGG
          [G,A]
          CAGATCATGAGGTCAGGAGATCGAGACCATCCTGGCCAACATGGTGAAACCCCATCTGTA
          CTAGAATACAAAAAAAAAAAAAAAAATTTGCTGGGCGTGGTGGCGTGCGCCTGTAGTCCCA
          GCTACTCGGGAGCTGAGTCAGGGGAATCGCTTGAACCCGGGAGGTGGAGGTTGCAGTGAG
          CCGAGATTGTGCCACTGCACTCCAGCCTGGTGACAGAGTGAGACTCCGTCTCAAACAAAA
```

FIGURE 3PPPP

```
             CAAAACAAAACAAAAAACAAAAAAAGAAAATCTTAGAAAAAGAAAATAAATTGTAATATT

166209       TTGGTAATAATATATATGTGATAATATGTATGTAATATTATTATAATGTAATATACAATA
             ATATTTGGTGTAACTGGTGACTCTGAGGCCAGTCTTTGATCGAACCTCTCAAGCTATGAT
             TTACATTATGGTCAATGTTAGCATAATGCAATTATCAGCAATCACTTGCTGTTGCTTTGA
             AAGTCAGAAGGATGGCTAATAAAAATCTTAGAAAAAGAAAACAGGCCGGGTGCAGTGGCT
             CACCCCTGTAATCCCAGCACTTTGGGAGGCTGAGGCGGACAGATCATGAGGTCAGGAGAT
             [C,T]
             GAGACCATCCTGGCCAACATGGTGAAACCCCATCTGTACTAGAATACAAAAAAAAAAAAA
             AAATTTGCTGGGCGTGGTGGCGTGCGCCTGTAGTCCCAGCTACTCGGGAGCTGAGTCAGG
             GGAATCGCTTGAACCCGGGAGGTGGAGGTTGCAGTGAGCCGAGATTGTGCCACTGCACTC
             CAGCCTGGTGACAGAGTGAGACTCCGTCTCAAACAAAACAAAACAAAACAAAAACAAAA
             AAAGAAAATCTTAGAAAAAGAAAATAAATTGTAATATTTCAGAATATTTGTTGGGGAGGA

166402       GGCTAATAAAAATCTTAGAAAAAGAAAACAGGCCGGGTGCAGTGGCTCACCCCTGTAATC
             CCAGCACTTTGGGAGGCTGAGGCGGACAGATCATGAGGTCAGGAGATCGAGACCATCCTG
             GCCAACATGGTGAAACCCCATCTGTACTAGAATACAAAAAAAAAAAAAAAATTTGCTGGG
             CGTGGTGGCGTGCGCCTGTAGTCCCAGCTACTCGGGAGCTGAGTCAGGGGAATCGCTTGA
             ACCCGGGAGGTGGAGGTTGCAGTGAGCCGAGATTGTGCCACTGCACTCCAGCCTGGTGAC
             [A,G]
             GAGTGAGACTCCGTCTCAAACAAAACAAAACAAAACAAAAACAAAAAAGAAAATCTTA
             GAAAAAGAAAATAAATTGTAATATTTCAGAATATTTGTTGGGGAGGATATGTGTGCTCAA
             GAAATATATACTGAGAACTTACCATTGATGCTAGAGATTGAATTGCCCCATGTCTACATG
             AAAAATGAATAGAATATAAACATTTTAAATTGAGCCATGTCTATCTGTATTATATTTCTT
             TTATAGAAATTCATGGAAATGGTATATTTTAACTGAATTATTAACACTGGGGACAATAGG

166529       TGGTGAAACCCCATCTGTACTAGAATACAAAAAAAAAAAAAAAATTTGCTGGGCGTGGTG
             GCGTGCGCCTGTAGTCCCAGCTACTCGGGAGCTGAGTCAGGGGAATCGCTTGAACCCGGG
             AGGTGGAGGTTGCAGTGAGCCGAGATTGTGCCACTGCACTCCAGCCTGGTGACAGAGTGA
             GACTCCGTCTCAAACAAAACAAAACAAAACAAAAACAAAAAAGAAAATCTTAGAAAAA
             GAAAATAAATTGTAATATTTCAGAATATTTGTTGGGGAGGATATGTGTGCTCAAGAAATA
             [T,C]
             ATACTGAGAACTTACCATTGATGCTAGAGATTGAATTGCCCCATGTCTACATGAAAAATG
             AATAGAATATAAACATTTTAAATTGAGCCATGTCTATCTGTATTATATTTCTTTTATAGA
             AATTCATGGAAATGGTATATTTTAACTGAATTATTAACACTGGGGACAATAGGCTTTAAT
             CATTATCTAATACCTGTACGTTGTTTTGAAATTCATAGCCCACCACCATTAATTTCAAAA
             TTGGGTTCTTACTCAAAGAGTGATGAAAAGGCACCAGTACCAAATGGTCTGGCCAAAATG

166567       AAAAAATTTGCTGGGCGTGGTGGCGTGCGCCTGTAGTCCCAGCTACTCGGGAGCTGAGTC
             AGGGGAATCGCTTGAACCCGGGAGGTGGAGGTTGCAGTGAGCCGAGATTGTGCCACTGCA
             CTCCAGCCTGGTGACAGAGTGAGACTCCGTCTCAAACAAAACAAAACAAAACAAAAACA
             AAAAAGAAAATCTTAGAAAAAGAAAATAAATTGTAATATTTCAGAATATTTGTTGGGGA
             GGATATGTGTGCTCAAGAAATATATACTGAGAACTTACCATTGATGCTAGAGATTGAATT
             [G,T]
             CCCCATGTCTACATGAAAAATGAATAGAATATAAACATTTTAAATTGAGCCATGTCTATC
             TGTATTATATTTCTTTTATAGAAATTCATGGAAATGGTATATTTTAACTGAATTATTAAC
             ACTGGGGACAATAGGCTTTAATCATTATCTAATACCTGTACGTTGTTTTGAAATTCATAG
             CCCACCACCATTAATTTCAAAATTGGGTTCTTACTCAAAGAGTGATGAAAAGGCACCAGT
             ACCAAATGGTCTGGCCAAAATGCTACATGGAACTAAATGCTGGGGATGGTCATACAATGA

166951       ATTCATGGAAATGGTATATTTTAACTGAATTATTAACACTGGGGACAATAGGCTTTAATC
             ATTATCTAATACCTGTACGTTGTTTTGAAATTCATAGCCCACCACCATTAATTTCAAAAT
             TGGGTTCTTACTCAAAGAGTGATGAAAAGGCACCAGTACCAAATGGTCTGGCCAAAATGC
             TACATGGAACTAAATGCTGGGGATGGTCATACAATGAGTTTTAAGTGGCTAGACCCTAAA
             TCAGAAGCACTTTCTTCTAATTAGCACCATGGTTCTTAATCCTTTCTGTACATTACAATC
             [G,A]
             CTCAGCAGCTTAATACAAATGTTGCTTCCCGGGGCCACACTCCACATCTTTCTGACTCTC
             TGATTTAATTGGTCCGAATGGGGCCTATACATCAGGTGTTTTTTAAAAGGTCTCCAAGTG
             ATTCTAATGTGTACCTGCATTGAGGACAGGGAAGGTGTAGGAAGCCTGATAACCTTTAC
             TCTCCAGCCTCATCCTCCAATCCCATGATTGTTTATGGGATTGTTGCTACACACCCAGCT
             TAGTCATAGCATTCTTACTCTAGCTTTTTTTTAGATGCAATTTTTATTTATTCTTAAAGA

167026       TACGTTGTTTTGAAATTCATAGCCCACCACCATTAATTTCAAAATTGGGTTCTTACTCAA
             AGAGTGATGAAAAGGCACCAGTACCAAATGGTCTGGCCAAAATGCTACATGGAACTAAAT
             GCTGGGGATGGTCATACAATGAGTTTTAAGTGGCTAGACCCTAAATCAGAAGCACTTTCT
```

FIGURE 3QQQQ

```
         TCTAATTAGCACCATGGTTCTTAATCCTTTCTGTACATTACAATCGCTCAGCAGCTTAAT
         ACAAATGTTGCTTCCCGGGGCCACACTCCACATCTTTCTGACTCTCTGATTTAATTGGTC
         [C,T]
         GAATGGGGCCTATACATCAGGTGTTTTTTAAAAGGTCTCCAAGTGATTCTAATGTGTACC
         TGCATTGAGGACCAGGGAAGGTGTAGGAAGCCTGATAACCTTTACTCTCCAGCCTCATCC
         TCCAATCCCATGATTGTTTATGGGATTGTTGCTACACACCCAGCTTAGTCATAGCATTCT
         TACTCTAGCTTTTTTTTAGATGCAATTTTTATTTATTCTTAAAGAAAAAGATTTCTTTAG
         CACCTTTATTCTAAAGAGCTCTTAATTGCTGTGCTTAGAACTTCTAAACAGTGAGCATTT

167086   AGAGTGATGAAAAGGCACCAGTACCAAATGGTCTGGCCAAAATGCTACATGGAACTAAAT
         GCTGGGGATGGTCATACAATGAGTTTTAAGTGGCTAGACCCTAAATCAGAAGCACTTTCT
         TCTAATTAGCACCATGGTTCTTAATCCTTTCTGTACATTACAATCGCTCAGCAGCTTAAT
         ACAAATGTTGCTTCCCGGGGCCACACTCCACATCTTTCTGACTCTCTGATTTAATTGGTC
         CGAATGGGGCCTATACATCAGGTGTTTTTTAAAAGGTCTCCAAGTGATTCTAATGTGTAC
         [C,T]
         TGCATTGAGGACCAGGGAAGGTGTAGGAAGCCTGATAACCTTTACTCTCCAGCCTCATCC
         TCCAATCCCATGATTGTTTATGGGATTGTTGCTACACACCCAGCTTAGTCATAGCATTCT
         TACTCTAGCTTTTTTTTAGATGCAATTTTTATTTATTCTTAAAGAAAAAGATTTCTTTAG
         CACCTTTATTCTAAAGAGCTCTTAATTGCTGTGCTTAGAACTTCTAAACAGTGAGCATTT
         GTCAAACATAGAATAGCAGAATGAAGGGGTTGGACCTCGGGTGAGGAGGGCTGTCGCATG

167517   TTTTTTTAGATGCAATTTTTATTTATTCTTAAAGAAAAAGATTTCTTTAGCACCTTTATT
         CTAAAGAGCTCTTAATTGCTGTGCTTAGAACTTCTAAACAGTGAGCATTTGTCAAACATA
         GAATAGCAGAATGAAGGGGTTGGACCTCGGGTGAGGAGGGCTGTCGCATGGTCTCTTTCG
         AGTGCCGGCGGGTGGGGGCTGCACATCTCCTCGCTTCTGGGCCCATTGATAAGTGACCTA
         AAAGTGCCTTTCGTTTTTTTTGGTGGGGGGTGAAAAAGCAATCTGTTTTGTACCCACAGC
         [G,A]
         GTGCACTTTAAACAGGAAGCCCTACTGGGGCCAGCCTTCTATGTGTCATTAAGTTTTTCA
         CGCCACACATCCTACCTATCATCATGCACCCATGTCATCGTTCTTTTAAAGGGTGCCAGTTT
         TTTGCTTAAGCACAAGGAGCTGTGACCTGTGTTGTCATCCCTGATGCATGTCATGCATGT
         GACTTCATGACATGTGGGTGACTTTTGATCTCTGAAGGACCAGGGACCCAGTCTGTGGAT
         CACCACTCTCTCCGTGGGTGGTTTGGGTCTTGTTCTCTAGCCCACCCAGCCAGGTGCAAT

167552   AAAAGATTTCTTTAGCACCTTTATTCTAAAGAGCTCTTAATTGCTGTGCTTAGAACTTCT
         AAACAGTGAGCATTTGTCAAACATAGAATAGCAGAATGAAGGGGTTGGACCTCGGGTGAG
         GAGGGCTGTCGCATGGTCTCTTTCGAGTGCCGGCGGGTGGGGGCTGCACATCTCCTCGCT
         TCTGGGCCCATTGATAAGTGACCTAAAAGTGCCTTTCGTTTTTTTTGGTGGGGGGTGAAA
         AAGCAATCTGTTTTGTACCCACAGCGGTGCACTTTAAACAGGAAGCCCTACTGGGGCCAG
         [G,C]
         CTTCTATGTGTCATTAAGTTTTTCACGCCACATCCTACCTATCATCATGCACCCATGTCA
         TCGTTCTTTTAAAGGGTGCCAGTTTTTTGCTTAAGCACAAGGAGCTGTGACCTGTGTTGT
         CATCCCTGATGCATGTCATGCATGTGACTTCATGACATGTGGGTGACTTTTGATCTCTGA
         AGGACCAGGGACCCAGTCTGTGGATCACCACTCTCTCCGTGGGTGGTTTGGGTCTTGTTC
         TCTAGCCCACCCAGCCAGGTGCAATTAGGAATAAAGGAAATAGCAAAGGAATTTTGCTCA

167775   TTTGGTGGGGGGTGAAAAAGCAATCTGTTTTGTACCCACAGCGGTGCACTTTAAACAGGA
         AGCCCTACTGGGGCCAGCCTTCTATGTGTCATTAAGTTTTTCACGCCACATCCTACCTAT
         CATCATGCACCCATGTCATCGTTCTTTTAAAGGGTGCCAGTTTTTTGCTTAAGCACAAGG
         AGCTGTGACCTGTGTTGTCATCCCTGATGCATGTCATGCATGTGACTTCATGACATGTGG
         GTGACTTTTGATCTCTGAAGGACCAGGGACCCAGTCTGTGGATCACCACTCTCTCCGTGG
         [C,G]
         TGGTTTGGGTCTTGTTCTCTAGCCCACCCAGCCAGGTGCAATTAGGAATAAAGGAAATAG
         CAAAGGAATTTTGCTCAAGGCCATGCCAAGCATTTCATCTCATATGAAAAGGAAAAGAGA
         GAGAGTGTGTGTGTGTTGGCTAGATTTAGGTAGAAAACAGGCTGGTGAGAAGCGTAGAAC
         TTGGTTAAAATTTCTAGCCAAAAGTAAGATTTTTAAAAAGATTTATTTCTGGATCCAATC
         CCTGTTGCCCATTTCTATGAATAATCACCATTTGTTTTAATGTGAATAATAGCACACAGC

167876   CACGCCACATCCTACCTATCATCATGCACCCATGTCATCGTTCTTTTAAAGGGTGCCAGT
         TTTTTGCTTAAGCACAAGGAGCTGTGACCTGTGTTGTCATCCCTGATGCATGTCATGCAT
         GTGACTTCATGACATGTGGGTGACTTTTGATCTCTGAAGGACCAGGGACCCAGTCTGTGG
         ATCACCACTCTCTCCGTGGGTGGTTTGGGTCTTGTTCTCTAGCCCACCCAGCCAGGTGCA
         ATTAGGAATAAAGGAAATAGCAAAGGAATTTTGCTCAAGGCCATGCCAAGCATTTCATCT
         [C,T]
         ATATGAAAAGGAAAAGAGAGAGAGTGTGTGTGTGTTGGCTAGATTTAGGTAGAAAACAGG
         CTGGTGAGAAGCGTAGAACTTGGTTAAAATTTCTAGCCAAAAGTAAGATTTTTAAAAAGA
```

FIGURE 3RRRR

```
           TTTATTTCTGGATCCAATCCCTGTTGCCCATTTCTATGAATAATCACCATTTGTTTTAAT
           GTGAATAATAGCACACAGCAAATTCAGCCCCCTGAGTTTTACCATTTTAAGCAATTGCTT
           TAGGCCCGTGAGGCATGTACTATTTATGAAGTTGCATGGGTAGTAATGGAAAACACAACA

172530     GGTTTCGGAGGCTACTTGAGATGTGATTGCTCCTAATGAACCTCCACGGGCCTTTTTAAC
           CTGTCGATGTGTTTATTTCAGATGGAGCAGGAAATGACCCGGTTACATCGGAGAGTGTCA
           GAGGTGGAGGCTGTGCTTAGTCAGAAGGAGGTGGAGCTGAAGGCCTCTGAGACTCAGAGA
           TCCCTCCTGGAGCAGGACCTTGCTACCTACATCACAGAATGCAGTGTGAGCCTTCCCTGA
           AGCCCCCTTCCCTTGGAGGTGGCACTTCCTGTTGTGTGTCTCATCCTGTTTCATGATG
           [A,G]
           CTCCATGAGGCACATCACAGCCAATGGCAGAGAGTAGAGAGAGGGAGAGCACAAAAGCAA
           GATCTGTGTTTTGCAGAGTAGTGAGAGCCAGGCGTAAGGTCCCCAAGAAATGAGATTGGA
           CTCATTTCCAGCAGAAAGTGCAGGTAGACGGCTGGTACCATGGAGTCTGGAGATGGGAGT
           AATTCATCTTTGCCGCAAGTTGCAAAAGATCTTAACATCTCCCATCCCAGCCTCTGTGGT
           CTGCGTTGTGTCTGACATGAGCAGCCTTGAGAACCAGACTCCCAACTATGTACAAGAAAA

172714     TCCTGGAGCAGGACCTTGCTACCTACATCACAGAATGCAGTGTGAGCCTTCCCTGAAGCC
           CCCTTCCCTTGGAGGTGGCACTTCCTGTTGTGTGTCTCATCCTGTTTCATGATGACTC
           CATGAGGCACATCACAGCCAATGGCAGAGAGTAGAGAGAGGGAGAGCACAAAAGCAAGAT
           CTGTGTTTTGCAGAGTAGTGAGAGCCAGGCGTAAGGTCCCCAAGAAATGAGATTGGACTC
           ATTTCCAGCAGAAAGTGCAGGTAGACGGCTGGTACCATGGAGTCTGGAGATGGGAGTAAT
           [T,C]
           CATCTTTGCCGCAAGTTGCAAAAGATCTTAACATCTCCCATCCCAGCCTCTGTGGTCTGC
           GTTGTGTCTGACATGAGCAGCCTTGAGAACCAGACTCCCAACTATGTACAAGAAAACTTA
           CTTTCAATCTTCCTGACATCAAATTTTCCATTGGCCAGAACCAGTGTAGTGACAAGAAAA
           TAGCCTTGAAAACCCAGACCCTCTGTCATTATTTACCATGTGACTTTCATTTTTTCTTTC
           CTTCACAAGAGTAGACTGTCTTCTTCTCCATTGTCTTGTTAAATTTTTCATTCAGGTGTT

173811     TGATTCTCCTGCCTCAGCCTCCCGAGTAGCTGGGACTACAGGCATGCACCACCATGCCCA
           GCTAATTTTTGTATTTTTAGTAAAGACGGGGTTTCACCATGTTGGCCAGGGTGGTCTCGA
           TCTCTTGACCTTGTGATCCGCCTGCCTCGGCCTCCCAAAGTGCTGGGATTACAGGTGTGA
           GCCACTGTGCCCAGCCCATAAATCAAAATTTTTTCAGCAATTGTTATACAAGTGGAACCT
           TACTCTTCAAATGCAATTGTCCAGTGTCTGGCTTAATGTCTGCTGTTGTCAGAAACCATG
           [C,T]
           GAATGGAGTAGATTCCCAGGTTATAAGGAGCCCCCAGGGAGGATGCGCGAGTCACTGGCT
           TCTCCAGGGGTCTCTGGTTTGGGGTTGCCTTGGTGCTGGGCACACTTCCTGGAGATTTTA
           CTGGACCAGCCTGAGGCCTTTGGGGCTCTGTGCAGATGCTCTACTTCTGACTTGTCTAGA
           GCTTTCTTCTAATTCTGGACTAAAAGCAAGCAGGAGTTTGGAGGATGATGGTGAGAATTC
           ACATCCCCGAGTTGGCTTTTGGAATGCAGTAGTTTGTGAGATTTAGTGTTTTTTTTAAGA

173812     GATTCTCCTGCCTCAGCCTCCCGAGTAGCTGGGACTACAGGCATGCACCACCATGCCCAG
           CTAATTTTTGTATTTTTAGTAAAGACGGGGTTTCACCATGTTGGCCAGGGTGGTCTCGAT
           CTCTTGACCTTGTGATCCGCCTGCCTCGGCCTCCCAAAGTGCTGGGATTACAGGTGTGAG
           CCACTGTGCCCAGCCCATAAATCAAAATTTTTTCAGCAATTGTTATACAAGTGGAACCTT
           ACTCTTCAAATGCAATTGTCCAGTGTCTGGCTTAATGTCTGCTGTTGTCAGAAACCATGT
           [C,T,G]
           AATGGAGTAGATTCCCAGGTTATAAGGAGCCCCCAGGGAGGATGCGCGAGTCACTGGCTT
           CTCCAGGGGTCTCTGGTTTGGGGTTGCCTTGGTGCTGGGCACACTTCCTGGAGATTTTAC
           TGGACCAGCCTGAGGCCTTTGGGGCTCTGTGCAGATGCTCTACTTCTGACTTGTCTAGAG
           CTTTCTTCTAATTCTGGACTAAAAGCAAGCAGGAGTTTGGAGGATGATGGTGAGAATTCA
           CATCCCCGAGTTGGCTTTTGGAATGCAGTAGTTTGTGAGATTTAGTGTTTTTTTTAAGAA
```

Chromosome map:
Chromosome 12

FIGURE 3SSSS

SEQUENCE LISTING

<160> NUMBER OF SEQ ID NOS: 4

<210> SEQ ID NO 1
<211> LENGTH: 1515
<212> TYPE: DNA
<213> ORGANISM: Human

<400> SEQUENCE: 1

```
ggggagatgt tgaagttcaa atatggagcg cggaatcctt tggatgctgg tgctgctgaa      60
cccattgcca accgggcctc caggctgaat ctgttcttcc aggggaaacc accctttatg     120
actcaacagc agatgtctcc tctttcccga aagggatat tagatgccct ctttgttctc      180
tttgaagaat gcagtcagcc tgctctgatg aagattaagc acgtgagcaa ctttgtccgg     240
aagtattccg acaccatagc tgagttacag gagctccagc cttcggcaaa ggacttcgaa     300
gtcagaagtc ttgtaggttg tggtcacttt gctgaagtgc aggtggtaag agagaaagca     360
accgggggaca tctatgctat gaaagtgatg aagaagaagg ctttattggc ccaggagcag     420
gtttcattt tgaggaaga gcggaacata ttatctcgaa gcacaagccc gtggatcccc        480
caattacagt atgcctttca ggacaaaaat caccttatc tggtcatgga atatcagcct      540
ggagggact tgctgtcact tttgaataga tatgaggacc agttagatga aacctgata         600
cagttttacc tagctgagct gattttggct gttcacagcg ttcatctgat gggatacgtg     660
catcgagaca tcaagcctga gaacattctc gttgaccgca caggacacat caagctggtg     720
gattttggat ctgccgcgaa aatgaattca aacaagatgg tgaatgccaa actcccgatt     780
gggaccccag attacatggc tcctgaagtg ctgactgtga tgaacgggga tggaaaaggc     840
acctacggcc tggactgtga ctggtggtca gtgggcgtga ttgcctatga tgatgatttat    900
gggagatccc ccttcgcaga gggaacctct gccagaacct tcaataacat tatgaatttc     960
cagcggtttt tgaaatttcc agatgacccc aaagtgagca gtgactttct tgatctgatt    1020
caaagcttgt tgtgcggcca gaaagagaga ctgaagtttg aaggtctttg ctgccatcct    1080
ttcttctcta aaattgactg gaacaacatt cgtaactctc ctccccccctt cgttcccacc    1140
ctcaagtccg acgatgacac ctccaatttt gatgaaccag agaagaattc gtgggtttca    1200
tcctctccgt gccagctgag ccccctcaggc ttctcgggtg aagaactgcc gtttgtgggg    1260
ttttcgtaca gcaaggcact ggggattctt ggtagatctg agtctgttgt gtcgggtctg    1320
gactcccctg ccaagactag ctccatggaa aagaaacttc tcatcaaaag caaagagcta    1380
caagactctc aggacaagtg tcacaaggta tttatttccg cagccggcct ccttccttgc    1440
tccaggatcc tcccgtccgt atatgccaag ggatccgccc ggggccgctg ctggctctga    1500
gccgcctgat ccgta                                                     1515
```

<210> SEQ ID NO 2
<211> LENGTH: 497
<212> TYPE: PRT
<213> ORGANISM: Human

<400> SEQUENCE: 2

```
Met Leu Lys Phe Lys Tyr Gly Ala Arg Asn Pro Leu Asp Ala Gly Ala
  1               5                  10                  15

Ala Glu Pro Ile Ala Asn Arg Ala Ser Arg Leu Asn Leu Phe Phe Gln
             20                  25                  30

Gly Lys Pro Pro Phe Met Thr Gln Gln Gln Met Ser Pro Leu Ser Arg
```

-continued

|  | 35 |  |  |  | 40 |  |  |  | 45 |  |  |  |
|---|---|---|---|---|---|---|---|---|---|---|---|---|
| Glu | Gly | Ile | Leu | Asp | Ala | Leu | Phe | Val | Leu | Phe | Glu | Glu | Cys | Ser | Gln |

Pro Ala Leu Met Lys Ile Lys His Val Ser Asn Phe Val Arg Lys Tyr
65                 70                  75                  80

Ser Asp Thr Ile Ala Glu Leu Gln Glu Leu Gln Pro Ser Ala Lys Asp
              85                  90                  95

Phe Glu Val Arg Ser Leu Val Gly Cys Gly His Phe Ala Glu Val Gln
              100                 105                 110

Val Val Arg Glu Lys Ala Thr Gly Asp Ile Tyr Ala Met Lys Val Met
              115                 120                 125

Lys Lys Lys Ala Leu Leu Ala Gln Glu Gln Val Ser Phe Phe Glu Glu
130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
                165                 170                 175

Gln Pro Gly Gly Asp Leu Leu Ser Leu Leu Asn Arg Tyr Glu Asp Gln
              180                 185                 190

Leu Asp Glu Asn Leu Ile Gln Phe Tyr Leu Ala Glu Leu Ile Leu Ala
              195                 200                 205

Val His Ser Val His Leu Met Gly Tyr Val His Arg Asp Ile Lys Pro
              210                 215                 220

Glu Asn Ile Leu Val Asp Arg Thr Gly His Ile Lys Leu Val Asp Phe
225                 230                 235                 240

Gly Ser Ala Ala Lys Met Asn Ser Asn Lys Met Val Asn Ala Lys Leu
                245                 250                 255

Pro Ile Gly Thr Pro Asp Tyr Met Ala Pro Glu Val Leu Thr Val Met
              260                 265                 270

Asn Gly Asp Gly Lys Gly Thr Tyr Gly Leu Asp Cys Asp Trp Trp Ser
              275                 280                 285

Val Gly Val Ile Ala Tyr Glu Met Ile Tyr Gly Arg Ser Pro Phe Ala
290                 295                 300

Glu Gly Thr Ser Ala Arg Thr Phe Asn Asn Ile Met Asn Phe Gln Arg
305                 310                 315                 320

Phe Leu Lys Phe Pro Asp Asp Pro Lys Val Ser Ser Asp Phe Leu Asp
                325                 330                 335

Leu Ile Gln Ser Leu Leu Cys Gly Gln Lys Glu Arg Leu Lys Phe Glu
              340                 345                 350

Gly Leu Cys Cys His Pro Phe Phe Ser Lys Ile Asp Trp Asn Asn Ile
              355                 360                 365

Arg Asn Ser Pro Pro Pro Phe Val Pro Thr Leu Lys Ser Asp Asp Asp
370                 375                 380

Thr Ser Asn Phe Asp Glu Pro Glu Lys Asn Ser Trp Val Ser Ser Ser
385                 390                 395                 400

Pro Cys Gln Leu Ser Pro Ser Gly Phe Ser Gly Glu Glu Leu Pro Phe
                405                 410                 415

Val Gly Phe Ser Tyr Ser Lys Ala Leu Gly Ile Leu Gly Arg Ser Glu
              420                 425                 430

Ser Val Val Ser Gly Leu Asp Ser Pro Ala Lys Thr Ser Ser Met Glu
              435                 440                 445

Lys Lys Leu Leu Ile Lys Ser Lys Glu Leu Gln Asp Ser Gln Asp Lys
450                 455                 460

-continued

```
Cys His Lys Val Phe Ile Ser Ala Ala Gly Leu Leu Pro Cys Ser Arg
465                 470                 475                 480

Ile Leu Pro Ser Val Tyr Ala Lys Gly Ser Ala Arg Gly Arg Cys Trp
                485                 490                 495

Leu
```

<210> SEQ ID NO 3
<211> LENGTH: 174493
<212> TYPE: DNA
<213> ORGANISM: Human
<220> FEATURE:
<221> NAME/KEY: misc_feature
<222> LOCATION: (1)...(174493)
<223> OTHER INFORMATION: n = A,T,C or G

<400> SEQUENCE: 3

| | | | | | |
|---|---|---|---|---|---|
| tacacctagc | aatagtcata | gaatgcacaa | atcttcaatg | ttagcaaata | atgccaaact | 60 |
| tttttttcaa | atttcaaaga | gattgtatcc | atttacacgc | ctacgggtac | tgtataagtg | 120 |
| tgtgtacttc | cacatcttcg | caaacactgt | cacatccttt | tgttgttgtt | gttctcgaat | 180 |
| ttgagtgtta | ttctttctca | ctgtgacttt | attttttcata | ttttctgatt | atgaacgagg | 240 |
| ttgacaactt | tcacacattt | gttggtcatc | tggatttcct | ttttggtgaa | gtgcctgttt | 300 |
| aagtatctcg | tctataattt | attttaaagt | gtcctttcag | acagtctcaa | tgactgtcac | 360 |
| caactccttg | cagggcagtc | agcccggaga | tagagtaatc | aaggtaggtt | gaagtcaagc | 420 |
| tcaaaacatt | cgctgcctca | gctgtagcag | aggaccactg | ggcttcccca | ggtaacaagt | 480 |
| acttctacct | tagccacatg | agagagaaag | aagaccaggc | agagcagcct | ggctgccttc | 540 |
| ctccttgcag | gtggccgaga | gcaggggaca | gcgccctggc | gacctcctca | gggatcctag | 600 |
| attaacagtc | gcgtcctcaa | acgcagcatc | ctgcgtaacc | gccaatttca | aacttccaag | 660 |
| acctgccctg | ctgattttgc | ccttcccttt | tcccgttgg | tcgcgagtca | aggaagatg | 720 |
| caatttgatt | ggctctcccc | ttcactttcc | tccatgcctt | tagggacatg | ggcggggcct | 780 |
| ggctgagacg | cccatgtcta | tcataggagc | ggagacgctg | attggtccaa | acacggctga | 840 |
| gacccgcccg | cgccgttcct | cgggttcaaa | cgcggcggcg | ggaggcgcgg | ggcggaacag | 900 |
| atcgcagacc | tgggggttcg | cagagcgtga | gtctgatccc | ccagacccaa | ttctaccgca | 960 |
| cccggctctg | caaggccagg | ggagggccgc | ctccacccat | acaagtcccg | ggtttccctc | 1020 |
| ccgccccggg | gagggcggcg | attccacccc | cagggctgcg | ggaggcctgg | agggtcttcc | 1080 |
| ggggctagct | gtgcgcgcgc | ccaccttcct | tgggagccga | ggggtcagcc | gagtggtgct | 1140 |
| ggggcaggag | gcttgctcct | cccctaaacc | aggcggagtg | ctttgtctct | tcagctctgc | 1200 |
| ctcctgtcag | cactaactgc | attattctgc | ccagtgtagt | cggccggttc | cttattatct | 1260 |
| gcgtgaactt | agccatttac | ttaacctctc | tgtttcagcg | tattcatacc | ccgtgcccac | 1320 |
| cccatcacct | catgatgccc | ccgcctcttt | cgctctgctc | cagtccgtct | ggcctcgctg | 1380 |
| ttgctggaga | ggccaggtcc | tgcctcagtg | cttttggctt | ggctgtttcg | tttgccacgg | 1440 |
| atgtctttct | ttccccagat | atcaacatgg | cttgctggtc | attcgcttca | ggtcttcaag | 1500 |
| tcttgggtca | aatggtggct | tctcagtgaa | gtccttatttg | accacactaa | aaattgcacc | 1560 |
| atctcacccc | cattgtcctt | tcttgctcg | attttgtttt | taccccatag | cacttaacac | 1620 |
| cttacaacaa | gctatatatt | ttgcttattt | cagtcattca | tttaataact | attcgcacct | 1680 |
| atttgtgtgc | caggctatgt | gtgcccccac | tgcatggggg | caaacatctc | tgcccttgtg | 1740 |

-continued

```
gagcttccat tctaagggggg gagataataa acacatttat aagtaagaga gtatgtcaga      1800
taagtgtatc atctcctgtc acagtgagtt aaaatctggt gtttaatctc catgattaga      1860
ctgagcttcc taaaactgga gtggtagctg attttcacct ccttgtccct gatatcttga      1920
gggagatcag gatctctcag gcccttcctg ctcaaaacat aggacacact tgacttttct      1980
gatatccttt cagcgccagt ggggagatgt tgaagttcaa atatggagcg cggaatcctt      2040
tggatgctgg tgctgctgaa cccattgcca gccgggcctc caggctgaat ctgttcttcc      2100
aggtaacagc ctaccctgcc aactttgctc acctgtgtgt gtccttggaa tctccttgtc      2160
actcaccttt gcttttattt atttgtttat ttatttagag tctcagtctc tcaggctgga      2220
gtacagtggt gcaatctcag ctcactgcaa cctccgcctc ctgggttcaa gcgattctcc      2280
tgcctcagcc tccagagtag ctgggactac agccgcctgc caccacaccc ggctaaattt      2340 tgtattttc ttttagtag agacggggtt tcaccatgtt ggccaggcta gggtcgaact      2400
cctgacctca agtgatccac ctgccttggc ctcctaaagt gctgggatta caggcatgaa      2460
ccgtgcccag cttgctttta ttataggacc agggataata ttttagggga aattctgttt      2520
tgttttgttt gaaacaaggt cttctgtcga ctctaggcct gtgccaccat gcctggctaa      2580 tttttttaatt ttttgtaggg atggggtctc actgtgttgc ccaggctgat atagaacacc      2640
tgacttcaag tgagcctctt gccttggcct cccaaagcac tggggttata ggtgtgagcc      2700
actgcacctg gccctctatt tagagttta tatgcactga ttcttttgga aaaagacac      2760 tgtgcagaag tagatagctg aacttgcctt agaagggaga tcttttcata tttctcacac      2820
tttacacttc tgtactaaag tttattcatt cattgattga ttggttgctt gcaagacagg      2880
gtcttgctct gtggctcagg ctggagtgca ttggcacaat cacggcttac tgcagccttg      2940
acctcctggg ctcaaacgat cctcccactt cagcttcctg agtagctggg accacaggtg      3000
tgtgccacca tacctggcta attttgtat tttttgtaga gatgaggttt caccatgttg      3060
cccaggcagg tctcgaattc ctgggctcaa gtgatctact tgtcacagct tctgcaagtg      3120
ttgggcttac aggcataagc ccctgtacca gggcaagttt gtccttttat tgaagaaaga      3180
aaaataaatg aacaaagatg cttttttaaaa ctacaatttc tgtgggtata atcctattca      3240
ttttcattgc agggatgttt attttttaag atttttttt ttttttttg agacagagtc      3300 ttcgctgtcg cccaggctgg agtgcagtgg cgcgatctcg gctcactgca ggctctgccc      3360
cccggggttc acgccattct cctgcctcag cctcccacgt agctgggact acaggcgccc      3420
gtcacctcgc ccggctaatt ttttgtattt ttagtagaga cggggtttca ctgtgttagc      3480
caggatggta ttttttaaga ttttaaaaaa agttttgatg aataccacac ctgtttaacc      3540
ctcattcctc tcaagataca catttctgtc accccagatg cgttaaaact taatatcata      3600
agattacttc caaatagatt tttaattctt ttgtttctga tgtatgtgga acactggtga      3660
agtagaaatc cttgtttgat ttatgtattc gtaagtcagg gggacaatag agaccatgaa      3720
gatttagaat tgaatcccag tcccagcact agttagctgc attactttgg gtgagtcagt      3780 tacctttct gagtccattt gctattcttt aaaataggtt gtagcctgta atgccagtat      3840
tttcggaggc tgaggcgggc ggattacttg aggtcacggg ttcagacca gcctggacaa      3900 cgtggtgaaa ccctgtctct actaaaaata tagaaaatta gctgggcatg gtggtcgcat      3960
gtacctgtaa tcccagctac ttgaaaagct gaagcaggag aatcatttga acccgggagg      4020
cggaggttgt cgtgagccga gatggtgcac tgcactccag cctgggcgac agagtgggta      4080
agactccatc tcaaaacaaa acaaaacaaa agaaaacaaa aaaataaaca tagaggttgt      4140
```

-continued

```
agtacctaat ccacagggtt gttgtgagga ttagatgaga tattcgattt aaagcactta   4200
gcaccttgcc tggctcttag taaactcctt ataaaaaatg gtaattattg ttaatactca   4260
gcatagaata gtattagtta taatattaat actaaatttg tttccttaat agtaattata   4320
tttgggaagg tagttatgta ggatacctgt aagatgatga atgatgaagt attcttgata   4380 acttttttt tttttccaaa atattggtat tgggtgttta aacagatgag agtggaaaca    4440
aattgaaagc ttaggttttt ctgtgggacc atccccatca gcatttttaag tcttgacata   4500 tctttcacaa atgaatagtc tgtctttaac cttagatggc tggagtgctg ccacgtttca   4560 gccccttat catgctactt taaaatatct ccaacttgct gggcgtggtg gctcacgcct    4620
gtaatcctag caatttggga ggctgaggtg ggtggattgc ttgaggtcag gagttcgaga   4680
gcagcccggg caacatggtg agcccctccg tttctactaa aaacacaaaa aatagctgac   4740
tgtgatggtg tgtgcctgta gtcccagcta ctcgggaggc tgaggcagga ggatcacttg   4800
agccctagag gcagaggttg cagtgagcta agattgtgcc actgcacttc agcacttcag   4860
cctaggcgac agagcaagac cctgtaaatt aaaaaaaaaa aaaaaagaa aggaaaaaa    4920 atttccaact tattaagggc ttatagtgtg ctgattatgt aatagttatg cttccaatg   4980 tgtctggcat agaactggca tgtttctgag tatctcactt cagcctcatg acagaggtaa   5040
ggactatttt taatttaaac tttaaatagg aggcaacagg ccaggtgtgg tggctcacac   5100
ctgtaatccc agtactttgg gaggctgagg caggtggatt gcttgagtcc aagagttcaa   5160
gactagcctg ggcaaaatgg tgaaacccca tctctacaaa aatataaat aattagtcag   5220 gcatggcggt gtgtgcctgt agtcccagct actcaggagg ctgaggtggg ggcatctctg   5280
gggccccgga ggcagaggtt gtagtgagtt gagattgcaa cactgcactc cagcctgggc   5340
aacagaacga gaccctgttt ctaaataaat acataaatag gaggcaacag atatagacag   5400
atatggaggt aggtaaggcc ttgcccaaga tcatacacgt tgggttttgc agatgaggcc   5460
aagatcagac tccatctttg gttggtctga ctccaaaggc tgaccacata gccattgggc   5520
cacagcacct gtgcacgtca gaatttatta agtatatctt gtatttagtc attataacag   5580
gaagacttat gggtaaaccc tcagttcatc tctttttaat gctgagatcc ccctgcccag   5640
taaagctatt attgcaagta tagtatatac ctatcatttg ccttgagtta tcaggtaagg   5700
atgctgtttg ttcttttccc atatagtgct gtttgaatga ggttgagata cagtagcaat   5760
tttgttttcc attcaggtga gtaccttaga ctgagtgtca ttttgtcttt tttacttcta   5820
ctcaacagga tttcctgaca tgttcgaggt cagtgattgt cagactttct gagccagcaa   5880
aatttcccaa attgctgggt agacacaggt tttccaactt tttattttgc caagtaagga   5940
tatataaaaa aaaataaaa agaaagacct attattttct ggcccttgta tttcataaag   6000 ggcatttta gaaacaacaa gacaggaaga acatcatctc agaataaagg accattttta   6060
aatttgaata catttagttt tataaaaaag atatcatgtg gtgttcattt tttctcattt   6120
cactgcaggc tgttgaaaac tttgttaaga accagtacta tatttgggaa ccctgctttt   6180
aattgatcta aactcttgaa gaatagaaga aacaaagcat tttattttc tgagttactg   6240 gcaactatta ctaaagtgac agatatggtg gccttgaatg cagtgcttcc caaacctgat   6300
tgaggtctga ctctcttggg gaccagggtc tcattctgtt gcccaggctg gagtgtggca   6360
gcacaatctt ggctcactgc agcctttact tctgggctc aagtgatcct tctacctcag   6420
tctcacaagt ggctaggact acaggaccat ggcactacac ctggctaatt ttttttttgtt   6480
```

-continued

```
tgtttgtaga gatgggatct cgctgtgttg ccctggctgg tcttgaactc ctgggctcaa    6540
gtgatcctcc caccttggcc tcccaaagtg ctagtattcc aggtgtgagc cacctctccc    6600
tgctggggaa cttgttaata aaacagattc taggctacag tctggaaaat tctaattcat    6660
ttggttgtgg gggaggggg cataggacca gagaatgtgt ttgtttgttt gtttgttttt    6720
cttaaattct ccagtgctgt tgtgattcaa atgcagccgg tctgtttctg ttatcaagtg    6780
ctgtgtaaca aagcactcac aaagtttaaa gcaacaatga tttatttttt cttaggattc    6840
tgtgggttgg ctggactcag ctaggtagtt ctgcttcatc ctgtgatgtc agctggggtc    6900
acttgtgggg ctacattcag ctgggattat gtctgggact ggaacatgtg ggtgctgact    6960
gctggctggg gcaccttagt gtttctcaca tggcctctct tctccatgag gtctttcagt    7020
agtatagccc aggactcgta acttttttt ttttttaag acagactgtc gccctgtcgc     7080
ccaggctgga gtgcagtggc acgatctctg ctcactgcaa cctccgcctc ctgggttcaa    7140
gcaattctcc tgccccagcc tcccgagtag ctgggattac aggcacgtgc ctccacgccc    7200
ggctaatgtt tgcatttta gtagagatgg gtttcacca cgttggtcag gctggtctcg     7260
aacttctgac ctcgcgatcc gcctgcctcg gcctcccaaa gtgttggaat tacaggtgtg    7320
agccactgca cctggctgac tcgtaacttt ttttgtaagt aataaatatt ttaggctttg    7380
tgggtcctgt agtctctgtt gcaaccactc aacttggcca tggtagcaca aaagcagcta    7440
aagacaatat gtaaatgatg ggtgtagctg tgttccagta aaacttataa aaagtccgtg    7500
ggctggattt ggtccaaggg ctacagattg cacaccctg gtctagccca agcatctgtg     7560
catggtggct ggcttcccaa aagtggaagc tgctaagctg cctttttttt tttttttt      7620 ttttttgaga gggagtctca ctgtgttgcc taggctggag tgcggtggtg tgatctcggc    7680
tcactgcaac ctccatctcc cgggtgcagg caattctcat gcctcaacct cccaggtagc    7740
tgggattacg ggtgcctacc accacgcctg gctaattttt gtattttggt agagacaggg    7800
tttcaccatg ttggccaggc tggtctcaaa ctcctgacct caagtgatcc acccgtcttg    7860
gcctcccaaa gtgctgggat tacagatgtg agccaccgtg tctggccgct tgacaagctt    7920
cttaaaggca ctgccctgaa ctggcacagt gtcacttgtg tcacattctt ttggttgaag    7980
agagtctcag agatggcaca gattcaaagg caggagaaat agactccagc gcttaaagta    8040
aggagtagca tgtgcctaca gaattggagg aactgttgga ggccatcttt gaagagagac    8100
caccactatc catggcttgg cacgtgggaa tcactgctct ataccagggt tgcagactca    8160 tgtcttggg ggccaggcag tgagtataaa tgagtcaagt gggccagttg gaagatggag    8220
tcagacctgc agtgaactcc caaacacatc tgctaccggg agggcagca ttactcagct    8280 ccagctcagc gtcatcaggc aggaaggcga ggcagtgttg ccggatgtgc cagtgtttca    8340
aaagaagcca gagactccat tttattttt ttgtatggaa tctcctgatt ttgaaatatt    8400
ggcagataat tcaaattatc ttaaacacta caggccaaac aaaacatatc tgtgggctag    8460
agacagtctg ccagtttgta actatttctc cagatcatga gtaaatttgg ctttacgatg    8520
gtcactcagt tcttattact ctaggttgtt caaatgaatt aaaaaagctg aaattatatg    8580
aataaacccc tgggcacaca tgaaagaagt gaaaaaccca ttgtttccta ttgtagaaac    8640
atggaagcat gtcagagcca gaggatccag aggaaatatt ctcactagcc tcagaccctc    8700
aggagtgagg gagcttttct tgttaatggc cacgcttgtg cagttttcct tcccaggtgc    8760
tggtgaaaga aacccacagt cttggaatca tggaagtgat accataatga ctgtcagttg    8820
acgttgcttt aaagaatgaa gccacagaat tgtgctgtta gcatgtcgtg agcagttagt    8880
```

-continued

```
tgagttggtg gcttgtaatt tactctgtgt ggatgttatt gatcaaagct tttcattatt      8940
gacagtgtct ccatctgctg tttgctgttt ttaggggaaa ccacccttta tgactcaaca      9000
gcagatgtct cctctttccc gagaagggat attagatgcc ctctttgttc tctttgaaga      9060
atgcagtcag cctgctctga tgaagattaa gcacgtgagc aactttgtcc cggaagtgta      9120
agtttgggga acttttcttt gaaaactgtc ctgagagaga aaaactagaa agatgcttga      9180
ggcagaatga gttactggtt gatagtagtc ggtaagaact ctggttctat ataagacaga      9240
tccaggttca aattcaggct gcacctctta tagctgggag accaggtaag ttgggcttct      9300
tggttgcaag cgacaaactt aattcaaaga ctgaatttag gccaggtgca atggctcata      9360
cctataatct cagcccttg ggaagctgag gtgggtgaat cgcttgagcc caggagttca      9420
agaccagctt gggcaacatg gtgaaacccc atctctacaa aaatacaaa aattagctgg       9480
gtatggtggc ttgcacccgt ggtcccagct gctgaggagg ctgaggtggg aggatcactg      9540
gagcccggga ggttgaggct caatgagctg tgattgtgcc attgcactcc agtctgggtg      9600
acagagtgag accctgtgtg aataaaagag tgaatttatt ggctcatgaa actgagaaat      9660
ccaggaatga gttaagtttt agctttaggc atagctagtt ccagagacct caataatatc      9720
ccgtggccct gtccttatac tcactcaggg ctgactttct attaggcaga gtaggcacgg      9780
tgcttaggat ctgtgatatt taattttaat gaatttaatt acttttaatt aactgaatta      9840
aattttaatt tgttttaaaa ttataggaaa atgaatatat ataatgtata atgattctgg      9900
attacattca tctttatact aatgtagtca taaaatataa ttttgtttt ttttggagac       9960
agagtcttgc cctattaccc aggctggatt gcagtggtat atcatggctc actgcagttt     10020
caaccttcta ggctcaagca atccttccac cccagtggct gggactacag gctcacacta     10080
ccacgcccag ctaattttg cttttttctc tgtagagata gggtcttact atgttaccca      10140
ggctggtttc aaactccagg cttgaagcag tcttcctgcc tcagcctccc aaagctttgg     10200
gattacaggt gtgagccacc atgcctggcc ccataaaata taattttga attctttttt      10260
gttttaatg gaggaagggg ctgaggaagg caaaagtacc tagggcctat gaagtcatat       10320
attggccttg ccttcaccct gtttctgact ttgcttgact tccatgtgat gaggcagttg     10380
gctgttagtg tcccagtttc atactcttac attagtgttt ttcaaccagt gggtgatttg     10440
acgttttcgg ttgtcagagc tagttggggg tggtggtgtg tgagtttggg gggaagggtc     10500
ctactgtcag ttaatgggtg aggccagaga tgccaccaaa caccttacag tgcacaaagc     10560
agccccata acacagaatt atgtagccca caatgccaac agtgctgaat ttgagaaacc      10620
ccaccttgta caacattgct gtgcaaccaa ccaccctaaa tattactgac ttaaaacaat     10680
agtcactgtg gctgggcgcg gtggctcatg cgtgtaagcc cagcgctttg ggaggctgag     10740
gcggcggatc acttgaggtc aggagttcca gaccagcctg ccaacatgg tgaaaccttg       10800
tctctactaa aaatacaaga attagctgaa tgtggcagcg ggcgcctgta atcccagcca     10860
tttgggaggc agaggcagga gaatcgcttg aacctgggag gtggaggttg cagtgagcca     10920
agatctcacc attgcactcc agcttgggca atgagtgaga ctctgtctta aaaaaaaaa      10980
aaagttattg tattacctct tgtgtgtgta ggttaattgg actcagctgg ggattcctct     11040
gctctgtatt acattggcca ggattgcagt cacctggggc tctcctgggc tggaatgtgt     11100
gagagggctt actcagtgtt tggtgccctg gcttggaggc tgggcccagc tgggcctctc     11160
tctcttcatg aagtttcagg gccttttgct gtccacatgg cacctctatg tggtctccaa     11220
```

```
atcagaagtc aaggaactac agcctgtgat gcctattttg taaagaaggt tttactggaa      11280
cacagcccta cccatgtgtt tgtacagtgc ctatggctgc tttcacatca taacagcatt      11340
ttatttcatt ttatttattt tttttgaga caaagtctca ctctggctgg agtgcagcag      11400
cacaatcata gctcactgca gcctccaact cttgggctca agcaatcctc ctgtctcagc      11460
ctcctcagta gctagtacta caggcccatg ccaccactaa tggctaattt tttaattttg      11520
tgtagagatg ggaccttgtg agattgccta ggctggtctt gaactcctgg cctcaagaaa      11580
tcctcccacc ttggcctccc aaaatgcttg gattacaggc atgagccact gtgcccagcc      11640
cacaacagca tttgagtagt tgtgatagag accaaatggc ctacaaagcc caaatagtt      11700 cctgtttggc ccatttcgaa aaggcttgct gacctctgag ctacatggtc tctctagcag      11760
gacagcctcg acggtagctc aggtttccaa aacacaaaag tggaagctgc caggctttct      11820 tagggggttat cctaggaggg acataggatc tctttgactg catttttattg tttgatgcat      11880 gctctggggc tgctcaaatt ccacctgaga ggaaactaca caaggtcatg aatcccaaga      11940 ggactgggc attgggtgct attttttggag actggctacc acaccctgcc caatggtaat      12000
cttcccttat ctagattaat acaaccccag ggaagattct aacttggctc tgctttgggt      12060
catttgcctc cctggaggtg aggtgttgtg atcggttttg ttggaatgcc caaagggtc      12120 aggcagtgt gattaccagg acctcatgga atgggggatg cgtggttatg caaggagcc      12180 ggggatgctg ggtagaaaaa aaatcagcat atgttcacta tagtgctctt cagtattta      12240 catgtacttt gttctcagtt ttctcatctg taaaatagga ataatgtata tccttttttt      12300
tttttttttt ttggagtctt gctctgttgt ccaggctgga gtacagtggc acaatctcag      12360
ctcactgcaa cctccgcatc ccgggttcaa gtgattctcc tgcctcagcc tcctcagtag      12420
ctgggactac aggcgtgcac caccacactc agctagtttt tgtatttta gtagagatgg      12480 ggtttcgcca tgttggccag gctggtctca aactcctgac ctcaagtgat ctgcctgcct      12540
cggcctccga aagtgctgga attacaggca tgagccacca cgcccattgg gaataatgta      12600
tatctaatga ggctgtgttg gaattgaatg agttaatgca cagaccagat ttgtcatgtt      12660
gcctggccca taggagacaa taaatggtac ccagtattaa taactgtgaa tgtcaacaac      12720
atttaatata ttgtatatct tcaaaatgta cttgaggtat ttgttcatca ttctgttttt      12780
gtttgaataa gctcgtgcct tcttttttgtg aatatttaaa tttataagta gcgagtggga      12840
ggggaaggaa gttatgtgat gaggctagct tactgagcca tctgcaggca ccttcattag      12900
tcttgagact gtcctctggt tacttaacag cagtgaatta tctagaatca tttagtgatc      12960
agaagacttg gtttagtgga atgtagattt ttttctaata gacccctctt ccagggaaat      13020
gtttcatatt tttgaagagg tttcctgggg agtgtttaag aggccatgat tgaaaatggg      13080
tgattacatt agtgtgtttt ctattcctcc cctttttgag tttctgttttt ggaatgtaag      13140 ctttgttttt ctacgtggag aagggtccct cagctgcttc tgcccaggtt ttttgaatct      13200
tcctataggg atggagattt ctttgggga ctgttagaga aaatgaaata gagtgtagct      13260
ctgaaggaga aggatgtctc cagcagaagt acctctagcc ttgggccaag ggagggaagg      13320
gaagggaacg agcatctggg aaccaggaa gggattttttg tctttcttaa ttactcttac      13380
atccccagtg cccaaaatag tgtctggcat atgttaagtc cttagtaaat acttgttgaa      13440
tgagtgtatg ctcagtgaac aaaataaatg gcaaacatta agcacagtat cagataattt      13500
gtgtaaaaaa tatacagcag tgttatacta aaacttgcac agaggccagg tgcagtggct      13560
cacgcctgta atcccagcac tgggaggccg aggtgggcag atctttgagc tcaggagttt      13620
```

```
gagaccaacc tgggcaacat gctgaaaccc tgtctataca aaaaatacaa aaagtagctg   13680
gggcatgggg acgcacatct gtggtcccag ctacttggga ggctgaggct ggagtaattg   13740
cttgaagctg ggaggtggag gttgcagtaa gccaagattg tgccactgca ccccagcctg   13800
ggtgacagag taagaccctg tctcaaaaca caaaacaaca cccccttcaa aaaaaatcca   13860
aaaccaccac cacaacaaaa aaacttacac agaaaagtgt tgataattgt caaaattggg   13920
ctgttattgg caatttgaca gtagctgaat tactaccatt tgagctatat tcactataga   13980
taagatcttc aatatattta caactttagt actaatggga aaatgataac ttttgaaaag   14040
tttttttttt ttcttattgc aaacaataca caatacaatg ttaaatatag aaggttaaac   14100
gtgcatctga gtctgtttgg gctgcgataa tagataccct agacttggca atttataaac   14160
aatagaaatt cattgctgac agttgtgaag actgggaagt ccaagatcaa ggcgccagcg   14220
aatctggtat ctggtgatgg ctccctgctt caaaaatggc gccttcttgc tgcatcttca   14280
cctggcagaa ggggcaaaca tgagtccttc agcttctttt tttttttttt tctatgttta   14340
aaacttttgg tccggcgtgg tggctcatgc ctgtaatcct agcactttgg gaggccgagg   14400
caggtgcatc atgaggtcaa gagatcgaga ccatcctggc caacatggtg aaaccccccc   14460
gtctctatac taaaaataca aaaattagcc aggcatggtg gcgtgtgctt gtagtcccag   14520
ctactcagga ggctgaggca ggagaattgc ttgaacctgg gaggcagagg ttgcagtgag   14580
ccaagattgc gccactgcac tccagcctgg caacagagta agactccgtc tcaaaacaaa   14640
caaacaaaaa aacaaaaaa aaacttttat tttaggttca tgggtaaatg tacaggtttg   14700
ttatgtaggt aaacttgtct tggggtttgt tatagattat ttcgtcaccc aggtactaag   14760
cctagtaacc aatagttatt ttttcagatt gtcctccctc ctcccaccct ctgtcctcta   14820
gtaggctcca atgtctgttg ttcccttctt agtgtccttg tgttctcatc ctttagctcc   14880
catttatatg tgagaacatg tggtatttgg ttttctgttc ctgcattagt ttgctaagga   14940
taatgtcagc ctcttttttt tttttttttt ttttttgat acagagtctc gctctgttgc   15000
ccaggttgga gtgcagtggt gcgatcttgg ctcactgcaa cctctgcctc ccgggttcaa   15060
gtgattctct tgccttagcc tcctgagtag ctgggactac aggtgcgcac caccatgcca   15120
ggctaatttt tgtatttag tagagatagg gttttcaccat gctggccacg ctggtctcca   15180
actcttgacc ttgtgatccg ccggcctcgt cttttttccca aagtgctgag attacaggtg   15240
tgagtcactg cacccggccc aatgtcagcc tcttttttag ggaagtgatt taatcacttc   15300
cctaaaagtc ctacctcgtt tttttttttg gttttttctt tttttttttt tttttttttt   15360 tttttttta ggtagagtct tgctctgtca cccaggctgg agtgcagtgg tgcgatcttg   15420
gctcactgca acctccacct cctgagttca agcaattctc ctgcctcagc ctcctgagta   15480
gctgggatta taggtgcctg ccaccacgcc tggctaattt ttttgtattt ttagtagagt   15540
tggggtttca ccatgttggc caggctggtc ttgaactcct gacctcaagt gatctgccca   15600
aaatgctggg attacaggcg ggagccactg tggccagccc ctgcaagtcc tacctcttaa   15660
tagtattaca ctgggattaa catttcaaca tgaattttgt agggggcagg ggcacaaacg   15720
tttagaatat agcacatcac atacatagtg agagaaaaat ccctcaaaat cttacctgag   15780
acaatcactg ccaacagatt gctgtatagt gtgccaattt tgtttgtgtg tgtgtgtgcc   15840
ttaaaaatat ttattatgga aatttaaaaa cgtaccccaa ggtggccagg tgtagggctc   15900
acgcctgtaa tcctggcact ttgggagccc gaggtgggtg tattacttga ggtcaggagt   15960
```

```
ttgagaccag cctggccaaa atggtgatac cagtctccta aaaatacaaa aattagccgg   16020
gtgtggtggg cacctgtagt tccagctact cgggagacca agtcatgaga attgcttgaa   16080
ccctggaggc agaggttgca gtgagccaag accatgccac tgcactccag ccagggtgac   16140
agagtgagac tccatcctag taaacaaaca aacaaacaaa caaaccaact aaccaaccag   16200
gataaaactc cctgtctgta aggagtatgt gttctaatgg atactgagcc atcttgttct   16260
gtttaacatg tgcctaatgt tcttttatat gggcggactt gtaggttgtt tcaacttttc   16320
tgttgatgaa cctttaggtg gtttctgatt attttttgtgt tacaacagtt ttcatcattc   16380
acatctttgt atgcatcttt tttgagcaca tgtgcaagta tttctgtgga caatggatga   16440
ttcctagaaa ttgaaagttt ggattactgt gttccaaaaa aggaagcaat acacccagct   16500
atgttggctt ttgctcttgg gtccagatga ttatctgaca aagttattct ctgattgcat   16560
tttcttttct tttcttttct tttttttttt tgagatggag tttcgctctt gttgcccagg   16620
ttggagtgca atggcgcgat cttggctcac tgcaacctct gcctcccagg ttcaagcgat   16680
tctcctgcct cagcctccta gtagctggga ttgcaggca tgcgccacga cacctggcta   16740
attttttgta tttttagtag agatgggatt tctccatatt ggtcaggctg gtcttgaact   16800
cttgacctca ggtgatccac ccgcttcagc ctcccaaagt gctgggatta caggcgtgag   16860
ccacagtgcc tggccctctg actgcatttt cacagtgttt tgggtcctta tctctacctc   16920
agtacctcaa tattcagtgc ccactgggcc cttagatact gcagctaaaa gtgcacaggg   16980
gtggagtgat gtgacggttt tggggtcaca gaagcagctg gtatagagag aagttgtgaa   17040
gttttttttt ttttttcctga cagagtct cgctgtatcc cctaggctgg agtgcagtgg   17100
cttgatctcg gctcactgca acctctgtct ccctggttca agtgattctt atgcctcagc   17160
ctcccgagta gctgggatta taggcatgtg tcaccatacc cagctaattt ttgtgttttt   17220
agtagagatg gggtttcacc atgttggcca ggctggtctt gagctcctga cctcaggtga   17280
tccgcccacc tgggcctccc aaagtgctgg gattacaggc ctgagccatt cgcctggtc   17340 tttttttttt tttttttaagt aatcataggc ttgaatgtag cctctcatct gttcacctta   17400
ataatccaaa agcctttaga taaagaaatg gagatttgga atggcttctc agaattccaa   17460
gagagtattg tcatggtttt gcctgcaaag caccgtggtc tgtctccttg tgcagttgag   17520
aaagctggtg gtcgccactg acaggcccag agttattaag ttggacactg ctttaagcaa   17580 cttttgtaaac aatccaaggc atactagaga attaggagag attggctttg tgtatgagca   17640
ataacaaaat caagttcaat ccagcaagtt tttggggaat tataattcaa aactcaaata   17700
cttgatctgg aagaaacttg gaagaggga aggaagacag gcttgttaca gcattgtcag   17760
ggtaaaagga aaataccgtg cagctttta ttttgcttct tcatggcatt ccccatgtag   17820
gtgccctaga tttgtttttt acagtggtca cgacttcatg tggatccacc caccactctt   17880
gcctggttcc ccaagggacc aagggaaggt gtattcagga tgattgctga agtgaggggt   17940
ggggtctgtg gctgagaaga ctctcaatac cgcggcactc attataagcc tctgacacag   18000
gagatttcaa ctccacccgt gcaacaaagg aacagggtgg gcaagagtag ttacagttgc   18060
aggctgagtg cgatggttca tgcctgtaat cccagtgctt tgggaagcca aggtgggagg   18120
attgcttgag tctaggagtt tgagaccagc ctgggtgaca taatgagacc ctacctgtac   18180
aaaaaaattt taaaaattag ccagattggt ggtgtgcgcc tatagtccca gctactctgg   18240
agaatgaggt gggtgagggt cccttgagtc caggagttcg aggctgcagt gagttatgat   18300
tctatgattt caccactgca ttccagcctg ggcgacagag caagattgtg ttctttttt   18360
```

```
tttttgagac ggagtctcac tctgtcaccc aggctgaagt gcagtggtac gatctctgct   18420
cactacaacc tgcacctccc aggttcaagt gattctctcc ctcagcctcc cgagcagctg   18480
agattaaaag cggccgcttg tgtgcagcta attttgtat tgttagtaga gatggggttt     18540
catcatgttg gtcaggcttg tcttgaactc ctgacctcag gtgatccacc cgcctcgccc   18600
tcccaaaatg ctgggattac aggcgtgagc tactgcgccc agccatttgt gtctcttaaa   18660
aaaaaaacta agaaaatgaa aaaaatgaca ttggccaatt cattaaaatg ccactcactg   18720
actgtggtat gaaatggctt tcccttgat ggaccgagtc tgtctcattg tgtgagccac     18780
ttgcagggct gagtatgact ctggaatgta gctcctaacc ttatctgctg cccagccatt   18840
gaaatggcca tcccttccag ttcccagaag attccagtgt gtgtttggga ttttaagaca   18900
gtctcttggt cttcagtgtg gcatctttct gccggatttt ccaggataat tttgattata   18960
agcattgcat tgcccttggt gtgtaatgcc tgtgtatgat gctgttccct tgtaacgtgc   19020
aggattaaat ttttgggtca gccactgctg ctcccttca ttcctgcagg tcattagagt      19080
catcgtacat ttagcgatgt ctcagatcag tgtatctaga gtgttaataa acatgttaga   19140
ttccaaatct actgtccatt taatccatac ttcatacgtt gaggatctct gactgaaaga   19200
ttagacttgg aaaaataata agactgtatg gtaagaaaac tatagttgca aatccatttg   19260
gacatgtagt atgtcagccc tgcagagcag atgtcagaac cccatttagt tctctgagtg   19320 ctaagcccctt ctgcccacca cgctgttttt ttttttgag atggagtctc gctctgtcac    19380
tcaggctgga gtgcagtggt gtgatctcgg ctcactgcaa gctctgtctc ccaggttcac   19440
gccattctcc tgcctcagcc tcccaagtag ctgggactac aggtgctcac caccatgccc   19500
agctaatttt ttgtatgttt ttggtagaga cggggtttca ctgtgttagc caggatggtc   19560
tggatctcct gaccttgtga tccaccgct tcggcctccc aaagtgctgg gattacaggc     19620
gtgagccact gctcctggcc cccacgcctt ttttttttt tggagacaga gtttcactct     19680
gtcacccaga ttggagtgct gtggcacaat ctcagctcat tgtgtcctct gcctcccagg   19740
ttcaagtgat tcttgtgcct cagcctcctg agtaggtgga attacaggcg tgcaccacaa   19800
cacctggcta attttgtat ttttagtaga tgggggttt caccatgttg gccaggctgg      19860
tctcgatctc ctgacctcca gtgatccact tgcctaggcc tcccaaagtg ttgggattac   19920
aggcgtcagc caccatgcct ggaccctct gccccttaa gcactgccac atattagatc      19980
tacgaaggct ttatggatac aatccaagga agatgaacct tgggctagtg ggataaaact   20040
aagcgcatgt agttagaatg gaatgatctg gaaaccaggt cccaagttgg tctaaattag   20100
actcatgttg actatgtcac actgtaaacc agtctaaatg ctaataagca tgcttgacca   20160
aacactgccc tgcagccttc agagaggaag aaggaaaaca taatttgtat cctctctccc   20220
tattttctga gtctatggga ttcaaattgt agctgccatg gaaactgtac tttggaattt   20280
ctagagccct taattttaac ttaacatata aaaacacttt tgtactgatt ttataattat   20340
tcatgatgga tgagaaagtg aatgtctttg acagtgaggg aagctatccg aatgctattt   20400 tcttttttt tttcttca taaagatgca tatatttgca tgctttatt acctggggct           20460 aactcttgca tcttttgcag attccgacac catagctgag ttacaggagc tccagccttc   20520
ggcaaaggac ttcgaagtca gaagtcttgt aggttgtggt cactttgctg aagtgcaggt   20580
ggtaagagag aaagcaaccg gggacatcta tgctatgaaa gtgatgaaga agaaggcttt   20640
attggcccag gagcaggtag gaggatttta acatcatgct tttccacttt ctgtaccgga   20700
```

```
gtgttcattg caaagacgat aatctgctgc actggcgtct aggatcaagc acgttttcct    20760
ctgtgactct atatttaatt atagttgggg caaaaaggtc tctcatgttc ttagctcatc    20820
ttcttgaact gatgttggct aattttgaag gctcacaaat tcctcttgat gtatcatgtt    20880
tctatcgttg taatttattt cagaaccaag gtggcctttt agctaatgaa tttaagatga    20940
tcttttatga ccattagctg aggactcagg atatacatat ggtggggtga atcagattgc    21000
ttttgtacac gctttaggta tttgtgttgt gggcatatgg atttggtttt aaaacaggcc    21060
tttgaagaaa tcaaataaca ttctttgtta tgtggctagg gagttgcttg tttgagagca    21120
ggtagaacgt tatctttttt gttgtggtat ttttctttct tttaaacaag gctactgtct    21180
ctagacatat tgattcattt gctgtgtttt agagagatgg ccgtcagcct tggaattcag    21240
agagtaattt attacttaca gacattttag tgcacatgat atgtctgata atgtacccag    21300
ctctgcagga agcttgcaaa aggaatagaa gtcccatggt tgctattttc agtgtttaaa    21360 acaaccttg gaaagtggag gaaaaatgca aatgtataaa gcaggtgctt accagctaaa    21420
gtatcacaga agtgggagag caattagcaa attaattaac gatgatgtga ggggagatgt    21480
tgtgggtgag caagggacag ttagggacag ttctcaccga tgggggggaaa tgtaggttct    21540 cggcagagag aagtgatgag aacatgttgg gtagaagtgt gacattctgg agtactagaa    21600
tgctatgcaa gtgtgtgtgt gtgggtgtgt gtgtgtgttc agtggttcag aacagactgg    21660
gaaatggcga aatgaggaca tttgggtggg gaggggaaa tgggtgggaa actcaagaac    21720 cttttttaa aaaattgtgg taaaatatat ataacataaa gtgtaccatt ttaaccattt    21780
ttaaatgtgc aactgagtgg tattcagtgc attcatgatg ttgtacaacc atgaccgctc    21840
tccatttcta gaattttttct atcatcccaa acagaaactc tctatccatt atacaatacc    21900
tccccattcc cccaagaacc agttttttgaa ttgcagtttta ctttgtgagg ctgttgggga    21960
ttatttaggc ctctggaagg aggaggttgg gatcagagtc tggccctgtg gacttcaatg    22020
actttgtgtg gcctccaatc agagaagcag cggagggcag gaagctgctt gtcagaatct    22080
gagagtgatg tggcttcttt gtttagcaat aaaatgtgag cacataatag aaaggaaaag    22140
tgacaggaca tggcagataa tttggaagag aggagtggaa gatgctcact cagcctccca    22200
gctcctgaga aagaactgtg tctcatcagt tcatactacc tgagcatctg ttgtatctgg    22260
tgtgtttcta ggtcctggag aagaggcatt acgtgtagcc ctgaccttgt gatgcttatg    22320
tttttgatgg gaaatagtgc gtgtaaaaag aaaataatcc aacaggccac acggcaggca    22380
aacaatagag atattcaaat aggtatacct tcctccaggt gaatggcctg aaatgaccgt    22440
gtggaagtgt gggctggggg cttataaaat tatacacata caggcgctaa ctaaagccgc    22500
ctattcattc cttaagagga tgcatagaaa agaaaagtag ggtccttaac tgagccattt    22560
ggaatttaag ggcatgagag aagccagcac aagcagtgaa gggaaggaaa agaagtgccc    22620
gagaggaggg agggatgctg ttctgcagac aaggcctgcc gcctgggaga ggcccgcacg    22680
cccacccagg gttctctgac agctggaagg ggtcttcaga gactgtttat attttattta    22740
tttatttatt tatttatttt gagacagagt ctctgtcacc caggctggag tgcagtggtg    22800
cgatctcagc tcactgcaag ctccgcctcc caggttcaca ccattctcct atctcagcct    22860
cccgagtagc tgggactaca ggcgcctgcc acaatgcccg gctaattttt ttgtaatttt    22920
agtagagacg gggttttacc tcgttagcca ggatggtctt gatctcctga cctcatgatt    22980
cgcccacctc ggcctcccaa agtgctggga ttacaggtgt gagccactgt gcctggccga    23040
ctgtttctac tattttagag agagggtctc actgtcatct gtgctggaat gcagtgatgc    23100
```

```
agtcatagct cactgcaccc tcaaactcct gggcttaagc gaccctcccg cctcagcctc   23160
ttaagtagct gggaccatag gcatgtgctg ccacacccag ttaactttat tatttattta   23220
tttatttaga gaatgagtct cattctgttg cccaggctag aggtgcagtg gcacgatctc   23280
ggctcactgc aacccgcct cccaggttca agcgattctt cttgctcagc ctcctgaata   23340
gctgggatta caggcacctg ccaccacacc tggctaattt ttgtattttt agtgcagagg   23400
gggggttttc accatgttgg tcaggctggt ctcgaactcc tgaccttgtg atctgcctgc   23460
ctcggcctcc caaagtgctg ggattacagg cgtgagccac cgtgcccggc ccactttatt   23520
attttaaaaa cattgtttta ttttatttt tttgagacag agtccgctgg agttcagtgg   23580
ccggatctca ctcactgcaa cctctgcctc ctgggttcaa gtgattcttg tgcttcagcc   23640
tctctagtag ctgggactac aggcgggtgc caccatgcct ggctaatgtt ttttgtatct   23700
ttttagtaga cacgggttt tgcccatgtt ggccaggctg gtctcgaact cctgacctca   23760
agtgatctgc ccactttagc ctctcaaagt acttgggatt acaggcgtga gccactgtgg   23820
ctagccccca gctaactta aaaaaaaaatt ttgtgggccg ggtgcagtgg ctcacgcctg   23880
taatcccagc actttggagg ccaagcaggg cggatcactt gaggtcggga gtttgagacc   23940
agcctgacca acatggagaa accctgtctc tactaaaaat acaaaaaatt agccgggtgt   24000
ggtggtgcat gcctgtaatc ccagctactt gggagctgag gcaggagaat tgcttgaatc   24060
tgggaggcag aggttgcagt gagcttagat cacgccactg cactcagcc tgggcaacaa   24120 gagcgaacac tccgtctcaa aaaaaaaaa taaattatgt agaggtggga tctccctatg   24180
ttgcccggac tggtcttgaa ctcctggcct caagtgatcc ttccatctcc cctcccaaa   24240 gtgttgggat tacaggcatg agccaccct cctggctgag actgcttatt ttatttattt   24300 ttaattttt tttgttttgag actgcttatt ttaatggaag cttcagggggt cagacggggt   24360 cagacagagt cattggtgag caagcaaagg tgtagactgt tcagttcagc cttccttgga   24420 cacctttat gtgccagaca aaagaaggat cagcatatca ggtgcagtaa attattgggg   24480
ttatgttggt gtttcccaaa tgtgttagat ttatccctgg tagtgttaaa tctcatgatt   24540
ttaggtagta tatggacaac ctatgtaaaa acatttaata gtttaatatt aactagcata   24600
tcaaaacctg tgactttgct cacgcctgta atcccagcac tttgggaggc caaggcggga   24660 ggatggttg ggcccaggag tttgaggcca gcctaggtaa catggtgaga ccctgtctct   24720
aaaacaaaac aaaacaaaac aaacaaacaa acaaataaac aaatccctg taacttgttc   24780 taacataac ctaaacaatt tttttattaa aattaaataa aaaaattgaa acagtaacca   24840
tttttttttt tttttttgga gacagagtct tgctttgtca cctagtctag agtgcagtgg   24900
cacaatctct gctcactgca acctctgcct tcaaacaatt ctcctgcctc aggcttctga   24960
gtaggtggga ttgattacag gtgcactcca ccatgcccag ctaattttttg tattttttagt  25020 agagacgggg tttcaccatg ttggctaggc tagtcttgaa ctcctgacct gcagtagtcc   25080
acgtgccttg gcctcccaaa gtgctgggat tacaatcaca aatttataga aaagttgcaa   25140
gtaccatgta gtcagggttc ttaagagaaa tggaaccagt aggagataga tatataatca   25200
tctcctagga ttataagttg acacataaga ctaaccgtca catacagtat aaacaacttt   25260
ttttcttaaa ccatttgata gatacacaca cactgatata catagaatat atatacacac   25320
acacagaatg tatatacaca tagaatatat gtgcatacag aatatataca cagaaatata   25380
tatgtacaca tgcatagaat atatttacat atatatgcat atatataatt tatttatttt   25440
```

```
aagcagttga tttatacagt ttttgttttt gttttttttt tgagacagag tctcactctg   25500
tcacccaggc tagagtgcag tggcgagatc tcagctcact gcaacctctg ccccgggtt    25560 ccagtgattc tcctgcctca gctccacaag tagcacacca ccatgcccag ctaattttg    25620 tattttttt agtagagacg aggtttcatc atgttggcca ggctggtctc gaactcctga    25680
cctcaagtga tccgcccgcc ttggcctccc aaagtgctgg gatttcaggc gtgagccacc   25740
acacctggct cccataatgt cttttagaat aaaacgatcg agttgaggat cacacgtgac   25800
acttaattgt cctgtctctt tagtctcctt caatctggag cagttctttg attttttcctg  25860 gactctcatg accttgacaa ttctgatgat ataggccag ttattttgta aaatttgaat    25920
ttgtctgatg ttgcttatgt ttagatttag ggtcttggtc tttggccgga atatctcaga   25980
caagatgctc tgttcttatt gcatcagagc agaagactct ctgtttcagt tgatcacatt   26040
tatgttgatg ctcactttga tcacttgatt aaggtggtgt cagttatgcc tttctacttg   26100
tagggttact ccttcctcct tcgtgatttt atttatttta ttttcttag acagggtc     26160 ttgcttggtt gcccaagctg gagtgcagtg gtgggatctt ggctcactgc agccttgaac   26220
tcctgggctc aagtaatcca cctgccacag cctcctgagt aactgggact gtaagcgaac   26280
accaccacac ccagctactt tttgtattgt agagatgggg tctcactgtg ttgtccaggc   26340
tggtctgtaa ctcctggcct caagcagtct tccggccttg gcctcccgaa gtgctgggat   26400
tacaggcatg agccactgca cccagcctcc tttgtaatta aaaagtatt ttatggggag    26460 ttactttcaa gtgatggaaa tatttatat ctatgtggac ttggattttc ctatttcagt    26520
cagtgagtta taatccattt ctgtcactag ttttatactt aaattgttcc caacttggcc   26580
actgagaacc ttttaggtt agcttttgtg tccttttcac atgtctccaa gattcattga   26640
atactttcct gctttctggt atagcaagat gttcaggttc ttttggtact tttactttct   26700
ctgccctggc tctggcatca gtcatttctc agaggagccc tgtgccttc agtgacaat     26760 ggtgtttaga ggccaagatc tggacattgg gtgttttcat tgctaccggt gtgtcactac   26820
tcccagaccc ctttcagtgg acagcactaa ggaatacaca tacgtatata caatatatcc   26880
acctacacat gtgcgtgcac tcacacacac acatatacat tacatctata tttgtgtatc   26940
catgtctata tattgaaaat tgtggctggg cacagtggct tatgcctta atctcagcat    27000 tttgggaggc tgaggcaaga ggatcacctg aagccaggag ttcaacacca gcttgggaaa   27060
cagagagaga ctctgtctct acaaaaataa aaagggaaaa ccatgagttc acaccgtgc    27120 ccccagttcc aatccaactt cacagggttc attttagttt tcacccttc catgtttgta    27180 attctcttct ctgacattat acccttaata tgtttactta ttttatgcat ctgtatgcat   27240
ccaatctact gtctttgttg gtatcccacc tcccctggt gggtccagat aatctgctct    27300
gggttgccct ttcacgtgga tgtcttcctt accctgtgtg ggcctgtgat actgggctgc   27360
ccccacacat gagtgctgcc ctcctcacgt tgcttgggac ggcactgtgt cctgggccac   27420
catgactttt ctcataacta gcgtggatgc ttaccttgtt ccacaccagt gaatggcttc    27480
aggaagagaa gaggaagaga aaaatattta catttaaaga aaggtagttt aaagaaatat   27540
gttaggtaaa gaattgagca ggtaatatac ggagctggca aaaattgtga ccaaagtagg   27600
tgaatgattg agatttatgc aattctgggc taagtgacag ccccttccct ttcccttccc   27660
ttcccctccc cttcccttt cttccctttc ccttccttt ccttccctt ccttccccct     27720 tccctccct ttccttccct ttccctcttc ttccttcctt cttctgttt tcttttccct    27780 tctttccttt gcctttttt tttttaaa gctagaaaca tcagtttagg cataaagaca     27840
```

```
gaggaaaagg cttctttttc ctctcacagt tctttataat tgtctaagca gtttcttttt    27900
tccctaggtt tcattttttg aggaagagcg aacatatta tctcgaagca caagcccgtg    27960
gatcccccaa ttacagtatg cctttcagga caaaaatcac ctttatctgg tgagtcttta    28020
catctgtctc tctggaatta gcctagcact ctgacactca gatgcctgtg gtagaactga    28080
atgttgttct tgcccatgtg gtctcattca tgcaaagact ttcttacctt acaggtgtct    28140
ccctggtttc ctcgttataa agatcaagag ctaacccatt tagaaacagc ctcattgggc    28200
tgaacgtggt ggctcacgcc tgtaatccca gcattttggg aggccgaggc gggtggatca    28260
cgaggtcagg agatcaagac catcctggct aacacagtga aaccccgtct ctactaaaaa    28320
tacagaaaaa ttagccgggc atggtgtcgg gtgcctgtag tcccagctac tcaggtggct    28380
aaggcaggac aatcgcttga acctgggaag cggagcttgc agtgagccga gattgcgcca    28440
ctgcactcca gcctgggtga cagagcaaga ctctatctca aaaaaaaaa aaagaaaaaa    28500 aaagaaacag cctcattgac agttggatat tgtagctgtg gctttcaggc aataataggg    28560
aatcatttat tggggaatag tctgtcatta tgtataagat aatcttgctt taattttttaa    28620 aaacttcctg tgttagcttg cttaggatta aaaaaatgat aatagtgcat ggttgttata    28680
agaaaatgca aacactgcag acatgcatga agttgaaggg aaagccccccc attttctttt    28740 ccttttcttt tttttttgaga cagagtctcg ctttgtcacc caggctggag tgcggtggca    28800
ctatctcggc tcactgcaat ctccacctcc caggttcaag agattcttct gcctcagctt    28860
ccctagtagc tgggattaca ggcacgtgtc accacgccca actaattttt gtatttttag    28920
tagagatggg gttttaccac gttggccggg ctggccgcaa actcctgacc tcaaatgatc    28980
cacctgcctc ggcctcccaa agtgttgtga ttacaggagt gagccactgt gcccggcctc    29040
tccgttttat tttctaatcc tcctccctag gggaagaaat gttaaatggt tacataagct    29100 ttcccttttct gaccccttaac tgtgctctgt aggagcatgg tgggggatgt ttcttttctt    29160
ttcttctttt tttgagacca ggtctcactt tgccacccag gctggagttc agtggcatga    29220
acatggctca ctgcagcctc gacttcctgg gctccagcaa acctcccacc tcagcctccc    29280
gggcatacac cactgtgcct ggctaatttt tgtattttta gtagagacgg ggttttgcca    29340
tgttgcccag gctggtttcg aagtcctgag ctcaagagat cttcctgcct tggccttcca    29400
aagtgctggg attacaggtg tgagccacca tgcccagctc cggtgggga tatttctata    29460 tccacatgtg tatagtttac tttataaaaa tggtatgtta ctctgtgctt ggctctccag    29520
cttgctgttg cctttcacca gtgtatccca gacatccttt cttccttgtc agtaacgcag    29580
gtctacttta ttctttgagc agtggcataa ttttccctga tgtgtatata tcataagtta    29640
gagaatgcta aaattcattt tggggccttg tttaggttct tgagggatta aattcctaaa    29700
tttaacaagt gtatcctgga aacaattttt gttcctgatt cagcccttaa aagaggacta    29760
tcatgttacc ttgaatggag ataaacaggc tcacgtaaga gaaaagggta agagggatga    29820
actcccactt atcttaaact tctactggcc cgttttgggg gaattgctg cttttattcc    29880 tgacctaaaa taaataagtt tatgtgtctt ggtttcatat tagttgagaa cccagtgcct    29940
ggagagaagt tttccttgtc ctctgagtga ggacattcac atatgaatct attggcagac    30000
tggctttgac tgaccacacg tgccttcaga accaatgcca cagctcttag gtttatggcc    30060
tgaaacaccc tttccttaca tattgcctta gaaactttcc ttccttgaga catggggcat    30120
ggaaccctca ccttcacaga tgaccttggt gtgtttctag ggttgctggt gttccaggac    30180
```

-continued

```
atctgttgca gatgcagtat ttaccttgtg ctctctgcat cataagcagc ttctcatgtt    30240
tgaatgtatt aacagacttt taattttttt tatttttgag acaaagtctc actctgtcac    30300
ccaggctagt gttacccagg ctggagtgca atggctcaat ctcagctcac tgcaacctcc    30360
acctcctggg ttcaagcgat tctcttgcct cagcctcccg agtagctggg attacaggtg    30420
catgacacca cgccctgcta atttttgtat ttttagtaga cacggggttt cgccatgttg    30480
gtggggctgg tctcaaactc ctgacctcag atgatctgcc cgccttggcc tcccaaagtg    30540
ctgggattac aggcgtgagc cactgcgcct tttcttttca tttttttttct gagatggagt    30600
cttttctctgt caccaggctg gagtacagtc atgcaatctc agctcactgc aacttccacc    30660
tcctgggtta aagtgattct cctgtcttag cctcctgtgt agctgggact acaggcgtgt    30720
gccactgtgc ccagctaatt tttatatttt tagtagagac ggggttttgc catgtgggtt    30780
aggctggtct tgaactcctg acctcaggtg atccacccgt cttggcctcc caaagtgctg    30840
gggttatagg cgtgagccac tgtgcccagc ctcaggcttc tttattaaga agaagttcgg    30900
gccaggtgtg gtggcttaca cctgtaatcc cagcaatttg ggaggccgag gtgggcagat    30960
caggaggtca ggagatcgag accatcctgg ctaacatggt gaaacctcgt ctctactaaa    31020
aatataaaaa attaggcagg tatggtggcg ggtgcctgta gtcccagcta ctcgggaggc    31080
tgagggagga gaacggtgtg aacctgggag gcggagcttg cagtgagccc agattgtgcc    31140
agtgcactcc agcctgggtg acagagcgag gctccgtctc aagaaaaaaa aaaaagacgt    31200
tcccttgaaa caacagggct tttgtttgtt ttggtttgtg tttgtttgtt attgttgttt    31260
tagatacgta ttttttttctt tcttttttttt ttttaagtga tgatgtctct gttgcagtgg    31320
catgatcata gctcactgta acctcaaatt gcagggctca agtgattctc ctgcttcacc    31380
ttcctgatta gctgggacaa caggtacaaa ccaccatgcc tagcgaattt ttaaattttt    31440
catagagact agggtctcac tatgttgcct aggctggttt cgaactcctg ccccaagtc    31500
atcctcctgc cttggcttcc caaattgttg ggatcacagg catgaatcac cacacccagc    31560
ctattttttag atattttaat tcgagctcta caggagggttt agaacactag cttgtgaaga    31620
taaacttcat tttcaaggcc acacagaatc taagtggtcc tggaattagg aagggctttg    31680
attttttgga ccaaagttga gagtccacag ttttctggtc taccttgcac tgctccataa    31740
actcatattt cttttctctg agctgaagag ctccccttct tggtgtctag tctcaggcaa    31800
cttattctta aaagtaagca ttattgaaat gctttgggat tttcacatca tcaaggtcca    31860
ttttggtaga ggcactgaca gattttgagt gttctgtgtg aaggaactca gttgaggatt    31920
tagtggtcca tgtggcaggc tactgctcag tagcttcagg gaaaccactg cttgcctccc    31980
ctgtggccag tgaggatgat cagaggagtc ccagcaggaa tgcccaaatg tagttttctt    32040
acatgttgat gggagtgcat tgtttcatgt ctaaacagtt ctcaaatcac atcttccgga    32100
gggtactatc tgggcacttt gataatttct cactttgatg tcaccgttct tattaccatc    32160
acctagttttt gtcatagtag aaataacttt ccttttctctg tgtgtgtgtg tgtgtgtgtg    32220
tgtgtgtgtg tgtgtgtgtt ttgagatgga gtcttgccgt gttgcccagg ctgtagtgca    32280
gtggcgtgtt ctcggctcac tgcaacctct gcctcccggg ttctcctgcc tcagcctccc    32340
gagtagttgg gattacaggc gtgtgacacc acgcctggct catttttgta ttttcagtag    32400
agatggggtt tcaccacttt ggccaggctg gtcttgaact cctgaccttg tgatccgccc    32460
accttgacct cccaaagtgc tgggattgca ggtgtgagcc accgcctg gctttttttt    32520
tttttttttt tgagacagag tcttgctctg ttgcccaggc tggagtgcag tggcgggatc    32580
```

-continued

```
ttggctcact gcagcctcca cctcctaggt tcaagcaatt cttctgcctc agcctcctga   32640
gtagctggga ttacaggtgc ccaccaccat gtccggcaaa tttttgtatt tttagtagag   32700
acagggtttc accatgttgg ccaggctggt ttctaactcc tgaccccagg tgatccgcct   32760
gcctcagcct cccagagtga tggaattaca ggcatgagcc actgcgcctg gccacctttg   32820
tcttcttagt tgtggattta actgctgtgg acatctgctt gggcatagcc ttcccggagt   32880
acctcttgga ttgggactgt ctgtgggttt ctgtgctagg acaggctccc agatgtagga   32940
ggcttcccca atgatctcac cactggcatc ggcatcctta gcttctactc agcttttcca   33000
tctgccatct gcaagatgg aaggttgttt tgtttttgtt tttgttttt ggtttatttt     33060
ttttgagata gagtctcgct ctgttgccaa ggctggagtt cagtggcgca atctcggctc   33120
agtgcaacct ccacctcctg ggttcaagtg attcacctgc ctcagcctct ggagtagctg   33180
ggattacagg cgcgtgccac catgttcgtt taatttttttg tattttttagt agagacgggg  33240
tttcaccgtg ttagccagga tggtctcgat cttctgacct catgatccgc ctgcttcagc   33300
ctcccagagt gctgggatta caggcgtgag ccaccgtgcc cagcctagga gggttcttaa   33360
tgcagctgtt ttttggagtt ctggttgcct cagcacactg ctacttgggt caatgacatt   33420
tttactccct tgtttttgtag ctcaattggg tattactgat gggattttgt aattattaat  33480
atttcttgt ctccatttc ttctcaagta ctttgttgct tttgagtaaa atgcttgcta     33540
agggtatagt tttcacataa aagctcaaat ttagcatgga aattaagata tgctcatacg   33600
tctgccatcc cttatctgta attctgaaat acctagagtt ctgaataacc tcaaattctt   33660
ttgttacttg tttatcagca aaacctgatt tgaactcagt ttttggcaaa acttgatcca   33720
agctctctta aggctctttt tagtctttat tcattccctt tagtgtgact tcccattttg   33780
ctataaaatt atgagtgtgt ttgattacaa ggtgatgtcc cagaccctac tgagggtgtt   33840
acataatata aactgtatgt atggctgggc gcggtggctt atacctgtaa tcccagcaac   33900
tttgggaggc cgaggcgagc ggataaccctt agttcaggag ttcaagccca gcctggccaa   33960
catggtgaaa ccccgtctct actaagaata caaaaattag ccaggcatga tggtgggcgc   34020
ctgtaatccc agctactcct taggctgagg caggagaatc acttgaaccc aggaggtgga   34080
ggttgcagtg agccaaggtc atgccactgc actccagcct gggcgacaaa gcaagaatct   34140
gtctcaaaaa aaaaaaaaaa aaagtgtgtg taccacttta cctttctaaa atctgaaaaa   34200
ttctgaatct ggaaacccat tctgcttcaa gataaatgga tcctagattt atatcggtac   34260
cgtacagtcc tgaaattcca tcctatctat tggccacttt tacatcaaca aaccttttgaa 34320
gtttggggaa acttacatat cacgctccct tggcagttga acattattta tttattttga   34380
gatggagtac tcgctttgcc caggctggag tgcagtggcg cgatcttggc tcactgcaac   34440
ctctgcctcc cgggttcaag caattctcct gcctcagcct cctgagtagc tgggattata   34500
ggcatgcaac accatgccca gctaattttt gtcttttag tagagacggg gtttcactat     34560
gttaaccagg ctgttctcga actcctgacc ttgtaatctt ccctcctcgg cctcccaaag   34620
tgctggaatt acaggcgtga accaccacgc ctggccctga agatacattt taaatcaatg   34680
aaaaaaacaa caggattcta cctcctatgg tatatccctc ctggctgtct cttctctcca   34740
gtcttgcctc tgctgtgtgg gtttcaggca tccatcttct ctactctgaa ttactgtgat   34800
aacctctgaa gtatttcccc tgccatctgt ctggcccttc tcccaggtct tccacatact   34860
gcagccaagt cagcccgctg ttgaaaccct tcaagactcc ctgctgtcct ctggatgaag   34920
```

-continued

```
tccagactct tccacgtgac ttaccaggcc tttcttgcac ttgtcccag ccacttactg    34980 tttctctctt tctaccttaa catcctgaac ttcctttggt tctttgacct tgcctctgac    35040 cttttttccat gctgttcact ctttccctgt tcaccttgct aactcctctt tctcttttctg  35100 ggttggatca gatttcactt cttccagaag cccttcctag accctatact tctggaatgg    35160
cgccttttga ctgtacgctc attgcaccct gtacttctcc tttatgagtg ggtgctggtc    35220
tgtcccacta ggctacttca tccataaagg gagagtagag ctttaccaag tcaatgctta    35280
agcaatattt attggatgaa tgtgtgatta atttcataga aatttgatgt gcattcaaat    35340
ttacttattg tattacggaa cttgcattat attctcagtg gagttatttt ctttcacgtg    35400
tgtaattcaa gatagactca gtgagatttt caaaatttgg aatgcagtgc aaggaaattg    35460
aacttgagtt cttttgcatt ttgatggtta aaaatttccc atttgtggtg acataccaca    35520
ataagccagt gaatgtggct tattgttttc tggtctatag aaaattgtcg caaactctgt    35580
cataatgtct ggttctatat aacaaagcta gtcctgtatt ctgcatgtgg ctgatggaaa    35640
cagtgctctg ttgatctggt tcatgaagaa atctgttcaa ttctgcataa cagatgcctt    35700
catcagtgtc cttccatgaa ggagctgatc ttcacaaaga acacatagtt ttgcatccca    35760
ccacttgcag tattttttt ttttttttt tttttttgag atgcagtctc gctctgtcac    35820
cctggctgga gtgcagtggc atgatctcag ctcagtgcaa cctctacctc ctgggttcaa    35880
ttgattctcc tgcctcagcc tcctgagtag ctgggattac aggcgcacac caccatgcct    35940
ggctaatttt tgttgtttta gtagagacgg agtttcacca tattggtcag gctggtctca    36000
aactcttgac ctcatgatct gcctgccttg gcgtcccaaa gtgttgggat tacaggcgtg    36060
agtcactgtg ccctgccagt attgttttgt ctaaattatt tgtgctgatg ttttccac     36120 tgtggttttc ttcagattac ccttgctctg agcctgcaat tgactcatga acttcttttc    36180
catgttctaa ccttacaatg acttccttgt gttcactcca aatgttttc cctggttgca    36240 tgtagagatg tattagctaa ggtacatgct tagctgctgt atcaaagaga ccctaatgta    36300
caacccaggc tggtagagca gctctgctgt atgtgttaat tcaggaccc aggttccttc    36360 catgttgtga ctccccccctt ccttaggatg ttgtcttctt ttacatggct gaagttgggc    36420
catttcatgt ctctgttcca gctgcctggt aggaaaaaag aacagaaatt cagagtaagc    36480
aaattctttt tctatagatg gatgcggaag ttggacacat catttcctct cacattttct    36540
cggccagaac gtagtcatgt gactgcacgt ctagctgcta aggagactgg gaatttactg    36600
tcggctgtgt ggcctctgtc aagctaaaat tcttattact gtggaataag ggaaggatgg    36660 atttggggc acaattaata gtctgtcaca gaggctaaaa cagctgcttt tggctgggca    36720
cggtggctca cacatgtaat ttcagcactt tgggaggccg aggcaagtgg atcacttgag    36780
atcaggaatt tgagaccagc ctggccaaca tggtgaaacc ctgtctctcc taaaaatata    36840
gaaattagcc gggcatggtg gcgggtacct gtaatccgag ctactccaga ggttgaggca    36900
ggagaattgc ttgaacctgg aaggcagagg ttgcagtgag ccaagatggt gccactgcac    36960
tccagcctgg gcgacagagc aagactccat ctcaaaaaaa aaaaaaagg ttaaataaac    37020 agctgctttt gtaggtgata caaggtacag ctaagctttg aagccaggcc tgtagtttca    37080
ccttccatat tcttactcaa ggcattatac ttctggatct gaaaccactg gatctgatgc    37140
cctgcttggg atgagttctt tatattatct tgctttcaac ccacacctgt gtaattttat    37200
gggcagcgtt tgtttcctat ataggaacaa tttgaaagtg ggctgttttct aggctttcat    37260 gaatagcagg ctatgctgtc attgggaatc tggagggagt taatgaacac aacttcattg    37320
```

-continued

```
tttactttag tgaaatgtgg cagcttatga tagttttgac agtgagacat gtgctgtttt    37380
gatctctcag ctaagattat ctgattttc aggcatgtct caaaactcac caggcctgct    37440
cacatgctgc tgcttctgaa gccagggttt ggaaaccagc tgcccatcag aatgaggctg    37500
tgacttagaa tattggttct tgttttatta ccattccttg tttggtctct ccagagtcac    37560
tggccttttc cgcttcaatt ttcttatcgg tgaaatgaga tattaattcc tcttattgac    37620
ttcaattcaa ttgctgagtg tattgttgcc tttgggaagt tctttgagtt ttctgtgcct    37680
ttgaaatagt tgttttttt tattctggtg ttttgaggca tgtttcaagt gagtgcattt    37740
acacttctac cattttagga gccacaattc agttatgttg tcccagcttg cttggcccca    37800
tccccagagt ttctgattca gtaggtctgg ggtggggccc aataatttgc atttcttctt    37860
cttttttcga gacagagtct gactgtgtca tccaagctgg agtgcagtgg cacgatcgta    37920
gctcattgta gcctcaaact cctgggctca agccgtcctc ccacctcacc ctcctgagta    37980
gctgggacta taggcatata ctaccatgcc ctgccacctt tttaattttt tgtaaggatg    38040
ggggtctcac tgtgttgctc aggctggtct tgaattcctg gctgaagtg atcctcctgc    38100
ttcagcctcc ccaaatgccg gcattcctgg catgagccac tgcacttggc caagactttg    38160
catttctaac tagtttccag gtaatgctgc tgctggtgta gggacctcat tttgagaacc    38220
attgttctat agctgtagct atagttagtt ctggttata gcttcttcct tttgtccctt    38280
cagtaatagt gtacacatcc gaaatccctg tccttgctct ttcaggccca ggcatggtat    38340
ctggtcctct tctgttgcta gccctggggt gcttcatcat cccaagttta tttttcttct    38400
cctaacctga acctttgtaa atagccccctt ccctaatgaa cgtcctcaat tccctgtttt    38460
gcgtgtcctg tctgtttctt ggcaagactc tggatgattc agtactcaat gaggattttt    38520
cgcatagatg gatgaaacag gctgggtttc atgttttcta agataaaggt gcttctctct    38580
tttctcttg gtcactttga ccaagaagaa aataacagag ttttattct caagaagaat    38640
aatatcgggg ccactctgct cagaggccac tctgctttga ggaccccttc tctcctccct    38700
catgccaaag atcaggaaca ttgggcagag cggataacga tgccgccagc gtcattacat    38760
tttcacggca ctttcagttg tgctgagcgt gcaaacattt caaggagaca tttctaagag    38820
gtggctagca cagcatgcct ctaatgccct atgtgaattg gaatagagta ctaaagaact    38880
gttcaatatt caccccatcc ccgcatatgc aagcatgcac gtgggttcat tgtatatgtg    38940
tgtgtgcacg tgtgcacaga cacatttgtc cttcgtttca aatgcaacac aatggatgga    39000
aattgccttc ctggtactgg ggtatggatg caaacaccaa cagagaagca gccgctactt    39060
ccaaactgaa cacatgtgag atttgccctt taattagcat ctgcagctgc tgccatcaga    39120
agggtctgtc tctgttggcc tgaaagtctt tgctttaaaa gagcaagtcc attatagctc    39180
caagccaggc tcgtctgtca gctgctgtgc tttctctgcc atcagcgggg ttgccacatt    39240
gttttgggct gtttcactct aggactcttt cctcctcctg tgcccccagc ctttgattac    39300
catgccttgg tgatcctcat ttgggtgacc tgcagctgct cattgtgtgt gcaggagaca    39360
tctccagtcc ttgtaaggag ggaagatcac tggcttcagt gctgatggac tggttatttt    39420
ccagcccttt gtcgtcagtg atcttgtctt gatatgcaga aaggctccag gtagtcactg    39480
aaaaaaatat aagcagcaga ggtgatggct atatgaaagt cacgtttcat caagggcatt    39540
gctgctatgg aaactttcaa ttcacttgga gtagggagcc atattggttc cacagcctcc    39600
tcagcagtgg gtcccaacac agtgctgggc tagctgcctc tgaatcaccg cagtagctcc    39660
```

```
ttttactata gattcctggg tcccacccat ggaatgtgat ccatgaagtc tggggttatt   39720
ccctggaatc ctttaagctc cctaagtggt tgggatggga aagagatatg ctttatgtta   39780
ctatacttct tattattatt attttaaaat tcttgccggg cgcagtggct cacacctgta   39840
atcccagcac attgggagac cgaggcgggt ggatcacttg aggtcaggag ttcgagactg   39900
gcctggccaa catgatgaaa tcccgtctct actaaaaata caaaaattag ctgggcatgg   39960
tggcgcatga ctgtagtccc agccactccg gaggctgagg caggagaatc gcttgaaccc   40020
gggaggcaga ggttgcagtg agccgagatc gtggcactgc actccagcct gggtaacaga   40080
gtgagacttc atctcaaaaa aacccaaaaa aacaaaaact cttttcatt ataccggaac    40140 gtcagcttta tggagtcggg gattttttct gttttattca ctgctgtttc cctaacatct   40200
agaatagtgg ctggcacgat aggcactcaa gtattgattt agatgagtct attttatttt   40260
cttttaaatt tttaattttt attagaggtg gggtctggct tgttgccca agctggtctc    40320 aaaactcctg gcctcaagcg attgtactgc ctcagcctcc caagggcta ggataggcat    40380 gagccaacat gcctggcttg tcttattttt aacaagcact tctggtgatt ctgatggaca   40440
atcaggcttg ggaagttcta acctagagga cctacagttg tcttggggta aagccaagg    40500 ctatcctggt ttttagaatc agtgccttac tgggcatctc tgaagagtaa aagtcaggga   40560
cagagttaca tttttggaca aaaccagatg ctgtgaatgg actcttggtc caacctggg    40620 tggcgacttg gtccttaact tcttcatcat tttctgctga ccctgttctt tggttcacag   40680
caagtcacct gataagaaga ctcaaagact gctagtttgt tactttagat gatgcttttg   40740
gaacctcttg gtaccatttt aacaatccaa acgtattta tgaaagcact caagtcctgg    40800
gtctttattg tatctttaag ctctaacagc atgatgatta aataagctgt ggttggccac   40860
acacaagcca tcttccccat ggcctccatt catactagaa tgagcagcta taccccagta   40920
gtatagtttt gggatatggg taacatcttg ggatagccac atttacttag taaatgtctg   40980
gcttacattc tcctaatggt gcactgttgg aattttttggt gtggtaacct ggaatagtgt   41040
tggtgggtca agtttgatta gcatctttga taaggacccg gtctatttag aggtttgtca   41100
ttgagtgtgt ctgtttttggc ctcatgttgt gaagcatgct gtgtagcagc tgttgtaatt   41160
tttgttgctt gttttctcaa tcaacccctgg ttttgaagaa atgggaagtt gttccactct   41220
tagactgatc tgacttggga ggggattttc agttcaggaa gttggatctt ctgaatggaa   41280
gcaaagaata catgtctttt tgccacttta caagctggcc ttgttttct gaactatttt    41340 actggtcatt gcaaatagaa tgtcaggagt agctgccaaa tactaagttg tgttcagttt   41400
gtcagttctt aagagttgcc ggtggctgct ctgctatgcg tatgactttc tcagccttaa   41460
acttacaagc catactgttt ttttcacatc tttaatacag ccataggaaa tttataactg   41520
tggcgtgtcg tcataaatat gcattgttct tattttaaga catttcagta ctaaaagtat   41580
aagtacttct gttattatct gtgaatttct ttccttcttc ttttttttgga tatttaagac   41640 cttttcgatg tcaatatata tttaaaacag acatataaat tagcattcac ccacataccc   41700
agggcctatg gagaaccagg ttgggatgag tgggtgagct acaggcagcc aggtggctcc   41760
tgtgggctcc tcgaggactg gggtgagtaa ctaatgtctg ctaggaactt ggggaagaa    41820 aggtgtgtat gttaggtgct gccccttct aagtgttcct cttgttcata attgatttt     41880 tttttttttt tttttttttt tttagaagga gtctcgctct gttgccaggc tggagtgcag   41940
tggtgtgatc tcagctcact gcaacctctg cctcccgggt tcaagtgatt ctcctgcctc   42000
agcctcccga gtagctggga ctacaggcat gcaccaccat gcccagctaa ttttttgtatt  42060
```

```
ttnnnnnnnn nnnnnnnnnn nnnnnnnnnn nnnnnnnnnn nnnnnnnnnn nnnnnnnnnn    42120
nnnnnnnnnn nnnnnnnnnn nnnnnnnnnn nnnnnnnnnn nnnnnnnnnn nnnnnnnnnn    42180
nnnnnnnnnn nnnnnnnnnn nnnnnnnnnn nnnnnnnnnn nnnnnnnnnn nnnnnnnnnn    42240
nnnnnnnnnn nnnnnnnnnn nnnnnnnnnn nnnnnnnnnn nnnnnnnnnn nnnnnnnnnn    42300
nnnnnnnnnn nnnnnnnnnn nnnnnnnnnn nnnnnnnnnn nnnnnnnnnn nnnnnnnnnn    42360
nnnnnnnnnn nnnnnnnnnn nnnnnnnnnn nnnnnnnnnn nnnnnnnnnn nnnnnnnnnn    42420
nnnnnnnnnn nnnnnnnnnn nnnnnnnnnn nnnnnnnnnn nnnnnnnnnn nnnnnnnnnn    42480
nnnnnnnnnn nnnnnnnnnn nnnnnnnnnn nnnnnnnnnn nnnnnnnnnn nnnnnnnnnn    42540
nnnnnnnnnn nnnnnnnnnn nnnnnnnnnn nnnnnnnnnn nnnnnnnnnn nnnnnnnnnn    42600
nnnnnnnnnn nnnnnnnnnn nnnnnnnnnn nnnnnnnnnn nnnnnnnnnn nnnnnnnnnn    42660
nnnnnnnnnn nnnnnnnnnn nnnnnnnnnn nnnnnnnnnn nnnnnnnnnn nnnnnnnnnn    42720
nnnnnnnnnn nnnnnnnnnn nnnnnnnnnn nnnnnnnnnn nnnnnnnnnn nnnnnnnnnn    42780
nnnnnnnnnn nnnnnnnnnn nnnnnnnnnn nnnnnnnnnn nnnnnnnnnn nnnnnnnnnn    42840
nnnnnnnnnn nnnnnnnnnn nnnnnnnnnn nnnnnnnnnn nnnnnnnnnn nnnnnnnnnn    42900
nnnnnnnnnn nnnnnnnnnn nnnnnnnnnn nnnnnnnnnn nnnnnnnnnn nnnnnnnnnn    42960
nnnnnnnnnn nnnnnnnnnn nnnnnnnnnn nnnnnnnnnn nnnnnnnnnn nnnnnnnnnn    43020
nnnnnnnnnn nnnnnnnnnn nnnnnnnnnn nnnnnnnnnn nnnnnnnnnn nnnnnnnnnn    43080
nnnnnnnnnn nnnnnnnnnn nnnnnnnnnn nnnnnnnnnn nnnnnnnnnn nnnnnnnnnn    43140
nnnnnnnnnn nnnnnnnnnn nnnnnnnnnn nnnnnnnnnn nnnnnnnnnn nnnnnnnnnn    43200
nnnnnnnnnn nnnnnnnnnn nnnnnnnnnn nnnnnnnnnn nnnnnnnnnn nnnnnnnnnn    43260
nnnnnnnnnn nnnnnnnnnn nnnnnnnnnn nnnnnnnnnn nnnnnnnnnn nnnnnnnnnn    43320
nnnnnnnnnn nnnnnnnnnn nnnnnnnnnn nnnnnnnnnn nnnnnnnnnn nnnnnnnnnn    43380
nnnnnnnnnn nnnnnnnnnn nnnnnnnnnn nnnnnnnnnn nnnnnnnnnn nnnnnnnnnn    43440
nnnnnnnnnn nnnnnnnnnn nnnnnnnnnn nnnnnnnnnn nnnnnnnnnn nnnnnnnnnn    43500
nnnnnnnnnn nnnnnnnnnn nnnnnnnnnn nnnnnnnnnn nnnnnnnnnn nnnnnnnnnn    43560
nnnnnnnnnn nnnnnnnnnn nnnnnnnnnn nnnnnnnnnn nnnnnnnnnn nnnnnnnnnn    43620
nnnnnnnnnn nnnnnnnnnn nnnnnnnnnn nnnnnnnnnn nnnnnnnnnn nnnnnnnnnn    43680
nnnnnnnnnn nnnnnnnnnn nnnnnnnnnn nnnnnnnnnn nnnnnnnnnn nnnnnnnnnn    43740
nnnnnnnnnn nnnnnnnnnn nnnnnnnnnn nnnnnnnnnn nnnnnnnnnn nnnnnnnnnn    43800
nnnnnnnnnn nnnnnnnnnn nnnnnnnnnn nnnnnnnnnn nnnnnnnnnn nnnnnnnnnn    43860
nnnnnnnnnn nnnnnnnnnn nnnnnnnnnn nnnnnnnnnn nnnnnnnnnn nnnnnnnnnn    43920
nnnnnnnnnn nnnnnnnnnn nnnnnnnnnn nnnnnnnnnn nnnnnnnnnn nnnnnnnnnn    43980
nnnnnnnnnn nnnnnnnnnn nnnnnnnnnn nnnnnnnnnn nnnnnnnnnn nnnnnnnnnn    44040
nnnnnnnnnn nnnnnnnnnn nnnnnnnnnn nnnnnnnnnn nnnnnnnnnn nnnnnnnnnn    44100
nnnnnnnnnn nnnnnnnnnn nnnnnnnnnn nnnnnnnnnn nnnnnnnnnn nnnnnnnnnn    44160
nnnnnnnnnn nnnnnnnnnn nnnnnnnnnn nnnnnnnnnn nnnnnnnnnn nnnnnnnnnn    44220
nnnnnnnnnn nnnnnnnnnn nnnnnnnnnn nnnnnnnnnn nnnnnnnnnn nnnnnnnnnn    44280
nnnnnnnnnn nnnnnnnnnn nnnnnnnnnn nnnnnnnnnn nnnnnnnnnn nnnnnnnnnn    44340
nnnnnnnnnn nnnnnnnnnn nnnnnnnnnn nnnnnnnnnn nnnnnnnnnn nnnnnnnnnn    44400
```

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 44460 |
| nnnnnnnnnn | nnnnnnnnnn | nnnnnnnnnn | nnnnnnnnnn | nnnnnnnnnn | nnnnnnnnnn | 44520 |
| nnnnnnnnnn | nnnnnnnnnn | nnnnnnnnnn | nnnnnnnnnn | nnnnnnnnnn | nnnnnnnnnn | 44580 |
| nnnnnnnnnn | nnnnnnnnnn | nnnnnnnnnn | nnnnnnnnnn | nnnnnnnnnn | nnnnnnnnnn | 44640 |
| nnnnnnnnnn | nnnnnnnnnn | nnnnnnnnnn | nnnnnnnnnn | nnnnnnnnnn | nnnnnnnnnn | 44700 |
| nnnnnnnnnn | nnnnnnnnnn | nnnnnnnnnn | nnnnnnnnnn | nnnnnnnnnn | nnnnnnnnnn | 44760 |
| nnnnnnnnnn | nnnnnnnnnn | nnnnnnnnnn | nnnnnnnnnn | nnnnnnnnnn | nnnnnnnnnn | 44820 |
| nnnnnnnnnn | nnnnnnnnnn | nnnnnnnnnn | nnnnnnnnnn | nnnnnnnnnn | nnnnnnnnnn | 44880 |
| nnnnnnnnnn | nnnnnnnnnn | nnnnnnnnnn | nnnnnnnnnn | nnnnnnnnnn | nnnnnnnnnn | 44940 |
| nnnnnnnnnn | nnnnnnnnnn | nnnnnnnnnn | nnnnnnnnnn | nnnnnnnnnn | nnnnnnnnnn | 45000 |
| nnnnnnnnnn | nnnnnnnnnn | nnnnnnnnnn | nnnnnnnnnn | nnnnnnnnnn | nnnnnnnnnn | 45060 |
| nnnnnnnnnn | nnnnnnnnnn | nnnnnnnnnn | nnnnnnnnnn | nnnnnnnnnn | nnnnnnnnnn | 45120 |
| nnnnnnnnnn | nnnnnnnnnn | nnnnnnnnnn | nnnnnnnnnn | nnnnnnnnnn | nnnnnnnnnn | 45180 |
| nnnnnnnnnn | nnnnnnnnnn | nnnnnnnnnn | nnnnnnnnnn | nnnnnnnnnn | nnnnnnnnnn | 45240 |
| nnnnnnnnnn | nnnnnnnnnn | nnnnnnnnnn | nnnnnnnnnn | nnnnnnnnnn | nnnnnnnnnn | 45300 |
| nnnnnnnnnn | nnnnnnnnnn | nnnnnnnnnn | nnnnnnnnnn | nnnnnnnnnn | nnnnnnnnnn | 45360 |
| nnnnnnnnnn | nnnnnnnnnn | nnnnnnnnnn | nnnnnnnnnn | nnnnnnnnnn | nnnnnnnnnn | 45420 |
| nnnnnnnnnn | nnnnnnnnnn | nnnnnnnnnn | nnnnnnnnnn | nnnnnnnnnn | nnnnnnnnnn | 45480 |
| nnnnnnnnnn | nnnnnnnnnn | nnnnnnnnnn | nnnnnnnnnn | nnnnnnnnnn | nnnnnnnnnn | 45540 |
| nnnnnnnnnn | nnnnnnnnnn | nnnnnnnnnn | nnnnnnnnnn | nnnnnnnnnn | nnnnnnnnnn | 45600 |
| nnnnnnnnnn | nnnnnnnnnn | nnnnnnnnnn | nnnnnnnnnn | nnnnnnnnnn | nnnnnnnnnn | 45660 |
| nnnnnnnnnn | nnnnnnnnnn | nnnnnnnnnn | nnnnnnnnnn | nnnnnnnnnn | nnnnnnnnnn | 45720 |
| nnnnnnnnnn | nnnnnnnnnn | nnnnnnnnnn | nnnnnnnnnn | nnnnnnnnnn | nnnnnnnnnn | 45780 |
| nnnnnnnnnn | nnnnnnnnnn | nnnnnnnnnn | nnnnnnnnnn | nnnnnnnnnn | nnnnnnnnnn | 45840 |
| nnnnnnnnnn | nnnnnnnnnn | nnnnnnnnnn | nnnnnnnnnn | nnnnnnnnnn | nnnnnnnnnn | 45900 |
| nnnnnnnnnn | nnnnnnnnnn | nnnnnnnnnn | nnnnnnnnnn | nnnnnnnnnn | nnnnnnnnnn | 45960 |
| nnnnnnnnnn | nnnnnnnnnn | nnnnnnnnnn | nnnnnnnnnn | nnnnnnnnnn | nnnnnnnnnn | 46020 |
| nnnnnnnnnn | nnnnnnnnnn | nnnnnnnnnn | nnnnnnnnnn | nnnnnnnnnn | nnnnnnnnnn | 46080 |
| nnnnnnnnnn | nnnnnnnnnn | nnnnnnnnnn | nnnnnnnnnn | nnnnnnnnnn | nnnnnnnnnn | 46140 |
| nnnnnnnnnn | nnnnnnnnnn | nnnnnnnnnn | nnnnnnnnnn | nnnnnnnnnn | nnnnnnnnnn | 46200 |
| nnnnnnnnnn | nnnnnnnnnn | nnnnnnnnnn | nnnnnnnnnn | nnnnnnnnnn | nnnnnnnnnn | 46260 |
| nnnnnnnnnn | nnnnnnnnnn | nnnnnnnnnn | nnnnnnnnnn | nnnnnnnnnn | nnnnnnnnnn | 46320 |
| nnnnnnnnnn | nnnnnnnnnn | nnnnnnnnnn | nnnnnnnnnn | nnnnnnnnnn | nnnnnnnnnn | 46380 |
| nnnnnnnnnn | nnnnnnnnnn | nnnnnnnnnn | nnnnnnnnnn | nnnnnnnnnn | nnnnnnnnnn | 46440 |
| nnnnnnnnnn | nnnnnnnnnn | nnnnnnnnnn | nnnnnnnnnn | nnnnnnnnnn | nnnnnnnnnn | 46500 |
| nnnnnnnnnn | nnnnnnnnnn | nnnnnnnnnn | nnnnnnnnnn | nnnnnnnnnn | nnnnnnnnnn | 46560 |
| nnnnnnnnnn | nnnnnnnnnn | nnnnnnnnnn | nnnnnnnnnn | nnnnnnnnnn | nnnnnnnnnn | 46620 |
| nnnnnnnnnn | nnnnnnnnnn | nnnnnnnnnn | nnnnnnnnnn | nnnnnnnnnn | nnnnnnnnnn | 46680 |
| nnnnnnnnnn | nnnnnnnnnn | nnnnnnnnnn | nnnnnnnnnn | nnnnnnnnnn | nnnnnnnnnn | 46740 |
| nnnnnnnnnn | nnnnnnnnnn | nnnnnnnnnn | nnnnnnnnnn | nnnnnnnnnn | nnnnnnnnnn | 46800 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 46860 |
| nnnnnnnnnn | nnnnnnnnnn | nnnnnnnnnn | nnnnnnnnnn | nnnnnnnnnn | nnnnnnnnnn | 46920 |
| nnnnnnnnnn | nnnnnnnnnn | nnnnnnnnnn | nnnnnnnnnn | nnnnnnnnnn | nnnnnnnnnn | 46980 |
| nnnnnnnnnn | nnnnnnnnnn | nnnnnnnnnn | nnnnnnnnnn | nnnnnnnnnn | nnnnnnnnnn | 47040 |
| nnnnnnnnnn | nnnnnnnnnn | nnnnnnnnnn | nnnnnnnnnn | nnnnnnnnnn | nnnnnnnnnn | 47100 |
| nnnnnnnnnn | nnnnnnnnnn | nnnnnnnnnn | nnnnnnnnnn | nnnnnnnnnn | nnnnnnnnnn | 47160 |
| nnnnnnnnnn | nnnnnnnnnn | nnnnnnnnnn | nnnnnnnnnn | nnnnnnnnnn | nnnnnnnnnn | 47220 |
| nnnnnnnnnn | nnnnnnnnnn | nnnnnnnnnn | nnnnnnnnnn | nnnnnnnnnn | nnnnnnnnnn | 47280 |
| nnnnnnnnnn | nnnnnnnnnn | nnnnnnnnnn | nnnnnnnnnn | nnnnnnnnnn | nnnnnnnnnn | 47340 |
| nnnnnnnnnn | nnnnnnnnnn | nnnnnnnnnn | nnnnnnnnnn | nnnnnnnnnn | nnnnnnnnnn | 47400 |
| nnnnnnnnnn | nnnnnnnnnn | nnnnnnnnnn | nnnnnnnnnn | nnnnnnnnnn | nnnnnnnnnn | 47460 |
| nnnnnnnnnn | nnnnnnnnnn | nnnnnnnnnn | nnnnnnnnnn | nnnnnnnnnn | nnnnnnnnnn | 47520 |
| nnnnnnnnnn | nnnnnnnnnn | nnnnnnnnnn | nnnnnnnnnn | nnnnnnnnnn | nnnnnnnnnn | 47580 |
| nnnnnnnnnn | nnnnnnnnnn | nnnnnnnnnn | nnnnnnnnnn | nnnnnnnnnn | nnnnnnnnnn | 47640 |
| nnnnnnnnnn | nnnnnnnnnn | nnnnnnnnnn | nnnnnnnnnn | nnnnnnnnnn | nnnnnnnnnn | 47700 |
| nnnnnnnnnn | nnnnnnnnnn | nnnnnnnnnn | nnnnnnnnnn | nnnnnnnnnn | nnnnnnnnnn | 47760 |
| nnnnnnnnnn | nnnnnnnnnn | nnnnnnnnnn | nnnnnnnnnn | nnnnnnnnnn | nnnnnnnnnn | 47820 |
| nnnnnnnnnn | nnnnnnnnnn | nnnnnnnnnn | nnnnnnnnnn | nnnnnnnnnn | nnnnnnnnnn | 47880 |
| nnnnnnnnnn | nnnnnnnnnn | nnnnnnnnnn | nnnnnnnnnn | nnnnnnnnnn | nnnnnnnnnn | 47940 |
| nnnnnnnnnn | nnnnnnnnnn | nnnnnnnnnn | nnnnnnnnnn | nnnnnnnnnn | nnnnnnnnnn | 48000 |
| nnnnnnnnnn | nnnnnnnnnn | nnnnnnnnnn | nnnnnnnnnn | nnnnnnnnnn | nnnnnnnnnn | 48060 |
| nnnnnnnnnn | nnnnnnnnnn | nnnnnnnnnn | nnnnnnnnnn | nnnnnnnnnn | nnnnnnnnnn | 48120 |
| nnnnnnnnnn | nnnnnnnnnn | nnnnnnnnnn | nnnnnnnnnn | nnnnnnnnnn | nnnnnnnnnn | 48180 |
| nnnnnnnnnn | nnnnnnnnnn | nnnnnnnnnn | nnnnnnnnnn | nnnnnnnnnn | nnnnnnnnnn | 48240 |
| nnnnnnnnnn | nnnnnnnnnn | nnnnnnnnnn | nnnnnnnnnn | nnnnnnnnnn | nnnnnnnnnn | 48300 |
| nnnnnnnnnn | nnnnnnnnnn | nnnnnnnnnn | nnnnnnnnnn | nnnnnnnnnn | nnnnnnnnnn | 48360 |
| nnnnnnnnnn | nnnnnnnnnn | nnnnnnnnnn | nnnnnnnnnn | nnnnnnnnnn | nnnnnnnnnn | 48420 |
| nnnnnnnnnn | nnnnnnnnnn | nnnnnnnnnn | nnnnnnnnnn | nnnnnnnnnn | nnnnnnnnnn | 48480 |
| nnnnnnnnnn | nnnnnnnnnn | nnnnnnnnnn | nnnnnnnnnn | nnnnnnnnnn | nnnnnnnnnn | 48540 |
| nnnnnnnnnn | nnnnnnnnnn | nnnnnnnnnn | nnnnnnnnnn | nnnnnnnnnn | nnnnnnnnnn | 48600 |
| nnnnnnnnnn | nnnnnnnnnn | nnnnnnnnnn | nnnnnnnnnn | nnnnnnnnnn | nnnnnnnnnn | 48660 |
| nnnnnnnnnn | nnnnnnnnnn | nnnnnnnnnn | nnnnnnnnnn | nnnnnnnnnn | nnnnnnnnnn | 48720 |
| nnnnnnnnnn | nnnnnnnnnn | nnnnnnnnnn | nnnnnnnnnn | nnnnnnnnnn | nnnnnnnnnn | 48780 |
| nnnnnnnnnn | nnnnnnnnnn | nnnnnnnnnn | nnnnnnnnnn | nnnnnnnnnn | nnnnnnnnnn | 48840 |
| nnnnnnnnnn | nnnnnnnnnn | nnnnnnnnnn | nnnnnnnnnn | nnnnnnnnnn | nnnnnnnnnn | 48900 |
| nnnnnnnnnn | nnnnnnnnnn | nnnnnnnnnn | nnnnnnnnnn | nnnnnnnnnn | nnnnnnnnnn | 48960 |
| nnnnnnnnnn | nnnnnnnnnn | nnnnnnnnnn | nnnnnnnnnn | nnnnnnnnnn | nnnnnnnnnn | 49020 |
| nnnnnnnnnn | nnnnnnnnnn | nnnnnnnnnn | nnnnnnnnnn | nnnnnnnnnn | nnnnnnnnnn | 49080 |
| nnnnnnnnnn | nnnnnnnnnn | nnnnnnnnnn | nnnnnnnnnn | nnnnnnnnnn | nnnnnnnnnn | 49140 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 49200 |
| nnnnnnnnnn | nnnnnnnnnn | nnnnnnnnnn | nnnnnnnnnn | nnnnnnnnnn | nnnnnnnnnn | 49260 |
| nnnnnnnnnn | nnnnnnnnnn | nnnnnnnnnn | nnnnnnnnnn | nnnnnnnnnn | nnnnnnnnnn | 49320 |
| nnnnnnnnnn | nnnnnnnnnn | nnnnnnnnnn | nnnnnnnnnn | nnnnnnnnnn | nnnnnnnnnn | 49380 |
| nnnnnnnnnn | nnnnnnnnnn | nnnnnnnnnn | nnnnnnnnnn | nnnnnnnnnn | nnnnnnnnnn | 49440 |
| nnnnnnnnnn | nnnnnnnnnn | nnnnnnnnnn | nnnnnnnnnn | nnnnnnnnnn | nnnnnnnnnn | 49500 |
| nnnnnnnnnn | nnnnnnnnnn | nnnnnnnnnn | nnnnnnnnnn | nnnnnnnnnn | nnnnnnnnnn | 49560 |
| nnnnnnnnnn | nnnnnnnnnn | nnnnnnnnnn | nnnnnnnnnn | nnnnnnnnnn | nnnnnnnnnn | 49620 |
| nnnnnnnnnn | nnnnnnnnnn | nnnnnnnnnn | nnnnnnnnnn | nnnnnnnnnn | nnnnnnnnnn | 49680 |
| nnnnnnnnnn | nnnnnnnnnn | nnnnnnnnnn | nnnnnnnnnn | nnnnnnnnnn | nnnnnnnnnn | 49740 |
| nnnnnnnnnn | nnnnnnnnnn | nnnnnnnnnn | nnnnnnnnnn | nnnnnnnnnn | nnnnnnnnnn | 49800 |
| nnnnnnnnnn | nnnnnnnnnn | nnnnnnnnnn | nnnnnnnnnn | nnnnnnnnnn | nnnnnnnnnn | 49860 |
| nnnnnnnnnn | nnnnnnnnnn | nnnnnnnnnn | nnnnnnnnnn | nnnnnnnnnn | nnnnnnnnnn | 49920 |
| nnnnnnnnnn | nnnnnnnnnn | nnnnnnnnnn | nnnnnnnnnn | nnnnnnnnnn | nnnnnnnnnn | 49980 |
| nnnnnnnnnn | nnnnnnnnnn | nnnnnnnnnn | nnnnnnnnnn | nnnnnnnnnn | nnnnnnnnnn | 50040 |
| nnnnnnnnnn | nnnnnnnnnn | nnnnnnnnnn | nnnnnnnnnn | nnnnnnnnnn | nnnnnnnnnn | 50100 |
| nnnnnnnnnn | nnnnnnnnnn | nnnnnnnnnn | nnnnnnnnnn | nnnnnnnnnn | nnnnnnnnnn | 50160 |
| nnnnnnnnnn | nnnnnnnnnn | nnnnnnnnnn | nnnnnnnnnn | nnnnnnnnnn | nnnnnnnnnn | 50220 |
| nnnnnnnnnn | nnnnnnnnnn | nnnnnnnnnn | nnnnnnnnnn | nnnnnnnnnn | nnnnnnnnnn | 50280 |
| nnnnnnnnnn | nnnnnnnnnn | nnnnnnnnnn | nnnnnnnnnn | nnnnnnnnnn | nnnnnnnnnn | 50340 |
| nnnnnnnnnn | nnnnnnnnnn | nnnnnnnnnn | nnnnnnnnnn | nnnnnnnnnn | nnnnnnnnnn | 50400 |
| nnnnnnnnnn | nnnnnnnnnn | nnnnnnnnnn | nnnnnnnnnn | nnnnnnnnnn | nnnnnnnnnn | 50460 |
| nnnnnnnnnn | nnnnnnnnnn | nnnnnnnnnn | nnnnnnnnnn | nnnnnnnnnn | nnnnnnnnnn | 50520 |
| nnnnnnnnnn | nnnnnnnnnn | nnnnnnnnnn | nnnnnnnnnn | nnnnnnnnnn | nnnnnnnnnn | 50580 |
| nnnnnnnnnn | nnnnnnnnnn | nnnnnnnnnn | nnnnnnnnnn | nnnnnnnnnn | nnnnnnnnnn | 50640 |
| nnnnnnnnnn | nnnnnnnnnn | nnnnnnnnnn | nnnnnnnnnn | nnnnnnnnnn | nnnnnnnnnn | 50700 |
| nnnnnnnnnn | nnnnnnnnnn | nnnnnnnnnn | nnnnnnnnnn | nnnnnnnnnn | nnnnnnnnnn | 50760 |
| nnnnnnnnnn | nnnnnnnnnn | nnnnnnnnnn | nnnnnnnnnn | nnnnnnnnnn | nnnnnnnnnn | 50820 |
| nnnnnnnnnn | nnnnnnnnnn | nnnnnnnnnn | nnnnnnnnnn | nnnnnnnnnn | nnnnnnnnnn | 50880 |
| nnnnnnnnnn | nnnnnnnnnn | nnnnnnnnnn | nnnnnnnnnn | nnnnnnnnnn | nnnnnnnnnn | 50940 |
| nnnnnnnnnn | nnnnnnnnnn | nnnnnnnnnn | nnnnnnnnnn | nnnnnnnnnn | nnnnnnnnnn | 51000 |
| nnnnnnnnnn | nnnnnnnnnn | nnnnnnnnnn | nnnnnnnnnn | nnnnnnnnnn | nnnnnnnnnn | 51060 |
| nnnnnnnnnn | nnnnnnnnnn | nnnnnnnnnn | nnnnnnnnnn | nnnnnnnnnn | nnnnnnnnnn | 51120 |
| nnnnnnnnnn | nnnnnnnnnn | nnnnnnnnnn | nnnnnnnnnn | nnnnnnnnnn | nnnnnnnnnn | 51180 |
| nnnnnnnnnn | nnnnnnnnnn | nnnnnnnnnn | nnnnnnnnnn | nnnnnnnnnn | nnnnnnnnnn | 51240 |
| nnnnnnnnnn | nnnnnnnnnn | nnnnnnnnnn | nnnnnnnnnn | nnnnnnnnnn | nnnnnnnnnn | 51300 |
| nnnnnnnnnn | nnnnnnnnnn | nnnnnnnnnn | nnnnnnnnnn | nnnnnnnnnn | nnnnnnnnnn | 51360 |
| nnnnnnnnnn | nnnnnnnnnn | nnnnnnnnnn | nnnnnnnnnn | nnnnnnnnnn | nnnnnnnnnn | 51420 |
| nnnnnnnnnn | nnnnnnnnnn | nnnnnnnnnn | nnnnnnnnnn | nnnnnnnnnn | nnnnnnnnnn | 51480 |
| nnnnnnnnnn | nnnnnnnnnn | nnnnnnnnnn | nnnnnnnnnn | nnnnnnnnnn | nnnnnnnnnn | 51540 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 51600 |
| nnnnnnnnnn | nnnnnnnnnn | nnnnnnnnnn | nnnnnnnnnn | nnnnnnnnnn | nnnnnnnnnn | 51660 |
| nnnnnnnnnn | nnnnnnnnnn | nnnnnnnnnn | nnnnnnnnnn | nnnnnnnnnn | nnnnnnnnnn | 51720 |
| nnnnnnnnnn | nnnnnnnnnn | nnnnnnnnnn | nnnnnnnnnn | nnnnnnnnnn | nnnnnnnnnn | 51780 |
| nnnnnnnnnn | nnnnnnnnnn | nnnnnnnnnn | nnnnnnnnnn | nnnnnnnnnn | nnnnnnnnnn | 51840 |
| nnnnnnnnnn | nnnnnnnnnn | nnnnnnnnnn | nnnnnnnnnn | nnnnnnnnnn | nnnnnnnnnn | 51900 |
| nnnnnnnnnn | nnnnnnnnnn | nnnnnnnnnn | nnnnnnnnnn | nnnnnnnnnn | nnnnnnnnnn | 51960 |
| nnnnnnnnnn | nnnnnnnnnn | nnnnnnnnnn | nnnnnnnnnn | nnnnnnnnnn | nnnnnnnnnn | 52020 |
| nnnnnnnnnn | nnnnnnnnnn | nnnnnnnnnn | nnnnnnnnnn | nnnnnnnnnn | nnnnnnnnnn | 52080 |
| nnnnnnnnnn | nnnnnnnnnn | nnnnnnnnnn | nnnnnnnnnn | nnnnnnnnnn | nnnnnnnnnn | 52140 |
| nnnnnnnnnn | nnnnnnnnnn | nnnnnnnnnn | nnnnnnnnnn | nnnnnnnnnn | nnnnnnnnnn | 52200 |
| nnnnnnnnnn | nnnnnnnnnn | nnnnnnnnnn | nnnnnnnnnn | nnnnnnnnnn | nnnnnnnnnn | 52260 |
| nnnnnnnnnn | nnnnnnnnnn | nnnnnnnnnn | nnnnnnnnnn | nnnnnnnnnn | nnnnnnnnnn | 52320 |
| nnnnnnnnnn | nnnnnnnnnn | nnnnnnnnnn | nnnnnnnnnn | nnnnnnnnnn | nnnnnnnnnn | 52380 |
| nnnnnnnnnn | nnnnnnnnnn | nnnnnnnnnn | nnnnnnnnnn | nnnnnnnnnn | nnnnnnnnnn | 52440 |
| nnnnnnnnnn | nnnnnnnnnn | nnnnnnnnnn | nnnnnnnnnn | nnnnnnnnnn | nnnnnnnnnn | 52500 |
| nnnnnnnnnn | nnnnnnnnnn | nnnnnnnnnn | nnnnnnnnnn | nnnnnnnnnn | nnnnnnnnnn | 52560 |
| nnnnnnnnnn | nnnnnnnnnn | nnnnnnnnnn | nnnnnnnnnn | nnnnnnnnnn | nnnnnnnnnn | 52620 |
| nnnnnnnnnn | nnnnnnnnnn | nnnnnnnnnn | nnnnnnnnnn | nnnnnnnnnn | nnnnnnnnnn | 52680 |
| nnnnnnnnnn | nnnnnnnnnn | nnnnnnnnnn | nnnnnnnnnn | nnnnnnnnnn | nnnnnnnnnn | 52740 |
| nnnnnnnnnn | nnnnnnnnnn | nnnnnnnnnn | nnnnnnnnnn | nnnnnnnnnn | nnnnnnnnnn | 52800 |
| nnnnnnnnnn | nnnnnnnnnn | nnnnnnnnnn | nnnnnnnnnn | nnnnnnnnnn | nnnnnnnnnn | 52860 |
| nnnnnnnnnn | nnnnnnnnnn | nnnnnnnnnn | nnnnnnnnnn | nnnnnnnnnn | nnnnnnnnnn | 52920 |
| nnnnnnnnnn | nnnnnnnnnn | nnnnnnnnnn | nnnnnnnnnn | nnnnnnnnnn | nnnnnnnnnn | 52980 |
| nnnnnnnnnn | nnnnnnnnnn | nnnnnnnnnn | nnnnnnnnnn | nnnnnnnnnn | nnnnnnnnnn | 53040 |
| nnnnnnnnnn | nnnnnnnnnn | nnnnnnnnnn | nnnnnnnnnn | nnnnnnnnnn | nnnnnnnnnn | 53100 |
| nnnnnnnnnn | nnnnnnnnnn | nnnnnnnnnn | nnnnnnnnnn | nnnnnnnnnn | nnnnnnnnnn | 53160 |
| nnnnnnnnnn | nnnnnnnnnn | nnnnnnnnnn | nnnnnnnnnn | nnnnnnnnnn | nnnnnnnnnn | 53220 |
| nnnnnnnnnn | nnnnnnnnnn | nnnnnnnnnn | nnnnnnnnnn | nnnnnnnnnn | nnnnnnnnnn | 53280 |
| nnnnnnnnnn | nnnnnnnnnn | nnnnnnnnnn | nnnnnnnnnn | nnnnnnnnnn | nnnnnnnnnn | 53340 |
| nnnnnnnnnn | nnnnnnnnnn | nnnnnnnnnn | nnnnnnnnnn | nnnnnnnnnn | nnnnnnnnnn | 53400 |
| nnnnnnnnnn | nnnnnnnnnn | nnnnnnnnnn | nnnnnnnnnn | nnnnnnnnnn | nnnnnnnnnn | 53460 |
| nnnnnnnnnn | nnnnnnnnnn | nnnnnnnnnn | nnnnnnnnnn | nnnnnnnnnn | nnnnnnnnnn | 53520 |
| nnnnnnnnnn | nnnnnnnnnn | nnnnnnnnnn | nnnnnnnnnn | nnnnnnnnnn | nnnnnnnnnn | 53580 |
| nnnnnnnnnn | nnnnnnnnnn | nnnnnnnnnn | nnnnnnnnnn | nnnnnnnnnn | nnnnnnnnnn | 53640 |
| nnnnnnnnnn | nnnnnnnnnn | nnnnnnnnnn | nnnnnnnnnn | nnnnnnnnnn | nnnnnnnnnn | 53700 |
| nnnnnnnnnn | nnnnnnnnnn | nnnnnnnnnn | nnnnnnnnnn | nnnnnnnnnn | nnnnnnnnnn | 53760 |
| nnnnnnnnnn | nnnnnnnnnn | nnnnnnnnnn | nnnnnnnnnn | nnnnnnnnnn | nnnnnnnnnn | 53820 |
| nnnnnnnnnn | nnnnnnnnnn | nnnnnnnnnn | nnnnnnnnnn | nnnnnnnnnn | nnnnnnnnnn | 53880 |

```
nnnnnnnnnn nnnnnnnnnn nnnnnnnnnn nnnnnnnnnn nnnnnnnnnn nnnnnnnnnn    53940
nnnnnnnnnn nnnnnnnnnn nnnnnnnnnn nnnnnnnnnn nnnnnnnnnn nnnnnnnnnn    54000
nnnnnnnnnn nnnnnnnnnn nnnnnnnnnn nnnnnnnnnn nnnnnnnnnn nnnnnnnnnn    54060
nnnnnnnnnn nnnnnnnnnn nnnnnnnnnn nnnnnnnnnn nnnnnnnnnn nnnnnnnnnn    54120
nnnnnnnnnn nnnnnnnnnn nnnnnnnnnn nnnnnnnnnn nnnnnnnnnn nnnnnnnnnn    54180
nnnnnnnnnn nnnnnnnnnn nnnnnnnnnn nnnnnnnnnn nnnnnnnnnn nnnnnnnnnn    54240
nnnnnnnnnn nnnnnnnnnn nnnnnnnnnn nnnnnnnnnn nnnnnnnnnn nnnnnnnnnn    54300
nnnnnnnnnn nnnnnnnnnn nnnnnnnnnn nnnnnnnnnn nnnnnnnnnn nnnnnnnnnn    54360
nnnnnnnnnn nnnnnnnnnn nnnnnnnnnn nnnnnnnnnn nnnnnnnnnn nnnnnnnnnn    54420
nnnnnnnnnn nnnnnnnnnn nnnnnnnnnn nnnnnnnnnn nnnnnnnnnn nnnnnnnnnn    54480
nnnnnnnnnn nnnnnnnnnn nnnnnnnnnn nnnnnnnnnn nnnnnnnnnn nnnnnnnnnn    54540
nnnnnnnnnn nnnnnnnnnn nnnnnnnnnn nnnnnnnnnn nnnnnnnnnn nnnnnnnnnn    54600
nnnnnnnnnn nnnnnnnnnn nnnnnnnnnn nnnnnnnnnn nnnnnnnnnn nnnnnnnnnn    54660
nnnnnnnnnn nnnnnnnnnn nnnnnnnnnn nnnnnnnnnn nnnnnnnnnn nnnnnnnnnn    54720
nnnnnnnnnn nnnnnnnnnn nnnnnnnnnn nnnnnnnnnn nnnnnnnnnn nnnnnnnnnn    54780
nnnnttctaa taactgtgct ttctactaca ttaagcctat tttttttttt tttttttttt    54840
tttgagatgg agtcttgctc tgttacccag gctggagtgc agtggcacaa tatcggctca    54900
ctgcaaccct gcctcctggg ttcaagcgat tttcctgcct cagcctcctg agtagctggg    54960
atcacgggtg cccaccacca tgcctggcta ttttttgtat ttttagtaga gatggggttt    55020
caccatgttg gctaggctgg tcttgaactc ttgacccttag gtgatccgcc tgcctcggcc    55080
tcccaaagta ttgggattac aggcatgagc cactgtgcct agcctgtgaa gctcatttct    55140
taaggctctg ataaatgtat atgttttagt ttcaaccaaa aggaaaagga acgtatttcc    55200 tagattttg tatctcacct aattttcatc tttctggaat gcttaataca tattttatg     55260 tacatacatt atttgttatt cttgagcctc ctcttgagtg aaaatttccc cttagatgac    55320
tcttggagct aatttatttc cttcccttta gctcactcac tcattcaatc attcaataac    55380
gagtgcgtta tcataccagg tactgttagg tagcaggttt acagggatga gcagaagaag    55440
caggccctct ctgccttctt tctttttcat cacactgaaa tcacagcgca ttgtgtgtgt    55500
gcaaaagtag agtgcagagg gaacatgcag aaaggagtta taggatagaa aaggtagcca    55560
aggaaagcag caagaacagc atgatttgtt cagggatctt taaatagctc atcattgttg    55620
gacagcaaag ggagagatgg ggaacgtggc aagatgagat gagaagggga gccgggtca    55680 agccatggag gacgctgaac ccctacaaag gaactaagcc tattgatgtg aacaggccac    55740
ttattttggg aacacgcctt tggtccaaag ggaagagggc acgaaacttc cttctctaaa    55800
aaacaaaaaa aaagaaactt gcatatatga gaaatacttt cttcactttg cagcatgaga    55860
aacggaatcc ctactaagga aataattctc ttatttttt tggaacagcg ttttttgaaa    55920
tttccagatg accccaaagt gagcagtgac tttcttgatc tgattcaaag cttgttgtgc    55980
ggccagaaag agagactgaa gtttgaaggt ctttgctgcc atcctttctt ctctaaaatt    56040
gactggaaca acattcgtaa ctgtaagtag ggctgttttc cttaatttgg gatgttggaa    56100
ttatgaaaca ctcaagagag atctgagatt gttctggccc aaagaagctt ctgtaaatta    56160
cataaataaa ggctttaatt atctacagga gtagtaaagg ctaatgatgt agctgtcttt    56220
gagtaataat tctgccttaa aattgttttgt gtagaactgg gtcatttatc aaactctgtg    56280
```

-continued

```
tttatgtggc ctttagaata ttatccctca gtaagttaga ggcacagatt aatggagttt    56340
gaaggttgtc acttggtttg acacagtttc ttccaaaaaa gtggatctag gtatttcatt    56400
cacatatcag gaaaaagact cagattaggc aacatgccca ggttgttctg ctaatggctg    56460
agtttaaaca aaaaccataa acacctccct gtgtttattc atttgtttcc ctcgataata    56520
tttgtctttg ctcacaagca tgtaaaacct ataatgtata tgcacagtag attcattcat    56580
acatcacttt ttataatcag ttagtgcaaa ctgaatgaat tcattaaaaa caaagacctg    56640
gtttattatc aacagaaacc acacaatgct cttttttctt ttaccagttg gtgatctttt    56700
aaaaatcctt ttaattcttg gatgtgttgt tgattgaatg tgttctactg aatgatcagc    56760
acggattaga gccagtagga aagcagttat cctgtttgag tatgtgtttt gtttttggtg    56820
atggagggag gttgggaaat ggaatctgtt tctaggtgtc aaaaccaggc ttctgattgg    56880
agatgtgtta taattataat tgcttgcacc ttcagctagg acatagtatg gtaaaaaatc    56940
agtattgtcc agttgtaaac catttgatg gtttctctaa ccttctgctg aaatatttaa     57000
gtaggtagca tttccataaa tctttcttgg caaatgtttt tattattcgg gtggccacat    57060
tgctttattt ttctaaataa atagacatct ccccccaaat ctccaaggtt cagaccttct    57120
aatcagtaat atattttcag ggcattcttc ctttttatgct tttagaaaga tgtaatagac    57180
tttcttttag atgctgttca agtacttaat cttttcttgt cttgccttt tatctctgta    57240 atcttcttga ataagcagtt aattttttt attcatgaac ctgctgatca tgtctaagaa     57300
tgtatctcca cttaagtaag tcagtgaatg gtgattacct gagtagagtt aaagtagtcc    57360
cccaccctcc tatctgtggc acatatgttc caagtctccc agtggatgtg tgaaactgat    57420
gatagtactg aaacccatct acctttttc ctgtgcatac atacctatgt tatataaagc     57480
ttaacttata aattaggcat aatatatttg actcccagct cccagtgtag tggctctgaa    57540
gactcacaaa atgtatttgc tttaaaaaat tctttttttt tttttgaga cggagttttg    57600 ctcttgttgc ccaggctgga gtgcagtggt gcgacctcag ctcactgcaa cctccgcctc    57660
ttgggttcaa gcgattctcc tgcctcagcc tcccaagtag ctgggattat aggcatgcac    57720
caccacaccc agctaatttt ctattttcg tagaaacggt ttttccatgt tggtcaggct     57780
gatcttgaac tcctgacctc aggtgatctg cctgcctcgg ccttccaaag tgctgggatt    57840
acaggtgtga gccaccacgc ctggccaaaa aattcttttta atttaagtaa atctttattt    57900
atttactttt gagacagagt ctcactctgt gggccaggca ggaatgcagt ggtgtgatca    57960
cggctcactg cagcctcgac ctcccatgct caagcagtcc tcccacctca gcctcctaag    58020
tagctaggac tacaggtgtg tgccatcaca ctctgctaat ttttttgtat ttgtagagac    58080
gcggtttcac caggttgccc aggctggtct tgaactcctg agctcaagtg atcctcctgc    58140
tttggcctcc caaatactg ggattacagg cgtgagccat tgcacccagc cctaatttta     58200
ataaatcttt tattttggaa tagtattaga tttatagaaa agttgcaaag atagtatgga    58260
agagttccca catacccttc acccagtttt ccccaacgtt aactcttttt tatatttatt    58320
tatttatttt ttgagacaca gtcttcccgt cgcccaggct ggagtgtggt ggcacgatct    58380
cggctcactg caacctccgc ctcctgggtt caagtgattc ttctgcctca gcctccgagt    58440
agctgggacc acaggtgtgc gccaccatgc ccggctactt tttgtatttt cagtagagac    58500
agggtttcac catgttggtc aggctgatct caagctcctg acctcaggtg atctgcctac    58560
cttagcctcc caaagtgctg ggattacaga catgagccac cgcacccagc ccccagtgtt    58620
```

```
aactcttaca taacagtgtc actgtctaag tgtttgaaaa actatttgtc aaaactaata   58680
ttggtacatt attgttaact acacttcaga cttttttttgg attttaccaa ttctcccact   58740
catgtccctt ttctgtttca ggaatcaatc cgtggtacca tattgcagtt agggtgttta   58800
tatttgatgg gactggtcct agtttagata cttagtgtag ctcagccagc aggtgggatc   58860
ttcatgccca ccgaggattg gtattgtgtt ttcctggtgg ttttatggca tttccgacta   58920
tgcagagagg catggtatta acttcagtgt ctcctagcaa attttcctgt ttttcaccaa   58980
cctctgatcc ctgcattatt tgcaatcaac tcagagattt gtgattgaaa acattgcttg   59040
actccatgct ctttaagcta ttttctaact aggtaactgt aacataaatt atgcttttat   59100
ctagcactgt ttttcataaa cacatgttga gtgattttca tcaaccgaaa tacttcgaat   59160
cattaagttt cccaagttca tggatgctgc ttaaatgcct ggtggttcca ggctgtcgaa   59220
tatttctgcc ttctgcaata agagattgtc ccttgttaaa agcaacatta gcctttgtgc   59280
ggtttcaccc ccaattcttc ttttttcttgt tgtaaccaat gaaaggaagt actgcttaac   59340
acagcaggta ataatcttct aaaactcatt atctcaagag gtggtcctgg caggatatat   59400
aaatgcaatt taagaaaggt cttggcaaat ttatgaatga cagaactggg agtggctacc   59460
gagagaaact aggatgcgcc tttgctttga cactgaggtc aggcgtagct tctgtaccct   59520
cctgggtcct gcctcttggg gttgctgcag gcagcacccc atgaaccagg catctgaccc   59580
agttccagga tactattct tccagcaagt cgaacactct gtgatgagtg actgccatgc   59640
tcatgggtca ccaggctctc attattctgt ttcatttcca gcctcccaca agattggttt   59700
ttcagctgct tatttattat tatcattatt tcaaggctgc tttccaagtt tcagtggggg   59760
gtttcctaag cgtaccagct gccctggttg tgcagttccg gtgatgtttc agatgctggg   59820
ccggattctg gctgtaccca gcctgatctt tctgggcttc aggaaagctg aagccaatca   59880
gagctcctct ttcatgcctt tgggattatg cttaccttgc ctggcatcgt gtacctgctc   59940
ccatccatgg gaaagttttg ctgtctggta ctgtcttcta tcaacatctt ttaagatatc   60000
ttcccccgag gcatcgtgat gtcaacggaa ccagcacact tgtacgtttt atgcaagact   60060
gccatatctc aacagtgaga aatgcataat ggaagtggtg atcacggatt atttcctagg   60120
acattatggc taatgcgcta gagaactcgg atggtctgtt gcgtctgaca tgggcttttt   60180
ctcttgagtt gtctttctttt tgctattctc tgaaagaaac aattcttgcc acatgatcct   60240 gattttttcag gtcctcagca tttgttagca gaaagtacac tttgtttcca tccggcagtg   60300
actcagtggt ggtcccatgc tgatgaaacg ctgagatagt cttcttccaa ataggtatcg   60360
ttttgattgt tgctgcttat ttgctagctg gccctcaata gtgacaatga aacctcaagt   60420
gtataatatg gttgctcagt aatcctgagg gaagacagtc tttggtttgg gggataggga   60480
ttctgtgcct acttagcttc aggtgaaagt cttacaaatt tttgtgtgta gaaataagca   60540
ccatgtacct ccttgggttt tttcttttttt tttctagtcc tttagtatgg tcaacaatat   60600
tgtttaggga gtacctattc tgtgctaacc actaggcatt caagtatatt acactatgct   60660
ccttcaaaac acttctgtca aatgtaagga ttattatacc cattttacag atgtggttac   60720
tgtggtaact tggccaaggt catagggcaa gtgaataagg gattctggat ttgggtggag   60780
gtctgtgtga ttccaaagcc catgctcttt ctacaatact atatatgcct ttgcataagt   60840
tattgttatt agtaataata tttgtgatga tggcaaataa taaaccatgt cacactagag   60900
agtgatttaa tctctaggtc tatttaagaa catttggaat tgcaggaatt ggatttttt   60960 ttttttttaa gtgatggagt cttgccatct ttgcccaggc tggtctcaaa cttgtgggct   61020
```

```
caagtgatca tcctccctct gcctcccaaa gtgatgggat tacagatatg agccaccatg   61080
cccagcctag aattgcagga atttttgaat tgatgattca ttctgatatt tgaatttcta   61140
cagtatgtta agtgcaatgt caggtgctgg tgctgtggct ccattgatga acacatttgg   61200
gtatggccct accttcattg aatttagagt ctaagagcct aaccggtctt ttgcttgaat   61260
agagctgtag tcctgttaaa ttgctgtacc tccaaatggt gggaagttta atgcttcgta   61320
ggcctcccct cactagttta ctgaaccaca tgtgcttgat ttttttttga gatgggtct   61380 cgctctgttg cccaggccgg agtgcagtgg cgtgatctcg gctcactgca agctccgcct   61440
cccaggttca cgccattctt ctgcctcagc ctcccgagta gctgggacta caggtgcccg   61500
ccaacacgcc cggctaattt ttttgtattt ttagtagaga cagggtttta ccatgttagc   61560
caggatggtc tcggtctgct gacctcgtga tccacctgcc tcagcctccc aaagtgctgg   61620
gattacaggc atgagccact gtgcctggcc ccacatgtgc ttgattttaa gcaaaataca   61680
gactataggc tgtgacctgg tgatctcttc cccacataca gcatcctgct aacctataac   61740
tctccccatg tctcagatct agcctgggaa aggacaatgt tggatcgatg gcccacttct   61800
aatcttggga tttctaatct caagatgagt tgagaagact caggatgtgt cctgttttct   61860
gtttatttag aacagggttt ctcagccttg gcactgttga catttggggc cagataattc   61920
tttgctgtgg gggctgttgt gtgaattgca ggatgttgaa cagcatcgct gtgctttctc   61980
catggatacc agtagcaccc tcccctgca gttgcaacaa ccaaaaatga ctctagacat   62040
tgcccagtct ccccttgggg gctacagtca ccttcagttg agaaccattg atttagaaga   62100
attggccagg ttattatcag gagagggaac atcacagtaa tctgaatctc tcaatactgc   62160
cactgttact gttaacgaac agcaaaacta ttacgtggag gcagtaggac cttgctactc   62220
agagtgtggt ccgtggaccg gcagcatcgg aatcatctag gagcttgtta gagcttcaga   62280
gactcaggcc tactgagtca gaagctgcat tttaataagg atccccaggg gatttctgtg   62340
catattagag ttgtgaagcc ctgcaagagg aagaaattgg atgctagcct cagagtttct   62400
tgctcatctt tgtgggtctt cctcgttttg tcttcgggct taaggtatgg ggaggccact   62460
ttttggctca ggactcctat gggtgaatgg gactgcttag aactgctggg ttttaggcct   62520
tgctttgagg aatttaaagc ttttctctta gatggacatt acatcgttca tacttcaa   62580 aatggtggtt tgacctaatc tctgccttct gatagcaaaa agatatttcc ttgactccct   62640 gaacccccact ttactgttgt cccatattgg atttttaatta agggtggaat aagtattctt   62700
cactaacatg tttatacatg tatgatatta ccatgccatt tattgagtgc ctagtatgtg   62760
ccaggagctc tgcaaagtgc tttatgctta ttattgttcc atttattctt ccccaaacct   62820
ctgtgaggca ggtcctatca ctagtccaca atacaaatga ggtcatggag cccgaagttg   62880
gcagtggtag gaatcaaact caggtctccc tgactctaaa ttctctttgc ctttgttttt   62940
ttgaaaaagt ggtatagccc atagcagaaa attcacatta tacagaaggt tatacggcga   63000
aaaatgcctc cttcccaccc cacgctcaac ccctctccct caagcgaacc actattgtca   63060
gtttctcata gaactttcca gaatattcta tgctcctata acactagcac aacctatcct   63120
cttaacaaca tctttatgct gcctcccaag aattcagtaa tttttttttt tttgagatgg   63180
agttttgctc tagttgccca ggctggagtg caatggcgtg atctcggctc attgcaacct   63240
ctgcctccca cgttcaagtg attctcttgc ctcagcctcc cgagtagctg ggattacagg   63300
catgcgccac tatgcttggc taattttgta tttttagtag agatggggtt tctccatgtt   63360
```

```
ggtcaggctg gtcttgaact cccaacctca ggtaatccgc ccacctcggc ctcccaaagt    63420
gttgagatta caggcgtgag ccaccgcacc tggccaaatt cagtaatttt tattggcagg    63480
ttattttccc gcatcattga aatgaatgaa gcaatcttta tacttcattc atttaagcat    63540
ggccctacca tgcttatcct tcgaatctgc cactcagcca ttggtttctg ataagcagtg    63600
ctcttctcaa atgaaaaccc cttatggctt tttttttttt ttaaacaagg ccacaggtga    63660
tatcatgatt ttgacattat ttttcattt attttgttta gtgtcctgcc tttagaattg     63720
cattatctca atggcttgtg catttagtgt gtgtgtgtgt gtgtgtgttg tgtgtgtgtg    63780
tgtgtggtat gtgagcacgc acatatttgt tttgggccct tttttttttt tttttgaga    63840 cagagtcttc ctctgtcagc caggctggag tgcagtggca caatctcggc tcactgcaac    63900
ttctgcctcc tgggttcaag caattctcct gcctcagcct cccacgcagc tgggattaca    63960
ggcatgcgcc accacgcctg gctaattttt ttgtattttt agtagagacg ggtttcaccg    64020
tgttggccag gctggtctcg aactcctgac ctcaggtaat ccgcccgcct cggcctccca    64080
aagtgctggg attacaggcg tgatgttttg gccttttaa agttcatctt gtttgtgtat     64140
tcatttgttt ggggcctttt aaagttcttc ttgtttgagg cttcctgtca tttgaagggt    64200
tatctggtca tgttttgttt tctaagctag ttccatgagg atcatagata tgcttctctg    64260
ttaggcttgg ttggccctta aacttgtctt ccttttggac actcacttac ttcagggca    64320 ggaggaagtg aggaagagga gttgggtctg tttggagtat cagcatggac gggaagggga    64380
gcaagaggga tgggatggta aagtagtgat ggtagaaatt caacttacta gaccaggagc    64440
gtgtgggcgc cacctactaa aacaaaaaag gaataatgaa gagctatagt cagtagctct    64500
tataatctct tatgggatat gtaggcaaat atttatgtgt ctcttcgggg ctgttctgtt    64560
tttagaaggt aaatgattgg taagaaaaaa taggccaaaa agagctaaat gcttatgaat    64620
taggattata ggattttccc ccactagtct gaatttagaa gctacttcca gagatgtcaa    64680
aaatatgtaa tattctactt tattccaaga taaattgagg gcaacttatt ctagaaataa    64740
ttgcaatatt aaaaatataa caatgaataa atagagaaat ctagatgaaa ggagtatgag    64800
gatagggaaa taaagttagg gttgaaagta aaaacaagga agttcctgtt aagttgccaa    64860
aggaagaatg atttgggact ctcagtctcc cagtgaccaa agcagaaagg agaatataaa    64920
cagttacaag agcccagtc gcatgaaaaa aaagtccaga atgctctgct cagaggagac    64980 ccaatttct gaatactgag ccctgaggaa tttcaccact gggtttccca taatgagac     65040 cccctgtgac ctggtgggcc ccatccctcg gaagtgtacc ctggcatttc cataggactg    65100
cttccttctg ggcctcttag tgcaagccag cagtgcaatg ccacatccaa gtttggtaaa    65160
tcaattctaa gtgagataaa ttaatgcctt ttttggggga agatgggaaa cagagtgggt    65220
ttgttggaga gcccataaat tggagtcttc aacccttaaa ttctcacttg cgggaaaacc    65280
tttcacaacc aagcaaacgt ggaaatgatt tggccaaaga ttcaaaatta tattaaacat    65340
ctgggactat attcagcagc caactttcta atcaattcta tgagtgtggt gattgcagtt    65400
atgctcattt tctgagggtg aagtttggat agaactaaaa agggcggttg gcaggaatca    65460
aaagagatga aagcctcagg acaaagagtt agaggcccag gtggttcatg actgagagtt    65520
tggaaatgat ttctggtgtc tcacttcaga gaaaataaat atagccaact ctgttcatcc    65580
gtggtgatgg aacattcaac tacagcactg gcagtttggg atctaagacc acccttccag    65640
cacttcaaaa ttctgactta taaggacac acacaaagaa cagatagcca gatagagacc     65700 aaaatacccca cttattctt ggcagggcaa gcacccagta agctctgatg cagggctctg    65760
```

-continued

```
gtaaatttgc ccatcctacc aacagagaag aatggtggcc tccectcatg aacgggtcg    65820 gagggggcc ttgccacaac aggggcctg atggaaataa ggggacaag agtgttcggt      65880 tggttgagtg cctgctatgc ctgtgcctag gcagtaaaag gggaagtttt aagtttggcc   65940
cttactttca agacatagta attctacctt ctagtaaaac atggccaaat aaatgtctgc   66000
ttttcatgag ccagataacc tccttcttct ttattggagg agtgagtaga agggtgagac   66060
tagccgggtg cgatgtctcc aacctgggcg aaagagcaag actccatctc aaaaaaaaaa   66120
aaaaaaatta agaataaatc ttttcactgt tggagaaaag ttttgagagg ccgaggtgag   66180
aggatcactt gaggccagga gtttgagact agcctgggca acatagcaag accctgtct   66240 ctatcaaaaa ataataataa aaaagctag ctgggtatgg tggtgtgcac ctgtaatccc    66300
agctacttgg gaggctgagg tgggaggatt gcttgagccc aggagttcaa gcttatagtg   66360
aactatgatt gcacccctgc actccctcct gggcatcaga gtgagacact gtctctaaaa   66420 aaaaaagtt ggagaaaagg atactaaaga gataaaaggg tactaaagag atcgggaagg    66480
cagcaaagaa tgaatctagt ctgatgtgtt attgggtgta cgtaattcat ggcggaaggt   66540
gctgaaaggg aaggttgcct gggcctacag caagcaggtg ctgatgaact agctcctttg   66600
ctattactta aatgtgtcct ggttgggcca gatgtggtgg ctcacacctg taatcccagc   66660
actttgggag gccaaggcgg acggatcact tgaggtcagg agttcgagac cagcctggcc   66720
aacatggtaa aaccccgtct ctactaaaaa tacaaaaaaa gtatccaggc atggtggcag   66780
gtgcttgtaa tcccagctac ttgggaggct gaagcatgag aattccttga acccgggagg   66840
tggaggttgc agtgagccga gatcatgcca ctgcacttcc aacctgggca aaagagcaag   66900
actgagttct caaaaaaaaa aaaaaaaaa attcctgggg aatatccacc agggtgaaaa    66960
attgggtata tccaaattca gctttgcaaa gaaatgcact catgactagt tgcaatttga   67020
aacgttcctc ttctgagtat ttctagccta tgtaggtgtt tcacagattg ctgagtacct   67080
agactgagag ggagagaaaa aaacaaagta aagctaaaat gttaagaagt ctggttaaag   67140
tgcaatccag aagtgaggga aagcatctct aaaagtatga atctttgggg aaacataact   67200
tgattaccaa aaacttaata ttaagcagcc tcataggaac atggctttg ggtatggcga    67260 gagccagcta gagctcacat ctccattgaa atccaccacc agagaggtta tctgcctagt   67320
tgttggcagc cagaccctgg cattgtttag attgattgat ggaaggctac tttgggaatg   67380
ctggcttcct tattcattga ctttaaagac agcattgtaa aaattgatca ccagcccaaa   67440
tcaatgttac cctgaagtat ttttatgact ttttggggag gcaaagagat gggataattt   67500
ttgatttatt taagtctatt gcaaactgga actccttttgt cttctttttg aactaccttt   67560
tttgtttttt tgagagagag tcttgctttg ttacccagac tagaaagcag tgatgcagtc   67620
acagctgact gcagccttga cctcccagac tccgatgatc ctcccatctc tcccatgtgc   67680
atcaccacac ccggctaatt ttttgtattt tttgtagaga cagggttttg ccatgttgcc   67740
caggctggtc ttgaactcct agactgaagt gatccacctg ctttggcctc ctaaaatgct   67800
gggattacaa gtgttagcca ccaggcccgg tcttgaactt cgtatataca gtgtgttgtg   67860
tgggcaagtc atgcctgacc acttcctagt gggaggggag aaactagagg gcttgcctga   67920
ggctttaggc aatgtaatct gttctcttgg gatcaattac ttatgcatat ttagtagcca   67980
gctctatttg ctgatcacct aatctgttct cttcgttcat tcccatgaga cttcgatatg   68040
ggatatcttc ctcttcttcc cattgcagcc ttttctctca gagttgttcc catgataaga   68100
```

-continued

```
actcccatca aaatctctgc tctaacatca gttgtcagat tttgccactt tttttttttt    68160
ttttttttctg agatgatgga atctcactct gctgcccagg ctggaggcag tgccaccatc    68220
tcggctcatt gcaacctctg tctcccgggt tgagggatt  ctcctgcctc agcctcccga    68280
gtagctgaga ttacaggagc accccaccac tccaggctaa ttttgtatt  tttttttagta   68340
gagatgggct ttcaccatat tggccaggtt ggtctcaaac tcctgacctt aaatgatctg    68400
cctgtctctg cttcccaaag tgctgggatt acaggtgtga gccactacgc ccagccacat    68460
tttgttactt ctttctgtaa cctgaatgtg aaaaactca  ctgtctttcc tccactctca    68520
caccataact gtcaacacca cagaagactt ctgtgaccaa atatgtggtc accaccaagc    68580
aagcagtaag ttctgcagtg gacaccacta ggcgtcctcc agttcagttc tggcactatc    68640
cgcctggaga tagggctcaa tcccacaggt ggaggtctca gtccccaaga atgtcccctc    68700
ttcaggcacc agttgcaagt ccaggcctct ggaacttctc gctgactggc ttcaaattgg    68760
ggttcctgca gcccctctt  tgagttcaat taattggcta gagctgctca cagaacttgg    68820
gaaacacat  ttactggttt attctaaagg acattgcaaa ggataaagat gaagaaatgc    68880
atagggcgag gtatggggga agggttgcga gcttccacgc cctccctggt cgccctccag    68940
gaacctccac gtgttcagct atccggaagc tctccaaact ctgtcctctt gggacctttc    69000
atggagacgc cattggatag gcatgatcaa caaccatgta gaaatgggat tgcacgaaaa    69060
ggctatgatc taatcctcat aggctgagtg gggaatccca gcaaggcctg tttgttcaga    69120
tccttctgta gcattcattc ctccaggtta tggggcagga ccccttctga atgggtct     69180
tctgacctac aatcagacaa ggcagaggaa atttctttat ggccagctcc aagtcagaaa    69240
ggtgggggaa gattagagtc ctgccttgag cagatgaaag gagggctgga ggaggtcaga    69300
gagagagaga ttctgttttt caaggcctgc ttctaaagcc taaagcaccc ctaaataaca    69360
aaagattgta acaaggacta tgggagtcat aagccaggaa ccgtggatga aaacctatat    69420
atatgtatat atatatctca taataattca aacctgtctc ctgttaatcc catcctctct    69480
gtttctgtta tcatttcctt agtgtagatc tgcctaagtg tagaatttgt agaatttgtc    69540
atgttgacta ttgtagactt gtcttttaga gtttctagca ctagcctctt ccacccatca    69600
ctattgagat gattgtatcc gtctcagtac tgacactaac ccagcactct ggttttacat    69660
ctgtcaatcc atcaagactt cactttcact ttcttccctg cctcattatt cactatgctc    69720
ttgggccatt gctctggctt ctggggcttt tctaaagtag cacttttccc cactccagcc    69780
catgaagata ccttttaacc agctcttgag attaaatccc ctccgtgaca ctttcctgca    69840
ggaacttgca aaaagtact  gcattcccca ctggcaaaac ttgccatcag ccagtttatg    69900
tattctctgc ttttcacacc catatcttga cctctgaaca acacacatat tctcctcttc    69960
atttatttca cagttctgtc ttcataacat tgataagtat gatcacatta gcgctctaga    70020
ttttaagcaa ctggaagata gctatttttt tggtactctt cctttaaatt tgaacatagt    70080
gtctaattag tcaattaaca tttttttaaa agggcgaggg acatcatggt agagagaacg    70140
aagttgaacg tgttttggt  tgaatattag cgcatgccca ctgtattcta ggcacagtcc    70200
tgattcatta tatcatcaca caataattat ttatgtgcct tcatccttta tgacacagtg    70260
ctggctctta ttcatctccc atttctgcaa tccatggtga tgattaaaag tcttaggagt    70320
tttacgaggc tcagtatttt ttttttttaa tatgctagtt cttcatgaat acattgggta    70380
ctctgaagca tatcatttcc tgggtttcct gaagtggtat gttgcgtgga atggcacatt    70440
aggtctaaat aattatcccc tatgtaaggt tcttgttttt cattcattct cttaaaaaat    70500
```

-continued

```
agatattaaa cattaaataa ggacagccag gtattgtttg aggtgttagt gggctatgct      70560
aaaaaatcaa aggtgggaat gaggcagctg gagctcaaag gagcatgtta gaaggagtcc      70620
caagaggaca aatccatttg gttcttcttt ccttgttttt tttcgaatat ttttgaggat      70680 gataatttt ttcccctcaa aagcttttaa tgaatgttag gattaaaaaa gagagagaga      70740
gaatttatag aagagaaatt aactatagct cctaaaatag ctctttgttt ctgaaagcct      70800
tgattctgct atctatttta taactgaaac aaaaacaaaa acaaaaacaa aaacaacct      70860 caagaagtta cttgtatagc ctctgccact aaggagactg tgttctgatg ttacctcaaa      70920
caggctgatt tattaaaata tttaaaaata tatatggaaa tattttttc tattttttt      70980 tttagtggct tttcccagtg aacaataggt cttactatat gatttcttat ttgtcattag      71040
tgaatgtggt gggtatgtgg cagctggggg agctgatgat tttataatac tgtatcagaa      71100
atgattagtg taggtactta ttaacatatt tctcagacaa aacaatcttg acttttaaaa      71160
cctcttcatt taattcaaac atcaagtacc ctgtttgtgg cctgtgttat gttaggtgct      71220
ctctttacaa gacctatttt cttgctattt aattatatat ttgcttagca aatatttact      71280
ctgcacctac taggtacctg gcactgtgct gtgtactgag gtgccatgtg tacctccatc      71340
aacatagact caagatcaat atgatttcag tgaactaaaa ataccttat tgaagcaaaa       71400 aaaaatcaca ttttgtaagg atcaaaaaag agacattta tataaggtac aagaaataga       71460
agaattatat ccccaagata tatgtgataa catacttgtt agttttgga cgtgaccaga       71520 ttttacacaa tccttaaaaa atgcagcaac cagattttaa agtagttctc taatctctct      71580
ttctgtgccc cattagatgt atattggatc ttctcattct gtctttgtct tttgacctct      71640
catgttttcc gtctctttgt ctctgtgtgt tgcattgtac acaaatgctt cttgaactgt      71700
ggtgtgcaca tgaatcacct ggggaccttg ttacaacgta ggttctgatt ccatgggtat      71760
ggggcagggc ctgagattct tagagaatta aattctaacc agctcctgag tggtggtgat      71820
aatgccagtg tgtagaccat agcttaagta tcaaggttct atgtgattcc ctcagatcta      71880
actgctagtt cactaagttt ctcttcagct gtatctagtc tgctatttaa catattcagt      71940
gaatttttaa ccttaaattc aagaacaaga ctttttattt ctggaagttc agtttggttc      72000
ctttcaaatg tacctggttc ttttttcaaag tgtcatgttc tttgataaga atttctacta      72060
atttaccttg ataataaaaa tttgtttcat ggctcatttt agattgttct tttatctgca      72120 gttttttggag ggctaattct cccatttctt gtatctgttg ttgcacccgt aagtgtagt      72180 tgttgattt tacttttaa ttgtgaattt atttctggta gggattggaa ggaggttgtt      72240 ggggtgggg tgggtgggg agaaaatcct gtgtgccctg ggttgcaaaa acaccctac       72300 aagttgttct ccacttgcat ctgccagtgc tccaagggct cagtgatcct ggaccagtag      72360
tcatgataat ttcttgaatt gtaacaggat actgtaaatg tggacactct acctgaggtt      72420
actgcttctt tctatctgct ttatttcctt cccactgaag ggccctggac aagggtaaac      72480
atctcatcac tttctgggtg gcagaatatt tccagttccc ccacttcttt ttggcttaag      72540
gctgtggctt tttcctctgc ctgaatgtgg ccctaagaag cccttctttt caaactttcc      72600
tgttgtactt gaccgactag ctgtctagag gtttatatcc ctagctttta atctttgctg      72660
tgaatatctt acctgttacc agctagtata tttcacattg acttctcttt ccttttttt      72720 ttttttttt tttttgagac ggtgtttcgc tcttgttccc caggctggag tgcagtggca      72780
cgatcttggc tcactgcaac ctccacctcc caggttcaag cgattctctt gcctcagcct      72840
```

```
cccaagtagc tgggactaca ggcatgcacc atcacatctg ctaattttt ttgtattttt    72900
aatagagatg gggttttacc atgttggcca ggctggcctt gaactcctga cctcaggtga    72960
tccacctgcc tcgccctccc aaggtgctgg gattacaggc atgagccact gtgcctggcc    73020
tacttcttct tccttttaac ttgaagatta tctgcccctt tttctaatct taaccgcatt    73080
aagctggctt tgagcatggc aagagtttta tagatgaatc ttattttata gtacaggatt    73140
tcaaaatcat aattatttca ctgagggtgg cttttaccct ccattaatta tacttctcac    73200
tcagaaatgg aattctattt tggtctccta agataaatt agtatatagt ggaaaggaat    73260
tataaagttc tgctaggaat taaatgatat gattaacaca aacatccaca tggatgtgtc    73320
tctgccctgt gcaggaaaga tgaacattca gtacagattc tgctctatgt cactagcttt    73380
caagacctgc aggttctctc ctaagcatgc aattcctgtg agcagtagca ataatagcag    73440
gtcatatttg tggagtgatt actgtatgct aagaactgtg gtaaacactt ttatatggat    73500
tattttattt aaacctccta atagtccatt gaaatagata ttgccatgtt gaaaactgag    73560
gttcagagag gttaagtgac ttacccagtg tcacagaact agtaagtggt gcagctggga    73620
tttgaactga gattccagaa caattgccat taaccacttt gcttccatat tagtatcatc    73680
tgcaaatctc tctccataaa tttcctcagt ctttatctga gtttccttat ttcaggaagg    73740
aaaacttctg ttttttgatcc ttatgaaata caatttccat taaaacttt tttttttgct    73800
attaaaaaag gtaccggata attgaaacca gactggattt gagcctgtgt tgatggaagt    73860
acacatggga tgtgggctga agtgttcaat ctaattttc tttccatcag ctaattttta    73920
aagtattaag caagtagatt ctgacactaa cagggaagat ttaaattctc ttgagagact    73980
ggaggtgtta ataattttc tggtagtgca catttttacat cttaaatctt cctcactctc    74040
ccacctcatc tcaatgtacc tgaagctctg ggaatgttct tttgtacttc tcaggaacag    74100
ccagacctct ggcttcatct cctctcccct ccacatccct ttcctgctcc aattacttcc    74160
cagcgccact tggatgttgt tgtcatcggg gaactttgga aacagccaga ttttttttgga    74220
gtctgtaagc agaaaacaga ctgcttgctg ctcatatctg gcacccagct ttgtccagaa    74280
aacgaggagt taaaagaag tctgggctgt gaagggctgt gacaactgtc ctaggggag    74340
ctctagcgag ccctggcggg cagtgactca tgctgctctg tcactgggat cagcactggc    74400
ccctggcagg caggcggcag ccaggtgggg ttccagccag agcacgcacg cacggagccg    74460
ggagcatgca gcctgcactg cgggggatgt gatgctcggc tctaactcgc ctggctggcc    74520
cgccacggac gcctcagctt gcaaccatgg taacgtttct ggcgggggac accccgggga    74580
gcccaccgcg atgggcagcc tcctggtgac tgatggacga gtgtccacct cccagaccga    74640
gagcgcttag taggtcggag gaagtggaga ggatgtaaca cgcccccagc cgggagtgaa    74700
gccctgagga ggtaggagcc gcatatgtcc atccgtgcat tcccaccgtc agcgcgcagg    74760
ggtgctgtag atcaccggta ggaactttat ttggctggtg cttcattatg ctgattaaac    74820
tgcagtggat ttgatgggca tgattgcgct ggggaagatg cataatgaac taaaaaaaaa    74880
aaaaagtggt taataagatc tcggagtcga cttgtccggg tatgaatgaa gtagactgca    74940
gtggtatcct aacaggagtt ccagaacctc acacatccct tttcctggtc cttcctctta    75000
tcccggttaa tccacgaaat gtagaagttc catcttattt caacgattag tgctaatcat    75060
taataattta gacctgtctg gaggagggaa tccataggtt taggtctcct agcatcctgg    75120
cactagccag cagctgctct gtaggagcct tctggaaaca gcaggaagga gcggcttccc    75180
cacgagttcc ccaagtgctt tcgttggccc aagtgctttc gttggcccaa gtgacctgtt    75240
```

-continued

```
tgagtttgct cttcagttta ccccaggcgg gaaggcagcc tgtctgcggg ttggtggcca    75300
tgttggcaga gaaggggtta atctcttgtt gctgtaggag ccgaggttgc gagctagatt    75360
gaaagcaggc gctgcagtgc catcgccagc gccgaaggag taagacgatc ttctccgcaa    75420
cagtgttgaa tccggctgaa atttttttc ctccccgcct cctttcttgt ttttctttaa    75480
ccagctcctc ccccttcgt tcccaccctc aagtctgacg atgacacctc caattttgat    75540
gaaccagaga agaattcgtg ggtttcatcc tctccgtgcc agctgagccc ctcaggcttc    75600
tcgggtgaag aactgccgtt tgtggggttt tcgtacagca aggcactggg gattcttggt    75660
agatctgagt aagtgaaaat ttgactttct aaagggacct gcattgatgc aaggcttttg    75720
gagccaaagg tggtggtggg ggggtggggg aataggtggg gggagtgcag tggagggaag    75780
ctgctagtca cctgcattgg gaaagcagtc tacctgttag gctttgcgg gggtagcctg    75840 ttaatattct cattttgcag tgtgtaaggt acctgttcct gtctgtggta tgataattgt    75900
caattgggta ctttgggtta gttttccaat ctttggtctt ctttaaaggg gagagagtgg    75960
gagatttcca gcagtgcaga tccccggtca aaggagaaat gtgcaggagt taagatgagc    76020
tgcccatcta tctaaccatc tatgtatctg tctctcaagt gggtggatgg gggttgctat    76080
cttggctgta taaagaatcc taaaaaccctt gtctcataag ctagaggttt cctgatgggt    76140
ttaactgagc tgcaagtggc tgaaccagag ctctaacaga gagatggtgc tcggctcctc    76200
tccaagtatg ctgcaagatc agggatctgg cagctgagcc tctctgagct ggtggagcgc    76260
tggcagccag agaaagcccc gttactgtga gccaccagga gggagtgtga tgtagccgag    76320
tcattgattc acagaaactg ggcttcatag ggggaaaaaa aaccaggaga ctagaaaatg    76380
gaaatataaa tatcactgta aacctcttga tctggtaggt ctttctccat tctcataaaa    76440
gctattgaaa aatgcattaa cagagcactt ggaattagag ggtcgaggct tccaggagcc    76500
tcctggaatt tctgtaaaat gcagtagctt ctgtggatgt gggaggtcag tatcttgcct    76560
cattctctca tgatacaatg acattctgtt ttcagaggag tgagttcccc agaagatctt    76620
ggactgatgg tgttatttgc cagccaccct ggtccctgca ctttcaggtt ctcagagggt    76680
aatgttgggt tagttgctgc ccacttagga gacgagcaga atttgatatt cttcttggca    76740
gcatctttcc ctctttgtgg tatttgtagc ttagatatcg atttataggg atgttatgtt    76800
ggttcctgga tggtgtctcc ctatgggtgc tattttgaca gtaacgttcc tgaaaagatt    76860
tcagagtgtt gtgggggaatt gggcatttga tacgaaataa ggttgtgggc tgtgattgaa    76920
tgtgagggag gtttttatgt tgcaagatgt tgaagtggtc tttcttgatc ccctctctgg    76980
gggctgggtt tcaaattcag gttggatttt ggtagtgtta gatgtgcctc tctgtctgat    77040
ttgctccaca accccaaagc aatctggatg gtggtgggag aggcagagtg ctaactagct    77100
gttgaatgtg ccatcagatg ggtttgaaac ggctcagcag gattgggagg ttttgccatt    77160
ggcatcaaag agcagggcag aagcggaggc ctgatgttga aggatgcatg gttagtgggc    77220
agtataacct tgacacacgc agcacactga aggtcacacg tcgtactgga aggacgtgtg    77280
gagagttcta gttctggtta gcagtgggct ggctgggtca gaatgcaagc ttgcttgggt    77340
gttggtcagt gatctgaaag acgagggagg attcgaggga gttagatttc aggggaaaag    77400
gcagaatgat atgggagatc ttaggcattg caattaatct gaagcagtgt gtgattaatt    77460
gcttattttt caggaagact tgaatgacat ctttctgttt ctcacagaaa gctcagttta    77520
gggagctctc tgacagggac atctcagtat taaggctgag gcactcgata aatatttgtt    77580
```

```
gatttaattt acctatgatc ctttcctcca gaagtgttta tattgcttat tgtatttgaa   77640
gatgtgctat ctcacctctg gtagtttaaa ctatatcctt agagcacaaa acgagctgct   77700
gttcctgacc caacagaatg tttaataaga ttcttatttc aaaaaaggtc catgcaaata   77760
aaactgtgta tttcttattt ggacgatggc atcagagtat tcctatcatt ggggaacttt   77820
aacgtttttt caaagcttgg caacgggtt  ggaatcagaa agattttctt tcatcttgcg   77880
tcttgttatg tgttattgct attggacttg gctactctgc tgtaggcagc cctgtgggtg   77940
atacctacaa gcatcatttt agaaattcat ccacctgttg gatgtagatg accctggaca   78000
tatcagattg tgattaatta gaaatctaat aaaagagagg cagtgatgaa attacttagc   78060
agctcctgca gttttattga caaaatttac ttggagagag ggggagacat tttctggggg   78120 taccacctt  gctgccagcg accctgtgtt tcttcctgag tttcttttc  ttttctcacc    78180 attttcagca tcacaggttt ttatttacac acattgatta cctgtgctgt tactcattct   78240
tcacaccact gaggaaattg cagatgctgc tgtactgtgc taggtaaatt gacctcagat   78300
ttgttaccag tgaattgaat gaaatgttca gaggtggagc tgaatgaacg aggagttttt   78360
gtggagaaat tggcagtgag aatgatttaa attctgtgat agctcctcgt ttttgggat    78420 ccttattttg ggaccccaga ctatttttaa gccattgagt gcatcattat tttaggctga   78480
gcaagaatct tgatgacagc gtttcaatgg ctgaggcgta gtgggagttc cttgcagctt   78540
gagttggtgg gagctggaga gtttctagag aactaggttt ggttgtcttt ggggtgggt    78600 tatggtgaaa ttagtcttgg agagtgagta gctgtctgat gcttcttttc cttttaacc    78660 agcaagagcc caaccaaat  ccccaagctc tgaatgcctg gctgttcctc tcagcctttc   78720
tttgcttgaa cttgacaata gtagggtagt aacaggaaac agcatgttaa agttttaaaa   78780
ataaaataga tctcagctct tttccttccc attagcaagg ggtacattta tttaggtttt   78840
tccttctaga ttgaggcact gcctcattta agttcttggt gaagccatgc atttctgcaa   78900
accataagta taaactctag aacgggggtg tccaatcttt tggcttcctt gggccacatg   78960
ggaagaagaa gaattgtctt gaggcacaca taaaatacac taatgatagc tgatgagcta   79020
aaaaaaaaaa aaaactcata aagttttaag aaagcttaca aacttgtaag ttttgagcca   79080
cattaaaaac catcctgggc tgcatgcagc ccccggggcc ttgggttgga caagcttgct   79140
gtagaaggta aaaatcagtt ggttttatgt ttttgtttta aacatgctgg ttgtatgctt   79200
ttggaagagt tggggaacac tgagggtaat gggatcttga tgggctgga  atttgtggga   79260 agatggtgtc tgggtaggct gttttaggga agggcactc  tcttcctttt gattcagaga   79320 ttttttccttt cttttcgggt ggttctgaaa acacagcgat ggatccaggc attcaaacac   79380
catggaggaa ggaagagtgg ctgttgccat tgcttcccga gttttctggg aaccagtttt   79440
tggtgcctct tccttgctct actgggcctt ctctgcatgt cagtttcttc aactgcgaag   79500
tggaaggaca gcgatacttt tcttacagga cttttgcggg gatggatgaa atacgtaaaa   79560
cacttggtct agtacctggc acatggaaaa gccttggtaa atgttcactg ttgttatttt   79620
tgttattact aatacactag tccatgtatg tatagtgtcc tcctatacac accaagaaa    79680 tatggaaagg actcagcaat gattaggtag tccaaagtca taccagattg gaaaccaagc   79740
ttcccaggcc ctgggacttt tctgctagag acacttcacg gttctgacca actacaaaga   79800
gttaatatgc agttgccaaa tacctgttgg taaaaggtgg atgttgggga ggagtggatt   79860
ggggaacaga attagaaggt ccagtcccag aatgggtacc ttcccatcaa gttgaacaag   79920
tcaaaacagg ttatgttgaa acaactgaga gaaagtaaag caaacaccat tgctgcagaa   79980
```

```
tatcatggta caaattggac atctttggga gttagcggag taaggcaaaa tccagtgagg    80040
gacgcttaat gggtaatgcc aattcacaat tcttgttaaa ttacattgct gatcttcctt    80100
ggaatgtctg tccattcccc caagtagact gtgatctcaa ggcaaggctg ggtcttattc    80160
atcctggttt tcctggagca gtaaatactt gtgctgggac tgggcttata agcatactaa    80220
tggaaagtaa aatatttggg ttggtttttt aaaaagacag tggatttgga tcagtggaga    80280
ggaaggtaga gggaatttca ggtgggcagg gtgctaacaa cagcccatcc ttacagggca    80340
ccaactgtgt tctaggctgt gttccaacca ctttacacag atgaattcat ttaaattgca    80400
caaccagccc aagaggaagg taccattatt attctcattt tggatgtgag gaaactgagg    80460
cgtggggaga tcaaacaact tgcctaaagt tatgtagctt tgagtggctt agctgagatt    80520
tgaaccctgt gggtataaac gccacagatg ggaaatttgt gtggggtacc caggttcatg    80580
tgcttgttag aagtggaagc tatttgtaga gaatcacgaa tgatgaggtt ggggcagggt    80640
gtgatgggag ctgacaggca ggtctaaatg ctgggattca ttttcagtct ctgtgtttat    80700
tgagtaggta gacggtatag ctcttggatt tctcagattt tttcctcttt tcatttagag    80760
actcttatct ggtgtgtgtg tgcccgcaca catacataaa cccacgcgta tatactcttt    80820
ccctgaatgt tcttatttgc taaagcttaa gcttggcaaa gagaggaaac tgcactgacc    80880
ttactctcca ccatatcttc aggctgatca tacacaagtt gcttaataag catttggtta    80940
atccatctaa atcattctta tggctgcaac tctcattttg ttgatgactc tactatctat    81000
gtctattcac atctacattt tgtactttg tttgcctccc atctgtcctg ggatggctga    81060
taccagtgga agacagcctg aactctccaa tcagtcctgt ttcctttta tgaaatactt    81120 ggaggttgga ggatcttccc ttaaaaagtg ttttcctttc tacatccagc caaaggctct    81180
tggtccttgt gcttgctacc tagatcccta ttggaaagag tcttgcctgc aatttgattt    81240
tttaaatagc agcaataaca gagtcgtctc tgctacacga agacatgcat ctgctgtatt    81300
tcccagacaa gttcaaaaac cttaactagc ttctgcccat ggttattgct ctcaagtgcc    81360
ttgtgttgtt cccatcccct cattatctgg attagatgtt taacatttgc ctgtgtgtgt    81420
tgtgttggat tttctcctct cctcttgctc attcaatttc ttccttctct tagccaagca    81480
cagcttgttc tcctacttgc cttattctgt tctctattta gactgtgcgt gcctgccttg    81540
cagccctggc aggaccattc caccgccttc tcatttgtct taaagatacc tttaggaaat    81600
ctaatccaga caatcctagc ccagtcctga agattaggct ccagaagatc tgtcaagtgt    81660
gttttttgct ggcctacaca tgctaatttg catggttgcc tgggatccct taagaagaca    81720
gtcattgact aaatggcgct acatgttccc aagctctgcg ccagtctggc aactcttcct    81780
ttgtctacgt gaatttctcc tagttctttc tgctttgctt gctgttcatc tcctgacctc    81840
tctccgacaa acttcctgaa agaagagcct gcactcaaca cctctttttt ccacctcttc    81900
aacaatactg aaatgactgt ctcagaagcc gttgattgta cctaaccacc aaatctggtg    81960
atttccatct caccacgtga taccattaat actacctttc ttcgagacaa cgttctactt    82020
tcttctcttc tgtattatgg acacttggtt tccctcctac ctctctgact gtcattctca    82080
ctcttttgtg gctgccatca ggctcttgca atgtacgtac catctcctca agttccatcc    82140
tcagttatct ttctagttgg ttcttggtga tctcattcag ttccttgact ttagttctta    82200 cctcccatg gcctcctccc atcgtacact gtgttcctca tcaccaggat gttttaccag    82260
tttctcacca tcccatcctc tgttcccttc ctacatagac agacccactc gctcactcag    82320
```

-continued

| | | | | |
|---|---|---|---|---|
| taagccacta | ggtgctagtt | ttggcttctt | cattttatgt | aagaaactac cacccttccct 82380 |
| acccttctag | gcaagaaagc | tgagtcatcg | taaattcttt | tctgcctccc ccgccatccc 82440 |
| atcagttgcc | aatttctcca | agtggtgcct | ctaggatgcc | acttgcatcc atcccatct 82500 |
| ttcttcctca | ttggcaccca | tcatggactc | ttgcttggtc | tggtgcagta gcctcctcag 82560 |
| tgattcccctt | gcctctggtt | ttcctggctg | taatccattc | tccacaaagg gtggaattct 82620 |
| tccaaagcat | aggttggatg | atgtcattca | ccggcttaca | ccttcaacag catcccagtg 82680 |
| tgctcataat | taatggctgc | tcctgaactt | ggtattcagt | cttggtatgc caagaccccca 82740 |
| gcctgccggc | tcatttgtgt | ctcctcatcc | cctactgaat | cacttcaata gtgttgtctg 82800 |
| gccaagctgt | tcaaggctca | ttaaggacag | gaccaggtct | tccttctttt gcctgaaaca 82860 |
| gtgccttgcc | cctggcaggt | cttcaatgaa | catttgttga | attgaattag actaaaatgg 82920 |
| ccagggatta | taccaattcc | ttctgcacag | tgtagacaac | tgctaatgga acctgttttc 82980 |
| tgtagagcac | ttcttgtgtt | cccagaacta | tgcgagtact | ttatgtgcat tatctcatta 83040 |
| aatcatcaca | atctcactgt | aactctatga | ggtagctgat | attatcccca ttttacaaat 83100 |
| gaagacactg | attcaggaag | attagattat | tttcctgagg | ttctgaaggt agaaacacat 83160 |
| ctaagacttg | gagcaatatc | tggttgcctc | tagaccactg | tactatctac cctgcctcta 83220 |
| agagccatga | ctttgctaga | ttatgcagga | gttatggact | tgtctaatag taaaggtaaa 83280 |
| agaattggtt | ttaatgagaa | tctactcttc | taggtactat | tctgagtgcc tgacaagcat 83340 |
| tctcatgtag | acccagcaat | aactcattat | tttacagata | gagaaaatga tgatcatgat 83400 |
| gcttgggtta | cttcttaggt | tcactcagct | cacatctggc | agagggtggt caacttttcc 83460 |
| aagttttaac | ttatttattt | atttattttg | agacagagtc | tcattctgtt gcccacgctg 83520 |
| gagtacggtg | acacaatctc | agcttattgc | aacctccgcc | tcccaggttc aagcgattct 83580 |
| tgtgcctcag | cctcccgtgt | agctgggatt | acaggtgcct | gccaccacgc ccagctaatt 83640 |
| ttgttttttgt | attttttagta | gaggctgggt | ttcaccatgt | tggccaggcc tgtcttgaac 83700 |
| tcctgacctc | aagtgatctg | ccagcctcgg | cctcccaaag | tgttgtgatt acagatgtga 83760 |
| gccaccacgc | ctggctcaac | ttttaacttt | agaactgata | taaacatgcc tattttttg 83820 |
| ggactgactg | tagcataccc | attcaaagtc | caggctttgg | aatcagacag acgtgggctg 83880 |
| aactcagggt | ttcacccctt | gcttgttgtg | tgaatgagac | atttcactgc tttcagcctc 83940 |
| aattccctca | tctgtaaagt | ggaaggtgta | aggtcgccta | tctgataggt ttgccatggg 84000 |
| gatatgaagc | acacttagtg | ttggtgccat | gagtagaatg | agtgttcatt tcatatttgt 84060 |
| taatgttatt | taggtccgag | gatgggtatg | gggtgctttg | gactctcttt ttctccctgc 84120 |
| ttccgcctta | taaagacatc | ttgctggttt | ctgcccattg | agagaatcca gctccacgtg 84180 |
| gggggcctga | cagatgtcct | aatatctcca | tccaattttt | tactctgaat ggagtctgtg 84240 |
| atgtatcact | tcaacctgca | ctttctataa | aatgctctcc | aggcttctgg taggatccag 84300 |
| tgccagtggg | aagtgtgcat | gttcccagcc | tagatgtcac | atgctcccac ccaccctgga 84360 |
| agcacttggg | tatcccctgg | atgggtaagt | ctgtgtgtca | ttgtgccatt cctgtctcag 84420 |
| aaccaatgct | gggcatctct | acttgcaggt | gctggaaagc | ttttcatgc cagcatacat 84480 |
| gcagcacact | tctcattttg | gattcccttta | tcccacggtg | acctttaaac tggctgcctg 84540 |
| ggggcacaga | agtactagca | caccattcac | ttatttattc | attcattcat tcattcattc 84600 |
| attcactcaa | caaatatatt | gttctagtcc | ttaaggcaca | actctgagca agacaggtaa 84660 |
| ggtctttact | ctcaagaagc | tagcatttgg | tggggagaaa | caaggagaa ataactactg 84720 |

-continued

```
tgcacatgtg aggcaattgc agatggtggt ctgcagaatt gggattgaga ctgcctgggg   84780
gtggccactt tagactgggt ccgcaaggaa aggttctctg agctgagcat gagtatttgt   84840
tcaagaaggc tgagttgcat cccaaggtga cacagctttt aagcccacac tgagcagctc   84900
tgaggtccta ggggctgttc gagaacctgg gatatagcac tgactatgag acaaaaatcc   84960
ctgtcttcat ggagcttaca tgatggggc agattcacat tcattcattt gttcattaat    85020
tcattaattc attcagctat ttgagagcct actatgtgcc aagcactttc taggcactgg   85080
agaagtaaca gtgaatgcaa aggagcaagc atccctgccc acacagagtg cattcttcca   85140
gaatatcaat aaggagtcgg ttagcaaaaa taagtgggaa gagtattcca gagagaggaa   85200 aaagggcaa aggccctgag ctgccacta acctatgggt gctcaatgaa cagaaggcat     85260
gtttgggtag ggggtactta aggatacaca aggaacatgg tctgagctga ggtcatcagg   85320
gcctttaggt atggactttg ctctaaattg cactgagtag gaagcttttg caggattttg   85380 aataggtca tggaatatct gggtcttatt tcacaaagtg tgcctctgac cattgtgtgg    85440
agggtggata gtgagggaca agagttggat ccagggaggg aagtgtggtt attgcagtca   85500
tcccaggtga gaggcaatga aattaacctg caaagtgagg cactggctta gaggtgggaa   85560
ctgaattaaa aatcatggga ctagctattc ttttattaat agcatgattt ttgataaatg   85620
attctggagc tacatattaa tcatttcaaa gcaagtgctc taatttaact agagaccact   85680
gctggttgtg tgtgtgagtg catatgtgtg tatgtatatg agtatgtgtg gtgtgtgtca   85740
gtatgtatat gtgtgtatgg tatatatata aatatatata ttgtgtgtgg tgggggaggg   85800
ggggtgcccc aaagctagac agactctgac tgtctttagg ggaatagtgt ttttgatatt   85860
tccaggtgtt cctgatgggc accattgtta ttttatttta tttttatttt attttgaga    85920 cggagtctca ctctgtcgcc aggctggagt gcagtggcgc tatctcggct caagacaacc   85980
tccgcctccc aggttcaagc aattctcctg cctcagcctc ccgagtagct aggactacag   86040
gtgcgtgcca ccacccgg ccaccattgt gtattttaaa gtgtgcttat aaaattagtt     86100
cagagccaga tgtggtggcc cacgcctgta atccaagcac tttgggaggc cgaggcgggt   86160
ggatcatgag gtcaggagac cgagaccatc cttgccaacg gggtggtgaa accccatctc   86220
tactaaaaat acaaaaaaat tagctgggta cagtggcgcg tgcctgtagt cccaactact   86280
ccggaggaca aggcaggaga attgcttgaa cctgggaggt agaggttgca gtgagccgag   86340
atcgcaccac tgcactccag cctggtgaca gaacaagact ccatctctaa ataaataaat   86400
aaaacaagtt cacaaatttc ggaatgctca atcttaaaag ccagtatatt tttggaaacg   86460
gaatgctgat gagtttttta ttttttgcag catattacat cttgcagttg catgtatttt   86520
tagtgctgtt ggccagcact aaaggtgggg ccctcagctg agctaattt gagtcccctc    86580 attttggctt caagtatact cattcttggt tttcccaaga atatctggga tttgtgatct   86640
gtgttatctg tggtttggtg tcgtattttg caggcatagg gtcctattcc taagggaata   86700
aatggatggc ttgatgctta agcacgaact taatcatcgc agtagtgatt aaagagtatt   86760
caacatgtac acttgcttgt aggaaggagt acacattgta ttctcttttg atatgcaata   86820
ttttattcat agcccctatta agtaatttt tttaacaaag ttatatggat tatttacagg   86880
tacatcacgg gaaaactgca ttttataatt ttcactgaaa tgttgaggtt acatgtaaag   86940 caattttat gtcatatctg atacatttta agaaaacatg tcttcctgtt acagcggtaa    87000
tgaccatgcc tgctctttct tctgtgtcat atgccattat ccctattaat actctttggg   87060
```

```
cttctataat tataaagcag atgtgtatat cagggagaga tgttgatttc agagtaagtt    87120
tttctagaaa atagaagctg gaaaaaaaag gaaaacccaa acttggcttc gtgctcgaag    87180
agacagcact gctgtgtgtg ggcgggtggc tgcgtgcacc cgctgctcag aagtgccttt    87240
tctctccatg gggataactg gctgtgtatc cgagatgtgg ccaggagtag gcaagcaacg    87300
tgtgggcagg ctgcatgttc ttttattagc atcttcattg tactgcatct cgtcgagccc    87360
agagcatgaa ctggcctggg tttctaatat ctaccctgct tcccacctaa ttactcccct    87420
gaaccctaaa gtgagggagg gagagttgct cttgtgggt gagctttccc tggggtggct    87480
gtgaaccaac ctggcatgtg gatgttcttg ggtatccaga gctgtcctgg actcaggctt    87540
ggagtcagct tcttagcact gaatgcagcc agtcatggat ggaggtcact gtatctcaca    87600
tgttccgctc tccctttcct ccatgacctt gcccctctga gcctctgtag cacttttctt    87660
gagtgtgtcc aaggccatct agctaagaag tagcagaaat gggatttgaa gccatgactg    87720
tttggtgata gagcctcagc tttgaactgg ggttctactg cctggcaccc ctgcacaaat    87780
catggtaacg tggtaggaga acatagaggt ataggggcaag cccctcctta atgccatgaa    87840
taatacccat cttataggat tgtggggagg actcagtgaa gtaacccgtg aagcactaaa    87900
cacgtgcctg acacgtgctc aataaatgag cacttgtcct gatgacaaag gtcgtggcat    87960
taattctctc tcctaggttg ttacttcctt gaggacagga attgtggctt ccttaatggc    88020
cactgcagca gagtttctca agttggcact attgacattt tgggctggat aattcttgtt    88080
gtgggagctg tcctgtggat tgtaggatgt tgagcagcat ctttggcctc tacccgctac    88140
atattaatag caccctagt catgaaaata aatgtctag acattgccaa actgcccctg    88200
ttgagaacca ctggtctgca ggtatctctc atggggatca cagggctttt atattctctt    88260
ctctgtctct ctctctccct ctctgggtgt ctctctctct cacacacacg cttagagaag    88320
gtggttaaaa aaaattttgt tgaagtttga gaattttgag aacaaaggaa aaattttgga    88380
aggcatttta atgaacagat agactctgtc ccattccatg gtcaacagaa tttcataatt    88440
agatagtttg tttactgcaa ctctgcaccc cattgcccat cattttagag ttccaaccag    88500
ttagaggatt tttcttgcaa actttcctta aagcagtgat agtatcagct ctttaaataa    88560
tactatgctt gatgaagtgg tacttttcgg gataatttga gaccagccga cttgctgctt    88620
gaagaggaca gggctatatt tggtaataat atatatgtga taatatgtat gtaatattat    88680
tataatgtaa tatacaataa tatttggtgt aactggtgac tctgaggcca gtcttttgatc    88740 gaacctctca agctatgatt tacattatgg tcaatgttag cataatgcaa ttatcagcaa    88800
tcacttgctt ttgctttgaa agtcagaagg atggctaata aaaatcttag aaaaagaaaa    88860
caggctgggc gcagtggctc acccctgtaa tcccagcact ttgggaggct gaggcgggca    88920
gatcatgagg tcaggagatc gagaccatcc tggccaacat ggtgaaaccc catctgtact    88980
agaatacaaa aaaaaaaaaa aaatttgctg ggcgtggtgg cgtgcgcctg tagtcccagc    89040
tactcgggag ctgagtcagg ggaatcgctt gaacccggga ggtggaggtt gcagtgagcc    89100
gagattgtgc cactgcactc cagcctggtg acagagtgag actccgtctc aaacaaaaca    89160
aaacaaaaca aaaacaaaa aagaaaatc ttagaaaaag aaaataaatt gtaatatttc    89220
agaatatttg ttggggagga tatgtgtgct caagaaatat atactgagaa cttaccattg    89280
atgctagaga ttgaattgcc ccatgtctac atgaaaaatg aatagaatat aaacatttta    89340
aattgagcca tgtctatctg tattatattt cttttataga aattcatgga aatggtatat    89400
tttaactgaa ttattaacac tggggacaat aggctttaat cattatctaa tacctgtacg    89460
```

-continued

```
ttgttttgaa attcatagcc caccaccatt aatttcaaaa ttgggttctt actcaaagag   89520
tgatgaaaag gcaccagtac caaatggtct ggccaaaatg ctacatggaa ctaaatgctg   89580
gggatggtca tacaatgagt tttaagtggc tagaccctaa atcagaagca ctttcttcta   89640
attagcacca tggttcttaa tcctttctgt acattacaat cgctcagcag cttaatacaa   89700
atgttgcttc ccggggccac actccacatc tttctgactc tctgatttaa ttggtccgaa   89760
tggggcctat acatcaggtg ttttttaaaa ggtctccaag tgattctaat gtgtacctgc   89820
attgaggacc agggaaggtg taggaagcct gataaccttt actctccagc ctcatcctcc   89880
aatcccatga ttgtttatgg gattgttgct acacacccag cttagtcata gcattcttac   89940
tctagctttt ttttagatgc aatttttatt tattcttaaa gaaaaagatt tctttagcac   90000
ctttattcta aagagctctt aattgctgtg cttagaactt ctaaacagtg agcatttgtc   90060
aaacatagaa tagcagaatg aagggttgg  acctcgggtg aggagggctg tcgcatggtc   90120
tctttcgagt gccggcgggt gggggctgca catctcctcg cttctgggcc cattgataag   90180
tgacctaaaa gtgccttcg  tttttttggg tggggggtga aaaagcaatc tgttttgtac   90240
ccacagcggt gcactttaaa caggaagccc tactggggcc agccttctat gtgtcattaa   90300 gttttttcacg ccacatccta cctatcatca tgcacccatg tcatcgttct tttaagggt   90360 gccagttttt tgcttaagca caaggagctg tgacctgtgt tgtcatccct gatgcatgtc   90420
atgcatgtga cttcatgaca tgtgggtgac ttttgatctc tgaaggacca gggacccagt   90480
ctgtggatca ccactctctc cgtgggtggt ttgggtcttg ttctctagcc cacccagcca   90540
ggtgcaatta ggaataaagg aaatagcaaa ggaattttgc tcaaggccat gccaagcatt   90600
tcatctcata tgaaaaggaa aagagagaga gtgtgtgtgt gttggctaga tttaggtaga   90660
aaacaggctg gtgagaagcg tagaacttgg ttaaaatttc tagccaaaag taagatttt    90720 aaaaagattt atttctggat ccaatccctg ttgcccattt ctatgaataa tcaccatttg   90780
ttttaatgtg aataatagca cacagcaaat tcagccccct gagttttacc attttaagca   90840
attgctttag gcccgtgagg catgtactat ttatgaagtt gcatgggtag taatggaaaa   90900
cacaacaatg acagtagtaa caggtgacat ttgtcgaaca cttgcagtgt gccaggcact   90960
gtgctgagag cattacatgc attatttcat ttaatccttc caagaactct ttgaagtagg   91020
ttggtaatta tggccatttt acaattgagg aaactgaggt tcggagatgt caaataacta   91080
gtcagtggtg ggggtcagat ttttcttttt tttttaaatt tatttgcttt ttttttttt    91140 tttttttgaga cggagtctca ctctgttgcc caggctgagt gctgtggtgc catcttggct   91200
cactgcaagt tccgcctccc gggttcacgc cattctcctg cctcagcctc cggagtagct   91260
gggactacag gcgcccacca ccaggcctgg ctaattttt  gtattttag  tagagacgag   91320 gtttcaccgt gttagccagg atggtctgga tctcctgacc tcgtgatccg cttgcctcgg   91380
ccccccaaag tgctgagatt acaggcatca gccaccgcgc ccggcctatt tgtttttttt   91440
tttaagagac aaggtcttgc tgtgttaccc agactggagt gcagtggtac aatcgtagct   91500
cactgtagcc ttgaactcct gggctcgagc gatcctccca ccccagcctc ccacgtagct   91560
gggactagag gcatgagcca ctatgcccga ctcatttta  aacatttttt atagagacgg   91620
ctgggtgtgg tacctgtaat cccagcactt tgggagactg aggcgggcgg attgcttgag   91680
cccaggaatt tgagaccagc ctgggcaaca tggagaaacc ccgtgtctac aaaaaataca   91740
aaaatcagct gggtgtggtg gtgcgtgcct gtagttccag ttactgggga ggctgaggta   91800
```

```
agagaatcac ttgagtctgg gaagtcgagg ctgcagtgac ctgggaccac cgcactccag   91860
cctgggcatc ggagtgagac tgtctttcaa aaataatttt atttatttat tttaaaaata   91920
gagacagggt attgctgtgt tgcccaggcc cgtcttgaac ttctggcctc aagtgatcct   91980
tctgcctcgg cctcccaaag tgttgagatt ataggcatgt gccactgtgc ccagcctgag   92040
attttgaaca gaggagcatg atgctgggcg ttgactcatt tggctgtgag tgtggaaagc   92100
tgtcactgga gtacagcaag tcagcactat caagccagcc cttgtcattg ccaggagctg   92160
cggggagaga ggtgttttgc attgctgcag ggaactgacc tcttttagtc agggaagtag   92220
tttgggcagt agaaagcaga acttgcacct gctggtaaga tctgagtggt cactgacaac   92280
cagctctgca accctgttac cagggcaaca agatgggcc caggggtagt ggtgggctct   92340
gccacatctc tctgtgcata agaacctttg ccacttgct ctggccttgt ctttcaccaa   92400
tcccagtgtt catatccagt gtaccaacca ctgagggcag ctgtcctgga atctgtctct   92460
catctctgcc cataattaac tgcttctggg cacagtgcat gagttacata gatgagtgtg   92520
ggtaagtttg ccctttctgt ggggggagca tcctttttggt ccactctcag gagggcatcc   92580
tatgttattt ttgtgatatt ttcctaagag ttgtataagc aagtgcatca gccaacttg   92640 tctaccccag ctccctcttg agaccagcag aaactattta tcaactgca gtttacgtaa   92700 cctctctggg cctcaatttc ctcatataaa atgaggataa taaatcgtat ctgctcatag   92760
agttgctgtg gggagtaaag agttcaaatg tatctgtcag tgaaggaaaa aagaaaaaaa   92820
aacaaaaaca aagagttcaa atatatctag cgttcaaaca gaaccaggta tgcagccagt   92880
gcccaatagg tgtatgagtt cctatggcc aatgtaacaa atgaccacaa acttagtggc   92940
ttaaaacaac acacatttat tatttttacag ttctggaggt cagaagtcta agatgatgcc   93000
aggcttggtg gctcaagcct gtaatcccag cactttggga ggctgaggtg gcaggatcac   93060
ttgaggtcag gagttccaga ctagcctagc caacatggtg aaaccccatc tctactaaaa   93120
atacaaaaat tagtcaggca cggtcacgag cacctgtaat cccaactact caggaggctg   93180
aggcaggaga attgcttgaa cccaggaggt ggaggttgca gtgagccgag gttgcagtga   93240
gccgaggttg caccactgca ctccagcctg gcaacagaa cgcgaccctg tttccaagaa   93300
aaaaaaaaag tccgggatga gttttactgg gctgagatca gtgtagacaa ggctgccctc   93360
tctctggagg ctctagggca gaatctgttt ccttgtcttt tccagcttct agaggttgcc   93420
tgcattcctt ggcttgtggc cccttcctcc gtgttcaaag ccattggtgt aacatcttca   93480
ggtctctgtg actccgatcc ttgcttccat cttataagga tccttgtgat ttcattgtac   93540
ccatccagat atcccaggag aatctttcca tcccaagatc cataacttaa atcccatctg   93600
caaagtccct tttgccatgt gtggtaatat attcacagct tgcagagatc aggacatggg   93660
catctttggg aaacgggaag ggggcattat ttgacctaac atcaagagca tgagatgttt   93720
ttgtaaaatg aaacaaatgt tgcagcttcc taatgcagct tcttaggccc acctgcaggc   93780 cccccttgacg ttggttttttc tctacctagg tctgttgtgt cgggtctgga ctcccctgcc   93840
aagactagct ccatggaaaa gaaacttctc atcaaaagca aagagctaca agactctcag   93900
gacaagtgtc acaaggtatt tatttccgca gccggcctcc ttccttgctc caggatcctc   93960
ccgtccgtat atgccaaggg atccgcccgg ggccgctgct ggctctgagc cgcctgatcc   94020
gtagagagtg aggcgctcct gccttcgctg aagtcgcgcc tccagcagct cagagggaga   94080
tgaattcggg ccttgctgtt gctgtaaatc ctttaaatct aaaccagagg aggccctgga   94140
tttaaacagt ccgtttctca gcatgaccca gccagatgtc tgcttcttcc ggcaggtggc   94200
```

-continued

```
ctgggtcctc acctgtggct gagatacatc ccatctgctt tgagtgatgc gaagtctctc    94260
ttcctagtct tttaaaactc ctgcttatgt cactgcggcc actgtgttga ttacgctcaa    94320
cgtctcttaa cattcactgt tcctgcccag aggcaacgct ctggaaacta ataagtcact    94380
gcttgcctgg gactcctaag agtgcagacg aataaatatc tccttgccct gtcctggatt    94440
tgtcctctag atctttgcaa ggagatgggg ggggatcaag atggatttgg gataaaatta    94500
aagtgacgtc tgcaaaaaca aaacaaaaac aaaagcaaac aggtgaaaaa tgatgattgt    94560
ggcttccttg ctaactgggt tagagaagtg atcaagtgtg aaccgggact tgaatgagag    94620
gagtgactta gcatttggtg actgtcctta acgaagaact gtgcgctcct gggcgaagaa    94680
acaatggtat ttccatccca acttaacttt tggcgaatta gccttagccc agaccaccag    94740
gtggtttcgg aggctacttg agatgtgatt gctcctaatg aacctccacg ggccttttta    94800
acctgtcgat gtgtttattt cagatggagc aggaaatgac ccggttacat cggagagtgt    94860
cagaggtgga ggctgtgctt agtcagaagg aggtggagct gaaggcctct gagactcaga    94920
gatccctcct ggagcaggac cttgctacct acatcacaga atgcagtgtg agccttccct    94980
gaagccccct tcccttggag gtggcacttc ctgttgtgtg tgtctcatcc tgtttcatga    95040
tgactccatg aggcacatca cagccaatgg cagagagtag agagagggag agcacaaaag    95100
caagatctgt gttttgcaga gtagtgagag ccaggcgtaa ggtccccaag aaatgagatt    95160
ggactcattt ccagcagaaa gtgcaggtag acggctggta ccatggagtc tggagatggg    95220
agtaattcat ctttgccgca agttgcaaaa gatcttaaca tctcccatcc cagcctctgt    95280
ggtctgcgtt gtgtctgaca tgagcagcct tgagaaccag actcccaact atgtacaaga    95340
aaacttactt tcaatcttcc tgacatcaaa ttttccattg gccagaacca gtgtagtgac    95400
aagaaaatag ccttgaaaac ccagaccctc tgtcattatt taccatgtga ctttcatttt    95460
ttctttcctt cacaagagta gactgtcttc ttctccattg tcttgttaaa tttttcattc    95520
aggtgttttt taatgtgccc aattaaacag tctcaagaag ttgaatcaca catttctaaa    95580
gttttttttca caagggagag gaaatctata gaacgtggct gattaagaat aactgctatg    95640
tttccattcc agacttggct gcctttcagt ggtgggtgaa gttattcagc tatgtatttc    95700
agatatagat ttcagtgcca ttgaagcatt aagggattct tatggatgaa aggtgtccag    95760
gaaaaataag ccaggaggta gaaatagacc acttggagtc ttaaatgaca actgggcaga    95820
ggatatgaag tcattgctac tttgaaagag gcatatgtac tttagggccc acaaataact    95880
gtagaaaaca ctttgtagct atccacatgg tggctgtaat agctactggg tcttaatagg    95940
ttttagtcct gaacatgcaa gtaagtatct cctaggacag gtagatggtg gcaggagaca    96000
ggctgatgca gtttccggct ggactaattt ttgtattgtt agtagagatg gggtttcatc    96060
atgttggtca ggcttgtctt gaactcctga cctcaggtga tccacccgcc tcgccctccc    96120
aaaatgctgg gattacaggc gtgagctact gcgcccagcc atttgtgtct cttaaaaaaa    96180
aaactaagaa aatgaaaaaa atgacattgg ccaattcatt aaaatgccac tcactgactg    96240
tggtatgaaa tggctttccc tttgatggac cgaagtctgt ctcattgtgt gagccacttg    96300
cagggctgag tatgactnnn nnnnnnnnn nnnnnnnnnn nnnnnnnnnn nnnnnnnnnn    96360
nnnnnnnnnn nnnnnnnnnn nnnnnnnnnn nnnnnnnnnn nnnnnnnnnn nnnnnnnnnn    96420
nnnnnnnnnn nnnnnnnnnn nnnnnnnnnn nnnnnnnnnn nnnnnnnnnn nnnnnnnnnn    96480
nnnnnnnnnn nnnnnnnnnn nnnnnnnnnn nnnnnnnnnn nnnnnnnnnn nnnnnnnnnn    96540
```

```
nnnnnnnnnn nnnnnnnnnn nnnnnnnnnn nnnnnnnnnn nnnnnnnnnn nnnnnnnnnn     96600
nnnnnnnnnn nnnnnnnnnn nnnnnnnnnn nnnnnnnnnn nnnnnnnnnn nnnnnnnnnn     96660
nnnnnnnnnn nnnnnnnnnn nnnnnnnnnn nnnnnnnnnn nnnnnnnnnn nnnnnnnnnn     96720
nnnnnnnnnn nnnnnnnnnn nnnnnnnnnn nnnnnnnnnn nnnnnnnnnn nnnnnnnnnn     96780
nnnnnnnnnn nnnnnnnnnn nnnnnnnnnn nnnnnnnnnn nnnnnnnnnn nnnnnnnnnn     96840
nnnnnnnnnn nnnnnnnnnn nnnnnnnnnn nnnnnnnnnn nnnnnnnnnn nnnnnnnnnn     96900
nnnnnnnnnn nnnnnnnnnn nnnnnnnnnn nnnnnnnnnn nnnnnnnnnn nnnnnnnnnn     96960
nnnnnnnnnn nnnnnnnnnn nnnnnnnnnn nnnnnnnnnn nnnnnnnnnn nnnnnnnnnn     97020
nnnnnnnnnn nnnnnnnnnn nnnnnnnnnn nnnnnnnnnn nnnnnnnnnn nnnnnnnnnn     97080
nnnnnnnnnn nnnnnnnnnn nnnnnnnnnn nnnnnnnnnn nnnnnnnnnn nnnntcggcc     97140
tcccaagtgc tgggattaca ggcgtgagcc actgctcctg gcccccacgc cttttttttt     97200
ttttggagac agagtttcac tctgtcaccc agattggagt gctgtggcac aatctcagct     97260
cattgtgtcc tctgcctccc aggttcaagt gattcttgtg cctcagcctc ctgagtaggt     97320
ggaattacag gcgtgcacca caacacctgg ctaattttttg tatttttagt agagatgggg     97380
tttcaccatg ttggccaggc tggtctcgat ctcctgacct ccagtgatcc acttgcctag     97440
gcctcccaaa gtgttgggat tacaggcgtc agccaccatg cctggacccc tctgcccctt     97500
taagcactgc cacatattag atctacgaag gctttatgga tacaatccaa ggaagatgaa     97560
ccttgggcta gtgggataaa actaagcgca tgtagttaga atggaatgat ctggaaacca     97620
ggtcccaagt tggtctaaat tagactcatg ttgactatgt cacactgtaa accagtctaa     97680
atgctaataa gcatgcttga ccaaacactg ccctgcagcc ttcagagagg aagaaggaaa     97740
acataatttg tatcctctct ccctattttc tgagtctatg ggattcaaat tgtagctgcc     97800
atggaaactg tactttggaa tttctagagc ccttaatttt aacttaacat ataaaaacac     97860
ttttgtactg atttttataat tattcatgat ggatgagaaa gtgaatgtct ttgacagtga     97920
gggaagctat ccgaatgcta ttttcttttt tttttttctt tcataaagat gcatatattt     97980
gcatgcttta tttacctggg gctaactctt gcatcttttg cagattccga caccatagct     98040
gagttacagg agctccagcc ttcggcaaag gacttcgaag tcagaagtct tgtaggttgt     98100
ggtcactttg ctgaagtgca ggtggtaaga gagaaagcaa ccggggacat ctatgctatg     98160
aaagtgatga agaagaaggc tttattggcc caggagcagg taggaggatt ttaacatcat     98220
gcttttccac tttctgtacc ggagtgttca ttgcaaagac gataatctgc tgcactggcg     98280
tctaggatca agcacgtttt cctctgtgac tctatattta attatagttg gggcaaaaag     98340
gtctctcatg ttcttagctc atcttcttga actgatgttg gctaattttg aaggctcaca     98400
aattcctctt gatgtatcat gtttctatcg ttgtaattta tttcagaacc aaggtggcct     98460
tttagctaat gaatttaaga tgatcttttta tgaccattag ctgaggactc aggatataca     98520
tatggtgggg tgaatcagat tgcttttgta cacgctttag gtatttgtgt tgtgggcata     98580
tggatttggt tttaaaacag gcctttgaag aaatcaaata acattctttg ttatgtggct     98640
agggagttgc ttgtttgaga gcaggtagaa cgttatcttt tttgttgtgg tatttttctt     98700
tcttttaaac aaggctactg tctctagaca tattgattca tttgctgtgt tttagagaga     98760
tggccgtcag ccttggaatt cagagagtaa tttattactt acagacattt tagtgcacat     98820
gatatgtctg ataatgtacc cagctctgca ggaagcttgc aaaaggaata gaagtcccat     98880
ggttgctatt tcagtgtttt aaaaacaacc ttggaaagtg gaggaaaaat gcaaatgtat     98940
```

-continued

```
aaagcaggtg cttaccagct aaagtatcac agaagtggga gagcaattag caaattaatt   99000
aacgatgatg tgaggggaga tgttgtgggt gagcaaggga cagttaggga cagttctcac   99060
cgatgggggg aaatgtaggt tctcggcaga gagaagtgat gagaacatgt tgggtagaag   99120
tgtgacattc tggagtacta gaatgctatg caagtgtgtg tgtgtgggtg tgtgtgtgtg   99180
ttcagtggtt cagaacagac tgggaaatgg cgaaatgagg acatttgggt ggggaggggg   99240
aaatgggtgg gaaactcaag aacctttttt taaaaaattg tggtaaaata tatataacat   99300
aaagtgtacc attttaacca tttttaaatg tgcaactgag tggtattcag tgcattcatg   99360
atgttgtaca accatgaccg ctctccattt ctagaatttt tctatcatcc caaacagaaa   99420
ctctctatcc attatacaat acctccccat tcccccaaga accagttttt gaattgcagt   99480
ttactttgtg aggctgttgg ggattattta ggcctctgga aggaggaggt tgggatcaga   99540
gtctggccct gtggacttca atgactttgt gtggcctcca atcagagaag cagcggaggg   99600
caggaagctg cttgtcagaa tctgagagtg atgtggcttc tttgtttagc aataaaatgt   99660
gagcacataa tagaaaggaa aagtgacagg acatggcaga taatttggaa gagaggagtg   99720
gaagatgctc actcagcctc ccagctcctg agaaagaact gtgtctcatc agttcatact   99780
acctgagcat ctgttgtatc tggtgtgttt ctaggtacct ggagaagagg cattacgtgt   99840
agccctgacc ttgtgatgct tatgtttttg atgggaaata gtgcgtgtaa aagaaaata   99900 atccaacagg ccacacggca ggcaaacaat agagatattc aaataggtat accttcctcc   99960
aggtgaatgg cctgaaatga ccgtgtggaa gtgtgggctg ggggcttata aaattataca  100020
catacaggcg ctaactaaag ccgcctattc attccttaag aggatgcata gaaaagaaaa  100080
gtagggtcct ttaactgagc ccatttgaat ttagggcctg agagaagcag cacaagcagt  100140
gaagggaaga aaaagaagtg cccgagagga gggagggatt ctgttctgca gacaaggcct  100200
gccgcctggg agaggcccgc acgcccaccc agggttctct gacagctgga aggggtcttc  100260
agagactgtt tatattttat ttatttattt atttatttat tntgagacag agtctctgtc  100320
acccaggctg gagtgcagtg gtgcgatctc agctcactgc aagctccgcc tcccaggttc  100380
acaccattct cctatctcag cctcccgagt agctgggact acaggcgcct gccacaatgc  100440
ccggctaatt ttttttgtaat tttagtagag acggggtttt acctgcgtta gccaggtatg  100500
gtcttgatct cctgacctca tgattcgccc acctcggcct cccaaagtgc tgggattaca  100560
ggtgtgagcc actgtgcctg gccgactgtt tctactattt tagagagagg gtctcactgt  100620
catctgtgct ggaatgcagt gatgcagtca tagctcactg caccctcaaa ctcctgggct  100680
taagcgaccc tcccgcctca gcctcttaag tagctgggac cataggcatg tgctgccaca  100740
cccagttaac tttattattt atttatttat ttagagaatg agtctcattc tgttgcccag  100800
gctagaggtg cagtggcacg atctcggctc actgcaaccc cgcctcccag gttcaagcga  100860
ttcttcttgc tcagcctcct gaatagctgg gattacaggc acctgccacc acacctggct  100920 aattttttgta tttttagtgc agagggggggn nnnnnnnnn nnnnnnnnnn nnnnnnnnnn  100980
nnnnnnnnnn nnnnnnnnnn nnnnnnnnnn nnnnnnnnnn nnnnnnnnnn nnnnnnnnnn  101040
nnnnnnnnnn nnnnnnnnnn nnnnnnnnnn nnnnnnnnnn nnnnnnnnnn nnnnnnnnnn  101100
nnnnnnnnnn nnnnnnnnnn nnnnnnnnnn nnnnnnnnnn nnnnnnnnnn nnnnnnnnnn  101160
nnnnnnnnnn nnnnnnnnnn nnnnnnnnnn nnnnnnnnnn nnnnnnnnnn nnnnnnnnnn  101220
nnnnnnnnnn nnnnnnnnnn nnnnnnnnnn nnnnnnnnnn nnnnnnnnnn nnnnnnnnnn  101280
```

```
nnnnnnnnnn nnnnnnnnnn nnnnnnnnnn nnnnnnnnnn nnnnnnnnnn nnnnnnnnnn    101340
nnnnnnnnnn nnnnnnnnnn nnnnnnnnnn nnnnnnnnnn nnnnnnnnnn nnnnnnnnnn    101400
nnnnnnnnnn nnnnnnnnnn nnnnnnnnnn nnnnnnnnnn nnnnnnnnnn nnnnnnnnnn    101460
nnnnnnnnnn nnnnnnnnnn nnnnnnnnnn nnnnnnnnnn nnnnnnnnnn nnnnnnnnnn    101520
nnnnnnnnnn nnnnnnnnnn nnnnnnnnnn nnnnnnnnnn nnnnnnnnnn nnnnnnnnnn    101580
nnnnnnnnnn nnnnnnnnnn nnnnnnnnnn nnnnnnnnnn nnnnnnnnnn nnnnnnnnnn    101640
nnnnnnnnnn nnnnnnnnnn nnnnnnnnnn nnnnnnnnnn nnnnnnnnnn nnnnnnnnnn    101700
nnnnnnnnnn nnnnnnnnnn nnnnnnnnnn nnnnnnnnnn nnnnnnnnnn nnnnnnnngt    101760
nnnnnnnnnn nnnnnnnnnn nnnnnnnnnn nnnnnnnnnn nnnnnnnnnn nnnnnnnnnn    101820
nnnnnnnnnn nnnnnnnnnn nnnnnnnnnn nnnnnnnnnn nnnnnnnnnn nnnnnnnnnn    101880
nnnnnnnnnn nnnnnnnnnn nnnnnnnnnn nnnnnnnnnn nnnnnnnnnn nnnnnnnnnn    101940
nnnnnnnnnn nnnnnnnnnn nnnnnnnnnn nnnnnnnnnn nnnnnnnnnn nnnnnnnnnn    102000
nnnnnnnnnn nnnnnnnnnn nnnnnnnnnn nnnnnnnnnn nnnnnnnnnn nnnnnnnnnn    102060
nnnnnnnnnn nnnnnnnnnn nnnnnnnnnn nnnnnnnnnn nnnnnnnnnn nnnnnnnnnn    102120
nnnnnnnnnn nnnnnnnnnn nnnnnnnnnn nnnnnnnnnn nnnnnnnnnn nnnnnnnnnn    102180
nnnnnnnnnn nnnnnnnnnn nnnnnnnnnn nnnnnnnnnn nnnnnnnnnn nnnnnnnnnn    102240
nnnnnnnnnn nnnnnnnnnn nnnnnnnnnn nnnnnnnnnn nnnnnnnnnn nnnnnnnnnn    102300
nnnnnnnnnn nnnnnnnnnn nnnnnnnnnn nnnnnnnnnn nnnnnnnnnn nnnnnnnnnn    102360
nnnnnnnnnn nnnnnnnnnn nnnnnnnnnn nnnnnnnnnn nnnnnnnnnn nnnnnnnnnn    102420
nnnnnnnnnn nnnnnnnnnn nnnnnnnnnn nnnnnnnnnn nnnnnnnnnn nnnnnnnnnn    102480
nnnnnnnnnn nnnnnnnnnn nnnnnnnnnn nnnnnnnnnn nnnnnnnnnn nnnnnnnnnn    102540
nnnnnnnnnn nnnnnnnnnn nnnnnnnnnn nnnnnnnnnn nnnnnnnnnn nnnnnnnnnn    102600
nnnnnnnnnn nnnnnnnnnn nnnnnnnnnn nnnnnnnnnn nnnnnnnnnn nnnnnnnnnn    102660
nnnnnnnnnn nnnnnnnnnn nnnnnnnnnn nnnnnnnnnn nnnnnnnnnn nnnnnnnnnn    102720
nnnnnnnnnn nnnnnnnnnn nnnnnnnnnn nnnnnnnnnn nnnnnnnnnn nnnnnnnnnn    102780
nnnnnnnnnn nnnnnnnnnn nnnnnnnnnn nnnnnntata tgtgcataca gaatatatac    102840
acagaaatat atatgtacac atgcatagaa tatatttaca tatatatgca tatatataat    102900
ttatttattt taagcagttg atttatacag tttttgtttt tgtttttttt ttgagacaga    102960
gtctcactct gtcacccagg ctagagtgca gtggcgagat ctcagctcac tgcaacctct    103020
gcccccgggt tccagtgatt ctcctgcctc agctccacaa gtagcacacc accatgccca    103080
gctaattttt gtattttttt tagtagagac gaggtttcat catgttggcc aggctggtct    103140
cgaactcctg acctcaagtg atccgcccgc cttggcctcc caaagtgctg ggatttcagg    103200
cgtgagccac cacacctggc tcccataatg tcttttagaa taaaacgatc gagttgagga    103260
tcacacgtga cacttaattg tcctgtctct ttagtctcct tcaatctgga gcagttcttt    103320
gatttttcct ggactctcat gaccttgaca attctgatga ttataggcca gttatttgt    103380
aaaatttgaa tttgtctgat gttgcttatg tttagattta gggtcttggt ctttggccgg    103440
aatatctcag acaagatgct ctgttcttat tgcatcagag cagaagactc tctgtttcag    103500
ttgatcacat ttatgttgat gctcactttg atcacttgat taaggtggtg tcagttatgc    103560
cttctctactt gtagggttac tccttcctcc ttcgtgattt tatttatttt attttcttc    103620
gagacagggt cttgcttggt tgcccaagct ggagtgcagt ggtgggatct tggctcactg    103680
```

```
cagccttgaa ctcctgggct caagtaatcc acctgccaca gcctcctgag taactgggac    103740
tgtaagcgaa caccaccaca cccagctact ttttgtattg tagagatggg gtctcactgt    103800
gttgtccagg ctggtctgta actcctggcc tcaagcagtc ttccggcctt ggcctcccga    103860
agtgctggga ttacaggcat gagccactgc acccagcctc ctttgtaatt aaaaaagtat    103920
tttatgggga gttactttca agtgatggaa atattttata tctatgtgga cttggatttt    103980
cctatttcag tcagtgagtt ataatccatt tctgtcacta gttttatact taaattgttc    104040
ccaacttggc cactgagaac cttttaggt tagcttttgt gtcctttca catgtctcca      104100
agattcattg aatactttcc tgctttctgg tatagcaaga tgttcaggtt cttttggtac    104160
ttttactttc tctgccctgg ctctggcatc agtcatttct cagaggagcc ctgtgccttt    104220
cagtggacaa tggtgtttag aggccaagat ctggacattg ggtgttttca ttgctaccgg    104280
tgtgtcacta ctcccagacc cctttcagtg gacagcacta aggaatacac atacgtatat    104340
acaatatatc cacctacaca tgtgcgtgca ctcacacaca cacatataca ttacatctat    104400
atttgtgtat ccatgtctat atattgaaaa ttgtggctgg gcacagtggc ttatgccttt    104460
aatctcagca ttttgggagg ctgaggcaag aggatcacct gaagccagga gttcaacacc    104520
agcttgggaa acagagagag actctgtctc tacaaaaata aaaagggaaa accatgagtt    104580
cacacccgtg cccccagttc caatccaact tcacagggtt cattttagtt ttcaccctt     104640
ccatgtttgt aattctcttc tctgacatta tacccttaat atgtttactt attttatgca    104700
tctgtatgca tccaatctac tgtctttgtt ggtatcccac ctcccttgg tgggtccaga     104760
taatctgctc tgggttgccc tttcacgtgg atgtcttcct tacccgtgt gggcctgtga     104820
tactgggctg ccccacaca tgagtgctgc cctcctcacg ttgcttggga cggcactgtg     104880
tcctgggcca ccatgacttt tctcataact agcgtggatg cttaccttgt tccacaccag    104940
tgaatggctt caggaagaga agaggaagag aaaaatattt acatttaaag aaaggtagtt    105000
taaagaaata tgttaggtaa agaattgagc aggtaatata cggagctggc aaaaattgtg    105060
accaaagtag gtgaatgatt gagatttatg caattctggg ctaagtgaca gcccttccc     105120
tttcccttcc cttcccctc ccttcccttt tcttcccttt cccttccctt tccttccctt    105180
tcccttcccc ttcccttccc tttccttccc tttccctctt cttccttcct tccttctgtt   105240
ttcttttccc ttcttttcct tgcctttttt ttttttttaa agctagaaac atcagtttag    105300
gcataaagac agaggaaaag gcttcttttt cctctcacag ttctttataa ttgtctaagc    105360
agtttctttt ttccctaggt ttcatttttt gaggaagagc ggaacatatt atctcgaagc    105420
acaagcccgg gatcccccaa ttannnnnnn nnnnnnnnn nnnnnnnnnn nnnnnnnnnn      105480
nnnnnnnnnn nnnnnnnnnn nnnnnnnnnn nnnnnnnnnn nnnnnnnnnn nnnnnnnnnn    105540
nnnnnnnnnn nnnnnnnnnn nnnnnnnnnn nnnnnnnnnn nnnnnnnnnn nnnnnnnnnn    105600
nnnnnnnnnn nnnnnnnnnn nnnnnnnnnn nnnnnnnnnn nnnnnnnnnn nnnnnnnnnn    105660
nnnnnnnnnn nnnnnnnnnn nnnnnnnnnn nnnnnnnnnn nnnnnnnnnn nnnnnnnnnn    105720
nnnnnnnnnn nnnnnnnnnn nnnnnnnnnn nnnnnnnnnn nnnnnnnnnn nnnnnnnnnn    105780
nnnnnnnnnn nnnnnnnnnn nnnnnnnnnn nnnnnnnnnn nnnnnnnnnn nnnnnnnnnn    105840
nnnnnnnnnn nnnnnnnnnn nnnnnnnnnn nnnnnnnnnn nnnnnnnnnn nnnnnnnnnn    105900
nnnnnnnnnn nnnnnnnnnn nnnnnnnnnn nnnnnnnnnn nnnnnnnnnn nnnnnnnnnn    105960
nnnnnnnnnn nnnnnnnnnn nnnnnnnnnn nnnnnnnnnn nnnnnnnnnn nnnnnnnnnn    106020
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 106080 |
| nnnnnnnnnn | nnnnnnnnnn | nnnnnnnnnn | nnnnnnnnnn | nnnnnnnnnn | nnnnnnnnnn | 106140 |
| nnnnnnnnnn | nnnnnnnnnn | nnnnnnnnnn | nnnnnnnnnn | nnnnnnnnnn | nnnnnnnnnn | 106200 |
| nnnnnnnnnn | nnnnnnnnnn | nnnnnnnnnn | nnnnnnnnnn | nnnnnnnnnn | nnnnnnnnnn | 106260 |
| nnnnnnnnnn | nnnnnnnnnn | nnnnnnnnnn | nnnnnnnnnn | nnnnnnnnnn | nnnnnnnnnn | 106320 |
| nnnnnnnnnn | nnnnnnnnnn | nnnnnnnnnn | nnnnnnnnnn | nnnnnnnnnn | nnnnnnnnnn | 106380 |
| nnnnnnnnnn | nnnnnnnnnn | nnnnnnnnnn | nnnnnnnnnn | nnnnnnnnnn | nnnnnnnnnn | 106440 |
| nnnnnnnnnn | nnnnnnnnnn | nnnnnnnnnn | nnnnnnnnnn | nnnnnnnnnn | nnnatggagt | 106500 |
| cttgctctgt | tgtccaggct | ggagtgcagt | ggtgtgatct | tggctcactg | caacctccgc | 106560 |
| ctcctgggtt | gaagcgattc | tcctgcctca | gcccctgaa  | tagctgggat | tacaggcatg | 106620 |
| tgccaccacg | cctggctaat | ttttgtattt | ttaatagaca | cggggtttca | ccatgttggt | 106680 |
| caggctggtc | tcgaactcct | gacctcaggt | gatctgcatg | cctaggcctc | ccaaagtgct | 106740 |
| gggattacag | gcatgagcca | ctgcgcctgg | ccaacttatt | taactttttt | gagacagggt | 106800 |
| ctcactctgt | cacccaggct | ggagtgcagt | ggcatgatca | tggctcactg | cagcctcaaa | 106860 |
| ttgcagggct | caagtgattc | tcctgcttca | ccttcctgat | tagctgggac | aacaggtaca | 106920 |
| aaccaccatg | cctagctaat | ttttaaattt | tctgtagaga | ctagggtctc | actatgttgc | 106980 |
| ccaggctggt | ttcgaactcc | tgagctcaag | agatcttcct | gccttggcct | tccaaagtgc | 107040 |
| tgggattaca | ggtgtgagcc | ccatgcccag | ctccggtggg | ggatatttct | atatccacat | 107100 |
| gtgtatagtt | tactttataa | aaatggtatg | ttactctgtg | cttggctctc | cagcttgctg | 107160 |
| ttgcctttca | ccagtgtatc | ccagacatcc | tttcttcctt | gtcagtaacg | caggtctact | 107220 |
| ttattctttg | agcagtggca | taattttccc | tgatgtgtat | atatcataag | ttagagaatg | 107280 |
| ctaaaattca | ttttggggcc | ttgtttaggt | tcttgaggga | ttaaattcct | aaatttaaca | 107340 |
| agtgtatcct | ggaaacaatt | tttgttcctg | attcagccct | taaaagagga | ctatcatgtt | 107400 |
| accttgaatg | gagataaaca | ggctcacgta | agagaaaagg | gtaagaggga | tgaactccca | 107460 |
| cttatcttaa | acttctactg | gcccgttttt | ggggaatttg | ctgcttttat | tcctgaccta | 107520 |
| aaataaataa | gtttatgtgt | cttggtttca | tattagttga | gaacccagtg | cctggagaga | 107580 |
| agttttcctt | gtcctctgag | tgaggacatt | cacatatgaa | tctattggca | gactggcttt | 107640 |
| gactgaccac | acgtgccttc | agaaccaatg | ccacagctct | taggtttatg | gcctgaaaca | 107700 |
| cccttttcctt | acatattgcc | ttagaaactt | tccttccttg | agacatgggg | catggaaccc | 107760 |
| tcaccttcac | agatgacctt | ggtgtgtttc | tagggttgct | ggtgttccag | gacatctgtt | 107820 |
| gcagatgcag | tatttacctt | gtgctctctg | catcataagc | agcttctcat | gtttgaatgt | 107880 |
| attaacagac | ttttaattt  | ttttattttt | gagacaaagt | ctcactctgt | cacccaggct | 107940 |
| agtgttaccc | aggctggagt | gcaatgnnnn | nnnnnnnnnn | nnnnnnnnnn | nnnnnnnnnn | 108000 |
| nnnnnnnnnn | nnnnnnnnnn | nnnnnnnnnn | nnnnnnnnnn | nnnnnnnnnn | nnnnnnnnnn | 108060 |
| nnnnnnnnnn | nnnnnnnnnn | nnnnnnnnnn | nnnnnnnnnn | nnnnnnnnnn | nnnnnnnnnn | 108120 |
| nnnnnnnnnn | nnnnnnnnnn | nnnnnnnnnn | nnnnnnnnnn | nnnnnnnnnn | nnnnnnnnnn | 108180 |
| nnnnnnnnnn | nnnnnnnnnn | nnnnnnnnnn | nnnnnnnnnn | nnnnnnnnnn | nnnnnnnnnn | 108240 |
| nnnnnnnnnn | nnnnnnnnnn | nnnnnnnnnn | nnnnnnnnnn | nnnnnnnnnn | nnnnnnnnnn | 108300 |
| nnnnnnnnnn | nnnnnnnnnn | nnnnnnnnnn | nnnnnnnnnn | nnnnnnnnnn | nnnnnnnnnn | 108360 |
| nnnnnnnnnn | nnnnnnnnnn | nnnnnnnnnn | nnnnnnnnnn | nnnnnnnnnn | nnnnnnnnnn | 108420 |

```
nnnnnnnnnn nnnnnnnnnn nnnnnnnnnn nnnnnnnnnn nnnnnnnnnn nnnnnnnnnn 108480
nnnnnnnnnn nnnnnnnnnn nnnnnnnnnn nnnnnnnnnn nnnnnnnnnn nnnnnnnnnn 108540
nnnnnnnnnn nnnnnnnnnn nnnnnnnnnn nnnnnnnnnn nnnnnnnnnn nnnnnnnnnn 108600
nnnnnnnnnn nnnnnnnnnn nnnnnnnnnn nnnnnnnnnn nnnnnnnnnn nnnnnnnnnn 108660
nnnnnnnnnn nnnnnnnnnn nnnnnnnnnn nnnnnnnnnn nnnnnnnnnn nnnnnnnnnn 108720
nnnnnnnnnn nnnnnnnnnn nnnnnnnnnn nnnnnnnnnn nnnnnnnnnn nnnnnnnnnn 108780
nnnnnnnnnn nnnnnnnnnn nnnnnnnnnn nnnnnnnnnn nnnnnnnnnn nnnnnnnnnn 108840
nnnnnnnnnn nnnnnnnnnn nnnnnnnnnn nnnnnnnnnn nnnnnnnnnn nnnnnnnnnn 108900
nnnnnnnnnn nnnnnnnnnn nnnnnnnnnn nnnnnnnnnn nnnnnnnnnn nnnnnnnnnn 108960
nnnnnnnnnn nnnnnnnnnn nnnnnnnnnn nnnnnnnnnn nnnnnnnnnn nnnnnnnnnn 109020
nnnnnnnnnn nnnnnnnnnn nnnnnnnnnn nnnnnnnnnn nnnnnnnnnn nnnnnnnnnn 109080
nnnnnnnnnn nnnnnnnnnn nnnnnnnnnn nnnnnnnnnn nnnnnnnnnn nnnnnnnnnn 109140
nnnnnnnnnn nnnnnnnnnn nnnnnnnnnn nnnnnnnnnn nnnnnnnnnn nnnnnnnnnn 109200
nnnnnnnnnn nnnnnnnnnn nnnnnnnnnn nnnnnnnnnn nnnnnnnnnn nnnnnnnnnn 109260
nnnnnnnnnn nnnnnnnnnn nnnnnnnnnn nnnnnnnnnn nnnnnnnnnn nnnnnnnnnn 109320
nnnnnnnnnn nnnnnnnnnn nnnnnnnnnn nnnnnnnnnn nnnnnnnnnn nnnnnnnnnn 109380
nnnnnnnnnn nnnnnnnnnn nnnnnnnnnn nnnnnnnnnn nnnnnnnnnn nnnnnnnnnn 109440
nnnnnnnnnn nnnnnnnnnn nnnnnnnnnn nnnnnnnnnn nnnnnnnnnn nnnnnnnnnn 109500
nnnnnnnnnn nnnnnnnnnn nnnnnnnnnn nnnnnnnnnn nnnnnnnnnn nnnnnnnnnn 109560
nnnnnnnnnn nnnnnnnnnn nnnnnnnnnn nnnnnnnnnn nnnnnnnnnn nnnnnnnnnn 109620
nnnnnnnnnn nnnnnnnnnn nnnnnnnnnn nnnnnnnnnn nnnnnnnnnn nnnnnnnnnn 109680
nnnnnnnnnn nnnnnnnnnn nnnnnnnnnn nnnnnnnnnn nnnnnnnnnn nnnnnnnnnn 109740
nnnnnnnnnn nnnnnnnnnn nnnnnnnnnn nnnnnnnnnn nnnnnnnnnn nnnnnnnnnn 109800
nnnnnnnnnn nnnnnnnnnn nnnnnnnnnn nnnnnnnnnn nnnnnnnnnn nnnnnnnnnn 109860
nnnnnnnnnn nnnnnnnnnn nnnnnnnnnn nnnnnnnnnn nnnnnnnnnn nnnnnnnnnn 109920
nnnnnnnnnn nnnnnnnnnn nnnnnnnnnn nnnnnnnnnn nnnnnnnnnn nnnnnnnnnn 109980
nnnnnnnnnn nnnnnnnnnn nnnnnnnnnn nnnnnnnnnn nnnnnnnnnn nnnnnnnnnn 110040
nnnnnnnnnn nnnnnnnnnn nnnnnnnnnn nnnnnnnnnn nnnnnnnnnn nnnnnnnnnn 110100
nnnnnnnnnn nnnnnnnnnn nnnnnnnnnn nnnnnnnnnn nnnnnnnnnn nnnnnnnnnn 110160
nnnnnnnnnn nnnnnnnnnn nnnnnnnnnn nnnnnnnnnn nnnnnnnnnn nnnnnnnnnn 110220
nnnnnnnnnn nnnnnnnnnn nnnnnnnnnn nnnnnnnnnn nnnnnnnnnn nnnnnnnnnn 110280
nnnnnnnnnn nnnnnnnnnn nnnnnnnnnn nnnnnnnnnn nnnnnnnnnn nnnnnnnnnn 110340
nnnnnnnnnn nnnnnnnnnn nnnnnnnnnn nnnnnnnnnn nnnnnnnnnn nnnnnnnnnn 110400
nnnnnnnnnn nnnnnnnnnn nnnnnnnnnn nnnnnnnnnn nnnnnnnnnn nnnnnnnnnn 110460
nnnnnnnnnn nnnnnnnnnn nnnnnnnnnn nnnnnnnnnn nnnnnnnnnn nnnnnnnnnn 110520
nnnnnnnnnn nnnnnnnnnn nnnnnnnnnn nnnnnnnnnn nnnnnnnnnn nnnnnnnnnn 110580
nnnnnnnnnn nnnnnnnnnn nnnnnnnnnn nnnnnnnnnn nnnnnnnnnn nnnnnnnnnn 110640
nnnnnnnnnn nnnnnnnnnn nnnnnnnnnn nnnnnnnnnn nnnnnnnnnn nnnnnnnnnn 110700
nnnnnnnnnn nnnnnnnnnn nnnnnnnnnn nnnnnnnnnn nnnnnnnnnn nnnnnnnnnn 110760
```

```
nnnnnnnnnn nnnnnnnnnn nnnnnnnnnn nnnnnnnnnn nnnnnnnnnn nnnnnnnnnn    110820
nnnnnnnnnn nnnnnnnnnn nnnnnnnnnn nnnnnnnnnn nnnnnnnnnn nnnnnnnnnn    110880
nnnnnnnnnn nnnnnnnnnn nnnnnnnnnn nnnnnnnnnn nnnnnnnnnn nnnnnnnnnn    110940
nnnnnnnnnn nnnnnnnnnn nnnnnnnnnn nnnnnnnnnn nnnnnnnnnn nnnnnnnnnn    111000
nnnnnnnnnn nnnnnnnnnn nnnnnnnnnn nnnnnnnnnn nnnnnnnnnn nnnnnnnnnn    111060
nnnnnnnnnn nnnnnnnnnn nnnnnnnnnn nnnnnnnnnn nnnnnnnnnn nnnnnnnnnn    111120
nnnnnnnnnn nnnnnnnnnn nnnnnnnnnn nnnnnnnnnn nnnnnnnnnn nnnnnnnnnn    111180
nnnnnnnnnn nnnnnnnnnn nnnnnnnnnn nnnnnnnnnn nnnnnnnnnn nnnnnnnnnn    111240
nnnnnnnnnn nnnnnnnnnn nnnnnnnnnn nnnnnnnnnn nnnnnnnnnn nnnnnnnnnn    111300
nnnnnnnnnn nnnnnnnnnn nnnnnnnnnn nnnnnnnnnn nnnnnnnnnn nnnnnnnnnn    111360
nnnnnnnnnn nnnnnnnnnn nnnnnnnnnn nnnnnnnnnn nnnnnnnnnn nnnnnnnnnn    111420
nnnnnnnnnn nnnnnnnnnn nnnnnnnnnn nnnnnnnnnn atattgaatc tgtgcaaagt    111480
cagctatcag tctgattgcc ctatcccaca aattgcatcc caggagatga ttagatgcaa    111540
taggtgaaag ttttcatgtt cctcagtggc attcagtgca tgaacaacca ttgtccacct    111600
aattcctctg catctacagc aagaaataga attttttgtgg agacttaaca tgctgtgtct    111660
tacttacata tgtatgcaaa aaaaaaaaaa aaagtcactt ttttcttt ttgagaccga      111720 gtcttgctct gtggcccagg ctggagcaca atcacggctc actgtaacct ccgctaccca    111780
ggttcaagtg attctcctgc ctcagcctcc ttgagtagct gggactacag gcacgtgcca    111840
ccatgcccag ctaatttttg tactttagt agaaatgggg ttttgccatg ttggccaggc     111900
tggtctcgaa ctcctgacct caggtgatcc acctgtcttg gcctcccaaa gtgtgggatt    111960
acaggcgtga accaccaacg cctggccctg aagatacatt ttaaatcaat gaaaaaaaac    112020
aacaggattc tacctcctat ggtatatccc tcctggctgt ctcttctctc cagtcttgcc    112080
tctgctgtgt gggtttcagg catccatctt ctctactctg aattactgtg ataacctctg    112140
aagtattttc cctgccatct gtctggccct tctcccaggt cttccacata ctgcagccaa    112200
gtcagcccgc tgttgaaacc cttcaagact ccctgctgtc tctggatga agtccagact     112260 cttccacgtg acttaccagg ccttttcttgc acttgtcccc agccacttac tgtttctctc   112320
tttctacctt aacatcctga acttcctttg gttcttgac cttgcctctg accttttttcc   112380 atgctgttca ctctttccct gttccacttg ctaactcctc tttctcttc tgggttggat    112440 cagatttcac ttcttccaga agcccttcct agaccctata cttctggaat ggcgcctttt    112500
gactgtacgc tcattgcacc ctgtacttct ccttttatgag tgggtgctgg tctgtcccac   112560
taggctactt catccataaa gggagagtag agctttacca agtcaatgct taagcaatat    112620
ttattggatg aatgtgtgat taatttcata gaaatttgat gtgcattcaa atttacttat    112680
tgtattacgg aacttgcatt atattctcag tggagttatt ttctttcacg tgtgtaattc    112740
aagatagact cagtgagatt ttcaaaattt ggaatgcagt gcaaggaaat tgaacttgag    112800
ttcttttgca ttttgatggt taaaaatttc ccatttgtgg tgacatacca caataagcca    112860
gtgaatgtgg cttattgttt tctggtctat agaaaattgt cgcaaactct gtcataatgt    112920
ctggttctat ataacaaagc tagtcctgta ttctgcatgt ggctgatgga aacagtgctc    112980
tgttgatctg gttcatgaag aaatctgttc aattctgcat aacagatgcc ttcatcagtg    113040
tccttccatg aaggagctga tcttcacaaa gaacacatag ttttgcatcc caccacttgc    113100
agtnnnnnnn nnnnnnnnnn nnnnnnnnnn nnnnnnnnnn nnnnnnnnnn nnnnnnnnnn    113160
```

-continued

```
nnnnnnnnnn nnnnnnnnnn nnnnnnnnnn nnnnnnnnnn nnnnnnnnnn nnnnnnnnnn  113220
nnnnnnnnnn nnnnnnnnnn nnnnnnnnnn nnnnnnnnnn nnnnnnnnnn nnnnnnnnnn  113280
nnnnnnnnnn nnnnnnnnnn nnnnnnnnnn nnnnnnnnnn nnnnnnnnnn nnnnnnnnnn  113340
nnnnnnnnnn nnnnnnnnnn nnnnnnnnnn nnnnnnnnnn nnnnnnnnnn nnnnnnnnnn  113400
nnnnnnncct actgtggttt tcttcagaat taccctttgct ctgagcctgc aattgactca  113460
tgaacttctt ttccatgttc taaccttaca atgacttcct tgtgttcact ccaaatgttt  113520
ttccctggtt gcatgtagag atgtattagc taaggtacat gcttagctgc tgtatcaaag  113580
agaccctaat gtacaaccca ggctggtaga gcagctctgc tgtatgtgtt aattcaggga  113640
cccaggttcc ttccatgttg tgactccccc cttcctagg atgttgtctt cttttacatg  113700
gctgaagttg ggccatttca tgtctctgtt ccagctgcct ggtaggaaaa agaacagaa  113760 attcagagta agcaaattct ttttctatag atggatgcgg aagttggaca catcatttcc  113820
tctcacattt tctcggccag aacgtagtca tgtgactgca cgtctagctg ctaaggagac  113880
tgggaattta ctgtcggctg tgtggcctct gtcaagctaa aattcttatt actgtggaat  113940
aagggaagga tggatttggg ggcacaatta atagtctgtc acagaggcta aaacagctgc  114000
ttttggctgg gcacggtggc tcacacatgt aatttcagca ctttgggagg ccgaggcaag  114060
tggatcactt gagatcagga atttgagacc agcctggcca acatggtgaa accctgtctc  114120
tcctaaaaat atagaaatta gccgggcatg gtggcgggta cctgtaatcc gagctactcc  114180
agaggttgag gcaggagaat tgcttgaacc tggaaggcag aggttgcagt gagccaagat  114240
ggtgccactg cactccagcc tgggcgacag agcaagactc catctcaaaa aaaaaaaaaa  114300
aggttaaata aacagctgct tttgtaggtg atacaaggta cagctaagct ttgaagccag  114360
gcctgtagtt tcaccttcca tattcttact caaggcatta tacttctgga tctgaaacca  114420
ctggatctga tgccctgctt gggatgagtt ctttatatta tcttgctttc aacccacacc  114480
tgtgtaattt tatgggcagc gttgtttcc tatataggaa caatttgaaa gtgggctgtt  114540
tctaggcttt catgaatagc aggctatgct gtcattggga atctggaggg agttaatgaa  114600
cacaacttca ttgtttactt tagtgaaatg tggcagctta tgatagtttt gacagtgaga  114660
catgtgctgt tttgatctct cagctaagat tatctgattt ttcaggcatg tctcaaaact  114720
caccaggcct gctcacatgc tgctgcttct gaagccaggg tttggaaacc agctgcccat  114780
cagaatgagg ctgtgactta gaatattggt tcttgtttta ttaccattcc ttgtttggtc  114840
tctccagagt cactggcctt ttccgcttca attttcttat cggtgaaatg agatattaat  114900
tcctcttatt gacttcaatt caattgctga gtgtattgtt gcctttggga agttctttga  114960
gttttctgtg cctttgaaat agttgttttt ttttattctg gtgttttgag gcatgtttca  115020
agtgagtgca tttacacttc taccatttta ggagccacaa ttcagttatg ttgtcccagc  115080
ttgcttggcc ccatccccag agtttctgat tcagtaggtc tggggtgggg cccaataatt  115140
tgcatttctt cttctttttt cgagacagag tctgactgtg tcatccaagc tggagtgcag  115200
tggcacgatc gtagctcatt gtagcctcaa actcctgggc tcaagccgtc ctcccacctc  115260
accctcctga gtagctggga ctataggcat atactaccat gccctgccac cttttttaatt  115320 ttttgtaagg atgggggtct cactgtgttg ctcaggctgg tcttgaattc ctgggctgaa  115380
gtgatcctcc tgcttcagcc tcccaaaatg ccggcattcc tggcatgagc cactgcactt  115440
ggccaagact ttgcatttct aactagtttc caggtaatgc tgctgctggt gtagggacct  115500
```

```
cattttgaga accattgttc tatagctgta gctatagtta gtttctggtt atagcttctt   115560 cctttgtcc  cttcagtaat agtgtacaca tccgaaatcc ctgtccttgc tctttcaggc   115620
ccaggcatgg tatctggtcc tcttctgttg ctagccctgg ggtgcttcat catcccaagt   115680
ttatttttct tctcctaacc tgaacctttg taaatagccc cttccctaat gaacgtcctc   115740
aattccctgt tttgcgtgtc ctgtctgttt cttggcaaga ctctggatga ttcagtactc   115800
aatgaggatt tttcgcatag atggatgaaa caggctgggt tcatgttttt ctaagataaa   115860
ggtgcttctc tcttttttctc ttggtcactt tgaccaagaa gaaaataaca gagttttttat 115920 tctcaagaag aataatatcg gggccactct gctcagaggc cactctgctt tgaggacccc   115980
ttctctcctc cctcatgcca aagatcagga acattgggca gagcggataa cgatgccgcc   116040
agcgtcatta cattttcacg gcactttcag ttgtgctgag cgtgcaaaca tttcaaggag   116100
acatttctaa gaggtggcta gcacagcatg cctctaatgc cctatgtgaa ttggaataga   116160
gtactaaaga actgttcaat attcaccccca tccccgcata tgcaagcatg cacgtgggtt   116220
cattgtatat gtgtgtgtgc acgtgtgcac agacacattt gtccttcgtt tcaaatgcaa   116280
cacaatggat ggaaattgcc ttcctggtac tggggtatgg atgcaaacac caacagagaa   116340
gcagccgcta cttccaaact gaacacatgt gagatttgcc cttttaattag catctgcagc    116400 tgctgccatc agaagggtct gtctctgttg gcctgaaagt ctttgcttta aaagagcaag   116460
tccattatag ctccaagcca ggctcgtctg tcagctgctg tgctttctct gccatcagcg   116520
gggttgccac attgttttgg gctgtttcac tctaggactc ttttcctcctc ctgtgcccccc  116580 agcctttgat taccatgcct tggtgatcct catttgggtg acctgcagct gctcattgtg    116640
tgtgcaggag acatctccag tccttgtaag gagggaagat cactggcttc agtgctgatg    116700
gactggttat tttccagccc tttgtcgtca gtgatcttgt cttgatatgc agaaaggctc    116760
caggtagtca ctgaaaaaaa tataagcagc agaggtgatg gctatatgaa agtcacgttt    116820
catcaagggc attgctgcta tggaaacttt caattcactt ggagtaggga gccatattgg    116880
ttccacagcc tcctcagcag tgggtcccaa cacagtgctg ggctagctgc ctctgaatca    116940
ccgcagtagc tcctttttact atagattcct gggtcccacc catggaatgt gatccatgaa   117000 gtctgggggtt attccctgga atcctttaag ctccctaagt ggttgggatg ggaaagagat   117060
atgctttatg ttactatact tcttattatt attattttaa aattcttgcc gggcgcagtg    117120
gctcacacct gtaatcccag cacattggga gaccgaggcg ggtggatcac ttgaggtcag   117180
gagttcgaga ctggcctggc caacatgatg aaatcccgtc tctactaaaa atacaaaaat   117240
tagctgggca tggtggcgca tgactgtagt cccagccact ccgaggctg aggcaggaga    117300 atcgcttgaa cccgggaggc agaggttgca gtgagccgag atcgtggcac tgcactccag   117360
cctgggtaac agagtgagac ttcatctcaa aaaaaaccca aaaaaacaaa actctttttc   117420
attataccgg aacgtcagct ttatggagtc ggggattttt tctgttttat tcactgctgt   117480
ttccctaaca tctagaatag tggctggcac gataggcact caagtattga tttagatgag   117540 tctatttat tttctttaa atttttaatt tttattagag gtggggtctg gctttgttgc    117600
ccaagctggt ctcaaaactc ctggcctcaa gcgattgtac tgcctcagcc tcccaaaggg    117660
ctaggatagg catgagccaa catgcctggc ttgtcttatt tttaacaagc acttctggtg    117720
attctgatgg acaatcaggc ttgggaagtt ctaacctaga ggacctacag ttgtcttggg    117780
gtagaagcca aggctatcct ggttttagaa atcagtgcct tactgggcat ctctgaagag    117840
taaaagtcag ggacagagtt acattttggg acaaaaccag atgctgtgaa tggactcttg    117900
```

```
gtcacaacct gggtggcgac ttggtcctta acttcttcat cattttctgc tgaccctgtt 117960
ctttggttca cagcaagtca cctgataaga agactcaaag actgctagtt tgttacttta 118020
gatgatgctt ttggaacctc ttggtaccat tttaacaatc caaacgtatt ttatgaaagc 118080
actcaagtcc tggtctttta ttgtatcttt aagctctaac agcatgatga ttgaataagc 118140
tgtggttggc cacacacaag ccatcttccc catggcctcc attcatacta gaatgagcag 118200 ctataccccca gtagtatagt tttgggatat gggtaacatc ttgggatagc cacatttact 118260
tagtaaatgt ctggcttaca ttctcctaat ggtgcactgt tggaatttttt ggtgtggtaa 118320 cctggaatag tgttggtggg tcaagtttga ttagcatctt tgataaggac ccggtctatt 118380
tagaggtttg tcattgagtg tgtctgtttt ggcctcatgt tgtgaagcat gctgtgtagc 118440
agctgttgta atttttgttg cttgttttct caatcaaccc tggttttgaa gaaatgggaa 118500
gttgttccac tcttagactg atctgacttg ggaggggatt ttcagttcag gaagttggat 118560
cttctgaatg gaagcaaaga atacatgtct ttttgccact ttacaagctg gctcttgttt 118620
tctgaactat tttactggtc attgcaaata gaatgtcagg agtagctgcc aaatactaag 118680
ttgtgttcag tttgtcagtt cttaagagtt gccggtggct gctctgctat gcgtatgact 118740
ttctcagcct taaacttaca agccatactg tttttttcac atctttaata cagccatagg 118800
aaatttataa ctgtggcgtg tcgtcataaa tatgcattgt tcttatttta agacatttca 118860
gtactaaaag tataagtact tctgttatta tctgtgaatt tctttccttc ttcttttttt 118920
ggatatttaa gacctttcg atgtcaatat atatttaaaa cagacatata aattagcatt 118980 caccacata cccagggcct atggagaacc aggttgggat gagtgggtga gctacaggca 119040
gccaggtggc tcctgtgggc tcctcgagga ctggggtgag taactaatgt ctgctaggaa 119100
cttgggggaa agaaggtgtg tatgttaggt gctgcccct tctaagtgtt cctcttgttc 119160
ataattgagt tttttttttt tttttttttt ttttagaagg agtctcgctc tgttgccagg 119220
ctggagtgca gtggtgtgat ctcagctcac tgcaacctct gcctcccggg ttcaagtgat 119280
tctcctgcct cagcctcccg agtagctggg actacaggca tgcaccacca tgcccagcta 119340
atttttgtat ttttagtaaa gacggggttt caccatgttg gccagggtgg tctcgatctc 119400
ttgaccttgt gatccgcctg cctcggcctc ccaaagtgct gggattacag gtgtgagcca 119460
ctgtgcccag cccataaatc aaaatttttt cagcaattgt tatacaagtg gaaccttact 119520
cttcaaatgc aattgtccag tgtctggctt aatgtctgct gttgtcagaa accatgtgaa 119580
tggagtagat tcccaggtta taaggagccc ccagggagga tgcgcgagtc actggcttct 119640 ccagggtct ctggtttggg gttgccttgg tgctgggcac acttcctgga gattttactg 119700
gaccagcctg aggcctttgg ggctctgtgc agatgctcta cttctgactt gtctagagct 119760
ttcttctaat tctggactaa aagcaagcag gagtttggag gatgatggtg agaattcaca 119820
tccccgagtt ggcttttgga atgcagtagt ttgtgagatt tagtgttttt tttaagaagt 119880
atattcagat cttgccttt tcccagaaag catatgagac aacttccaag acatttatag 119940
catggctaat aaaatgggaa atcagggcga aggacaggag aactcaataa gggttaacat 120000
ggctacagcg attgtctaaa tgggttcttt ttgctggcca gagcagaaag gatcatgcag 120060
taaagtgggg gggaagaaag ggaattgaat ggtaggtgaa gacttcatgt tggtgccagg 120120
cactgtgcca ggcctccta ggaccttgtc ttactcaatc ctcacacagt gctgcaagag 120180
gattagtctt atccctgttt tagagaggat gaaactgaaa ggcagcgagg tgaagtcacc 120240
```

```
                                                         -continued agcaggaggc tgaagccgcc caggctaact ggccttatag ctacctaggg actcaggaat   120300
atcacacctg tttatcatca aaaggagaaa ggatttcagt tccttggggt agaagagttt   120360 cttttttgcta atcaaacatt ttacttgagg cttcatattc ttcttcaaga ttttttttcct   120420 gtgtatgtac caacacatgt aataattcct tgtttatttc aaaaaagggg ttgtacttta   120480
ttctttacaa gatttcactt tatattgtca tggacaattt tccatggcag tatgaataaa   120540
tggaatctgt ttgttttttaa tatctttgtc ttatcccatt gtttacatat gtcatatttt   120600
agccagtctc taactgatgg atagctgaat gatttccatg ttttttttccc ctgttacaaa   120660 caatactgca aggaatctat ttatctttct atttatctgc aaactattgt aagtacctgt   120720
aaattgttag aagtggaatt actaggtcaa agggggatatt ttcacattta aattttgaat   120780
agaggctgtc agttgccttc cacactgact ataaaaggaa aagattgtat cacatttatt   120840
gcaagccttc tgtattctgc tgggtgctga ggggaataca gaaaggatat aagagtggtt   120900
gccctctagg aatatccgtc tacactgtac ctaatcctag ggaatgtctg gggtgtcaac   120960
ttgtgggtgg gaaagtgggt ggatttaatt caactgttca agcttgcctt gcaaacactg   121020
tgcatggtgt ctgggactag tctttcatta tattgattcc cctgggtaac agatgtaatt   121080
tccttagggc agggacttca tcctacatga cttacagcgt gccttacaca tcttctttgc   121140
tttgtggaga ccttgttatt ataacacgtc aggtgatatt cgaggatcta attgaggcat   121200
tccctatttt tgggtgtgtg aagaattaat aactttggca ttctatacag gtcatggaat   121260
atcagcctgg agggacttg ctgtcacttt tgaatagata tgaggaccag ttagatgaaa   121320
acctgataca gttttaccta gctgagctga ttttggctgt tcacagcgtt catctgatgg   121380
gatacgtgca tcggtaagtg agactctggt agcatttta tgctgaggat tttcctgtgt   121440
cgcataagag ttcctgcatg gaaatgagtg gatgagtgat ttcaagatca agataacgcc   121500
nnnnnnnnnn nnnnnnnnnn nnnnnnnnnn nnnnnnnnnn nnnnnnnnnn nnnnnnnnnn   121560
nnnnnnnnnn nnnnnnnnnn nnnnnnnnnn nnnnnnnnnn nnnnnnnnnn nnnnnnnnnn   121620
nnnnnnnnnn nnnnnnnnnn nnnnnnnnnn nnnnnnnnnn nnnnnnnnnn nnnnnnnnnn   121680
nnnnnnnnnn nnnnnnnnnn nnnnnnnnnn nnnnnnnnnn nnnnnnnnnn nnnnnnnnnn   121740
nnnnnnnnnn nnnnnnnnnn nnnnnnnnnn nnnnnnnnnn nnnnnnnnnn nnnnnnnnnn   121800
nnnnnnnnnn nnnnnnnnnn nnnnnnnnnn nnnnnnnnnn nnnnnnnnnn nnnnnnnnnn   121860
nnnnnnnnnn nnnnnnnnnn nnnnnnnnnn nnnnnnnnnn nnnnnnnnnn nnnnnnnnnn   121920
nnnnnnnnnn nnnnnnnnnn nnnnnnnnnn nnnnnnnnnn nnnnnnnnnn nnnnnnnnnn   121980
nnnnnnnnnn nnnnnnnnnn nnnnnnnnnn nnnnnnnnnn nnnnnnnnnn nnnnnnnnnn   122040
nnnnnnnnnn nnnnnnnnnn nnnnnnnnnn nnnnnnnnnn nnnnnnnnnn nnnnnnnnnn   122100
nnnnnnnnnn nnnnnnnnnn nnnnnnnnnn nnnnnnnnnn nnnnnnnnnn nnnnnnnnnn   122160
nnnnnnnnnn nnnnnnnnnn nnnnnnnnnn nnnnnnnnnn nnnnnnnnnn nnnnnnnnnn   122220
nnnnnnnnnn nnnnnnnnnn nnnnnnnnnn nnnnnnnnnn nnnnnnnnnn nnnnnnnnnn   122280
nnnnnnnnnn nnnnnnnnnn nnnnnnnnnn nnnnnnnnnn nnnnnnnnnn nnnnnnnnnn   122340
nnnnnnnnnn nnnnnnnnnn nnnnnnnnnn nnnnnnnnnn nnnnnnnnnn nnnnnnnnnn   122400
nnnnnnnnnn nnnnnnnnnn nnnnnnnnnn nnnnnnnnnn nnnnnnnnnn nnnnnnnnnn   122460
nnnnnnnnnn nnnnnnnnnn nnnnnnnnnn nnnnnnnnnn nnnnnnnnnn nnnnnnnnnn   122520
nnnnnnnnnn nnnnnnnnnn nnnnnnnnnn nnnnnnnnnn nnnnnnnnnn nnnnnnnnnn   122580
nnnnnnnnnn nnnnnnnnnn nnnnnnnnnn nnnnnnnnnn nnnnnnnnnn nnnnnnnnnn   122640
```

```
nnnnnnnnnn nnnnnnnnnn nnnnnnnnnn nnnnnnnnnn nnnnnnnnnn nnnnnnnnnn    122700
nnnnnnnnnn nnnnnnnnnn nnnnnnnnnn nnnnnnnnnn nnnnnnnnnn nnnnnnnnnn    122760
nnnnnnnnnn nnnnnnnnnn nnnnnnnnnn nnnnnnnnnn nnnnnnnnnn nnnnnnnnnn    122820
nnnnnnnnnn nnnnnnnnnn nnnnnnnnnn nnnnnnnnnn nnnnnnnnnn nnnnnnnnnn    122880
nnnnnnnnnn nnnnnnnnnn nnnnnnnnnn nnnnnnnnnn nnnnnnnnnn nnnnnnnnnn    122940
nnnnnnnnnn nnnnnnnnnn nnnnnnnnnn nnnnnnnnnn nnnnnnnnnn nnnnnnnnnn    123000
nnnnnnnnnn nnnnnnnnnn nnnnnnnnnn nnnnnnnnnn nnnnnnnnnn nnnnnnnnnn    123060
nnnnnnnnnn nnnnnnnnnn nnnnnnnnnn nnnnnnnnnn nnnnnnnnnn nnnnnnnnnn    123120
nnnnnnnnnn nnnnnnnnnn nnnnnnnnnn nnnnnnnnnn nnnnnnnnnn nnnnnnnnnn    123180
nnnnnnnnnn nnnnnnnnnn nnnnnnnnnn nnnnnnnnnn nnnnnnnnnn nnnnnnnnnn    123240
nnnnnnnnnn nnnnnnnnnn nnnnnnnnnn nnnnnnnnnn nnnnnnnnnn nnnnnnnnnn    123300
nnnnnnnnnn nnnnnnnnnn nnnnnnnnnn nnnnnnnnnn nnnnnnnnnn nnnnnnnnnn    123360
nnnnnnnnnn nnnnnnnnnn nnnnnnnnnn nnnnnnnnnn nnnnnnnnnn nnnnnnnnnn    123420
nnnnnnnnnn nnnnnnnnnn nnnnnnnnnn nnnnnnnnnn nnnnnnnnnn nnnnnnnnnn    123480
nnnnnnnnnn nnnnnnnnnn nnnnnnnnnn nnnnnnnnnn nnnnnnnnnn nnnnnnnnnn    123540
nnnnnnnnnn nnnnnnnnnn nnnnnnnnnn nnnnnnnnnn nnnnnnnnnn nnnnnnnnnn    123600
nnnnnnnnnn nnnnnnnnnn nnnnnnnnnn nnnnnnnnnn nnnnnnnnnn nnnnnnnnnn    123660
nnnnnnnnnn nnnnnnnnnn nnnnnnnnnn nnnnnnnnnn nnnnnnnnnn nnnnnnnnnn    123720
nnnnnnnnnn nnnnaaaaaa ctgatgctag tgaaaatgca taatttaaga ggttagagaa    123780
gctgctcttc aaaatgcccc ccaagtctga gagttaaatc ctttacataa aggacaatat    123840
gtaaaatttt cttttctttt ttctttttt tttgagacgg agtctcgctc tgtcccccag    123900
gctggagtgc agtggcgcga tctcggctca ctgcaagctc cgccccctg ggttcacgcc     123960 attctcctgc ctcagcctcc cgagtagctg ggactgcaag cgcccgccac catgcccagc    124020 taatttttg tatttttagt agagacgggg tttcaccgtg ttagccagga tggtctcgat     124080
ctcctgacct cgtgatccac tcgcttcggc ctcccaaagt gctgggatta caggcataag    124140
ccactgcgcc cggctctttt ttttcttaaa ctgcttccag aaagtggat attattaggt     124200 tgatgttaag aaaaggcttg gagttgcatt aacttttgc tttctagcat ctggcctgtc     124260
tgttctgcag acctgagacc tacttgagat aattttcttg gtgttcaggc ccttggaaaa    124320
ataagttccc tatgttgtcc agtgtcaaag tttctcaacc tcagcactat tcttttttttc   124380 aggttatttt cttgtaatct gttcacttga tcattacatt aagaattaga ttatattgct    124440
ataactacaa agcattttat gttttaaaaa ttatgtacaa tttagaaaca ggcatgaaaa    124500
cttaggtatt aaatttagtg gaataaagca cagaaaaaaa gttaaaataa tgcagtttta   124560
tcacttagga ttaaacattt atatgggccg ggtgtagtgc ctcacacctg taatcccagc    124620
acgtttggag gtcgaggcgg gaggattgct ggagtttgag accagcctgg gcaacaaaat    124680
gagacctagt ctctacaaaa aatcaaaaaa ttagccagac atggtagtac atgcttgtag    124740
ctccagccac atgggaggcc aagacagtag gatcgctgga gcgaaggagg ttgaggctgc    124800
aatgaccgtg tttgcaccat tgcattccag cctgggcgac agaacaagac cctgtcttaa    124860
aacaaattta tatgctgcat tcgtgaaatt aaaaaaaaat catggattta gaaataaatt    124920
gaagcaaggt acattgacag tgtaacctca gcactactga cattttgatc tgaataattc    124980
```

```
tttgttgtgg gggatgcgct gtataagatg tttagctgca tccctgactc ctacctccta   125040
gatgccatta gcaccctccc ctccagatgt gataaccaaa aatgtctcta gacattgcca   125100
gatgtgcctg gggtaggagg gttgggggaa gtgggglttg agaaccctta gttgatcatg   125160
cctgcagtag gttgagaagc atcagaaagc taattaatta gacaggaata tgtgtttgca   125220
gtaagaaaac ctcagcaaac taatcaagtt ccaaagttac tgcttggtaa ataaatagga   125280
attaagaata agaccctatc tctgtgtctg gggtcattct cttcggagct cttggtggag   125340
agacagggtt cccagtttca attttttagt gcttcagact gccctttttca gttataattg   125400 taacaacctt cactccaggt ggggagcctc ccaggtttat ttacaacaag gctcaatctc   125460
tgattatttt ggtcaaggag atatgacact ctataccaca cacttgagaa tattgcctct   125520 cttttttctct tgagctttta gggttggaac gtgacaggca gataaggaat ttttttgcatt   125580 aagtgcaaag tccttttttct tatagaagag caataatctg cacactagat caagtcaagt   125640
gtggatataa aattataatt tttgggggga tatttttaat agtggttttg ggttaaacat   125700 atttcctttta aatgaaatgt ctgtaggcct aaagtaggtt ctaaatgttg cctgtactca   125760
tagtatacca tataaaatat aatccacatt tactggaact accatatatt acttacccca   125820
aatcaatcaa tcccttccct atcaccccca cgtaagatct tcgtattttg gatacctgtg   125880
aatcttagat ctgttcagtt ttccattatc cattgtctta tttcaagctt ctcattcaga   125940
atgttgcttt ggagtatttt ctgttagtaa acacagggcc tagtgactct aggacctgct   126000
gtgtgactta ggtcacccac ttcactttat tagaatctca aagaatggtg aacagctgag   126060
ttccaatctg tctcatttgg ctctcatgaa acagtcata aggagattgt agataaacca   126120
cattatatag catagtaagt gataatcaac cccatttggc agttgcaacc ccacaagaga   126180 tagcccttt tagatttgtg taggagtgaa aagctttatt ttccacaaga ggaacgacat   126240
agtaagaact cctttccccc ctgcttctgc aggtatatgc ttatgcccta ggcaacttga   126300
tgggtaaagt taggtttaaa tagttttatt tgtaagctct tctcttctct tctcttctct   126360
tctcttctct tctcttctct tcttttcttt caagacagag tcttgctctg tcacccaggc   126420
tggagtgcag tgggcgacct tggctcactg caacctccgc ctcctgggtt caagagattc   126480
tcctgcctca gctccccgag tagctgggat tacaggtgcc cgccaccatg cctggctaat   126540
ttttgtattt ttagtagaga tggggtttca ccatgttgaa gcatttagg aaagggggtta   126600 ggaggaggaa gacannnnnn nnnnnnnnnn nnnnnnnnnn nnnnnnnnnn nnnnnnnnnn   126660
nnnnnnnnnn nnnnnntctc cccctttctc ccaaaatatg gcagactctt ctgtccccta   126720
gtcattctca tatagtcttc tgaacttgtt tattttcttc cctgttaata cagtaaaaat   126780
taactaagtt ggccaggagt ggtggcacat gcctgtaatc ccagcacttt gggaggccga   126840
ggcgagcaga tcacctgagg tcaggagttt gagaccagcc tggccaacat ggtgaaaccc   126900
tgtctctact aaaaaaaaat tgtaaaagtt agctgggtgt ggtggtgcgc acctgtagtc   126960
ccagctattc ggaggctga gcagggagaa ttgcttgaac ccaggggctg gaggttcag   127020 tgagccaaga tcgcgccact gcactctagc ctgggcgaca gagcagtctt taaaaaaaaa   127080
aaaaaattaa ctaagttaag tagtacttgg gccctatcag atagtgtcct cctgcaggca   127140
ggctgggccc ctactacagt ttcactttta atatctcacc gagattagct gactgaattg   127200
ccaccagagg agagtgaaag catattgcaa aatcataatc aggacatgtg agattatgtg   127260
ttgaacaggt ttaatgtgct tggggggtcag tgactaatgg gaacttagca gtcattaact   127320
gtcattaaaa acgtttgtta attactatta cacacttaga gatttgttaa ttaacaaaga   127380
```

```
gtaatgcctt tgctaatcac tattatgcac ttaagaggaa gccagtgggt attttccct   127440 tcatagcttt ctagtacaaa ttaataaaat ttagaaaatt agaaaatgat tgtgcataaa   127500
tgtgtataat catgtatctg ttagggggca aaaattagtt ggggaattat ctttctttga   127560
taagtcttat cattagtttg aaaatggggc attggcaatt catactgttt ggctgggttg   127620
tcctgagaaa cactccccag tcaattctgt ttttgcaact ctttggttgt gaacaagtga   127680
ctgccctgtg agctgcaaat aaggagaact gaatattcct gaacagtctg tggcaataaa   127740
aatgaaatcc agtaagtgca aatggtatgt attcaacaat tgcgtagtta ggtcctgcaa   127800
ggtaattaga cataaaggat aagtatttaa tcaacaatat agtagcattt tcattaccta   127860
gtcaaatcaa gatgttacag ttttccttct cttgttttgt tatttaaaaa atatctattg   127920
tggccaggct ccgtggctca cacttgtaat cccagcactt tgggaggcca agatgggtgg   127980
atcacgaggt caagagatcg agaccatcct ggccaaacat agtgaaaccc cgtctctact   128040
aaaaatacaa aaattatctg ggtgtggtgg catgcacctg tagtcgcagt tactcgagag   128100
gctgaggcaa gagaattgct tgaacctggg aggaggaggt tgcagtgagc tgagatcgca   128160
gcactgcact ccagcctggt gacagagcga gactccatct cggaaaaaaa aaaaaatcta   128220
ttggttattg ttggtgcatt ttaaccaaaa ccctttagtt taaccctaac ctgtgctgag   128280
ctctttaaca tttacataca tattaaaaaa cagaatcagc ccagatttcc caacatatta   128340
agtcttctcc ttgacttaag ctactttcag ttcttcaagc ttaagtcacc ctgtggtttt   128400
gtcttaggcc aaatattttc cctttgtct cccttctgt ctatcaagcc aagcctgcct   128460
gtgggttttg gatagtgtga ccatctggct ttcttgaagg ggcacttaca ggggaagttt   128520
tattgcccaa accggtggac aatccatgtc aggaatgatt atatcacact gctttctggg   128580
tttagggctt ggaaaaacct gtatcagagc gtgggcccta gggaagaggt aaaaagagag   128640
gagagggaag aataggtctg tttcatataa cgagaaagtc tcatggcaga ggaatggatg   128700
agattcaagt tacaggctgg aagagcttca tccagaatca gccccgggga gaggagacct   128760
catcacgtcc tcactaaaca ttcactttcc tctccacacc cagttaaagt aaagcaaatt   128820
tacttccttg gtgaaaagcc cagccttcaa ggtatgtgga cttacccaca aaatctcttg   128880
gctcactcag tttcacttac catcgtttaa tgaggaaaaa gttctttttgt accatgtaac   128940 tgctgacctg agagaagccc attatgatat agagttatag gacagctggc caacacacta   129000
tatagctaaa atcagggcct ctctgttttg atggggagaa aagttagaga aggaatcttt   129060
agacttcaaa tttcatggct cagtaaaacg tcaaaataat tttgaagacc aaagggggttg   129120 ccagcttact aggctgccta gacagggtg ggtatgaggg gaagaaagcc tgcttctttc   129180
atcaacagca tatccagaaa caaggacat ttaaacacta aaaagtcag aaggacaaat   129240 tctcagaaaa aaaggacagt cctttaaatg ggttacattt agctttataa aatgccctcc   129300
tgtattgtcc taatctttct ttgccaaggt caagtgcttg ggtgccattg gattataagc   129360
ccctgggttt ctgaacggtg ggggagggaa ccacaggaac aagggttagg ggtgaggaaa   129420
aagaactcat taaccttggg ccctgggtgg aagttaatta tcatgtcttg ccctgtgggt   129480
gggttgaagt aggaacgtta attccaaagg cagttttcca aattttttgaa cttgagattt   129540 gtaaatattat cttgccagtt agccaccagt tctcttctct tttttctttt cttttcttac   129600
agtctcgctg tcacccaggc tgcagtgtaa tggcgcaatc ttggctcact gcaacctccg   129660
cctcccaggt tcaagcgatt cttgtgcctc agcctcccga gtagctggga ccacaggtgt   129720
```

-continued

```
gcaccaccac acctgactaa ttttgtatt tttaatagag atgggcttc accatgttgg   129780 ccatgctggt ctcaaactcc tggcctcaaa tgatccaccc accttggcct cccaaagtgt   129840
tgggattaca ggcatgggcc actgcacctg gccaactgcc agttttctag taatggttag   129900
gttgatattt tagattcatt tttagagttt attatcattt tgctgttatc ataagagaag   129960
ttccatcatg tcaataactt gtattaggaa agacatcttc cattcccggt atatccaact   130020
ctcattcgta taactgaagg ctgtgtgtat atcatcaaca attcttgccc ttttgccctt   130080
ggattgcatt atatgctgtg tgctttttt ttttttaaa ttagtaaagc gtttgcattt   130140
cctgacagtg tgccacttga cagctggttt aagtgcctgg gagaatagta atcagtggca   130200
aatcagcttg tgtctgaaat gtggctgttg gcagtctact tgaggataat tgaaagtttg   130260
ctgtattcgt tttattgatg ggattctagg tgaatgccaa actcccgatt gggaccccag   130320
attacatggc tcctgaagtg ctgactgtga tgaacgggga tggaaaaggc acctacggcc   130380
tggactgtga ctggtggtca gtgggcgtga ttgcctatga gatgatttat gggagatccc   130440
ccttcgcaga gggaacctct gccagaacct tcaataacat tatgaatttc caggtaaaga   130500
gtccttagaa gatttcgaag tcacattgag aaacgttatt taaaaattgt gcgaatgagg   130560
ctgggccgtg ggtggctcat gcctgtaatc ccggcacttt gggaggccga ggtgggtgga   130620
tcacgaggtc aggagatcga gaccatcctg gctaacatgg tgaaacccca tctctactaa   130680
aaaatacaaa aaaattagcc agttgtggtg gtgggcgcct gtagtcccag ctannnnnnn   130740
nnnnnnnnnn nnnnnnnnnn nnnnnnnnnn nnnnnnnnnn nnnnnnnnnn nnnnnnnnnn   130800
nnnnnnnnnn nnnnnnnnnn nnnnnnnnnn nnnnnnnnnn nnnnnnnnnn nnnnnnnnnn   130860
nnnnnnnnnn nnnnnnnnnn nnnnnnnnnn nnnnnnnnnn nnnnnnnnnn nnnnnnnnnn   130920
nnnnnnnnnn nnnnnnnnnn nnnnnnnnnn nnnnnnnnnn nnnnnnnnnn nnnnnnnnnn   130980
nnnnnnnnnn nnnnnnnnnn nnnnnnnnnn nnnnnnnnnn nnnnnnnnnn nnnnnnnnnn   131040
nnnnnnnnnn nnnnnnnnnn nnnnnnnnnn nnnnnnnnnn nnnnnnnnnn nnnnnnnnnn   131100
nnnnnnnnnn nnnnnnnnnn nnnnnnnnnn nnnnnnnnnn nnnnnnnnnn nnnnnnnnnn   131160
nnnnnnnnnn nnnnnnnnnn nnnnnnnnnn nnnnnnnnnn nnnnnnnnnn nnnnnnnnnn   131220
nnnnnnnnnn nnnnnnnnnn nnnnnnnnnn nnnnnnnnnn nnnnnnnnnn nnnnnnnnnn   131280
nnnnnnnnnn nnnnnnnnnn nnnnnnnnnn nnnnnnnnnn nnnnnnnnnn nnnnnnnnnn   131340
nnnnnnnnnn nnnnnnnnnn nnnnnnnnnn nnnnnnnnnn nnnnnnnnnn nnnnnnnnnn   131400
nnnnnnnnnn nnnnnnnnnn nnnnnnnnnn nnnnnnnnnn nnnnnnnnnn nnnnnnnnnn   131460
nnnnnnnnnn nnnnnnnnnn nnnnnnnnnn nnnnnnnnnn nnnnnnnnnn nnnnnnnnnn   131520
nnnnnnnnnn nnnnnnnnnn nnnnnnnnnn nnnnnnnnnn nnnnnnnnnn nnnnnnnnnn   131580
nnnnnnnnnn nnnnnnnnnn nnnnnnnnnn nnnnnnnnnn nnnnnnnnnn nnnnnnnnnn   131640
nnnnnnnnnn nnnnnnnnnn nnnnnnnnnn nnnnnnnnnn nnnnnnnnnn nnnnnnnnnn   131700
nnnnnnnnnn nnnnnnnnnn nnnnnnnnnn nnnnnnnnnn nnnnnnnnnn nnnnnnnnnn   131760
nnnnnnnnnn nnnnnnnnnn nnnnnnnnnn nnnnnnnnnn nnnnnnnnnn nnnnnnnnnn   131820
nnnnnnnnnn nnnnnnnnnn nnnnnnnnnn nnnnnnnnnn nnnnnnnnnn nnnnnnnnnn   131880
nnnnnnnnnn nnnnnnnnnn nnnnnnnnnn nnnnnnnnnn nnnnnnnnnn nnnnnnnnnn   131940
nnnnnnnnnn nnnnnnnnnn nnnnnnnnnn nnnnnnnnnn nnnnnnnnnn nnnnnnnnnn   132000
nnnnnnnnnn nnnnnnnnnn nnnnnnnnnn nnnnnnnnnn nnnnnnnnnn nnnnnnnnnn   132060
nnnnnnnnnn nnnnnnnnnn nnnnnnnnnn nnnnnnnnnn nnnnnnnnnn nnnnnnnnnn   132120
```

-continued

```
nnnnnnnnnn nnnnnnnnnn nnnnnnnnnn nnnnnnnnnn nnnnnnnnnn nnnnnnnnnn    132180
nnnnnnnnnn nnnnnnnnnn nnnnnnnnnn nnnnnnnnnn nnnnnnnnnn nnnnnnnnnn    132240
nnnnnnnnnn nnnnnnnnnn nnnnnnnnnn nnnnnnnnnn nnnnnnnnnn nnnnnnnnnn    132300
nnnnnnnnnn nnnnnnnnnn nnnnnnnnnn nnnnnnnnnn nnnnnnnnnn nnnnnnnnnn    132360
nnnnnnnnnn nnnnnnnnnn nnnnnnnnnn nnnnnnnnnn nnnnnnnnnn nnnnnnnnnn    132420
nnnnnnnnnn nnnnnnnnnn nnnnnnnnnn nnnnnnnnnn nnnnnnnnnn nnnnnnnnnn    132480
nnnnnnnnnn nnnnnnnnnn nnnnnnnnnn nnnnnnnnnn nnnnnnnnnn nnnnnnnnnn    132540
nnnnnnnnnn nnnnnnnnnn nnnnnnnnnn nnnnnnnnnn nnnnnnnnnn nnnnnnnnnn    132600
nnnnnnnnnn nnnnnnnnnn nnnnnnnnnn nnnnnnnnnn nnnnnnnnnn nnnnnnnnnn    132660
nnnnnnnnnn nnnnnnnnnn nnnnnnnnnn nnnnnnnnnn nnnnnnnnnn nnnnnnnnnn    132720
nnnnnnnnnn nnnnnnnnnn nnnnnnnnnn nnnnnnnnnn nnnnnnnnnn nnnnnnnnnn    132780
nnnnnnnnnn nnnnnnnnnn nnnnnnnnnn nnnnnnnnnn nnnnnnnnnn nnnnnnnnnn    132840
nnnnnnnnnn nnnnnnnnnn nnnnnnnnnn nnnnnnnnnn nnnnnnnnnn nnnnnnnnnn    132900
nnnnnnnnnn nnnnnnnnnn nnnnnnnnnn nnnnnnnnnn nnnnnnnnnn nnnnnnnnnn    132960
nnnnnnnnnn nnnnnnnnnn nnnnnnnnnn nnnnnnnnnn nnnnnnnnnn nnnnnnnnnn    133020
nnnnnnnnnn nnnnnnnnnn nnnnnnnnnn nnnnnnnnnn nnnnnnnnnn nnnnnnnnnn    133080
nnnnnnnnnn nnnnnnnnnn nnnnnnnnnn nnnnnnnnnn nnnnnnnnnn nnnnnnnnnn    133140
nnnnnnnnnn nnnnnnnnnn nnnnnnnnnn nnnnnnnnnn nnnnnnnnnn nnnnnnnnnn    133200
nnnnnnnnnn nnnnnnnnnn nnnnnnnnnn nnnnnnnnnn nnnnnnnnnn nnnnnnnnnn    133260
nnnnnnnnnn nnnnnnnnnn nnnnnnnnnn nnnnnnnnnn nnnnnnnnnn nnnnnnnnnn    133320
nnnnnnnnnn nnnnnnnnnn nnnnnnnnnn nnnnnnnnnn nnnnnnnnnn nnnnnnnnnn    133380
nnnnnnnnnn nnnnnnnnnn nnnnnnnnnn nnnnnnnnnn nnnnnnnnnn nnnnnnnnnn    133440
nnnnnnnnnn nnnnnnnnnn nnnnnnnnnn nnnnnnnnnn nnnnnnnnnn nnnnnnnnnn    133500
nnnnnnnnnn nnnnnnnnnn nnnnnnnnnn nnnnnnnnnn nnnnnnnnnn nnnnnnnnnn    133560
nnnnnnnnnn nnnnnnnnnn nnnnnnnnnn nnnnnnnnnn nnnnnnnnnn nnnnnnnnnn    133620
nnnnnnnnnn nnnnnnnnnn nnnnnnnnnn nnnnnnnnnn nnnnnnnnnn nnnnnnnnnn    133680
nnnnnnnnnn nnnnnnnnnn nnnnnnnnnn nnnnnnnnnn nnnnnnnnnn nnnnnnnnnn    133740
nnnnnnnnnn nnnnnnnnnn nnnnnnnnnn nnnnnnnnnn nnnnnnnnnn nnnnnnnnnn    133800
nnnnnnnnnn nnnnnnnnnn nnnnnnnnnn nnnnnnnnnn nnnnnnnnnn nnnnnnnnnn    133860
nnnnnnnnnn nnnnnnnnnn nnnnnnnnnn nnnnnnnnnn nnnnnnnnnn nnnnnnnnnn    133920
nnnnnnnnnn nnnnnnnnnn nnnnnnnnnn nnnnnnnnnn nnnnnnnnnn nnnnnnnnnn    133980
nnnnnnnnnn nnnnnnnnnn nnnnnnnnnn nnnnnnnnnn nnnnnnnnnn nnnnnnnnnn    134040
nnnnnnnnnn nnnnnnnnnn nnnnnnnnnn nnnnnnnnnn nnnnnnnnnn nnnnnnnnnn    134100
nnnnnnnnnn nnnnnnnnnn nnnnnnnnnn nnnnnnnnnn nnnnnnnnnn nnnnnnnnnn    134160
nnnnnnnnnn nnnnnnnnnn nnnnnnnnnn nnnnnnnnnn nnnnnnnnnn nnnnnnnnnn    134220
nnnnnnnnnn nnnnnnnnnn nnnnnnnnnn nnnnnnnnnn nnnnnnnnnn nnnnnnnnnn    134280
nnnnnnnnnn nnnnnnnnnn nnnnnnnnnn nnnnnnnnnn nnnnnnnnnn nnnnnnnnnn    134340
nnnnnnnnnn nnnnnnnnnn nnnnnnnnnn nnnnnnnnnn nnnnnnnnnn nnnnnnnnnn    134400
nnnnnnnnnn nnattgcttt attttctaa ataaatagac atctccccc aaatctccaa       134460
```

```
ggttcagacc ttctaatcag taatatattt tcagggcatt cttccttta tgcttttaga    134520 aagatgtaat agactttctt ttagatgctg ttcaagtact taatcttttc ttgtcttgcc    134580
tttttatctc tgtaatcttc ttgaataagc agttaatttt ttttattcat gaacctgctg    134640
atcatgtcta agaatgtatc tccacttaag taagtcagtg aatggtgatt acctgagtag    134700
agttaaagta gtcccccacc ctcctatctg tggcacatat gttccaagtc tcccagtgga    134760
tgtgtgaaac tgatgatagt actgaaaccc atctacctt tttcctgtgc atacatacct    134820
atgttatata aagcttaact tataaattag gcataatata tttgactccc agctcccagt    134880
gtagtggctc tgcagactca caaaatgtat ttgctttaaa aaattctttt tttttttttt    134940
gagacggagt tttgctcttg ttgcccaggc tggagtgcag tggtgcgacc tcagctcact    135000
gcaacctccg cctcttgggt tcaagcgatt ctcctgcctc agcctcccaa gtagctggga    135060
ttataggcat gcaccaccac acccagctaa ttttctattt ttcgtagaaa cggtttttcc    135120
atgttggtca ggctgatctt gaactcctga cctcaggtga tctgcctgcc tcggccttcc    135180
aaagtgctgg gattacaggt gtgagccacc acgcctggcc aaaaaattct tttaatttaa    135240
gtaaatcttt atttatttac ttttgagaca gagtctcact ctgtgggcca ggcaggaatg    135300
cagtggtgtg atcacggctc actgcagcct cgacctccca tgctcaagca gtcctcccac    135360
ctcagcctcc taagtagcta ggactacagg tgtgtgccat cacactctgc taattttttt    135420
gtatttgtag agacgcggtt tcaccaggtt gcccaggctg gtcttgaact cctgagctca    135480
agtgatcctc ctgctttggc ctcccaaaat actgggatta caggcgtgag ccattgcacc    135540
cagccctaat tttaataaat ctttatttt ggaatagtat tagatttata gaaaagttgc    135600
aaagatagta tggaagagtt cccacatacc cttcacccag ttttccccaa nnnnnnnnnn    135660
nnnnnnnnnn nnnnnnnnnn nnnnnnnnnn nnnnnnnnnn tatttattta tttattttt    135720 gagacacagt cttcccgtcg cccaggctgg agtgtggtgg cacgatctcg gctcactgca    135780
acctccgcct cctgggttca agtgattctt ctgcctcagc ctccgagtag ctgggaccac    135840
aggtgtgcgc caccatgccc ggctactttt tgtattttca gtagagacag ggtttcacca    135900
tgttggtcag gctgatctca agctcctgac ctcaggtgat ctgcctacct agcctcccaa    135960
aagtgctggg attacagaca tgagccaccg cacccagccc ccagtgttaa ctcttacata    136020
acagtgtcac tgtctaagtg tttgaaaaac tatttgtcaa aactaatatt ggtacattat    136080
tgttaactac acttcagact tttttggat tttaccaatt ctcccactca tgtcccttt    136140 ctgtttcagg aatcaatccg tggtaccata ttgcagttag ggtgtttata tttgatggga    136200
ctggtcctag tttagatact tagtgtagct cagccagcag gtgggatctt catgcccacc    136260
gaggattggt attgtgtttt cctggtggtt ttatggcatt tccgactatg cagagaggca    136320
tggtattaac ttcagtgtct cctagcaaat tttcctgttt ttcaccaacc tctgatccct    136380
gcattatttg caatcaactc agagatttgt gattgaaaac attgcttgac tccatgctct    136440
ttaagctatt ttctaactag gtaactgtaa cataaattat gcttttatct agcactgttt    136500
ttcataaaca catgttgagt gattttcatc aaccgaaata cttcgaatca ttaagtttcc    136560
caagttcatg gatgctgctt aaatgcctgg tggttccagg ctgtcgaata tttctgcctt    136620
ctgcaataag agattgtccc ttgttaaaag caacattagc ctttgtgcgg tttcaccccc    136680
aattcttctt tttcttgttg taaccaatga aggaagtac tgcttaacac agcaggtaat    136740
aatcttctaa aactcattat ctcaagaggt ggtcctgcca ggatatataa atgcaattta    136800
agaaaggtct tggcaaattt atgaatgaca gaactgggag tggctaccga gagaaactag    136860
```

```
gatgcgcctt tgctttgaca ctgaggtcag gcgtagcttc tgtaccctcc tgggtcctgc    136920 ctcttgggt tgctgcaggc agcaccccat gaaccaggca tctgacccag ttccaggata    136980
cttattcttc cagcaagtcg aacactctgt gatgagtgac tgccatgctc atgggtcacc    137040
aggctctcat tattctgttt catttccagc ctcccacaag attggttttt cagctgctta    137100
tttattatta tcattatttc aaggctgctt tccaagtttc agtgggggt ttcctaagcg     137160 taccagctgc cctggttgtg cagttccggt gatgtttcag atgctgggcc ggattctggc    137220
tgtacccagc ctgatctttc tgggcttcag gaaagctgaa gccaatcaga gctcctcttt    137280
catgcctttg ggattatgct taccttgcct ggcatcgtgt acctgctccc atccatggga    137340 aagtttgct gtctggtact gtcttctatc aacatctttt aagatatctt ccccgaggc     137400 atcgtgatgt caacggaacc agcacacttg tacgttttat gcaagactgc catatctcaa    137460
cagtgagaaa tgcataatgg aagtggtgat cacggattat ttcctaggac attatggcta    137520
atgcgctaga gaactcggat ggtctgttgc gtctgacatg gctttttct cttgagttgt     137580 ctttcttttg ctattctctg aaagaaacaa ttcttgccac atgatcctga tttttcaggt    137640
cctcagcatt tgttagcaga aagtacactt tgtttccatc cggcagtgac tcagtggtgg    137700
tcccatgctg atgaaacgct gagatagtct tcttccaaat aggtatcgtt ttgattgttg    137760
ctgcttattt gctagctggc cctcaatagt gacaatgaaa cctcaagtgt ataatatggt    137820
tgctcagtaa tcctgaggga agacagtctt tggtttgggg gatagggatt ctgtgcctac    137880
ttagcttcag gtgaaagtct tacaaatttt tgtgtgtaga aataagcacc atgtacctcc    137940
ttgggttttt tctttttttt tctagtcctt tagtatggtc aacaatattg tttagggagt    138000
acctattctg tgctaaccac taggcattca agtatattac actatgctcc ttcaaaacac    138060
ttctgtcaaa tgtaaggatt attataccca ttttacagat gtggttactg tggtaacttg    138120
gccaaggtca tagggcaagt gaataaggga ttctggattt gggtggaggt ctgtgtgatt    138180
ccaaagccca tgctctttct acaatactat atatgccttt gcataagtta ttgttattag    138240
taataatatt tgtgatgatg gcaaataata aaccatgtca cactagagag tgatttaatc    138300
tctaggtcta tttaagaaca tttggaattg caggaattgg atttttttt tttttttaagt   138360 gatggagtct tgccatcttt gcccaggctg gtctcaaact tgtgggctca agtgatcatc    138420
ctccctctgc ctcccaaagt gatgggatta cagatatgag ccaccatgcc cagcctagaa    138480
ttgcaggaat ttttgaattg atgattcatt ctgatatttg aatttctaca gtatgttaag    138540
tgcaatgtca ggtgctggtg ctgtggctcc attgatgaac acatttgggt atggccctac    138600
cttcattgaa tttagagtct aagagcctaa ccggtctttt gcttgaatag agctgtagtc    138660
ctgttaaatt gctgtacctc caaatggtgg gaagtttaat gcttcgtagg cctcccctca    138720
ctagtttact gaaccacatg tgcttgattt ttttttgann nnnnnnnnnn nnnnnnnnnn    138780
nnnnnnnnnn nnnnnnnnnn nnnnnnnnnn nnnnnnnnnn nnnnnnnnnn ctcactgcaa    138840
gctccgcctc ccaggttcac gccattcttc tgcctcagcc tcccgagtag ctgggactac    138900
aggtgcccgc caacacggcc cggctaattt ttttgtattt ttagtagaga cagggtttta    138960
ccatgttagc caggatggtc tcggtctgct gacctcgtga tccacctgcc tcagcctccc    139020
aaagtgctgg gattacaggc atgagccact gtgcctggcc ccacatgtgc ttgattttaa    139080
gcaaaataca gactataggc tgtgacctgg tgatctcttc cccacataca gcatcctgct    139140
aacctataac tctccccatg tctcagatct agcctgggaa aggacaatgt tggatcgatg    139200
```

-continued

```
gcccacttct aatcttggga tttctaatct caagatgagt tgagaagact caggatgtgt 139260
cctgttttct gtttatttag aacagggttt ctcagccttg gcactgttga catttggggc 139320
cagataattc tttgctgtgg gggctgttgt gtgaattgca ggatgttgaa cagcatcgct 139380
gtgctttctc catggatacc agtagcaccc tccccctgca gttgcaacaa ccaaaaatga 139440
ctctagacat tgcccagtct cccctttgggg gctacagtca ccttcagttg agaaccattg 139500
atttagaaga attggccagg ttattatcag gagagggaac atcacagtaa tctgaatctc 139560
tcaatactgc cactgttact gttaacgaac agcaaaacta ttacgtggag gcagtaggac 139620
cttgctactc agagtgtggt ccgtggaccg gcagcatcgg aatcatctag gagcttgtta 139680
gagcttcaga gactcaggcc tactgagtca gaagctgcat tttaataagg atccccaggg 139740
gatttctgtg catattagag ttgtgaagcc ctgcaagagg aagaaattgg atgctagcct 139800 cagagttttct tgctcatctt tgtgggtctt cctacgtttt gtcttcggc ttaaggtatg 139860 gggaggccac tttttggctc aggactccta tgggtgaatg ggactgctta gaactgctgg 139920
gttttaggcc ttgctttgag gaatttaaag cttttctctt agatggacat tacatcgttc 139980
atatacttca aaatggtggt ttgacctaat ctctgccttc tgatagcaaa aagatatttc 140040
cttgactccc tgaaccccac tttactgttg tcccatattg gattttaatt aagggtggaa 140100
taagtattct tcactaacat gtttatacat gtatgatatt accatgccat ttattgagtg 140160
cctagtatgt gccaggagct ctgcaaagtg ctttatgctt attattgttc catttattct 140220
tccccaaacc tctgtgaggc aggtcctatc actagtccac aatacaaatg aggtcatgga 140280
gcccgaagtt ggcagtggta ggaatcaaac tcaggtctcc ctgactctaa attctctttg 140340
cctttgtttt tttgaaaaag tggtatagcc catagcagaa aattcacatt atacagaagg 140400
ttatacggcg aaaaatgcct ccttcccacc ccacgctcaa cccctctccc tcaagcggaa 140460
ccactattgt cagtttctca tagaactttc cagaatattc tatgctccta taacactagc 140520
acaacctatc ctcttaacaa catctttatg ctgcctccca agaattcagt aattttttt 140580 tttttgagat ggagttttgc tctagttgcc caggctggag tgcaatggcg tgatctcggc 140640
tcattgcaac ctctgcctcc cacgttcaag tgattctctt gcctcagcct cccgagtagc 140700
tgggattaca ggcatgcgcc actatgcttg gctaattttg tattttagt agagatgggg 140760 tttctcccat gttggtcagg ctggtcttga actcccaacc tcaggtaatc cgcccacctc 140820
ggcctcccaa agtgttgaga ttacaggcgt gagccaccgc acctggccaa attcagtaat 140880
ttttattggc aggttatttt cccgcatcat tnnnnnnnn nnnnnnnnnn nnnnnnnnnn 140940
nnnnnnnnnn nnnnnnnnnn nnnnnnnnnn nnnnnnnnnn nnnnnnnnnn nnnnnnnnnn 141000
nnnnnnnnnn nnnnnnnnnn nnnnnnnnnn nnnnnnnnnn nnnnnnnnnn nnnnnnnnnn 141060
nnnnnnnnnn nnnnnnnnnn nnnnnnnnnn nnnnnnnnnn nnnnnnnnnn nnnnnnnnnn 141120
nnnnnnnnnn nnnnnnnnnn nnnnnnnnnn nnnnnnnnnn nnnnnnnnnn nnnnnnnnnn 141180
nnnnnnnnnn nnnnnnnnnn nnnnnnnnnn nnnnnnnnnn nnnnnnnnnn nnnnnnnnnn 141240
nnnnnnnnnn nnnnnnnnnn nnnnnnnnnn nnnnnnnnnn nnnnnnnnnn nnnnnnnnnn 141300
nnnnnnnnnn nnnnnnnnnn nnnnnnnnnn nnnnnnnnnn nnnnnnnnnn nnnnnnnnnn 141360
nnnnnnnnnn nnnnnnnnnn nnnnnnnnnn nnnnnnnnnn nnnnnnnnnn nnnnnnnnnn 141420
nnnnnnnnnn nnnnnnnnnn nnnnnnnnnn nnnnnnnnnn nnnnnnnnnn nnnnnnnnnn 141480
nnnnnnnnnn nnnnnnnnnn nnnnnnnnnn nnnnnnnnnn nnnnnnnnnn nnnnnnnnnn 141540
nnnnnnnnnn nnnnnnnnnn nnnnnnnnnn nnnnnnnnnn nnnnnnnnnn nnnnnnnnnn 141600
```

```
nnnnnnnnnn nnnnnnnnnn nnnnnnnnnn nnnnnnnnnn nnnnnnnnnn nnnnnnnnnn 141660
nnnnnnnnnn nnnnnnnnnn nnnnnnnnnn nnnnnnnnnn nnnnnnnnnn nnnnnnnnnn 141720
nnnnnnnnnn nnnnnnnnnn nnnnnnnnnn nnnnnnnnnn nnnnnnnnnn nnnnnnnnnn 141780
nnnnnnnnnn nnnnnnnnnn nnnnnnnnnn nnnnnnnnnn nnnnnnnnnn nnnnnnnnnn 141840
nnnnnnnnnn nnnnnnnnnn nnnnnnnnnn nnnnnnnnnn nnnnnnnnnn nnnnnnnnnn 141900
nnnnnnnnnn nnnnnnnnnn nnnnnnnnnn nnnnnnnnnn nnnnnnnnnn nnnnnnnnnn 141960
nnnnnnnnnn nnnnnnnnnn nnnnnnnnnn nnnnnnnnnn nnnnnnnnnn nnnnnnnnnn 142020
nnnnnnnnnn nnnnnnnnnn nnnnnnnnnn nnnnnnnnnn nnnnnnnnnn nnnnnnnnnn 142080
nnnnnnnnnn nnnnnnnnnn nnnnnnnnnn nnnnnnnnnn nnnnnnnnnn nnnnnnnnnn 142140
nnnnnnnnnn nnnnnnnnnn nnnnnnnnnn nnnnnnnnnn nnnnnnnnnn nnnnnnnnnn 142200
nnnnnnnnnn nnnnnnnnnn nnnnnnnnnn nnnnnnnnnn nnnnnnnnnn nnnnnnnnnn 142260
nnnnnnnnnn nnnnnnnnnn nnnnnnnnnn nnnnnnnnnn nnnnnnnnnn nnnnnnnnnn 142320
nnnnnnnnnn nnnnnnnnnn nnnnnnnnnn nnnnnnnnnn nnnnnnnnnn nnnnnnnnnn 142380
nnnnnnnnnn nnnnnnnnnn nnnnnnnnnn nnnnnnnnnn nnnnnnnnnn nnnnnnnnnn 142440
nnnnnnnnnn nnnnnnnnnn nnnnnnnnnn nnnnnnnnnn nnnnnnnnnn nnnnnnnnnn 142500
nnnnnnnnnn nnnnnnnnnn nnnnnnnnnn nnnnnnnnnn nnnnnnnnnn nnnnnnnnnn 142560
nnnnnnnnnn nnnnnnnnnn nnnnnnnnnn nnnnnnnnnn nnnnnnnnnn nnnnnnnnnn 142620
nnnnnnnnnn nnnnnnnnnn nnnnnnnnnn nnnnnnnnnn nnnnnnnnnn nnnnnnnnnn 142680
nnnnnnnnnn nnnnnnnnnn nnnnnnnnnn nnnnnnnnnn nnnnnnnnnn nnnnnnnnnn 142740
nnnnnnnnnn nnnnnnnnnn nnnnnnnnnn nnnnnnnnnn nnnnnnnnnn nnnnnnnnnn 142800
nnnnnnnnnn nnnnnnnnnn nnnnnnnnnn nnnnnnnnnn nnnnnnnnnn nnnnnnnnnn 142860
nnnnnnnnnn nnnnnnnnnn nnnnnnnnnn nnnnnnnnnn nnnnnnnnnn nnnnnnnnnn 142920
nnnnnnnnnn nnnnnnnnnn nnnnnnnnnn nnnnnnnnnn nnnnnnnnnn nnnnnnnnnn 142980
nnnnnnnnnn nnnnnnnnnn nnnnnnnnnn nnnnnnnnnn nnnnnnnnnn nnnnnnnnnn 143040
nnnnnnnnnn nnnnnnnnnn nnnnnnnnnn nnnnnnnnnn nnnnnnnnnn nnnnnnnnnn 143100
nnnnnnnnnn nnnnnnnnnn nnnnnnnnnn nnnnnnnnnn nnnnnnnnnn nnnnnnnnnn 143160
nnnnnnnnnn nnnnnnnnnn nnnnnnnnnn nnnnnnnnnn nnnnnnnnnn nnnnnnnnnn 143220
nnnnnnnnnn nnnnnnnnnn nnnnnnnnnn nnnnnnnnnn nnnnnnnnnn nnnnnnnnnn 143280
nnnnnnnnnn nnnnnnnnnn nnnnnnnnnn nnnnnnnnnn nnnnnnnnnn nnnnnnnnnn 143340
nnnnnnnnnn nnnnnnnnnn nnnnnnnnnn nnnnnnnnnn nnnnnnnnnn nnnnnnnnnn 143400
nnnnnnnnnn nnnnnnnnnn nnnnnnnnnn nnnnnnnnnn nnnnnnnnnn nnnnnnnnnn 143460
nnnnnnnnnn nnnnnnnnnn nnnnnnnnnn nnnnnnnnnn nnnnnnnnnn nnnnnnnnnn 143520
nnnnnnnnnn nnnnnnnnnn nnnnnnnnnn nnnnnnnnnn nnnnnnnnnn nnnnnnnnnn 143580
nnnnnnnnnn nnnnnnnnnn nnnnnnnnnn nnnnnnnnnn nnnnnnnnnn nnnnnnnnnn 143640
nnnnnnnnnn nnnnnnnnnn nnnnnnnnnn nnnnnnnnnn nnnnnnnnnn nnnnnnnnnn 143700
nnnnnnnnnn nnnnnnnnnn nnnnnnnnnn nnnnnnnnnn nnnnnnnnnn nnnnnnnnnn 143760
nnnnnnnnnn nnnnnnnnnn nnnnnnnnnn nnnnnnnnnn nnnnnnnnnn nnnnnnnnnn 143820
nnnnnnnnnn nnnnnnnnnn nnnnnnnnnn nnnnnnnnnn nnnnnnnnnn nnnnnnnnnn 143880
nnnnnnnnnn nnnnnnnnnn nnnnnnnnnn nnnnnnnnnn nnnnnnnnnn nnnnnnnnnn 143940
```

```
nnnnnnnnnn nnnnnnnnnn nnnnnnnnnn nnnnnnnnnn nnnnnnnnnn nnnnnnnnnn 144000
nnnnnnnnnn nnnnnnnnnn nnnnnnnnnn nnnnnnnnnn nnnnnnnnnn nnnnnnnnnn 144060
nnnnnnnnnn nnnnnnnnnn nnnnnnnnnn nnnnnnnnnn nnnnnnnnnn nnnnnnnnnn 144120
nnnnnnnnnn nnnnnnnnnn nnnnnnnnnn nnnnnnnnnn nnnnnnnnnn nnnnnnnnnn 144180
nnnnnnnnnn nnnnnnnnnn nnnnnnnnnn nnnnnnnnnn nnnnnnnnnn nnnnnnnnnn 144240
nnnnnnnnnn nnnnnnnnnn nnnnnnnnnn nnnnnnnnnn nnnnnnnnnn nnnnnnnnnn 144300
nnnnnnnnnn nnnnnnnnnn nnnnnnnnnn nnnnnnnnnn nnnnnnnnnn nnnnnnnnnn 144360
nnnnnnnnnn nnnnnnnnnn nnnnnnnnnn nnnnnnnnnn nnnnnnnnnn nnnnnnnnnn 144420
nnnnnnnnnn nnnnnnnnnn nnnnnnnnnn nnnnnnnnnn nnnnnnnnnn nnnnnnnnnn 144480
nnnnnnnnnn nnnnnnnnnn nnnnnnnnnn nnnnnnnnnn nnnnnnnnnn nnnnnnnnnn 144540
nnnnnnnnnn nnnnnnnnnn nnnnnnnnnn nnnnnnnnnn nnnnnnnnnn nnnnnnnnnn 144600
nnnnnnnnnn nnnnnnnnnn nnnnnnnnnn nnnnnnnnnn nnnnnnnnnn nnnnnnnnnn 144660
nnnnnnnnnn nnnnnnnnnn nnnnnnnnnn nnnnnnnnnn nnnnnnnnnn nnnnnnnnnn 144720
nnnnnnnnnn nnnnnnnnnn nnnnnnnnnn nnnnnnnnnn nnnnnnnnnn nnnnnnnnnn 144780
nnnnnnnnnn nnnnnnnnnn nnnnnnnnnn nnnnnnnnnn nnnnnnnnnn nnnnnnnnnn 144840
nnnnnnnnnn nnnnnnnnnn nnnnnnnnnn nnnnnnnnnn nnnnnnnnnn nnnnnnnnnn 144900
nnnnnnnnnn nnnnnnnnnn nnnnnnnnnn nnnnnnnnnn nnnnnnnnnn nnnnnnnnnn 144960
nnnnnnnnnn nnnnnnnnnn nnnnnnnnnn nnnnnnnnnn nnnnnnnnnn nnnnnnnnnn 145020
nnnnnnnnnn nnnnnnnnnn nnnnnnnnnn nnnnnnnnnn nnnnnnnnnn nnnnnnnnnn 145080
nnnnnnnnnn nnnnnnnnnn nnnnnnnnnn nnnnnnnnnn nnnnnnnnnn nnnnnnnnnn 145140
nnnnnnnnnn nnnnnnnnnn nnnnnnnnnn nnnnnnnnnn nnnnnnnnnn nnnnnnnnnn 145200
nnnnnnnnnn nnnnnnnnnn nnnnnnnnnn nnnnnnnnnn nnnnnnnnnn nnnnnnnnnn 145260
nnnnnnnnnn nnnnnnnnnn nnnnnnnnnn nnnnnnnnnn nnnnnnnnnn nnnnnnnnnn 145320
nnnnnnnnnn nnnnnnnnnn nnnnnnnnnn nnnnnnnnnn nnnnnnnnnn nnnnnnnnnn 145380
nnnnnnnnnn nnnnnnnnnn nnnnnnnnnn nnnnnnnnnn nnnnnnnnnn nnnnnnnnnn 145440
nnnnnnnnnn nnnnnnnnnn nnnnnnnnnn nnnnnnnnnn nnnnnnnnnn nnnnnnnnnn 145500
nnnnnnnnnn nnnnnnnnnn nnnnnnnnnn nnnnnnnnnn nnnnnnnnnn nnnnnnnnnn 145560
nnnnnnnnnn nnnnnnnnnn nnnnnnnnnn nnnnnnnnnn nnnnnnnnnn nnnnnnnnnn 145620
nnnnnnnnnn nnnnnnnnnn nnnnnnnnnn nnnnnnnnnn nnnnnnnnnn nnnnnnnnnn 145680
nnnnnnnnnn nnnnnnnnnn nnnnnnnnnn nnnnnnnnnn nnnnnnnnnn nnnnnnnnnn 145740
nnnnnnnnnn nnnnnnnnnn nnnnnnnnnn nnnnnnnnnn nnnnnnnnnn nnnnnnnnnn 145800
nnnnnnnnnn nnnnnnnnnn nnnnnnnnnn nnnnnnnnnn nnnnnnnnnn nnnnnnnnnn 145860
nnnnnnnnnn nnnnnnnnnn nnnnnnnnnn nnnnnnnnnn nnnnnnnnnn nnnnnnnnnn 145920
nnnnnnnnnn nnnnnnnnnn nnnnnnnnnn nnnnnnnnnn nnnnnnnnnn nnnnnnnnnn 145980
nnnnnnnnnn nnnnnnnnnn nnnnnnnnnn nnnnnnnnnn nnnnnnnnnn nnnnnnnnnn 146040
nnnnnnnnnn nnnnnnnnnn nnnnnnnnnn nnnnnnnnnn nnnnnnnnnn nnnnnnnnnn 146100
nnnnnnnnnn nnnnnnnnnn nnnnnnnnnn nnnnnnnnnn nnnnnnnnnn nnnnnnnnnn 146160
nnnnnnnnnn nnnnnnnnnn nnnnnnnnnn nnnnnnnnnn nnnnnnnnnn nnnnnnnnnn 146220
nnnnnnnnnn nnnnnnnnnn nnnnnnnnnn nnnnnnnnnn nnnnnnnnnn nnnnnnnnnn 146280
nnnnnnnnnn nnnnnnnnnn nnnnnnnnnn nnnnnnnnnn nnnnnnnnnn nnnnnnnnnn 146340
```

-continued

```
nnnnnnnnnn nnnnnnnnnn nnnnnnnnnn nnnnnnnnnn nnnnnnnnnn nnnnnnaatt 146400
caaaacctgt ctcctgttaa tcccatcctc tctgtttctg ttatcatttc cttagtgtag 146460
atctgcctaa gtgtagaatt tgtagaattt gtcatgttga ctattgtaga cttgtctttt 146520
agagtttcta gcactagcct cttccaccca tcactattga gatgattgta tccgtctcag 146580
tactgacact aacccagcac tctggtttta catctgtcaa tccatcaaga cttcactttc 146640
actttcttcc ctgcctcatt attcactatg ctcttgggcc attgctctgg cttctggggc 146700
tttttctaaag tagcactttt ccccactcca gcccatgaag atacctttta accagctctt 146760
gagattaaat cccctccgtg acactttcct gcaggaactt gcaaaaaagt actgcattcc 146820
ccactggcaa aacttgccat cagccagttt atgtattctc tgcttttcac acccatatct 146880
tgacctctga acaacacaca tattctcctc ttcatttatt tcacagttct gtcttcataa 146940
cattgataag tatgatcaca ttagcgctct agattttaag caactggaag atagctattt 147000
ttttggtact cttcctttaa atttgaacat agtgtctaat tagtcaatta acatttttt 147060
aaagggcga gggacatcat ggtagagaga acgaagttga acgtgttttt ggttgaatat 147120
tagcgcatgc ccactgtatt ctaggcacag tcctgattca ttatatcatc acacaataat 147180
tatttatgtg ccttcatcct ttatgacaca gtgctggctc ttattcatct cccatttctg 147240
caatccatgg tgatgattaa aagtcttagg agttttacga ggctcagtat tttttttttt 147300
taatatgcta gttcttcatg aatacattgg gtactctgaa gcatatcatt tcctgggttt 147360
cctgaagtgg tatgttgcgt ggaatggcac attaggtcta ataattatc ccctatgtaa 147420
ggggtcttgt ttttcattca ttctcttaaa aaatagatat taaacattaa ataaggacag 147480
ccaggnnnnn nnnnnnnnnn nnnnnnnnnn nnnnnnnnnn nnnnnnnnnn nnnnnnnnnn 147540
nnnnnnnnnn nnnnnnnnnn nnnnnnnnnn nnnnnnnnnn nnnnnnnnnn nnnnnnnnnn 147600
nnnnnnnnnn nnnnnnnnnn nnnnnnnnnn nnnnnnnnnn nnnnnnnnnn nnnnnnnnnn 147660
nnnnnnnnnn nnnnnnnnnn nnnnnnnnnn nnnnnnnnnn nnnnnnnnnn nnnnnnnnnn 147720
nnnnnnnnnn nnnnnnnnnn nnnnnnnnnn nnnnnnnnnn nnnnnnnnnn nnnnnnnnnn 147780
nnnnnnnnnn nnnnnnnnnn nnnnnnnnnn nnnnnnnnnn nnnnnnnnnn nnnnnnnnnn 147840
nnnnnnnnnn nnnnnnnnnn nnnnnnnnnn nnnnnnnnnn nnnnnnnnnn nnnnnnnnnn 147900
nnnnnnnnnn nnnnnnnnnn nnnnnnnnnn nnnnnnnnnn nnnnnnnnnn nnnnnnnnnn 147960
nnnnnnnnnn nnnnnnnnnn nnnnnnnnnn nnnnnnnnnn nnnnnnnnnn nnnnnnnnnn 148020
nnnnnnnnnn nnnnnnnnnn nnnnnnnnnn nnnnnnnnnn nnnnnnnnnn nnnnnnnnnn 148080
nnnnnnnnnn nnnnnnnnnn nnnnnnnnnn nnnnnnnnnn nnnnnnnnnn nnnnnnnnnn 148140
nnnnnnnnnn nnnnnnnnnn nnnnnnnnnn nnnnnnnnnn nnnnnnnnnn nnnnnnnnnn 148200
nnnnnnnnnn nnnnnnnnnn nnnnnnnnnn nnnnnnnnnn nnnnnnnnnn nnnnnnnnnn 148260
nnnnnnnnnn nnnnnnnnnn nnnnnnnnnn nnnnnnnnnn nnnnnnnnnn nnnnnnnnnn 148320
nnnnnnnnnn nnnnnnnnnn nnnnnnnnnn nnnnnnnnnn nnnnnnnnnn nnnnnnnnnn 148380
nnnnnnnnnn nnnnnnnnnn nnnnnnnnnn nnnnnnnnnn nnnnnnnnnn nnnnnnnnnn 148440
nnnnnnnnnn nnnnnnnnnn nnnnnnnnnn nnnnnnnnnn nnnnnnnnnn nnnnnnnnnn 148500
nnnnnnnnnn nnnnnnnnnn nnnnnnnnnn nnnnnnnnnn nnnnnnnnnn nnnnnnnnnn 148560
nnnnnnnnnn nnnnnnnnnn nnnnnnnnnn nnnnnnnnnn nnnnnnnnnn nnnnnnnnnn 148620
nnnnnnnnnn nnnnnnnnnn nnnnnnnnnn nnnnnnnnnn nnnnnnnnnn nnnnnnnnnn 148680
```

-continued

| | | | | | |
|---|---|---|---|---|---|
| nnnnnnnnnn | nnnnnnnnnn | nnnnnnnnnn | nnnnnnnnnn | nnnnnnnnnn | nnnnnnnnnn 148740 |
| nnnnnnnnnn | nnnnnnnnnn | nnnnnnnnnn | nnnnnnnnnn | nnnnnnnnnn | nnnnnnnnnn 148800 |
| nnnnnnnnnn | nnnnnnnnnn | nnnnnnnnnn | nnnnnnnnnn | nnnnnnnnnn | nnnnnnnnnn 148860 |
| nnnnnnnnnn | nnnnnnnnnn | nnnnnnnnnn | nnnnnnnnnn | nnnnnnnnnn | nnnnnnnnnn 148920 |
| nnnnnnnnnn | nnnnnnnnnn | nnnnnnnnnn | nnnnnnnnnn | nnnnnnnnnn | nnnnnnnnnn 148980 |
| nnnnnnnnnn | nnnnnnnnnn | nnnnnnnnnn | nnnnnnnnnn | nnnnnnnnnn | nnnnnnnnnn 149040 |
| nnnnnnnnnn | nnnnnnnnnn | nnnnnnnnnn | nnnnnnnnnn | nnnnnnnnnn | nnnnnnnnnn 149100 |
| nnnnnnnnnn | nnnnnnnnnn | nnnnnnnnnn | nnnnnnnnnn | nnnnnnnnnn | nnnnnnnnnn 149160 |
| nnnnnnnnnn | nnnnnnnnnn | nnnnnnnnnn | nnnnnnnnnn | nnnnnnnnnn | nnnnnnnnnn 149220 |
| nnnnnnnnnn | nnnnnnnnnn | nnnnnnnnnn | nnnnnnnnnn | nnnnnnnnnn | nnnnnnnnnn 149280 |
| nnnnnnnnnn | nnnnnnnnnn | nnnnnnnnnn | nnnnnnnnnn | nnnnnnnnnn | nnnnnnnnnn 149340 |
| nnnnnnnnnn | nnnnnnnnnn | nnnnnnnnnn | nnnnnnnnnn | nnnnnnnnnn | nnnnnnnnnn 149400 |
| nnnnnnnnnn | nnnnnnnnnn | nnnnnnnnnn | nnnnnnnnnn | nnnnnnnnnn | nnnnnnnnnn 149460 |
| nnnnnnnnnn | nnnnnnnnnn | nnnnnnnnnn | nnnnnnnnnn | nnnnnnnnnn | nnnnnnnnnn 149520 |
| nnnnnnnnnn | nnnnnnnnnn | nnnnnnnnnn | nnnnnnnnnn | nnnnnnnnnn | nnnnnnnnnn 149580 |
| nnnnnnnnnn | nnnnnnnnnn | nnnnnnnnnn | nnnnnnnnnn | nnnnnnnnnn | nnnnnnnnnn 149640 |
| nnnnnnnnnn | nnnnnnnnnn | nnnnnnnnnn | nnnnnnnnnn | nnnnnnnnnn | nnnnnnnnnn 149700 |
| nnnnnnnnnn | nnnnnnnnnn | nnnnnnnnnn | nnnnnnnnnn | nnnnnnnnnn | nnnnnnnnnn 149760 |
| nnnnnnnnnn | nnnnnnnnnn | nnnnnnnnnn | nnnnnnnnnn | nnnnnnnnnn | nnnnnnnnnn 149820 |
| nnnnnnnnnn | nnnnnnnnnn | nnnnnnnnnn | nnnnnnnnnn | nnnnnnnnnn | nnnnnnnnnn 149880 |
| nnnnnnnnnn | nnnnnnnnnn | nnnnnnnnnn | nnnnnnnnnt | tccttttttt | tttttttttt 149940 |
| tttttttgaga | cggtgtttcg | ctcttgttcc | ccaggctgga | gtgcagtggc | acgatcttgg 150000 |
| ctcactgcaa | cctccacctc | ccaggttcaa | gcgattctct | tgcctcagcc | tcccaagtag 150060 |
| ctgggactac | aggcatgcac | catcacatct | ggctaatttt | tttgtatttt | taatagagat 150120 |
| ggggttttac | catgttggcc | aggctggcct | tgaactcctg | acctcaggtg | atccacctgc 150180 |
| ctcgccctcc | caaggtgctg | ggattacagg | catgagccac | tgtgcctggc | ctacttcttc 150240 |
| ttccttttaa | cttgaagatt | atctgcccct | ttttctaatc | ttaaccgcat | taagctggct 150300 |
| ttgagcatgg | caagagtttt | atagatgaat | cttatttat | agtacaggat | ttcaaaatca 150360 |
| taattatttc | actgagggtg | gcttttaccc | tccattaatt | atacttctca | ctcagaaatg 150420 |
| gaattctatt | ttggtctcct | aaagataaat | tagtatatag | tggaaaggaa | tttataaagtt 150480 |
| ctgctaggaa | ttaaatgata | tgattaacac | aaacatccac | atggatgtgt | ctctgccctg 150540 |
| tgcaggaaag | atgaacattc | agtacagatt | ctgctctatg | tcactagctt | tcaagacctg 150600 |
| caggttctct | cctaagcatg | caattcctgt | gagcagtagc | aataatagca | ggtcatattt 150660 |
| gtggagtgat | tactgtatgc | taagaactgt | ggtaaacact | tttatatgga | ttatttatt 150720 |
| taaacctcct | aatagtccat | tgaaatagat | attgccatgt | tgaaaactga | ggttcagaga 150780 |
| ggttaagtga | cttacccagt | gtcacagaac | tagtaagtgg | tgcagctggg | atttgaactg 150840 |
| agattccaga | acaattgcca | ttaaccactt | tgcttccata | ttagtatcat | ctgcaaatct 150900 |
| ctctccataa | atttcctcag | tctttatctg | agtttcctta | tttcaggaag | gaaaacttct 150960 |
| gttttttgatc | cttatgaaat | acaatttcca | ttaaaactt | tttttttgc | tattaaaaaa 151020 |
| ggtaccggat | aattgaaacc | agactggatt | tgagcctgtg | ttgatggaag | tacacatggg 151080 |

```
atgtgggctg aagtgttcaa tctaatttt  ctttccatca gctaattttt aaagtattaa  151140
gcaagtagat tctgacacta acagggaaga tttaaattct cttgagagac tggaggtgtt  151200
aaataatttt ctggtagtgc acattttaca tcttaaatct tcctcactct cccacctcat  151260
ctcaatgtac ctgaagctct gggaatgttc ttttgtactt ctcaggaaca gccagacctc  151320
tggcttcatc tcctctcccc tccacatccc tttcctgctc caattacttc ccagcgccac  151380
ttggatgttg ttgtcatcgg ggaactttgg aaacagccag attttttttgg agtctgtaag  151440
cagaaaacag actgcttgct gctcatatct ggcacccagc tttgtccaga aaacgaggag  151500
ttaaaaagaa gtctgggctg tgaagggctg tgacaactgt cctaggggga gctctagcga  151560
gccctggcgg gcagtgactc atgctgctct gtcactggga tcagcactgg ccctggcag   151620
gcaggcggca gccaggtggg gttccagcca gagcacgcac gcacggagcc gggagcatgc  151680
agcctgcact gcggggatg  tgatgctcgg ctctaactcg cctggctggc ccgccacgga   151740
cgcctcagct tgcaaccatg gtaacgtttc tggcggggga caccccgggg agcccaccgc  151800
gatgggcagc ctcctggtga ctgatggacg agtgtccacc tcccagaccg agagcgctta  151860
gtaggtcgga ggaagtggag aggatgtaac acgcccccag ccgggagtga agccctgagg  151920
aggtaggagc cgcatatgtc catccgtgca ttcccaccgt cagcgcgcag gggtgctgta   151980
gatcaccggt aggaacttta tttggctggt gcttcattat gctgattaaa ctgcagtgga  152040
tttgatgggc atgattgcgc tggggaagat gcataatgaa ctaaaaaaaa aaaaagtgg   152100
ttaataagat ctcggagtcg acttgtccgg gtatgaatga agtagactgc agtggtatcc  152160
taacaggagt tccagaacct cacacatccc ttttcctggt ccttcctctt atcccggtta  152220
atccacgaaa tgtagaagtt ccatcttatt tcaacgatta gtgctaatca ttaataattt  152280
agacctgtct ggaggaggga atccataggt ttaggtctcc tagcatcctg gcactagcca  152340
gcagctgctc tgtaggagcc ttctggaaac agcaggaagg agcggcttcc ccacgagttc  152400
cccaagtgct ttcgttggcc caagtgcttt cgttggccca agtgacctgt ttgagtttgc  152460
tcttcagttt accccaggcg ggaaggcagc ctgtctgcgg gttggtggcc atgttggcag  152520
agaaggggtt aatctcttgt tgctgtagga gccgaggttg cgagctagat tgaaagcagg  152580
cgctgcagtg ccatcgccag cgccgaagga gtaagacgat cttctccgca acagtgttga  152640
atccggctga aattttttt  cctccccgcc tcctttcttg ttttttcttta accagctcct  152700
ccccccttcg ttcccaccct caagtctgac gatgacacct ccaattttga tgaaccagag  152760
aagaattcgt gggtttcatc ctctccgtgc cagctgagcc cctcaggctt ctcgggtgaa  152820
gaactgccgt ttgtggggtt ttcgtacagc aaggcactgg ggattcttgg tagatctgag  152880
taagtgaaaa tttgactttc taaagggacc tgcattgatg caaggctttt ggagccaaag  152940
gtggtggtgg ggggtgggg  gaataggtgg ggggagtgca gtggagggaa gctgctagtc  153000
acctgcattg ggaaagcagt ctacctgtta gggctttgcg ggggtagcct gttaatattc  153060
tcattttgca gtgtgtaagg tacctgttcc tgtctgtggt atgataattg tcaattgggt  153120
actttgggtt agttttccaa tctttggtct tctttaaagg ggagagagtg ggagatttcc  153180
agcagtgcag atccccggtc aaaggagaaa tgtgcaggag ttaagatgag ctgcccatct  153240
atctaaccat ctatgtatct gtctctcaag tgggtggatg ggggttgcta tcttggctgt  153300
ataaagaatc ctaaaaacct tgtctcataa gctagaggtt tcctgatggg tttaactgag  153360
ctgcaagtgg ctgaaccaga gctctaacag agagatggtg ctcggctcct ctccaagtat  153420
```

```
gctgcaagat cagggatctg gcagctgagc ctctctgagc tggtgagcg ctggcagcca  153480 gagaaagccc cgttactgtg agccaccagg agggagtgtg atgtagccga gtcattgatt  153540
cacagaaact gggcttcata gggggaaaaa aaaccaggag actagaaaat ggaaatataa  153600
atatcactgt aaacctcttg atctggtagg tctttctcca ttctcataaa agctattgaa  153660
aaatgcatta acagagcact tggaattaga gggtcgaggc ttccaggagc ctcctggaat  153720
ttctgtaaaa tgcagtagct tctgtggatg tgggaggtca gtatcttgcc tcattctctc  153780
atgatacaat gacattctgt tttcagagga gtgagttccc cagaagatct tggactgatg  153840
gtgttatttg ccagccaccc tggtccctgc actttcaggt tctcagaggg taatgttggg  153900
ttagttgctg cccacttagg agacgagcag aatttgatat tcttcttggc agcatctttc  153960
cctctttgtg gtatttgtag cttagatatc gatttatagg gatgttatgt tggttcctgg  154020
atggtgtctc cctatgggtg ctattttgac agtaacgttc ctgaaaagat ttcagagtgt  154080
tgtggggaat tgggcatttg atacgaaata aggttgtggg ctgtgattga atgtgaggga  154140 ggttttttatg ttgcaagatg ttgaagtggt ctttcttgat cccctctctg ggggctgggg  154200
ttcaaattca ggttggattt tggtagtgtt agatgtgcct ctctgtctga tttgctccac  154260
aaccccaaag caatctggat ggtggtggga gaggcagagt gctaactagc tgttgaatgt  154320
gccatcagat gggttttgaaa cggctcagca ggattgggag gttttgccat ggcatcaaa  154380 gagcagggca gaagcggagg cctgatgttg aaggatgcat ggttagtggg cagtataacc  154440
ttgacacacg cagcacactg aaggtcacac gtcgtactgg aaggacgtgt ggagagttct  154500
agttctggtt agcagtgggc tggctgggtc agaatgcaag cttgcttggg tgttggtcag  154560
tgatctgaaa gacgagggag gattcgaggg agttagattt caggggaaaa ggcagaatga  154620
tatgggagat cttaggcatt gcaattaatc tgaagcagtg tgtgattaat tgcttatttt  154680
tcaggaagac ttgaatgaca tctttctgtt tctcacagaa agctcagttt agggagctct  154740
ctgacaggga catctcagta ttaaggctga ggcactcgat aaatatttgt tgatttaatt  154800
tacctatgat cctttcctcc agaagtgttt atattgctta ttgtatttga agatgtgcta  154860
tctcacctct ggtagtttaa actatatcct tagagcacaa aacgagctgc tgttcctgac  154920
ccaacagaat gtttaataag attcttattt caaaaaggt ccatgcaaat aaaactgtgt  154980
atttcttatt tggacgatgg catcagagta ttcctatcat tggggaactt taacgttttt  155040
tcaaagcttg gcaacgggt tggaatcaga aagattttct ttcatcttgc gtcttgttat  155100
gtgttattgc tattggactt ggctactctg ctgtaggcag ccctgtgggt gatacctaca  155160
agcatcattt tagaaattca tccacctgtt ggatgtagat gaccctggac atatcagatt  155220
gtgattaatt agaaatctaa taaaagagag gcagtgatga aattacttag cagctcctgc  155280
agttttattg acaaaattta cttggagaga ggggagaca ttttctgggg gtaccaccttt  155340 tgctgccagc gaccctgtgt ttcttcctga gtttcttttt cttttctcac catttcagc  155400 atcacaggtt tttatttaca cacattgatt acctgtgctg ttactcattc ttcacaccac  155460
tgaggaaatt gcagatgctg ctgtactgtg ctaggtaaat tgacctcaga tttgttacca  155520
gtgaattgaa tgaaatgttc agaggtggag ctgaatgaac gaggagtttt tgtggagaaa  155580
ttggcagtga gaatgattta aattctgtga tagctcctcg ttttttggga tccttatttt  155640
gggaccccag actatttta agccattgag tgcatcatta tttaggctg agcaagaatc  155700 ttgatgacag cgtttcaatg gctgaggcgt agtgggagtt ccttgcagct tgagttggtg  155760
ggagctggag agtttctaga gaactaggtt tggttgtctt tggggtgggg ttatggtgaa  155820
```

```
attagtcttg gagagtgagt agctgtctga tgcttctttt ccttttttaac cagcaagagc    155880 ccaaaccaaa tccccaagct ctgaatgcct ggctgttcct ctcagccttt ctttgcttga    155940
acttgacaat agtagggtag taacaggaaa cagcatgtta aagttttaaa aataaaatag    156000
atctcagctc ttttccttcc cattagcaag gggtacattt atttaggttt ttccttctag    156060
attgaggcac tgcctcattt aagttcttgg tgaagccatg catttctgca aaccataagt    156120
ataaactcta gaacgggggt gtccaatctt ttggcttcct tgggccacat gggaagaaga    156180
agaattgtct tgaggcacac ataaaataca ctaatgatag ctgatgagct aaaaaaaaaa    156240
aaaaactcat aaagttttaa gaaagcttac aaacttgtaa gttttgagcc acattaaaaa    156300
ccatcctggg ctgcatgcag cccccggggc cttggttgg acaagcttgc tgtagaaggt     156360
aaaaatcagt tggttttatg ttttttgttt aaacatgctg gttgtatgct tttggaagag    156420
ttggggaaca ctgagggtaa tgggatcttg atggggctgg aatttgtggg aagatggtgt    156480 ctggtaggc tgttttttagg aaggggcact ctcttccttt tgattcagag attttttcctt    156540 tcttttcggg tggttctgaa aacacagcga tggatccagg cattcaaaca ccatggagga    156600
aggaagagtg gctgttgcca ttgcttcccg agttttctgg gaaccagttt ttggtgcctc    156660
ttccttgctc tactggggct tctctgcatg tcagtttctt caactgcgaa gtggaaggac    156720
agcgatactt ttcttacagg acttttgcgg ggatggatga aatacgtaaa acacttggtc    156780
tagtacctgg cacatggaaa agccttggta aatgttcact gttgttattt ttgttattac    156840
taatacacta gtccatgtat gtatagtgtc ctcctataca caccaagaga atatggaaag    156900
gactcagcaa tgattaggta gtccaaagtc ataccagatt ggaaaccaag cttcccaggc    156960
cctgggactt ttctgctaga gacacttcac ggttctgacc aactacaaag agttaatatg    157020
cagttgccaa atacctgttg gtaaaaggtg gatgttgggg aggagtggat tgggaacag     157080 aattagaagg tccagtccca gaatgggtac cttcccatca agttgaacaa gtcaaaacag    157140
gttatgttga aacaactgag agaaagtaaa gcaaacacca ttgctgcaga atatcatggt    157200
acaaattgga catctttggg agttagcgga gtaaggcaaa atccagtgag ggacgcttaa    157260
tgggtaatgc caattcacaa ttcttgttaa attacattgc tgatcttcct tggaatgtct    157320
gtccattccc ccaagtagac tgtgatctca aggcaaggct gggtcttatt catcctggtt    157380
ttcctggagc agtaaatact tgtgctggga ctgggcttat aagcatacta atggaaagta    157440
aaatatttgg gttggttttt taaaaagaca gtggatttgg atcagtggag aggaaggtag    157500
agggaatttc aggtgggcag ggtgctaaca acagcccatc cttacagggc accaactgtg    157560
ttctaggctg tgttccaacc actttacaca gatgaattca tttaaattgc acaaccagcc    157620
caagaggaag gtaccattat tattctcatt ttggatgtga ggaaactgag gcgtggggag    157680
atcaaacaac ttgcctaaag ttatgtagct ttgagtggct tagctgagat ttgaaccctg    157740
tgggtataaa tgccacagat gggaaatttg tgtggggtac cccagggttc atgtgcttgt    157800
tagaagtgga agctatttgt agagaatcac gaatgatgag gttggggcag ggtgtgatgg    157860
gagctgacag gcaggtctaa atgctgggat tccattttca gtctctgtgt ttattgagta    157920
ggtagacggt atagctcttg gatttctcag attttttcct cttttcattt agagactctt    157980
atctggtgtg tgtgtgcccg cacacataca taaacccacg cgtatatact ctttccctga    158040
atgttcttat ttgctaaagc ttaagcttgg caaagagagg aaactgcact gaccttactc    158100
tccaccatat cttcaggctg atcatacaca agttgcttaa taagcatttg gttaatccat    158160
```

-continued

```
ctaaatcatt cttatggctg caactctcat tttgttgatg actctactat ctatgtctat  158220
tcacatctac attttgtact tttgtttgcc tcccatctgt cctgggatgg ctgataccag  158280
tggaagacag cctgaactct ccaatcagtc ctgtttcctt tttatgaaat acttggaggt  158340
tggaggatct tcccttaaaa agtgttttcc tttctacatc cagccaaagg ctcttggtcc  158400
ttgtgcttgc tacctagatc cctattggaa agagtcttgc ctgcaatttg attttttaaa  158460
tagcagcaat aacagagtcg tctctgctac acgaagacat gcatctgctg tatttcccag  158520
acaagttcaa aaaccttaac tagcttctgc ccatggttat tgctctcaag tgccttgtgt  158580
tgttcccatc ccctcattat ctggattaga tgtttaacat ttgcctgtgt gtgttgtgtt  158640
ggattttctc ctctcctctt gctcattcaa tttcttcctt ctcttagcca agcacagctt  158700
gttctcctac ttgccttatt ctgttctcta tttagactgt gcgtgcctgc cttgcagccc  158760
tggcaggacc attccaccgc cttctcattt gtcttaaaga tacctttagg aaatctaatc  158820
cagacaatcc tagcccagtc ctgaagatta ggctccagaa gattctgtca agtgtgtttt  158880
ttgctggcct acacatgcta atttgcatgg ttgcctggga tcccttaaga agacagtcat  158940
tgactaaatg gcgctacatg ttcccaagct ctgcgccagt ctggcaactc ttcctttgtc  159000
tacgtgaatt tctcctagtt ctttctgctt tgcttgctgt tcatctcctg acctctctcc  159060
gacaaacttc nnnnnnnnnn nnnnnnnnnn nnnnnnnnnn nnnnnnnnnn nnnnnnnnnn  159120
nnnnnnnnnn nnnnnnnnnn nnnnnnnnnn nnnnnnnnnn nnnnnnnnnn nnnnnnnnnn  159180
nnnnnnnnnn nnnnnnnnnn nnnnnnnnnn nnnnnnnnnn nnnnnnnnnn nnnnnnnnnn  159240
nnnnnnnnnn nnnnnnnnnn nnnnnnnnnn nnnnnnnnnn nnnnnnnnnn nnnnnnnnnn  159300
nnnnnnnnnn nnnnnnnnnn nnnnnnnnnn nnnnnnnnnn nnnnnnnnnn nnnnnnnnnn  159360
nnnnnnnnnn nnnnnnnnnn nnnnnnnnnn nnnnnnnnnn nnnnnnnnnn nnnnnnnnnn  159420
nnnnnnnnnn nnnnnnnnnn nnnnnnnnnn nnnnnnnnnn nnnnnnnnnn nnnnnnnnnn  159480
nnnnnnnnnn nnnnnnnnnn nnnnnnnnnn nnnnnnnnnn nnnnnnnnnn nnnnnnnnnn  159540
nnnnnnnnnn nnnnnnnnnn nnnnnnnnnn nnnnnnnnnn nnnnnnnnnn nnnnnnnnnn  159600
nnnnnnnnnn nnnnnnnnnn nnnnnnnnnn nnnnnnnnnn nnnnnnnnnn nnnnnnnnnn  159660
nnnnnnnnnn nnnnnnnnnn nnnnnnnnnn nnnnnnnnnn nnnnnnnnnn nnnnnnnnnn  159720
nnnnnnnnnn nnnnnnnnnn nnnnnnnnnn nnnnnnnnnn nnnnnnnnnn nnnnnnnnnn  159780
nnnnnnnnnn nnnnnnnnnn nnnnnnnnnn nnnnnnnnnn nnnnnnnnnn nnnnnnnnnn  159840
nnnnnnnnnn nnnnnnnnnn nnnnnnnnnn nnnnnnnnnn nnnnnnnnnn nnnnnnnnnn  159900
nnnnnnnnnn nnnnnnnnnn nnnnnnnnnn nnnnnnnnnn nnnnnnnnnn nnnnnnnnnn  159960
nnnnnnnnnn nnnnnnnnnn nnnnnnnnnn nnnnnnnnnn nnnnnnnnnn nnnnnnnnnn  160020
nnnnnnnnnn nnnnnnnnnn nnnnnnnnnn nnnnnnnnnn nnnnnnnnnn nnnnnnnnnn  160080
nnnnnnnnnn nnnnnnnnnn nnnnnnnnnn nnnnnnnnnn nnnnnnnnnn nnnnnnnnnn  160140
nnnnnnnnnn nnnnnnnnnn nnnnnnnnnn nnnnnnnnnn nnnnnnnnnn nnnnnnnnnn  160200
nnnnnnnnnn nnnnnnnnnn nnnnnnnnnn nnnnnnnnnn nnnnnnnnnn nnnnnnnnnn  160260
nnnnnnnnnn nnnnnnnnnn nnnnnnnnnn nnnnnnnnnn nnnnnnnnnn nnnnnnnnnn  160320
nnnnnnnnnn nnnnnnnnnn nnnnnnnnnn nnnnnnnnnn nnnnnnnnnn nnnnnnnnnn  160380
nnnnnnnnnn nnnnnnnnnn nnnnnnnnnn nnnnnnnnnn nnnnnnnnnn nnnnnnnnnn  160440
nnnnnnnnnn nnnnnnnnnn nnnnnnnnnn nnnnnnnnnn nnnnnnnnnn nnnnnnnnnn  160500
nnnnnnnnnn nnnnnnnnnn nnnnnnnnnn nnnnnnnnnn nnnnnnnnnn nnnnnnnnnn  160560
```

```
nnnnnnnnnn nnnnnnnnnn nnnnnnnnnn nnnnnnnnnn nnnnnnnnnn nnnnnnnnnn    160620
nnnnnnnnnn nnnnnnnnnn nnnnnnnnnn nnnnnnnnnn nnnnnnnnnn nnnnnnnnnn    160680
nnnnnnnnnn nnnnnnnnnn nnnnnnnnnn nnnnnnnnnn nnnnnnnnnn nnnnnnnnnn    160740
nnnnnnnnnn nnnnnnnnnn nnnnnnnnnn nnnnnnnnnn nnnnnnnnnn nnnnnnnnnn    160800
nnnnnnnnnn nnnnnnnnnn nnnnnnnnnn nnnnnnnnnn nnnnnnnnnn nnnnnnnnnn    160860
nnnnnnnnnn nnnnnnnnnn nnnnnnnnnn nnnnnnnnnn nnnnnnnnnn nnnnnnnnnn    160920
nnnnnnnnnn nnnnnnnnnn nnnnnnnnnn nnnnnnnnnn nnnnnnnnnn nnnnnnnnnn    160980
nnnnnnnnnn nnnnnnnnnn nnnnnnnnnn nnnnnnnnnn nnnnnnnnnn nnnnnnnnnn    161040
nnnnnnnnnn nnnnnnnnnn nnnnnnnnnn nnnnnnnnnn nnnnnnnnnn nnnnnnnnnn    161100
nnnnnnnnnn nnnnnnnnnn nnnnnnnnnn nnnnnnnnnn nnnnnnnnnn nnnnnnnnnn    161160
nnnnnnnnnn nnnnnnnnnn nnnnnnnnnn nnnnnnnnnn nnnnnnnnnn nnnnnnnnnn    161220
nnnnnnnnnn nnnnnnnnnn nnnnnnnnnn nnnnnnnnnn nnnnnnnnnn nnnnnnnnnn    161280
nnnnnnnnnn nnnnnnnnnn nnnnnnnnnn nnnnnnnnnn nnnnnnnnnn nnnnnnnnnn    161340
nnnnnnnnnn nnnnnnnnnn nnnnnnnnnn nnnnnnnnnn nnnnnnnnnn nnnnnnnnnn    161400
nnnnnnnnnn nnnnnnnnnn nnnnnnnnnn nnnnnnnnnn nnnnnnnnnn nnnnnnnnnn    161460
nnnnnnnnnn nnnnnnnnnn nnnnnnnnnn nnnnnnnnnn nnnnnnnnnn nnnnnnnnnn    161520
nnnnnnnnnn nnnnnnnnnn nnnnnnnnnn nnnnnnnnnn nnnnnnnnnn nnnnnnnnnn    161580
nnnnnnnnnn nnnnnnnnnn nnnnnnnnnn nnnnnnnnnn nnnnnnnnnn nnnnnnnnnn    161640
nnnnnnnnnn nnnnnnnnnn nnnnnnnnnn nnnnnnnnnn nnnnnnnnnn nnnnnnnnnn    161700
nnnnnnnnnn nnnnnnnnnn nnnnnnnnnn nnnnnnnnnn nnnnnnnnnn nnnnnnnnnn    161760
nnnnnnnnnn nnnnnnnnnn nnnnnnnnnn nnnnnnnnnn nnnnnnnnnn nnnnnnnnnn    161820
nnnnnnnnnn nnnnnnnnnn nnnnnnnnnn nnnnnnnnnn nnnnnnnnnn nnnnnnnnnn    161880
nnnnnnnnnn nnnnnnnnnn nnnnnnnnnn nnnnnnnnnn nnnnnnnnnn nnnnnnnnnn    161940
nnnnnnnnnn nnnnnnnnnn nnnnnnnnnn nnnnnnnnnn nnnnnnnnnn nnnnnnnnnn    162000
nnnnnnnnnn nnnnnnnnnn nnnnnnnnnn nnnnnnnnnn nnnnnnnnnn nnnnnnnnnn    162060
nnnnnnnnnn nnnnnnnnnn nnnnnnnnnn nnnnnnnnnn nnnnnnnnnn nnnnnnnnnn    162120
nnnnnnnnnn nnnnnnnnnn nnnnnnnnnn nnnnnnnnnn nnnnnnnnnn nnnnnnnnnn    162180
nnnnnnnnnn nnnnnnnnnn nnnnnnnnnn nnnnnnnnnn nnnnnnnnnn nnnnnnnnnn    162240
nnnnnnnnnn nnnnnnnnnn nnnnnnnnnn nnnnnnnnnn nnnnnnnnnn nnnnnnnnnn    162300
nnnnnnnnnn nnnnnnnnnn nnnnnnnnnn nnnnnnnnnn nnnnnnnnnn nnnnnnnnnn    162360
nnnnnnnnnn nnnnnnnnnn nnnnnnnnnn nnnnnnnnnn nnnnnnnnnn nnnnnnnnnn    162420
nnnnnnnnnn nnnnnnnnnn nnnnnnnnnn nnnnnnnnnn nnnnnnnnnn nnnnnnnnnn    162480
nnnnnnnnnn nnnnnnnnnn nnnnnnnnnn nnnnnnnnnn nnnnnnnnnn nnnnnnnnnn    162540
nnnnnnnnnn nnnnnnnnnn nnnnnnnnnn nnnnnnnnnn nnnnnnnnnn nnnnnnnnnn    162600
nnnnnnnnnn nnnnnnnnnn nnnnnnnnnn nnnnnnnnnn nnnnnnnnnn nnnnnnnnnn    162660
nnnnnnnnnn nnnnnnnnnn nnnnnnnnnn nnnnnnnnnn nnnnnnnnnn nnnnnnnnnn    162720
nnnnnnnnnn nnnnnnnnnn nnnnnnnnnn nnnnnnnnnn nnnnnnnnnn nnnnnnnnnn    162780
nnnnnnnnnn nnnnnnnnnn nnnnnnnnnn nnnnnnnnnn nnnnnnnnnn nnnnnnnnnn    162840
nnnnnnnnnn nnnnnnnnnn nnnnnnnnnn nnnnnnnnnn nnnnnnnnnn nnnnnnnnnn    162900
```

```
nnnnnnnnnn nnnnnnnnnn nnnnnnnnnn nnnnnnnnnn nnnnnnnnnn nnnnnnnnnn  162960
nnnnnnnnnn nnnnnnnnnn nnnnnnnnnn nnnnnnnnnn nnnnnnnnnn nnnnnnnnnn  163020
nnnnnnnnnn nnnnnnnnnn nnnnnnnnnn nnnnnnnnnn nnnnnnnnnn nnnnnnnnnn  163080
nnnnnnnnnn nnnnnnnnnn nnnnnnnnnn nnnnnnnnnn nnnnnnnnnn nnnnnnnnnn  163140
nnnnnnnnnn nnnnnnnnnn nnnnnnnnnn nnnnnnnnnn nnnnnnnnnn nnnnnnnnnn  163200
nnnnnnnnnn nnnnnnnnnn nnnnnnnnnn nnnnnnnnnn nnnnnnnnnn nnnnnnnnnn  163260
nnnnnnnnnn nnnnnnnnnn nnnnnnnnnn nnnnnnnnnn nnnnnnnnnn nnnnnnnnnn  163320
nnnnnnnnnn nnnnnnnnnn nnnnnnnnnn nnnnnnnnnn nnnnnnnnnn nnnnnnnnnn  163380
nnnnnnnnnn nnnnnnnnnn nnnnnnnnnn nnnnnnnnnn nnnnnnnnnn nnnnnnnnnn  163440
nnnnnnnnnn nnnnnnnnnn nnnnnnnnnn nnnnnnnnnn nnnnnnnnnn nnnnnnnnnn  163500
nnnnnnnnnn nnnnnnnnnn nnnnnnnnnn nnnnnnnnnn nnnnnnnnnn nnnnnnnnnn  163560
nnnnnnnnnn nnnnnnnnnn nnnnnnnnnn nnnnnnnnnn nnnnnnnnnn nnnnnnnnnn  163620
nnnnnnnnnn nnnnnnnnnn nnnnnnnnnn nnnnnnnnnn nnnnnnnnnn nnnnnnnnnn  163680
nnnnnnnnnn nnnnnnnnnn nnnnnnnnnn nnnnnnnnnn nnnnnnnnnn nnnnnnnnnn  163740
nnnnnnnnnn nnnnnnnnnn nnnnnnnnnn nnnnnnnnnn nnnnnnnnnn nnnnnnnnnn  163800
nnnnnnnnnn nnnnnnnnnn nnnnnnnnnn nnnnnnnnnn nnnnnnnnnn nnnnnnnnnn  163860
nnnnnnnnnn nnnnnnnnnn nnnnnnnnnn nnnnnnnnnn nnnnnnnnnn nnnnnnnnnn  163920
nnnnnnnnnn nnnnnnnnnn nnnnnnnnnn nnnnnnnnnn nnnnnnnnnn nnnnnnnnnn  163980
nnnnnnnnnn nnnnnnnnnn nnnnnnnnnn nnnnnnnnnn nnnnnnnnnn nnnnnnnnnn  164040
nnnnnnnnnn nnnnnnnnnn nnnnnnnnnn nnnnnnnnnn nnnnnnnnnn nnnnnnnnnn  164100
nnnnnnnnnn nnnnnnnnnn nnnnnnnnnn nnnnnnnnnn nnnnnnnnnn nnnnnnnnnn  164160
nnnnnnnnnn nnnnnnnnnn nnnnnnnnnn nnnnnnnnnn nnnnnnnnnn nnnnnnnnnn  164220
nnnnnnnnnn nnnnnnnnnn nnnnnnnnnn nnnnnnnnnn nnnnnnnnnn nnnnnnnnnn  164280
nnnnnnnnnn nnnnnnnnnn nnnnnnnnnn nnnnnnnnnn nnnnnnnnnn nnnnnnnnnn  164340
nnnnnnnnnn nnnnnnnnnn nnnnnnnnnn nnnnatttca gagtaagttt ttctagaaaa  164400
tagaagctgg aaaaaaaagg aaacccaaa  cttggcttcg tgctcgaaga cacagcactg  164460
ctgtgtgtgg gcgggtggct gcgtgcaccc gctgctcaga agtgccttt  ctctccatgg  164520
ggataactgg ctgtgtatcc gagatgtggc caggagtagg caagcaacgt gtgggcaggc  164580
tgcatgttct tttattagca tcttcattgt actgcatctc gtcgagccca gagcatgaac  164640
tggcctgggt ttctaatatc taccctgctt cccacctaat tactccctg  aaccctaaag  164700
tgagggaggg agagttgctc ttgtgggtg  agctttccct ggggtggctg tgaaccaacc  164760
tggcatgtg  atgttcttgg gtatccagag ctgtcctgga ctcaggcttg gagtcagctt  164820
cttagcactg aatgcagcca gtcatggatg gaggtcactg tatctcacat gttccgctct  164880
cccttcctc  catgaccttg cccctctgag cctctgtagc acttttcttg agtgtgtcca  164940
aggccatcta gctaagaagt agcagaaatg ggatttgaag ccatgactgt ttggtgatag  165000
agcctcagct ttgaactggg gttctactgc ctggcacccc tgcacaaatc atggtaacgt  165060
ggtaggagaa catagaggta tagggcaagc ccctccttaa tgccatgaat aatacccatc  165120
ttataggatt gtgggagga  ctcagtgaag taacccgtga agcactaaac acgtgcctga  165180
cacgtgctca ataaatgagc acttgtcctg atgacaaagg tcgtggcatt aattctctct  165240
cctaggttgt tacttccttg aggacaggaa ttgtggcttc cttaatggcc actgcagcag  165300
```

```
agtttctcaa gttggcacta ttgacatttt gggctggata attcttgttg tgggagctgt   165360
cctgtggatt gtaggatgtt gagcagcatc tttggcctct acccgctaca tattaatagc   165420
acccctagtc atgaaaataa aatgtctaga cattgccaaa ctgcccctgt tgagaaccac   165480
tggtctgcag gtatctctca tggggatcac agggctttta tattctcttc tctgtctctc   165540
tctctccctc tctgggtgtc tctctctctc acacacacgc ttagagaagg tggttaaaaa   165600
aaattttgtt gaagtttgag aattttgaga acaaaggaaa aattttggaa ggcattttaa   165660
tgaacagata gactctgtcc cattccatgg tcaacgaatt tcataatta gatagtttgt   165720 ttactgcaac tctgcacccc attgcccatc attttagagt tccaaccagt tagaggattt   165780
ttcttgcaaa ctttccttaa agcagtgata gtatcagctc tttaaataat actatgcttg   165840
atgaagtggt acttttcggg ataatttgag accagccgac ttgctgcttg aagaggacag   165900
ggctatattt ggtaataata tatatgtgat aatatgtatg taatattatt ataatgtaat   165960
atacaataat atttggtgta actggtgact ctgaggccag tctttgatcg aacctctcaa   166020
gctatgattt acattatggt caatgttagc ataatgcaat tatcagcaat cacttgctgt   166080
tgctttgaaa gtcagaagga tggctaataa aaatcttaga aaagaaaac aggccgggtg   166140 cagtggctca cccctgtaat cccagcactt tgggaggctg aggcggacag atcatgaggt   166200
caggagatcg agaccatcct ggccaacatg gtgaaacccc atctgtacta gaatacaaaa   166260
aaaaaaaaaa aatttgctgg gcgtggtggc gtgcgcctgt agtcccagct actcgggagc   166320
tgagtcaggg gaatcgcttg aacccgggag gtggaggttg cagtgagccg agattgtgcc   166380
actgcactcc agcctggtga cagagtgaga ctccgtctca aacaaaacaa acaaaaacaa   166440 aaacaaaaa aagaaaatct tagaaaaaga aaataaattg taatatttca gaatatttgt   166500
tggggaggat atgtgtgctc aagaaatata tactgagaac ttaccattga tgctagagat   166560
tgaattgccc catgtctaca tgaaaaatga atagaatata aacattttaa attgagccat   166620
gtctatctgt attatatttc ttttatagaa attcatggaa atggtatatt ttaactgaat   166680
tattaacact ggggacaata ggctttaatc attatctaat acctgtacgt tgttttgaaa   166740
ttcatagccc accaccatta atttcaaaat tgggttctta ctcaaagagt gatgaaaagg   166800
caccagtacc aaatggtctg gccaaaatgc tacatggaac taaatgctgg ggatggtcat   166860
acaatgagtt ttaagtggct agaccctaaa tcagaagcac tttcttctaa ttagcaccat   166920
ggttcttaat cctttctgta cattacaatc gctcagcagc ttaatacaaa tgttgcttcc   166980
cggggccaca ctccacatct ttctgactct ctgatttaat tggtccgaat ggggcctata   167040
catcaggtgt tttttaaaag gtctccaagt gattctaatg tgtacctgca ttgaggacca   167100
gggaaggtgt aggaagcctg ataacccttta ctctccagcc tcatcctcca atcccatgat   167160
tgtttatggg attgttgcta cacacccagc ttagtcatag cattcttact ctagcttttt   167220
tttagatgca attttttattt attcttaaag aaaaagattt ctttagcacc tttattctaa   167280
agagctctta attgctgtgc ttagaacttc taaacagtga gcatttgtca aacatagaat   167340
agcagaatga aggggttgga cctcgggtga ggagggctgt cgcatggtct ctttcgagtg   167400
ccggcgggtg ggggctgcac atctcctcgc ttctgggccc attgataagt gacctaaaag   167460
tgcctttcgt ttttttttggt gggggtgaa aaagcaatct gttttgtacc cacagcggtg   167520
cactttaaac aggaagccct actggggcca gccttctatg tgtcattaag ttttcacgc   167580 cacatcctac ctatcatcat gcacccatgt catcgttctt ttaaagggtg ccagttttt   167640
```

-continued

```
gcttaagcac aaggagctgt gacctgtgtt gtcatccctg atgcatgtca tgcatgtgac    167700
ttcatgacat gtgggtgact tttgatctct gaaggaccag ggacccagtc tgtggatcac    167760
cactctctcc gtgggtggtt tgggtcttgt tctctagccc acccagccag gtgcaattag    167820
gaataaagga aatagcaaag gaattttgct caaggccatg ccaagcattt catctcatat    167880
gaaaaggaaa agagagagag tgtgtgtgtg ttggctagat ttaggtagaa aacaggctgg    167940
tgagaagcgt agaacttggt taaaatttct agccaaaagt aagatttta aaaagattta     168000 tttctggatc caatccctgt tgcccatttc tatgaataat caccatttgt tttaatgtga    168060
ataatagcac acagcaaatt cagcccctg agttttacca ttttaagcaa ttgctttagg     168120
cccgtgaggc atgtactatt tatgaagttg catgggtagt aatggaaaac acaacaatga    168180
cagtagtaac aggtgacatt tgtcgaacac ttgcagtgtg ccaggcactg tgctgagagc    168240
attacatgca ttatttcatt taatccttcc aagaactctt tgaagtaggt tggtaattat    168300
ggccatttta caattgagga aactgaggtt cggagatgtc aaataactag tcagtggtgg    168360
ggtcagattt ttcttttttt tttaaattta tttgctttt tttttttttt tttttttttg    168420
agacggagtc tcactctgtt gcccaggctg annnnnnnnn nnnnnnnnnn nnnnnnnnnn    168480
nnnnnnnnnn nnnnnnnnnn nnnnnnnnnn nnnnnnnnnn nnnnnnnnnn nnnnnnnnnn    168540
nnnnnnnnnn nnnnnnnnnn nnnnnnnnnn nnnnnnnnnn nnnnnnnnnn nnnnnnnnnn    168600
nnnnnnnnnn nnnnnnnnnn nnnnnnnnnn nnnnnnnnnn nnnnnnnnnn nnnnnnnnnn    168660
nnnnnnnnnn nnnnnnnnnn nnnnnnnnnn nnnnnnnnnn nnnnnnnnnn nnnnnnnnnn    168720
nnnnnnnnnn nnnnnnnnnn nnnnnnnnnn nnnnnnnnnn nnnnnnnnnn nnnnnnnnnn    168780
nnnnnnnnnn nnnnnnnnnn nnnnnnnnnn nnnnnnnnnn nnnnnnnnnn nnnnnnnnnn    168840
nnnnnnnnnn nnnnnnnnnn nnnnnnnnnn nnnnnnnnnn nnnnnnnnnn nnnnnnnnnn    168900
nnnnnnnnnn nnnnnnnnnn nnnnnnnnnn nnnnnnnnnn nnnnnnnnnn nnnnnnnnnn    168960
nnnnnnnnnn nnnnnnnnnn nnnnnnnnnn nnnnnnnnnn nnnnnnnnnn nnnnnnnnnn    169020
nnnnnnnnnn nnnnnnnnnn nnnnnnnnnn nnnnnnnnnn nnnnnnnnnn nnnnnnnnnn    169080
nnnnnnnnnn nnnnnnnnnn nnnnnnnnnn nnnnnnnnnn nnnnnnnnnn nnnnnnnnnn    169140
nnnnnnnnnn nnnnnnnnnn nnnnnnnnnn nnnnnnnnnn nnnnnnnnnn nnnnnnnnnn    169200
nnnnnnnnnn nnnnnnnnnn nnnnnnnnnn nnnnnnnnnn nnnnnnnnnn nnnnnnnnnn    169260
nnnnnnnnnn nnnnnnnnnn nnnnnnnnnn nnnnnnnnnn nnnnnnnnnn nnnnnnnnnn    169320
nnnnnnnnnn nnnnnnnnnn nnnnnnnnnn nnnnnnnnnn nnnnnnnnnn nnnnnnnnnn    169380
nnnnnnnnnn nnnnnnnnnn nnnnnnnnnn nnnnnnnnnn nnnnnnnnnn nnnnnnnnnn    169440
nnnnnnnnnn nnnnnnnnnn nnnnnnnnnn nnnnnnnnnn nnnnnnnnnn nnnnnnnnnn    169500
nnnnnnnnnn nnnnnnnnnn nnnnnnnnnn nnnnnnnnnn nnnnnnnnnn nnnnnnnnnn    169560
nnnnnnnnnn nnnnnnnnnn nnnnnnnnnn nnnnnnnnnn nnnnnnnnnn nnnnnnnnnn    169620
nnnnnnnnnn nnnnnnnnnn nnnnnnnnnn nnnnnnnnnn nnnnnnnnnn nnnnnnnnnn    169680
nnnnnnnnnn nnnnnnnnnn nnnnnnnnnn nnnnnnnnnn nnnnnnnnnn nnnnnnnnnn    169740
nnnnnnnnnn nnnnnnnnnn nnnnnnnnnn nnnnnnnnnn nnnnnnnnnn nnnnnnnnnn    169800
nnnnnnnnnn nnnnnnnnnn nnnnnnnnnn nnnnnnnnnn nnnnnnnnnn nnnnnnnnnn    169860
nnnnnnnnnn nnnnnnnnnn nnnnnnnnnn nnnnnnnnnn nnnnnnnnnn nnnnnnnnnn    169920
nnnnnnnnnn nnnnnnnnnn nnnnnnnnnn nnnnnnnnnn nnnnnnnnnn nnnnnnnnnn    169980
nnnnnnnnnn nnnnnnnnnn nnnnnnnnnn nnnnnnnnnn nnnnnnnnnn nnnnnnnnnn    170040
```

```
nnnnnnnnnn nnnnnnnnnn nnnnnnnnnn nnnnnnnnnn nnnnnnnnnn nnnnnnnnnn  170100
nnnnnnnnnn nnnnnnnnnn nnnnnnnnnn nnnnnnnnnn nnnnnnnnnn nnnnnnnnnn  170160
nnnnnnnnnn nnnnnnnnnn nnnnnnnnnn nnnnnnnnnn nnnnnnnnnn nnnnnnnnnn  170220
nnnnnnnnnn nnnnnnnnnn nnnnnnnnnn nnnnnnnnnn nnnnnnnnnn nnnnnnnnnn  170280
nnnnnnnnnn nnnnnnnnnn nnnnnnnnnn nnnnnnnnnn nnnnnnnnnn nnnnnnnnnn  170340
nnnnnnnnnn nnnnnnnnnn nnnnnnnnnn nnnnnnnnnn nnnnnnnnnn nnnnnnnnnn  170400
nnnnnnnnnn nnnnnnnnnn nnntggctta aaacaacaca catttattat tttacagttc  170460
tggaggtcag aagtctaaga tgatgccagg cttggtggct caagcctgta atcccagcac  170520
tttgggaggc tgaggtggca ggatcacttg aggtcaggag ttccagacta gcctagccaa  170580
catggtgaaa ccccatctct actaaaaata caaaaattag tcaggcacgg tcacgagcac  170640
ctgtaatccc aactactcag gaggctgagg caggagaatt gcttgaaccc aggaggtgga  170700
ggttgcagtg agccgaggtt gcagtgagcc gaggttgcac cactgcactc cagcctgggc  170760
aacagaacgc gaccctgttt ccaagaaaaa aaaaagtcc gggatgagtt ttactgggct  170820
gagatcagtg tagacaaggc tgccctctct ctggaggctc tagggcagaa tctgtttcct  170880
tgtcttttcc agcttctaga ggttgcctgc attccttggc ttgtggcccc ttcctccgtg  170940
ttcaaagcca ttggtgtaac atcttcaggt ctctgtgact ccgatccttg cttccatctt  171000
ataaggatcc ttgtgatttc attgtaccca tccagatatc ccaggagaat cttccatcc  171060 caagatccat aacttaaatc ccatctgcaa agtccctttt gccatgtgtg gtaatatatt  171120
cacagcttgc agagatcagg acatgggcat cttgggaaa cgggaagggg gcattatttg  171180
acctaacatc aagagcatga gatgtttttg taaaatgaaa caaatgttgc agcttcctaa  171240
tgcagcttct taggcccacc tgcaggcccc cttgacgttg gttttctct acctaggtct  171300 gttgtgtcgg gtctggactc ccctgccaag actagctcca tggaaaagaa acttctcatc  171360
aaaagcaaag agctacaaga ctctcaggac aagtgtcaca aggtatttat ttccgcagcc  171420
ggcctccttc cttgctccag gatcctcccg tccgtatatg ccaagggatc cgcccggggc  171480
cgctgctggc tctgagccgc ctgatccgta gagagtgagg cgctcctgcc ttcgctgaag  171540
tcgcgcctcc agcagctcag agggagatga attcgggcct tgctgttgct gtaaatcctt  171600
taaatctaaa ccagaggagg ccctggattt aaacagtccg tttctcagca tgacccagcc  171660
agatgtctgc ttcttccggc aggtggcctg ggtcctcacc tgtggctgag atacatccca  171720
tctgctttga gtgatgcgaa gtctctcttc ctagtctttt aaaactcctg cttatgtcac  171780
tgcggccact gtgttgatta cgctcaacgt ctcttaacat tcactgttcc tgcccagagg  171840
caacgctctg gaaactaata agtcactgct tgcctgggac tcctaagagt gcagcgaat  171900 aaatatctcc ttgccctgtc ctggatttgt cctctagatc tttgcaagga gatgggggg  171960 gatcaagatg gatttgggat aaaattaaag tgacgtctgc aaaacaaaa caaaacaaa  172020 agcaaacagg tgaaaatga tgattgtggc ttccttgcta actgggttag agaagtgatc  172080
aagtgtgaac cgggacttga atgagaggag tgacttagca tttggtgact gtccttaacg  172140
aagaactgtg cgctcctggg cgaagaaaca atggtatttc catcccaact taacttttgg  172200
cgaattagcc ttagcccaga ccaccaggtg gtttcggagg ctacttgaga tgtgattgct  172260
cctaatgaac ctccacgggc cttttaacc tgtcgatgtg tttatttcag atggagcagg  172320
aaatgacccg gttacatcgg agagtgtcag aggtggaggc tgtgcttagt cagaaggagg  172380
```

-continued

```
tggagctgaa ggcctctgag actcagagat ccctcctgga gcaggacctt gctacctaca 172440
tcacagaatg cagtgtgagc cttccctgaa gccccttcc cttggaggtg gcacttcctg 172500
ttgtgtgtgt ctcatcctgt ttcatgatga ctccatgagg cacatcacag ccaatggcag 172560
agagtagaga gagggagagc acaaaagcaa gatctgtgtt ttgcagagta gtgagagcca 172620
ggcgtaaggt ccccaagaaa tgagattgga ctcatttcca gcagaaagtg caggtagacg 172680
gctggtacca tggagtctgg agatgggagt aattcatctt tgccgcaagt tgcaaaagat 172740
cttaacatct cccatcccag cctctgtggt ctgcgttgtg tctgacatga gcagccttga 172800
gaaccagact cccaactatg tacaagaaaa cttactttca atcttcctga catcaaattt 172860
tccattggcc agaaccagtg tagtgacaag aaaatagcct tgaaaaccca gaccctctgt 172920
cattatttac catgtgactt tcatttttc tttccttcac aagagtagac tgtcttcttc 172980
tccattgtct tgttaaattt ttcattcagg tgttttttaa tgtgcccaat taaacagtct 173040
caagaagttg aatcacacat ttctaaagtt tttttcacaa gggagaggaa atctatagaa 173100
cgtggctgat taagaataac tgctatgttt ccattccaga cttggctgcc tttcagtggt 173160
gggtgaagtt attcagctat gtatttcaga tatagatttc agtgccatga agcataaggg 173220
nnnnnnnnnn nnnnnnnnnn nnnnnnnnnn nnnnnnnnnn nnnnnnnnnn nnnnnnnnnn 173280
nnnnnnnnnn nnnnnnnnnn nnnnnnnnnn nnnnnnnnnn nnnnnnnnnn nnnnnnnnnn 173340
nnnnnnnnnn nnnnnnnnnn nnnnnnnnnn nnnnnnnnnn nnnnnnnnnn nnnnnnnnnn 173400
nnnnnnnnnn nnnnnnnnnn nnnnnnnnnn nnnnnnnnnn nnnnnnnnnn nnnnnnnnnn 173460
nnnnnnnnnn nnnnnnnnnn nnnnnnnnnn nnnnnnnnnn nnnnnnnnnn tgattctcct 173520
gcctcagcct cccgagtagc tgggactaca ggcatgcacc accatgccca gctaattttt 173580
gtattttag taaagacggg gtttcaccat gttggccagg gtggtctcga tctcttgacc 173640
ttgtgatccg cctgcctcgg cctcccaaag tgctgggatt acaggtgtga gccactgtgc 173700
ccagcccata aatcaaaatt ttttcagcaa ttgttataca agtggaacct tactcttcaa 173760
atgcaattgt ccagtgtctg gcttaatgtc tgctgttgtc agaaaccatg tgaatgagt 173820
agattcccag gttataagga gccccaggg aggatgcgcg agtcactggc ttctccaggg 173880
gtctctggtt tggggttgcc ttggtgctgg gcacacttcc tggagatttt actgaccag 173940
cctgaggcct ttggggctct gtgcagatgc tctacttctg acttgtctag agctttcttc 174000
taattctgga ctaaaagcaa gcaggagttt ggaggatgat ggtgagaatt cacatccccg 174060
agttggcttt tggaatgcag tagtttgtga gatttagtgt ttttttaag aagtatattc 174120
agatcttgcc ttttcccag aaagcatatg agacaacttc caagacattt atagcatggc 174180
taataaaatg ggaaatcagg gcgaaggaca ggagaactca ataagggtta acatggctac 174240
agcgattgtc taaatgggtt cttttgctg gccagagcag aaaggatcat gcagtaaagt 174300
ggggggaag aaaggggaatt gaatggtagg tgaagacttc atgttggtgc caggcactgt 174360
gccaggccct cctaggacct tgtcttactc aatcctcaca cagtgctgca agaggattag 174420
tcttatccct gttttagaga ggatgaaact gaaaggcagc gaggtgaagt caccagcagg 174480
aggctgaagc cgc                                                    174493
```

<210> SEQ ID NO 4
<211> LENGTH: 494
<212> TYPE: PRT
<213> ORGANISM: Mus Musculus

<400> SEQUENCE: 4

```
Met Leu Lys Phe Lys Tyr Gly Val Arg Asn Pro Pro Glu Ala Ser Ala
 1               5                  10                  15

Ser Glu Pro Ile Ala Ser Arg Ala Ser Arg Leu Asn Leu Phe Phe Gln
            20                  25                  30

Gly Lys Pro Pro Leu Met Thr Gln Gln Gln Met Ser Ala Leu Ser Arg
            35                  40                  45

Glu Gly Met Leu Asp Ala Leu Phe Ala Leu Phe Glu Glu Cys Ser Gln
    50                  55                  60

Pro Ala Leu Met Lys Met Lys His Val Ser Ser Phe Val Gln Lys Tyr
65                  70                  75                  80

Ser Asp Thr Ile Ala Glu Leu Arg Glu Leu Gln Pro Ser Ala Arg Asp
                85                  90                  95

Phe Glu Val Arg Ser Leu Val Gly Cys Gly His Phe Ala Glu Val Gln
                100                 105                 110

Val Val Arg Glu Lys Ala Thr Gly Asp Val Tyr Ala Met Lys Ile Met
            115                 120                 125

Lys Lys Lys Ala Leu Leu Ala Gln Glu Gln Val Ser Phe Phe Glu Glu
        130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn Asn Leu Tyr Leu Val Met Glu Tyr
                165                 170                 175

Gln Pro Gly Gly Asp Phe Leu Ser Leu Leu Asn Arg Tyr Glu Asp Gln
            180                 185                 190

Leu Asp Glu Ser Met Ile Gln Phe Tyr Leu Ala Glu Leu Ile Leu Ala
            195                 200                 205

Val His Ser Val His Gln Met Gly Tyr Val His Arg Asp Ile Lys Pro
210                 215                 220

Glu Asn Ile Leu Ile Asp Arg Thr Gly Glu Ile Lys Leu Val Asp Phe
225                 230                 235                 240

Gly Ser Ala Ala Lys Met Asn Ser Asn Lys Val Asp Ala Lys Leu Pro
                245                 250                 255

Ile Gly Thr Pro Asp Tyr Met Ala Pro Glu Val Leu Thr Val Met Asn
            260                 265                 270

Glu Asp Arg Arg Gly Thr Tyr Gly Leu Asp Cys Asp Trp Trp Ser Val
            275                 280                 285

Gly Val Val Ala Tyr Glu Met Val Tyr Gly Lys Thr Pro Phe Thr Glu
            290                 295                 300

Gly Thr Ser Ala Arg Thr Phe Asn Asn Ile Met Asn Phe Gln Arg Phe
305                 310                 315                 320

Leu Lys Phe Pro Asp Asp Pro Lys Val Ser Ser Glu Leu Leu Asp Leu
            325                 330                 335

Leu Gln Ser Leu Leu Cys Val Gln Lys Glu Arg Leu Lys Phe Glu Gly
            340                 345                 350

Leu Cys Cys His Pro Phe Phe Ala Arg Thr Asp Trp Asn Asn Ile Arg
            355                 360                 365

Asn Ser Pro Pro Pro Phe Val Pro Thr Leu Lys Ser Asp Asp Asp Thr
370                 375                 380

Ser Asn Phe Asp Glu Pro Glu Lys Asn Ser Trp Ala Phe Ile Leu Cys
385                 390                 395                 400

Val Pro Ala Glu Pro Leu Ala Phe Ser Gly Glu Glu Leu Pro Phe Val
            405                 410                 415
```

-continued

```
Gly Phe Ser Tyr Ser Lys Ala Leu Gly Tyr Leu Gly Arg Ser Glu Ser
            420                 425                 430

Val Val Ser Ser Leu Asp Ser Pro Ala Lys Val Ser Ser Met Glu Lys
            435                 440                 445

Lys Leu Leu Ile Lys Ser Lys Glu Leu Gln Asp Ser Gln Asp Lys Cys
        450                 455                 460

His Lys Val Ser Ile Ser Thr Ala Gly Leu Arg Pro Cys Ser Arg Ile
465                 470                 475                 480

Leu Gln Ser Ile Tyr Ala Glu Gly Ser Ala Gly Gly His Cys
                485                 490
```

ISOLATED HUMAN KINASE PROTEINS, NUCLEIC ACID MOLECULES ENCODING HUMAN KINASE PROTEINS, AND USES THEREOF

RELATED APPLICATIONS

The present application is a divisional of U.S. application Ser. No. 09/804,471, filed on Mar. 13, 2001 and issued on Nov. 12, 2002 as U.S. Pat. No. 6,479,269.

FIELD OF THE INVENTION

The present invention is in the field of kinase proteins that are related to the rho/rac-interacting citron kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A–XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books,* Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine,* McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

Activated Rho GTPases trigger distinctive kinase cascades. In particular, the Rho-binding serine/threonine kinase (ROCK) binds to Rho, and its kinase activity is moderately stimulated by this association. The citron molecule (Madaule et al., 1995), a specific interactor of Rho and Rac, shares a significant degree of structural homology with ROCK; however, its lack of a kinase domain raised the question of its biologic function. By PCR of a mouse primary keratinocyte cDNA library, Di Cunto et al. (1998) identified a novel serine/threonine kinase, CRIK (citron Rho-interacting kinase), belonging to the myotonic dystrophy kinase family. CRIK can be expressed as at least 2 isoforms, one of which encompasses the previously reported form of citron in almost its entirety. The long form of CRIK is a 240-kD protein in which the kinase domain is followed by the sequence of citron. The short form, CRIK-SK (short kinase), is an approximately 54-kD protein that consists mostly of the kinase domain. CRIK and CRIK-SK proteins are capable of phosphorylating exogenous substrates as well as of autophosphorylation, when tested by in vitro kinase assays after expression into COS-7 cells. CRIK kinase activity is increased several-fold by coexpression of constitutively active Rho, while active Rac has more limited effects. Kinase activity of the endogenous CRIK is indicated by in vitro kinase assays after immunoprecipitation with antibodies recognizing the citron moiety of the protein. When expressed in keratinocytes, full-length CRIK, but not CRIK-SK, localizes into corpuscular cytoplasmic structures and elicits recruitment of actin into these structures. The previously reported Rho-associated kinases ROCK1 and ROCK2 are ubiquitously expressed. Northern blot analysis of mouse tissues revealed a restricted pattern of expression limited to keratinocytes, brain, spleen, lung, kidney, and an especially strong signal in testis. No expression was detectable in heart, liver, or skeletal muscle. The CRIK protein contains a kinase domain, a coiled-coil domain, a leucine-rich domain, a Rho-Rac binding domain, a zinc finger region, a pleckstrin homology domain, and a putative SH3-binding domain. Di Cunto et al. (1998) reported cloning the human homolog of the CRIK kinase domain. They stated that the human homolog of citron is contained within a PAC clone mapping to chromosome 12q.

Di Cunto et al. (2000) generated mice deficient in citron kinase by targeted disruption. Citron-K-/-mice grow at slower rates, are severely ataxic, and die before adulthood as a consequence of fatal seizures. Their brains display defective neurogenesis, with dramatic depletion of microneurons in the olfactory bulb, hippocampus, and cerebellum. These abnormalities arise during development of the central nervous system due to altered cytokinesis and massive apoptosis. Di Cunto et al (2000) concluded that citron-K is essential for cytokinesis in vivo, in specific neuronal precursors only. Moreover, they suggested a novel molecular mechanism for a subset of human malformation syndromes of the central nervous system. For a review, see Di Cunto et al., *J Biol Chem* 1998 Nov 6;273(45):29706–11; Di Cunto, et al., *Neuron* 28: 115–127, 2000; Madaule et al., *FEBS Lett.* 377: 243–248, 1995; Nagase et al., *DNA Res.* 6: 63–70, 1999.

Kinase proteins, particularly members of the rho/rac-interacting citron kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the rho/rac-interacting citron kinase subfamily.

SUMMARY OF THE INVENTION

The present invention is based in part on the identification of amino acid sequences of human kinase peptides and proteins that are related to the rho/rac-interacting citron kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the brain glioblastoma, uterus tumor, colon, normal nervous system, tumor nervous system.

DESCRIPTION OF THE FIGURE SHEETS

FIGS. 1A–1C provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the brain glioblastoma, uterus tumor, colon, normal nervous system, tumor nervous system.

FIGS. 2A–2E provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3SSSS provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. 148 SNPs, including 6 indels, have been identified in the gene encoding the kinase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the rho/rac-interacting citron kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the rho/rac-interacting citron kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the rho/rac-interacting citron kinase subfamily and the expression pattern observed. Experimental data as provided in FIG. 1 indicates expression in the brain glioblastoma, uterus tumor, colon, normal nervous system, tumor nervous system. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known rho/rac-interacting citron kinase family or subfamily of kinase proteins.

Specific Embodiments

Peptide Molecules

The present invention provides nucleic acid sequences that encode protein molecules that have been identified as being members of the kinase family of proteins and are related to the rho/rac-interacting citron kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the brain glioblastoma, uterus tumor, colon, normal nervous system, tumor nervous system. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO: 1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 12 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. As indicated by the data presented in FIG. 3, the map position was determined to be on chromosome 12 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., Science 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., J. Mol. Biol. 224:899–904 (1992); de Vos et al. Science 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties, 2nd Ed., T. E. Creighton, W. H. Freeman and Company, New York (1993). Many detailed reviews are available on this subject, such as by Wold, F., Posttranslational Covalent Modification of Proteins, B. C. Johnson, Ed., Academic Press, New York 1–12 (1983); Seifter et al. (Meth. Enzymol. 182: 626–646 (1990)) and Rattan et al. (Ann. N.Y. Acad. Sci. 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Substantial chemical and structural homology exists between the rho/rac-interacting citron kinase protein described herein and mouse Cirton Rho-interacting kinase (CRIK) (see FIG. 1). As discussed in the background, mouse CRIK are known in the art to be involved in phosphorylating exogenous substrates as well as autophosphorylation., and have be may play a role in central nervous system S. Accordingly, the rho/rac-interacting citron kinase protein, and the encoding gene, provided by the present invention is useful for treating, preventing, and/or diagnosing disorder related to the cytokinesis and massive apoptosis.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. A large percentage of pharmaceutical agents are being developed that modulate the activity of kinase proteins, particularly members of the rho/rac-interacting citron kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the brain glioblastoma, uterus tumor, colon, normal nervous system, tumor nervous system. Such uses can readily be determined using the information provided herein, that which is known in the art, and routine experimentation.

The proteins of the present invention (including variants and fragments that may have been disclosed prior to the present invention) are useful for biological assays related to kinases that are related to members of the rho/rac-interacting citron kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the brain glioblastoma, uterus tumor, colon, normal nervous system, tumor nervous system. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind to or otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the brain glioblastoma, uterus tumor, colon, normal nervous system, tumor nervous system. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the brain glioblastoma, uterus tumor, colon, normal nervous system, tumor nervous system. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the brain glioblastoma, uterus tumor, colon, normal nervous system, tumor nervous system. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction.

FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^3H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the brain glioblastoma, uterus tumor, colon, normal nervous system, tumor nervous system. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the brain glioblastoma, uterus tumor, colon, normal nervous system, tumor nervous system. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the brain glioblastoma, uterus tumor, colon, normal nervous system, tumor nervous system. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 12 by ePCR.

FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 148 SNPs, including 6 indels, have been identified in the gene encoding the kinase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 12 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the brain glioblastoma, uterus tumor, colon, normal nervous system, tumor nervous system. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the brain glioblastoma, uterus tumor, colon, normal nervous system, tumor nervous system.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements. As indicated by the data presented in FIG. 3, the map position was determined to be on chromosome 12 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the brain glioblastoma, uterus tumor, colon, normal nervous system, tumor nervous system by a virtual northern blot. In addition, PCR-based tissue screening panel indicates expression in a pooled tissues such as brain, heart, kidney, lung, spleen, testis, leukocyte. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 148 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion E. coli expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example E. coli. (Wada et al., *Nucleic Acids Res.* 20:2111–2118 (1992)).

The nucleic acid molecules can also be expressed by expression vectors that are operative in yeast. Examples of vectors for expression in yeast e.g., S. cerevisiae include pYepSec1 (Baldari, et al., *EMBO J* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual*. 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *